(12) United States Patent
zur Megede et al.

(10) Patent No.: US 7,618,642 B2
(45) Date of Patent: Nov. 17, 2009

(54) EXPRESSION CASSETTES ENCODING MODIFIED HUMAN IMMUNODEFICIENCY VIRUS TYPE 1 SUBTYPE C ENVELOPE GLYCOPROTEINS

(75) Inventors: Jan zur Megede, San Francisco, CA (US); Susan Barnett, San Francisco, CA (US); Ying Lian, Vallejo, CA (US); Susan Engelbrecht, Tygerberg (ZA); Estrelita Janse van Rensburg, Tygerberg (ZA)

(73) Assignee: Novartis Vaccines and Diagnostics, Inc., Emeryville, CA (US)

(*) Notice: Subject to any disclaimer, the term of this patent is extended or adjusted under 35 U.S.C. 154(b) by 357 days.

(21) Appl. No.: 09/899,575

(22) Filed: Jul. 5, 2001

(65) Prior Publication Data

US 2003/0223961 A1    Dec. 4, 2003

Related U.S. Application Data

(63) Continuation-in-part of application No. 09/610,313, filed on Jul. 5, 2000.

(51) Int. Cl.
- A61K 39/21 (2006.01)
- C12P 21/06 (2006.01)
- C07H 21/04 (2006.01)

(52) U.S. Cl. .................. 424/208.1; 424/188.1; 435/69.1; 536/23.72

(58) Field of Classification Search .............. 424/188.1, 424/208.1; 536/23.72
See application file for complete search history.

(56) References Cited

FOREIGN PATENT DOCUMENTS

| | | |
|---|---|---|
| WO | WO 97/31115 | 8/1997 |
| WO | WO 99/41397 | 8/1999 |
| WO | WO 00/15819 | 3/2000 |
| WO | WO 03/004620 A2 | 1/2003 |

OTHER PUBLICATIONS

2008, Instructions to Authors, J. Virol. 82(1):1-19.*

Johnson, P. R. , et al., 1992, Identification of overlapping HLA class I-restricted cytotoxic T cell epitopes in a conserved region of the human immunodeficiency virus type 1 envelope glycoprotein: definition of minimum eptiopes and analysis of the effects of sequence variation, J. Exp. Med. 175:961-971.*

Dai, L. C., et al., 1992, Mutation of human immunodeficiency virus type 1 at amino acid 585 on gp41 results in loss of killing by CD8+ A24-restricted cytotoxic T lymphocytes, J. Virol. 66(5):3151-3154.*

Watkins, B. A., et al., Immune escape by human immunodeficiency virus type 1 from neutralizing antibodies: evidence for multiple pathways, J. Virol. 67(12):7493-7500.*

Fenoglio, D., et al., 2000, Natural analogue peptides of HIV-1 gp120 T-helper epitope antagonize response of gp120-specific human CD4 T-cell clones, JAIDS 23:1-7.*

McLain, L., et al., Different effects of a single amino acid substitution on three adjacent epitopes in the gp41 C-terminal tail of a neutralizing antibody escape mutant of human immunodeficiency virus type 1, Arch. Virol. 146:157-166.*

(Continued)

Primary Examiner—Jeffrey S. Parkin
(74) Attorney, Agent, or Firm—Regina Bautista; Helen Lee

(57) ABSTRACT

The present invention relates to polynucleotides encoding immunogenic HIV type C polypeptides. Uses of the polynucleotides in applications including DNA immunization, generation of packaging cell lines, and production of HIV Type C proteins are also described.

20 Claims, 114 Drawing Sheets

```
gp140mod.TV1.delV2   (SEQ ID NO:120)

1 gaattcatgc gcgtgatggg cacccagaag aactgccagc agtggtggat ctggggcatc
  61 ctgggcttct ggatgctgat gatctgcaac acgaggacc tgtgggtgac cgtgtactac
 121 ggcgtgcccg tgtggcgcga cgccaagacc accctgttct gcgccagcga cgccaaggcc
 181 tacgagaccg aggtgcacaa cgtgtgggcc acccacgcct ggtgccac cgaccccaac
 241 ccccaggaga tcgtgctggg caacgtgacc gagaacttca acatgtggaa gaacgacatg
 301 gccgaccaga tgcacgagga cgtgatcagc ctgtgggacc agagcctgaa gccctgcgtg
 361 aagctgaccc ccctgtgcgt gaccctgaac tgcaccgaca ccaacgtgac cggcaacgc
 421 accgtgaccg gcaacagcac caacaacacc aacggcacg gcatctacaa catcgaggag
 481 atgaagaact gcagcttcaa cgccggcgcc ggccgcctga tcaactgcaa caccagcacc
 541 atcacccagg cctgcccaa ggtgagcttc gacccatcc ccatccacta ctgcgcccc
 601 gccggctacg ccatcctgaa gtgcaacaac agaccttca acggcaccgg ccctgctac
 661 aacgtgagca ccgtgcagtg cacccacggc atcaagccgg tggtgagcac ccagctgctg
 721 ctgaacggca gcctggccga ggagggcatc atcatccgca gcgagaacct gaccgagaac
 781 accaagacca tcatcgtgca cctgaacgag agcgtggaga tcaactgcac ccgccccaac
 841 aacaacaccc gcaagagcgt gcgcatcggc cccggccagg ccttctacgc caccaacgac
 901 gtgatcggca acatccgcca ggcccactgc aacatcagca ccgaccgctg gaacaagacc
 961 ctgcagcagg tgatgaagaa gctgggcgag cacttcccca acaagaccat ccagttcaag
1021 ccccacgccg gcggcgacct ggagatcacc atgcacagct tcaactgccg cggcgagttc
1081 ttctactgca acaccagcaa cctgttcaac agcacctacc acagcaacaa cggcacctac
1141 aagtacaacg gcaacagcag cagcccatc acctgcagt gcaagatcaa gcagatcgtg
1201 cgcatgtggc agggcgtggg ccaggccacc tacgccccc ccatcgccgg caacatcacc
1261 tgccgcagca acatcaccgg catcctgctg accgcgacg gcggcttcaa caccaaccgac
1321 aacaccgaga ccttccgcc cggcgggcgc gacatgcgcg acaactggcg cagcgagctg
1381 tacaagtaca aggtggtgga gatcaagccc ctgggcatcg ccccccaccaa ggccaaggcgc
1441 cgcgtggtgc agcgcgagaa gcgcgccgtg ggcatcggcg ccgtgttcct gggcttcctg
1501 ggcgccgccg gcagcaccat gggcgccgcc agcatcaccc tgaccgtgca ggcccgccag
1561 ctgctgagcg gcatcgtgca gcagcagagc aacctgctga agcatcga ggccagcag
1621 cacatgctgc agctgaccgt gtgggcatc aagcagctgc agccccgcgt gctggccatc
1681 gagcgctacc tgaaggacca gcagctgctg ggcatctggg gctgcagggg ccgcctgatc
1741 tgcaccaccg ccgtgccctg gaacagcagc tggagcaaca agagcgagaa ggacatctgg
1801 gacaacatga cctggatgca gtgggaccgc gagtcagca actacaccgg cctgatctac
1861 aacctgctgg aggacagcca gaaccagcag gagaagaacg agaaggacct gctggagctg
1921 gacaagtgga caaacctgtg gaactggttc gacatcagca actggccctg gtacatctaa
1981 ctcgag
```

OTHER PUBLICATIONS

Liu, Y., et al., 2006, Selection on the human immunodeficiency virus type 1 proteome following primary infection, J. Virol. 80(19):9519-9529.*

Burton, D. R., and J. P. Moore, 1998, Why do we not have an HIV vaccine and how can we make one?, Nat. Med. Vacc. Suppl. 4(5):495-498.*

Desrosiers, R. C., 2004, Prospects for an AIDS vaccine, Nat. Med. 10(3):221-223.*

Pantaleo, G., and R. A. Koup, 2004, Correlates of immune protection in HIV-1 infection: what we know, what we don't know, what we should know, Nat. Med. 10(8):806-810.*

Haas et al., "Cytotoxin T-Cell Responses to HIV-1 Reverse Transcriptase, Integrase and Protease," AIDS, 12:1427-1436 (1998).

Hamajima, et al., "The Combination of DNA and Peptide Vaccines Induces Strong Immunities Against HIV-1 in Both Humoral and CMI," 11$^{TH}$ International AIDS Conference, Vancouver, Britich Columbia, Jul. 7-12; 11:6 (abstract No. Mo.A.151) (1996).

Kent, et al., "A Recombinant Avipoxvirus HIV-1 Vaccine Expressing Interferon-Gamma is Safe and Immunogenic in Macaques," Vaccine 18:2250-2256 (2000).

Williamson, et al., "Designing HIV-1 Subtype C Vaccines for South Africa," South African Journal of Science, 96:318-324 (2000).

Kolaskar et al., "A semi-empirical method for prediction of antigenic determinants." FEBS Lett. (1990) 276:172-4.

Barnett et al., "The ability of an oligomeric human immunodeficiency virus type 1 (HIV-1) envelope antigen to elicit neutralizing antibodies against primary HIV-1 isolates is improved following partial deletion of the second hypervariable region," J Virol. Jun. 2001;75(12):5526-40.

Lee et al., "A single point mutation in HIV-1 V3 loop alters the immunogenic properties of rgp120," Arch Virol. 2000;145(10):2087-103.

Chang et al., "Human immunodeficiency virus type 1 subtype E envelope recombinant peptides containing naturally immunogenic epitopes," J Infect Dis. Aug. 2000;182(2):442-50.

Brusic et al., "Prediction of MHC class II-binding peptides using an evolutionary algorithm and artificial neural network," *Bioinformatics* 14(2):121-30, 1998.

Carter, "Epitope Mapping of a Protein Using the Geysen (PEPSCAN) Procedure," *Methods Mol. Biol.* 36:207-23, 1994.

Davenport et al., "An empirical method for th prediction of T-cell epitopes," *Immunogenetics* 42:392-97, 1995.

Feller & De La Cruz, "Identigying antigenic T-cell sites," *Nature* 349(6311):720-21, 1991.

Geysen et al., "Use of peptide synthesis to probe viral antigens for epitopes to a resolution of a single amino acid," *Proc. Natl. Acad. Sci. USA 81*, 3998-4002, 1984.

Hopp, "Retrospective: 12 Years of Antigenic Determinant Predictions and More," *Peptide Research* 6:183-90, 1993.

Jameson et al., "The antigenic index: a novel algorithm for predicting antigenic determinants," *CABIOS* 4(1):1818-86, 1988.

Maksyutov & Zagrebelnaya, "ADEPT: a computer program for prediction of protein antigenic determinants," *Comput. Appl. Biosci.* 9(3):291-97, 1993.

Meister et al., "Two novel T cell epitope prediction algorithms based on MHC-binding motifs; comparison of predicted and published epitopes from *Mycobacterium tuberculosis* and HIV protein sequences," *Vaccine* 13(6):581-91, 1995.

Roberts et al., "Prediction of HIV Peptide Epitopes by a Noval Algorithm," *AIDS Res. Hum. Retroviruses* 12(7):593-610, 1996.

Welling et al., "Prediction of sequential antigenic regions in proteins," *FEBS Lett.* 188:215-18, 1985.

* cited by examiner

Gag_AF110965_BW_mod
ATGGGCGCCCGCGCCAGCATCCTGCGCGGCGGCAAGCTGGACGCCTGGGAGCGCATCCGCC
TGCGCCCCGGCGGCAAGAAGTGCTACATGATGAAGCACCTGGTGTGGGCCAGCCGCGAGCT
GGAGAAGTTCGCCCTGAACCCCGGCCTGCTGGAGACCAGCGAGGGCTGCAAGCAGATCATC
CGCCAGCTGCACCCCGCCCTGCAGACCGGCAGCGAGGAGCTGAAGAGCCTGTTCAACACCG
TGGCCACCCTGTACTGCGTGCACGAGAAGATCGAGGTCCGCGACACCAAGGAGGCCCTGGA
CAAGATCGAGGAGGAGCAGAACAAGTGCCAGCAGAAGATCCAGCAGGCCGAGGCCGCCGAC
AAGGGCAAGGTGAGCCAGAACTACCCCATCGTGCAGAACCTGCAGGGCCAGATGGTGCACC
AGGCCATCAGCCCCCGCACCCTGAACGCCTGGGTGAAGGTGATCGAGGAGAAGGCCTTCAG
CCCCGAGGTGATCCCCATGTTCACCGCCCTGAGCGAGGGCGCCACCCCCCAGGACCTGAAC
ACGATGTTGAACACCGTGGGCGGCCACCAGGCCGCCATGCAGATGCTGAAGGACACCATCA
ACGAGGAGGCCGCCGAGTGGGACCGCGTGCACCCCGTGCACGCCGGCCCCATCGCCCCCGG
CCAGATGCGCGAGCCCCGCGGCAGCGACATCGCCGGCACCACCAGCACCCTGCAGGAGCAG
ATCGCCTGGATGACCAGCAACCCCCCCATCCCCGTGGGCGACATCTACAAGCGGTGGATCA
TCCTGGGCCTGAACAAGATCGTGCGGATGTACAGCCCCGTGAGCATCCTGGACATCAAGCA
GGGCCCCAAGGAGCCCTTCCGCGACTACGTGGACCGCTTCTTCAAGACCCTGCGCGCCGAG
CAGAGCACCCAGGAGGTGAAGAACTGGATGACCGACACCCTGCTGGTGCAGAACGCCAACC
CCGACTGCAAGACCATCCTGCGCGCTCTCGGCCCCGGCGCCAGCCTGGAGGAGATGATGAC
CGCCTGCCAGGGCGTGGGCGGCCCCAGCCACAAGGCCCGCGTGCTGGCCGAGGCGATGAGC
CAGGCCAACACCAGCGTGATGATGCAGAAGAGCAACTTCAAGGGCCCCCGGCGCATCGTCA
AGTGCTTCAACTGCGGCAAGGAGGGCCACATCGCCCGCAACTGCCGCGCCCCCCGCAAGAA
GGGCTGCTGGAAGTGCGGCAAGGAGGGCCACCAGATGAAGGACTGCACCGAGCGCCAGGCC
AACTTCCTGGGCAAGATCTGGCCCAGCCACAAGGGCCGCCCCGGCAACTTCCTGCAGAGCC
GCCCCGAGCCCACCGCCCCCCCGCCGAGAGCTTCCGCTTCGAGGAGACCACCCCCGGCCA
GAAGCAGGAGAGCAAGGACCGCGAGACCCTGACCAGCCTGAAGAGCCTGTTCGGCAACGAC
CCCCTGAGCCAGTAA

Figure 1

Gag_AF110967_BW_mod
ATGGGCGCCCGCGCCAGCATCCTGCGCGGCGAGAAGCTGGACAAGTGGGAGAAGATCCGCC
TGCGCCCCGGCGGCAAGAAGCACTACATGCTGAAGCACCTGGTGTGGGCCAGCCGCGAGCT
GGAGGGCTTCGCCCTGAACCCCGGCCTGCTGGAGACCGCCGAGGGCTGCAAGCAGATCATG
AAGCAGCTGCAGCCCGCCCTGCAGACCGGCACCGAGGAGCTGCGCAGCCTGTACAACACCG
TGGCCACCCTGTACTGCGTGCACGCCGGCATCGAGGTCCGCGACACCAAGGAGGCCCTGGA
CAAGATCGAGGAGGAGCAGAACAAGTCCCAGCAGAAGACCCAGCAGGCCAAGGAGGCCGAC
GGCAAGGTGAGCCAGAACTACCCCATCGTGCAGAACCTGCAGGGCCAGATGGTGCACCAGG
CCATCAGCCCCCGCACCCTGAACGCCTGGGTGAAGGTGATCGAGGAGAAGGCCTTCAGCCC
CGAGGTGATCCCCATGTTCACCGCCCTGAGCGAGGGCGCCACCCCCCAGGACCTGAACACG
ATGTTGAACACCGTGGGCGGCCACCAGGCCGCCATGCAGATGCTGAAGGACACCATCAACG
AGGAGGCCGCCGAGTGGGACCGCCTGCACCCCGTGCAGGCCGGCCCCGTGGCCCCCGGCCA
GATGCGCGACCCCGCGGCAGCGACATCGCCGGCGCCACCAGCACCCTGCAGGAGCAGATC
GCCTGGATGACCAGCAACCCCCCCGTGCCCGTGGGCGACATCTACAAGCGGTGGATCATCC
TGGGCCTGAACAAGATCGTGCGGATGTACAGCCCCGTGAGCATCCTGGACATCCGCCAGGG
CCCCAAGGAGCCCTTCCGCGACTACGTGGACCGCTTCTTCAAGACCCTGCGCGCCGAGCAG
GCCACCCAGGACGTGAAGAACTGGATGACCGAGACCCTGCTGGTGCAGAACGCCAACCCCG
ACTGCAAGACCATCCTGCGCGCTCTCGGCCCCGGCGCCACCCTGGAGGAGATGATGACCGC
CTGCCAGGGCGTGGGCGGCCCCGGCCACAAGGCCCGCGTGCTGGCCGAGGCGATGAGCCAG
GCCAACAGCGTGAACATCATGATGCAGAAGAGCAACTTCAAGGGCCCCCGGCGCAACGTCA
AGTGCTTCAACTGCGGCAAGGAGGGCCACATCGCCAAGAACTGCCGCGCCCCCGCAAGAA
GGGCTGCTGGAAGTGCGGCAAGGAGGGCCACCAGATGAAGGACTGCACCGAGCGCCAGGCC
AACTTCCTGGGCAAGATCTGGCCCAGCCACAAGGGCCGCCCCGGCAACTTCCTGCAGAACC
GCAGCGAGCCCGCCGCCCCCACCGTGCCCACCGCCCCCCCGCCGAGAGCTTCCGCTTCGA
GGAGACCACCCCCGCCCCCAAGCAGGAGCCCAAGGACCGCGAGCCCTACCGCGAGCCCCTG
ACCGCCCTGCGCAGCCTGTTCGGCAGCGGCCCCCTGAGCCAGTAA

Env_AF110968_C_BW_opt

--> signal peptide (1-81)
ATGGCGCGTGATGGGCATCCTGAAGAACTACCAGCAGTGGTGGATGTGGGGCATCCTGGGCTTCTGGATGCTGATCA
\/--> gp120/140/160 (82)
TCAGCAGCGTGGTGGGCAACCTGTGGGTGACCGTGTACTACGGCGTGCCCGTGTGGAAGGAGGCCAAGACCACCCT
GTTCTGCACCAGCGACGCCAAGGCCTACGAGACCGAGGTGCACAACGTGTGGGCCACCCACGCCTGCGTGCCCACC
GACCCCAACCCCCAGGAGATCGTGCTGGAGAACGTGACCGAGAACTTCAACATGTGGAAGAACGACATGGTGGACC
AGATGCACGAGGACATCATCAGCCTGTGGGACCAGAGCCTGAAGCCCTGCGTGAAGCTGACCCCCCTGTGCGTGAC
CCTGAAGTGCCGCAACGTGAACGCCACCAACAACATCAACAGCATGATCGACAACAGCAACAAGGGCGAGATGAAG
AACTGCAGCTTCAACGTGACCACCGAGCTGCGCGACCGCAAGCAGGAGGTGCACGCCCTGTTCTACCGCCTGGACG
TGGTGCCCCTGCAGGGCAACAACAGCAACGAGTACCGCCTGATCAACTGCAACACCAGCGCCATCACCCAGGCCTG
CCCCAAGGTGAGCTTCGACCCCATCCCCATCCACTACTGCACCCCCGCCGGCTACGCCATCCTGAAGTGCAACAAC
CAGACCTTCAACGGCACCGGCCCCTGCAACAACGTGAGCAGCGTGCAGTGCGCCCACGGCATCAAGCCCGTGGTGA
GCACCCAGCTGCTGCTGAACGGCAGCCTGGCCAAGGGCGAGATCATCATCCGCAGCGAGAACCTGGCCAACAACGC
CAAGATCATCATCGTGCAGCTGAACAAGCCCGTGAAGATCGTGTGCGTGCGCCCCAACAACAACACCCGCAAGAGC
GTGCGCATCGGCCCCGGCCAGACCTTCTACGCCACCGGCGAGATCATCGGCGACATCCGCCAGGCCTACTGCATCA
TCAACAAGACCGAGTGGAACAGCACCCTGCAGGGCGTGAGCAAGAAGCTGGAGGAGCACTTCAGCAAGAAGGCCAT
CAAGTTCGAGCCCAGCAGCGGCGGCGACCTGGAGATCACCACCCACAGCTTCAACTGCCGCGGCGAGTTCTTCTAC
TGCGACACCAGCCAGCTGTTCAACAGCACCTACAGCCCCAGCTTCAACGGCACCGAGAACAAGCTGAACGGCACCA
TCACCATCACCTGCCGCATCAAGCAGATCATCAACATGTGGCAGAAGGTGGGCCGCGCCATGTACGCCCCCCCCAT
CGCCGGCAACCTGACCTGCGAGAGCAACATCACCGGCCTGCTGCTGACCCGCGACGGCGGCAAGACCGGCCCCAAC
GACACCGAGATCTTCCGCCCCGGCGGCGGCGACATGCGCGACAACTGGCGCAACGAGCTGTACAAGTACAAGGTGG
gp120(1512)<--\/-->(1513)gp41
TGGAGATCAAGCCCCTGGGCGTGGCCCCCACCGAGGCCAAGCGCCGCGTGGTGGAGCGCGAGAAGCGCGCCGTGGG
CATCGGCGCCGTGTTCCTGGGCTTCCTGGGCGCCGCCGGCAGCACCATGGGCGCCGCCAGCATCACCCTGACCGTG
CAGGCCCGCCTGCTGCTGAGCGGCATCGTGCAGCAGCAGAACAACCTGCTGCGCGCCATCGAGGCCCAGCAGCACC
TGCTGCAGCTGACCGTGTGGGGCATCAAGCAGCTGCAGACCCGCATCCTGGCCGTGGAGCGCTACCTGAAGGACCA
GCAGCTGCTGGGCATCTGGGGCTGCAGCGGCAAGCTGATCTGCACCACCGCCGTGCCCTGGAACAGCAGCTGGAGC
AACCGCAGCCACGACGAGATCTGGGACAACATGACCTGGATGCAGTGGGACCGCGAGATCAACAACTACACCGACA
CCATCTACCGCCTGCTGGAGGAGAGCCAGAACCAGCAGGAGAAGAACGAGAAGGACCTGCTGGCCCTGGACAGCTG
gp140(2025)<--\/
GCAGAACCTGTGGAACTGGTTCAGCATCACCAACTGGCTGTGGTACATCAAGATCTTCATCATGATCGTGGGCGGC
CTGATCGGCCTGCGCATCATCTTCGCCGTGCTGAGCATCGTGAACCGCGTGCGCCAGGGCTACAGCCCCCTGCCCT
TCCAGACCCTGACCCCCAACCCCCGCGAGCCCGACCGCCTGGGCCGCATCGAGGAGGAGGGCGGCGAGCAGGACCG
CGGCCGCAGCATCCGCCTGGTGAGCGGCTTCCTGGCCCTGGCCTGGGACGACCTGCGCAGCCTGTGCCTGTTCAGC
TACCACCGCCTGCGCGACTTCATCCTGATCGCCGCCCGCGTGCTGGAGCTGCTGGGCCAGCGCGGCTGGGAGGCCC
TGAAGTACCTGGGCAGCCTGGTGCAGTACTGGGGCCTGGAGCTGAAGAAGAGCGCCATCAGCCTGCTGGACACCAT
CGCCATCGCCGTGGCCGAGGGCACCGACCGCATCATCGAGTTCATCCAGCGCATCTGCCGCGCCATCCGCAACATC
gp160, gp41(2547)<--\
CCCGCCGCATCCGCCAGGGCTTCGAGGCCGCCCTGCAGTAA

Fig. 4

Env_AF110975_C_BW_opt

--> signal peptide (1-72) \/-->
ATGCGCGTGCGCGGCATCCTGCGCAGCTGGCAGCAGTGGTGGATCTGGGGCATCCTGGGCTTCTGGATCTGCAGCG
gp120/140/160 (72)
GCCTGGGCAACCTGTGGGTGACCGTGTACGACGGCGTGCCCGTGTGGCGCGAGGCCAGCACCACCCTGTTCTGCGC

CAGCGACGCCAAGGCCTACGAGAAGGAGGTGCACAACGTGTGGGCCACCCACGCCTGCGTGCCCACCGACCCCAAC

CCCCAGGAGATCGAGCTGGACAACGTGACCGAGAACTTCAACATGTGGAAGAACGACATGGTGGACCAGATGCACG

AGGACATCATCAGCCTGTGGGACCAGAGCCTGAAGCCCCGCGTGAAGCTGACCCCCCTGTGCGTGACCCTGAAGTG

CACCAACTACAGCACCAACTACAGCAACACCATGAACGCCACCAGCTACAACAACAACACCACCGAGGAGATCAAG

AACTGCACCTTCAACATGACCACCGAGCTGCGCGACAAGAAGCAGCAGGTGTACGCCCTGTTCTACAAGCTGGACA

TCGTGCCCCTGAACAGCAACAGCAGCGAGTACCGCCTGATCAACTGCAACACCAGCGCCATCACCCAGGCCTGCCC

CAAGGTGAGCTTCGACCCCATCCCCATCCACTACTGCGCCCCCGCCGGCTACGCCATCCTGAAGTGCAAGAACAAC

ACCAGCAACGGCACCGGCCCCTGCCAGAACGTGAGCACCGTGCAGTGCACCCACGGCATCAAGCCCGTGGTGAGCA

CCCCCCTGCTGCTGAACGGCAGCCTGGCCGAGGGCGGCGAGATCATCATCCGCAGCAAGAACCTGAGCAACAACGC

CTACACCATCATCGTGCACCTGAACGACAGCGTGGAGATCGTGTGCACCCGCCCCAACAACAACACCCGCAAGGGC

ATCCGCATCGGCCCCGGCCAGACCTTCTACGCCACCGAGAACATCATCGGCGACATCCGCCAGGCCCACTGCAACA

TCAGCGCCGGCGAGTGGAACAAGGCCGTGCAGCGCGTGAGCGCCAAGCTGCGCGAGCACTTCCCCAACAAGACCAT

CGAGTTCCAGCCCAGCAGCGGCGGCGACCTGGAGATCACCACCCACAGCTTCAACTGCCGCGGCGAGTTCTTCTAC

TGCAACACCAGCAAGCTGTTCAACAGCAGCTACAACGGCACCAGCTACCGCGGCACCGAGAGCAACAGCAGCATCA

TCACCCTGCCCTGCCGCATCAAGCAGATCATCGACATGTGGCAGAAGGTGGGCCGCGCCATCTACGCCCCCCCCAT

CGAGGGCAACATCACCTGCAGCAGCAGCATCACCGGCCTGCTGCTGGCCCGCGACGGCGGCCTGGACAACATCACC

ACCGAGATCTTCCGCCCCCAGGGCGGCGACATGAAGGACAACTGGCGCAACGAGCTGTACAAGTACAAGGTGGTGG
gp120 (1509)<--\/-->(1510) gp41
AGATCAAGCCCCTGGGCGTGGCCCCCACCGAGGCCAAGCGCCGCGTGGTGGAGCGCGAGAAGCGCGCCGTGGGCAT

CGGCGCCGTGATCTTCGGCTTCCTGGGCGCCGCCGGCAGCAACATGGGCGCCGCCAGCATCACCCTGACCGCCCAG

GCCCGCCAGCTGCTGAGCGGCATCGTGCAGCAGCAGAGCAACCTGCTGCGCGCCATCGAGGCCCAGCAGCACATGC

TGCAGCTGACCGTGTGGGGCATCAAGCAGCTGCAGGCCCGCGTGCTGGCCATCGAGCGCTACCTGAAGGACCAGCA

GCTGCTGGGCATCTGGGGCTGCAGCGGCAAGCTGATCTGCACCACCACCGTGCCCTGGAACAGCAGCTGGAGCAAC

AAGACCCAGGGCGAGATCTGGGAGAACATGACCTGGATGCAGTGGGACAAGGAGATCAGCAACTACACCGGCATCA

TCTACCGCCTGCTGGAGGAGAGCCAGAACCAGCAGGAGCAGAACGAGAAGGACCTGCTGGCCCTGGACAGCCGCAA
gp140 (2022)<--\/
CAACCTGTGGAGCTGGTTCAACATCAGCAACTGGCTGTGGTACATCAAGATCTTCATCATGATCGTGGGCGGCCTG

ATCGGCCTGCGCATCATCTTCGCCGTGCTGAGCATCGTGAACCGCGTGCGCCAGGGCTACAGCCCCCTGAGCTTCC

AGACCCTGACCCCCAACCCCCGCGGCCTGGACCGCCTGGGCCGCATCGAGGAGGAGGGCGGCGAGCAGGACCGCGA

CCGCAGCATCCGCCTGGTGCAGGGCTTCCTGGCCCTGGCCTGGGACGACCTGCGCAGCCTGTGCCTGTTCAGCTAC

CACCGCCTGCGCGACCTGATCCTGGTGACCGCCCGCGTGGTGGAGCTGCTGGGCCGCAGCAGCCCCCGCGGCCTGC

AGCGCGGCTGGGAGGCCCTGAAGTACCTGGGCAGCCTGGTGCAGTACTGGGGCCTGGAGCTGAAGAAGAGCGCCAC

CAGCCTGCTGGACAGCATCGCCATCGCCGTGGCCGAGGGCACCGACCGCATCATCGAGGTGATCCAGCGCATCTAC
gp160, gp41 (2565)<--
CGCGCCTTCTGCAACATCCCCCGCCGCGTGCGCCAGGGCTTCGAGGCCGCCCTGCAGTAA

Gag_AF110965_BW_opt
ATGGGCGCCCGCGCCAGCATCCTGCGCGGCGGCAAGCTGGACGCCTGGGAGCGCATCCGCCTGCGCCCCGG

CGGCAAGAAGTGCTACATGATGAAGCACCTGGTGTGGGCCAGCCGCGAGCTGGAGAAGTTCGCCCTGAACC

CCGGCCTGCTGGAGACCAGCGAGGGCTGCAAGCAGATCATCCGCCAGCTGCACCCCGCCCTGCAGACCGGC

AGCGAGGAGCTGAAGAGCCTGTTCAACACCGTGGCCACCCTGTACTGCGTGCACGAGAAGATCGAGGT[G/C]CG

CGACACCAAGGAGGCCCTGGACAAGATCGAGGAGGAGCAGAACAAGTGCCAGCAGAAGATCCAGCAGGCCG

AGGCCGCCGACAAGGGCAAGGTGAGCCAGAACTACCCCATCGTGCAGAACCTGCAGGGCCAGATGGTGCAC

CAGGCCATCAGCCCCCGCACCCTGAACGCCTGGGTGAAGGTGATCGAGGAGAAGGCCTTCAGCCCCGAGGT

GATCCCCATGTTCACCGCCCTGAGCGAGGGCGCCACCCCCCAGGACCTGAACA[C/G]CATG[C/T]GAACACCGTGG

GCGGCCACCAGGCCGCCATGCAGATGCTGAAGGACACCATCAACGAGGAGGCCGCCGAGTGGGACCGCGTG

CACCCCGTGCACGCCGGCCCCATCGCCCCCGGCCAGATGCGCGAGCCCCGCGGCAGCGACATCGCCGGCAC

CACCAGCACCCTGCAGGAGCAGATCGCCTGGATGACCAGCAACCCCCCCATCCCCGTGGGCGACATCTACA

AGC[C/G]TGGATCATCCTGGGCCTGAACAAGATCGTGCG[C/G]ATGTACAGCCCCGTGAGCATCCTGGACATCAAG

CAGGGCCCCAAGGAGCCCTTCCGCGACTACGTGGACCGCTTCTTCAAGACCCTGCGCGCCGAGCAGAGCAC

CCAGGAGGTGAAGAACTGGATGACCGACACCCTGCTGGTGCAGAACGCCAACCCCGACTGCAAGACCATCC

TGCGCGC[C/T]CT[G/C]GGCCCCGGCGCCAGCCTGGAGGAGATGATGACCGCCTGCCAGGGCGTGGGCGGCCCCAGC

CACAAGGCCCGCGTGCTGGCCGAGGC[C/G]ATGAGCCAGGCCAACACCAGCGTGATGATGCAGAAGAGCAACTT

CAAGGGCCCCCG[C/G]GCATCG[T/G]AAGTGCTTCAACTGCGGCAAGGAGGGCCACATCGCCCGCAACTGCCGCG

CCCCCCGCAAGAAGGGCTGCTGGAAGTGCGGCAAGGAGGGCCACCAGATGAAGGACTGCACCGAGCGCCAG

GCCAACTTCCTGGGCAAGATCTGGCCCAGCCACAAGGGCCGCCCCGGCAACTTCCTGCAGAGCCGCCCCGA

GCCCACCGCCCCCCCGCCGAGAGCTTCCGCTTCGAGGAGACCACCCCCGGCCAGAAGCAGGAGAGCAAGG

ACCGCGAGACCCTGACCAGCCTGAAGAGCCTGTTCGGCAACGACCCCCTGAGCCAGTAA

Figure 5

Gag_AF110967_BW_opt
ATGGGCGCCCGCGCCAGCATCCTGCGCGGCGAGAAGCTGGACAAGTGGGAGAAGATCCGCCTGCGCCCCGG
CGGCAAGAAGCACTACATGCTGAAGCACCTGGTGTGGGCCAGCCGCGAGCTGGAGGGCTTCGCCCTGAACC
CCGGCCTGCTGGAGACCGCCGAGGGCTGCAAGCAGATCATGAAGCAGCTGCAGCCCGCCCTGCAGACCGGC
ACCGAGGAGCTGCGCAGCCTGTACAACACCGTGGCCACCCTGTACTGCGTGCACGCCGGCATCGAGGT[C]G
 [G]
CGACACCAAGGAGGCCCTGGACAAGATCGAGGAGGAGCAGAACAA[G][AG]CAGCAGAAGACCCAGCAGGCCA
 [AC]
AGGAGGCCGACGGCAAGGTGAGCCAGAACTACCCCATCGTGCAGAACCTGCAGGGCCAGATGGTGCACCAG
GCCATCAGCCCCCGCACCCTGAACGCCCTGGGTGAAGGTGATCGAGGAGAAGGCCTTCAGCCCCGAGGTGAT
CCCCATGTTCACCGCCCTGAGCGAGGGCGCCACCCCCCAGGACCTGAACA[C][CATGC]TGAACACCGTGGGCG
 [G][T]
GCCACCAGGCCGCCATGCAGATGCTGAAGGACACCATCAACGAGGAGGCCGCCGAGTGGGACCGCCTGCAC
CCCGTGCAGGCCGGCCCCGTGGCCCCCGGCCAGATGCGCGACCCCCGCGGCAGCGACATCGCCGGCGCCAC
CAGCACCCTGCAGGAGCAGATCGCCTGGATGACCAGCAACCCCCCCGTGCCCGTGGGCGACATCTACAAGC
[C][C]GGATCATCCTGGGCCTGAACAAGATCGTGC[C][C]ATGTACAGCCCCGTGAGCATCCTGGACATCCGCCAG
[G]                                 [G]
GGCCCCAAGGAGCCCTTCCGCGACTACGTGGACCGCTTCTTCAAGACCCTGCGCGCCGAGCAGGCCACCCA
GGACGTGAAGAACTGGATGACCGAGACCCTGCTGGTGCAGAACGCCAACCCCGACTGCAAGACCATCCTGC
GCG[CCTG]GGCCCCGGCGCCACCCTGGAGGAGATGATGACCGCCTGCCAGGGCGTGGGCGGCCCCGGCCAC
 [T][C]
AAGGCCCGCGTGCTGGCCGAGG[C]TGAGCCAGGCCAACAGCGTGAACATCATGATGCAGAAGAGCAACTT
                       [G]
CAAGGGCCCCC[C][G]GCAACGT[G]AAGTGCTTCAACTGCGGCAAGGAGGGCCACATCGCCAAGAACTGCCGCG
           [G][C]         [C]
CCCCCCGCAAGAAGGGCTGCTGGAAGTGCGGCAAGGAGGGCCACCAGATGAAGGACTGCACCGAGCGCCAG
GCCAACTTCCTGGGCAAGATCTGGCCCAGCCACAAGGGCCGCCCCGGCAACTTCCTGCAGAACCGCAGCGA
GCCCGCCGCCCCCACCGTGCCCACCGCCCCCCCGCCGAGAGCTTCCGCTTCGAGGAGACCACCCCCGCCC
CCAAGCAGGAGCCCAAGGACCGCGAGCCCTACCGCGAGCCCCTGACCGCCCTGCGCAGCCTGTTCGGCAGC
GGCCCCCTGAGCCAGTAA

*Figure 6*

PR975(+) (SEQ ID NO:30)

```
GTCGACGCCACCATGGCCGAGGCCATGAGCCAGGCCACCAGCGCCAACATCCTGAT
GCAGCGCAGCAACTTCAAGGGCCCCAAGCGCATCATCAAGTGCTTCAACTGCGGCAA
GGAGGGCCACATCGCCCGCAACTGCCGCGCCCCCGCAAGAAGGGCTGCTGGAAGT
GCGGCAAGGAGGGCCACCAGATGAAGGACTGCACCGAGCGCCAGGCCAACTTCTTC
CGCGAGGACCTGGCCTTCCCCCAGGGCAAGGCCCGCGAGTTCCCCAGCGAGCAGAA
CCGCGCCAACAGCCCCACCAGCCGCGAGCTGCAGGTGCGCGGCGACAACCCCCGCA
GCGAGGCCGGCGCCGAGCGCCAGGGCACCCTGAACTTCCCCAGATCACCCTGTGGC
AGCGCCCCTGGTGAGCATCAAGGTGGGCGGCCAGATCAAGGAGGCCCTGCTGGAC
ACCGGCGCCGACGACACCGTGCTGGAGGAGATGAGCCTGCCCGGCAAGTGGAAGCC
CAAGATGATCGGCGGCATCGGCGGCTTCATCAAGGTGCGCCAGTACGACCAGATCCT
GATCGAGATCTGCGGCAAGAAGGCCATCGGCACCGTGCTGATCGGCCCCACCCCCGT
GAACATCATCGGCCGCAACATGCTGACCCAGCTGGGCTGCACCCTGAACTTCCCCAT
CAGCCCCATCGAGACCGTGCCCGTGAAGCTGAAGCCCGGCATGGACGGCCCCAAGG
TGAAGCAGTGGCCCCTGACCGAGGAGAAGATCAAGGCCCTGACCGCCATCTGCGAG
GAGATGGAGAAGGAGGGCAAGATCACCAAGATCGGCCCCGAGAACCCCTACAACAC
CCCCGTGTTCGCCATCAAGAAGAAGGACAGCACCAAGTGGCGCAAGCTGGTGGACT
TCCGCGAGCTGAACAAGCGCACCCAGGACTTCTGGGAGGTGCAGCTGGGCATCCCCC
ACCCCGCCGGCCTGAAGAAGAAGAAGAGCGTGACCGTGCTGGACGTGGGCGACGCC
TACTTCAGCGTGCCCCTGGACGAGGACTTCCGCAAGTACACCGCCTTCACCATCCCC
AGCATCAACAACGAGACCCCCGGCATCCGCTACCAGTACAACGTGCTGCCCCAGGGC
TGGAAGGGCAGCCCCAGCATCTTCCAGAGCAGCATGACCAAGATCCTGGAGCCCTTC
CGCGCCCGCAACCCCGAGATCGTGATCTACCAGTACATGGACGACCTGTACGTGGGC
AGCGACCTGGAGATCGGCCAGCACCGCGCCAAGATCGAGGAGCTGCGCAAGCACCT
GCTGCGCTGGGGCTTCACCACCCCCGACAAGAAGCACCAGAAGGAGCCCCCCTTCCT
GTGGATGGGCTACGAGCTGCACCCCGACAAGTGGACCGTGCAGCCCATCGAGCTGCC
CGAGAAGGAGAGCTGGACCGTGAACGACATCCAGAAGCTGGTGGGCAAGCTGAACT
GGGCCAGCCAGATCTACCCCGGCATCAAGGTGCGCCAGCTGTGCAAGCTGCTGCGCG
GCGCCAAGGCCCTGACCGACATCGTGCCCCTGACCGAGGAGGCCGAGCTGGAGCTG
GCCGAGAACCGCGAGATCCTGCGCGAGCCCGTGCACGGCGTGTACTACGACCCCAG
CAAGGACCTGGTGGCCGAGATCCAGAAGCAGGGCCACGACCAGTGGACCTACCAGA
TCTACCAGGAGCCCTTCAAGAACCTGAAGACCGGCAAGTACGCCAAGATGCGCACC
GCCCACACCAACGACGTGAAGCAGCTGACCGAGGCCGTGCAGAAGATCGCCATGGA
GAGCATCGTGATCTGGGGCAAGACCCCCAAGTTCCGCCTGCCCATCCAGAAGGAGAC
CTGGGAGACCTGGTGGACCGACTACTGGCAGGCCACCTGGATCCCCGAGTGGGAGTT
CGTGAACACCCCCCCCTGGTGAAGCTGTGGTACCAGCTGGAGAAGGAGCCCATCAT
CGGCGCCGAGACCTTCTACGTGGACGGCGCCGCCAACCGCGAGACCAAGATCGGCA
AGGCCGGCTACGTGACCGACCGGGGCCGGCAGAAGATCGTGAGCCTGACCGAGACC
ACCAACCAGAAGACCGAGCTGCAGGCCATCCAGCTGGCCCTGCAGGACAGCGGCAG
CGAGGTGAACATCGTGACCGACAGCCAGTACGCCCTGGGCATCATCCAGGCCCAGCC
CGACAAGAGCGAGAGCGAGCTGGTGAACCAGATCATCGAGCAGCTGATCAAGAAGG
AGAAGGTGTACCTGAGCTGGGTGCCCGCCCACAAGGGCATCGGCGGCAACGAGCAG
ATCGACAAGCTGGTGAGCAAGGGCATCCGCAAGGTGCTGTTCCTGGACGGCATCGAT
GGCGGCATCGTGATCTACCAGTACATGGACGACCTGTACGTGGGCAGCGGCGGCCCT
AGGATCGATTAAAAGCTTCCCGGGGCTAGCACCGGTGAATTC
```

FIGURE 8

PR975YM (SEQ ID NO:31)
GTCGACGCCACCATGGCCGAGGCCATGAGCCAGGCCACCAGCGCCAACATCCTGAT
GCAGCGCAGCAACTTCAAGGGCCCCAAGCGCATCATCAAGTGCTTCAACTGCGGCAA
GGAGGGCCACATCGCCCGCAACTGCCGCGCCCCCGCAAGAAGGGCTGCTGGAAGT
GCGGCAAGGAGGGCCACCAGATGAAGGACTGCACCGAGCGCCAGGCCAACTTCTTC
CGCGAGGACCTGGCCTTCCCCCAGGGCAAGGCCCGCGAGTTCCCCAGCGAGCAGAA
CCGCGCCAACAGCCCCACCAGCCGCGAGCTGCAGGTGCGCGGCGACAACCCCCGCA
GCGAGGCCGGCGCCGAGCGCCAGGGCACCCTGAACTTCCCCCAGATCACCCTGTGGC
AGCGCCCCTGGTGAGCATCAAGGTGGGCGGCCAGATCAAGGAGGCCCTGCTGGAC
ACCGGCGCCGACGACACCGTGCTGGAGGAGATGAGCCTGCCCGGCAAGTGGAAGCC
CAAGATGATCGGCGGCATCGGCGGCTTCATCAAGGTGCGCCAGTACGACCAGATCCT
GATCGAGATCTGCGGCAAGAAGGCCATCGGCACCGTGCTGATCGGCCCCACCCCCGT
GAACATCATCGGCCGCAACATGCTGACCCAGCTGGGCTGCACCCTGAACTTCCCCAT
CAGCCCCATCGAGACCGTGCCCGTGAAGCTGAAGCCCGGCATGGACGGCCCCAAGG
TGAAGCAGTGGCCCCTGACCGAGGAGAAGATCAAGGCCCTGACCGCCATCTGCGAG
GAGATGGAGAAGGAGGGCAAGATCACCAAGATCGGCCCCGAGAACCCCTACAACAC
CCCCGTGTTCGCCATCAAGAAGAAGGACAGCACCAAGTGGCGCAAGCTGGTGGACT
TCCGCGAGCTGAACAAGCGCACCCAGGACTTCTGGGAGGTGCAGCTGGGCATCCCCC
ACCCCGCCGGCCTGAAGAAGAAGAAGAGCGTGACCGTGCTGGACGTGGGCGACGCC
TACTTCAGCGTGCCCCTGGACGAGGACTTCCGCAAGTACACCGCCTTCACCATCCCC
AGCATCAACAACGAGACCCCCGGCATCCGCTACCAGTACAACGTGCTGCCCCAGGGC
TGGAAGGGCAGCCCCAGCATCTTCCAGAGCAGCATGACCAAGATCCTGGAGCCCTTC
CGCGCCCGCAACCCCGAGATCGTGATCTACCAGGCCCCCCTGTACGTGGGCAGCGAC
CTGGAGATCGGCCAGCACCGCGCCAAGATCGAGGAGCTGCGCAAGCACCTGCTGCG
CTGGGGCTTCACCACCCCCGACAAGAAGCACCAGAAGGAGCCCCCCTTCCTGTGGAT
GGGCTACGAGCTGCACCCCGACAAGTGGACCGTGCAGCCCATCGAGCTGCCCGAGA
AGGAGAGCTGGACCGTGAACGACATCCAGAAGCTGGTGGGCAAGCTGAACTGGGCC
AGCCAGATCTACCCCGGCATCAAGGTGCGCCAGCTGTGCAAGCTGCTGCGCGGCGCC
AAGGCCCTGACCGACATCGTGCCCCTGACCGAGGAGGCCGAGCTGGAGCTGGCCGA
GAACCGCGAGATCCTGCGCGAGCCCGTGCACGGCGTGTACTACGACCCCAGCAAGG
ACCTGGTGGCCGAGATCCAGAAGCAGGGCCACGACCAGTGGACCTACCAGATCTAC
CAGGAGCCCTTCAAGAACCTGAAGACCGGCAAGTACGCCAAGATGCGCACCGCCCA
CACCAACGACGTGAAGCAGCTGACCGAGGCCGTGCAGAAGATCGCCATGGAGAGCA
TCGTGATCTGGGGCAAGACCCCCAAGTTCCGCCTGCCCATCCAGAAGGAGACCTGGG
AGACCTGGTGGACCGACTACTGGCAGGCCACCTGGATCCCCGAGTGGGAGTTCGTGA
ACACCCCCCCCCTGGTGAAGCTGTGGTACCAGCTGGAGAAGGAGCCCATCATCGGCG
CCGAGACCTTCTACGTGGACGGCGCCGCCAACCGCGAGACCAAGATCGGCAAGGCC
GGCTACGTGACCGACCGGGGCCGGCAGAAGATCGTGAGCCTGACCGAGACCACCAA
CCAGAAGACCGAGCTGCAGGCCATCCAGCTGGCCCTGCAGGACAGCGGCAGCGAGG
TGAACATCGTGACCGACAGCCAGTACGCCCTGGGCATCATCCAGGCCCAGCCCGACA
AGAGCGAGAGCGAGCTGGTGAACCAGATCATCGAGCAGCTGATCAAGAAGGAGAAG
GTGTACCTGAGCTGGGTGCCCGCCCACAAGGGCATCGGCGGCAACGAGCAGATCGA
CAAGCTGGTGAGCAAGGGCATCCGCAAGGTGCTGTTCCTGGACGGCATCGATGGCG
GCATCGTGATCTACCAGTACATGGACGACCTGTACGTGGGCAGCGGCGGCCCTAGGA
TCGATTAAAAGCTTCCCGGGGCTAGCACCGGTGAATTC

FIGURE 9

PR975YMWM (SEQ ID NO:32)

GTCGACGCCACCATGGCCGAGGCCATGAGCCAGGCCACCAGCGCCAACATCCTGAT
GCAGCGCAGCAACTTCAAGGGCCCCAAGCGCATCATCAAGTGCTTCAACTGCGGCAA
GGAGGGCCACATCGCCCGCAACTGCCGCGCCCCCGCAAGAAGGGCTGCTGGAAGT
GCGGCAAGGAGGGCCACCAGATGAAGGACTGCACCGAGCGCCAGGCCAACTTCTTC
CGCGAGGACCTGGCCTTCCCCCAGGGCAAGGCCCGCGAGTTCCCCAGCGAGCAGAA
CCGCGCCAACAGCCCCACCAGCCGCGAGCTGCAGGTGCGCGGCGACAACCCCCGCA
GCGAGGCCGGCGCCGAGCGCCAGGGCACCCTGAACTTCCCCCAGATCACCCTGTGGC
AGCGCCCCTGGTGAGCATCAAGGTGGGCGGCCAGATCAAGGAGGCCCTGCTGGAC
ACCGGCGCCGACGACACCGTGCTGGAGGAGATGAGCCTGCCCGGCAAGTGGAAGCC
CAAGATGATCGGCGGCATCGGCGGCTTCATCAAGGTGCGCCAGTACGACCAGATCCT
GATCGAGATCTGCGGCAAGAAGGCCATCGGCACCGTGCTGATCGGCCCCACCCCCGT
GAACATCATCGGCCGCAACATGCTGACCCAGCTGGGCTGCACCCTGAACTTCCCCAT
CAGCCCCATCGAGACCGTGCCCGTGAAGCTGAAGCCCGGCATGGACGGCCCCAAGG
TGAAGCAGTGGCCCCTGACCGAGGAGAAGATCAAGGCCCTGACCGCCATCTGCGAG
GAGATGGAGAAGGAGGGCAAGATCACCAAGATCGGCCCCGAGAACCCCTACAACAC
CCCCGTGTTCGCCATCAAGAAGAAGGACAGCACCAAGTGGCGCAAGCTGGTGGACT
TCCGCGAGCTGAACAAGCGCACCCAGGACTTCTGGGAGGTGCAGCTGGGCATCCCCC
ACCCCGCCGGCCTGAAGAAGAAGAAGAGCGTGACCGTGCTGGACGTGGGCGACGCC
TACTTCAGCGTGCCCCTGGACGAGGACTTCCGCAAGTACACCGCCTTCACCATCCCC
AGCATCAACAACGAGACCCCCGGCATCCGCTACCAGTACAACGTGCTGCCCCAGGGC
TGGAAGGGCAGCCCCAGCATCTTCCAGAGCAGCATGACCAAGATCCTGGAGCCCTTC
CGCGCCCGCAACCCCGAGATCGTGATCTACCAGGCCCCCCTGTACGTGGGCAGCGAC
CTGGAGATCGGCCAGCACCGCGCCAAGATCGAGGAGCTGCGCAAGCACCTGCTGCG
CTGGGGCTTCACCACCCCCGACAAGAAGCACCAGAAGGAGCCCCCCTTCCTGCCCAT
CGAGCTGCACCCCGACAAGTGGACCGTGCAGCCCATCGAGCTGCCCGAGAAGGAGA
GCTGGACCGTGAACGACATCCAGAAGCTGGTGGGCAAGCTGAACTGGGCCAGCCAG
ATCTACCCCGGCATCAAGGTGCGCCAGCTGTGCAAGCTGCTGCGCGGCGCCAAGGCC
CTGACCGACATCGTGCCCCTGACCGAGGAGGCCGAGCTGGAGCTGGCCGAGAACCG
CGAGATCCTGCGCGAGCCCGTGCACGGCGTGTACTACGACCCCAGCAAGGACCTGGT
GGCCGAGATCCAGAAGCAGGGCCACGACCAGTGGACCTACCAGATCTACCAGGAGC
CCTTCAAGAACCTGAAGACCGGCAAGTACGCCAAGATGCGCACCGCCCACACCAAC
GACGTGAAGCAGCTGACCGAGGCCGTGCAGAAGATCGCCATGGAGAGCATCGTGAT
CTGGGGCAAGACCCCCAAGTTCCGCCTGCCCATCCAGAAGGAGACCTGGGAGACCT
GGTGGACCGACTACTGGCAGGCCACCTGGATCCCCGAGTGGGAGTTCGTGAACACCC
CCCCCCTGGTGAAGCTGTGGTACCAGCTGGAGAAGGAGCCCATCATCGGCGCCGAG
ACCTTCTACGTGGACGGCGCCGCCAACCGCGAGACCAAGATCGGCAAGGCCGGCTA
CGTGACCGACCGGGGCCGGCAGAAGATCGTGAGCCTGACCGAGACCACCAACCAGA
AGACCGAGCTGCAGGCCATCCAGCTGGCCCTGCAGGACAGCGGCAGCGAGGTGAAC
ATCGTGACCGACAGCCAGTACGCCCTGGGCATCATCCAGGCCCAGCCCGACAAGAG
CGAGAGCGAGCTGGTGAACCAGATCATCGAGCAGCTGATCAAGAAGGAGAAGGTGT
ACCTGAGCTGGGTGCCCGCCCACAAGGGCATCGGCGGCAACGAGCAGATCGACAAG
CTGGTGAGCAAGGGCATCCGCAAGGTGCTGTTCCTGGACGGCATCGATGGCGGCATC
GTGATCTACCAGTACATGGACGACCTGTACGTGGGCAGCGGCGGCCCTAGGATCGAT
TAAAAGCTTCCCGGGGCTAGCACCGGTGAATTC

FIGURE 10

8_5_ZA (SEQ ID NO:33)

```
   1 TGGAAGGGTT AATTTACTCC AAGAAAAGGC AAGAAATCCT TGATTTGTGG GTCTATCACA
  61 CACAAGGCTT CTTCCCTGAT TGGCAAAACT ACACACCGGG GCCAGGGGTC AGATATCCAC
 121 TGACCTTTGG ATGGTGCTAC AAGCTAGTGC CAGTTGACCC AGGGGAGGTG GAAGAGGCCA
 181 ACGGAGGAGA AGACAACTGT TTGCTACACC CTATGAGCCA ACATGGAGCA GAGGATGAAG
 241 ATAGAGAAGT ATTAAAGTGG AAGTTTGACA GCCTCCTAGC ACGCAGACAC ATGGCCCGCG
 301 AGCTACATCC GGAGTATTAC AAAGACTGCT GACACAGAAG GGACTTTCCG CCTGGGACTT
 361 TCCACTGGGG CGTTCCGGGA GGTGTGGTCT GGGCGGGACT TGGGAGTGGT CAACCCTCAG
 421 ATGCTGCATA TAAGCAGCTG CTTTTCGCCT GTACTGGGTC TCTCTCGGTA GACCAGATCT
 481 GAGCCTGGGA GCCCTCTGGC TATCTAGGGA ACCCACTGCT TAAGCCTCAA TAAAGCTTGC
 541 CTTGAGTGCT TTAAGTAGTG TGTGCCCATC TGTTGTGTGA CTCTGGTAAC TAGAGATCCC
 601 TCAGACCCTT TGTGGTAGTG TGGAAAATCT CTAGCAGTGG CGCCCGAACA GGGACCAGAA
 661 AGTGAAAGTG AGACCAGAGG AGATCTCTCG ACGCAGGACT CGGCTTGCTG AAGTGCACAC
 721 GGCAAGAGGC GAGAGGGGCG GCTGGTGAGT ACGCCAATTT TACTTGACTA GCGGAGGCTA
 781 GAAGGAGAGA GATGGGTGCG AGAGCGTCAA TATTAAGCGG CGGAAAATTA GATAAATGGG
 841 AAAGAATTAG GTTAAGGCCA GGGGAAAGA AACATTATAT GTTAAAACAT CTAGTATGGG
 901 CAAGCAGGGA GCTGGAAAGA TTTGCACTTA ACCCTGGCCT GTTAGAAACA TCAGAAGGCT
 961 GTAAACAAAT AATAAAACAG CTACAACCAG CTCTTCAGAC AGGAACAGAG GAACTTAGAT
1021 CATTATTCAA CACAGTAGCA ACTCTCTATT GTGTACATAA AGGGATAGAG GTACGAGACA
1081 CCAAGGAAGC CTTAGACAAG ATAGAGGAAG AACAAAACAA ATGTCAGCAA AAAGCACAAC
1141 AGGCAAAAGC AGCTGACGAA AAGGTCAGTC AAAATTATCC TATAGTACAG AATGCCCAAG
1201 GGCAAATGGT ACACCAAGCT ATATCACCTA GAACATTGAA TGCATGGATA AAAGTAATAG
1261 AGGAAAAGGC TTTCAATCCA GAGGAAATAC CCATGTTTAC AGCATTATCA GAAGGAGCCA
1321 CCCCACAAGA TTTAAACACA ATGTTAAATA CAGTGGGGGG ACATCAAGCA GCCATGCAAA
1381 TGTTAAAAGA TACCATCAAT GAGGAGGCTG CAGAATGGGA TAGGACACAT CCAGTACATG
1441 CAGGGCCTGT TGCACCAGGC CAGATGAGAG AACCAAGGGG AAGTGACATA GCAGGAACTA
1501 CTAGTACCCT TCAGGAACAA ATAGCATGGA TGACAAGTAA TCCACCTATT CCAGTAGAAG
1561 ACATCTATAA AAGATGGATA ATTCTGGGGT TAAATAAAAT AGTAAGAATG TATAGCCCTG
1621 TTAGCATTTT GGACATAAAA CAAGGGCCAA AAGAACCCTT TAGAGACTAT GTAGACCGGT
1681 TCTTTAAAAC CTTAAGAGCT GAACAAGCTA CACAAGATGT AAAGAATTGG ATGACAGACA
1741 CCTTGTTGGT CCAAAATGCG AACCCAGATT GTAAGACCAT TTTAAGAGCA TTAGGACCAG
1801 GGGCCTCATT AGAAGAAATG ATGACAGCAT GTCAGGGAGT GGGAGGACCT AGCCATAAAG
1861 CAAGAGTGTT GGCTGAGGCA ATGAGCCAAG CAAACAGTAA CATACTAGTG CAGAGAAGCA
1921 ATTTTAAAGG CTCTAACAGA ATTATTAAAT GTTTCAACTG TGGCAAAGTA GGGCACATAG
1981 CCAGAAATTG CAGGGCCCCT AGGAAAAAGG GCTGTTGGAA ATGTGGACAG GAAGGACACC
2041 AAATGAAAGA CTGTACTGAG AGGCAGGCTA ATTTTTTAGG GAAAATTTGG CCTTCCCACA
2101 AGGGGAGGCC AGGGAATTTC CTCCAGAACA GACCAGAGCC AACAGCCCCA CCAGCAGAAC
2161 CAACAGCCCC ACCAGCAGAG AGCTTCAGGT TCGAGGAGAC AACCCCCGTG CCGAGGAAGG
2221 AGAAAGAGAG GGAACCTTTA ACTTCCCTCA AATCACTCTT TGGCAGCGAC CCCTTGTCTC
2281 AATAAAAGTA GAGGGCCAGA TAAAGGAGGC TCTCTTAGAC ACAGGAGCAG ATGATACAGT
2341 ATTAGAAGAA ATAGATTTGC CAGGGAAATG GAAACCAAAA ATGATAGGGG GAATTGGAGG
2401 TTTTATCAAA GTAAGACAGT ATGATCAAAT ACTTATAGAA ATTGTGGAA AAAAGGCTAT
2461 AGGTACAGTA TTAGTAGGGC CTACACCAGT CAACATAATT GGAAGAAATC TGTTAACTCA
2521 GCTTGGATGC ACACTAAATT TTCCAATTAG TCCTATTGAA ACTGTACCAG TAAAATTAAA
2581 ACCAGGAATG GATGGCCCAA AGGTCAAACA ATGGCCATTG ACAGAAGAAA AAATAAAAGC
2641 ATTAACAGCA ATTTGTGAGG AAATGGAGAA GGAAGGAAAA ATTACAAAAA TTGGGCCTGA
2701 TAATCCATAT AACACTCCAG TATTTGCCAT AAAAAAGAAG GACAGTACTA AGTGGAGAAA
2761 ATTAGTAGAT TTCAGGGAAC TCAATAAAAG AACTCAAGAC TTTTGGGAAG TTCAATTAGG
2821 AATACCACAC CCAGCAGGAT TAAAAAAGAA AAAATCAGTG ACAGTGCTAG ATGTGGGGGA
2881 TGCATATTTT TCAGTTCCTT TAGATGAAAG CTTCAGGAAA TATACTGCAT TCACCATACC
```

FIGURE 11

```
2941 TAGTATAAAC AATGAAACAC CAGGGATTAG ATATCAATAT AATGTGCTGC CACAGGGATG
3001 GAAAGGATCA CCAGCAATAT TCCAGAGTAG CATGACAAAA ATCTTAGAGC CCTTCAGAGC
3061 AAAAAATCCA GACATAGTTA TCTATCAATA TATGGATGAC TTGTATGTAG GATCTGACTT
3121 AGAAATAGGG CAACATAGAG CAAAAATAGA AGAGTTAAGG GAACATTTAT TGAAATGGGG
3181 ATTTACAACA CCAGACAAGA AACATCAAAA AGAACCCCCA TTTCTTTGGA TGGGGTATGA
3241 ACTCCATCCT GACAAATGGA CAGTACAACC TATACTGCTG CCAGAAAAGG ATAGTTGGAC
3301 TGTCAATGAT ATACAGAAGT TAGTGGGAAA ATTAAACTGG GCAAGTCAGA TTTACCCAGG
3361 GATTAAAGTA AGGCAACTCT GTAAACTCCT CAGGGGGGCC AAAGCACTAA CAGACATAGT
3421 ACCACTAACT GAAGAAGCAG AATTAGAATT GGCAGAGAAC AGGGAAATTT AAGAGAACC
3481 AGTACATGGA GTATATTATG ATCCATCAAA AGACTTGATA GCTGAAATAC AGAAACAGGG
3541 GCATGAACAA TGGACATATC AAATTTATCA AGAACCATTT AAAAATCTGA AAACAGGGAA
3601 GTATGCAAAA ATGAGGACTA CCCACACTAA TGATGTAAAA CAGTTAACAG AGGCAGTGCA
3661 AAAAATAGCC ATGGAAAGCA TAGTAATATG GGAAAGACT CCTAAATTTA GACTACCCAT
3721 CCAAAAAGAA ACATGGGAGA CATGGTGGAC AGACTATTGG CAAGCCACCT GGATCCCTGA
3781 GTGGGAGTTT GTTAATACCC CTCCCCTAGT AAAATTATGG TACCAACTAG AAAAAGATCC
3841 CATAGCAGGA GTAGAAACTT TCTATGTAGA TGGAGCAACT AATAGGGAAG CTAAAATAGG
3901 AAAAGCAGGG TATGTTACTG ACAGAGGAAG GCAGAAAATT GTTACTCTAA CTAACACAAC
3961 AAATCAGAAG ACTGAGTTAC AAGCAATTCA GCTAGCTCTG CAGGATTCAG GATCAGAAGT
4021 AAACATAGTA ACAGACTCAC AGTATGCATT AGGAATCATT CAAGCACAAC CAGATAAGAG
4081 TGACTCAGAG ATATTTAACC AAATAATAGA ACAGTTAATA AACAAGGAAA GAATCTACCT
4141 GTCATGGGTA CCAGCACATA AAGGAATTGG GGGAAATGAA CAAGTAGATA AATTAGTAAG
4201 TAAGGGAATT AGGAAAGTGT TGTTTCTAGA TGGAATAGAT AAAGCTCAAG AAGAGCATGA
4261 AAGGTACCAC AGCAATTGGA GAGCAATGGC TAATGAGTTT AATCTGCCAC CCATAGTAGC
4321 AAAAGAAATA GTAGCTAGCT GTGATAAATG TCAGCTAAAA GGGGAAGCCA TACATGGACA
4381 AGTCGACTGT AGTCCAGGGA TATGGCAATT AGATTGTACC CATTTAGAGG GAAAAATCAT
4441 CCTGGTAGCA GTCCATGTAG CTAGTGGCTA CATGGAAGCA GAGGTTATCC CAGCAGAAAC
4501 AGGACAAGAA ACAGCATATT TTATATTAAA ATTAGCAGGA AGATGGCCAG TCAAAGTAAT
4561 ACATACAGAC AATGGCAGTA ATTTTACCAG TACTGCAGTT AAGGCAGCCT GTTGGTGGGC
4621 AGGTATCCAA CAGGAATTTG GAATTCCCTA CAATCCCCAA AGTCAGGGAG TGGTAGAATC
4681 CATGAATAAA GAATTAAAGA AAATAATAGG ACAAGTAAGA GATCAAGCTG AGCACCTTAA
4741 GACAGCAGTA CAAATGGCAG TATTCATTCA CAATTTTAAA AGAAAAGGGG GAATTGGGGG
4801 GTACAGTGCA GGGGAAAGAA TAATAGACAT AATAGCAACA GACATACAAA CTAAAGAATT
4861 ACAAAAACAA ATTATAAGAA TTCAAAATTT TCGGGTTTAT TACAGAGACA GCAGAGACCC
4921 TATTTGGAAA GGACCAGCCG AACTACTCTG GAAAGGTGAA GGGGTAGTAG TAATAGAAGA
4981 TAAAGGTGAC ATAAAGGTAG TACCAAGGAG GAAAGCAAAA ATCATTAGAG ATTATGGAAA
5041 ACAGATGGCA GGTGCTGATT GTGTGGCAGG TGGACAGGAT GAAGATTAGA GCATGGAATA
5101 GTTTAGTAAA GCACCATATG TATATATCAA GGAGAGCTAG TGGATGGGTC TACAGACATC
5161 ATTTTGAAAG CAGACATCCA AAAGTAAGTT CAGAAGTACA TATCCCATTA GGGGATGCTA
5221 GATTAGTAAT AAAAACATAT TGGGGTTTGC AGACAGGAGA AAGAGATTGG CATTTGGGTC
5281 ATGGAGTCTC CATAGAATGG AGACTGAGAG AATACAGCAC ACAAGTAGAC CCTGACCTGG
5341 CAGACCAGCT AATTCACATG CATTATTTTG ATTGTTTTAC AGAATCTGCC ATAAGACAAG
5401 CCATATTAGG ACACATAGTT TTTCCTAGGT GTGACTATCA AGCAGGACAT AAGAAGGTAG
5461 GATCTCTGCA ATACTTGGCA CTGACAGCAT TGATAAAACC AAAAAAGAGA AAGCCACCTC
5521 TGCCTAGTGT TAGAAAATTA GTAGAGGATA GATGGAACGA CCCCCAGAAG ACCAGGGGCC
5581 GCAGAGGGAA CCATACAATG AATGGACACT AGAGATTCTA GAAGAACTCA AGCAGGAAGC
5641 TGTCAGACAC TTTCCTAGAC CATGGCTCCA TAGCTTAGGA CAATATATCT ATGAAACCTA
5701 TGGGGATACT TGGACGGGAG TTGAAGCTAT AATAAGAGTA CTGCAACAAC TACTGTTCAT
5761 TCATTTCAGA ATTGGATGCC AACATAGCAG AATAGGCATC TTGCGACAGA GAAGAGCAAG
5821 AAATGGAGCC AGTAGATCCT AAACTAAAGC CCTGGAACCA TCCAGGAAGC CAACCTAAAA
5881 CAGCTTGTAA TAATTGCTTT TGCAAACACT GTAGCTATCA TTGTCTAGTT TGCTTTCAGA
```

FIGURE 11 CONTINUED

```
5941 CAAAAGGTTT AGGCATTTCC TATGGCAGGA AGAAGCGGAG ACAGCGACGA AGCGCTCCTC
6001 CAAGTGGTGA AGATCATCAA AATCCTCTAT CAAAGCAGTA AGTACACATA GTAGATGTAA
6061 TGGTAAGTTT AAGTTTATTT AAAGGAGTAG ATTATAGATT AGGAGTAGGA GCATTGATAG
6121 TAGCACTAAT CATAGCAATA ATAGTGTGGA CCATAGCATA TATAGAATAT AGGAAATTGG
6181 TAAGACAAAA GAAAATAGAC TGGTTAATTA AAAGAATTAG GGAAAGAGCA GAAGACAGTG
6241 GCAATGAGAG TGATGGGGAC ACAGAAGAAT TGTCAACAAT GGTGGATATG GGGCATCTTA
6301 GGCTTCTGGA TGCTAATGAT TTGTAACACG GAGGACTTGT GGGTCACAGT CTACTATGGG
6361 GTACCTGTGT GGAGAGAAGC AAAAACTACT CTATTCTGTG CATCAGATGC TAAAGCATAT
6421 GAGACAGAAG TGCATAATGT CTGGGCTACA CATGCTTGTG TACCCACAGA CCCCAACCCA
6481 CAAGAAATAG TTTTGGGAAA TGTAACAGAA AATTTTAATA TGTGGAAAAA TAACATGGCA
6541 GATCAGATGC ATGAGGATAT AATCAGTTTA TGGGATCAAA GCCTAAAGCC ATGTGTAAAG
6601 TTGACCCCAC TCTGTGTCAC TTTAAACTGT ACAGATACAA ATGTTACAGG TAATAGAACT
6661 GTTACAGGTA ATACAAATGA TACCAATATT GCAAATGCTA CATATAAGTA TGAAGAAATG
6721 AAAAATTGCT CTTTCAATGC AACCACAGAA TTAAGAGATA AGAAACATAA AGAGTATGCA
6781 CTCTTTTATA AACTTGATAT AGTACCACTT AATGAAAATA GTAACAACTT TACATATAGA
6841 TTAATAAATT GCAATACCTC AACCATAACA CAAGCCTGTC CAAAGGTCTC TTTTGACCCG
6901 ATTCCTATAC ATTACTGTGC TCCAGCTGAT TATGCGATTC TAAAGTGTAA TAATAAGACA
6961 TTCAATGGGA CAGGACCATG TTATAATGTC AGCACAGTAC AATGTACACA TGGAATTAAG
7021 CCAGTGGTAT CAACTCAACT ACTGTTAAAT GGTAGTCTAG CAGAAGAAGG GATAATAATT
7081 AGATCTGAAA ATTTGACAGA GAATACCAAA ACAATAATAG TACATCTTAA TGAATCTGTA
7141 GAGATTAATT GTACAAGGCC CAACAATAAT ACAAGGAAAA GTGTAAGGAT AGGACCAGGA
7201 CAAGCATTCT ATGCAACAAA TGACGTAATA GGAAACATAA GACAAGCACA TTGTAACATT
7261 AGTACAGATA GATGGAATAA AACTTTACAA CAGGTAATGA AAAAATTAGG AGAGCATTTC
7321 CCTAATAAAA CAATAAAATT TGAACCACAT GCAGGAGGGG ATCTAGAAAT TACAATGCAT
7381 AGCTTTAATT GTAGAGGAGA ATTTTTCTAT TGCAATACAT CAAACCTGTT TAATAGTACA
7441 TACTACCCTA AGAATGGTAC ATACAAATAC AATGGTAATT CAAGCTTACC CATCACACTC
7501 CAATGCAAAA TAAAACAAAT TGTACGCATG TGGCAAGGGG TAGGACAAGC AATGTATGCC
7561 CCTCCCATTG CAGGAAACAT AACATGTAGA TCAAACATCA CAGGAATACT ATTGACACGT
7621 GATGGGGGAT TTAACAACAC AAACAACGAC ACAGAGGAGA CATTCAGACC TGGAGGAGGA
7681 GATATGAGGG ATAACTGGAG AAGTGAATTA TATAAATATA AAGTGGTAGA AATTAAGCCA
7741 TTGGGAATAG CACCCACTAA GGCAAAAAGA AGAGTGGTGC AGAGAAAAAA AAGAGCAGTG
7801 GGAATAGGAG CTGTGTTCCT TGGGTTCTTG GGAGCAGCAG GAAGCACTAT GGGCGCAGCG
7861 TCAATAACGC TGACGGTACA GGCCAGACAA CTGTTGTCTG GTATAGTGCA ACAGCAAAGC
7921 AATTTGCTGA AGGCTATAGA GGCGCAACAG CATATGTTGC AACTCACAGT CTGGGGCATT
7981 AAGCAGCTCC AGGCGAGAGT CCTGGCTATA GAAAGATACC TAAAGGATCA ACAGCTCCTA
8041 GGGATTTGGG GCTGCTCTGG AAGACTCATC TGCACCACTG CTGTGCCTTG GAACTCCAGT
8101 TGGAGTAATA AATCTGAAGC AGATATTTGG GATAACATGA CTTGGATGCA GTGGGATAGA
8161 GAAATTAATA ATTACACAGA AACAATATTC AGGTTGCTTG AAGACTCGCA AAACCAGCAG
8221 GAAAAGAATG AAAAAGATTT ATTAGAATTG GACAAGTGGA ATAATCTGTG GAATTGGTTT
8281 GACATATCAA ACTGGCTGTG GTATATAAAA ATATTCATAA TGATAGTAGG AGGCTTGATA
8341 GGTTTAAGAA TAATTTTTGC TGTGCTCTCT ATAGTGAATA GAGTTAGGCA GGGATACTCA
8401 CCTTTGTCAT TTCAGACCCT TACCCCAAGC CCGAGGGGAC TCGACAGGCT CGGAGGAATC
8461 GAAGAAGAAG GTGGAGAGCA AGACAGAGAC AGATCCATAC GATTGGTGAG CGGATTCTTG
8521 TCGCTTGCCT GGGACGATCT GCGGAGCCTG TGCCTCTTCA GCTACCACCG CTTGAGAGAC
8581 TTCATATTAA TTGCAGTGAG GGCAGTGGAA CTTCTGGGAC ACAGCAGTCT CAGGGGACTA
8641 CAGAGGGGGT GGGAGATCCT TAAGTATCTG GGAAGTCTTG TGCAGTATTG GGGTCTAGAG
8701 CTAAAAAAGA GTGCTATTAG TCCGCTTGAT ACCATAGCAA TAGCAGTAGC TGAAGGAACA
8761 GATAGGATTA TAGAATTGGT ACAAAGAATT TGTAGAGCTA TCCTCAACAT ACCTAGGAGA
8821 ATAAGACAGG GCTTTGAAGC AGCTTTGCTA TAAAATGGGA GGCAAGTGGT CAAAACGCAG
8881 CATAGTTGGA TGGCCTGCAG TAAGAGAAAG AATGAGAAGA ACTGAGCCAG CAGCAGAGGG
8941 AGTAGGAGCA GCGTCTCAAG ACTTAGATAG ACATGGGGCA CTTACAAGCA GCAACACACC
```

FIGURE 11 CONTINUED

```
9001 TGCTACTAAT GAAGCTTGTG CCTGGCTGCA AGCACAAGAG GAGGACGGAG ATGTAGGCTT
9061 TCCAGTCAGA CCTCAGGTAC CTTTAAGACC AATGACTTAT AAGAGTGCAG TAGATCTCAG
9121 CTTCTTTTTA AAAGAAAAGG GGGGACTGGA AGGGTTAATT TACTCTAGGA AAAGGCAAGA
9181 AATCCTTGAT TTGTGGGTCT ATAACACACA AGGCTTCTTC CCTGATTGGC AAAACTACAC
9241 ATCGGGGCCA GGGGTCCGAT TCCCACTGAC CTTTGGATGG TGCTTCAAGC TAGTACCAGT
9301 TGACCCAAGG GAGGTGAAAG AGGCCAATGA AGGAGAAGAC AACTGTTTGC TACACCCTAT
9361 GAGCCAACAT GGAGCAGAGG ATGAAGATAG AGAAGTATTA AAGTGGAAGT TTGACAGCCT
9421 TCTAGCACAC AGACACATGG CCCGCGAGCT ACATCCGGAG TATTACAAAG ACTGCTGACA
9481 CAGAAGGGAC TTTCCGCCTG GGACTTTCCA CTGGGCGTT CCGGGAGGTG TGGTCTGGGC
9541 GGGACTTGGG AGTGGTCACC CTCAGATGCT GCATATAAGC AGCTGCTTTT CGCTTGTACT
9601 GGGTCTCTCT CGGTAGACCA GATCTGAGCC TGGGAGCTCT CTGGCTATCT AGGGAACCCA
9661 CTGCTTAGGC CTCAATAAAG CTTGCCTTGA GTGCTCTAAG TAGTGTGTGC CCATCTGTTG
9721 TGTGACTCTG GTAACTAGAG ATCCCTCAGA CCCTTTGTGG TAGTGTGGAA AATCTCTAGC
9781 A
```

FIGURE 11 CONTINUED

SEQ ID NO:34

GCTGAGGCAATGAGCCAAGCAACCAGCGCAAACATACTGATGCAGAGAAGCAATTT
CAAAGGCCCTAAAAGAATTATTAAATGTTTCAACTGTGGCAAGGAAGGGCACATAG
CTAGAAATTGTAGGGCCCCTAGGAAAAAAGGCTGTTGGAAATGTGGAAAGGAAGGA
CACCAAATGAAAGACTGTACTGAGAGGCAGGCTAA

FIGURE 12

975Pol wt until 6aa Int: (SEQ ID NO:35)
TTTTTTAGGGAAGATTTGGCCTTCCCACAAGGGAAGGCCAGGGAATTTCCTTCAGAA
CAGAACAGAGCCAACAGCCCCACCAGCAGAGAGCTTCAAGTTCGAGGAGACAACCC
CCGCTCCGAAGCAGGAGCCGAAAGACAGGGAACCCTTAATTTCCCTCAAATCACTCT
TTGGCAGCGACCCCTTGTCTCAATAAAAGTAGGGGGTCAAATAAAGGAGGCTCTCTT
AGACACAGGAGCTGATGATACAGTATTAGAAGAAATGAGTTTGCCAGGAAAATGGA
AACCAAAAATGATAGGAGGAATTGGAGGTTTTATCAAAGTAAGACAGTATGATCAA
ATACTTATAGAAATTTGTGGAAAAAAGGCTATAGGTACAGTATTAATAGGACCTACA
CCTGTCAACATAATTGGAAGGAATATGTTGACTCAGCTTGGATGCACACTAAATTTT
CCAATTAGTCCCATTGAAACTGTGCCAGTAAAATTAAAGCCAGGAATGGATGGCCCA
AAGGTTAAACAATGGCCATTGACAGAAGAGAAAATAAAAGCATTAACAGCAATTTG
TGAAGAAATGGAGAAAGAAGGAAAAATTACAAAAATTGGGCCTGAAAATCCATATA
ACACTCCAGTATTTGCCATAAAAAAGAAGGACAGTACTAAGTGGAGAAAGTTAGTA
GATTTCAGGGAACTTAATAAAAGAACTCAAGACTTTTGGGAAGTTCAATTAGGAATA
CCACACCCAGCAGGGTTAAAAAAGAAAAAATCAGTGACAGTACTGGATGTGGGGGA
TGCATATTTTTCAGTTCCTTTAGATGAGGACTTCAGGAAATATACTGCATTCACCATA
CCTAGTATAAACAATGAAACACCAGGGATTAGATATCAATATAATGTGCTTCCACAG
GGATGGAAAGGATCACCATCAATATTCCAGAGTAGCATGACAAAAATCTTAGAGCC
CTTTAGAGCAAGAAATCCAGAAATAGTCATCTATCAATATATGGATGACTTGTATGT
AGGATCTGACTTAGAAATAGGGCAACATAGAGCAAAAATAGAGGAGTTAAGAAAAC
ATCTGTTAAGGTGGGGATTTACCACACCGGACAAGAAACATCAGAAAGAACCCCCA
TTTCTTTGGATGGGGTATGAACTCCATCCTGACAAATGGACAGTACAGCCTATAGAG
TTGCCAGAAAAGGAAAGCTGGACTGTCAATGATATACAGAAGTTAGTGGGAAAATT
AAATTGGGCCAGTCAGATTTACCCAGGAATTAAAGTAAGGCAACTTTGTAAACTCCT
TAGGGGGGCCAAAGCACTAACAGATATAGTACCACTAACTGAAGAAGCAGAATTAG
AATTGGCAGAGAACAGGGAAATTCTAAGAGAACCAGTACATGGAGTATATTATGAC
CCATCAAAAGACTTGGTAGCTGAAATACAGAAACAGGGGCATGACCAATGGACATA
TCAAATTTACCAAGAACCATTCAAAAACCTGAAAACAGGGAAGTATGCAAAAATGA
GGACTGCCCACACTAATGATGTAAAACAGTTAACAGAGGCAGTGCAAAAAATAGCT
ATGGAAAGCATAGTAATATGGGGAAAGACTCCTAAATTTAGACTACCCATCCAAAA
AGAAACATGGGAGACATGGTGGACAGACTATTGGCAAGCCACCTGGATTCCTGAGT
GGGAGTTTGTTAATACCCCTCCCTTAGTAAAATTATGGTACCAGCTAGAGAAAGAAC
CCATAATAGGAGCAGAAACTTTCTATGTAGATGGAGCAGCTAATAGGGAAACTAAA
ATAGGAAAAGCAGGGTATGTTACTGACAGAGGAAGGCAGAAAATTGTTTCTCTAAC
AGAAACAACAAATCAGAAGACTGAATTACAAGCAATTCAGCTAGCTTTGCAAGATTC
AGGATCAGAAGTAAACATAGTAACAGACTCACAGTATGCATTAGGAATCATTCAAG
CACAACCAGATAAGAGTGAATCAGAGTTAGTCAACCAAATAATAGAACAATTAATA
AAAAAGGAAAAGGTCTACCTGTCATGGGTACCAGCACATAAAGGAATTGGAGGAAA
TGAACAAATAGATAAATTAGTAAGTAAGGGAATCAGGAAAGTGCTGTTTCTAGATG
GAATAGAT

FIGURE 13

SEQ ID NO:36

GGCGGCATCGTGATCTACCAGTACATGGACGACCTGTACGTGGGCAGCGGCG
GC

FIGURE 14

SEQ ID NO: 37

GGIVIYQYMDDLYVGSGG

FIGURE 15

12_5/1ZA (SEQ ID NO:45)

```
TGGAAGGGTTAATTTACTCCAGGAAAAGGCAAGAGATCCTTGATTTATGGGTCTATC
ACACACAAGGCTACTTCCCTGATTGGCAAAACTACACACCGGGACCAGGGGTCAGA
TATCCACTGACCTTTGGATGGTGCTTCAAGCTAGTGCCAGTTGACCCAAGGGAAGTA
GAAGAGGCCAACGGAGGAGAAGACAACTGTTTGCTACACCCTATGAGCCAGTATGG
AATGGATGATGAACACAAAGAAGTGTTACAGTGGAAGTTTGACAGCAGCCTAGCAC
GCAGACACCTGGCCCGCGAGCTACATCCGGATTATTACAAAGACTGCTGACACAGA
AGGGACTTTCCGCCTGGGACTTTCCACTGGGGCGTTCCAGGGGGAGTGGTCTGGGCG
GGACTGGGAGTGGCCAGCCCTCAGATGCTGCATATAAGCAGCGGCTTTTCGCCTGTA
CTGGGTCTCTCTAGGTAGACCAGATCCGAGCCTGGGAGCTCTCTGTCTATCTGGGGA
ACCCACTGCTTAGGCCTCAATAAAGCTTGCCTTGAGTGCTCTAAGTAGTGTGTGCCC
ATCTGTTGTGTGACTCTGGTAACTCTGGTAACTAGAGATCCCTCAGACCCTTGTGGT
AGTGTGGAAAATCTCTAGCAGTGGCGCCCGAACAGGGACTTGAAAGCGAAAGTGAG
ACCAGAGAAGATCTCTCGACGCAGGACTCGGCTTGCTGAAGTGCACTCGGCAAGAG
GCGAGGGGGGCGACTGGTGAGTACGCCAAAATTTTTTTGACTAGCGGAGGCTAGA
AGGAGAGAGATGGGTGCGAGAGCGTCAATATTAAGAGGGGGAAAATTAGACAAAT
GGGAAAAAATTAGGTTACGGCCAGGGGGGAGAAAACACTATATGCTAAAACACCTA
GTATGGGCAAGCAGAGAGCTGGAAAGATTTGCAGTTAACCCTGGCCTTTTAGAGAC
ATCAGACGGATGTAGAC AAATAATAAAACAGCTACAACCAGCTCTTCAGA
CAGGAACAGAGGAAATTAGATCATTATTTAACACAGTAGCAACTCTCTATTGTGTAC
ATAAAGGGATAGATGTACGAGACACCAAGGAAGCCTTAGACAAGATAGAGGAGGA
ACAAAACAAATGTCAGCAAAAAACACAGCAGGCGGAAGCGGCTGACAAAAGGTC
AGTCAAAATTATCCTATAGTGCAGAACCTCCAAGGGCAAATGGTACACCAGGCCAT
ATCACCTAGAACCTTGAATGCATGGGTAAAAGTAATAGAGGAGAAGGCTTTTAGCC
CAGAGGTAATACCCATGTTTACAGCATTATCAGAAGGAGCCACCCCACAAGATTTA
AACACCATGTTAAATACAGTGGGGGGACATCAAGCAGCCATGCAAATGTTAAAAG
ATACCATCAATGAGGAGGCTGCAGAATGGGATAGGTTACATCCAGTACATGCAGGG
CCTGTTGCACCAGGCCAGATGAGAGAACCAAGGGGAAGTGACATAGCAGGAACTA
CTAGTACCCTTCAAGAACAAATAGCATGGATGACAAGTAACCCACCTATCCCAGTA
GGGGACATCTATAAAAGGTGGATAATTCTGGGGTTAAATAAAATAGTAAGAATGTA
CAGCCCTGTCAGCATTTTAGACATAAAACAAGGACCAAAGGAACCCTTTAGAGACT
ATGTAGACCGGTTCTTCAAAACTTTAAGAGCTGAACAATCTACACAAGAGGTAAAA
AATTGGATGACAGACACCTTGTTAGTCCAAAATGCGAACCCAGATTGTAAGACCATT
TTAAGAGCATTAGGACCAGGGGCTTCATTAGAAGAAATGATGACAGCATGTCAGGG
AGTGGGAGGACCTAGCCACAAAGCAAGAGTTTTGGCTGAGGCAATGAGCCAAGCAA
ACAATACAAGTGTAATGATACAGAAAAGCAATTTTAAAGGCCCTAGAAGAGCTGTT
AAATGTTTCAACTGTGGCAGGGAAGGGCACATAGCCAGGAATTGCAGGGCCCCTAG
GAAAAGGGGCTGTTGGAAATGTGGAAAGGAAGGACACCAAATGAAAGACTGTACT
GAGAGGCAGGCTAATTTTTAGGGAAATTTGGCCTTCCCACAAGGGGAGGCCAGG
GAATTTCCTTCAGAGCAGACCAGAGCCAACAGCCCCACCACTAGAACCAACAGCCC
CACCAGCAGAGAGCTTCAAGTTCAAGGAGACTCCGAAGCAGGAGCCGAAAGACAG
GGAACCTTTAACTTCCCTCAAATCACTCTTTGGCAGCGACCCCTTGTCTCAATAAAA
```

FIGURE 16

```
GTAGCGGGCCAAACAAAGGAGGCTCTTTTAGATACAGGAGCAGATGATACAGTACT
AGAAGAAATAAACTTGCCAGGAAAATGGAAACCAAAAATGATAGGAGGAATTGGA
GGTTTTATCAAAGTAAGACAGTATGATCAAATACTTATAGAAATTTGTGGAAAAAGG
GCTATAGGTACAGTATTAGTAGGACCTACACCTGTCAACATAATTGGAAGAAATCTG
TTGACTCAGCTTGGATGCACACTAAATTTTCCAATTAGCCCCATTGAAACTGTACCA
GTAAAATTAAAGCCAGGAATGGATGGCCCAAAGGTTAAACAATGGCCATTGACAGA
AGAAAAAATAAAAGCATTAACAGAAATTTGTGAGGAAATGGAGAAGGAAGGAAAA
ATTACAAAAATTGGGCCTGAAAATCCATATAACACTCCAGTATTTGCCATAAAGAAG
AAGGACAGTACAAAGTGGAGAAAATTAGTAGATTTCAGGGAACTCAATAAAAGAAC
TCAAGACTTTTGGGAAGTCCAATTAGGAATACCACACCCAGCAGGGTTAAAAAAGA
AAAAATCAGTGACAGTACTGGATGTGGGAGATGCATATTTTTCAGTCCCTTTAGATG
AGAGCTTCAGAAAATATACTGCATTCACCATACCTAGTATAAACAATGAAACACCA
GGGATTAGATATCAATATAATGTTCTTCCACAGGGATGGAAAGGATCACCAGCAA
TATTCCAGAGTAGCATGACAAGAATCTTAGAGCCCTTTAGAACACAAAACCCAGAA
GTAGTTATCTATCAATATATGGATGACTTATATGTAGGATCTGACTTAGAAATAGGG
CAACATAGAGCAAAAATAGAGGAGTTAAGAGGACACCTATTGAAATGGGGATTTAC
CACACCAGACAAGAAACATCAGAAAGAACCCCCATTTCTTTGGATGGGGTATGAAC
TCCATCCTGACAAATGGACAGTACAGCCTATACAGCTGCCAGAAAAGGAGAGCTGG
ACTGTCAATGATATACAGAAGTTAGTGGGAAAGTTAAACTGGGCAAGTCAGATTTA
CCCAGGGATTAAAGTAAGGCAACTGTGTAAACTCCTTAGGGGAGCCAAAGCACTAA
CAGACATAGTGCCACTGACTGAAGAAGCAGAATTAGAATTGGCTGAGAACAGGGA
AATTCTAAAAGAACCAGTACATGGAGTATATTATGACCCATCAAAAGATTTAATAG
CTGAAATACAGAAACAGGGGAATGACCAATGGACATATCAAATTTACCAAGAACC
ATTTAAAAATCTGAGAACAGGAAAGTATGCAAAAATGAGGACTGCCCACACTAATG
ATGTGAAACAGTTAGCAGAGGCAGTGCAAAAGATAACCCAGGAAAGCATAGTAATA
TGGGGAAAAACTCCTAAATTTAGACTACCCATCCCAAAAGAAACATGGGAGACATG
GTGGTCAGACTATTGGCAAGCCACCTGGATTCCTGAGTGGGAGTTTGTCAATACCCC
TCCCCTAGTAAAATTGTGGTACCAGCTGGAAAAAGAACCCATAGTAGGGGCAGAAA
CTTTCTATGTAGATGGAGCAGCCAATAGGGAAACTAAAATAGGAAAAGCAGGGTAT
GTCACTGACAAAGGAAGGCAGAAAGTTGTTTCCTTCACTGAAACAACAAATCAGAA
GACTGAATTACAAGCAATTCAGCTAGCTTGCAGGATTCAGGGCCAGAAGTAAACA
TAGTAACAGACTCACAGTATGCATTAGGAATCATTCAAGCACAACCAGATAAGAGT
GAATCAGAATTAGTCAGTCAAATAATAGAACAGTTGATAAAAAGGAAAAAGTCTA
CCTATCATGGGTACCAGCACATAAAGGAATTGGAGGAAATGAACAAGTAGACAAAT
TAGTAAGTAGTGGAATCAGAAAAGTACTGTTTCTAGATGGAATAGATAAAGCTCAA
GAAGAGCATGAAAAATATCACAGCAATTGGAGAGCAATGGCTAGTGAGTTTAATCT
GCCACCCATAGTAGCAAAGGAAATAGTAGCCAGCTGTGATAAATGTCAGCTAAAAG
GGGAAGCCATGCATGGACAAGTCGACTGTAGTCCAGGAATATGGCAATTAGACTGT
ACACATTTAGAAGGAAAAATCATCCTAGTAGCAGTCCATGTAGCCAGTGGCTACAT
GGAAGCAGAGGTTATCCCAGCAGAAACAGGACAAGAAACAGCATACTTTATACTAA
AATTAGCAGGAAGATGGCCAGTCAAAGTAATACATACAGATAATGGCAGTAATTTC
ACCAGTACCGCAGTTAAGGCAGCCTGTTGGTGGGCAGATATCCAACGGGAATTTGG
AATTCCCTACAATCCCCAAAGTCAAGGAGTAGTAGAATCCATGAATAAAGAATTAA
```

FIGURE 16 CONTINUED

```
AGAAAATCATAGGGCAAGTAAGAGATCAAGCTGAGCACCTTAAGACAGCAGTACAA
ATGGCAGTATTCATTCACAATTTTAAAAGAAAAGGGGGGATTGGGGGGTACAGTGC
AGGGGAGAGAATAATAGACATAATAGCATCAGACATACAAACTAAAGAATTACAAA
AACAAATTATAAAAATTCAAAATTTTCGGGTTTATTACAGAGACAGCAGAGACCCTA
TTTGGAAAGGACCAGCCAAACTACTCTGGAAAGGTGAAGGGGCAGTAGTAATACAA
GATAATAGTGATATAAAGGTAGTACCAAGAAGGAAAGCAAAAATCATTAAGGACTA
TGGAAAACAGATGGCAGGTGCTGATTGTGTGGCAGGTAGACAGGATGAAGATTAGA
ACATGGCACAGTTTAGTAAAGCACCATATGTATGTTTCGAGGAGAGCTGATGGATGG
TTCTACAGACATCATTATGAAAGCAGACACCCAAAAGTAAGTTCAGAAGTACACAT
CCCATTAGGAGATGCCAGGTTAGTAATAAAAACATATTGGGGTCTGCAGACAGGAG
AAAGAGCTTGGCATTTGGGTCACGGAGTCTCCATAGAATGGAGATTGAGAAGATAT
AGCACACAAGTAGACCCTGACCTGACAGACCAACTAATTCATATGCATTATTTTGAT
TGTTTTGCAGAATCTGCCATAAGGAAAGCCATACTAGGACAGATAGTTAGCCCTAA
GTGTGACTATCAAGCAGGACATAACAAGGTAGGATCTCTACAATACTTGGCACTGA
CAGCATTGATAAAACCAAAAAAGATAAAGCCACCTCTGCCTAGTGTTAGGAAATTA
GTAGAGGATAGATGGAACAAGCCCCAGAAGACCAGGGGCCGCAGAGGGAACCATA
CAATGAATGGACACTAGAGCTTTTAGAAGAACTCAAGCAGGAAGCTGTCAGACACT
TTCCTAGACCATGGCTCCATAACTTAGGACAACATATCTATGAAACCTATGGAGATA
CTTGGACAGGAGTTGAAGCAATAATAAGAATCCTGCAACAATTACTGTTTATTCATT
TCAGGATTGGGTGCCATCATAGCAGAATAGGCATTTGCGACAGAGAAGAGCAAGA
AATGGAGCCAATAGATCCTAACCTAGAACCCTGGAACCATCCAGGAAGTCAGCCTA
AAACTGCTTGTAATGGGTGTTACTGTAAACGTTGCAGCTATCATTGTCTAGTTTGCTT
TCAGAAAAAAGGCTTAGGCATTTACTATGGCAGGAAGAAGCGGAGACAGCGACGAA
GCGCTCCTCCAAGCAATAAAGATCATCAAGATCCTCTACCAAAGCAGTAAGTACCG
AATAGTATATGTAATGTTAGATTTAACTGCAAGAATAGATTCTAGATTAGGAATAGG
AGCATTGATAGTAGCACTAATCATAGCAATAATAGTGTGGACCATAGTATATATAG
AATATAGGAAATTGGTAAGGCAAAGGAAAATAGACTGGTTAGTTAAAAGGATTAGG
GAAAGAGCAGAAGACAGTGGCAATGAGAGCGAGGGGGATACTGAAGAATTATCGA
CACTGGTGGATATGGGGCATCTTAGGCTTTTGGATGCTAATGATGTGTAATGTGAA
GGGCTTGTGGGTCACAGTCTACTACGGGGTACCTGTGGGAGAGAAGCAAAAACT
ACTCTATTTTGTGCATCAGATGCTAAAGCATATGAGAAAGAAGTGCATAATGTCTG
GGCTACACATGCCTGTGTACCCACAGACCCCAACCCACAAGAAGTGATTTTGGGC
AATGTAACAGAAAATTTTAACATGTGGAAAAATGACATGGTGGATCAGATGCAGG
AAGATATAATCAGTTTATGGGATCAAAGCCTTAAGCCATGTGTAAAATTGACCCCA
CTCTGTGTCACTTTAAACTGTACAAATGCAACTGTTAACTACAATAATACCTCTAAA
GACATGAAAAATTGCTCTTTCTATGTAACCACAGAATTAAGAGATAAGAAAAAGAA
AGAAAATGCACTTTTTATAGACTTGATATAGTACCACTTAATAATAGGAAGAATGG
GAATATTAACAACTATAGATTAATAAATTGTAATACCTCAGCCATAACACAAGCCTG
TCCAAAAGTCTCGTTTGACCCAATTCCTATACATTATTGTGCTCCAGCTGGTTATGCG
CCTCTAAAATGTAATAATAAGAAATTCAATGGAATAGGACCATGCGATAATGTCAG
CACAGTACAATGTACACATGGAATTAAGCCAGTGGTATCAACTCAATTACTGTTAAA
TGGTAGCCTAGCAGAAGAAGAGATAATAATTAGATCTGAAAATCTGACAAACAATG
TCAAAACAATAATAGTACATCTTAATGAATCTATAGAGATTAAATGTACAAGACC
```

FIGURE 16 CONTINUED

```
TGGCAATAATACAAGAAAGAGTGTGAGAATAGGACCAGGACAAGCATTCTATGCA
ACAGGAGACATAATAGGAGATATAAGACAAGCACATTGTAACATTAGTAAAAATGA
ATGGAATACAACTTTACAAAGGGTAAGTCAAAAATTACAAGAACTCTTCCCTAATA
GTACAGGGATAAAATTTGCACCACACTCAGGAGGGGACCTAGAAATTACTACACAT
AGCTTTAATTGTGGAGGAGAATTTTTCTATTGCAATACAACAGACCTGTTTAATAGT
ACATACAGTAATGGTACATGCACTAATGGTACATGCATGTCTAATAATACAGAGCG
CATCACACTCCAATGCAGAATAAAACAAATTATAAACATGTGGCAGGAGGTAGGAC
GAGCAATGTATGCCCCTCCCATTGCAGGAAACATAACATGTAGATCAAATATTACA
GGACTACTATTAACACGTGATGGAGGAGATAATAATACTGAAACAGAGACATTCAG
ACCTGGAGGAGGAGACATGAGGGACAATTGGAGAAGTGAATTATATAAATACAAG
GTGGTAGAAATTAAACCATTAGGAGTAGCACCCACTGCTGCAAAAAGGAGAGTGGT
GGAGAGAGAAAAAAGAGCAGTAGGAATAGGAGCTGTGTTCCTTGGGTTCTTGGGAG
CAGCAGGAAGCACTATGGGCGCAGCATCAATAACGCTGACGGTACAGGCCAGACAA
TTATTGTCTGGTATAGTGCAACAGCAAAGTAATTTGCTGAGGGCTATAGAGGCGCAA
CAGCATATGTTGCAACTCACGGTCTGGGGCATTAAGCAGCTCCAGGCAAGAGTCCTG
GCTATAGAGAGATACCTACAGGATCAACAGCTCCTAGGACTGTGGGGCTGCTCTGG
AAAACTCATCTGCACCACTAATGTGCTTTGGAACTCTAGTTGGAGTAATAAAACTCA
AAGTGATATTTGGGATAACATGACCTGGATGCAGTGGGATAGGGAAATTAGTAATT
ACACAAACACAATATACAGGTTGCTTGAAGACTCGCAAAGCCAGCAGGAAAGAAA
TGAAAAAGATTTACTAGCATTGGACAGGTGGAACAATCTGTGGAATTGGTTTAGCAT
AACAAATTGGCTGTGGTATATAAAAATATTCATAATGATAGTAGGAGGCTTGATAG
GTTTAAGAATAATTTTTGCTGTGCTCTCTAGTAAATAGAGTTAGGCAGGGATACT
CACCCTTGTCATTGCAGACCCTTATCCCAAACCCGAGGGGACCCGACAGGCTCGGA
GGAATCGAAGAAGAAGGTGGAGAGCAAGACAGCAGCAGATCCATTCGATTAGTGA
GCGGATTCTTGACACTTGCCTGGGACGACCTACGAAGCCTGTGCCTCTTCTGCTACC
ACCGATTGAGAGACTTCATATTAATTGTAGTGAGAGCAGTGGAACTTCTGGGACAC
AGTAGTCTCAGGGGACTGCAGAGGGGGTGGGGAACCCTTAAGTATTTGGGGAGTCT
TGTGCAATATTGGGGTCTAGAGTTAAAAAAGAGTGCTATTAATCTGCTTGATACTAT
AGCAATAGCAGTAGCTGAAGGAACAGATAGGATTCTAGAATTCATACAAAACCTTT
GTAGAGGTATCCGCAACGTACCTAGAAGAATAAGACAGGGCTTCGAAGCAGCTTTG
CAATAAAATGGGGGGCAAGTGGTCAAAAAGCAGTATAATTGGATGGCCTGAAGTAA
GAGAAAGAATCAGACGAACTAGGTCAGCAGCAGAGGGAGTAGGATCAGCGTCTCA
AGACTTAGAGAAACATGGGGCACTTACAACCAGCAACACAGCCCACAACAATGCTG
CTTGCGCCTGGCTGGAAGCGCAAGAGGAGGAAGGAGAAGTAGGCTTTCCAGTCAGA
CCTCAGGTACCTTTAAGACCAATGACTTATAAAGCAGCAATAGATCTCAGCTTCTTT
TTAAAAGAAAAGGGGGGACTGGAAGGGTTAATTTACTCCAAGAAAAGGCAAGAGAT
CCTTGATTTGTGGGTTTATAACACACAAGGCTTCTTCCCTGATTGGCAAAACTACAC
ACCGGGACCAGGGGTCAGATTTCCACTGACCTTTGGATGGTACTTCAAGCTAGAGCC
AGTCGATCCAAGGGAAGTAGAAGAGGCCAATGAAGGAGAAAACAACTGTTTACTAC
ACCCTATGAGCCAGCATGGAATGGAGGATGAAGACAGAGAAGTATTAAGATGGAAG
TTTGACAGTACGCTAGCACGCAGACACATGGCCCGCGAGCTACATCCGGAGTATTAC
AAAGACTGCTGACACAGAAGGGACTTTCCGCTGGGACTTTCCACTGGGGCGTTCCAG
GAGGTGTGGTCTGGGCGGGACAGGGGAGTGGTCAGCCCTGAGATGCTGCATATAAG
CAGCTGCTTTTCGCCTGTACTGGGTCTCTCTAGGTAGACCAGATCTGAGCCCGGGAG
```

FIGURE 16 CONTINUED

CTCTCTGGCTATCTAGGGAACCCACTGCTTAAGCCTCAATAAAGCTTGCCTTGAGTG
CCTTGAGTAGTGTGTGCCCGTCTGTTGTGTGACTCTGGTAACTAGAGATCCCTCAGA
CCACTTGTGGTAGTGTGGAAAATCTCTAGCA

FIGURE 16 CONTINUED

>C4_Env_TV1_C_ZA_opt_short (SEQ ID NO:46)

CATCACCCTGCAGTGCAAGATCAAGCAGATCGTGCGCATGTGGCAGGGCGTGGGCCAGGCCATGTACGCCCCCCCCATCG
CCGGCAACATCACCTGC

FIGURE 17

>C4_Env_TV1_C_ZA_opt (SEQ ID NO:47)

CTGCCCATCACCCTGCAGTGCAAGATCAAGCAGATCGTGCGCATGTGGCAGGGCGTGGGCCAGGCCATGTACGCCCCCCC
CATCGCCGGCAACATCACCTGCCGCAGCAACATCACCGGCATCCTGCTGACCCGCGACGGCGGC

FIGURE 18

>C4_Env_TV1_C_ZA_wt (SEQ ID NO:48)

TTACCCATCACACTCCAATGCAAAATAAAACAAATTGTACGCATGTGGCAAGGGGTAGGACAAGCAATGTATGCCCCTCC
CATTGCAGGAAACATAACATGTAGATCAAACATCACAGGAATACTATTGACACGTGATGGGGGA

FIGURE 19

>Envgp160_TV1_C_ZAopt (SEQ ID NO:49)

ATGCGCGTGATGGGCACCCAGAAGAACTGCCAGCAGTGGTGGATCTGGGGCATCCTGGGCTTCTGGATGCTGATGATCTG
CAACACCGAGGACCTGTGGGTGACCGTGTACTACGGCGTGCCCGTGTGGCGCGAGGCCAAGACCACCCTGTTCTGCGCCA
GCGACGCCAAGGCCTACGAGACCGAGGTGCACAACGTGTGGGCCACCCACGCCTGCGTGCCCACCGACCCCAACCCCCAG
GAGATCGTGCTGGGCAACGTGACCGAGAACTTCAACATGTGGAAGAACAACATGGCCGACCAGATGCACGAGGACATCAT
CAGCCTGTGGGACCAGAGCCTGAAGCCCTGCGTGAAGCTGACCCCCCTGTGCGTGACCCTGAACTGCACCGACACCAACG
TGACCGGCAACCGCACCGTGACCGGCAACACCAACGACACCAACATCGCCAACGCCACCTACAAGTACGAGGAGATGAAG
AACTGCAGCTTCAACGCCACCACCGAGCTGCGCGACAAGAAGCACAAGGAGTACGCCCTGTTCTACAAGCTGGACATCGT
GCCCCTGAACGAGAACAGCAACAACTTCACCTACCGCCTGATCAACTGCAACACCAGCACCATCACCCAGGCCTGCCCCA
AGGTGAGCTTCGACCCCATCCCCATCCACTACTGCGCCCCCGCCGACTACGCCATCCTGAAGTGCAACAACAAGACCTTC
AACGGCACCGGCCCCTGCTACAACGTGAGCACCGTGCAGTGCACCCACGGCATCAAGCCCGTGGTGAGCACCCAGCTGCT
GCTGAACGGCAGCCTGGCCGAGGAGGGCATCATCATCCGCAGCGAGAACCTGACCGAGAACACCAAGACCATCATCGTGC
ACCTGAACGAGAGCGTGGAGATCAACTGCACCCGCCCCAACAACAACACCCGCAAGAGCGTGCGCATCGGCCCCGGCCAG
GCCTTCTACGCCACCAACGACGTGATCGGCAACATCCGCCAGGCCCACTGCAACATCAGCACCGACCGCTGGAACAAGAC
CCTGCAGCAGGTGATGAAGAAGCTGGGCGAGCACTTCCCCAACAAGACCATCAAGTTCGAGCCCCACGCCGGCGGCGACC
TGGAGATCACCATGCACAGCTTCAACTGCCGCGGCGAGTTCTTCTACTGCAACACCAGCAACCTGTTCAACAGCACCTAC
TACCCCAAGAACGGCACCTACAAGTACAACGGCAACAGCAGCCTGCCCATCACCCTGCAGTGCAAGATCAAGCAGATCGT
GCGCATGTGGCAGGGCGTGGGCCAGGCCATGTACGCCCCCCCCATCGCCGGCAACATCACCTGCCGCAGCAACATCACCG
GCATCCTGCTGACCCGCGACGGCGGCTTCAACAACACCAACAACGACACCGAGGAGACCTTCCGCCCCGGCGGCGGCGAC
ATGCGCGACAACTGGCGCAGCGAGCTGTACAAGTACAAGGTGGTGGAGATCAAGCCCCTGGGCATCGCCCCCACCAAGGC
CAAGCGCCGCGTGGTGCAGCGCAAGAAGCGCGCCGTGGGCATCGGCGCCGTGTTCCTGGGCTTCCTGGGCGCCGCCGGCA
GCACCATGGGCGCCGCCAGCATCACCCTGACCGTGCAGGCCCGCCAGCTGCTGAGCGGCATCGTGCAGCAGCAGAGCAAC
CTGCTGAAGGCCATCGAGGCCCAGCAGCACATGCTGCAGCTGACCGTGTGGGGCATCAAGCAGCTGCAGGCCCGCGTGCT
GGCCATCGAGCGCTACCTGAAGGACCAGCAGCTGCTGGGCATCTGGGGCTGCAGCGGCCGCCTGATCTGCACCACCGCCG
TGCCCTGGAACAGCAGCTGGAGCAACAAGAGCGAGGCCGACATCTGGGACAACATGACCTGGATGCAGTGGGACCGCGAG
ATCAACAACTACACCGAGACCATCTTCCGCCTGCTGGAGGACAGCCAGAACCAGCAGGAGAAGAACGAGAAGGACCTGCT
GGAGCTGGACAAGTGGAACAACCTGTGGAACTGGTTCGACATCAGCAACTGGCTGTGGTACATCAAGATCTTCATCATGA
TCGTGGGCGGCCTGATCGGCCTGCGCATCATCTTCGCCGTGCTGAGCATCGTGAACCGCGTGCGCCAGGGCTACAGCCCC
CTGAGCTTCCAGACCCTGACCCCCAGCCCCCGCGGCCTGGACCGCCTGGGCGGCATCGAGGAGGAGGGCGGCGAGCAGGA
CCGCGACCGCAGCATCCGCCTGGTGAGCGGCTTCCTGAGCCTGGCCTGGGACGACCTGCGCAGCCTGTGCCTGTTCAGCT
ACCACCGCCTGCGCGACTTCATCCTGATCGCCGTGCGCGCCGTGGAGCTGCTGGGCCACAGCAGCCTGCGCGGCCTGCAG
CGCGGCTGGGAGATCCTGAAGTACCTGGGCAGCCTGGTGCAGTACTGGGGCCTGGAGCTGAAGAAGAGCGCCATCAGCCC
CCTGGACACCATCGCCATCGCCGTGGCCGAGGGCACCGACCGCATCATCGAGCTGGTGCAGCGCATCTGCCGCGCCATCC
TGAACATCCCCCGCCGCATCCGCCAGGGCTTCGAGGCCGCCCTGCTGTAA

FIGURE 20

>Envgp160_TV1_C_ZAwt (SEQ ID NO:50)

```
ATGAGAGTGATGGGGACACAGAAGAATTGTCAACAATGGTGGATATGGGGCATCTTAGGCTTCTGGATGCTAATGATTTG
TAACACGGAGGACTTGTGGGTCACAGTCTACTATGGGGTACCTGTGTGGAGAGAAGCAAAAACTACTCTATTCTGTGCAT
CAGATGCTAAAGCATATGAGACAGAAGTGCATAATGTCTGGGCTACACATGCTTGTGTACCCACAGACCCCAACCCACAA
GAAATAGTTTTGGGAAATGTAACAGAAAATTTTAATATGTGGAAAAATAACATGGCAGATCAGATGCATGAGGATATAAT
CAGTTTATGGGATCAAAGCCTAAAGCCATGTGTAAAGTTGACCCCACTCTGTGTCACTTTAAACTGTACAGATACAAATG
TTACAGGTAATAGAACTGTTACAGGTAATACAAATGATACCAATATTGCAAATGCTACATATAAGTATGAAGAAATGAAA
AATTGCTCTTTCAATGCAACCACAGAATTAAGAGATAAGAAACATAAAGAGTATGCACTCTTTTATAAACTTGATATAGT
ACCACTTAATGAAAATAGTAACAACTTTACATATAGATTAATAAAATTGCAATACCTCAACCATAACACAAGCCTGTCCAA
AGGTCTCTTTTGACCCGATTCCTATACATTACTGTGCTCCAGCTGATTATGCGATTCTAAAGTGTAATAATAAGACATTC
AATGGGACAGGACCATGTTATAATGTCAGCACAGTACAATGTACACATGGAATTAAGCCAGTGGTATCAACTCAACTACT
GTTAAATGGTAGTCTAGCAGAAGAAGGGATAATAATTAGATCTGAAAATTTGACAGAGAATACCAAAACAATAATAGTAC
ATCTTAATGAATCTGTAGAGATTAATTGTACAAGGCCCAACAATAATACAAGGAAAGTGTAAGGATAGGACCAGGACAA
GCATTCTATGCAACAAATGACGTAATAGGAAACATAAGACAAGCACATTGTAACATTAGTACAGATAGATGGAATAAAAC
TTTACAACAGGTAATGAAAAAATTAGGAGAGCATTTCCCTAATAAAACAATAAAATTTGAACCACATGCAGGAGGGGATC
TAGAAATTACAATGCATAGCTTTAATTGTAGAGGAGAATTTTTCTATTGCAATACATCAAACCTGTTTAATAGTACATAC
TACCCTAAGAATGGTACATACAAATACAATGGTAATTCAAGCTTACCCATCACACTCCAATGCAAAATAAAACAAATTGT
ACGCATGTGGCAAGGGGTAGGACAAGCAATGTATGCCCCTCCCATTGCAGGAAACATAACATGTAGATCAAACATCACAG
GAATACTATTGACACGTGATGGGGGATTTAACAACACAAACAACGACACAGAGGAGACATTCAGACCTGGAGGAGGAGAT
ATGAGGGATAACTGGAGAAGTGAATTATATAAATATAAAGTGGTAGAAATTAAGCCATTGGGAATAGCACCCACTAAGGC
AAAAAGAAGAGTGGTGCAGAGAAAAAAAGAGCAGTGGGAATAGGAGCTGTGTTCCTTGGGTTCTTGGGAGCAGCAGGAA
GCACTATGGGCGCAGCGTCAATAACGCTGACGGTACAGGCCAGACAACTGTTGTCTGGTATAGTGCAACAGCAAAGCAAT
TTGCTGAAGGCTATAGAGGCGCAACAGCATATGTTGCAACTCACAGTCTGGGGCATTAAGCAGCTCCAGGCGAGAGTCCT
GGCTATAGAAAGATACCTAAAGGATCAACAGCTCCTAGGGATTTGGGGCTGCTCTGGAAGACTCATCTGCACCACTGCTG
TGCCTTGGAACTCCAGTTGGAGTAATAAATCTGAAGCAGATATTTGGGATAACATGACTTGGATGCAGTGGGATAGAGAA
ATTAATAATTACACAGAAACAATATTCAGGTTGCTTGAAGACTCGCAAAACCAGCAGGAAAAGAATGAAAAAGATTTATT
AGAATTGGACAAGTGGAATAATCTGTGGAATTGGTTTGACATATCAAACTGGCTGTGGTATATAAAAATATTCATAATGA
TAGTAGGAGGCTTGATAGGTTTAAGAATAATTTTTGCTGTGCTCTCTATAGTGAATAGAGTTAGGCAGGGATACTCACCT
TTGTCATTTCAGACCCTTACCCCAAGCCCGAGGGGACTCGACAGGCTCGGAGGAATCGAAGAAGAAGGTGGAGAGCAAGA
CAGAGACAGATCCATACGATTGGTGAGCGGATTCTTGTCGCTTGCCTGGGACGATCTGCGGAGCCTGTGCCTCTTCAGCT
ACCACCGCTTGAGAGACTTCATATTAATTGCAGTGAGGGCAGTGGAACTTCTGGGACACAGCAGTCTCAGGGGACTACAG
AGGGGGTGGGAGATCCTTAAGTATCTGGGAAGTCTTGTGCAGTATTGGGGTCTAGAGCTAAAAAAGAGTGCTATTAGTCC
GCTTGATACCATAGCAATAGCAGTAGCTGAAGGAACAGATAGGATTATAGAATTGGTACAAAGAATTTGTAGAGCTATCC
TCAACATACCTAGGAGAATAAGACAGGGCTTTGAAGCAGCTTTGCTATAA
```

FIGURE 21

>Gag_TV1_C_ZAopt (SEQ ID NO:51)
ATGGGCGCCCGCGCCAGCATCCTGAGCGGCGGCAAGCTGGACAAGTGGGAGCGCATCCGCCTGCGCCCCGGCGGCAAGAA
GCACTACATGCTGAAGCACCTGGTGTGGGCCAGCCGCGAGCTGGAGCGCTTCGCCCTGAACCCCGGCCTGCTGGAGACCA
GCGAGGGCTGCAAGCAGATCATCAAGCAGCTGCAGCCCGCCCTGCAGACCGGCACCGAGGAGCTGCGCAGCCTGTTCAAC
ACCGTGGCCACCCTGTACTGCGTGCACAAGGGCATCGAGGTGCGCGACACCAAGGAGGCCCTGGACAAGATCGAGGAGGA
GCAGAACAAGTGCCAGCAGAAGGCCCAGCAGGCCAAGGCCGCCGACGAGAAGGTGAGCCAGAACTACCCCATCGTGCAGA
ACGCCCAGGGCCAGATGGTGCACCAGGCCATCAGCCCCCGCACCCTGAACGCCTGGATCAAGGTGATCGAGGAGAAGGCC
TTCAACCCCGAGGAGATCCCCATGTTCACCGCCCTGAGCGAGGGCGCCACCCCCCAGGACCTGAACACCATGCTGAACAC
CGTGGGCGGCCACCAGGCCGCCATGCAGATGCTGAAGGACACCATCAACGAGGAGGCCGCCGAGTGGGACCGCACCCACC
CCGTGCACGCCGGCCCCGTGGCCCCCGGCCAGATGCGCGAGCCCCGCGGCAGCGACATCGCCGGCACCACCAGCACCCTG
CAGGAGCAGATCGCCTGGATGACCAGCAACCCCCCCATCCCCGTGGAGGACATCTACAAGCGCTGGATCATCCTGGGCCT
GAACAAGATCGTGCGCATGTACAGCCCCGTGAGCATCCTGGACATCAAGCAGGGCCCCAAGGAGCCCTTCCGCGACTACG
TGGACCGCTTCTTCAAGACCCTGCGCGCCGAGCAGGCCACCCAGGACGTGAAGAACTGGATGACCGACACCCTGCTGGTG
CAGAACGCCAACCCCGACTGCAAGACCATCCTGCGCGCCCTGGGCCCCGGCGCCAGCCTGGAGGAGATGATGACCGCCTG
CCAGGGCGTGGGCGGCCCCAGCCACAAGGCCCGCGTGCTGGCCGAGGCCATGAGCCAGGCCAACAGCAACATCCTGGTGC
AGCGCAGCAACTTCAAGGGCAGCAACCGCATCATCAAGTGCTTCAACTGCGGCAAGGTGGGCCACATCGCCCGCAACTGC
CGCGCCCCCCGCAAGAAGGGCTGCTGGAAGTGCGGCCAGGAGGGCCACCAGATGAAGGACTGCACCGAGCGCCAGGCCAA
CTTCCTGGGCAAGATCTGGCCCAGCCACAAGGGCCGCCCCGGCAACTTCCTGCAGAACCGCCCCGAGCCCACCGCCCCCC
CCGCCGAGCCCACCGCCCCCCCCGCCGAGAGCTTCCGCTTCGAGGAGACCACCCCCGTGCCCCGCAAGGAGAAGGAGCGC
GAGCCCCTGACCAGCCTGAAGAGCCTGTTCGGCAGCGACCCCCTGAGCCAGTAA

FIGURE 22

>Gag_TV1_C_ZAwt (SEQ ID NO:52)

ATGGGTGCGAGAGCGTCAATATTAAGCGGCGGAAAATTAGATAAATGGGAAAGAATTAGGTTAAGGCCAGGGGGAAAGAA
ACATTATATGTTAAAACATCTAGTATGGGCAAGCAGGGAGCTGGAAAGATTTGCACTTAACCCTGGCCTGTTAGAAACAT
CAGAAGGCTGTAAACAAATAATAAAACAGCTACAACCAGCTCTTCAGACAGGAACAGAGGAACTTAGATCATTATTCAAC
ACAGTAGCAACTCTCTATTGTGTACATAAAGGGATAGAGGTACGAGACACCAAGGAAGCCTTAGACAAGATAGAGGAAGA
ACAAAACAAATGTCAGCAAAAAGCACAACAGGCAAAAGCAGCTGACGAAAAGGTCAGTCAAAATTATCCTATAGTACAGA
ATGCCCAAGGGCAAATGGTACACCAAGCTATATCACCTAGAACATTGAATGCATGGATAAAAGTAATAGAGGAAAAGGCT
TTCAATCCAGAGGAAATACCCATGTTTACAGCATTATCAGAAGGAGCCACCCCACAAGATTTAAACACAATGTTAAATAC
AGTGGGGGGACATCAAGCAGCCATGCAAATGTTAAAAGATACCATCAATGAGGAGGCTGCAGAATGGGATAGGACACATC
CAGTACATGCAGGGCCTGTTGCACCAGGCCAGATGAGAGAACCAAGGGGAAGTGACATAGCAGGAACTACTAGTACCCTT
CAGGAACAAATAGCATGGATGACAAGTAATCCACCTATTCCAGTAGAAGACATCTATAAAAGATGGATAATTCTGGGGTT
AAATAAAATAGTAAGAATGTATAGCCCTGTTAGCATTTTGGACATAAAACAAGGGCCAAAAGAACCCTTTAGAGACTATG
TAGACCGGTTCTTTAAAACCTTAAGAGCTGAACAAGCTACACAAGATGTAAAGAATTGGATGACAGACACCTTGTTGGTC
CAAAATGCGAACCCAGATTGTAAGACCATTTTAAGAGCATTAGGACCAGGGGCCTCATTAGAAGAAATGATGACAGCATG
TCAGGGAGTGGGAGGACCTAGCCATAAAGCAAGAGTGTTGGCTGAGGCAATGAGCCAAGCAAACAGTAACATACTAGTGC
AGAGAAGCAATTTTAAAGGCTCTAACAGAATTATTAAATGTTTCAACTGTGGCAAAGTAGGGCACATAGCCAGAAATTGC
AGGGCCCCTAGGAAAAAGGGCTGTTGGAAATGTGGACAGGAAGGACACCAAATGAAAGACTGTACTGAGAGGCAGGCTAA
TTTTTTAGGGAAAATTTGGCCTTCCCACAAGGGGAGGCCAGGGAATTTCCTCCAGAACAGACCAGAGCCAACAGCCCCAC
CAGCAGAACCAACAGCCCCACCAGCAGAGAGCTTCAGGTTCGAGGAGACAACCCCCGTGCCGAGGAAGGAGAAAGAGAGG
GAACCTTTAACTTCCCTCAAATCACTCTTTGGCAGCGACCCCTTGTCTCAATAA

FIGURE 23

>Gag_TV1_ZA_MHRopt (SEQ ID NO:53)

GACATCAAGCAGGGCCCCAAGGAGCCCTTCCGCGACTACGTGGACCGCTTCTTCAAGACC

FIGURE 24

>Gag_TV1_ZA_MHRwt (SEQ ID NO:54)

GACATAAAACAAGGGCCAAAAGAACCCTTTAGAGACTATGTAGACCGGTTCTTTAAAACC

FIGURE 25

>Nef_TV1_C_ZAopt (SEQ ID NO:55)

ATGGGCGGCAAGTGGAGCAAGCGCAGCATCGTGGGCTGGCCCGCCGTGCGCGAGCGCATGCGCCGCACCGAGCCCGCCGC
CGAGGGCGTGGGCGCCGCCAGCCAGGACCTGGACCGCCACGGCGCCCTGACCAGCAGCAACACCCCCGCCACCAACGAGG
CCTGCGCCTGGCTGCAGGCCCAGGAGGAGGACGGCGACGTGGGCTTCCCCGTGCGCCCCCAGGTGCCCCTGCGCCCCATG
ACCTACAAGAGCGCCGTGGACCTGAGCTTCTTCCTGAAGGAGAAGGGCGGCCTGGAGGGCCTGATCTACAGCCGCAAGCG
CCAGGAGATCCTGGACCTGTGGGTGTACAACACCCAGGGCTTCTTCCCCGACTGGCAGAACTACACCAGCGGCCCCGGCG
TGCGCTTCCCCCTGACCTTCGGCTGGTGCTTCAAGCTGGTGCCCGTGGACCCCGCGAGGTGAAGGAGGCCAACGAGGGC
GAGGACAACTGCCTGCTGCACCCCATGAGCCAGCACGGCGCCGAGGACGAGGACCGCGAGGTGCTGAAGTGGAAGTTCGA
CAGCCTGCTGGCCCACCGCCACATGGCCCGCGAGCTGCACCCCGAGTACTACAAGGACTGCTGA

FIGURE 26

>Nef_TV1_C_ZAwt (SEQ ID NO:56)
ATGGGAGGCAAGTGGTCAAAACGCAGCATAGTTGGATGGCCTGCAGTAAGAGAAAGAATGAGAAGAACTGAGCCAGCAGC
AGAGGGAGTAGGAGCAGCGTCTCAAGACTTAGATAGACATGGGGCACTTACAAGCAGCAACACACCTGCTACTAATGAAG
CTTGTGCCTGGCTGCAAGCACAAGAGGAGGACGGAGATGTAGGCTTTCCAGTCAGACCTCAGGTACCTTTAAGACCAATG
ACTTATAAGAGTGCAGTAGATCTCAGCTTCTTTTTAAAAGAAAAGGGGGGACTGGAAGGGTTAATTTACTCTAGGAAAAG
GCAAGAAATCCTTGATTTGTGGGTCTATAACACACAAGGCTTCTTCCCTGATTGGCAAAACTACACATCGGGGCCAGGGG
TCCGATTCCCACTGACCTTTGGATGGTGCTTCAAGCTAGTACCAGTTGACCCAAGGGAGGTGAAAGAGGCCAATGAAGGA
GAAGACAACTGTTTGCTACACCCTATGAGCCAACATGGAGCAGAGGATGAAGATAGAGAAGTATTAAAGTGGAAGTTTGA
CAGCCTTCTAGCACACAGACACATGGCCCGCGAGCTACATCCGGAGTATTACAAAGACTGCTGA

FIGURE 27

\>NefD125G_TV1_C_ZAopt (SEQ ID NO:57)

ATGGGCGGCAAGTGGAGCAAGCGCAGCATCGTGGGCTGGCCCGCCGTGCGCGAGCGCATGCGCCGCACCGAGCCCGCCGC
CGAGGGCGTGGGCGCCGCCAGCCAGGACCTGGACCGCCACGGCGCCCTGACCAGCAGCAACACCCCCGCCACCAACGAGG
CCTGCGCCTGGCTGCAGGCCCAGGAGGAGGACGGCGACGTGGGCTTCCCCGTGCGCCCCCAGGTGCCCCTGCGCCCCATG
ACCTACAAGAGCGCCGTGGACCTGAGCTTCTTCCTGAAGGAGAAGGGCGGCCTGGAGGGCCTGATCTACAGCCGCAAGCG
CCAGGAGATCCTGGACCTGTGGGTGTACAACACCCAGGGCTTCTTCCCCGGCTGGCAGAACTACACCAGCGGCCCCGGCG
TGCGCTTCCCCCTGACCTTCGGCTGGTGCTTCAAGCTGGTGCCCGTGGACCCCCGCGAGGTGAAGGAGGCCAACGAGGGC
GAGGACAACTGCCTGCTGCACCCCATGAGCCAGCACGGCGCCGAGGACGAGGACCGCGAGGTGCTGAAGTGGAAGTTCGA
CAGCCTGCTGGCCCACCGCCACATGGCCCGCGAGCTGCACCCCGAGTACTACAAGGACTGCTGA

FIGURE 28

>p15RNaseH_TV1_C_ZAopt (SEQ ID NO:58)

ACCTTCTACGTGGACGGCGCCACCAACCGCGAGGCCAAGATCGGCAAGGCCGGCTACGTGACCGACCGCGGCCGCCAGAA
GATCGTGACCCTGACCAACACCACCAACCAGAAGACCGAGCTGCAGGCCATCCAGCTGGCCCTGCAGGACAGCGGCAGCG
AGGTGAACATCGTGACCGACAGCCAGTACGCCCTGGGCATCATCCAGGCCCAGCCCGACAAGAGCGACAGCGAGATCTTC
AACCAGATCATCGAGCAGCTGATCAACAAGGAGCGCATCTACCTGAGCTGGGTGCCCGCCCACAAGGGCATCGGCGGCAA
CGAGCAGGTGGACAAGCTGGTGAGCAAGGGCATC

FIGURE 29

>p15RNaseH_TV1_C_Zawt (SEQ ID NO:59)

ACTTTCTATGTAGATGGAGCAACTAATAGGGAAGCTAAAATAGGAAAAGCAGGGTATGTTACTGACAGAGGAAGGCAGAA
AATTGTTACTCTAACTAACACAACAAATCAGAAGACTGAGTTACAAGCAATTCAGCTAGCTCTGCAGGATTCAGGATCAG
AAGTAAACATAGTAACAGACTCACAGTATGCATTAGGAATCATTCAAGCACAACCAGATAAGAGTGACTCAGAGATATTT
AACCAAATAATAGAACAGTTAATAAACAAGGAAAGAATCTACCTGTCATGGGTACCAGCACATAAAGGAATTGGGGGAAA
TGAACAAGTAGATAAATTAGTAAGTAAGGGAATT

FIGURE 30

>p31Int_TV1_C_Zaopt (SEQ ID NO:60)

```
CGCAAGGTGCTGTTCCTGGACGGCATCGACAAGGCCCAGGAGGAGCACGAGCGCTACCACAGCAACTGGCGCGCCATGGC
CAACGAGTTCAACCTGCCCCCCATCGTGGCCAAGGAGATCGTGGCCAGCTGCGACAAGTGCCAGCTGAAGGGCGAGGCCA
TCCACGGCCAGGTGGACTGCAGCCCCGGCATCTGGCAGCTGGACTGCACCCACCTGGAGGGCAAGATCATCCTGGTGGCC
GTGCACGTGGCCAGCGGCTACATGGAGGCCGAGGTGATCCCCGCCGAGACCGGCCAGGAGACCGCCTACTTCATCCTGAA
GCTGGCCGGCCGCTGGCCCGTGAAGGTGATCCACACCGACAACGGCAGCAACTTCACCAGCACCGCCGTGAAGGCCGCCT
GCTGGTGGGCCGGCATCCAGCAGGAGTTCGGCATCCCCTACAACCCCCAGAGCCAGGGCGTGGTGGAGAGCATGAACAAG
GAGCTGAAGAAGATCATCGGCCAGGTGCGCGACCAGGCCGAGCACCTGAAGACCGCCGTGCAGATGGCCGTGTTCATCCA
CAACTTCAAGCGCAAGGGCGGCATCGGCGGCTACAGCGCCGGCGAGCGCATCATCGACATCATCGCCACCGACATCCAGA
CCAAGGAGCTGCAGAAGCAGATCATCCGCATCCAGAACTTCCGCGTGTACTACCGCGACAGCCGCGACCCCATCTGGAAG
GGCCCCGCCGAGCTGCTGTGGAAGGGCGAGGGCGTGGTGGTGATCGAGGACAAGGGCGACATCAAGGTGGTGCCCCGCCG
CAAGGCCAAGATCATCCGCGACTACGGCAAGCAGATGGCCGGCGCCGACTGCGTGGCCGGCGGCCAGGACGAGGAC
```

FIGURE 31

>p31Int_TV1_C_ZAwt (SEQ ID NO:61)

```
AGGAAAGTGTTGTTTCTAGATGGAATAGATAAAGCTCAAGAAGAGCATGAAAGGTACCACAGCAATTGGAGAGCAATGGC
TAATGAGTTTAATCTGCCACCCATAGTAGCAAAAGAAATAGTAGCTAGCTGTGATAAATGTCAGCTAAAAGGGGAAGCCA
TACATGGACAAGTCGACTGTAGTCCAGGGATATGGCAATTAGATTGTACCCATTTAGAGGGAAAAATCATCCTGGTAGCA
GTCCATGTAGCTAGTGGCTACATGGAAGCAGAGGTTATCCCAGCAGAAACAGGACAAGAAACAGCATATTTTATATTAAA
ATTAGCAGGAAGATGGCCAGTCAAAGTAATACATACAGACAATGGCAGTAATTTTACCAGTACTGCAGTTAAGGCAGCCT
GTTGGTGGGCAGGTATCCAACAGGAATTTGGAATTCCCTACAATCCCCAAAGTCAGGGAGTGGTAGAATCCATGAATAAA
GAATTAAAGAAAATAATAGGACAAGTAAGAGATCAAGCTGAGCACCTTAAGACAGCAGTACAAATGGCAGTATTCATTCA
CAATTTTAAAAGAAAAGGGGGAATTGGGGGGTACAGTGCAGGGGAAAGAATAATAGACATAATAGCAACAGACATACAAA
CTAAAGAATTACAAAAACAAATTATAAGAATTCAAAATTTTCGGGTTTATTACAGAGACAGCAGAGACCCTATTTGGAAA
GGACCAGCCGAACTACTCTGGAAAGGTGAAGGGGTAGTAGTAATAGAAGATAAAGGTGACATAAAGGTAGTACCAAGGAG
GAAAGCAAAAATCATTAGAGATTATGGAAAACAGATGGCAGGTGCTGATTGTGTGGCAGGTGGACAGGATGAAGAT
```

FIGURE 32

>Pol_TV1_C_ZAopt (SEQ ID NO:62)

```
TTCTTCCGCGAGAACCTGGCCTTCCCCCAGGGCGAGGCCCGCGAGTTCCCCCCCGAGCAGACCCGCGCCAACAGCCCCAC
CAGCCGCACCAACAGCCCCACCAGCCGCGAGCTGCAGGTGCGCGGCGACAACCCCCGCGCCGAGGAGGGCGAGCGCGAGG
GCACCTTCAACTTCCCCCAGATCACCCTGTGGCAGCGCCCCCTGGTGAGCATCAAGGTGGAGGGCCAGATCAAGGAGGCC
CTGCTGGACACCGGCGCCGACGACACCGTGCTGGAGGAGATCGACCTGCCCGGCAAGTGGAAGCCCAAGATGATCGGCGG
CATCGGCGGCTTCATCAAGGTGCGCCAGTACGACCAGATCCTGATCGAGATCTGCGGCAAGAAGGCCATCGGCACCGTGC
TGGTGGGCCCCACCCCCGTGAACATCATCGGCCGCAACCTGCTGACCCAGCTGGGCTGCACCCTGAACTTCCCCATCAGC
CCCATCGAGACCGTGCCCGTGAAGCTGAAGCCCGGCATGGACGGCCCCAAGGTGAAGCAGTGGCCCCTGACCGAGGAGAA
GATCAAGGCCCTGACCGCCATCTGCGAGGAGATGGAGAAGGAGGGCAAGATCACCAAGATCGGCCCCGACAACCCCTACA
ACACCCCCGTGTTCGCCATCAAGAAGAAGGACAGCACCAAGTGGCGCAAGCTGGTGGACTTCCGCGAGCTGAACAAGCGC
ACCCAGGACTTCTGGGAGGTGCAGCTGGGCATCCCCCACCCCGCCGGCCTGAAGAAGAAGAAGAGCGTGACCGTGCTGGA
CGTGGGCGACGCCTACTTCAGCGTGCCCCTGGACGAGAGCTTCCGCAAGTACACCGCCTTCACCATCCCCAGCATCAACA
ACGAGACCCCCGGCATCCGCTACCAGTACAACGTGCTGCCCCAGGGCTGGAAGGGCAGCCCCGCCATCTTCCAGAGCAGC
ATGACCAAGATCCTGGAGCCCTTCCGCGCCAAGAACCCCGACATCGTGATCTACCAGTACATGGACGACCTGTACGTGGG
CAGCGACCTGGAGATCGGCCAGCACCGCGCCAAGATCGAGGAGCTGCGCGAGCACCTGCTGAAGTGGGGCTTCACCACCC
CCGACAAGAAGCACCAGAAGGAGCCCCCCTTCCTGTGGATGGGCTACGAGCTGCACCCCGACAAGTGGACCGTGCAGCCC
ATCCTGCTGCCCGAGAAGGACAGCTGGACCGTGAACGACATCCAGAAGCTGGTGGGCAAGCTGAACTGGGCCAGCCAGAT
CTACCCCGGCATCAAGGTGCGCCAGCTGTGCAAGCTGCTGCGCGGCGCCAAGGCCCTGACCGACATCGTGCCCCTGACCG
AGGAGGCCGAGCTGGAGCTGGCCGAGAACCGCGAGATCCTGCGCGAGCCCGTGCACGGCGTGTACTACGACCCCAGCAAG
GACCTGATCGCCGAGATCCAGAAGCAGGGCCACGAGCAGTGGACCTACCAGATCTACCAGGAGCCCTTCAAGAACCTGAA
GACCGGCAAGTACGCCAAGATGCGCACCACCCACACCAACGACGTGAAGCAGCTGACCGAGGCCGTGCAGAAGATCGCCA
TGGAGAGCATCGTGATCTGGGGCAAGACCCCCAAGTTCCGCCTGCCCATCCAGAAGGAGACCTGGGAGACCTGGTGGACC
GACTACTGGCAGGCCACCTGGATCCCCGAGTGGGAGTTCGTGAACACCCCCCCCTGGTGAAGCTGTGGTACCAGCTGGA
GAAGGACCCCATCGCCGGCGTGGAGACCTTCTACGTGGACGGCGCCACCAACCGCGAGGCCAAGATCGGCAAGGCCGGCT
ACGTGACCGACCGCGGCCGCCAGAAGATCGTGACCCTGACCAACACCACCAACCAGAAGACCGAGCTGCAGGCCATCCAG
CTGGCCCTGCAGGACAGCGGCAGCGAGGTGAACATCGTGACCGACAGCCAGTACGCCCTGGGCATCATCCAGGCCCAGCC
CGACAAGAGCGACAGCGAGATCTTCAACCAGATCATCGAGCAGCTGATCAACAAGGAGCGCATCTACCTGAGCTGGGTGC
CCGCCCACAAGGGCATCGGCGGCAACGAGCAGGTGGACAAGCTGGTGAGCAAGGGCATCCGCAAGGTGCTGTTCCTGGAC
GGCATCGACAAGGCCCAGGAGGAGCACGAGCGCTACCACAGCAACTGGCGCGCCATGGCCAACGAGTTCAACCTGCCCCC
CATCGTGGCCAAGGAGATCGTGGCCAGCTGCGACAAGTGCCAGCTGAAGGGCGAGGCCATCCACGGCCAGGTGGACTGCA
GCCCCGGCATCTGGCAGCTGGACTGCACCCACCTGGAGGGCAAGATCATCCTGGTGGCCGTGCACGTGGCCAGCGGCTAC
ATGGAGGCCGAGGTGATCCCCGCCGAGACCGGCCAGGAGACCGCCTACTTCATCCTGAAGCTGGCCGGCCGCTGGCCCGT
GAAGGTGATCCACACCGACAACGGCAGCAACTTCACCAGCACCGCCGTGAAGGCCGCCTGCTGGTGGCCGGCATCCAGC
AGGAGTTCGGCATCCCCTACAACCCCCAGAGCCAGGGCGTGGTGGAGAGCATGAACAAGGAGCTGAAGAAGATCATCGGC
CAGGTGCGCGACCAGGCCGAGCACCTGAAGACCGCCGTGCAGATGGCCGTGTTCATCCACAACTTCAAGCGCAAGGGCGG
CATCGGCGGCTACAGCGCCGGCGAGCGCATCATCGACATCATCGCCACCGACATCCAGACCAAGGAGCTGCAGAAGCAGA
TCATCCGCATCCAGAACTTCCGCGTGTACTACCGCGACAGCCGCGACCCCATCTGGAAGGGCCCCGCCGAGCTGCTGTGG
AAGGGCGAGGGCGTGGTGGTGATCGAGGACAAGGGCGACATCAAGGTGGTGCCCCGCCGCAAGGCCAAGATCATCCGCGA
CTACGGCAAGCAGATGGCCGGCGCCGACTGCGTGGCCGGCGGCCAGGACGAGGAC
```

FIGURE 33

>Pol_TV1_C_ZAwt (SEQ ID NO:63)

```
TTTTTTAGGGAAAATTTGGCCTTCCCACAAGGGGAGGCCAGGGAATTTCCTCCAGAACAGACCAGAGCCAACAGCCCCAC
CAGCAGAACCAACAGCCCCACCAGCAGAGAGCTTCAGGTTCGAGGAGACAACCCCCGTGCCGAGGAAGGAGAAAGAGAGG
GAACCTTTAACTTCCCTCAAATCACTCTTTGGCAGCGACCCCTTGTCTCAATAAAAGTAGAGGGCCAGATAAAGGAGGCT
CTCTTAGACACAGGAGCAGATGATACAGTATTAGAAGAAATAGATTTGCCAGGGAAATGGAAACCAAAAATGATAGGGGG
AATTGGAGGTTTTATCAAAGTAAGACAGTATGATCAAATACTTATAGAAATTTGTGGAAAAAAGGCTATAGGTACAGTAT
TAGTAGGGCCTACACCAGTCAACATAATTGGAAGAAATCTGTTAACTCAGCTTGGATGCACACTAAATTTTCCAATTAGT
CCTATTGAAACTGTACCAGTAAAATTAAAACCAGGAATGGATGGCCCAAAGGTCAAACAATGGCCATTGACAGAAGAAAA
AATAAAAGCATTAACAGCAATTTGTGAGGAAATGGAGAAGGAAGGAAAAATTACAAAAATTGGGCCTGATAATCCATATA
ACACTCCAGTATTTGCCATAAAAAAGAAGGACAGTACTAAGTGGAGAAAATTAGTAGATTTCAGGGAACTCAATAAAAGA
ACTCAAGACTTTTGGGAAGTTCAATTAGGAATACCACACCCAGCAGGATTAAAAAAGAAAAAATCAGTGACAGTGCTAGA
TGTGGGGGATGCATATTTTTCAGTTCCTTTAGATGAAAGCTTCAGGAAATATACTGCATTCACCATACCTAGTATAAACA
ATGAAACACCAGGGATTAGATATCAATATAATGTGCTGCCACAGGGATGGAAAGGATCACCAGCAATATTCCAGAGTAGC
ATGACAAAAATCTTAGAGCCCTTCAGAGCAAAAAATCCAGACATAGTTATCTATCAATATATGGATGACTTGTATGTAGG
ATCTGACTTAGAAATAGGGCAACATAGAGCAAAAATAGAAGAGTTAAGGGAACATTTATTGAAATGGGGATTTACAACAC
CAGACAAGAAACATCAAAAAGAACCCCCATTTCTTTGGATGGGGTATGAACTCCATCCTGACAAATGGACAGTACAACCT
ATACTGCTGCCAGAAAAGGATAGTTGGACTGTCAATGATATACAGAAGTTAGTGGGAAAATTAAACTGGGCAAGTCAGAT
TTACCCAGGGATTAAAGTAAGGCAACTCTGTAAACTCCTCAGGGGGGCCAAAGCACTAACAGACATAGTACCACTAACTG
AAGAAGCAGAATTAGAATTGGCAGAGAACAGGGAAATTTTAAGAGAACCAGTACATGGAGTATATTATGATCCATCAAAA
GACTTGATAGCTGAAATACAGAAACAGGGGCATGAACAATGGACATATCAAATTTATCAAGAACCATTTAAAAATCTGAA
AACAGGGAAGTATGCAAAAATGAGGACTACCCACACTAATGATGTAAAACAGTTAACAGAGGCAGTGCAAAAAATAGCCA
TGGAAAGCATAGTAATATGGGGAAAGACTCCTAAATTTAGACTACCCATCCAAAAAGAAACATGGGAGACATGGTGGACA
GACTATTGGCAAGCCACCTGGATCCCTGAGTGGGAGTTTGTTAATACCCCTCCCCTAGTAAAATTATGGTACCAACTAGA
AAAAGATCCCATAGCAGGAGTAGAAACTTTCTATGTAGATGGAGCAACTAATAGGGAAGCTAAAATAGGAAAAGCAGGGT
ATGTTACTGACAGAGGAAGGCAGAAAATTGTTACTCTAACTAACACAACAAATCAGAAGACTGAGTTACAAGCAATTCAG
CTAGCTCTGCAGGATTCAGGATCAGAAGTAAACATAGTAACAGACTCACAGTATGCATTAGGAATCATTCAAGCACAACC
AGATAAGAGTGACTCAGAGATATTTAACCAAATAATAGAACAGTTAATAAACAAGGAAAAGAATCTACCTGTCATGGGTAC
CAGCACATAAAGGAATTGGGGGAAATGAACAAGTAGATAAATTAGTAAGTAAGGGAATTAGGAAAGTGTTGTTTCTAGAT
GGAATAGATAAAGCTCAAGAAGAGCATGAAAGGTACCACAGCAATTGGAGAGCAATGGCTAATGAGTTTAATCTGCCACC
CATAGTAGCAAAAGAAATAGTAGCTAGCTGTGATAAATGTCAGCTAAAAGGGGAAGCCATACATGGACAAGTCGACTGTA
GTCCAGGGATATGGCAATTAGATTGTACCCATTTAGAGGGAAAAATCATCCTGGTAGCAGTCCATGTAGCTAGTGGCTAC
ATGGAAGCAGAGGTTATCCCAGCAGAAACAGGACAAGAAACAGCATATTTTATATTAAAATTAGCAGGAAGATGGCCAGT
CAAAGTAATACATACAGACAATGGCAGTAATTTTACCAGTACTGCAGTTAAGGCAGCCTGTTGGTGGGCAGGTATCCAAC
AGGAATTTGGAATTCCCTACAATCCCCAAAGTCAGGGAGTGGTAGAATCCATGAATAAAGAATTAAAGAAAATAATAGGA
CAAGTAAGAGATCAAGCTGAGCACCTTAAGACAGCAGTACAAATGGCAGTATTCATTCACAATTTTAAAAGAAAGGGGG
AATTGGGGGGTACAGTGCAGGGGAAAGAATAATAGACATAATAGCAACAGACATACAAACTAAAGAATTACAAAAACAAA
TTATAAGAATTCAAAATTTTCGGGTTTATTACAGAGACAGCAGAGACCCTATTTGGAAAGGACCAGCCGAACTACTCTGG
AAAGGTGAAGGGGTAGTAGTAATAGAAGATAAAGGTGACATAAAGGTAGTACCAAGGAGGAAAGCAAAAATCATTAGAGA
TTATGGAAAACAGATGGCAGGTGCTGATTGTGTGGCAGGTGGACAGGATGAAGAT
```

FIGURE 34

>Prot_TV1_C_ZAopt (SEQ ID NO:64)

CCCCAGATCACCCTGTGGCAGCGCCCCCTGGTGAGCATCAAGGTGGAGGGCCAGATCAAGGAGGCCCTGCTGGACACCGG
CGCCGACGACACCGTGCTGGAGGAGATCGACCTGCCCGGCAAGTGGAAGCCCAAGATGATCGGCGGCATCGGCGGCTTCA
TCAAGGTGCGCCAGTACGACCAGATCCTGATCGAGATCTGCGGCAAGAAGGCCATCGGCACCGTGCTGGTGGGCCCCACC
CCCGTGAACATCATCGGCCGCAACCTGCTGACCCAGCTGGGCTGCACCCTGAACTTC

FIGURE 35

>Prot_TV1_C_ZAwt (SEQ ID NO:65)

CCTCAAATCACTCTTTGGCAGCGACCCCTTGTCTCAATAAAAGTAGAGGGCCAGATAAAGGAGGCTCTCTTAGACACAGG
AGCAGATGATACAGTATTAGAAGAAATAGATTTGCCAGGGAAATGGAAACCAAAAATGATAGGGGGAATTGGAGGTTTTA
TCAAAGTAAGACAGTATGATCAAATACTTATAGAAATTTGTGGAAAAAAGGCTATAGGTACAGTATTAGTAGGGCCTACA
CCAGTCAACATAATTGGAAGAAATCTGTTAACTCAGCTTGGATGCACACTAAATTTT

FIGURE 36

>Protina_TV1_C_ZAopt (SEQ ID NO:66)

```
CCCCAGATCACCCTGTGGCAGCGCCCCCTGGTGAGCATCAAGGTGGAGGGCCAGATCAAGGAGGCCCTGCTGGCCACCGG
CGCCGACGACACCGTGCTGGAGGAGATCGACCTGCCCGGCAAGTGGAAGCCCAAGATGATCGGCGGCATCGGCGGCTTCA
TCAAGGTGCGCCAGTACGACCAGATCCTGATCGAGATCTGCGGCAAGAAGGCCATCGGCACCGTGCTGGTGGGCCCCACC
CCCGTGAACATCATCGGCCGCAACCTGCTGACCCAGCTGGGCTGCACCCTGAACTTC
```

FIGURE 37

>Protina_TV1_C_ZAwt (SEQ ID NO:67)

CCTCAAATCACTCTTTGGCAGCGACCCCTTGTCTCAATAAAAGTAGAGGGCCAGATAAAGGAGGCTCTCTTAGCCACAGG
AGCAGATGATACAGTATTAGAAGAAATAGATTTGCCAGGGAAATGGAAACCAAAAATGATAGGGGGAATTGGAGGTTTTA
TCAAAGTAAGACAGTATGATCAAATACTTATAGAAATTTGTGGAAAAAAGGCTATAGGTACAGTATTAGTAGGGCCTACA
CCAGTCAACATAATTGGAAGAAATCTGTTAACTCAGCTTGGATGCACACTAAATTTT

FIGURE 38

>ProtinaRTmut_TV1_C_ZAopt (SEQ ID NO:68)

```
CCCCAGATCACCCTGTGGCAGCGCCCCCTGGTGAGCATCAAGGTGGAGGGCCAGATCAAGGAGGCCCTGCTGGCCACCGG
CGCCGACGACACCGTGCTGGAGGAGATCGACCTGCCCGGCAAGTGGAAGCCCAAGATGATCGGCGGCATCGGCGGCTTCA
TCAAGGTGCGCCAGTACGACCAGATCCTGATCGAGATCTGCGGCAAGAAGGCCATCGGCACCGTGCTGGTGGGCCCCACC
CCCGTGAACATCATCGGCCGCAACCTGCTGACCCAGCTGGGCTGCACCCTGAACTTCCCCATCAGCCCCATCGAGACCGT
GCCCGTGAAGCTGAAGCCCGGCATGGACGGCCCCAAGGTGAAGCAGTGGCCCCTGACCGAGGAGAAGATCAAGGCCCTGA
CCGCCATCTGCGAGGAGATGGAGAAGGAGGGCAAGATCACCAAGATCGGCCCCGACAACCCCTACAACACCCCCGTGTTC
GCCATCAAGAAGAAGGACAGCACCAAGTGGCGCAAGCTGGTGGACTTCCGCGAGCTGAACAAGCGCACCCAGGACTTCTG
GGAGGTGCAGCTGGGCATCCCCCACCCCGCCGGCCTGAAGAAGAAGAAGAGCGTGACCGTGCTGGACGTGGGCGACGCCT
ACTTCAGCGTGCCCCTGGACGAGAGCTTCCGCAAGTACACCGCCTTCACCATCCCCAGCATCAACAACGAGACCCCCGGC
ATCCGCTACCAGTACAACGTGCTGCCCCAGGGCTGGAAGGGCAGCCCCGCCATCTTCCAGAGCAGCATGACCAAGATCCT
GGAGCCCTTCCGCGCCAAGAACCCCGACATCGTGATCTACCAGGCCCCCCTGTACGTGGGCAGCGACCTGGAGATCGGCC
AGCACCGCGCCAAGATCGAGGAGCTGCGCGAGCACCTGCTGAAGTGGGGCTTCACCACCCCCGACAAGAAGCACCAGAAG
GAGCCCCCCTTCCTGCCCATCGAGCTGCACCCCGACAAGTGGACCGTGCAGCCCATCCTGCTGCCCGAGAAGGACAGCTG
GACCGTGAACGACATCCAGAAGCTGGTGGGCAAGCTGAACTGGGCCAGCCAGATCTACCCCGGCATCAAGGTGCGCCAGC
TGTGCAAGCTGCTGCGCGGCGCCAAGGCCCTGACCGACATCGTGCCCCTGACCGAGGAGGCCGAGCTGGAGCTGGCCGAG
AACCGCGAGATCCTGCGCGAGCCCGTGCACGGCGTGTACTACGACCCCAGCAAGGACCTGATCGCCGAGATCCAGAAGCA
GGGCCACGAGCAGTGGACCTACCAGATCTACCAGGAGCCCTTCAAGAACCTGAAGACCGGCAAGTACGCCAAGATGCGCA
CCACCCACACCAACGACGTGAAGCAGCTGACCGAGGCCGTGCAGAAGATCGCCATGGAGAGCATCGTGATCTGGGGCAAG
ACCCCCAAGTTCCGCCTGCCCATCCAGAAGGAGACCTGGGAGACCTGGTGGACCGACTACTGGCAGGCCACCTGGATCCC
CGAGTGGGAGTTCGTGAACACCCCCCCCCTGGTGAAGCTGTGGTACCAGCTGGAGAAGGACCCCATCGCCGGCGTGGAGA
CCTTCTACGTGGACGGCGCCACCAACCGCGAGGCCAAGATCGGCAAGGCCGGCTACGTGACCGACCGCGGCCGCCAGAAG
ATCGTGACCCTGACCAACACCACCAACCAGAAGACCGAGCTGCAGGCCATCCAGCTGGCCCTGCAGGACAGCGGCAGCGA
GGTGAACATCGTGACCGACAGCCAGTACGCCCTGGGCATCATCCAGGCCCAGCCCGACAAGAGCGACAGCGAGATCTTCA
ACCAGATCATCGAGCAGCTGATCAACAAGGAGCGCATCTACCTGAGCTGGGTGCCCGCCCACAAGGGCATCGGCGGCAAC
GAGCAGGTGGACAAGCTGGTGAGCAAGGGCATCCGCAAGGTGCTG
```

FIGURE 39

>ProtinaRTmut_TV1_C_ZAwt (SEQ ID NO:69)

CCTCAAATCACTCTTTGGCAGCGACCCCTTGTCTCAATAAAAGTAGAGGGCCAGATAAAGGAGGCTCTCTTAGCCACAGG
AGCAGATGATACAGTATTAGAAGAAATAGATTTGCCAGGGAAATGGAAACCAAAAATGATAGGGGGAATTGGAGGTTTTA
TCAAAGTAAGACAGTATGATCAAATACTTATAGAAATTTGTGGAAAAAAGGCTATAGGTACAGTATTAGTAGGGCCTACA
CCAGTCAACATAATTGGAAGAAATCTGTTAACTCAGCTTGGATGCACACTAAATTTTCCAATTAGTCCTATTGAAACTGT
ACCAGTAAAATTAAAACCAGGAATGGATGGCCCAAAGGTCAAACAATGGCCATTGACAGAAGAAAAAATAAAAGCATTAA
CAGCAATTTGTGAGGAAATGGAGAAGGAAGGAAAAATTACAAAAATTGGGCCTGATAATCCATATAACACTCCAGTATTT
GCCATAAAAAAGAAGGACAGTACTAAGTGGAGAAAATTAGTAGATTTCAGGGAACTCAATAAAAGAACTCAAGACTTTTG
GGAAGTTCAATTAGGAATACCACACCCAGCAGGATTAAAAAAGAAAAAATCAGTGACAGTGCTAGATGTGGGGGATGCAT
ATTTTTCAGTTCCTTTAGATGAAAGCTTCAGGAAATATACTGCATTCACCATACCTAGTATAAACAATGAAACACCAGGG
ATTAGATATCAATATAATGTGCTGCCACAGGGATGGAAAGGATCACCAGCAATATTCCAGAGTAGCATGACAAAAATCTT
AGAGCCCTTCAGAGCAAAAAATCCAGACATAGTTATCTATCAAGCCCCGTTGTATGTAGGATCTGACTTAGAAATAGGGC
AACATAGAGCAAAAATAGAAGAGTTAAGGGAACATTTATTGAAATGGGGATTTACAACACCAGACAAGAAACATCAAAAA
GAACCCCCATTTCTTCCCATCGAACTCCATCCTGACAAATGGACAGTACAACCTATACTGCTGCCAGAAAAGGATAGTTG
GACTGTCAATGATATACAGAAGTTAGTGGGAAAATTAAACTGGGCAAGTCAGATTTACCCAGGGATTAAAGTAAGGCAAC
TCTGTAAACTCCTCAGGGGGGCCAAAGCACTAACAGACATAGTACCACTAACTGAAGAAGCAGAATTAGAATTGGCAGAG
AACAGGGAAATTTTAAGAGAACCAGTACATGGAGTATATTATGATCCATCAAAAGACTTGATAGCTGAAATACAGAAACA
GGGGCATGAACAATGGACATATCAAATTTATCAAGAACCATTTAAAAATCTGAAAACAGGGAAGTATGCAAAAATGAGGA
CTACCCACACTAATGATGTAAAACAGTTAACAGAGGCAGTGCAAAAAATAGCCATGGAAAGCATAGTAATATGGGGAAAG
ACTCCTAAATTTAGACTACCCATCCAAAAAGAAACATGGGAGACATGGTGGACAGACTATTGGCAAGCCACCTGGATCCC
TGAGTGGAGTTTGTTAATACCCCTCCCCTAGTAAAATTATGGTACCAACTAGAAAAAGATCCCATAGCAGGAGTAGAAA
CTTTCTATGTAGATGGAGCAACTAATAGGGAAGCTAAAATAGGAAAAGCAGGGTATGTTACTGACAGAGGAAGGCAGAAA
ATTGTTACTCTAACTAACACAACAAATCAGAAGACTGAGTTACAAGCAATTCAGCTAGCTCTGCAGGATTCAGGATCAGA
AGTAAACATAGTAACAGACTCACAGTATGCATTAGGAATCATTCAAGCACAACCAGATAAGAGTGACTCAGAGATATTTA
ACCAAATAATAGAACAGTTAATAAACAAGGAAAGAATCTACCTGTCATGGGTACCAGCACATAAAGGAATTGGGGGAAAT
GAACAAGTAGATAAATTAGTAAGTAAGGGAATTAGGAAAGTGTTG

FIGURE 40

>ProtwtRTwt_TV1_C_ZAopt (SEQ ID NO:70)

```
CCCCAGATCACCCTGTGGCAGCGCCCCCTGGTGAGCATCAAGGTGGAGGGCCAGATCAAGGAGGCCCTGCTGGACACCGG
CGCCGACGACACCGTGCTGGAGGAGATCGACCTGCCCGGCAAGTGGAAGCCCAAGATGATCGGCGGCATCGGCGGCTTCA
TCAAGGTGCGCCAGTACGACCAGATCCTGATCGAGATCTGCGGCAAGAAGGCCATCGGCACCGTGCTGGTGGGCCCCACC
CCCGTGAACATCATCGGCCGCAACCTGCTGACCCAGCTGGGCTGCACCCTGAACTTCCCCATCAGCCCCATCGAGACCGT
GCCCGTGAAGCTGAAGCCCGGCATGGACGGCCCCAAGGTGAAGCAGTGGCCCCTGACCGAGGAGAAGATCAAGGCCCTGA
CCGCCATCTGCGAGGAGATGGAGAAGGAGGGCAAGATCACCAAGATCGGCCCCGACAACCCCTACAACACCCCCGTGTTC
GCCATCAAGAAGAAGGACAGCACCAAGTGGCGCAAGCTGGTGGACTTCCGCGAGCTGAACAAGCGCACCCAGGACTTCTG
GGAGGTGCAGCTGGGCATCCCCCACCCCGCCGGCCTGAAGAAGAAGAAGAGCGTGACCGTGCTGGACGTGGGCGACGCCT
ACTTCAGCGTGCCCCTGGACGAGAGCTTCCGCAAGTACACCGCCTTCACCATCCCCAGCATCAACAACGAGACCCCCGGC
ATCCGCTACCAGTACAACGTGCTGCCCCAGGGCTGGAAGGGCAGCCCCGCCATCTTCCAGAGCAGCATGACCAAGATCCT
GGAGCCCTTCCGCGCCAAGAACCCCGACATCGTGATCTACCAGTACATGGACGACCTGTACGTGGGCAGCGACCTGGAGA
TCGGCCAGCACCGCGCCAAGATCGAGGAGCTGCGCGAGCACCTGCTGAAGTGGGGCTTCACCACCCCCGACAAGAAGCAC
CAGAAGGAGCCCCCCTTCCTGTGGATGGGCTACGAGCTGCACCCCGACAAGTGGACCGTGCAGCCCATCCTGCTGCCCGA
GAAGGACAGCTGGACCGTGAACGACATCCAGAAGCTGGTGGGCAAGCTGAACTGGGCCAGCCAGATCTACCCCGGCATCA
AGGTGCGCCAGCTGTGCAAGCTGCTGCGCGGCGCCAAGGCCCTGACCGACATCGTGCCCCTGACCGAGGAGGCCGAGCTG
GAGCTGGCCGAGAACCGCGAGATCCTGCGCGAGCCCGTGCACGGCGTGTACTACGACCCCAGCAAGGACCTGATCGCCGA
GATCCAGAAGCAGGGCCACGAGCAGTGGACCTACCAGATCTACCAGGAGCCCTTCAAGAACCTGAAGACCGGCAAGTACG
CCAAGATGCGCACCGCCCACACCAACGACGTGAAGCAGCTGACCGAGGCCGTGCAGAAGATCGCCATGGAGAGCATCGTG
ATCTGGGGCAAGACCCCCAAGTTCCGCCTGCCCATCCAGAAGGAGACCTGGGAGACCTGGTGGACCGACTACTGGCAGGC
CACCTGGATCCCCGAGTGGGAGTTCGTGAACACCCCCCCCCTGGTGAAGCTGTGGTACCAGCTGGAGAAGGACCCCATCG
CCGGCGTGGAGACCTTCTACGTGGACGGCGCCACCAACCGCGAGGCCAAGATCGGCAAGGCCGGCTACGTGACCGACCGC
GGCCGCCAGAAGATCGTGACCCTGACCAACACCACCAACCAGAAGACCGAGCTGCAGGCCATCCAGCTGGCCCTGCAGGA
CAGCGGCAGCGAGGTGAACATCGTGACCGACAGCCAGTACGCCCTGGGCATCATCCAGGCCCAGCCCGACAAGAGCGACA
GCGAGATCTTCAACCAGATCATCGAGCAGCTGATCAACAAGGAGCGCATCTACCTGAGCTGGGTGCCCGCCCACAAGGGC
ATCGGCGGCAACGAGCAGGTGGACAAGCTGGTGAGCAAGGGCATCCGCAAGGTGCTG
```

FIGURE 41

>ProtwtRTwt_TV1_C_ZAwt(SEQ ID NO:71)

```
CCTCAAATCACTCTTTGGCAGCGACCCCTTGTCTCAATAAAAGTAGAGGGCCAGATAAAGGAGGCTCTCTTAGACACAGG
AGCAGATGATACAGTATTAGAAGAAATAGATTTGCCAGGGAAATGGAAACCAAAAATGATAGGGGGAATTGGAGGTTTTA
TCAAAGTAAGACAGTATGATCAAATACTTATAGAAATTTGTGGAAAAAAGGCTATAGGTACAGTATTAGTAGGGCCTACA
CCAGTCAACATAATTGGAAGAAATCTGTTAACTCAGCTTGGATGCACACTAAATTTTCCAATTAGTCCTATTGAAACTGT
ACCAGTAAAATTAAAACCAGGAATGGATGGCCCAAAGGTCAAACAATGGCCATTGACAGAAGAAAAAATAAAAGCATTAA
CAGCAATTTGTGAGGAAATGGAGAAGGAAGGAAAAATTACAAAAATTGGGCCTGATAATCCATATAACACTCCAGTATTT
GCCATAAAAAAGAAGGACAGTACTAAGTGGAGAAAATTAGTAGATTTCAGGGAACTCAATAAAAGAACTCAAGACTTTTG
GGAAGTTCAATTAGGAATACCACACCCAGCAGGATTAAAAAAGAAAAAATCAGTGACAGTGCTAGATGTGGGGATGCAT
ATTTTTCAGTTCCTTTAGATGAAAGCTTCAGGAAATATACTGCATTCACCATACCTAGTATAAACAATGAAACACCAGGG
ATTAGATATCAATATAATGTGCTGCCACAGGGATGGAAAGGATCACCAGCAATATTCCAGAGTAGCATGACAAAAATCTT
AGAGCCCTTCAGAGCAAAAAATCCAGACATAGTTATCTATCAATATATGGATGACTTGTATGTAGGATCTGACTTAGAAA
TAGGGCAACATAGAGCAAAAATAGAAGAGTTAAGGGAACATTTATTGAAATGGGGATTTACAACACCAGACAAGAAACAT
CAAAAAGAACCCCCATTTCTTTGGATGGGGTATGAACTCCATCCTGACAAATGGACAGTACAACCTATACTGCTGCCAGA
AAAGGATAGTTGGACTGTCAATGATATACAGAAGTTAGTGGGAAAATTAAACTGGGCAAGTCAGATTTACCCAGGGATTA
AAGTAAGGCAACTCTGTAAACTCCTCAGGGGGGCCAAAGCACTAACAGACATAGTACCACTAACTGAAGAAGCAGAATTA
GAATTGGCAGAGAACAGGGAAATTTTAAGAGAACCAGTACATGGAGTATATTATGATCCATCAAAAGACTTGATAGCTGA
AATACAGAAACAGGGGCATGAACAATGGACATATCAAATTTATCAAGAACCATTTAAAAATCTGAAAACAGGGAAGTATG
CAAAAATGAGGACTACCCACACTAATGATGTAAAACAGTTAACAGAGGCAGTGCAAAAAATAGCCATGGAAAGCATAGTA
ATATGGGGAAAGACTCCTAAATTTAGACTACCCCATCCAAAAAGAAACATGGGAGACATGGTGGACAGACTATTGGCAAGC
CACCTGGATCCCTGAGTGGGAGTTTGTTAATACCCCTCCCCTAGTAAAATTATGGTACCAACTAGAAAAAGATCCCATAG
CAGGAGTAGAAACTTTCTATGTAGATGGAGCAACTAATAGGGAAGCTAAAATAGGAAAAGCAGGGTATGTTACTGACAGA
GGAAGGCAGAAAATTGTTACTCTAACTAACACAACAAATCAGAAGACTGAGTTACAAGCAATTCAGCTAGCTCTGCAGGA
TTCAGGATCAGAAGTAAACATAGTAACAGACTCACAGTATGCATTAGGAATCATTCAAGCACAACCAGATAAGAGTGACT
CAGAGATATTTAACCAAATAATAGAACAGTTAATAAACAAGGAAAGAATCTACCTGTCATGGGTACCAGCACATAAAGGA
ATTGGGGGAAATGAACAAGTAGATAAATTAGTAAGTAAGGGAATTAGGAAAGTGTTG
```

FIGURE 42

>RevExon1_TV1_C_ZAopt(SEQ ID NO:72)

ATGGCCGGCCGCAGCGGCGACAGCGACGAGGCCCTGCTGCAGGTGGTGAAGATCATCAAGATCCTGTACCAGAGC

FIGURE 43

>RevExon1_TV1_C_ZAwt(SEQ ID NO:73)

ATGGCAGGAAGAAGCGGAGACAGCGACGAAGCGCTCCTCCAAGTGGTGAAGATCATCAAAATCCTCTATCAAAGCA

FIGURE 44

>RevExon2_TV1_C_ZAopt-2(SEQ ID NO:74)

CCCTACCCCAAGCCCGAGGGCACCCGCCAGGCCCGCCGCAACCGCCGCCGCCGCTGGCGCGCCCGCCAGCGCCAGATCCA
CACCATCGGCGAGCGCATCCTGGTGGCCTGCCTGGGCCGCAGCGCCGAGCCCGTGCCCCTGCAGCTGCCCCCCCTGGAGC
GCCTGCACATCAACTGCAGCGAGGGCAGCGGCACCAGCGGCACCCAGCAGAGCCAGGGCACCACCGAGGGCGTGGGCGAC
CCCTAA

FIGURE 45

\>RevExon2_TV1_C_ZAwt(SEQ ID NO:75)

ACCCTTACCCCAAGCCCGAGGGGACTCGACAGGCTCGGAGGAATCGAAGAAGAAGGTGGAGAGCAAGACAGAGACAGATC
CATACGATTGGTGAGCGGATTCTTGTCGCTTGCCTGGGACGATCTGCGGAGCCTGTGCCTCTTCAGCTACCACCGCTTGA
GAGACTTCATATTAATTGCAGTGAGGGCAGTGGAACTTCTGGGACACAGCAGTCTCAGGGGACTACAGAGGGGGTGGGAG
ATCCTTAA

FIGURE 46

RT_TV1_C_ZAopt (SEQ ID NO:76)

CCCATCAGCCCCATCGAGACCGTGCCCGTGAAGCTGAAGCCCGGCATGGACGGCCCCA
AGGTGAAGCAGTGGCCCCTGACCGAGGAGAAGATCAAGGCCCTGACCGCCATCTGCG
AGGAGATGGAGAAGGAGGGCAAGATCACCAAGATCGGCCCCGACAACCCCTACAACA
CCCCCGTGTTCGCCATCAAGAAGAAGGACAGCACCAAGTGGCGCAAGCTGGTGGACTT
CCGCGAGCTGAACAAGCGCACCCAGGACTTCTGGGAGGTGCAGCTGGGCATCCCCCAC
CCCGCCGGCCTGAAGAAGAAGAAGAGCGTGACCGTGCTGGACGTGGGCGACGCCTAC
TTCAGCGTGCCCCTGGACGAGAGCTTCCGCAAGTACACCGCCTTCACCATCCCCAGCA
TCAACAACGAGACCCCCGGCATCCGCTACCAGTACAACGTGCTGCCCCAGGGCTGGAA
GGGCAGCCCCGCCATCTTCCAGAGCAGCATGACCAAGATCCTGGAGCCCTTCCGCGCC
AAGAACCCCGACATCGTGATCTACCAGTACATGGACGACCTGTACGTGGGCAGCGACC
TGGAGATCGGCCAGCACCGCGCCAAGATCGAGGAGCTGCGCGAGCACCTGCTGAAGT
GGGGCTTCACCACCCCCGACAAGAAGCACCAGAAGGAGCCCCCCTTCCTGTGGATGGG
CTACGAGCTGCACCCCGACAAGTGGACCGTGCAGCCCATCCTGCTGCCCGAGAAGGAC
AGCTGGACCGTGAACGACATCCAGAAGCTGGTGGGCAAGCTGAACTGGGCCAGCCAG
ATCTACCCCGGCATCAAGGTGCGCCAGCTGTGCAAGCTGCTGCGCGGCGCCAAGGCCC
TGACCGACATCGTGCCCCTGACCGAGGAGGCCGAGCTGGAGCTGGCCGAGAACCGCG
AGATCCTGCGCGAGCCCGTGCACGGCGTGTACTACGACCCCAGCAAGGACCTGATCGC
CGAGATCCAGAAGCAGGGCCACGAGCAGTGGACCTACCAGATCTACCAGGAGCCCTT
CAAGAACCTGAAGACCGGCAAGTACGCCAAGATGCGCACCACCCACACCAACGACGT
GAAGCAGCTGACCGAGGCCGTGCAGAAGATCGCCATGGAGAGCATCGTGATCTGGGG
CAAGACCCCCAAGTTCCGCCTGCCCATCCAGAAGGAGACCTGGGAGACCTGGTGGACC
GACTACTGGCAGGCCACCTGGATCCCCGAGTGGGAGTTCGTGAACACCCCCCCCCTGG
TGAAGCTGTGGTACCAGCTGGAGAAGGACCCCATCGCCGGCGTGGAGACCTTCTACGT
GGACGGCGCCACCAACCGCGAGGCCAAGATCGGCAAGGCCGGCTACGTGACCGACCG
CGGCCGCCAGAAGATCGTGACCCTGACCAACACCACCAACCAGAAGACCGAGCTGCA
GGCCATCCAGCTGGCCCTGCAGGACAGCGGCAGCGAGGTGAACATCGTGACCGACAG
CCAGTACGCCCTGGGCATCATCCAGGCCCAGCCCGACAAGAGCGACAGCGAGATCTTC
AACCAGATCATCGAGCAGCTGATCAACAAGGAGCGCATCTACCTGAGCTGGGTGCCCG
CCCACAAGGGCATCGGCGGCAACGAGCAGGTGGACAAGCTGGTGAGCAAGGGCATCC
GCAAGGTGCTG

FIGURE 47

>RT_TV1_C_ZAwt(SEQ ID NO:77)

```
CCAATTAGTCCTATTGAAACTGTACCAGTAAAATTAAAACCAGGAATGGATGGCCCAAAGGTCAAACAATGGCCATTGAC
AGAAGAAAAAATAAAAGCATTAACAGCAATTTGTGAGGAAATGGAGAAGGAAGGAAAAATTACAAAAATTGGGCCTGATA
ATCCATATAACACTCCAGTATTTGCCATAAAAAAGAAGGACAGTACTAAGTGGAGAAAATTAGTAGATTTCAGGGAACTC
AATAAAAGAACTCAAGACTTTTGGGAAGTTCAATTAGGAATACCACACCCAGCAGGATTAAAAAAGAAAAAATCAGTGAC
AGTGCTAGATGTGGGGGATGCATATTTTTCAGTTCCTTTAGATGAAAGCTTCAGGAAATATACTGCATTCACCATACCTA
GTATAAACAATGAAACACCAGGGATTAGATATCAATATAATGTGCTGCCACAGGGATGGAAAGGATCACCAGCAATATTC
CAGAGTAGCATGACAAAAATCTTAGAGCCCTTCAGAGCAAAAAATCCAGACATAGTTATCTATCAATATATGGATGACTT
GTATGTAGGATCTGACTTAGAAATAGGGCAACATAGAGCAAAAATAGAAGAGTTAAGGGAACATTTATTGAAATGGGGAT
TTACAACACCAGACAAGAAACATCAAAAAGAACCCCCATTTCTTTGGATGGGGTATGAACTCCATCCTGACAAATGGACA
GTACAACCTATACTGCTGCCAGAAAAGGATAGTTGGACTGTCAATGATATACAGAAGTTAGTGGGAAAATTAAACTGGGC
AAGTCAGATTTACCCAGGGATTAAAGTAAGGCAACTCTGTAAACTCCTCAGGGGGGCCAAAGCACTAACAGACATAGTAC
CACTAACTGAAGAAGCAGAATTAGAATTGGCAGAGAACAGGGAAATTTTAAGAGAACCAGTACATGGAGTATATTATGAT
CCATCAAAAGACTTGATAGCTGAAATACAGAAACAGGGGCATGAACAATGGACATATCAAATTTATCAAGAACCATTTAA
AAATCTGAAAACAGGGAAGTATGCAAAAATGAGGACTACCCACACTAATGATGTAAAACAGTTAACAGAGGCAGTGCAAA
AAATAGCCATGGAAAGCATAGTAATATGGGAAAGACTCCTAAATTTAGACTACCCATCCAAAAAGAAACATGGGAGACA
TGGTGGACAGACTATTGGCAAGCCACCTGGATCCCTGAGTGGGAGTTTGTTAATACCCCTCCCCTAGTAAAATTATGGTA
CCAACTAGAAAAAGATCCCATAGCAGGAGTAGAAACTTTCTATGTAGATGGAGCAACTAATAGGGAAGCTAAAATAGGAA
AAGCAGGGTATGTTACTGACAGAGGAAGGCAGAAAATTGTTACTCTAACTAACACAACAAATCAGAAGACTGAGTTACAA
GCAATTCAGCTAGCTCTGCAGGATTCAGGATCAGAAGTAAACATAGTAACAGACTCACAGTATGCATTAGGAATCATTCA
AGCACAACCAGATAAGAGTGACTCAGAGATATTTAACCAAATAATAGAACAGTTAATAAACAAGGAAAGAATCTACCTGT
CATGGGTACCAGCACATAAAGGAATTGGGGGAAATGAACAAGTAGATAAATTAGTAAGTAAGGGAATTAGGAAAGTGTTG
```

FIGURE 48

>RTmut_TV1_C_ZAopt(SEQ ID NO:78)

CCCATCAGCCCCATCGAGACCGTGCCCGTGAAGCTGAAGCCCGGCATGGACGGCCCCAAGGTGAAGCAGTGGCCCCTGAC
CGAGGAGAAGATCAAGGCCCTGACCGCCATCTGCGAGGAGATGGAGAAGGAGGGCAAGATCACCAAGATCGGCCCCGACA
ACCCCTACAACACCCCCGTGTTCGCCATCAAGAAGAAGGACAGCACCAAGTGGCGCAAGCTGGTGGACTTCCGCGAGCTG
AACAAGCGCACCCAGGACTTCTGGGAGGTGCAGCTGGGCATCCCCCACCCCGCCGGCCTGAAGAAGAAGAAGAGCGTGAC
CGTGCTGGACGTGGGCGACGCCTACTTCAGCGTGCCCCTGGACGAGAGCTTCCGCAAGTACACCGCCTTCACCATCCCCA
GCATCAACAACGAGACCCCCGGCATCCGCTACCAGTACAACGTGCTGCCCCAGGGCTGGAAGGGCAGCCCCGCCATCTTC
CAGAGCAGCATGACCAAGATCCTGGAGCCCTTCCGCGCCAAGAACCCCGACATCGTGATCTACCAGGCCCCCCTGTACGT
GGGCAGCGACCTGGAGATCGGCCAGCACCGCGCCAAGATCGAGGAGCTGCGCGAGCACCTGCTGAAGTGGGGCTTCACCA
CCCCCGACAAGAAGCACCAGAAGGAGCCCCCCTTCCTGCCCATCGAGCTGCACCCCGACAAGTGGACCGTGCAGCCCATC
CTGCTGCCCGAGAAGGACAGCTGGACCGTGAACGACATCCAGAAGCTGGTGGGCAAGCTGAACTGGGCCAGCCAGATCTA
CCCCGGCATCAAGGTGCGCCAGCTGTGCAAGCTGCTGCGCGGCGCCAAGGCCCTGACCGACATCGTGCCCCTGACCGAGG
AGGCCGAGCTGGAGCTGGCCGAGAACCGCGAGATCCTGCGCGAGCCCGTGCACGGCGTGTACTACGACCCCAGCAAGGAC
CTGATCGCCGAGATCCAGAAGCAGGGCCACGAGCAGTGGACCTACCAGATCTACCAGGAGCCCTTCAAGAACCTGAAGAC
CGGCAAGTACGCCAAGATGCGCACCGCCCACACCAACGACGTGAAGCAGCTGACCGAGGCCGTGCAGAAGATCGCCATGG
AGAGCATCGTGATCTGGGGCAAGACCCCCAAGTTCCGCCTGCCCATCCAGAAGGAGACCTGGGAGACCTGGTGGACCGAC
TACTGGCAGGCCACCTGGATCCCCGAGTGGGAGTTCGTGAACACCCCCCCCCTGGTGAAGCTGTGGTACCAGCTGGAGAA
GGACCCCATCGCCGGCGTGGAGACCTTCTACGTGGACGGCGCCACCAACCGCGAGGCCAAGATCGGCAAGGCCGGCTACG
TGACCGACCGCGGCCGCCAGAAGATCGTGACCCTGACCAACACCACCAACCAGAAGACCGAGCTGCAGGCCATCCAGCTG
GCCCTGCAGGACAGCGGCAGCGAGGTGAACATCGTGACCGACAGCCAGTACGCCCTGGGCATCATCCAGGCCCAGCCCGA
CAAGAGCGACAGCGAGATCTTCAACCAGATCATCGAGCAGCTGATCAACAAGGAGCGCATCTACCTGAGCTGGGTGCCCG
CCCACAAGGGCATCGGCGGCAACGAGCAGGTGGACAAGCTGGTGAGCAAGGGCATCCGCAAGGTGCTG

FIGURE 49

>RTmut_TV1_C_ZAwt(SEQ ID NO:79)

CCAATTAGTCCTATTGAAACTGTACCAGTAAAATTAAAACCAGGAATGGATGGCCCAAAGGTCAAACAATGGCCATTGAC
AGAAGAAAAAATAAAAGCATTAACAGCAATTTGTGAGGAAATGGAGAAGGAAGGAAAAATTACAAAAATTGGGCCTGATA
ATCCATATAACACTCCAGTATTTGCCATAAAAAAGAAGGACAGTACTAAGTGGAGAAAATTAGTAGATTTCAGGGAACTC
AATAAAAGAACTCAAGACTTTTGGGAAGTTCAATTAGGAATACCACACCCAGCAGGATTAAAAAAGAAAAAATCAGTGAC
AGTGCTAGATGTGGGGGATGCATATTTTTCAGTTCCTTTAGATGAAAGCTTCAGGAAATATACTGCATTCACCATACCTA
GTATAAACAATGAAACACCAGGGATTAGATATCAATATAATGTGCTGCCACAGGGATGGAAAGGATCACCAGCAATATTC
CAGAGTAGCATGACAAAAATCTTAGAGCCCTTCAGAGCAAAAAATCCAGACATAGTTATCTATCAAGCCCCGTTGTATGT
AGGATCTGACTTAGAAATAGGGCAACATAGAGCAAAAATAGAAGAGTTAAGGGAACATTTATTGAAATGGGGATTTACAA
CACCAGACAAGAAACATCAAAAAGAACCCCCATTTCTTCCCATCGAACTCCATCCTGACAAATGGACAGTACAACCTATA
CTGCTGCCAGAAAAGGATAGTTGGACTGTCAATGATATACAGAAGTTAGTGGGAAAATTAAACTGGGCAAGTCAGATTTA
CCCAGGGATTAAAGTAAGGCAACTCTGTAAACTCCTCAGGGGGGCCAAAGCACTAACAGACATAGTACCACTAACTGAAG
AAGCAGAATTAGAATTGGCAGAGAACAGGGAAATTTTAAGAGAACCAGTACATGGAGTATATTATGATCCATCAAAAGAC
TTGATAGCTGAAATACAGAAACAGGGGCATGAACAATGGACATATCAAATTTATCAAGAACCATTTAAAAATCTGAAAAC
AGGGAAGTATGCAAAAATGAGGACTACCCACACTAATGATGTAAAACAGTTAACAGAGGCAGTGCAAAAAATAGCCATGG
AAAGCATAGTAATATGGGGAAAGACTCCTAAATTTAGACTACCCATCCAAAAAGAAACATGGGAGACATGGTGGACAGAC
TATTGGCAAGCCACCTGGATCCCTGAGTGGGAGTTTGTTAATACCCCTCCCCTAGTAAAATTATGGTACCAACTAGAAAA
AGATCCCATAGCAGGAGTAGAAACTTTCTATGTAGATGGAGCAACTAATAGGGAAGCTAAAATAGGAAAAGCAGGGTATG
TTACTGACAGAGGAAGGCAGAAAATTGTTACTCTAACTAACACAACAAATCAGAAGACTGAGTTACAAGCAATTCAGCTA
GCTCTGCAGGATTCAGGATCAGAAGTAAACATAGTAACAGACTCACAGTATGCATTAGGAATCATTCAAGCACAACCAGA
TAAGAGTGACTCAGAGATATTTAACCAAATAATAGAACAGTTAATAAACAAGGAAAGAATCTACCTGTCATGGGTACCAG
CACATAAAGGAATTGGGGGAAATGAACAAGTAGATAAATTAGTAAGTAAGGGAATTAGGAAAGTGTTG

FIGURE 50

>TatC22Exon1_TV1_C_ZAopt(SEQ ID NO:80)

ATGGAGCCCGTGGACCCCAAGCTGAAGCCCTGGAACCACCCCGGCAGCCAGCCCAAGACCGCCGGCAACAACTGCTTCTG
CAAGCACTGCAGCTACCACTGCCTGGTGTGCTTCCAGACCAAGGGCCTGGGCATCAGCTACGGCCGCAAGAAGCGCCGCC
AGCGCCGCAGCGCCCCCCCCAGCGGCGAGGACCACCAGAACCCCCTGAGCAAGCAG

FIGURE 51

>TatExon1_TV1_C_ZAopt(SEQ ID NO:81)
ATGGAGCCCGTGGACCCCAAGCTGAAGCCCTGGAACCACCCCGGCAGCCAGCCCAAGACCGCCTGCAACAACTGCTTCTG
CAAGCACTGCAGCTACCACTGCCTGGTGTGCTTCCAGACCAAGGGCCTGGGCATCAGCTACGGCCGCAAGAAGCGCCGCC
AGCGCCGCAGCGCCCCCCCCAGCGGCGAGGACCACCAGAACCCCCTGAGCAAGCAG

FIGURE 52

>TatExon1_TV1_C_ZAwt(SEQ ID NO:82)

ATGGAGCCAGTAGATCCTAAACTAAAGCCCTGGAACCATCCAGGAAGCCAACCTAAAACAGCTTGTAATAATTGCTTTTG
CAAACACTGTAGCTATCATTGTCTAGTTTGCTTTCAGACAAAAGGTTTAGGCATTTCCTATGGCAGGAAGAAGCGGAGAC
AGCGACGAAGCGCTCCTCCAAGTGGTGAAGATCATCAAAATCCTCTATCAAAGCAG

FIGURE 53

\>TatExon2_TV1_C_ZAopt(SEQ ID NO:83)

CCCCTGCCCCAGGCCCGCGGCGACAGCACCGGCAGCGAGGAGAGCAAGAAGAAGGTGGAGAGCAAGACCGAGACCGACCC
CTACGACTGGTGA

FIGURE 54

>TatExon2_TV1_C_ZAwt(SEQ ID NO:84)

CCCTTACCCCAAGCCCGAGGGGACTCGACAGGCTCGGAGGAATCGAAGAAGAAGGTGGAGAGCAAGACAGAGACAGATCC
ATACGATTGGTGA

FIGURE 55

>Vif_TV1_C_ZAopt(SEQ ID NO:85)
ATGGAGAACCGCTGGCAGGTGCTGATCGTGTGGCAGGTGGACCGCATGAAGATCCGCGCCTGGAACAGCCTGGTGAAGCA
CCACATGTACATCAGCCGCCGCGCCAGCGGCTGGGTGTACCGCCACCACTTCGAGAGCCGCCACCCCAAGGTGAGCAGCG
AGGTGCACATCCCCCTGGGCGACGCCCGCCTGGTGATCAAGACCTACTGGGGCCTGCAGACCGGCGAGCGCGACTGGCAC
CTGGGCCACGGCGTGAGCATCGAGTGGCGCCTGCGCGAGTACAGCACCCAGGTGGACCCCGACCTGGCCGACCAGCTGAT
CCACATGCACTACTTCGACTGCTTCACCGAGAGCGCCATCCGCCAGGCCATCCTGGGCCACATCGTGTTCCCCCGCTGCG
ACTACCAGGCCGGCCACAAGAAGGTGGGCAGCCTGCAGTACCTGGCCCTGACCGCCCTGATCAAGCCCAAGAAGCGCAAG
CCCCCCCTGCCCAGCGTGCGCAAGCTGGTGGAGGACCGCTGGAACGACCCCCAGAAGACCCGCGGCCGCCGCGGCAACCA
CACCATGAACGGCCACTAG

FIGURE 56

>Vif_TV1_C_ZAwt(SEQ ID NO:86)

ATGGAAAACAGATGGCAGGTGCTGATTGTGTGGCAGGTGGACAGGATGAAGATTAGAGCATGGAATAGTTTAGTAAAGCA
CCATATGTATATATCAAGGAGAGCTAGTGGATGGGTCTACAGACATCATTTTGAAAGCAGACATCCAAAAGTAAGTTCAG
AAGTACATATCCCATTAGGGGATGCTAGATTAGTAATAAAAACATATTGGGGTTTGCAGACAGGAGAAAGAGATTGGCAT
TTGGGTCATGGAGTCTCCATAGAATGGAGACTGAGAGAATACAGCACACAAGTAGACCCTGACCTGGCAGACCAGCTAAT
TCACATGCATTATTTTGATTGTTTTACAGAATCTGCCATAAGACAAGCCATATTAGGACACATAGTTTTTCCTAGGTGTG
ACTATCAAGCAGGACATAAGAAGGTAGGATCTCTGCAATACTTGGCACTGACAGCATTGATAAAACCAAAAAAGAGAAAG
CCACCTCTGCCTAGTGTTAGAAAATTAGTAGAGGATAGATGGAACGACCCCCAGAAGACCAGGGGCCGCAGAGGGAACCA
TACAATGAATGGACACTAG

FIGURE 57

>Vpr_TV1_C_ZAopt(SEQ ID NO:87)

ATGGAGCGCCCCCCCGAGGACCAGGGCCCCCAGCGCGAGCCCTACAACGAGTGGACCCTGGAGATCCTGGAGGAGCTGAA
GCAGGAGGCCGTGCGCCACTTCCCCCGCCCCTGGCTGCACAGCCTGGGCCAGTACATCTACGAGACCTACGGCGACACCT
GGACCGGCGTGGAGGCCATCATCCGCGTGCTGCAGCAGCTGCTGTTCATCCACTTCCGCATCGGCTGCCAGCACAGCCGC
ATCGGCATCCTGCGCCAGCGCCGCGCCCGCAACGGCGCCAGCCGCAGC

FIGURE 58

>Vpr_TV1_C_ZAwt(SEQ ID NO:88)

ATGGAACGACCCCCAGAAGACCAGGGGCCGCAGAGGGAACCATACAATGAATGGACACTAGAGATTCTAGAAGAACTCAA
GCAGGAAGCTGTCAGACACTTTCCTAGACCATGGCTCCATAGCTTAGGACAATATATCTATGAAACCTATGGGGATACTT
GGACGGGAGTTGAAGCTATAATAAGAGTACTGCAACAACTACTGTTCATTCATTTCAGAATTGGATGCCAACATAGCAGA
ATAGGCATCTTGCGACAGAGAAGAGCAAGAAATGGAGCCAGTAGATCC

FIGURE 59

>Vpu_TV1_C_ZAopt(SEQ ID NO:89)

ATGGTGAGCCTGAGCCTGTTCAAGGGCGTGGACTACCGCCTGGGCGTGGGCGCCCTGATCGTGGCCCTGATCATCGCCAT
CATCGTGTGGACCATCGCCTACATCGAGTACCGCAAGCTGGTGCGCCAGAAGAAGATCGACTGGCTGATCAAGCGCATCC
GCGAGCGCGCCGAGGACAGCGGCAACGAGAGCGACGGCGACACCGAGGAGCTGAGCACCATGGTGGACATGGGCCACCTG
CGCCTGCTGGACGCCAACGACCTGTAA

FIGURE 60

>Vpu_TV1_C_ZAwt(SEQ ID NO:90)

ATGGTAAGTTTAAGTTTATTTAAAGGAGTAGATTATAGATTAGGAGTAGGAGCATTGATAGTAGCACTAATCATAGCAAT
AATAGTGTGGACCATAGCATATATAGAATATAGGAAATTGGTAAGACAAAAGAAAATAGACTGGTTAATTAAAAGAATTA
GGGAAAGAGCAGAAGACAGTGGCAATGAGAGTGATGGGGACACAGAAGAATTGTCAACAATGGTGGATATGGGGCATCTT
AGGCTTCTGGATGCTAATGATTTGTAA

FIGURE 61 dna revexon1_2TV1_C_ZAop   (SEQ ID NO:91)

ATGGCCGGCCGCAGCGGCGACAGCGACGAGGCCCTGCTGCAGGTGGTGAAGATCATC
AAGATCCTGTACCAGAGCCCCTACCCCAAGCCCGAGGGCACCCGCCAGGCCCGCCGCA
ACCGCCGCCGCCGCTGGCGCGCCCGCCAGCGCCAGATCCACACCATCGGCGAGCGCAT
CCTGGTGGCCTGCCTGGGCCGCAGCGCCGAGCCCGTGCCCCTGCAGCTGCCCCCCCTG
GAGCGCCTGCACATCAACTGCAGCGAGGGCAGCGGCACCAGCGGCACCCAGCAGAGC
CAGGGCACCACCGAGGGCGTGGGCGACCCCTAA

FIGURE 62 dna Revexon1_2_TV1_C_ZAwt (SEQ ID NO:92)

ATGGCAGGAAGAAGCGGAGACAGCGACGAAGCGCTCCTCCAAGTGGTGAAGATCATC
AAAATCCTCTATCAAAGCAACCCTTACCCCAAGCCCGAGGGGACTCGACAGGCTCGGA
GGAATCGAAGAAGAAGGTGGAGAGCAAGACAGAGACAGATCCATACGATTGGTGAGC
GGATTCTTGTCGCTTGCCTGGGACGATCTGCGGAGCCTGTGCCTCTTCAGCTACCACCG
CTTGAGAGACTTCATATTAATTGCAGTGAGGGCAGTGGAACTTCTGGGACACAGCAGT
CTCAGGGGACTACAGAGGGGGTGGGAGATCCTTAA

FIGURE 63 dna TatC22Exon1_2_TV1_C_ZAopt  (SEQ ID NO:93)

ATGGAGCCCGTGGACCCCAAGCTGAAGCCCTGGAACCACCCCGGCAGCCAGCCCAAG
ACCGCCGGCAACAACTGCTTCTGCAAGCACTGCAGCTACCACTGCCTGGTGTGCTTCC
AGACCAAGGGCCTGGGCATCAGCTACGGCCGCAAGAAGCGCCGCCAGCGCCGCAGCG
CCCCCCCCAGCGGCGAGGACCACCAGAACCCCCTGAGCAAGCAGCCCCTGCCCCAGGC
CCGCGGCGACAGCACCGGCAGCGAGGAGAGCAAGAAGAAGGTGGAGAGCAAGACCG
AGACCGACCCCTACGACTGGTGA

FIGURE 64 dna TatExon1_2_TV1_C_ZAopt (SEQ ID NO:94)

ATGGAGCCCGTGGACCCCAAGCTGAAGCCCTGGAACCACCCCGGCAGCCAGCCCAAG
ACCGCCTGCAACAACTGCTTCTGCAAGCACTGCAGCTACCACTGCCTGGTGTGCTTCCA
GACCAAGGGCCTGGGCATCAGCTACGGCCGCAAGAAGCGCCGCAGCGCCGCAGCGCC
CCCCCCAGCGGCGAGGACCACCAGAACCCCCTGAGCAAGCAGCCCCTGCCCCAGGCCC
GCGGCGACAGCACCGGCAGCGAGGAGAGCAAGAAGAAGGTGGAGAGCAAGACCGAG
ACCGACCCCTACGACTGGTGA

FIGURE 65 dna TatExon1_2_TV1_C_ZAwt (SEQ ID NO:95)

ATGGAGCCAGTAGATCCTAAACTAAAGCCCTGGAACCATCCAGGAAGCCAACCTAAA
ACAGCTTGTAATAATTGCTTTTGCAAACACTGTAGCTATCATTGTCTAGTTTGCTTTCA
GACAAAAGGTTTAGGCATTTCCTATGGCAGGAAGAAGCGGAGACAGCGACGAAGCGC
TCCTCCAAGTGGTGAAGATCATCAAAATCCTCTATCAAAGCAGCCCTTACCCCAAGCC
CGAGGGGACTCGACAGGCTCGGAGGAATCGAAGAAGAAGGTGGAGAGCAAGACAGA
GACAGATCCATACGATTGGTGA

FIGURE 66

NefD125G-Myr_TV1_C_ZAopt (SEQ ID NO:96)

ATGGCCGGCAAGTGGAGCAAGCGCAGCATCGTGGGCTGGCCCGCCGTGCGC
GAGCGCATGCGCCGCACCGAGCCCGCCGCCGAGGGCGTGGGCGCCGCCAGC
CAGGACCTGGACCGCCACGGCGCCCTGACCAGCAGCAACACCCCCGCCACCA
ACGAGGCCTGCGCCTGGCTGCAGGCCCAGGAGGAGGACGGCGACGTGGGCT
TCCCCGTGCGCCCCCAGGTGCCCCTGCGCCCCATGACCTACAAGAGCGCCGT
GGACCTGAGCTTCTTCCTGAAGGAGAAGGGCGGCCTGGAGGGCCTGATCTAC
AGCCGCAAGCGCCAGGAGATCCTGGACCTGTGGGTGTACAACACCCAGGGCT
TCTTCCCCGGCTGGCAGAACTACACCAGCGGCCCCGGCGTGCGCTTCCCCCTG
ACCTTCGGCTGGTGCTTCAAGCTGGTGCCCGTGGACCCCGCGAGGTGAAGG
AGGCCAACGAGGGCGAGGACAACTGCCTGCTGCACCCCATGAGCCAGCACG
GCGCCGAGGACGAGGACCGCGAGGTGCTGAAGTGGAAGTTCGACAGCCTGC
TGGCCCACCGCCACATGGCCCGCGAGCTGCACCCCGAGTACTACAAGGACTG
CTGA

FIGURE 67

Envgp160_TV2_C_ZAopt (SEQ ID NO:97)

```
ATGCGCGCCCGCGGCATCCTGAAGAACTACCGCCACTGGTGGATCTGGGGCATCCT
GGGCTTCTGGATGCTGATGATGTGCAACGTGAAGGGCCTGTGGGTGACCGTGTACTA
CGGCGTGCCCGTGGGCCGCGAGGCCAAGACCACCCTGTTCTGCGCCAGCGACGCCA
AGGCCTACGAGAAGGAGGTGCACAACGTGTGGGCCACCCACGCCTGCGTGCCCACC
GACCCCAACCCCCAGGAGGTGATCCTGGGCAACGTGACCGAGAACTTCAACATGTG
GAAGAACGACATGGTGGACCAGATGCAGGAGGACATCATCAGCCTGTGGGACCAGA
GCCTGAAGCCCTGCGTGAAGCTGACCCCCTGTGCGTGACCCTGAACTGCACCAACG
CCACCGTGAACTACAACAACACCAGCAAGGACATGAAGAACTGCAGCTTCTACGTG
ACCACCGAGCTGCGCGACAAGAAGAAGAAGGAGAACGCCCTGTTCTACCGCCTGGA
CATCGTGCCCCTGAACAACCGCAAGAACGGCAACATCAACAACTACCGCCTGATCA
ACTGCAACACCAGCGCCATCACCCAGGCCTGCCCCAAGGTGAGCTTCGACCCCATCC
CCATCCACTACTGCGCCCCCGCCGGCTACGCCCCCCTGAAGTGCAACAACAAGAAG
TTCAACGGCATCGGCCCCTGCGACAACGTGAGCACCGTGCAGTGCACCCACGGCAT
CAAGCCCGTGGTGAGCACCCAGCTGCTGCTGAACGGCAGCCTGGCCGAGGAGGAGA
TCATCATCCGCAGCGAGAACCTGACCAACAACGTGAAGACCATCATCGTGCACCTG
AACGAGAGCATCGAGATCAAGTGCACCCGCCCCGGCAACAACACCCGCAAGAGCGT
GCGCATCGGCCCCGGCCAGGCCTTCTACGCCACCGGCGACATCATCGGCGACATCC
GCCAGGCCCACTGCAACATCAGCAAGAACGAGTGGAACACCACCCTGCAGCGCGTG
AGCCAGAAGCTGCAGGAGCTGTTCCCCAACAGCACCGGCATCAAGTTCGCCCCCCA
CAGCGGCGGCGACCTGGAGATCACCACCCACAGCTTCAACTGCGGCGGCGAGTTCT
TCTACTGCAACACCACCGACCTGTTCAACAGCACCTACAGCAACGGCACCTGCACCA
ACGGCACCTGCATGAGCAACAACACCGAGCGCATCACCCTGCAGTGCCGCATCAAG
CAGATCATCAACATGTGGCAGGAGGTGGGCCGCGCCATGTACGCCCCCCCCATCGC
CGGCAACATCACCTGCCGCAGCAACATCACCGGCCTGCTGCTGACCCGCGACGGCG
GCGACAACAACACCGAGACCGAGACCTTCCGCCCCGGCGGCGGCGACATGCGCGAC
AACTGGCGCAGCGAGCTGTACAAGTACAAGGTGGTGGAGATCAAGCCCCTGGGCGT
GGCCCCCACCGCCGCCAAGCGCCGCGTGGTGGAGCGCGAGAAGCGCGCCGTGGGCA
TCGGCGCCGTGTTCCTGGGCTTCCTGGGCGCCGCCGGCAGCACCATGGGCGCCGCCA
GCATCACCCTGACCGTGCAGGCCCGCCAGCTGCTGAGCGGCATCGTGCAGCAGCAG
AGCAACCTGCTGCGCGCCATCGAGGCCCAGCAGCACATGCTGCAGCTGACCGTGTG
GGGCATCAAGCAGCTGCAGGCCCGCGTGCTGGCCATCGAGCGCTACCTGCAGGACC
AGCAGCTGCTGGGCCTGTGGGGCTGCAGCGGCAAGCTGATCTGCACCACCAACGTG
CTGTGGAACAGCAGCTGGAGCAACAAGACCCAGAGCGACATCTGGGACAACATGAC
CTGGATGCAGTGGGACCGCGAGATCAGCAACTACACCAACACCATCTACCGCCTGC
TGGAGGACAGCCAGAGCCAGCAGGAGCGCAACGAGAAGGACCTGCTGGCCCTGGA
CCGCTGGAACAACCTGTGGAACTGGTTCAGCATCACCAACTGGCTGTGGTACATCAA
GATCTTCATCATGATCGTGGGCGGCCTGATCGGCCTGCGCATCATCTTCGCCGTGCT
GAGCCTGGTGAACCGCGTGCGCCAGGGCTACAGCCCCCTGAGCCTGCAGACCCTGA
TCCCCAACCCCCGCGGCCCCGACCGCCTGGGCGGCATCGAGGAGGAGGGCGGCGAG
CAGGACAGCAGCCGCAGCATCCGCCTGGTGAGCGGCTTCCTGACCCTGGCCTGGGA
CGACCTGCGCAGCCTGTGCCTGTTCTGCTACCACCGCCTGCGCGACTTCATCCTGAT
CGTGGTGCGCGCCGTGGAGCTGCTGGGCCACAGCAGCCTGCGCGGCCTGCAGCGCG
GCTGGGGCACCCTGAAGTACCTGGGCAGCCTGGTGCAGTACTGGGGCCTGGAGCTG
AAGAAGAGCGCCATCAACCTGCTGGACACCATCGCCATCGCCGTGGCCGAGGGCAC
CGACCGCATCCTGGAGTTCATCCAGAACCTGTGCCGCGGCATCCGCAACGTGCCCCG
CCGCATCCGCCAGGGCTTCGAGGCCGCCCTGCAGTAA
```

FIGURE 68

Envgp160_TV2_C_ZAwt (SEQ ID NO:98)

ATGAGAGCGAGGGGGGATACTGAAGAATTATCGACACTGGTGGATATGGGGCATCTT
AGGCTTTTGGATGCTAATGATGTGTAATGTGAAGGGCTTGTGGGTCACAGTCTACTA
CGGGGTACCTGTGGGGAGAGAAGCAAAAACTACTCTATTTTGTGCATCAGATGCTA
AAGCATATGAGAAGAAGTGCATAATGTCTGGGCTACACATGCCTGTGTACCCACA
GACCCCAACCCACAAGAAGTGATTTTGGGCAATGTAACAGAAAATTTTAACATGTG
GAAAAATGACATGGTGGATCAGATGCAGGAAGATATAATCAGTTTATGGGATCAAA
GCCTTAAGCCATGTGTAAAATTGACCCCACTCTGTGTCACTTTAAACTGTACAAATG
CAACTGTTAACTACAATAATACCTCTAAAGACATGAAAAATTGCTCTTTCTATGTAA
CCACAGAATTAAGAGATAAGAAAAAGAAAGAAAATGCACTTTTTTATAGACTTGAT
ATAGTACCACTTAATAATAGGAAGAATGGGAATATTAACAACTATAGATTAATAAA
TTGTAATACCTCAGCCATAACACAAGCCTGTCCAAAAGTCTCGTTTGACCCAATTCC
TATACATTATTGTGCTCCAGCTGGTTATGCGCCTCTAAAATGTAATAATAAGAAATT
CAATGGAATAGGACCATGCGATAATGTCAGCACAGTACAATGTACACATGGAATTA
AGCCAGTGGTATCAACTCAATTACTGTTAAATGGTAGCCTAGCAGAAGAAGAGATA
ATAATTAGATCTGAAAATCTGACAAACAATGTCAAAACAATAATAGTACATCTTAAT
GAATCTATAGAGATTAAATGTACAAGACCTGGCAATAATACAAGAAAGAGTGTGAG
AATAGGACCAGGACAAGCATTCTATGCAACAGGAGACATAATAGGAGATATAAGAC
AAGCACATTGTAACATTAGTAAAAATGAATGGAATACAACTTTACAAAGGGTAAGT
CAAAAATTACAAGAACTCTTCCCTAATAGTACAGGGATAAAATTTGCACCACACTCA
GGAGGGGACCTAGAAATTACTACACATAGCTTTAATTGTGGAGGAGAATTTTTCTAT
TGCAATACAACAGACCTGTTTAATAGTACATACAGTAATGGTACATGCACTAATGGT
ACATGCATGTCTAATAATACAGAGCGCATCACACTCCAATGCAGAATAAAACAAAT
TATAAACATGTGGCAGGAGGTAGGACGAGCAATGTATGCCCCTCCCATTGCAGGAA
ACATAACATGTAGATCAAATATTACAGGACTACTATTAACACGTGATGGAGGAGAT
AATAATACTGAAACAGAGACATTCAGACCTGGAGGAGGAGACATGAGGGACAATTG
GAGAAGTGAATTATATAAATACAAGGTGGTAGAAATTAAACCATTAGGAGTAGCAC
CCACTGCTGCAAAAAGGAGAGTGGTGGAGAGAGAAAAAAGAGCAGTAGGAATAGG
AGCTGTGTTCCTTGGGTTCTTGGGAGCAGCAGGAAGCACTATGGGCGCAGCATCAAT
AACGCTGACGGTACAGGCCAGACAATTATTGTCTGGTATAGTGCAACAGCAAAGTA
ATTTGCTGAGGGCTATAGAGGCGCAACAGCATATGTTGCAACTCACGGTCTGGGGC
ATTAAGCAGCTCCAGGCAAGAGTCCTGGCTATAGAGAGATACCTACAGGATCAACA
GCTCCTAGGACTGTGGGGCTGCTCTGGAAAACTCATCTGCACCACTAATGTGCTTTG
GAACTCTAGTTGGAGTAATAAAACTCAAAGTGATATTTGGGATAACATGACCTGGAT
GCAGTGGGATAGGGAAATTAGTAATTACACAAACACAATATACAGGTTGCTTGAAG
ACTCGCAAAGCCAGCAGGAAAGAAATGAAAAAGATTTACTAGCATTGGACAGGTGG
AACAATCTGTGGAATTGGTTTAGCATAACAAATTGGCTGTGGTATATAAAAATATTC
ATAATGATAGTAGGAGGCTTGATAGGTTTAAGAATAATTTTGCTGTGCTCTCTA
GTAAATAGAGTTAGGCAGGGATACTCACCCTTGTCATTGCAGACCCTTATCCCAAAC
CCGAGGGGACCCGACAGGCTCGGAGGAATCGAAGAAGAAGGTGGAGAGCAAGACA
GCAGCAGATCCATTCGATTAGTGAGCGGATTCTTGACACTTGCCTGGGACGACCTAC
GAAGCCTGTGCCTCTTCTGCTACCACCGATTGAGAGACTTCATATTAATTGTAGTGA
GAGCAGTGGAACTTCTGGGACACAGTAGTCTCAGGGGACTGCAGAGGGGGTGGGA
ACCCTTAAGTATTTGGGGAGTCTTGTGCAATATTGGGGTCTAGAGTTAAAAAGAGT
GCTATTAATCTGCTTGATACTATAGCAATAGCAGTAGCTGAAGGAACAGATAGGATT
CTAGAATTCATACAAAACCTTTGTAGAGGTATCCGCAACGTACCTAGAAGAATAAG
ACAGGGCTTCGAAGCAGCTTTGCAATAA

FIGURE 69

Gag_TV2_C_ZAopt (SEQ ID NO:99)

ATGGGCGCCCGCGCCAGCATCCTGCGCGGCGGCAAGCTGGACAAGTGGGAG
AAGATCCGCCTGCGCCCCGGCGGCCGCAAGCACTACATGCTGAAGCACCTGG
TGTGGGCCAGCCGCGAGCTGGAGCGCTTCGCCGTGAACCCCGGCCTGCTGGA
GACCAGCGACGGCTGCCGCCAGATCATCAAGCAGCTGCAGCCCGCCCTGCAG
ACCGGCACCGAGGAGATCCGCAGCCTGTTCAACACCGTGGCCACCCTGTACT
GCGTGCACAAGGGCATCGACGTGCGCGACACCAAGGAGGCCCTGGACAAGA
TCGAGGAGGAGCAGAACAAGTGCCAGCAGAAGACCCAGCAGGCCGAGGCCG
CCGACAAGAAGGTGAGCCAGAACTACCCCATCGTGCAGAACCTGCAGGGCC
AGATGGTGCACCAGGCCATCAGCCCCGCACCCTGAACGCCTGGGTGAAGGT
GATCGAGGAGAAGGCCTTCAGCCCCGAGGTGATCCCCATGTTCACCGCCCTG
AGCGAGGGCGCCACCCCCCAGGACCTGAACACCATGCTGAACACCGTGGGC
GGCCACCAGGCCGCCATGCAGATGCTGAAGGACACCATCAACGAGGAGGCC
GCCGAGTGGGACCGCCTGCACCCCGTGCACGCCGGCCCCGTGGCCCCCGGCC
AGATGCGCGAGCCCCGCGGCAGCGACATCGCCGGCACCACCAGCACCCTGCA
GGAGCAGATCGCCTGGATGACCAGCAACCCCCCCATCCCCGTGGGCGACATC
TACAAGCGCTGGATCATCCTGGGCCTGAACAAGATCGTGCGCATGTACAGCC
CCGTGAGCATCCTGGACATCAAGCAGGGCCCCAAGGAGCCCTTCCGCGACTA
CGTGGACCGCTTCTTCAAGACCCTGCGCGCCGAGCAGAGCACCCAGGAGGTG
AAGAACTGGATGACCGACACCCTGCTGGTGCAGAACGCCAACCCCGACTGCA
AGACCATCCTGCGCGCCCTGGGCCCCGGCGCCAGCCTGGAGGAGATGATGAC
CGCCTGCCAGGGCGTGGGCGGCCCCAGCCACAAGGCCCGCGTGCTGGCCGAG
GCCATGAGCCAGGCCAACAACACCAGCGTGATGATCCAGAAGAGCAACTTC
AAGGGCCCCCGCCGCGCCGTGAAGTGCTTCAACTGCGGCCGCGAGGGCCACA
TCGCCCGCAACTGCCGCGCCCCCGCAAGCGCGGCTGCTGGAAGTGCGGCAA
GGAGGGCCACCAGATGAAGGACTGCACCGAGCGCCAGGCCAACTTCCTGGG
CAAGATCTGGCCCAGCCACAAGGGCCGCCCCGGCAACTTCCTGCAGAGCCGC
CCCGAGCCCACCGCCCCCCCCTGGAGCCCACCGCCCCCCCGCCGAGAGCT
TCAAGTTCAAGGAGACCCCCAAGCAGGAGCCCAAGGACCGCGAGCCCCTGA
CCAGCCTGAAGAGCCTGTTCGGCAGCGACCCCCTGAGCCAGTAA

FIGURE 70

Gag_TV2_C_ZAwt (SEQ ID NO:100)

ATGGGTGCGAGAGCGTCAATATTAAGAGGGGGAAAATTAGACAAATGGGAA
AAAATTAGGTTACGGCCAGGGGGGAGAAAACACTATATGCTAAAACACCTA
GTATGGGCAAGCAGAGAGCTGGAAAGATTTGCAGTTAACCCTGGCCTTTTAG
AGACATCAGACGGATGTAGACAAATAATAAAACAGCTACAACCAGCTCTTCA
GACAGGAACAGAGGAAATTAGATCATTATTTAACACAGTAGCAACTCTCTAT
TGTGTACATAAAGGGATAGATGTACGAGACACCAAGGAAGCCTTAGACAAG
ATAGAGGAGGAACAAAACAAATGTCAGCAAAAAACACAGCAGGCGGAAGCG
GCTGACAAAAGGTCAGTCAAAATTATCCTATAGTGCAGAACCTCCAAGGGC
AAATGGTACACCAGGCCATATCACCTAGAACCTTGAATGCATGGGTAAAAGT
AATAGAGGAGAAGGCTTTTAGCCCAGAGGTAATACCCATGTTTACAGCATTA
TCAGAAGGAGCCACCCCACAAGATTTAAACACCATGTTAAATACAGTGGGGG
GACATCAAGCAGCCATGCAAATGTTAAAAGATACCATCAATGAGGAGGCTGC
AGAATGGGATAGGTTACATCCAGTACATGCAGGGCCTGTTGCACCAGGCCAG
ATGAGAGAACCAAGGGGAAGTGACATAGCAGGAACTACTAGTACCCTTCAA
GAACAAATAGCATGGATGACAAGTAACCCACCTATCCCAGTAGGGGACATCT
ATAAAAGGTGGATAATTCTGGGGTTAAATAAAATAGTAAGAATGTACAGCCC
TGTCAGCATTTTAGACATAAAACAAGGACCAAAGGAACCCTTTAGAGACTAT
GTAGACCGGTTCTTCAAAACTTTAAGAGCTGAACAATCTACACAAGAGGTAA
AAAATTGGATGACAGACACCTTGTTAGTCCAAAATGCGAACCCAGATTGTAA
GACCATTTTAAGAGCATTAGGACCAGGGGCTTCATTAGAAGAAATGATGACA
GCATGTCAGGGAGTGGGAGGACCTAGCCACAAAGCAAGAGTTTTGGCTGAG
GCAATGAGCCAAGCAAACAATACAAGTGTAATGATACAGAAAGCAATTTTA
AAGGCCCTAGAAGAGCTGTTAAATGTTTCAACTGTGGCAGGGAAGGGCACAT
AGCCAGGAATTGCAGGGCCCCTAGGAAAAGGGGCTGTTGGAAATGTGGAAA
GGAAGGACACCAAATGAAAGACTGTACTGAGAGGCAGGCTAATTTTTTAGGG
AAAATTTGGCCTTCCCACAAGGGGAGGCCAGGGAATTTCCTTCAGAGCAGAC
CAGAGCCAACAGCCCCACCACTAGAACCAACAGCCCCACCAGCAGAGAGCT
TCAAGTTCAAGGAGACTCCGAAGCAGGAGCCGAAAGACAGGGAACCTTTAA
CTTCCCTCAAATCACTCTTTGGCAGCGACCCCTTGTCTCAATAA

FIGURE 71

Nef_TV2_C_ZAopt (SEQ ID NO:101)

ATGGGCGGCAAGTGGAGCAAGAGCAGCATCATCGGCTGGCCCGAGGTGCGC
GAGCGCATCCGCCGCACCCGCAGCGCCGCCGAGGGCGTGGGCAGCGCCAGC
CAGGACCTGGAGAAGCACGGCGCCCTGACCACCAGCAACACCGCCCACAAC
AACGCCGCCTGCGCCTGGCTGGAGGCCCAGGAGGAGGAGGGCGAGGTGGGC
TTCCCCGTGCGCCCCCAGGTGCCCCTGCGCCCCATGACCTACAAGGCCGCCAT
CGACCTGAGCTTCTTCCTGAAGGAGAAGGGCGGCCTGGAGGGCCTGATCTAC
AGCAAGAAGCGCCAGGAGATCCTGGACCTGTGGGTGTACAACACCCAGGGC
TTCTTCCCCGACTGGCAGAACTACACCCCCGGCCCCGGCGTGCGCTTCCCCCT
GACCTTCGGCTGGTACTTCAAGCTGGAGCCCGTGGACCCCGCGAGGTGGAG
GAGGCCAACGAGGGCGAGAACAACTGCCTGCTGCACCCCATGAGCCAGCAC
GGCATGGAGGACGAGGACCGCGAGGTGCTGCGCTGGAAGTTCGACAGCACC
CTGGCCCGCCGCCACATGGCCCGCGAGCTGCACCCCGAGTACTACAAGGACT
GCTGA

FIGURE 72

Nef_TV2_C_ZAwt (SEQ ID NO:102)

ATGGGGGGCAAGTGGTCAAAAAGCAGTATAATTGGATGGCCTGAAGTAAGA
GAAAGAATCAGACGAACTAGGTCAGCAGCAGAGGGAGTAGGATCAGCGTCT
CAAGACTTAGAGAAACATGGGGCACTTACAACCAGCAACACAGCCCACAAC
AATGCTGCTTGCGCCTGGCTGGAAGCGCAAGAGGAGGAAGGAGAAGTAGGC
TTTCCAGTCAGACCTCAGGTACCTTTAAGACCAATGACTTATAAAGCAGCAAT
AGATCTCAGCTTCTTTTTAAAAGAAAAGGGGGGACTGGAAGGGTTAATTTAC
TCCAAGAAAAGGCAAGAGATCCTTGATTTGTGGGTTTATAACACACAAGGCT
TCTTCCCTGATTGGCAAAACTACACACCGGGACCAGGGGTCAGATTTCCACT
GACCTTTGGATGGTACTTCAAGCTAGAGCCAGTCGATCCAAGGGAAGTAGAA
GAGGCCAATGAAGGAGAAAACAACTGTTTACTACACCCTATGAGCCAGCATG
GAATGGAGGATGAAGACAGAGAAGTATTAAGATGGAAGTTTGACAGTACGC
TAGCACGCAGACACATGGCCCGCGAGCTACATCCGGAGTATTACAAAGACTG
CTGA

FIGURE 73

Pol_TV2_C_ZAopt (SEQ ID NO:103)

```
TTCTTCCGCGAGAACCTGGCCTTCCCCCAGGGCGAGGCCCGCGAGTTCCCCAGCGAGCAGACC
CGCGCCAACAGCCCCACCACCCGCACCAACAGCCCCACCAGCCGCGAGCTGCAGGTGCAGGG
CGACAGCGAGGCCGGCGCCGAGCGCCAGGGCACCTTCAACTTCCCCCAGATCACCCTGTGGC
AGCGCCCCCTGGTGAGCATCAAGGTGGCCGGCCAGACCAAGGAGGCCCTGCTGGACACCGGC
GCCGACGACACCGTGCTGGAGGAGATCAACCTGCCCGGCAAGTGGAAGCCCAAGATGATCGG
CGGCATCGGCGGCTTCATCAAGGTGCGCCAGTACGACCAGATCCTGATCGAGATCTGCGGCA
AGCGCGCCATCGGCACCGTGCTGGTGGGCCCCACCCCCGTGAACATCATCGGCCGCAACCTGC
TGACCCAGCTGGGCTGCACCCTGAACTTCCCCATCAGCCCCATCGAGACCGTGCCCGTGAAGC
TGAAGCCCGGCATGGACGGCCCCAAGGTGAAGCAGTGGCCCCTGACCGAGGAGAAGATCAAG
GCCCTGACCGAGATCTGCGAGGAGATGGAGAAGGAGGGCAAGATCACCAAGATCGGCCCCG
AGAACCCCTACAACACCCCCGTGTTCGCCATCAAGAAGAAGGACAGCACCAAGTGGCGCAAG
CTGGTGGACTTCCGCGAGCTGAACAAGCGCACCCAGGACTTCTGGGAGGTGCAGCTGGGCAT
CCCCCACCCCGCCGGCCTGAAGAAGAAGAAGAGCGTGACCGTGCTGGACGTGGGCGACGCCT
ACTTCAGCGTGCCCCTGGACGAGAGCTTCCGCAAGTACACCGCCTTCACCATCCCCAGCATCA
ACAACGAGACCCCCGGCATCCGCTACCAGTACAACGTGCTGCCCCAGGGCTGGAAGGGCAGC
CCCGCCATCTTCCAGAGCAGCATGACCCGCATCCTGGAGCCCTTCCGCACCCAGAACCCCGAG
GTGGTGATCTACCAGTACATGGACGACCTGTACGTGGGCAGCGACCTGGAGATCGGCCAGCA
CCGCGCCAAGATCGAGGAGCTGCGCGGCCACCTGCTGAAGTGGGGCTTCACCACCCCCGACA
AGAAGCACCAGAAGGAGCCCCCCTTCCTGTGGATGGGCTACGAGCTGCACCCCGACAAGTGG
ACCGTGCAGCCCATCCAGCTGCCCGAGAAGGAGAGCTGGACCGTGAACGACATCCAGAAGCT
GGTGGGCAAGCTGAACTGGGCCAGCCAGATCTACCCCGGCATCAAGGTGCGCCAGCTGTGCA
AGCTGCTGCGCGGCGCCAAGGCCCTGACCGACATCGTGCCCCTGACCGAGGAGGCCGAGCTG
GAGCTGGCCGAGAACCGCGAGATCCTGAAGGAGCCCGTGCACGGCGTGTACTACGACCCCAG
CAAGGACCTGATCGCCGAGATCCAGAAGCAGGGCAACGACCAGTGGACCTACCAGATCTACC
AGGAGCCCTTCAAGAACCTGCGCACCGGCAAGTACGCCAAGATGCGCACCGCCCACACCAAC
GACGTGAAGCAGCTGGCCGAGGCCGTGCAGAAGATCACCCAGGAGAGCATCGTGATCTGGGG
CAAGACCCCCAAGTTCCGCCTGCCCATCCCCAAGGAGACCTGGGAGACCTGGTGGAGCGACT
ACTGGCAGGCCACCTGGATCCCCGAGTGGGAGTTCGTGAACACCCCCCCCCTGGTGAAGCTGT
GGTACCAGCTGGAGAAGGAGCCCATCGTGGGCGCCGAGACCTTCTACGTGGACGGCGCCGCC
AACCGCGAGACCAAGATCGGCAAGGCCGGCTACGTGACCGACAAGGGCCGCCAGAAGGTGG
TGAGCTTCACCGAGACCACCAACCAGAAGACCGAGCTGCAGGCCATCCAGCTGGCCCTGCAG
GACAGCGGCCCCGAGGTGAACATCGTGACCGACAGCCAGTACGCCCTGGGCATCATCCAGGC
CCAGCCCGACAAGAGCGAGAGCGAGCTGGTGAGCCAGATCATCGAGCAGCTGATCAAGAAG
GAGAAGGTGTACCTGAGCTGGGTGCCCGCCCACAAGGGCATCGGCGGCAACGAGCAGGTGGA
CAAGCTGGTGAGCAGCGGCATCCGCAAGGTGCTGTTCCTGGACGGCATCGACAAGGCCCAGG
AGGAGCACGAGAAGTACCACAGCAACTGGCGCGCCATGGCCAGCGAGTTCAACCTGCCCCCC
ATCGTGGCCAAGGAGATCGTGGCCAGCTGCGACAAGTGCCAGCTGAAGGGCGAGGCCATGCA
CGGCCAGGTGGACTGCAGCCCCGGCATCTGGCAGCTGGACTGCACCCACCTGGAGGGCAAGA
TCATCCTGGTGGCCGTGCACGTGGCCAGCGGCTACATGGAGGCCGAGGTGATCCCCGCCGAG
ACCGGCCAGGAGACCGCCTACTTCATCCTGAAGCTGGCCGGCCGCTGGCCCGTGAAGGTGATC
CACACCGACAACGGCAGCAACTTCACCAGCACCGCCGTGAAGGCCGCCTGCTGGTGGGCCGA
CATCCAGCGCGAGTTCGGCATCCCCTACAACCCCCAGAGCCAGGGCGTGGTGGAGAGCATGA
ACAAGGAGCTGAAGAAGATCATCGGCCAGGTGCGCGACCAGGCCGAGCACCTGAAGACCGCC
GTGCAGATGGCCGTGTTCATCCACAACTTCAAGCGCAAGGGCGGCATCGGCGGCTACAGCGC
CGGCGAGCGCATCATCGACATCATCGCCAGCGACATCCAGACCAAGGAGCTGCAGAAGCAGA
TCATCAAGATCCAGAACTTCCGCGTGTACTACCGCGACAGCCGCGACCCCATCTGGAAGGGCC
CCGCCAAGCTGCTGTGGAAGGGCGAGGGCGCCGTGGTGATCCAGGACAACAGCGACATCAAG
GTGGTGCCCCGCCGCAAGGCCAAGATCATCAAGGACTACGGCAAGCAGATGGCCGGCGCCGA
CTGCGTGGCCGGCCGCCAGGACGAGGAC
```

FIGURE 74

Pol_TV2_C_ZAwt (SEQ ID NO:104)

```
TTTTTTAGGGAAAATTTGGCCTTCCCACAAGGGGAGGCCAGGGAATTTCCTTCAGAGCAGACC
AGAGCCAACAGCCCCACCACTAGAACCAACAGCCCCACCAGCAGAGAGCTTCAAGTTCAAGG
AGACTCCGAAGCAGGAGCCGAAAGACAGGGAACCTTTAACTTCCCTCAAATCACTCTTTGGCA
GCGACCCCTTGTCTCAATAAAAGTAGCGGGCCAAACAAGGAGGCTCTTTTAGATACAGGAG
CAGATGATACAGTACTAGAAGAAATAAACTTGCCAGGAAAATGGAAACCAAAAATGATAGG
AGGAATTGGAGGTTTTATCAAAGTAAGACAGTATGATCAAATACTTATAGAAATTTGTGGAAA
AAGGGCTATAGGTACAGTATTAGTAGGACCTACACCTGTCAACATAATTGGAAGAAATCTGTT
GACTCAGCTTGGATGCACACTAAATTTTCCAATTAGCCCCATTGAAACTGTACCAGTAAAATT
AAAGCCAGGAATGGATGGCCCAAAGGTTAAACAATGGCCATTGACAGAAGAAAAATAAAA
GCATTAACAGAAATTTGTGAGGAAATGGAGAAGGAAGGAAAATTACAAAAATTGGGCCTGA
AAATCCATATAACACTCCAGTATTTGCCATAAAGAAGAAGGACAGTACAAAGTGGAGAAAAT
TAGTAGATTTCAGGGAACTCAATAAAAGAACTCAAGACTTTTGGGAAGTCCAATTAGGAATA
CCACACCCAGCAGGGTTAAAAAAGAAAAAATCAGTGACAGTACTGGATGTGGGAGATGCATA
TTTTTCAGTCCCTTTAGATGAGAGCTTCAGAAAATATACTGCATTCACCATACCTAGTATAAAC
AATGAAACACCAGGGATTAGATATCAATATAATGTTCTTCCACAGGGATGGAAAGGATCACC
AGCAATATTCCAGAGTAGCATGACAAGAATCTTAGAGCCCTTTAGAACACAAAACCCAGAAG
TAGTTATCTATCAATATATGGATGACTTATATGTAGGATCTGACTTAGAAATAGGGCAACATA
GAGCAAAAATAGAGGAGTTAAGAGGACACCTATTGAAATGGGGATTTACCACACCAGACAAG
AAACATCAGAAAGAACCCCCATTTCTTTGGATGGGGTATGAACTCCATCCTGACAAATGGACA
GTACAGCCTATACAGCTGCCAGAAAAGGAGAGCTGGACTGTCAATGATATACAGAAGTTAGT
GGGAAAGTTAAACTGGGCAAGTCAGATTTACCCAGGGATTAAAGTAAGGCAACTGTGTAAAC
TCCTTAGGGGAGCCAAAGCACTAACAGACATAGTGCCACTGACTGAAGAAGCAGAATTAGAA
TTGGCTGAGAACAGGGAAATTCTAAAAGAACCAGTACATGGAGTATATTATGACCCATCAAA
AGATTTAATAGCTGAAATACAGAAACAGGGGAATGACCAATGGACATATCAAATTTACCAAG
AACCATTTAAAAATCTGAGAACAGGAAAGTATGCAAAAATGAGGACTGCCCACACTAATGAT
GTGAAACAGTTAGCAGAGGCAGTGCAAAAGATAACCCAGGAAAGCATAGTAATATGGGGAA
AAACTCCTAAATTTAGACTACCCATCCCAAAAGAAACATGGGAGACATGGTGGTCAGACTATT
GGCAAGCCACCTGGATTCCTGAGTGGGAGTTTGTCAATACCCCTCCCCTAGTAAAATTGTGGT
ACCAGCTGGAAAAAGAACCCATAGTAGGGGCAGAAACTTTCTATGTAGATGGAGCAGCCAAT
AGGGAAACTAAAATAGGAAAAGCAGGGTATGTCACTGACAAAGGAAGGCAGAAAGTTGTTTC
CTTCACTGAAACAACAAATCAGAAGACTGAATTACAAGCAATTCAGCTAGCTTTGCAGGATTC
AGGGCCAGAAGTAAACATAGTAACAGACTCACAGTATGCATTAGGAATCATTCAAGCACAAC
CAGATAAGAGTGAATCAGAATTAGTCAGTCAAATAATAGAACAGTTGATAAAAAAGGAAAAA
GTCTACCTATCATGGGTACCAGCACATAAAGGAATTGGAGGAAATGAACAAGTAGACAAATT
AGTAAGTAGTGGAATCAGAAAAGTACTGTTTCTAGATGGAATAGATAAAGCTCAAGAAGAGC
ATGAAAAATATCACAGCAATTGGAGAGCAATGGCTAGTGAGTTTAATCTGCCACCCATAGTA
GCAAAGGAAATAGTAGCCAGCTGTGATAAATGTCAGCTAAAAGGGGAAGCCATGCATGGACA
AGTCGACTGTAGTCCAGGAATATGGCAATTAGACTGTACACATTTAGAAGGAAAAATCATCCT
AGTAGCAGTCCATGTAGCCAGTGGCTACATGGAAGCAGAGGTTATCCCAGCAGAAACAGGAC
AAGAAACAGCATACTTTATACTAAAATTAGCAGGAAGATGGCCAGTCAAAGTAATACATACA
GATAATGGCAGTAATTTCACCAGTACCGCAGTTAAGGCAGCCTGTTGGTGGGCAGATATCCAA
CGGGAATTTGGAATTCCCTACAATCCCCAAAGTCAAGGAGTAGTAGAATCCATGAATAAAGA
ATTAAAGAAAATCATAGGGCAAGTAAGAGATCAAGCTGAGCACCTTAAGACAGCAGTACAAA
TGGCAGTATTCATTCACAATTTTAAAAGAAAGGGGGGATTGGGGGGTACAGTGCAGGGGAG
AGAATAATAGACATAATAGCATCAGACATACAAACTAAAGAATTACAAAAACAAATTATAAA
AATTCAAAATTTTCGGGTTTATTACAGAGACAGCAGAGACCCTATTTGGAAAGGACCAGCCAA
ACTACTCTGGAAAGGTGAAGGGGCAGTAGTAATACAAGATAATAGTGATATAAAGGTAGTAC
CAAGAAGGAAAGCAAAAATCATTAAGGACTATGGAAAACAGATGGCAGGTGCTGATTGTGTG
GCAGGTAGACAGGATGAAGAT
```

FIGURE 75

RevExon1_TV2_C_ZAopt (SEQ ID NO:105)

ATGGCCGGCCGCAGCGGCGACAGCGACGAGGCCCTGCTGCAGGCCATCAAG
ATCATCAAGATCCTGTACCAGAGC

FIGURE 76

RevExon1_TV2_C_ZAwt (SEQ ID NO:106)

ATGGCAGGAAGAAGCGGAGACAGCGACGAAGCGCTCCTCCAAGCAATAAAG
ATCATCAAGATCCTCTACCAAAGCA

FIGURE 77

RevExon2_TV2_C_ZAopt (SEQ ID NO:107)

CCCTACCCCAAGCCCGAGGGCACCCGCCAGGCCCGCCGCAACCGCCGCCGCC
GCTGGCGCGCCCGCCAGCAGCAGATCCACAGCATCAGCGAGCGCATCCTGGA
CACCTGCCTGGGCCGCCCCACCAAGCCCGTGCCCCTGCTGCTGCCCCCCATCG
AGCGCCTGCACATCAACTGCAGCGAGAGCAGCGGCACCAGCGGCACCCAGT
AGAGCCAGGGCACCGCCGAGGGCGTGGGCAACCCCTAA

FIGURE 78

RevExon2_TV2_C_ZAwt (SEQ ID NO:108)

ACCCTTATCCCAAACCCGAGGGGACCCGACAGGCTCGGAGGAATCGAAGAA
GAAGGTGGAGAGCAAGACAGCAGCAGATCCATTCGATTAGTGAGCGGATTCT
TGACACTTGCCTGGGACGACCTACGAAGCCTGTGCCTCTTCTGCTACCACCGA
TTGAGAGACTTCATATTAATTGTAGTGAGAGCAGTGGAACTTCTGGGACACA
GTAGTCTCAGGGGACTGCAGAGGGGGTGGGGAACCCTTAA

FIGURE 79

TatExon1_TV2_C_ZAopt (SEQ ID NO:109)

ATGGAGCCCATCGACCCCAACCTGGAGCCCTGGAACCACCCCGGCAGCCAGC
CCAAGACCGCCTGCAACGGCTGCTACTGCAAGCGCTGCAGCTACCACTGCCT
GGTGTGCTTCCAGAAGAAGGGCCTGGGCATCTACTACGGCCGCAAGAAGCGC
CGCCAGCGCCGCAGCGCCCCCCCCAGCAACAAGGACCACCAGGACCCCCTGC
CCAAGCAG

FIGURE 80

TatExon1_TV2_C_ZAwt (SEQ ID NO:110)

ATGGAGCCAATAGATCCTAACCTAGAACCCTGGAACCATCCAGGAAGTCAGC
CTAAAACTGCTTGTAATGGGTGTTACTGTAAACGTTGCAGCTATCATTGTCTA
GTTTGCTTTCAGAAAAAAGGCTTAGGCATTTACTATGGCAGGAAGAAGCGGA
GACAGCGACGAAGCGCTCCTCCAAGCAATAAAGATCATCAAGATCCTCTACC
AAAGCAG

FIGURE 81

TatExon2_TV2_C_ZAopt (SEQ ID NO:111)

CCCCTGAGCCAGACCCGCGGCGACCCCACCGGCAGCGAGGAGAGCAAGAAG
AAGGTGGAGAGCAAGACCGCCGCCGACCCCTTCGACTAG

FIGURE 82

TatExon2_TV2_C_ZAwt (SEQ ID NO:112)

CCCTTATCCCAAACCCGAGGGGACCCGACAGGCTCGGAGGAATCGAAGAAG
AAGGTGGAGAGCAAGACAGCAGCAGATCCATTCGATTAG

FIGURE 83

Vif_TV2_C_ZAopt (SEQ ID NO:113)

ATGGAGAACCGCTGGCAGGTGCTGATCGTGTGGCAGGTGGACCGCATGAAGA
TCCGCACCTGGCACAGCCTGGTGAAGCACCACATGTACGTGAGCCGCCGCGC
CGACGGCTGGTTCTACCGCCACCACTACGAGAGCCGCCACCCCAAGGTGAGC
AGCGAGGTGCACATCCCCCTGGGCGACGCCCGCCTGGTGATCAAGACCTACT
GGGGCCTGCAGACCGGCGAGCGCGCCTGGCACCTGGGCCACGGCGTGAGCA
TCGAGTGGCGCCTGCGCCGCTACAGCACCCAGGTGGACCCCGACCTGACCGA
CCAGCTGATCCACATGCACTACTTCGACTGCTTCGCCGAGAGCGCCATCCGC
AAGGCCATCCTGGGCCAGATCGTGAGCCCCAAGTGCGACTACCAGGCCGGCC
ACAACAAGGTGGGCAGCCTGCAGTACCTGGCCCTGACCGCCCTGATCAAGCC
CAAGAAGATCAAGCCCCCCTGCCCAGCGTGCGCAAGCTGGTGGAGGACCGC
TGGAACAAGCCCCAGAAGACCCGCGGCCGCCGCGGCAACCACACCATGAAC
GGCCACTAG

FIGURE 84

Vif_TV2_C_ZAwt (SEQ ID NO:114)

ATGGAAAACAGATGGCAGGTGCTGATTGTGTGGCAGGTAGACAGGATGAAG
ATTAGAACATGGCACAGTTTAGTAAAGCACCATATGTATGTTTCGAGGAGAG
CTGATGGATGGTTCTACAGACATCATTATGAAAGCAGACACCCAAAAGTAAG
TTCAGAAGTACACATCCCATTAGGAGATGCCAGGTTAGTAATAAAAACATAT
TGGGGTCTGCAGACAGGAGAAAGAGCTTGGCATTTGGGTCACGGAGTCTCCA
TAGAATGGAGATTGAGAAGATATAGCACACAAGTAGACCCTGACCTGACAG
ACCAACTAATTCATATGCATTATTTTGATTGTTTTGCAGAATCTGCCATAAGG
AAAGCCATACTAGGACAGATAGTTAGCCCTAAGTGTGACTATCAAGCAGGAC
ATAACAAGGTAGGATCTCTACAATACTTGGCACTGACAGCATTGATAAAACC
AAAAAAGATAAAGCCACCTCTGCCTAGTGTTAGGAAATTAGTAGAGGATAGA
TGGAACAAGCCCCAGAAGACCAGGGGCCGCAGAGGGAACCATACAATGAAT
GGACACTAG

FIGURE 85

Vpr_TV2_C_ZAopt (SEQ ID NO:115)

ATGGAGCAGGCCCCCGAGGACCAGGGCCCCCAGCGCGAGCCCTACAACGAG
TGGACCCTGGAGCTGCTGGAGGAGCTGAAGCAGGAGGCCGTGCGCCACTTCC
CCCGCCCCTGGCTGCACAACCTGGGCCAGCACATCTACGAGACCTACGGCGA
CACCTGGACCGGCGTGGAGGCCATCATCCGCATCCTGCAGCAGCTGCTGTTC
ATCCACTTCCGCATCGGCTGCCACCACAGCCGCATCGGCATCCTGCGCCAGC
GCCGCGCCCGCAACGGCGCCAACCGCAGC

FIGURE 86

Vpr_TV2_C_ZAwt (SEQ ID NO:116)

ATGGAACAAGCCCCAGAAGACCAGGGGCCGCAGAGGGAACCATACAATGAA
TGGACACTAGAGCTTTTAGAAGAACTCAAGCAGGAAGCTGTCAGACACTTTC
CTAGACCATGGCTCCATAACTTAGGACAACATATCTATGAAACCTATGGAGA
TACTTGGACAGGAGTTGAAGCAATAATAAGAATCCTGCAACAATTACTGTTT
ATTCATTTCAGGATTGGGTGCCATCATAGCAGAATAGGCATTTTGCGACAGA
GAAGAGCAAGAAATGGAGCCAATAGATCC

FIGURE 87

Vpu_TV2_C_ZAopt (SEQ ID NO:117)

ATGCTGGACCTGACCGCCCGCATCGACAGCCGCCTGGGCATCGGCGCCCTGA
TCGTGGCCCTGATCATCGCCATCATCGTGTGGACCATCGTGTACATCGAGTAC
CGCAAGCTGGTGCGCCAGCGCAAGATCGACTGGCTGGTGAAGCGCATCCGCG
AGCGCGCCGAGGACAGCGGCAACGAGAGCGAGGGCGACACCGAGGAGCTGA
GCACCCTGGTGGACATGGGCCACCTGCGCCTGCTGGACGCCAACGACGTGTA
A

FIGURE 88

Vpu_TV2_C_ZAwt (SEQ ID NO:118)

ATGTTAGATTTAACTGCAAGAATAGATTCTAGATTAGGAATAGGAGCATTGA
TAGTAGCACTAATCATAGCAATAATAGTGTGGACCATAGTATATATAGAATA
TAGGAAATTGGTAAGGCAAAGGAAAATAGACTGGTTAGTTAAAAGGATTAG
GGAAAGAGCAGAAGACAGTGGCAATGAGAGCGAGGGGGATACTGAAGAATT
ATCGACACTGGTGGATATGGGGCATCTTAGGCTTTTGGATGCTAATGATGTGT
AA

FIGURE 89 gp120mod.TV1.delV2 (SEQ ID NO:119)

```
   1 gaattcatgc gcgtgatggg cacccagaag aactgccagc agtggtggat ctggggcatc
  61 ctgggcttct ggatgctgat gatctgcaac accgaggacc tgtgggtgac cgtgtactac
 121 ggcgtgcccg tgtggcgcga cgccaagacc accctgttct cgccagcga cgccaaggcc
 181 tacgagaccg aggtgcacaa cgtgtgggcc acccacgcct gcgtgcccac cgaccccaac
 241 ccccaggaga tcgtgctggg caacgtgacc gagaacttca catgtggaa gaacgacatg
 301 gccgaccaga tgcacgagga cgtgatcagc ctgtgggacc agagcctgaa gccctgcgtg
 361 aagctgaccc ccctgtgcgt gaccctgaac tgcaccgaca ccaacgtgac cggcaaccgc
 421 accgtgaccg gcaacagcac caacaacacc aacggcaccg gcatctacaa catcgaggag
 481 atgaagaact gcagcttcaa cgccggcgcc ggccgcctga tcaactgcaa caccagcacc
 541 atcacccagg cctgccccaa ggtgagcttc gaccccatcc ccatccacta ctgcgccccc
 601 gccggctacg ccatcctgaa gtgcaacaac aagaccttca cggcaccgg cccctgctac
 661 aacgtgagca ccgtgcagtg cacccacggc atcaagcccg tggtgagcac ccagctgctg
 721 ctgaacggca gcctggccga ggagggcatc atcatccgca gcgagaacct gaccgagaac
 781 accaagacca tcatcgtgca cctgaacgag agcgtggaga tcaactgcac ccgccccaac
 841 aacaacaccc gcaagagcgt gcgcatcggc cccggccagg ccttctacgc caccaacgac
 901 gtgatcggca acatccgcca ggcccactgc aacatcagca ccgaccgctg gaacaagacc
 961 ctgcagcagg tgatgaagaa gctgggcgag cacttcccca acaagaccat ccagttcaag
1021 ccccacgccg gcggcgacct ggagatcacc atgcacagct caactgccg cggcgagttc
1081 ttctactgca acaccagcaa cctgttcaac agcacctacc acagcaacaa cggcacctac
1141 aagtacaacg gcaacagcag cagccccatc accctgcagt gcaagatcaa gcagatcgtg
1201 cgcatgtggc agggcgtggg ccaggccacc tacgccccc ccatcgccgg caacatcacc
1261 tgccgcagca acatcaccgg catcctgctg acccgcgacg gcggcttcaa caccaccaac
1321 aacaccgaga ccttccgccc cggcggcggc gacatgcgcg acaactggcg cagcgagctg
1381 tacaagtaca aggtggtgga gatcaagccc ctgggcatcg cccccaccaa ggccaagcgc
1441 cgcgtggtgc agcgcgagaa gcgctaactc gag
```

FIGURE 90 gp140mod.TV1.delV2   (SEQ ID NO:120)

```
   1 gaattcatgc gcgtgatggg cacccagaag aactgccagc agtggtggat ctggggcatc
  61 ctgggcttct ggatgctgat gatctgcaac accgaggacc tgtgggtgac cgtgtactac
 121 ggcgtgcccg tgtggcgcga cgccaagacc accctgttct cgccagcga cgccaaggcc
 181 tacgagaccg aggtgcacaa cgtgtgggcc acccacgcct gcgtgcccac cgaccccaac
 241 ccccaggaga tcgtgctggg caacgtgacc gagaacttca acatgtggaa gaacgacatg
 301 gccgaccaga tgcacgagga cgtgatcagc ctgtgggacc agagcctgaa gccctgcgtg
 361 aagctgaccc ccctgtgcgt gaccctgaac tgcaccgaca ccaacgtgac cggcaaccgc
 421 accgtgaccg gcaacagcac caacaacacc aacggcaccg gcatctacaa catcgaggag
 481 atgaagaact gcagcttcaa cgccggcgcc ggccgcctga tcaactgcaa caccagcacc
 541 atcacccagg cctgccccaa ggtgagcttc gaccccatcc ccatcacta ctgcgccccc
 601 gccggctacg ccatcctgaa gtgcaacaac aagaccttca cggcaccgg ccctgctac
 661 aacgtgagca ccgtgcagtg cacccacggc atcaagcccg tggtgagcac ccagctgctg
 721 ctgaacggca gcctggccga ggagggcatc atcatccgca gcgagaacct gaccgagaac
 781 accaagacca tcatcgtgca cctgaacgag agcgtggaga tcaactgcac ccgccccaac
 841 aacaacaccc gcaagagcgt gcgcatcggc cccggccagg ccttctacgc caccaacgac
 901 gtgatcggca acatccgcca ggcccactgc aacatcagca ccgaccgctg aacaagacc
 961 ctgcagcagg tgatgaagaa gctgggcgag cacttcccca caagaccat ccagttcaag
1021 ccccacgccg gcggcgacct ggagatcacc atgcacagct tcaactgccg gcgcgagttc
1081 ttctactgca acaccagcaa cctgttcaac agcacctacc acagcaacaa cggcacctac
1141 aagtacaacg caacagcag cagccccatc accctgcagt gcaagatcaa gcagatcgtg
1201 cgcatgtggc agggcgtggg ccaggccacc tacgccccc ccatcgccgg caacatcacc
1261 tgccgcagca acatcaccgg catcctgctg acccgcgacg gcggcttcaa caccaccaac
1321 aacaccgaga ccttccgccc cggcggcggc gacatgcgcg acaactggcg cagcgagctg
1381 tacaagtaca aggtggtgga gatcaagccc ctgggcatcg cccccaccaa ggccaagcgc
1441 cgcgtggtgc agcgcgagaa gcgcgccgtg ggcatcggcg ccgtgttcct gggcttcctg
1501 ggcgccgccg cagcaccat gggcgccgcc agcatcaccc tgaccgtgca ggcccgccag
1561 ctgctgagcg gcatcgtgca gcagcagagc aacctgctga aggccatcga ggcccagcag
1621 cacatgctgc agctgaccgt gtggggcatc aagcagctgc aggcccgcgt gctggccatc
1681 gagcgctacc tgaaggacca gcagctgctg ggcatctggg gctgcagcgg ccgcctgatc
1741 tgcaccaccg ccgtgccctg gaacagcagc tggagcaaca gagcgagaa ggacatctgg
1801 gacaacatga cctggatgca gtgggaccgc gagatcagca actacaccgg cctgatctac
1861 aacctgctgg aggacagcca gaaccagcag gagaagaacg agaaggacct gctggagctg
1921 gacaagtgga caacctgtg gaactggttc gacatcagca ctggccctg gtacatctaa
1981 ctcgag
```

FIGURE 91 gp140mod.TV1.mut7.delV2 (SEQ ID NO:121)

```
   1 gaattcatgc gcgtgatggg cacccagaag aactgccagc agtggtggat ctggggcatc
  61 ctgggcttct ggatgctgat gatctgcaac accgaggacc tgtgggtgac cgtgtactac
 121 ggcgtgcccg tgtggcgcga cgccaagacc ccctgttct gcgccagcga cgccaaggcc
 181 tacgagaccg aggtgcacaa cgtgtgggcc acccacgcct gcgtgcccac cgaccccaac
 241 ccccaggaga tcgtgctggg caacgtgacc gagaacttca acatgtggaa gaacgacatg
 301 gccgaccaga tgcacgagga cgtgatcagc ctgtgggacc agagcctgaa gccctgcgtg
 361 aagctgaccc ccctgtgcgt gaccctgaac tgcaccgaca ccaacgtgac cggcaaccgc
 421 accgtgaccg gcaacagcac caacaacacc aacggcaccg gcatctacaa catcgaggag
 481 atgaagaact gcagcttcaa cgccggcgcc ggccgcctga tcaactgcaa caccagcacc
 541 atcacccagg cctgccccaa ggtgagcttc gacccatcc ccatccacta ctgcgccccc
 601 gccggctacg ccatcctgaa gtgcaacaac aagaccttca cggcaccgg cccctgctac
 661 aacgtgagca ccgtgcagtg cacccacggc atcaagcccg tggtgagcac ccagctgctg
 721 ctgaacggca gcctggccga ggagggcatc atcatccgca gcgagaacct gaccgagaac
 781 accaagacca tcatcgtgca cctgaacgag agcgtggaga tcaactgcac ccgccccaac
 841 aacaacaccc gcaagagcgt gcgcatcggc cccggccagg ccttctacgc caccaacgac
 901 gtgatcggca acatccgcca ggcccactgc aacatcagca ccgaccgctg gaacaagacc
 961 ctgcagcagg tgatgaagaa gctgggcgag cacttcccca acaagaccat ccagttcaag
1021 ccccacgccg gcggcgacct ggagatcacc atgcacagct caactgccg cggcgagttc
1081 ttctactgca acaccagcaa cctgttcaac agcacctacc acagcaacaa cggcacctac
1141 aagtacaacg gcaacagcag cagccccatc accctgcagt gcagatcaa gcagatcgtg
1201 cgcatgtggc agggcgtggg ccaggccacc tacgcccccc ccatcgccgg caacatcacc
1261 tgccgcagca acatcaccgg catcctgctg acccgcgacg gcggcttcaa caccaccaac
1321 aacaccgaga ccttccgccc cggcggcggc gacatgcgcg acaactggcg cagcgagctg
1381 tacaagtaca aggtggtgga gatcaagccc ctgggcatcg ccccaccaa ggccatcagc
1441 agcgtggtgc agagcgagaa gagcgccgtg ggcatcggcg ccgtgttcct gggcttcctg
1501 ggcgccgccg cagcaccat gggcgccgcc agcatcaccc tgaccgtgca ggcccgccag
1561 ctgctgagcg gcatcgtgca gcagcagagc aacctgctga ggccatcga ggcccagcag
1621 cacatgctgc agctgaccgt gtggggcatc aagcagctgc aggcccgcgt gctggccatc
1681 gagcgctacc tgaaggacca gcagctgctg ggcatctggg gctgcagcgg ccgcctgatc
1741 tgcaccaccg ccgtgccctg gaacagcagc tggagcaaca gagcgagaa ggacatctgg
1801 gacaacatga cctggatgca gtgggaccgc gagatcagca actacaccgg cctgatctac
1861 aacctgctgg aggacagcca gaaccagcag gagaagaacg agaaggacct gctggagctg
1921 gacaagtgga caacctgtg gaactggttc gacatcagca actggccctg gtacatctaa
1981 ctcgag
```

FIGURE 92 gp160mod.TV1.delV1V2 (SEQ ID NO:122)

```
   1 gaattcatgc gcgtgatggg cacccagaag aactgccagc agtggtggat ctggggcatc
  61 ctgggcttct ggatgctgat gatctgcaac accgaggacc tgtgggtgac cgtgtactac
 121 ggcgtgcccg tgtggcgcga cgccaagacc accctgttct cgccagcga cgccaaggcc
 181 tacgagaccg aggtgcacaa cgtgtgggcc acccacgcct gcgtgcccac cgaccccaac
 241 ccccaggaga tcgtgctggg caacgtgacc gagaacttca acatgtggaa gaacgacatg
 301 gccgaccaga tgcacgagga cgtgatcagc ctgtgggacc agagcctgaa gccctgcgtg
 361 aagctgaccc ccctgtgcgt gggcgccggc aactgcaaca ccagcaccat cacccaggcc
 421 tgccccaagg tgagcttcga ccccatcccc atccactact gcgcccccgc cggctacgcc
 481 atcctgaagt gcaacaacaa gaccttcaac ggcaccggcc ctgctacaa cgtgagcacc
 541 gtgcagtgca cccacggcat caagcccgtg gtgagcaccc agctgctgct gaacggcagc
 601 ctggccgagg agggcatcat catccgcagc gagaacctga ccgagaacac caagaccatc
 661 atcgtgcacc tgaacgagag cgtggagatc aactgcaccc gccccaacaa caacacccgc
 721 aagagcgtgc gcatcggccc cggccaggcc ttctacgcca ccaacgacgt gatcggcaac
 781 atccgccagg cccactgcaa catcagcacc gaccgctgga caagaccct gcagcaggtg
 841 atgaagaagc tgggcgagca cttccccaac aagaccatcc agttcaagcc ccacgccggc
 901 ggcgacctgg agatcaccat gcacagcttc aactgccgcg gcgagttctt ctactgcaac
 961 accagcaacc tgttcaacag cacctaccac agcaacaacg gcacctacaa gtacaacggc
1021 aacagcagca gccccatcac cctgcagtgc aagatcaagc agatcgtgcg catgtggcag
1081 ggcgtgggcc aggccaccta cgccccccc atcgccggca acatcacctg ccgcagcaac
1141 atcaccggca tcctgctgac ccgcgacggc ggcttcaaca ccaccaacaa caccgagacc
1201 ttccgccccg gcggcggcga catgcgcgac aactggcgca gcgagctgta caagtacaag
1261 gtggtggaga tcaagcccct gggcatcgcc ccaccaagg ccaagcgccg cgtggtgcag
1321 cgcgagaagc gcgccgtggg catcggcgcc gtgttcctgg gcttcctggg cgccgccggc
1381 agcaccatgg gcgccgccag catcaccctg accgtgcagg cccgccagct gctgagcggc
1441 atcgtgcagc agcagagcaa cctgctgaag gccatcgagg cccagcagca catgctgcag
1501 ctgaccgtgt ggggcatcaa gcagctgcag gcccgcgtgc tggccatcga gcgctacctg
1561 aaggaccagc agctgctggg catctggggc tgcagcggcc gctgatctg caccaccgcc
1621 gtgccctgga acagcagctg gagcaacaag agcgagaagg acatctggga caacatgacc
1681 tggatgcagt gggaccgcga gatcagcaac tacaccggcc tgatctacaa cctgctggag
1741 gacagccaga accagcagga gaagaacgag aaggacctgc tggagctgga caagtggaac
1801 aacctgtgga actggttcga catcagcaac tggccctggt acatcaagat cttcatcatg
1861 atcgtgggcg gcctgatcgg cctgcgcatc atcttcgccg tgctgagcat cgtgaaccgc
1921 gtgcgccagg gctacagccc cctgagcttc cagaccctga cccccagccc ccgcggcctg
1981 gaccgcctgg gcggcatcga ggaggagggc ggcgagcagg accgcgaccg cagcatccgc
2041 ctggtgagcg gcttcctgag cctggcctgg gacgacctgc gcaacctgtg cctgttcagc
2101 taccaccgcc tgcgcgactt catcctgatc gccgtgcgcg ccgtggagct gctgggccac
2161 agcagcctgc gcggcctgca gcgcggctgg gagatcctga agtacctggg cagcctggtg
2221 cagtactggg gcctggagct gaagaagagc gccatcagcc tgctggacac catcgccatc
2281 accgtggccg agggcaccga ccgcatcatc gagctggtgc agcgcatctg ccgcgccatc
2341 ctgaacatcc ccgccgcat ccgccagggc ttcgaggccg ccctgctgta actcgag
```

FIGURE 93 gp160mod.TV1.delV2 (SEQ ID NO:123)

```
   1 gaattcatgc gcgtgatggg cacccagaag aactgccagc agtggtggat ctggggcatc
  61 ctgggcttct ggatgctgat gatctgcaac accgaggacc tgtgggtgac cgtgtactac
 121 ggcgtgcccg tgtggcgcga cgccaagacc accctgttct gcgccagcga cgccaaggcc
 181 tacgagaccg aggtgcacaa cgtgtgggcc acccacgcct gcgtgcccac cgaccccaac
 241 ccccaggaga tcgtgctggg caacgtgacc gagaacttca acatgtggaa gaacgacatg
 301 gccgaccaga tgcacgagga cgtgatcagc ctgtgggacc agagcctgaa gccctgcgtg
 361 aagctgaccc ccctgtgcgt gaccctgaac tgcaccgaca ccaacgtgac cggcaaccgc
 421 accgtgaccg gcaacagcac caacaacacc aacggcaccg catctacaa catcgaggag
 481 atgaagaact gcagcttcaa cgccggcgcc ggccgcctga tcaactgcaa caccagcacc
 541 atcacccagg cctgccccaa ggtgagcttc gaccccatcc ccatccacta ctgcgccccc
 601 gccggctacg ccatcctgaa gtgcaacaac aagaccttca cggcaccgg ccctgctac
 661 aacgtgagca ccgtgcagtg cacccacggc atcaagcccg tggtgagcac ccagctgctg
 721 ctgaacggca gcctggccga ggagggcatc atcatccgca gcgagaacct gaccgagaac
 781 accaagacca tcatcgtgca cctgaacgag agcgtggaga tcaactgcac ccgccccaac
 841 aacaacaccc gcaagagcgt gcgcatcggc cccggccagg ccttctacgc caccaacgac
 901 gtgatcggca acatccgcca ggcccactgc aacatcagca ccgaccgctg gaacaagacc
 961 ctgcagcagg tgatgaagaa gctgggcgag cacttcccca caagaccat ccagttcaag
1021 ccccacgccg gcggcgacct ggagatcacc atgcacagct caactgccg cggcgagttc
1081 ttctactgca caccagcaa cctgttcaac agcacctacc acagcaacaa cggcacctac
1141 aagtacaacg gcaacagcag cagccccatc accctgcagt gcaagatcaa gcagatcgtg
1201 cgcatgtggc agggcgtggg ccaggccacc tacgcccccc ccatcgccgg caacatcacc
1261 tgccgcagca acatcaccgg catcctgctg acccgcgacg cggcttcaa caccaccaac
1321 aacaccgaga ccttccgccc cggcggcggc gacatgcgcg acaactggcg cagcgagctg
1381 tacaagtaca aggtggtgga gatcaagccc ctgggcatcg cccccaccaa ggccaagcgc
1441 cgcgtggtgc agcgcgagaa gcgcgccgtg gcatcggcg ccgtgttcct gggcttcctg
1501 ggcgccgccg gcagcaccat gggcgccgcc agcatcaccc tgaccgtgca ggcccgccag
1561 ctgctgagcg gcatcgtgca gcagcagagc aacctgctga aggccatcga ggcccagcag
1621 cacatgctgc agctgaccgt gtggggcatc aagcagctgc aggcccgcgt gctggccatc
1681 gagcgctacc tgaaggacca gcagctgctg ggcatctggg gctgcagcgg ccgcctgatc
1741 tgcaccaccg ccgtgccctg gaacagcagc tggagcaaca agagcgagaa ggacatctgg
1801 gacaacatga cctggatgca gtgggaccgc gagatcagca actacaccgg cctgatctac
1861 aacctgctgg aggacagcca gaaccagcag gagaagaacg agaaggacct gctggagctg
1921 gacaagtgga caacctgtg gaactggttc gacatcagca ctggccctg gtacatcaag
1981 atcttcatca tgatcgtggg cggcctgatc ggcctgcgca tcatcttcgc cgtgctgagc
2041 atcgtgaacc gcgtgcgcca gggctacagc cccctgagct tccagaccct gacccccagc
2101 ccccgcggcc tggaccgcct gggcggcatc gaggaggagg cggcgagca ggaccgcgac
2161 cgcagcatcc gcctggtgag cggcttcctg agcctggcct gggacgacct gcgcaacctg
2221 tgcctgttca gctaccaccg cctgcgcgac ttcatcctga tgccgtgcg cgccgtggag
2281 ctgctgggcc acagcagcct gcgcggcctg cagcgcggct gggagatcct gaagtacctg
2341 ggcagcctgg tgcagtactg gggcctggag ctgaagaaga gcgccatcag cctgctggac
2401 accatcgcca tcaccgtggc cgagggcacc gaccgcatca tcgagctggt gcagcgcatc
2461 tgccgcgcca tcctgaacat ccccgccgc atccgccagg cttcgaggc cgccctgctg
2521 taactcgag
```

FIGURE 94 gp160mod.TV1.mut7.delV2 (SEQ ID NO:124)

```
   1 gaattcatgc gcgtgatggg cacccagaag aactgccagc agtggtggat ctggggcatc
  61 ctgggcttct ggatgctgat gatctgcaac accgaggacc tgtgggtgac cgtgtactac
 121 ggcgtgcccg tgtggcgcga cgccaagacc accctgttct gcgccagcga cgccaaggcc
 181 tacgagaccg aggtgcacaa cgtgtgggcc acccacgcct gcgtgcccac cgaccccaac
 241 ccccaggaga tcgtgctggg caacgtgacc gagaacttca catgtggaa gaacgacatg
 301 gccgaccaga tgcacgagga cgtgatcagc ctgtgggacc agagcctgaa gccctgcgtg
 361 aagctgaccc ccctgtgcgt gaccctgaac tgcaccgaca ccaacgtgac cggcaaccgc
 421 accgtgaccg gcaacagcac caacaacacc aacggcaccg gcatctacaa catcgaggag
 481 atgaagaact gcagcttcaa cgccggcgcc ggccgcctga tcaactgcaa caccagcacc
 541 atcacccagg cctgccccaa ggtgagcttc gaccccatcc ccatccacta ctgcgccccc
 601 gccggctacg ccatcctgaa gtgcaacaac aagaccttca acggcaccgg ccctgctac
 661 aacgtgagca ccgtgcagtg cacccacggc atcaagcccg tggtgagcac ccagctgctg
 721 ctgaacggca gcctggccga ggagggcatc atcatccgca gcgagaacct gaccgagaac
 781 accaagacca tcatcgtgca cctgaacgag agcgtggaga tcaactgcac ccgccccaac
 841 aacaacaccc gcaagagcgt gcgcatcggc cccggccagg ccttctacgc caccaacgac
 901 gtgatcggca acatccgcca ggcccactgc aacatcagca ccgaccgctg gaacaagacc
 961 ctgcagcagg tgatgaagaa gctgggcgag cacttcccca acaagaccat ccagttcaag
1021 ccccacgccg gcggcgacct ggagatcacc atgcacagct caactgccg cggcgagttc
1081 ttctactgca caccagcaa cctgttcaac agcacctacc acagcaacaa cggcacctac
1141 aagtacaacg gcaacagcag cagccccatc accctgcagt gcagatcaa gcagatcgtg
1201 cgcatgtggc agggcgtggg ccaggccacc tacgcccccc ccatcgccgg caacatcacc
1261 tgccgcagca acatcaccgg catcctgctg acccgcgacg gcggcttcaa caccaccaac
1321 aacaccgaga ccttccgccc cggcggcggc gacatgcgcg acaactggcg cagcgagctg
1381 tacaagtaca aggtggtgga gatcaagccc ctgggcatcg cccccaccaa ggccatcagc
1441 agcgtggtgc agagcgagaa gagcgccgtg ggcatcggcg ccgtgttcct gggcttcctg
1501 ggcgccgccg gcagcaccat gggcgccgcc agcatcaccc tgaccgtgca ggcccgccag
1561 ctgctgagcg gcatcgtgca gcagcagagc aacctgctga ggccatcga ggcccagcag
1621 cacatgctgc agctgaccgt gtggggcatc aagcagctgc aggcccgcgt gctggccatc
1681 gagcgctacc tgaaggacca gcagctgctg ggcatctggg gctgcagcgg ccgcctgatc
1741 tgcaccaccg ccgtgccctg gaacagcagc tggagcaaca gagcgagaa ggacatctgg
1801 gacaacatga cctggatgca gtgggaccgc gagatcagca actacaccgg cctgatctac
1861 aacctgctgg aggacagcca gaaccagcag gagaagaacg agaaggacct gctggagctg
1921 gacaagtgga acaacctgtg gaactggttc gacatcagca ctggccctg gtacatcaag
1981 atcttcatca tgatcgtggg cggcctgatc ggcctgcgca tcatcttcgc cgtgctgagc
2041 atcgtgaacc gcgtgcgcca gggctacagc cccctgagct ccagaccct gacccccagc
2101 cccgcggcc tggaccgcct gggcggcatc gaggaggagg cggcgagca ggaccgcgac
2161 cgcagcatcc gcctggtgag cggcttcctg agcctggcct gggacgacct gcgcaacctg
2221 tgcctgttca gctaccaccg cctgcgcgac ttcatcctga tgccgtgcg cgccgtggag
2281 ctgctgggcc acagcagcct gcgcggcctg cagcgcggct gggagatcct gaagtacctg
2341 ggcagcctgg tgcagtactg gggcctggag ctgaagaaga gcgccatcag cctgctggac
2401 accatcgcca tccgtggc cgagggcacc gaccgcatca tcgagctggt gcagcgcatc
2461 tgccgcgcca tcctgaacat cccccgccgc atccgccagg gcttcgaggc cgccctgctg
2521 taactcgag
```

FIGURE 95 gp160mod.TV1.tpa1 (SEQ ID NO:125)

1 gtcgacgcca ccatggatgc aatgaagaga gggctctgct gtgtgctgct gctgtgtgga
61 gcagtcttcg tttcgcccag cgccagcacc gaggacctgt gggtgaccgt gtactacggc
121 gtgcccgtgt ggcgcgacgc caagaccacc ctgttctgcg ccagcgacgc caaggcctac
181 gagaccgagg tgcacaacgt gtgggccacc cacgcctgcg tgcccaccga ccccaacccc
241 caggagatcg tgctgggcaa cgtgaccgag aacttcaaca tgtggaagaa cgacatggcc
301 gaccagatgc acgaggacgt gatcagcctg tgggaccaga gcctgaagcc ctgcgtgaag
361 ctgacccccc tgtgcgtgac cctgaactgc accgacacca acgtgaccgg caaccgcacc
421 gtgaccggca acagcaccaa caacaccaac ggcaccggca tctacaacat cgaggagatg
481 aagaactgca gcttcaacgc caccaccgag ctgcgcgaca agaagcacaa ggagtacgcc
541 ctgttctacc gcctggacat cgtgcccctg aacgagaaca gcgacaactt cacctaccgc
601 ctgatcaact gcaacaccag caccatcacc caggcctgcc ccaaggtgag cttcgacccc
661 atccccatcc actactgcgc ccccgccggc tacgccatcc tgaagtgcaa caacaagacc
721 ttcaacggca ccggcccctg ctacaacgtg agcaccgtgc agtgcaccca cggcatcaag
781 cccgtggtga gcacccagct gctgctgaac ggcagcctgg ccgaggaggg catcatcatc
841 cgcagcgaga acctgaccga gaacaccaag accatcatcg tgcacctgaa cgagagcgtg
901 gagatcaact gcacccgccc caacaacaac acccgcaaga gcgtgcgcat cggccccggc
961 caggccttct acgccaccaa cgacgtgatc ggcaacatcc gccaggccca ctgcaacatc
1021 agcaccgacc gctggaacaa gaccctgcag caggtgatga agaagctggg cgagcacttc
1081 cccaacaaga ccatccagtt caagccccac gccggcggcg acctggagat caccatgcac
1141 agcttcaact gccgcggcga gttcttctac tgcaacacca gcaacctgtt caacagcacc
1201 taccacagca acaacggcac ctacaagtac aacggcaaca gcagcagccc catcaccctg
1261 cagtgcaaga tcaagcagat cgtgcgcatg tggcagggcg tgggccaggc cacctacgcc
1321 ccccccatcg ccggcaacat cacctgccgc agcaacatca ccggcatcct gctgacccgc
1381 gacggcggct tcaacaccac caacaacacc gagaccttcc gccccggcgg cggcgacatg
1441 cgcgacaact ggcgcagcga gctgtacaag tacaaggtgg tggagatcaa gcccctgggc
1501 atcgccccca ccaaggccaa gcgccgcgtg gtgcagcgcg agaagcgcgc cgtgggcatc
1561 ggcgccgtgt tcctgggctt cctgggcgcc gccggcagca ccatgggcgc cgccagcatc
1621 accctgaccg tgcaggcccg ccagctgctg agcggcatcg tgcagcagca gagcaacctg
1681 ctgaaggcca tcgaggccca gcagcacatg ctgcagctga ccgtgtgggg catcaagcag
1741 ctgcaggccc gcgtgctggc catcgagcgc tacctgaagg accagcagct gctgggcatc
1801 tggggctgca gcggccgcct gatctgcacc accgccgtgc cctggaacag cagctggagc
1861 aacaagagcg agaaggacat ctgggacaac atgacctgga tgcagtggga ccgcgagatc
1921 agcaactaca ccggcctgat ctacaacctg ctggaggaca gccagaacca gcaggagaag
1981 aacgagaagg acctgctgga gctggacaag tggaacaacc tgtggaactg gttcgacatc
2041 agcaactggc cctggtacat caagatcttc atcatgatcg tgggcggcct gatcggcctg
2101 cgcatcatct tcgccgtgct gagcatcgtg aaccgcgtgc gccagggcta cagccccctg
2161 agcttccaga ccctgacccc cagcccccgc ggcctggacc gcctgggcgg catcgaggag
2221 gagggcggcg agcaggaccg cgaccgcagc atccgcctgg tgagcggctt cctgagcctg
2281 gcctgggacg acctgcgcaa cctgtgcctg ttcagctacc accgcctgcg cgacttcatc
2341 ctgatcgccg tgcgcgccgt ggagctgctg ggccacagca gcctgcgcgg cctgcagcgc
2401 ggctgggaga tcctgaagta cctgggcagc ctggtgcagt actggggcct ggagctgaag
2461 aagagcgcca tcagcctgct ggacaccatc gccatcaccg tggccgaggg caccgaccgc
2521 atcatcgagc tggtgcagcg catctgccgc gccatcctga acatcccccg ccgcatccgc
2581 cagggcttcg aggccgccct gctgtaactc gag

FIGURE 96 gp160mod.TV1 (SEQ ID NO:126)

```
   1 gaattcatgc gcgtgatggg cacccagaag aactgccagc agtggtggat ctggggcatc
  61 ctgggcttct ggatgctgat gatctgcaac accgaggacc tgtgggtgac cgtgtactac
 121 ggcgtgcccg tgtggcgcga cgccaagacc accctgttct gcgccagcga cgccaaggcc
 181 tacgagaccg aggtgcacaa cgtgtgggcc acccacgcct gcgtgcccac cgaccccaac
 241 ccccaggaga tcgtgctggg caacgtgacc gagaacttca catgtggaa gaacgacatg
 301 gccgaccaga tgcacgagga cgtgatcagc ctgtgggacc agagcctgaa gccctgcgtg
 361 aagctgaccc ccctgtgcgt gaccctgaac tgcaccgaca ccaacgtgac cggcaaccgc
 421 accgtgaccg gcaacagcac caacaacacc aacggcaccg gcatctacaa catcgaggag
 481 atgaagaact gcagcttcaa cgccaccacc gagctgcgcg acaagaagca caggagtac
 541 gccctgttct accgcctgga catcgtgccc ctgaacgaga acagcgacaa cttcacctac
 601 cgcctgatca actgcaacac cagcaccatc acccaggcct gccccaaggt gagcttcgac
 661 cccatcccca tccactactg cgcccccgcc ggctacgcca tcctgaagtg caacaacaag
 721 accttcaacg gcaccggccc ctgctacaac gtgagcaccg tgcagtgcac ccacggcatc
 781 aagcccgtgg tgagcaccca gctgctgctg aacggcagcc tggccgagga gggcatcatc
 841 atccgcagcg agaacctgac cgagaacacc aagaccatca tcgtgcacct gaacgagagc
 901 gtggagatca actgcacccg ccccaacaac aacacccgca gagcgtgcg catcggcccc
 961 ggccaggcct ctacgccac caacgacgtg atcggcaaca tccgccaggc ccactgcaac
1021 atcagcaccg accgctggaa caagaccctg cagcaggtga tgaagaagct gggcgagcac
1081 ttccccaaca agaccatcca gttcaagccc cacgccggcg cgacctgga tcaccatg
1141 cacagcttca ctgccgcgg cgagttcttc tactgcaaca ccagcaacct gttcaacagc
1201 acctaccaca gcaacaacgg cacctacaag tacaacggca acagcagcag ccccatcacc
1261 ctgcagtgca agatcaagca gatcgtgcgc atgtggcagg gcgtgggcca ggccacctac
1321 gccccccca tcgccggcaa catcacctgc cgcagcaaca tcaccggcat cctgctgacc
1381 cgcgacggcg gcttcaacac caccaacaac accgagacct tccgccccgg cggcggcgac
1441 atgcgcgaca ctggcgcag cgagctgtac aagtacaagg tggtggagat caagcccctg
1501 ggcatcgccc ccaccaaggc caagcgccgc gtggtgcagc gcgagaagcg cgccgtgggc
1561 atcggcgccg tgttcctggg cttcctgggc gccgccggca gcaccatggg cgccgccagc
1621 atcaccctga ccgtgcaggc ccgccagctg ctgagcggca tcgtgcagca gcagagcaac
1681 ctgctgaagg ccatcgaggc ccagcagcac atgctgcagc tgaccgtgtg gggcatcaag
1741 cagctgcagg cccgcgtgct ggccatcgag cgctacctga aggaccagca gctgctgggc
1801 atctggggct gcagcggccg cctgatctgc accaccgccg tgccctggaa cagcagctgg
1861 agcaacaaga gcgagaagga catctgggac aacatgacct ggatgcagtg ggaccgcgag
1921 atcagcaact acaccggcct gatctacaac ctgctggagg acagccagaa ccagcaggag
1981 aagaacgaga aggacctgct ggagctggac aagtggaaca acctgtggaa ctggttcgac
2041 atcagcaact ggccctggta catcaagatc ttcatcatga tcgtgggcgg cctgatcggc
2101 ctgcgcatca tcttcgccgt gctgagcatc gtgaaccgcg tgcgccaggg ctacagcccc
2161 ctgagcttcc agaccctgac ccccagcccc cgcggcctgg accgcctggg cggcatcgag
2221 gaggagggcg gcgagcagga ccgcgaccgc agcatccgcc tggtgagcgg cttcctgagc
2281 ctggcctggg acgacctgcg caacctgtgc ctgttcagct accaccgcct gcgcgacttc
2341 atcctgatcg ccgtgcgcgc cgtggagctg ctgggccaca gcagcctgcg cggcctgcag
2401 cgcggctggg agatcctgaa gtacctgggc agcctggtgc agtactgggg cctggagctg
2461 aagaagagcg ccatcagcct gctggacacc atcgccatca ccgtggccga gggcaccgac
2521 cgcatcatcg agctggtgca gcgcatctgc cgcgccatcc tgaacatccc ccgccgcatc
2581 cgccagggct cgaggccgc cctgctgtaa ctcgag
```

FIGURE 97 gp160mod.TV1.wtLnative (SEQ ID NO:127)

```
   1 gaattcatga gagtgatggg gacacagaag aattgtcaac aatggtggat atggggcatc
  61 ttaggcttct ggatgctaat gatttgtaac accgaggacc tgtgggtgac cgtgtactac
 121 ggcgtgcccg tgtggcgcga cgccaagacc accctgttct gcgccagcga cgccaaggcc
 181 tacgagaccg aggtgcacaa cgtgtgggcc acccacgcct gcgtgcccac cgaccccaac
 241 ccccaggaga tcgtgctggg caacgtgacc gagaacttca acatgtggaa gaacgacatg
 301 gccgaccaga tgcacgagga cgtgatcagc ctgtgggacc agagcctgaa gccctgcgtg
 361 aagctgaccc ccctgtgcgt gaccctgaac tgcaccgaca ccaacgtgac cggcaaccgc
 421 accgtgaccg gcaacagcac caacaacacc aacggcaccg gcatctacaa catcgaggag
 481 atgaagaact gcagcttcaa cgccaccacc gagctgcgcg acaagaagca caaggagtac
 541 gccctgttct accgcctgga catcgtgccc ctgaacgaga cagcgacaa cttcacctac
 601 cgcctgatca actgcaacac cagcaccatc acccaggcct gccccaaggt gagcttcgac
 661 cccatcccca tccactactg cgccccccgcc ggctacgcca tcctgaagtg caacaacaag
 721 accttcaacg gcaccggccc ctgctacaac gtgagcaccg tgcagtgcac ccacggcatc
 781 aagcccgtgg tgagcaccca gctgctgctg aacggcagcc tggccgagga gggcatcatc
 841 atccgcagcg agaacctgac cgagaacacc aagaccatca tcgtgcacct gaacgagagc
 901 gtggagatca actgcacccg ccccaacaac aacacccgca gagcgtgcg catcggcccc
 961 ggccaggcct tctacgccac caacgacgtg atcggcaaca tccgccaggc ccactgcaac
1021 atcagcaccg accgctggaa caagaccctg cagcaggtga tgaagaagct gggcgagcac
1081 ttccccaaca agaccatcca gttcaagccc cacgccggcg gcgacctgga gatcaccatg
1141 cacagcttca ctgccgcgg cgagttcttc tactgcaaca ccagcaacct gttcaacagc
1201 acctaccaca gcaacaacgg cacctacaag tacaacggca acagcagcag ccccatcacc
1261 ctgcagtgca gatcaagca gatcgtgcgc atgtggcagg gcgtgggcca ggccacctac
1321 gccccccccca tcgccggcaa catcacctgc cgcagcaaca tcaccggcat cctgctgacc
1381 cgcgacggcg gcttcaacac caccaacaac accgagacct tccgccccgg cggcggcgac
1441 atgcgcgaca actggcgcag cgagctgtac aagtacaagg tggtggagat caagcccctg
1501 ggcatcgccc ccaccaaggc caagcgccgc gtggtgcagc gcgagaagcg cgccgtgggc
1561 atcggcgccg tgttcctggg cttcctgggc gccgccggca gcaccatggg cgccgccagc
1621 atcaccctga ccgtgcaggc ccgccagctg ctgagcggca tcgtgcagca gcagagcaac
1681 ctgctgaagg ccatcgaggc ccagcagcac atgctgcagc tgaccgtgtg gggcatcaag
1741 cagctgcagg cccgcgtgct ggccatcgag cgctacctga aggaccagca gctgctgggc
1801 atctggggct gcagcggccg cctgatctgc accaccgccg tgccctggaa cagcagctgg
1861 agcaacaaga gcgagaagga catctgggac aacatgacct ggatgcagtg ggaccgcgag
1921 atcagcaact acaccggcct gatctacaac ctgctggagg acagccagaa ccagcaggag
1981 aagaacgaga aggacctgct ggagctggac aagtggaaca cctgtggaa ctggttcgac
2041 atcagcaact ggccctggta catcaagatc ttcatcatga tcgtgggcgg cctgatcggc
2101 ctgcgcatca tcttcgccgt gctgagcatc gtgaaccgcg tgcgccaggg ctacagcccc
2161 ctgagcttcc agaccctgac ccccagcccc cgcggcctgg accgcctggg cggcatcgag
2221 gaggagggcg gcgagcagga ccgcgaccgc agcatccgcc tggtgagcgg cttcctgagc
2281 ctggcctggg acgacctgcg caacctgtgc ctgttcagct accaccgcct gcgcgacttc
2341 atcctgatcg ccgtgcgcgc cgtggagctg ctgggccaca gcagcctgcg cggcctgcag
2401 cgcggctggg agatcctgaa gtacctgggc agcctggtgc agtactgggg cctggagctg
2461 aagaagagcg ccatcagcct gctggacacc atcgccatca ccgtggccga gggcaccgac
2521 cgcatcatcg agctggtgca gcgcatctgc cgcgccatcc tgaacatccc ccgccgcatc
2581 cgccagggct cgaggccgc cctgctgtaa ctcgag
```

FIGURE 98

Wild-type Env gp160 (8_2_ZA) (SEQ ID NO:128)

```
   1 atgagagtga tggggacaca gaagaattgt caacaatggt ggatatgggg catcttaggc
  61 ttctggatgc taatgatttg taacacggag gacttgtggg tcacagtcta ctatggggta
 121 cctgtgtgga gagacgcaaa aactactcta ttctgtgcat cagatgctaa agcatatgag
 181 acagaagtgc ataatgtctg ggctacacat gcctgtgtac ccacagaccc caacccacaa
 241 gaaatagttt tgggaaatgt aacagaaaat tttaatatgt ggaaaaatga catggcagat
 301 cagatgcatg aggatgtaat cagtttatgg gatcaaagcc taaagccatg tgtaaagttg
 361 accccactct gtgtcacttt aaactgtaca gatacaaatg ttacaggtaa tagaactgtt
 421 acaggtaata gtaccaataa tacaaatggt acaggtattt ataacattga gaaaatgaaa
 481 aattgctctt tcaatgcaac cacagaatta agagataaga acataaaga gtatgcactc
 541 ttttatagac ttgatatagt accacttaat gagaatagtg acaacttt a c atatagatta
 601 ataaattgca ataccctcaac cataacacaa gcctgtccaa aggtctcttt tgacccgatt
 661 cctatacatt actgtgctcc agctggttat gcgattctaa agtgtaataa taagacattc
 721 aatgggacag gaccatgtta taatgtcagc acagtacaat gtacacatgg aattaagcca
 781 gtggtatcaa ctcaattact gttaaatggt agtctagcag aagaagggat aataattaga
 841 tctgaaaaatt tgacagagaa taccaaaaca ataatagtac accttaatga atctgtagag
 901 attaattgta caagacccaa caataataca agaaaaagta taaggatagg accaggacaa
 961 gcattctatg caacaaatga tgtaatagga aacataagac aagcacattg taacattagt
1021 acagatagat ggaacaaaac tttacaacag gtaatgaaaa aattaggaga gcatttccct
1081 aataaaacaa tacaatttaa accacatgca ggaggggatc tagaaattac aatgcatagc
1141 tttaattgta gaggagaatt tttctattgt aatacatcaa acctgtttaa tagcacatac
1201 cactctaata tggtacata caaatacaat ggtaattcaa gctcacccat cacactccaa
1261 tgtaaaataa aacaaattgt acgcatgtgg caaggggtag gacaagcaac gtatgcccct
1321 cccattgcag gaaacataac atgtagatca aacatcacag gaatactatt gacacgtgat
1381 ggaggattta caccacaaa caacacagag acattcagac ctggaggagg agatatgagg
1441 gataactgga gaagtgaatt atataaatat aaagtagtag aaattaagcc attgggaata
1501 gcacccacta aggcaaaaag aagagtggtg cagagagaaa aaagagcagt gggaatagga
1561 gctgtgttcc ttgggttctt gggagcagca ggaagcacta tgggcgcagc gtcaataacg
1621 ctgacggtac aggccagaca actgttgtct ggtatagtgc aacagcaaag caatttgctg
1681 aaggctatag aggcgcaaca gcatatgttg caactcacag tctggggcat taagcagctc
1741 caggcgagag tcctggctat agaaagatac ctaaaggatc aacagctcct agggatttgg
1801 ggctgctctg gaagactcat ctgcaccact gctgtgcctt ggaactccag ttggagtaat
1861 aaatctgaaa aagatatttg ggataacatg acttggatgc agtgggatag agaaattagt
1921 aattacacag gcttaatata caatttgctt gaagactcgc aaaaccagca ggaaaagaat
1981 gaaaaagatt tattagaatt ggacaagtgg aacaatctgt ggaattggtt tgacatatca
2041 aactggccgt ggtatataaa aatattcata atgatagtag gaggcttgat aggtttaaga
2101 ataattttg ctgtgctttc tatagtgaat agagttaggc agggatactc accttgtca
2161 tttcagaccc ttaccccaag cccgagggga ctcgacaggc tcggaggaat cgaagaagaa
2221 ggtggagagc aagacagaga cagatccata cgattggtga gcggattctt gtcgcttgcc
2281 tgggacgatc tgcggaacct gtgcctcttc agctaccacc gcttgagaga cttcatatta
2341 attgcagtga gggcagtgga acttctggga cacagcagtc tcaggggact acagaggggg
2401 tgggaaatcc ttaagtatct gggaagtctt gtgcaatatt ggggtctaga gctaaaaaag
2461 agtgctatta gtctgcttga taccatagca ataacagtag ctgaaggaac agataggatt
2521 atagaattag tacaaagaat ttgtagagct atcctcaaca tacctagaag aataagacag
2581 ggctttgaag cagctttgct ataa
```

FIGURE 99 gp140mod.TV1.tpa1 (SEQ ID NO:131)

```
   1 atggatgcaa tgaagagagg gctctgctgt gtgctgctgc tgtgtggagc agtcttcgtt
  61 tcgcccagcg ccagcaccga ggacctgtgg gtgaccgtgt actacggcgt gcccgtgtgg
 121 cgcgacgcca agaccaccct gttctgcgcc agcgacgcca aggcctacga gaccgaggtg
 181 cacaacgtgt gggcacccca cgcctgcgtg cccaccgacc caaccccca ggagatcgtg
 241 ctgggcaacg tgaccgagaa cttcaacatg tggaagaacg acatggccga ccagatgcac
 301 gaggacgtga tcagcctgtg ggaccagagc ctgaagccct gcgtgaagct gacccccctg
 361 tgcgtgaccc tgaactgcac cgacaccaac gtgaccggca ccgcaccgt gaccggcaac
 421 agcaccaaca acaccaacgg caccggcatc tacaacatcg aggagatgaa gaactgcagc
 481 ttcaacgcca ccaccgagct gcgcgacaag aagcacaagg agtacgccct gttctaccgc
 541 ctggacatcg tgcccctgaa cgagaacagc gacaacttca cctaccgcct gatcaactgc
 601 aacaccagca ccatcaccca ggcctgcccc aaggtgagct cgaccccat ccccatccac
 661 tactgcgccc ccgccggcta cgccatcctg aagtgcaaca acaagacctt caacggcacc
 721 ggccccctgct acaacgtgag caccgtgcag tgcacccacg gcatcaagcc cgtggtgagc
 781 acccagctgc tgctgaacgg cagcctggcc gaggagggca tcatcatccg cagcgagaac
 841 ctgaccgaga acaccaagac catcatcgtg cacctgaacg agagcgtgga gatcaactgc
 901 acccgcccca caacaacac ccgcaagagc gtgcgcatcg ccccggcca ggccttctac
 961 gccaccaacg acgtgatcgg caacatccgc caggcccact gcaacatcag caccgaccgc
1021 tggaacaaga ccctgcagca ggtgatgaag aagctgggcg agcacttccc caacaagacc
1081 atccagttca gccccacgc cggcggcgac ctggagatca ccatgcacag cttcaactgc
1141 cgcggcgagt tcttctactg caacaccagc aacctgttca acagcaccta ccacagcaac
1201 aacggcacct acaagtacaa cggcaacagc agcagcccca tcaccctgca gtgcaagatc
1261 aagcagatcg tgcgcatgtg gcagggcgtg ggccaggcca cctacgcccc ccccatcgcc
1321 ggcaacatca cctgccgcag caacatcacc ggcatcctgc tgacccgcga cggcggcttc
1381 aacaccacca caacaccga ccttccgc ccggcggcg cgacatgcg cgacaactgg
1441 cgcagcgagc tgtacaagta caaggtggtg gagatcaagc ccctgggcat cgccccacc
1501 aaggccaagc gccgcgtggt gcagcgcgag aagcgcgccg tgggcatcgg cgccgtgttc
1561 ctgggcttcc tgggcgccgc cggcagcacc atgggcgccg ccagcatcac cctgaccgtg
1621 caggcccgcc agctgctgag cggcatcgtg cagcagcaga gcaacctgct gaaggccatc
1681 gaggcccagc agcacatgct gcagctgacc gtgtggggca tcaagcagct gcaggcccgc
1741 gtgctggcca tcgagcgcta cctgaaggac cagcagctgc tgggcatctg gggctgcagc
1801 ggccgcctga tctgcaccac cgccgtgccc tggaacagca gctggagcaa caagagcgag
1861 aaggacatct gggacaacat gacctggatg cagtgggacc gcgagatcag caactacacc
1921 ggcctgatct acaacctgct ggaggacagc cagaaccagc aggagaagaa cgagaaggac
1981 ctgctggagc tggacaagtg gaacaacctg tggaactggt tcgacatcag caactggccc
2041 tggtacatct aa
```

FIGURE 100 gp140mod.TV1 (SEQ ID NO:132)

```
   1 gaattcatgc gcgtgatggg cacccagaag aactgccagc agtggtggat ctggggcatc
  61 ctgggcttct ggatgctgat gatctgcaac accgaggacc tgtgggtgac cgtgtactac
 121 ggcgtgcccg tgtggcgcga cgccaagacc accctgttct cgccagcga cgccaaggcc
 181 tacgagaccg aggtgcacaa cgtgtgggcc acccacgcct gcgtgccac cgaccccaac
 241 ccccaggaga tcgtgctggg caacgtgacc gagaacttca catgtggaa gaacgacatg
 301 gccgaccaga tgcacgagga cgtgatcagc ctgtgggacc agagcctgaa gccctgcgtg
 361 aagctgaccc ccctgtgcgt gaccctgaac tgcaccgaca ccaacgtgac cggcaaccgc
 421 accgtgaccg gcaacagcac caacaacacc aacggcaccg catctacaa catcgaggag
 481 atgaagaact gcagcttcaa cgccaccacc gagctgcgcg acaagaagca caaggagtac
 541 gccctgttct accgcctgga catcgtgccc ctgaacgaga acagcgacaa cttcacctac
 601 cgcctgatca actgcaacac cagcaccatc acccaggcct gccccaaggt gagcttcgac
 661 cccatcccca tccactactg cgccccgcc ggctacgcca tcctgaagtg caacaacaag
 721 accttcaacg gcaccggccc ctgctacaac gtgagcaccg tgcagtgcac ccacggcatc
 781 aagcccgtgg tgagcaccca gctgctgctg aacggcagcc tggccgagga gggcatcatc
 841 atccgcagcg agaacctgac cgagaacacc aagaccatca tcgtgcacct gaacgagagc
 901 gtggagatca actgcacccg ccccaacaac aacacccgca gagcgtgcg catcggcccc
 961 ggccaggcct tctacgccac caacgacgtg atcggcaaca tccgccaggc ccactgcaac
1021 atcagcaccg accgctggaa caagaccctg cagcaggtga tgaagaagct gggcgagcac
1081 ttccccaaca agaccatcca gttcaagccc cacgccggcg cgacctgga tcaccatg
1141 cacagcttca ctgccgcgg cgagttcttc tactgcaaca ccagcaacct gttcaacagc
1201 acctaccaca gcaacaacgg cacctacaag tacaacggca acagcagcag ccccatcacc
1261 ctgcagtgca agatcaagca gatcgtgcgc atgtggcagg cgtgggcca ggccacctac
1321 gcccccccca tcgccggcaa catcacctgc cgcagcaaca tcaccggcat cctgctgacc
1381 cgcgacggcg gcttcaacac caccaacaac accgagacct tcgccccgg cggcggcgac
1441 atgcgcgaca actggcgcag cgagctgtac aagtacaagg tggtggagat caagcccctg
1501 ggcatcgccc ccaccaaggc caagcgccgc gtggtgcagc gcgagaagcg cgccgtgggc
1561 atcggcgccg tgttcctggg cttcctgggc gccgccggca gcaccatggg cgccgccagc
1621 atcaccctga ccgtgcaggc ccgccagctg ctgagcggca tcgtgcagca gcagagcaac
1681 ctgctgaagg ccatcgaggc ccagcagcac atgctgcagc tgaccgtgtg gggcatcaag
1741 cagctgcagg cccgcgtgct ggccatcgag cgctacctga aggaccagca gctgctgggc
1801 atctggggct gcagcggccg cctgatctgc accaccgccg tgccctggaa cagcagctgg
1861 agcaacaaga gcgagaagga catctgggac aacatgacct ggatgcagtg ggaccgcgag
1921 atcagcaact acaccggcct gatctacaac ctgctggagg acagccagaa ccagcaggag
1981 aagaacgaga aggacctgct ggagctggac aagtggaaca acctgtggaa ctggttcgac
2041 atcagcaact ggccctggta catctaactc gag
```

FIGURE 101 gp140mod.TV1.wtLnative (SEQ ID NO:133)

```
   1 gaattcatga gagtgatggg gacacagaag aattgtcaac aatggtggat atggggcatc
  61 ttaggcttct ggatgctaat gatttgtaac accgaggacc tgtgggtgac cgtgtactac
 121 ggcgtgcccg tgtggcgcga cgccaagacc accctgttct gcgccagcga cgccaaggcc
 181 tacgagaccg aggtgcacaa cgtgtgggcc acccacgcct gcgtgcccac cgaccccaac
 241 ccccaggaga tcgtgctggg caacgtgacc gagaacttca catgtggaa gaacgacatg
 301 gccgaccaga tgcacgagga cgtgatcagc ctgtgggacc agagcctgaa gccctgcgtg
 361 aagctgaccc ccctgtgcgt gaccctgaac tgcaccgaca ccaacgtgac cggcaaccgc
 421 accgtgaccg gcaacagcac caacaacacc aacggcaccg gcatctacaa catcgaggag
 481 atgaagaact gcagcttcaa cgccaccacc gagctgcgcg acaagaagca aggagtac
 541 gccctgttct accgcctgga catcgtgccc ctgaacgaga acagcgacaa cttcacctac
 601 cgcctgatca actgcaacac cagcaccatc acccaggcct gccccaaggt gagcttcgac
 661 cccatcccca tccactactg cgccccgcc ggctacgcca tcctgaagtg caacaacaag
 721 accttcaacg gcaccggccc tgctacaac gtgagcaccg tgcagtgcac ccacggcatc
 781 aagcccgtgg tgagcaccca gctgctgctg aacggcagcc tggccgagga gggcatcatc
 841 atccgcagcg agaacctgac cgagaacacc aagaccatca tcgtgcacct gaacgagagc
 901 gtggagatca actgcacccg ccccaacaac aacacccgca gagcgtgcg catcggcccc
 961 ggccaggcct ctacgccac caacgacgtg atcggcaaca tccgccaggc ccactgcaac
1021 atcagcaccg accgctggaa caagaccctg cagcaggtga tgaagaagct gggcgagcac
1081 ttccccaaca agaccatcca gttcaagccc cacgccggcg gcgacctgga gatcaccatg
1141 cacagcttca ctgccgcgg cgagttcttc tactgcaaca ccagcaacct gttcaacagc
1201 acctaccaca gcaacaacgg cacctacaag tacaacggca acagcagcag ccccatcacc
1261 ctgcagtgca gatcaagca gatcgtgcgc atgtggcagg cgtgggcca ggccacctac
1321 gcccccccca tcgccggcaa catcacctgc cgcagcaaca tcaccggcat cctgctgacc
1381 cgcgacggcg gcttcaacac caccaacaac accgagacct tccgccccgg cggcggcgac
1441 atgcgcgaca ctggcgcag cgagctgtac aagtacaagg tggtggagat caagcccctg
1501 ggcatcgccc ccaccaaggc caagcgccgc gtggtgcagc gcgagaagcg cgccgtgggc
1561 atcggcgccg tgttcctggg cttcctgggc gccgccggca gcaccatggg cgccgccagc
1621 atcaccctga ccgtgcaggc ccgccagctg ctgagcggca tcgtgcagca gcagagcaac
1681 ctgctgaagg ccatcgaggc ccagcagcac atgctgcagc tgaccgtgtg gggcatcaag
1741 cagctgcagg cccgcgtgct ggccatcgag cgctacctga aggaccagca gctgctgggc
1801 atctggggct gcagcggccg cctgatctgc accaccgccg tgccctggaa cagcagctgg
1861 agcaacaaga gcgagaagga catctgggac aacatgacct ggatgcagtg ggaccgcgag
1921 atcagcaact acaccggcct gatctacaac ctgctggagg acagccagaa ccagcaggag
1981 aagaacgaga aggacctgct ggagctggac aagtggaaca cctgtggaa ctggttcgac
2041 atcagcaact ggccctggta catctaactc gag
```

FIGURE 102

NefD125G_TV2_C_ZAopt (SEQ ID NO:134)

ATGGGCGGCAAGTGGAGCAAGAGCAGCATCATCGGCTGGCCCGAGGTGCGC
GAGCGCATCCGCCGCACCCGCAGCGCCGCCGAGGGCGTGGGCAGCGCCAGC
CAGGACCTGGAGAAGCACGGCGCCCTGACCACCAGCAACACCGCCCACAAC
AACGCCGCCTGCGCCTGGCTGGAGGCCCAGGAGGAGGAGGGCGAGGTGGGC
TTCCCCGTGCGCCCCAGGTGCCCCTGCGCCCCATGACCTACAAGGCCGCCAT
CGACCTGAGCTTCTTCCTGAAGGAGAAGGGCGGCCTGGAGGGCCTGATCTAC
AGCAAGAAGCGCCAGGAGATCCTGGACCTGTGGGTGTACAACACCCAGGGC
TTCTTCCCCGGCTGGCAGAACTACACCCCCGGCCCCGGCGTGCGCTTCCCCCT
GACCTTCGGCTGGTACTTCAAGCTGGAGCCCGTGGACCCCGCGAGGTGGAG
GAGGCCAACGAGGGCGAGAACAACTGCCTGCTGCACCCCATGAGCCAGCAC
GGCATGGAGGACGAGGACCGCGAGGTGCTGCGCTGGAAGTTCGACAGCACC
CTGGCCCGCCGCCACATGGCCCGCGAGCTGCACCCCGAGTACTACAAGGACT
GCTGA

FIGURE 103

NefD125G-Myr_TV2_C_ZAopt (SEQ ID NO:135)

ATGGCCGGCAAGTGGAGCAAGAGCAGCATCATCGGCTGGCCCGAGGTGCGC
GAGCGCATCCGCCGCACCCGCAGCGCCGCCGAGGGCGTGGGCAGCGCCAGC
CAGGACCTGGAGAAGCACGGCGCCCTGACCACCAGCAACACCGCCCACAAC
AACGCCGCCTGCGCCTGGCTGGAGGCCCAGGAGGAGGAGGGCGAGGTGGGC
TTCCCCGTGCGCCCCCAGGTGCCCCTGCGCCCCATGACCTACAAGGCCGCCAT
CGACCTGAGCTTCTTCCTGAAGGAGAAGGGCGGCCTGGAGGGCCTGATCTAC
AGCAAGAAGCGCCAGGAGATCCTGGACCTGTGGGTGTACAACACCCAGGGC
TTCTTCCCCGGCTGGCAGAACTACACCCCCGGCCCCGGCGTGCGCTTCCCCCT
GACCTTCGGCTGGTACTTCAAGCTGGAGCCCGTGGACCCCGCGAGGTGGAG
GAGGCCAACGAGGGCGAGAACAACTGCCTGCTGCACCCCATGAGCCAGCAC
GGCATGGAGGACGAGGACCGCGAGGTGCTGCGCTGGAAGTTCGACAGCACC
CTGGCCCGCCGCCACATGGCCCGCGAGCTGCACCCCGAGTACTACAAGGACT
GCTGA

FIGURE 104

↓: is the regions for β-sheet deletions

*: is the N-linked glycosylation sites for subtype C TV1 and TV2. Possible mutation (N→ Q) or deletions can be performed.

```
                 1                                                50
SF162       (1)  ----MDAMKRGLCCVLLLCGAVFVSPSAVEKLWVTVYYGVPVWKEATTTL
TV1.8_2     (1)  MRVMGTQKNCQQWWIWGILGFWMLMICNTEDLWVTVYYGVPVWREAKTTL
TV1.8_5     (1)  MRVMGTQKNCQQWWIWGILGFWMLMICNTEDLWVTVYYGVPVWREAKTTL
TV2.12-5/1  (1)  MRARGILKNYRHWWIWGILGFWMLMMCNVKGLWVTVYYGVPVGREAKTTL
Consensus   (1)  MRVMGTQKNCQQWWIWGILGFWMLMICNVEDLWVTVYYGVPVWREAKTTL 51                                              100
SF162       (47) FCASDAKAYDTEVHNVWATHACVPTDPNPQEIVLENVTENFNMWKNNMVE
TV1.8_2     (51) FCASDAKAYETEVHNVWATHACVPTDPNPQEIVLGNVTENFNMWKNDMAD
TV1.8_5     (51) FCASDAKAYETEVHNVWATHACVPTDPNPQEIVLGNVTENFNMWKNNMAD
TV2.12-5/1  (51) FCASDAKAYEKEVHNVWATHACVPTDPNPQEVVLGNVTENFNMWKNDMVD
Consensus   (51) FCASDAKAYETEVHNVWATHACVPTDPNPQEIVLGNVTENFNMWKNNMVD β2/V1V2/β3
                 101                                             150
SF162       (97) QMHEDIISLWDQSLKPCVKLTPLCVTLHCTNLKNATNTK-----SSN---
TV1.8_2    (101) QMHEDVISLWDQSLKPCVKLTPLCVTLNCTDTNVTGNRTVTGNSTNNTNG
TV1.8_5    (101) QMHEDIISLWDQSLKPCVKLTPLCVTLNCTDTNVTGNRTVTGNTNDTNIA
TV2.12-5/1 (101) QMQEDIISLWDQSLKPCVKLTPLCVTLNCTNATVNYN--------NTS---
Consensus  (101) QMHEDIISLWDQSLKPCVKLTPLCVTLNCTNTNVTGNRTVTGNSNSN   A 151                                            *200
SF162      (139) WKEMDRGEIKNCSFKVTTSIRNKMQKEYALFYKLDVVPIDN----DNTSY
TV1.8_2    (151) TGIYNIEEMKNCSFNATTELRDKKHKEYALFYKLDIVPLN--ENSDNFTY
TV1.8_5    (151) NATYKYEEMKNCSFNATTELRDKKHKEYALFYKLDIVPLN--ENSNNFTY
TV2.12-5/1 (141) ------KEMKNCSFYVTTELRDKKKKENALFYKLDIVPLNNRKNGNINNY
Consensus  (151)  A Y   EEMKNCSFNVTTELRDKKHKEYALFYKLDIVPLNN ENSNNFTY 201                                             250
SF162      (185) RLINCNTSVITQACPKVSFEPIPIHYCAPAGFAILKCNDKKFNGTGPCTN
TV1.8_2    (199) RLINCNTSTITQACPKVSFDPIPIHYCAPAGYAILKCNNKTFNGTGPCYN
TV1.8_5    (199) RLINCNTSTITQACPKVSFDPIPIHYCAPADYAILKCNNKTFNGTGPCYN
TV2.12-5/1 (185) RLINCNTSAITQACPKVSFDPIPIHYCAPAGYAPLKCNNKKFNGIGPCDN
Consensus  (201) RLINCNTSTITQACPKVSFDPIPIHYCAPAGYAILKCNNKTFNGTGPCYN 251                                             300
SF162      (235) VSTVQCTHGIRPVVSTQLLLNGSLAEEGVVIRSENFTDNAKTIIVQLKES
TV1.8_2    (249) VSTVQCTHGIKPVVSTQLLLNGSLAEEGIIIRSENLTENTKTIIVHLNES
TV1.8_5    (249) VSTVQCTHGIKPVVSTQLLLNGSLAEEGIIIRSENLTENTKTIIVHLNES
TV2.12-5/1 (235) VSTVQCTHGIKPVVSTQLLLNGSLAEEEIIIRSENLTNNVKTIIVHLNES
Consensus  (251) VSTVQCTHGIKPVVSTQLLLNGSLAEEGIIIRSENLTENTKTIIVHLNES 301*                                           *350
SF162      (285) VEINCTRPNNNTRKSITIGPGRAFYATGDIIGDIRQAHCNISGEKWNNTL
TV1.8_2    (299) VEINCTRPNNNTRKSVRIGPGQAFYATNDVIGNIRQAHCNISTDRWNKTL
TV1.8_5    (299) VEINCTRPNNNTRKSVRIGPGQAFYATNDVIGNIRQAHCNISTDRWNKTL
TV2.12-5/1 (285) IEIKCTRPGNNTRKSVRIGPGQAFYATGDIIGDIRQAHCNISKNEWNTTL
Consensus  (301) VEINCTRPNNNTRKSVRIGPGQAFYATNDIIGNIRQAHCNISTDRWNKTL
```

FIGURE 105A

```
                        351         *                              *    400
       SF162   (335) KQIVTKLQAQFGNKT-IVFKQSSGGPEIVM......G.........
       TV1.8_2 (349) QQVMKKLGEHFPNKT-IQFKPHA..L.ITM....R..P.YCNTSNL..
       TV1.8_5 (349) QQVMKKLGEHFPNKT-IKFEPHA..L.ITM....R..P.YCNTSNL..
      TV2.12-5/1 (335) QRVSQKLQELFPNSTGIKFAPH...L.ITT....G..P.YCNTTDL..
     Consensus (351) QQVMKKLQEHPPNKT IKFKPHA..L.ITM....R..P.YCNTSNL..

401      *         *           ↓  β20/β21  ↓   450
       SF162   (384) STWNN------TIGPN-NTNGT..P.RIK.INR..EV.K.MYA.P.R.
       TV1.8_2 (398) STYHS---NNGTYKYNGNSSSP..Q.KIK.IVRM..GQ.T.A.P.A.
       TV1.8_5 (398) STYYP---KNGTYKYNGNSSLP..Q.KIK.IVRM..GQ.M.A.P.A.
      TV2.12-5/1 (385) STYSNGTCTNGTCMSN--NTER..LQ.RIK.INM..EV.R.M.A.P.A.
     Consensus (401) STYHN    NGTYKYNGNSS PITLQCKIKQIIRMWQGVGQAMYAPPIAG

*
                       451     *           *    *                    500
       SF162   (427) QIRCS...........KEISNP--TI.R...D.......SELY....
       TV1.8_2 (445) NITCR...........FNTTNN--TET.R...D.R.NWRSELY....
       TV1.8_5 (445) NITCR...........FNNTNNDTE.T.R...D.R.NWRSELY....
      TV2.12-5/1 (433) NITCR...........DNNTET---ET.R...D.R.NWRSELY....
     Consensus (451) NITCRSNITGILLTRDGGFNNTNT  TETFRPGGGDMRDNWRSELYKYKV 501                                          550
       SF162   (475) K.E....A.TK.R..QRE.R.TL.A...........AR..T..
       TV1.8_2 (493) E.K.L.IA.TK.R..QRE.R.VGIGAVF.G..............
       TV1.8_5 (495) E.K.L..A.TK.R..QRK.R.VGIGAVF.G..............
      TV2.12-5/1 (480) E.K.L.VA.TA.R..E.E.R.VGIGAVF.G..............
     Consensus (501) VEIKPLGIAPTKAKRRVVQREKRAVGIGAVFLGFLGAAGSTMGAASITLT 551                                          600
       SF162   (525) .QAR.LLSG.VQQ.N.LRA.EAQ.Q.LQLTVWG.KQLQARV.A.ER..K
       TV1.8_2 (543) .QAR.LLSG.VQQ.SN.L.A.EAQQ.MLQLTVWG.KQLQARV.A.ER..K
       TV1.8_5 (545) .QAR.LLSG.VQQ.SN.L.A.EAQQ.MLQLTVWG.KQLQARV.A.ER..K
      TV2.12-5/1 (530) .QA..LLSG.VQQ.SN.L.A.EAQQ.MLQLTVWG.KQLQARV.A.ER..Q
     Consensus (551) VQARQLLSGIVQQQSNLLKAIEAQQHMLQLTVWGIKQLQARVLAIERYLK

*
                       601              *    *       *              650
       SF162   (575) DQ...I.........A.P.N.S.S.K.SLDQI....ME...D.
       TV1.8_2 (593) DQ..LGI..C...L.CTTA.PWNS.WSNK.SEKDI.D.TWMQDR.ISN.
       TV1.8_5 (595) DQ..LGI..C...L.CTTA.PWNS.WSNK.SEADI.D.TWMQDR.IEN.
      TV2.12-5/1 (580) DQ..LGI..C...L.CTTN.L..S.W.NK.TQSDI.D.TWMQDR.ISN.
     Consensus (601) DQQLLGIWGCSGKLICTTAVPWNSSWSNKSEADIWDNMTWMQWDREISNY 651                                          700
       SF162   (625) .NL.YT...S.N.QEK.QE..EK.ASI.N.D.SK.L...I.....
       TV1.8_2 (643) .GL.YN.LED.N.QEK.EKD.LE..K.NNL.N.D.SN.P.Y.I.I.I.
       TV1.8_5 (645) .ET.FR.LED.N.QQE..EKD.IE..K.NNL.N.D.SN.L.Y.I.I.I.
      TV2.12-5/1 (630) .NT.YR.LED.G.QEK.EKD.LA..K.NNL.N.S.TN.L.Y.I.I.I.
     Consensus (651) TNTIYRLLEDSQNQQEKNEKDLLELDKWNNLWNWFDISNWLWYIKIFIMI 701                                          750
       SF162   (675) ......T.L.I.N.V.Q.Y.P..F.T.F....RG.D.PE......
       TV1.8_2 (693) .GGLIGL.I.A.L.I.NRVRQGYSPLSFQTLT.S..GL.LG.I...GG
       TV1.8_5 (695) .GGLIGL.I.A.L.I.NRVRQGYSPLSFQTLT.S..GL.LG.I...GG
      TV2.12-5/1 (680) .GGLIGL.I.A.L.I.NRVRQGYSPLSLQTLI.N..G..LG.I...GG
     Consensus (701) VGGLIGLRIIFAVLSIVNRVRQGYSPLSFQTLTPSPRGPDRLGGIEEEGG
```

FIGURE 105B

```
                    751                                              800
SF162      (725)  ERDRDRSSP HGL I  I    SL  FSY  L DL  AA IV    R-
TV1.8_2    (743)  EQDRDRSIR SFLS A   LN  SY   DF  AV A     HS
TV1.8_5    (745)  EQDRDRSIR SFLS A   RS  SY  L D F  AV A     HS
TV2.12-5/1 (730)  EQDSSRSIR SFLT A   RS  C   L D F  VV A     HS
Consensus  (751)  EQDRDRSIRLVSGFLSLAWDDLRSLCLFSYHRLRDFILIAVRAVELLGHS
                    801                                              850
SF162      (774)  ------  EA  WN    IQ   N  SLF A AV     I
TV1.8_2    (793)  SLRGLQ  EI  L S V  GL  K  ISLL T A V     I
TV1.8_5    (795)  SLRGLQ  EI  L S V  GL  K  ISPL T A V     I
TV2.12-5/1 (780)  SLRGLQ  GT  L S V  GL  K  INLL T A V     I
Consensus  (801)  SLRGLQRGWEILKYLGSLVQYWGLELKKSAISLLDTIAIAVAEGTDRIIE
                    851              876
SF162      (818)  VAQRIGRAFLHI    R   RA L-
TV1.8_2    (843)  LVQRICRAILNI    R   EA L-
TV1.8_5    (845)  LVQRICRAILNI    R   EA L-
TV2.12-5/1 (830)  FIQNLCRGIRN     R   EA Q-
Consensus  (851)  LVQRICRAILNIPRRIRQGFEAALL
```

EXPRESSION CASSETTES ENCODING MODIFIED HUMAN IMMUNODEFICIENCY VIRUS TYPE 1 SUBTYPE C ENVELOPE GLYCOPROTEINS

CROSS-REFERENCE TO RELATED APPLICATIONS

This application is a continuation-in-part of U.S. Ser. No. 09/610,313, filed Jul. 5, 2000.

This application incorporates by reference the contents of a 263 KB text file created Sep. 19, 2008 and named "SN_09899575 sequence_listing.txt," which is the sequence listing for this application.

TECHNICAL FIELD

Polynucleotides encoding antigenic Type C HIV polypeptides (e.g. Gag, Pol, Vif, Vpr, Tat, Rev, Vim, Env, and Nef) are described, as are uses of these polynucleotides and polypeptide products in immunogenic compositions. Also described are polynucleotide sequences from South African variants of HIV Type C.

BACKGROUND OF THE INVENTION

Acquired immune deficiency syndrome (AIDS) is recognized as one of the greatest health threats facing modern medicine. There is, as yet, no cure for this disease. In 1983-1984, three groups independently identified the suspected etiological agent of AIDS. See, e.g., Barre-Sinoussi et al. (1983) Science 220:868-871; Montagnier et al., in Human T-Cell Leukemia Viruses (Gallo, Essex & Gross, eds., 1984); Vilmer et al. (1984) The Lancet 1:753; Popovic et al. (1984) Science 224:497-500; Levy et al. (1984) Science 225:840-842. These isolates were variously called lymphadenopathy-associated virus (LAV), human T-cell lymphotropic virus type III (HTLV-III), or AIDS-associated retrovirus (ARV). All of these isolates are strains of the same virus, and were later collectively named Human Immunodeficiency Virus (HIV). With the isolation of a related AIDS-causing virus, the strains originally called HIV are now termed HIV-1 and the related virus is called HIV-2 See, e.g., Guyader et al. (1987) Nature 326:662-669; Brun-Vezinet et al. (1986) Science 233: 343-346; Clavel et al. (1986) Nature 324:691-695.

A great deal of information has been gathered about the HIV virus, however, to date an effective vaccine has not been identified. Several targets for vaccine development have been examined including the env and gag gene products encoded by HIV. gag gene products include, but are not limited to, Gag-polymerase and Gag-protease. env gene products include, but are not limited to, monomeric gp120 polypeptides, oligomeric gp140 polypeptides and gp160 polypeptides Haas, et al., (*Current Biology* 6(3):315-324, 1996) suggested that selective codon usage by HIV-1 appeared to account for a substantial fraction of the inefficiency of viral protein synthesis. Andre, et al., (*J. Virol.* 72(2):1497-1503, 1998) described an increased immune response elicited by DNA vaccination employing a synthetic gp120 sequence with modified codon usage. Schneider, et al., (*J Virol.* 71(7): 4892-4903, 1997) discuss inactivation of inhibitory (or instability) elements (INS) located within the coding sequences of the Gag and Gag-protease coding sequences.

The Gag proteins of HIV-1 are necessary for the assembly of virus-like particles. HIV-1 Gag proteins are involved in many stages of the life cycle of the virus including, assembly, virion maturation after particle release, and early post-entry steps in virus replication. The roles of HIV-1 Gag proteins are numerous and complex (Freed, E.G., Virology 251:1-15, 1998).

Wolf, et al., (PCT International Application, WO 96/30523, published 3 Oct. 1996; European Patent Application, Publication No. 0 449 116 Al, published 2 Oct. 1991) have described the use of altered pr55 Gag of HIV-1 to act as a non-infectious retroviral-like particulate carrier, in particular, for the presentation of immunologically important epitopes. Wang, et al., (Virology 200:524-534, 1994) describe a system to study assembly of HIV Gag-β-galactosidase fusion proteins into virions. They describe the construction of sequences encoding HIV Gag-β-galactosidase fusion proteins, the expression of such sequences in the presence of HIV Gag proteins, and assembly of these proteins into virus particles.

Shiver, et al., (PCT International Application, WO 98/34640, published 13 Aug. 1998) described altering HIV-1 (CAM1) gag coding sequences to produce synthetic DNA molecules encoding HIV Gag and modifications of HIV Gag. The codons of the synthetic molecules were codons preferred by a projected host cell.

Recently, use of HIV Env polypeptides in immunogenic compositions has been described. (see, U.S. Pat. No. 5,846,546 to Hurwitz et al., issued Dec. 8, 1998, describing immunogenic compositions comprising a mixture of at least four different recombinant virus that each express a different HIV Env variant; and U.S. Pat. No. 5,840,313 to Vahlne et al., issued Nov. 24, 1998, describing peptides which correspond to epitopes of the HIV-1 gp120 protein). In addition, U.S. Pat. No. 5,876,731 to Sia et al, issued Mar. 2, 1999 describes candidate vaccines against HIV comprising an amino acid sequence of a T-cell epitope of Gag linked directly to an amino acid sequence of a B-cell epitope of the V3 loop protein of an HIV-1 isolate containing the sequence GPGR (SLQ ID NO: 150). There remains a need for antigenic HIV polypeptides, particularly Type C isolates.

SUMMARY OF THE INVENTION

Described herein are novel Type C HIV sequences, for example, 8_5_TV1_C.ZA, 8_2_TV1_C.ZA and 12-5_1_TV2_C.ZA, polypeptides encoded by these novel sequences, and synthetic expression cassettes generated from these and other Type C HIV sequences.

In certain embodiments, the present invention relates synthetic expression cassettes encoding HIV Type C polypeptides, including Env, Gag, Pol, Prot, Vpr, Vpu, Vif, Nef, Tat, Rev and/or fragments thereof. In addition, the present invention also relates to improved expression of HIV Type C polypeptides and production of virus-like particles. Synthetic expression cassettes encoding the HIV polypeptides (e.g., Gag-, pol-, protease (prot)-, reverse transcriptase, integrase, RNAseH, Tat, Rev, Nef, Vpr, Vpu, Vif and/or Env-containing polypeptides) are described, as are uses of the expression cassettes.

Thus, one aspect of the present invention relates to expression cassettes and polynucleotides contained therein. The expression cassettes typically include an HIV polypeptide encoding sequence inserted into an expression vector backbone. In one embodiment, an expression cassette comprises a polynucleotide sequence encoding one or more Pol-containing polypeptides, wherein the polynucleotide sequence comprises a sequence having at least about 85%, preferably about 90%, more preferably about 95%, and more preferably about 98% sequence (and any integers between these values) identity to the sequences taught in the present specification. The polynucleotide sequences encoding Pol-containing polypeptides include, but are not limited to, those shown in SEQ ID NO:30, SEQ ID NO:31; SEQ ID NO:32; SEQ ID NO:62; SEQ ID NO: 103; SEQ ID NO:58; SEQ ID NO:60; SEQ ID NO:64; SEQ ID NO:66; SEQ ID NO:68; SEQ ID NO:70; SEQ ID NO:76; and SEQ ID NO:78.

The polynucleotides encoding the HIV polypeptides of the present invention may also include sequences encoding additional polypeptides. Such additional polynucleotides encoding polypeptides may include, for example, coding sequences for other viral proteins (e.g., hepatitis B or C or other HIV proteins, such as, polynucleotide sequences encoding an HIV Gag polypeptide, polynucleotide sequences encoding an HIV Env polypeptide and/or polynucleotides encoding one or more of Vif, Vpr, Tat, Rev, Vpu and Nef); cytokines or other transgenes. In one embodiment, the sequence encoding the HIV Pol polypeptide(s) can be modified by deletions of coding regions corresponding to reverse transcriptase and integrase. Such deletions in the polymerase polypeptide can also be made such that the polynucleotide sequence preserves T-helper cell and CTL epitopes. Other antigens of interest may be inserted into the polymerase as well.

In another embodiment, an expression cassette comprises a polynucleotide sequence encoding a polypeptide including an HIV Gag-containing polypeptide, wherein the polynucleotide sequence encoding the Gag polypeptide comprises a sequence having at least about 85%, preferably about 90%, more preferably about 95%, and most preferably about 98% sequence identity to the sequences taught in the present specification. The polynucleotide sequences encoding Gag-containing polypeptides include, but are not limited to, the following polynucleotides: nucleotides 844-903 of FIG. 1 (a Gag major homology region) (SEQ ID NO: 1); nucleotides 841-900 of FIG. 2 (a Gag major homology region) (SEQ ID NO:2); FIG. 24 (SEQ ID NO:53, a Gag major homology region); the sequence presented as FIG. 1 (SEQ ID NO:3); the sequence presented as FIG. 22 (SEQ ID NO:5 1); the sequence presented as FIG. 70 (SEQ ID NO:99); and the sequence presented as FIG. 2 (SEQ ID NO:4). As noted above, the polynucleotides encoding the Gag-containing polypeptides of the present invention may also include sequences encoding additional polypeptides.

In another embodiment, an expression cassette comprises a polynucleotide sequence encoding a polypeptide including an HIV Env-containing polypeptide, wherein the polynucleotide sequence encoding the Env polypeptide comprises a sequence having at least about 85%, preferably about 90%, more preferably about 95%, and most preferably about 98% sequence identity to the sequences taught in the present specification. The polynucleotide sequences encoding Env-containing polypeptides include, but are not limited to, the following polynucleotides: nucleotides 1213-1353 of FIG. 3 (SEQ ID NO: 5) (encoding an Env common region); the sequence presented as FIG. 17 (SEQ ID NO:46) (encoding a 97 nucleotide long Env common region); SEQ ID NO:47 (encoding a 144 nucleotide long Env common region); nucleotides 82-15 12 of FIG. 3 (SEQ ID NO:6) (encoding a gp120 polypeptide); nucleotides 82-2025 of FIG. 3 (SEQ ID NO:7) (encoding a gp140 polypeptide); nucleotides 82-2547 of FIG. 3 (SEQ ID NO: 8) (encoding a gp160polypeptide); SEQ ID NO:49 (encoding a gp160 polypeptide); nucleotides 1-2547 of FIG. 3 (SEQ ID NO:9) (encoding a gp41 polypeptide with signal sequence); nucleotides 1513-2547 of FIG. 3 (SEQ ID NO: 10) (encoding a gp140 polypeptide); nucleotides 1210-1353 of FIG. 4 (SEQ ID NO: 11) (encoding an Env common region); nucleotides 73-1509 of FIG. 4 (SEQ ID NO: 12) (encoding a gp120 polypeptide); nucleotides 73-2022 of FIG. 4 (SEQ ID NO: 13) (encoding a gp140 polypeptide); nucleotides 73-2565 of FIG. 4 (SEQ ID NO: 14) (encoding a gp160 polypeptide); nucleotides 1-2565 of FIG. 4 (SEQ ID NO: 15) (encoding a gp160 polypeptide with signal sequence); the sequence presented as FIG. 20 (SEQ ID NO:49) (encoding a gp160 polypeptide); the sequence presented as FIG. 68 (SEQ ID NO:97) (encoding a gp160 polypeptide); nucleotides 1510-2565 of FIG. 4 (SEQ ID NO: 16) (encoding a gp41 polypeptide); nucleotides 7 to 1464 of FIG. 90 (SEQ ID NO:119) (encoding a gp120 polypeptide with modified wild type signal sequence); nucleotides 7 to 1977 of FIG. 91 (SEQ ID NO: 120) (encoding a gp140 polypeptide including signal sequence modified from wild-type 8_2_TV 1_C.ZA (e.g., "modified wild type leader sequence")); nucleotides 7 to 1977 of FIG. 92 (SEQ ID NO: 121) (encoding a gp140 polypeptide with modified wild type 8_2_TV 1_C.ZA signal sequence); nucleotides 7 to 2388 of FIG. 93 (SEQ ID NO: 122) (encoding a gp160 polypeptide with modified wild type signal sequence); nucleotides 7 to 2520 of FIG. 94 (SEQ ID NO: 123) (encoding a gp160 polypeptide with modified wild type 8_2_TV 1_C.ZA signal sequence); nucleotides 7 to 2520 of FIG. 95 SEQ ID NO: 124) (encoding a gp160 polypeptide with modified wild type 8_2_TY1_C.ZA signal sequence); nucleotides 13 to 2604 of FIG. 96 (SEQ ID NO: 125) (encoding a gp160 polypeptide with TPA1 signal sequence); nucleotides 7 to 2607 of FIG. 97 (SEQ ID NO: 126) (encoding a gp160 polypeptide with modified wild type 8_2_TY1_C.ZA signal sequence); nucleotides 1 to 2049 of FIG. 100 (SEQ ID NO:131) (encoding a gp140 polypeptide with TPAI signal sequence); nucleotides 7 to 1607 of FIG. 98 (SEQ ID NO: 126) (encoding a gp160 polypeptide with wild type 8_2 TV1_C.ZA signal sequence); nucleotides 7 to 2064 of SEQ ID NO: 132 (encoding a gp140 polypeptide with modified wild-type 8_2_TY1_C.ZA leader sequence); and nucleotides 7 to 2064 of SEQ ID NO: 133 (encoding a gp140 polypeptide with wild-type 8_2_TV1_C.ZA leader sequence).

In certain embodiments, the Env-encoding sequences will contain further modifications, for instance mutation of the cleavage site to prevent the cleavage of a gp140 polypeptide into a gp120 polypeptide and a gp41 polypeptide (SEQ ID NO:121 and SEQ ID NO:124) or deletion of variable regions V1 and/or V2 (SEQ ID NO:119; SEQ ID NO:120; SEQ ID NO:121; SEQ ID NO:122; SEQ ID NO:123; and SEQ ID NO:124).

In another embodiment, an expression cassette comprises a polynucleotide sequence encoding a polypeptide including an HIV Nef-containing polypeptide, wherein the polynucleotide sequence encoding the Nef polypeptide comprises a sequence having at least about 85%, preferably about 90%, more preferably about 95%, and most preferably about 98% sequence identity to the sequences taught in the present specification. The polynucleotide sequences encoding Nef-containing polypeptides include, but are not limited to, the following polynucleotides: the sequence presented in FIG. 26 SEQ ID NO:55); the sequence presented in FIG. 72 (SEQ ID NO: 101); the sequence presented in FIG. 28 (SEQ ID NO:57); the sequence presented in FIG. 67 (SEQ ID NO:96); the sequence presented in FIG. 103 (SEQ ID NO: 134); and the sequence presented in FIG. 104 (SEQ ID NO: 135).

In another embodiment, an expression cassette comprises a polynucleotide sequence encoding a polypeptide including an HIV Rev-containing polypeptide, wherein the polynucleotide sequence encoding the Rev polypeptide comprises a sequence having at least about 85%, preferably about 90%, more preferably about 95&, and most preferably about 98% sequence identity to the sequences taught in the present specification. The polynucleotide sequences encoding Rev -containing polypeptides include, but are not limited to, the following polynucleotides: the sequence presented in FIG. 43 (SEQ ID NO:72); the sequence presented in FIG. 76 (SEQ ID NO: 105); the sequence presented in FIG. 45 (SEQ ID NO:74); the sequence presented in FIG. 78 (SEQ ID NO: 107); and the sequence presented in FIG. 62 (SEQ ID NO:91).

In another embodiment, an expression cassette comprises a polynucleotide sequence encoding a polypeptide including an HIV Tat-containing polypeptide, wherein the polynucleotide sequence encoding the Tat polypeptide comprises a sequence having at least about 85%, preferably about 90%, more preferably about 95%, and most preferably about 98% sequence identity to the sequences taught in the present specification. The polynucleotide sequences encoding Tat-containing polypeptides include, but are not limited to, the following polynucleotides: the sequence presented in FIG. 51 (SEQ ID NO: 80); the sequence presented in FIG. 80 (SEQ ID NO: 109); the sequence presented in FIG. 52 (SEQ ID NO:81); the sequence presented in FIG. 54 (SEQ ID NO: 83); and the sequence presented in FIG. 82 (SEQ ID NO: 111).

In another embodiment, an expression cassette comprises a polynucleotide sequence encoding a polypeptide including an HIV Vif-containing polypeptide, wherein the polynucleotide sequence encoding the Vif polypeptide comprises a sequence having at least about 85%, preferably about 90%, more preferably about 95%, and most preferably about 98% sequence identity to the sequences taught in the present specification. The polynucleotide sequences encoding Vif-containing polypeptides include, but are not limited to, the following polynucleotides: the sequence presented in FIG. 56 (SEQ ID NO: 85); and the sequence presented in FIG. 84 (SEQ ID NO: 113).

In another embodiment, an expression cassette comprises a polynucleotide sequence encoding a polypeptide including an HIV Vpr-containing polypeptide, wherein the polynucleotide sequence encoding the Vpr polypeptide comprises a sequence having at least about 85%, preferably about 90%, more preferably about 95%, and most preferably about 98% sequence identity to the sequences taught in the present specification. The polynucleotide sequences encoding Vpr-containing polypeptides include, but are not limited to, the following polynucleotides: the sequence presented in FIG. 58 (SEQ ID NO:87); and the sequence presented in FIG. 86 SEQ ID NO: 115).

In another embodiment, an expression cassette comprises a polynucleotide sequence encoding a polypeptide including an HIV Vpu-containing polypeptide, wherein the polynucleotide sequence encoding the Vpu polypeptide comprises a sequence having at least about 85%, preferably about 90%, more preferably about 95%, and most preferably about 98% sequence identity to the sequences taught in the present specification. The polynucleotide sequences encoding Vpu-containing polypeptides include, but are not limited to, the following polynucleotides: the sequence presented in FIG. 60 (SEQ ID NO:89); and the sequence presented in FIG. 88 (SEQ ID NO:117).

Further embodiments of the present invention include purified polynucleotides of any of the sequences described herein. Exemplary polynucleotide sequences encoding Gag-containing polypeptides include, but are not limited to, the following polynucleotides: nucleotides 844-903 of FIG. 1 (SEQ ID NO:1) (a Gag major homology region); nucleotides 841-900 of FIG. 2 (SEQ ID NO:2) (a Gag major homology region); the sequence presented as FIG. 1 (SEQ ID NO:3); the sequence presented as FIG. 2 (SEQ ID NO:4); the sequence presented as FIG. 22 (SEQ ID NO:51); the sequence presented as FIG. 70 (SEQ ID NO:99); and the sequence presented as FIG. 24 (SEQ ID NO:53) (a Gag major homology region).

Exemplary polynucleotide sequences encoding Env-containing polypeptides include, but are not limited to, the following polynucleotides: nucleotides 1213-1353 of FIG. 3 (SEQ ID NO:5) (encoding an Env common region); the sequence presented as FIG. 17 (SEQ ID NO:46) (encoding a 97 nucleotide long Env common region); SEQ ID NO:47 (encoding a 144 nucleotide long Env common region); nucleotides 82-1512 of FIG. 3 (SEQ ID NO:6) (encoding a gp120 polypeptide); nucleotides 82-2025 of FIG. 3 (SEQ ID NO:7) (encoding a gp140 polypeptide); nucleotides 82-2547 of FIG. 3 (SEQ ID NO:8) (encoding a gp160 polypeptide); SEQ ID NO:49 (encoding a gp160 polypeptide); nucleotides 1-2547 of FIG. 3 (SEQ ID NO:9) (encoding a gp160 polypeptide with signal sequence); nucleotides 1513-2547 of FIG. 3 (SEQ ID NO:10) (encoding a gp41 polypeptide); nucleotides 1210-1353 of FIG. 4 (SEQ ID NO:11) (encoding an Env common region); nucleotides 73-1509 of FIG. 4 (SEQ ID NO:12) (encoding a gp120 polypeptide); nucleotides 73-2022 of FIG. 4 (SEQ ID NO:13) (encoding a gp140 polypeptide); nucleotides 73-2565 of FIG. 4 (SEQ ID NO:14) (encoding a gp160 polypeptide); nucleotides 1-2565 of FIG. 4 (SEQ ID NO:15) (encoding a gp160 polypeptide with signal sequence); the sequence presented as FIG. 20 (SEQ ID NO:49) (encoding a gp160 polypeptide); the sequence presented as FIG. 68 (SEQ ID NO:97) (encoding a gp160 polypeptide); nucleotides 1510-2565 of FIG. 4 (SEQ ID NO:16) (encoding a gp41 polypeptide); nucleotides 7 to 1464 of FIG. 90 (SEQ ID NO:119) (encoding a gp120 polypeptide with modified wild type signal sequence); nucleotides 7 to 1977 of FIG. 91 (SEQ ID NO:120) (encoding a gp140 polypeptide including signal sequence modified from wild-type 8_2_TV1_C.ZA (e.g., "modified wild type leader sequence")); nucleotides 7 to 1977 of FIG. 92 (SEQ ID NO:121) (encoding a gp140 polypeptide with modified wild type 8_2_TV1_C.ZA signal sequence); nucleotides 7 to 2388 of FIG. 93 (SEQ ID NO:122) (encoding a gp160 polypeptide with modified wild type signal sequence); nucleotides 7 to 2520 of FIG. 94 (SEQ ID NO:123) (encoding a gp160 polypeptide with modified wild type 8_2_TV1_C.ZA signal sequence); nucleotides 7 to 2520 of FIG. 95 (SEQ ID NO:124) (encoding a gp160 polypeptide with modified wild type 8_2_TV1_C.ZA signal sequence); nucleotides 13 to 2604 of FIG. 96 (SEQ ID NO:125) (encoding a gp160 polypeptide with TPA1 signal sequence); nucleotides 7 to 2607 of FIG. 97 (SEQ ID NO:126) (encoding a gp160 polypeptide with modified wild type 8_2_TV1_C.ZA signal sequence); nucleotides 1 to 2049 of FIG. 100 (SEQ ID NO:131) (encoding a gp140 polypeptide with TPA1 signal sequence); nucleotides 7 to 1607 of FIG. 98 (SEQ ID NO:126) (encoding a gp160 polypeptide with wild type 8_2_TV1_C.ZA signal sequence); nucleotides 7 to 2064 of SEQ ID NO:132 (encoding a gp140 polypeptide with modified wild-type 8_2_TV1_C.ZA leader sequence); and nucleotides 7 to 2064 of SEQ ID NO:133 (encoding a gp140 polypeptide with wild-type 8_2_TV1_C.ZA leader sequence).

Exemplary purified polynucleotides encoding additional HIV polynucleotides include: Pol-encoding polynucleotides (e.g., SEQ ID NO:30, SEQ ID NO:31; SEQ ID NO:32; SEQ ID NO:62; SEQ ID NO:103; SEQ ID NO:58; SEQ ID NO:60; SEQ ID NO:64; SEQ ID NO:66; SEQ ID NO:68; SEQ ID NO:70; SEQ ID NO:76; and SEQ ID NO:78); Nef-encoding polynucleotides (e.g., SEQ ID NO:55; SEQ ID NO:101; SEQ ID NO:57; SEQ ID NO:96); Rev-encoding polynucleotides (e.g., SEQ ID NO:72; SEQ ID NO:105; SEQ ID NO:74); SEQ ID NO:107; SEQ ID NO:91); Tat-encoding polynucleotides (e.g., SEQ ID NO:80; SEQ ID NO:109; SEQ ID NO:81; SEQ ID NO:83; SEQ ID NO:111); Vif-encoding polynucleotides (e.g., SEQ ID NO:85; SEQ ID NO:113); and Vpr-encoding polynucleotides (e.g., SEQ ID NO:87; SEQ ID NO:115); Vpu-encoding polynucleotides (e.g., SEQ ID NO:89; SEQ ID NO:117).

In other embodiments, the present invention relates to native HIV polypeptide-encoding sequences obtained from novel Type C strains; fragments of these native sequences; expression cassettes containing these wild-type sequences; and uses of these sequences, fragments and expression cassettes. Exemplary full length sequences are shown in SEQ ID NO:33 and SEQ ID NO:45. Exemplary fragments coding for various HIV gene products include: the sequence presented in FIG. 19 (SEQ ID NO:48) (an Env-encoding sequence); the sequence presented in FIG. 69 (SEQ ID NO:98) (an Env-encoding sequence); the sequence presented in FIG. 21 (SEQ ID NO:50) (a gp160 polypeptide); the sequence presented in FIG. 23 (SEQ ID NO:52) (a Gag polypeptide); the sequence presented in FIG. 71 (SEQ ID NO:100) (a Gag polypeptide); the sequence presented in FIG. 25 (SEQ ID NO:54) (a Gag polypeptide); the sequence presented in FIG. 27 (SEQ ID NO:56) (a Nef polypeptide); the sequence presented in FIG. 73 (SEQ ID NO:102) (a Nef polypeptide); the sequence presented in FIG. 30 (SEQ ID NO:59) (a p15RNAseH polypeptide); the sequence presented in FIG. 32 (SEQ ID NO:61) (a p31Integrase polypeptide); the sequence presented in FIG. 34 (SEQ ID NO:63) (a Pol polypeptide); the sequence presented in FIG. 75 (SEQ ID NO:104) (a Pol polypeptide); the sequence presented in FIG. 36 (SEQ ID NO:65) (a Prot polypeptide); the sequence presented in FIG. 38 (SEQ ID NO:67) (a inactivated Prot polypeptide); the sequence presented in FIG. 40 (SEQ ID NO:69) (an inactivated Prot and RT polypeptide); the sequence presented in FIG. 42 (SEQ ID NO:71) (a Prot and RT polypeptide); the sequence presented in FIG. 44 (SEQ ID NO:73) (a Rev polypeptide); the sequence presented in FIG. 77 (SEQ ID NO:106) (a Rev polypeptide); the sequence presented in FIG. 46 (SEQ ID NO:75) (a Rev polypeptide); the sequence presented in FIG. 79 (SEQ ID NO:108) (a Rev polypeptide); the sequence presented in FIG. 48 (SEQ ID NO:77) (an RT polypeptide); the sequence presented in FIG. 50 (SEQ ID NO:79) (a mutated RT polypeptide); the sequence presented in FIG. 53 (SEQ ID NO:82) (a Tat polypeptide); the sequence presented in FIG. 81 (SEQ ID NO:110) (a Tat polypeptide); the sequence presented in FIG. 55 (SEQ ID NO:84) (a Tat polypeptide); the sequence presented in FIG. 83 (SEQ ID NO:112) (a Tat polypeptide); the sequence presented in FIG. 57 (SEQ ID NO:86) (a Vif polypeptide); the sequence presented in FIG. 85 (SEQ ID NO:114) (a Vif polypeptide); the sequence presented in FIG. 59 (SEQ ID NO:88) (a Vpr polypeptide); the sequence presented in FIG. 82 (SEQ ID NO:116) (a Vpr polypeptide); the sequence presented in FIG. 61 (SEQ ID NO:90) (a Vpu polypeptide); the sequence presented in FIG. 89 (SEQ ID NO:118) (a Vpu polypeptide); the sequence presented in FIG. 63 (SEQ ID NO:92) (a Rev polypeptide); and the sequence presented in FIG. 66 (SEQ ID NO:95) (a Tat polypeptide).

The native and synthetic polynucleotide sequences encoding the HIV polypeptides of the present invention typically have at least about 85%, preferably about 90%, more preferably about 95%, and most preferably about 98% sequence identity to the sequences taught herein. Further, in certain embodiments, the polynucleotide sequences encoding the HIV polypeptides of the invention will exhibit 100% sequence identity to the sequences taught herein.

The polynucleotides of the present invention can be produced by recombinant techniques, synthetic techniques, or combinations thereof.

The present invention further includes recombinant expression systems for use in selected host cells, wherein the recombinant expression systems employ one or more of the polynucleotides and expression cassettes of the present invention. In such systems, the polynucleotide sequences are operably linked to control elements compatible with expression in the selected host cell. Numerous expression control elements are known to those in the art, including, but not limited to, the following: transcription promoters, transcription enhancer elements, transcription termination signals, polyadenylation sequences, sequences for optimization of initiation of translation, and translation termination sequences. Exemplary transcription promoters include, but are not limited to those derived from CMV, CMV+intron A, SV40, RSV, HIV-Ltr, MMLV-ltr, and metallothionein.

In another aspect the invention includes cells comprising one or more of the expression cassettes of the present invention where the polynucleotide sequences are operably linked to control elements compatible with expression in the selected cell. In one embodiment such cells are mammalian cells. Exemplary mammalian cells include, but are not limited to, BHK, VERO, HT1080, 293, RD, COS-7, and CHO cells. Other cells, cell types, tissue types, etc., that may be useful in the practice of the present invention include, but are not limited to, those obtained from the following: insects (e.g., *Trichoplusia ni* (Tn5) and Sf9), bacteria, yeast, plants, antigen presenting cells (e.g., macrophage, monocytes, dendritic cells, B-cells, T-cells, stem cells, and progenitor cells thereof), primary cells, immortalized cells, tumor-derived cells.

In a further aspect, the present invention includes compositions for generating an immunological response, where the composition typically comprises at least one of the expression cassettes of the present invention and may, for example, contain combinations of expression cassettes (such as one or more expression cassettes carrying a Pol-polypeptide-encoding polynucleotide, one or more expression cassettes carrying a Gag-polypeptide-encoding polynucleotide, one or more expression cassettes carrying accessory polypeptide-encoding polynucleotides (e.g., native or synthetic Vpu, Vpr, Nef, Vif, Tat, Rev), and/or one or more expression cassettes carrying an Env-polypeptide-encoding polynucleotide). Such compositions may further contain an adjuvant or adjuvants. The compositions may also contain one or more Type C HIV polypeptides. The Type C HIV polypeptides may correspond to the polypeptides encoded by the expression cassette(s) in the composition, or may be different from those encoded by the expression cassettes. An example of the polynucleotide in the expression cassette encoding the same polypeptide as is being provided in the composition is as follows: the polynucleotide in the expression cassette encodes the Gag-polypeptide of FIG. 1 (SEQ ID NO:3), and the polypeptide (SEQ ID NO: 17) is the polypeptide encoded by the sequence shown in FIG. 1. An example of the polynucleotide in the expression cassette encoding a different polypeptide as is being provided in the composition is as follows: an expression cassette having a polynucleotide encoding a Gag-polymerase polypeptide, and herein.

In another aspect the present invention includes methods of immunization of a subject. In the method any of the above described compositions are into the subject under conditions that are compatible with expression of the expression cassette(s) in the subject. In one embodiment, the expression cassettes (or polynucleotides of the present invention) can be introduced using a gene delivery vector. The gene delivery vector can, for example, be a non-viral vector or a viral vector. Exemplary viral vectors include, but are not limited to Sindbis-virus derived vectors, retroviral vectors, and lentiviral vectors. Compositions useful for generating an immunological response can also be delivered using a particulate carrier. Further, such compositions can be coated on, for example, gold or tungsten particles and the coated particles delivered to the subject using, for example, a gene gun. The compositions can also be formulated as liposomes. In one embodiment of this method, the subject is a mammal and can, for example, be a human.

In a further aspect, the invention includes methods of generating an immune response in a subject. Any of the expression cassettes described herein can be expressed in a suitable cell to provide for the expression of the Type C HIV polypeptides encoded by the polynucleotides of the present invention. The polypeptide(s) are then isolated (e.g., substantially purified) and administered to the subject in an amount sufficient to elicit an immune response. In certain embodiments, the methods comprise administration of one or more of the expression cassettes or polynucleotides of the present invention, using any of the gene delivery techniques described herein. In other embodiments, the methods comprise co-administration of one or more of the expression cassettes or polynucleotides of the present invention and one or more polypeptides, wherein the polypeptides can be expressed from these polynucleotides or can be other subtype C HIV polypeptides. In other embodiments, the methods comprise co-administration of multiple expression cassettes or polynucleotides of the present invention. In still further embodiments, the methods comprise co-administration of multiple polypeptides, for example polypeptides expressed from the polynucleotides of the present invention and/or other subtype C HIV polypeptides.

The invention further includes methods of generating an immune response in a subject, where cells of a subject are transfected with any of the above-described expression cassettes or polynucleotides of the present invention, under conditions that permit the expression of a selected polynucleotide and production of a polypeptide of interest (e.g., encoded by any expression cassette of the present invention). By this method an immunological response to the polypeptide is elicited in the subject. Transfection of the cells may be performed ex vivo and the transfected cells are reintroduced into the subject. Alternately, or in addition, the cells may be transfected in vivo in the subject. The immune response may be humoral and/or cell-mediated (cellular). In a further embodiment, this method may also include administration of an Type C HIV polypeptides before, concurrently with, and/or after introduction of the expression cassette into the subject.

These and other embodiments of the present invention will readily occur to those of ordinary skill in the art in view of the disclosure herein.

BRIEF DESCRIPTION OF THE FIGURES

FIG. 1 (SEQ ID NO:3) shows the nucleotide sequence of a polynucleotide encoding a synthetic Gag polypeptide. The nucleotide sequence shown was obtained by modifying type C strain AF110965 and include further modifications of INS.

FIG. 2 (SEQ ID NO:4) shows the nucleotide sequence of a polynucleotide encoding a synthetic Gag polypeptide. The nucleotide sequence shown was obtained by modifying type C strain AF110967 and include further modifications of INS.

FIG. 3 (SEQ ID NO:9) shows the nucleotide sequence of a polynucleotide encoding a synthetic Env polypeptide. The nucleotide sequence depicts gp160 (including a signal peptide) and was obtained by modifying type C strain AF110968. The arrows indicate the positions of various regions of the polynucleotide, including the sequence encoding a signal peptide (nucleotides 1-81) (SEQ ID NO:18), a gp120 polypeptide (nucleotides 82-1512) (SEQ ID NO:6), a gp41 polypeptide (nucleotides 1513-2547) (SEQ ID NO:10), a gp140 polypeptide (nucleotides 82-2025) (SEQ ID NO:7) and a gp160 polypeptide (nucleotides 82-2547) (SEQ ID NO:8). The codons encoding the signal peptide are modified (as described herein) from the native HIV-1 signal sequence.

FIG. 4 (SEQ ID NO:15) shows the nucleotide sequence of a polynucleotide encoding a synthetic Env polypeptide. The nucleotide sequence depicts gp160 (including a signal peptide) and was obtained by modifying type C strain AF110975. The arrows indicate the positions of various regions of the polynucleotide, including the sequence encoding a signal peptide (nucleotides 1-72) (SEQ ID NO:19), a gp120 polypeptide (nucleotides 73-1509) (SEQ ID NO:12), a gp41 polypeptide (nucleotides 1510-2565) (SEQ ID NO:16), a gp140 polypeptide (nucleotides 73-2022) (SEQ ID NO:13), and a gp160 polypeptide (nucleotides 73-2565) (SEQ ID NO:14). The codons encoding the signal peptide are modified (as described herein) from the native HIV-1 signal sequence.

FIG. 5 shows the location of some remaining INS in synthetic Gag sequences derived from AF110965. The changes made to these sequences are boxed in the Figures. The top line depicts a codon modified sequence of Gag polypeptides from the indicated strains (SEQ ID NO:20). The nucleotide(s) appearing below the line in the boxed region(s) depicts changes made to remove further INS and correspond to the sequence depicted in FIG. 1 (SEQ ID NO:3).

FIG. 6 shows the location of some remaining INS in synthetic Gag sequences derived from AF110967. The changes made to these sequences are boxed in the Figures. The top line depicts a modified sequence of Gag polypeptides from the indicated strains (SEQ ID NO:21). The nucleotide(s) appearing below the line in the boxed region(s) depicts changes made to remove further INS and correspond to the sequence depicted in FIG. 2 (SEQ ID NO:4).

FIG. 7 is a schematic depicting the selected domains in the Pol region of HIV. YMDD (SLQ ID NO: 148); WMGY (SLQ ID NO: 149).

FIG. 8 (SEQ ID NO:30) depicts the nucleotide sequence of the synthetic construct designated PR975(+). "(+)" indicates that the reverse transcriptase is functional. This construct includes sequence from p2 (nucleotides 16 to 54 of SEQ ID NO:30); p7 (nucleotides 55 to 219 of SEQ ID NO:30); p1/p6 (nucleotides 220-375 of SEQ ID NO:30); prot (nucleotides 376 to 672 of SEQ ID NO:30), reverse transcriptase (nucleotides 673 to 2352 of SEQ ID NO:30); and 6 amino acids of integrase shown in FIG. 7 (nucleotides 2353 to 2370 of SEQ ID NO:30). In addition, the construct contains a multiple cloning site (MCS, nucleotides 2425 to 2463 of SEQ ID NO:30) for insertion of a transgene and a YMDD (SEQ ID NO: 148) epitope cassette (nucleotides 2371 to 2424 of SEQ ID NO:30).

FIG. 9 (SEQ ID NO:31) depicts the nucleotide sequence of the synthetic construct designated PR975YM. As illustrated in FIG. 7,. the RT region includes a mutation in the catalytic center (mut. cat. center). "YM" refers to constructs in which the nucleotides encode the amino acids AP instead of YMDD (SEQ ID NO: 148) in this region. Reverse transcriptase is not functional in this construct. This construct includes sequence from the p2 (nucleotides 16 to 54 of SEQ ID NO:3 1); p7

(nucleotides 55 to 219 of SEQ ID NO:31); p1/p6 (nucleotides 220 to 375 of SEQ ID NO:31); prot (nucleotides 376 to 672 of SEQ ID NO:31); and reverse transcriptase (nucleotides 673 to 2346 of SEQ ID NO:31) shown in FIG. 7, although the reverse transcriptase protein is not functional. In addition, the construct contains a multiple cloning site (MCS, nucleotides 2419 to 2457 of SEQ ID NO:31) for insertion of a transgene and a YMDD (SEQ ID NO: 148) epitope cassette (nucleotides 2365 to 2418 of SEQ ID NO:31).

FIG. 10 (SEQ ID NO:32) depicts the nucleotide sequence of the synthetic construct designated PR975YMWM. "YM" refers to constructs in which the nucleotides encode the amino acids AP instead of YMDD (SEQ ID NO: 148) in this region. "WM" refers to constructs in which the nucleotides encode amino acids PT instead of WMGY (SEQ ID NO: 149) in this region. This construct includes sequence from the p2 (nucleotides 16 to 54 of SEQ ID NO:32); p7 (nucleotides 55 to 219 of SEQ ID NO:32); p1/p6 (nucleotides 220 to 375 of SEQ ID NO:32); prot (nucleotides 376 to 672 of SEQ ID NO:32); and reverse transcriptase (nucleotides 673 to 2340 of SEQ ID NO:32) shown in FIG. 7, although the reverse transcriptase protein is not functional. In addition, the construct contains a multiple cloning site (MCS, nucleotides 2413 to 2451 of SEQ ID NO:32) for insertion of a transgene and a YMDD (SEQ ID NO: 148) epitope cassette (nucleotides 2359 to 2412 of SEQ ID NO:32).

FIG. 11 (SEQ ID NO:33) depicts the nucleotide sequence of 8_5_TV1_C.ZA. Various regions are shown in Table A.

FIG. 12 (SEQ ID NO:34) depicts the wild type nucleotide sequence of AF110975 Pol from p2gag until p7gag.

FIG. 13 (SEQ ID NO:35) depicts the wild type nucleotide sequence of AF110975 Pol from p1 through the first 6 amino acids of the integrase protein.

FIG. 14 (SEQ ID NO:36) depicts the nucleotide sequence of a cassette encoding Ile178 through Serine 191 of reverse transcriptase.

Figure 15:
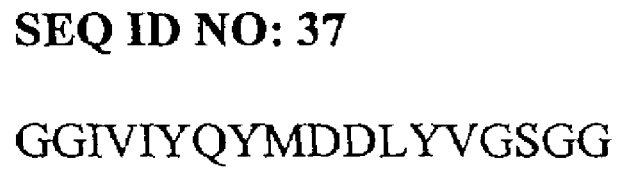

FIG. 15 (SEQ ID NO:37) shows amino acid sequence which includes an epitope in the region of the catalytic center of the reverse transcriptase protein.

FIG. 16 (SEQ ID NO:45) depicts the nucleotide sequence of 12-5_1_TV2_C.ZA.

FIG. 17 (SEQ ID NO:46) depicts the nucleotide sequence of a synthetic Env-encoding polynucleotide derived from 8_5_TV1_C.ZA. The sequence corresponds to a short (97 base pair) common region.

FIG. 18 (SEQ ID NO:47) depicts the nucleotide sequence of a synthetic Env-encoding polynucleotide derived from 8_5_TV1_C.ZA. The sequence corresponds to a common region in Env.

FIG. 19 (SEQ ID NO:48) depicts the wild-type nucleotide sequence of 8_5_TV1_C.ZA Env.

FIG. 20 (SEQ ID NO:49) depicts the nucleotide sequence of a synthetic Env gp160-encoding polynucleotide derived from 8_5_TV1_C.ZA.

FIG. 21 (SEQ ID NO:50) depicts the wild-type nucleotide sequence of 8_5_TV1_C.ZA Env gp160.

FIG. 22 (SEQ ID NO:51) depicts the nucleotide sequence of a synthetic Gag-encoding polynucleotide derived from 8_5_TV1_C.ZA.

FIG. 23 (SEQ ID NO:52) depicts the wild-type nucleotide sequence of 8_5_TV1_C.ZA Gag.

FIG. 24 (SEQ ID NO:53) depicts the nucleotide sequence of a synthetic Gag-encoding polynucleotide (major homology region) derived from 8_5_TV1_C.ZA.

FIG. 25 (SEQ ID NO:54) depicts the wild-type nucleotide sequence of 8_5_TV1_C.ZA Gag major homology region.

FIG. 26 (SEQ ID NO:55) depicts the nucleotide sequence of a synthetic Nef-encoding polynucleotide derived from 8_5_TV1_C.ZA.

FIG. 27 (SEQ ID NO:56) depicts the wild-type nucleotide sequence of 8_5_TV1_C.ZA Nef.

FIG. 28 (SEQ ID NO:57) depicts the nucleotide sequence of a synthetic Nef-encoding polynucleotide derived from 8_5_TV1_C.ZA. The sequence includes a mutation at position 125 which results in a non-functional gene product.

FIG. 29 (SEQ ID NO:58) depicts the nucleotide sequence of a synthetic RNAseH-encoding polynucleotide derived from 8_5_TV1_C.ZA. RnaseH is a functional domain of the Pol gene, corresponding to p15 (Table A).

FIG. 30 (SEQ ID NO:59) depicts the wild-type nucleotide sequence of 8_5_TV1_C.ZA RNAseH.

FIG. 31 (SEQ ID NO:60) depicts the nucleotide sequence of a synthetic integrase (Int)-encoding polynucleotide derived from 8_5_TV1_C.ZA. Int is a functional domain of the Pol gene, corresponding to p31 (Table A).

FIG. 32 (SEQ ID NO:61) depicts the wild-type nucleotide sequence of 8_5_TV1_C.ZA Int.

FIG. 33 (SEQ ID NO:62) depicts the nucleotide sequence of a synthetic Pol-encoding polynucleotide derived from 8_5_TV1_C.ZA.

FIG. 34 (SEQ ID NO:63) depicts the wild-type nucleotide sequence of 8_5_TV1_C.ZA Pol.

FIG. 35 (SEQ ID NO:64) depicts the nucleotide sequence of a synthetic protease (prot)-encoding polynucleotide derived from 8_5_TV1_C.ZA.

FIG. 36 (SEQ ID NO:65) depicts the wild-type nucleotide sequence of 8_5_TV1_C.ZA Prot.

FIG. 37 (SEQ ID NO:66) depicts the nucleotide sequence of a synthetic protease (prot)-encoding polynucleotide derived from 8_5_TV1_C.ZA containing a mutation in which results in inactivation of the protease.

FIG. 38 (SEQ ID NO:67) depicts the wild-type nucleotide sequence of 8_5_TV1_C.ZA inactivated Prot.

FIG. 39 (SEQ ID NO:68) depicts the nucleotide sequence of a synthetic protease (prot)-encoding polynucleotide and a synthetic reverse transcriptase (RT)-encoding polynucleotide, both derived from 8_5_TV1_C.ZA. The Prot and RT sequences both contain a mutation which results in inactivation of the gene product.

FIG. 40 (SEQ ID NO:69) depicts the wild-type nucleotide sequence of 8_5_TV1_C.ZA inactivated Prot/mutated RT.

FIG. 41 (SEQ ID NO:70) depicts the nucleotide sequence of a synthetic protease (prot)-encoding polynucleotide and a synthetic reverse transcriptase (RT)-encoding polynucleotide, both derived from 8_5_TV1_C.ZA.

FIG. 42 (SEQ ID NO:71) depicts the wild-type nucleotide sequence of 8_5_TV1_C.ZA Prot and RT.

FIG. 43 (SEQ ID NO:72) depicts the nucleotide sequence of a synthetic rev-encoding polynucleotide derived from 8_5_TV1_C.ZA. The synthetic sequence depicted corresponds to exon 1 of rev. Wild-type rev has two exons.

FIG. 44 (SEQ ID NO:73) depicts the wild-type nucleotide sequence of 8_5_TV1_C.ZA exon 1 of Rev.

FIG. 45 (SEQ ID NO:74) depicts the nucleotide sequence of a synthetic rev-encoding polynucleotide derived from 8_5_TV1_C.ZA. The synthetic sequence depicted corresponds to exon 2 of rev.

FIG. 46 (SEQ ID NO:75) depicts the wild-type nucleotide sequence of 8_5_TV1_C.ZA exon 2 of Rev.

FIG. 47 (SEQ ID NO:76) depicts the nucleotide sequence of a synthetic RT-encoding polynucleotide derived from 8_5_TV1_C.ZA.

FIG. 48 (SEQ ID NO:77) depicts the wild-type nucleotide sequence of 8_5_TV1_C.ZA RT.

FIG. 49 (SEQ ID NO:78) depicts the nucleotide sequence of a synthetic RT-encoding polynucleotide derived from 8_5_TV1_C.ZA. The synthetic polynucleotide includes a mutation in the RT coding sequence which renders the gene product inactive.

FIG. 50 (SEQ ID NO:79) depicts the wild-type nucleotide sequence of 8_5_TV1_C.ZA RT including a mutation which inactivates the RT gene product.

FIG. 51 (SEQ ID NO:80) depicts the nucleotide sequence of a synthetic Tat-encoding polynucleotide derived from 8_5_TV1_C.ZA. The synthetic sequence depicted corresponds to exon 1 of Tat and further includes a mutation that renders the Tat gene product non-functional. Wild-type Tat has two exons.

FIG. 52 (SEQ ID NO:81) depicts the nucleotide sequence of a synthetic Tat-encoding polynucleotide derived from 8_5_TV1_C.ZA. The synthetic sequence depicted corresponds to exon 1 of Tat.

FIG. 53 (SEQ ID NO:82) depicts the wild-type nucleotide sequence of 8_5_TV1_C.ZA exon 1 of Tat.

FIG. 54 (SEQ ID NO:83) depicts the nucleotide sequence of a synthetic Tat-encoding polynucleotide derived from 8_5_TV1_C.ZA. The synthetic sequence depicted corresponds to exon 2 of Tat.

FIG. 55 (SEQ ID NO:84) depicts the wild-type nucleotide sequence of 8_5_TV1_C.ZA exon 2 of Tat.

FIG. 56 (SEQ ID NO:85) depicts the nucleotide sequence of a synthetic Vif-encoding polynucleotide derived from 8_5_TV1_C.ZA.

FIG. 57 (SEQ ID NO:86) depicts the wild-type nucleotide sequence of 8_5_TV1_C.ZA Vif.

FIG. 58 (SEQ ID NO:87) depicts the nucleotide sequence of a synthetic Vpr-encoding polynucleotide derived from 8_5_TV1_C.ZA.

FIG. 59 (SEQ ID NO:88) depicts the wild-type nucleotide sequence of 8_5_TV1_C.ZA Vpr.

FIG. 60 (SEQ ID NO:89) depicts the nucleotide sequence of a synthetic Vpu-encoding polynucleotide derived from 8_5_TV1_C.ZA.

FIG. 61 (SEQ ID NO:90) depicts the wild-type nucleotide sequence of 8_5_TV1_C.ZA Vpu.

FIG. 62 (SEQ ID NO:91) depicts the nucleotide sequence of a synthetic rev-encoding polynucleotide derived from 8_5_TV1_C.ZA. The synthetic sequence depicted corresponds to exons 1 and 2 of rev.

FIG. 63 (SEQ ID NO:92) depicts the wild-type nucleotide sequence of exons 1 and 2 of rev derived from 8_5_TV1_C.ZA.

FIG. 64 (SEQ ID NO:93) depicts the nucleotide sequence of a synthetic Tat-encoding polynucleotide derived from 8_5_TV1_C.ZA. The synthetic polynucleotide includes both exons 1 and 2 of Tat and further includes a mutation in exon 1 which renders the gene product non-functional.

FIG. 65 (SEQ ID NO:94) depicts the nucleotide sequence of a synthetic Tat-encoding polynucleotide derived from 8_5_TV1_C.ZA. The synthetic polynucleotide includes both exons 1 and 2 of Tat.

FIG. 66 (SEQ ID NO:95) depicts the wild-type nucleotide sequence of exons 1 and 2 of Tat derived from 8_5_TV1_C.ZA.

FIG. 67 (SEQ ID NO:96) depicts the nucleotide sequence of a synthetic Nef-encoding polynucleotide derived from 8_5_TV1_C.ZA. The sequence includes a mutation at position 125 which results in a non-functional gene product and a mutation that eliminates the myristoylation site of the Nef gene product.

FIG. 68 (SEQ ID NO:97) depicts the nucleotide sequence of a synthetic Env gp160-encoding polynucleotide derived from 12-5_1_TV2_C.ZA.

FIG. 69 (SEQ ID NO:98) depicts the wild-type nucleotide sequence of Env gp160 derived from 12-5_1_TV2_C.ZA.

FIG. 70 (SEQ ID NO:99) depicts the nucleotide sequence of a synthetic Gag-encoding polynucleotide derived from 12-5_1_TV2_C.ZA.

FIG. 71 (SEQ ID NO:100) depicts the wild-type nucleotide sequence of Gag derived from 12-5_1_TV2_C.ZA.

FIG. 72 (SEQ ID NO:101) depicts the nucleotide sequence of a synthetic Nef-encoding polynucleotide derived from 12-5_1_TV2_C.ZA.

FIG. 73 (SEQ ID NO:102) depicts the wild-type nucleotide sequence of Nef derived from 12-5_1_TV2_C.ZA.

FIG. 74 (SEQ ID NO:103) depicts the nucleotide sequence of a synthetic Pol-encoding polynucleotide derived from 12-5_1_TV2_C.ZA.

FIG. 75 (SEQ ID NO:104) depicts the wild-type nucleotide sequence of Pol derived from 12-5_1_TV2_C.ZA.

FIG. 76 (SEQ ID NO:105) depicts the nucleotide sequence of a synthetic Rev-encoding polynucleotide derived from exon 1 of Rev from 12-5_1_TV2_C.ZA.

FIG. 77 (SEQ ID NO:106) depicts the wild-type nucleotide sequence of exon 1 of Rev derived from 12-5_1_TV2_C.ZA.

FIG. 78 (SEQ ID NO:107) depicts the nucleotide sequence of a synthetic Rev-encoding polynucleotide derived from exon 2 of Rev from 12-5_1_TV2_C.ZA.

FIG. 79 (SEQ ID NO:108) depicts the wild-type nucleotide sequence of exon 2 of Rev derived from 12-5_1_TV2_C.ZA.

FIG. 80 (SEQ ID NO:109) depicts the nucleotide sequence of a synthetic Tat-encoding polynucleotide derived from exon 1 of Tat from 12-5_1_TV2_C.ZA.

FIG. 81 (SEQ ID NO:110) depicts the wild-type nucleotide sequence of exon 1 of Tat derived from 12-5_1_TV2_C.ZA.

FIG. 82 (SEQ ID NO:111) depicts the nucleotide sequence of a synthetic Tat-encoding polynucleotide derived from exon 2 of Tat from 12-5_1_TV2_C.ZA.

FIG. 83 (SEQ ID NO:112) depicts the wild-type nucleotide sequence of exon 2 of Tat derived from 12-5_1_TV2_C.ZA.

FIG. 84 (SEQ ID NO:113) depicts the nucleotide sequence of a synthetic Vif-encoding polynucleotide derived from 12-5_1_TV2_C.ZA.

FIG. 85 (SEQ ID NO:114) depicts the wild-type nucleotide sequence of Vif derived from 12-5_1_TV2_C.ZA.

FIG. 86 (SEQ ID NO:115) depicts the nucleotide sequence of a synthetic Vpr-encoding polynucleotide derived from 12-5_1_TV2_C.ZA.

FIG. 87 (SEQ ID NO:116) depicts the wild-type nucleotide sequence of Vpr derived from 12-5_1_TV2_C.ZA.

FIG. 88 (SEQ ID NO:117) depicts the nucleotide sequence of a synthetic Vpu-encoding polynucleotide derived from 12-5_1_TV2_C.ZA.

FIG. 89 (SEQ ID NO:118) depicts the wild-type nucleotide sequence of Vpu derived from 12-5_1_TV2_C.ZA.

FIG. 90 (SEQ ID NO:119) depicts the nucleotide sequence of a synthetic Env gp120-encoding polynucleotide derived from 8_2_$_{TV}$1_C.ZA. The V2 region is deleted. The sequence includes: an EcoRI restriction site (nucleotides 1 to 6); a codon modified signal peptide leader sequence (nucleotides 7 to 87); a gp120 coding sequence (nucleotides 88 to 1464); a stop codon (nucleotides 1465 to 1467); an XhoI restriction site (nucleotides 1468 to 1473).

FIG. 91 (SEQ ID NO:120) depicts the nucleotide sequence of a synthetic Env gp140-encoding polynucleotide derived from 8_2_TV1_C.ZA. The V2 region is deleted. The sequence includes: an EcoRI restriction site (nucleotides 1 to 6); a modified signal peptide leader sequence (nucleotides 7 to 87); a gp140 coding sequence (nucleotides 88 to 1977); a stop codon (nucleotides 1978 to 1980); an XhoI restriction site (nucleotides 1981 to 1986).

FIG. 92 (SEQ ID NO:121) depicts the nucleotide sequence of a synthetic Env gp140-encoding polynucleotide derived from 8_2_TV1_C.ZA. The V2 region is deleted and the sequence includes mutations in the cleavage site that prevent the cleavage of a gp140 polypeptide into a gp120 polypeptide and a gp41 polypeptide. The sequence includes: an EcoRI restriction site (nucleotides 1 to 6); a modified signal peptide leader sequence (nucleotides 7 to 87); gp140 coding sequence (nucleotides 88 to 1977); a stop codon (nucleotides 1978 to 1980); an XhoI restriction site (nucleotides 1981 to 1986).

FIG. 93 (SEQ ID NO:122) depicts the nucleotide sequence of a synthetic Env gp160-encoding polynucleotide derived from 8_2_TV1_C.ZA. The V1/V2 regions are deleted. The sequence includes: an EcoRI restriction site (nucleotides 1 to 6); a modified signal peptide leader sequence (nucleotides 7 to 87); gp160 coding sequence (nucleotides 88 to 2388); a stop codon (nucleotides 2389 to 2391); an XhoI restriction site (nucleotides 2392 to 2397).

FIG. 94 (SEQ ID NO:123) depicts the nucleotide sequence of a synthetic Env gp160-encoding polynucleotide derived from 8_2_TV1_C.ZA. The V2 region is deleted. The sequence includes: an EcoRI restriction site (nucleotides 1 to 6); a modified signal peptide leader sequence (nucleotides 7 to 87); a gp160 coding sequence (nucleotides 88 to 2520); a stop codon (nucleotides 2521 to 2523); an XhoI restriction site (nucleotides 2524 to 2529).

FIG. 95 (SEQ ID NO:124) depicts the nucleotide sequence of a synthetic Env gp160-encoding polynucleotide derived from 8_2_TV1_C.ZA. The V2 region is deleted and the cleavage site is mutated. The sequence includes: an EcoRI restriction site (nucleotides 1 to 6); a modified signal peptide leader sequence (nucleotides 7 to 87); a gp160 coding sequence (nucleotides 88 to 2520); a stop codon (nucleotides 2521 to 2523); an XhoI restriction site (nucleotides 2524 to 2529).

FIG. 96 (SEQ ID NO:125) depicts the nucleotide sequence of a synthetic Env gp160-encoding polynucleotide derived from 8_2_TV1_C.ZA. The nucleotide sequence includes a TPA1 leader sequence. The sequence includes: a SalI restriction site (nucleotides 1 to 6); a Kozak sequence (nucleotides 7 to 12); a TPA1 signal peptide leader sequence (nucleotides 13 to 87); a gp160 coding sequence (nucleotides 88 to 2604); a stop codon (nucleotides 2605 to 2607); an XhoI restriction site (nucleotides 2608 to 2613).

FIG. 97 (SEQ ID NO:126) depicts the nucleotide sequence of a synthetic Env gp160-encoding polynucleotide derived from 8_2_TV1_C.ZA. The sequence includes: an EcoRI restriction site (nucleotides 1 to 6); a modified signal peptide leader sequence (nucleotides 7 to 87); a gp160 coding sequence (nucleotides 8 to 2607); a stop codon (nucleotides 2608 to 2610); an XhoI restriction site (nucleotides 2611 to 2616).

FIG. 98 (SEQ ID NO:127) depicts the nucleotide sequence of a synthetic Env gp160-encoding polynucleotide derived from 8_2_TV1_C.ZA. The nucleotide sequence includes a wild type leader sequence. The sequence includes: an EcoRI restriction site (nucleotides 1 to 6); a native (unmodified) signal peptide leader sequence (nucleotides 7 to 87); a gp160 coding sequence (nucleotides 88 to 2607); a stop codon (nucleotides 2608 to 2610); an XhoI restriction site (nucleotides 2611 to 2616).

FIG. 99 (SEQ ID NO:128) depicts the nucleotide sequence of wild type gp160 derived from 8_2_TV1_C.ZA.

FIG. 100 (SEQ ID NO:131) depicts the nucleotide sequence of a synthetic Env gp140-encoding polynucleotide derived from 8_2_TV1_C.ZA. The nucleotide sequence includes a TPA1 leader sequence (nucleotides 1-75); a gp140 coding sequence (nucleotides 76 to 2049); a stop codon (nucleotides 2050 to 2052)

FIG. 101 (SEQ ID NO:132) depicts the nucleotide sequence of a synthetic gp140-encoding polynucleotide derived from 8_2_TV1_C.ZA. The nucleotide sequence includes an EcoRI restriction site (nucleotides 1 to 6); a leader sequence modified from the TV1_C.ZA wild-type leader sequence (nucleotides 7 to 87); a gp140 coding sequence (nucleotides 88 to 2064); a stop codon (nucleotides 2065 to 2067); a XhoI restriction site (nucleotides 2068 to 2073).

FIG. 102 (SEQ ID NO:133) depicts the nucleotide sequence of a synthetic gp140-encoding polynucleotide derived from 8_2_TV1_C.ZA. The nucleotide sequence includes wild-type TV1_C.ZA unmodified leader sequence. The nucleotide sequence includes a restriction site (nucleotides 1 to 6); a wild type leader sequence (nucleotides 7 to 87); a gp140 coding sequence (nucleotides 88 to 2064); a stop codon (nucleotides 2065 to 2067); a XhoI restriction site (nucleotides 2068-2073).

FIG. 103 (SEQ ID NO:134) depicts the nucleotide sequence of a synthetic Nef-encoding polynucleotide derived from 12-5_1_TV2_C.ZA. The sequence includes a mutation at position 125 which results in a non-functional gene product.

FIG. 104 (SEQ ID NO:135) depicts the nucleotide sequence of a synthetic Nef-encoding polynucleotide derived from 12-5_1_TV2_C.ZA. The synthetic polynucleotide includes a mutation that eliminates the myristoylation site of the Nef gene product.

FIG. 105A-105C depicts an alignment of Env polypeptides from various HIV isolates (SEQ ID NOS:143-147). The regions between the arrows indicate regions (of TV1 and TV2 clones) in the beta and/or bridging sheet region(s) that can be deleted and/or truncated. The "*" denotes N-linked glycosylation sites (of TV1 and TV2 clones), one or more of which can be modified (e.g., deleted and/or mutated).

DETAILED DESCRIPTION OF THE INVENTION

Figure 7:
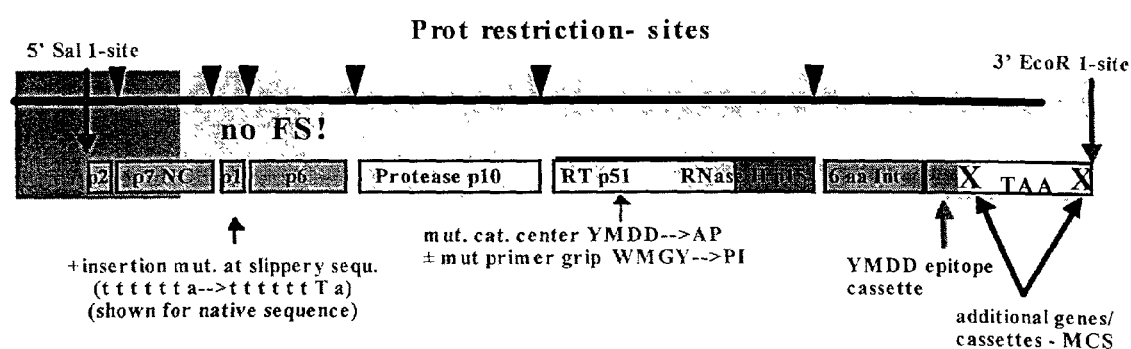

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences,* 18th Edition (Easton, Pa.: Mack Publishing Company, 1990); *Methods In Enzymology* (S. Colowick and N. Kaplan, eds., Academic Press, Inc.); and *Handbook of Experimental Immunology*, Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Short Protocols in Molecular Biology*, 4th ed. (Ausubel et al. eds., 1999, John Wiley & Sons); *Molecular Biology Techniques: An Intensive Laboratory Course*, (Ream et al., eds., 1998, Academic Press); PCR (*Introduction to Biotechniques Series*), 2nd ed. (Newton & Graham eds., 1997, Springer Verlag).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, for example, reference to "an antigen" includes a mixture of two or more such agents.

1. Definitions

In describing the present invention, the following terms will be employed, and are intended to be defined as indicated below.

"Synthetic" sequences, as used herein, refers to Type C HIV polypeptide-encoding polynucleotides whose expression has been modified as described herein, for example, by codon substitution and inactivation of inhibitory sequences. "Wild-type" or "native" sequences, as used herein, refers to polypeptide encoding sequences that are essentially as they are found in nature, e.g., Gag, Pol, Vif, Vpr, Tat, Rev, Vpu, Env and/or Nef encoding sequences as found in Type C isolates, e.g., AF110965, AF110967, AF110968, AF110975, 8_5_TV1_C.ZA, 8_2_TV1_C.ZA or 12-5_1_TV2_C.ZA. The various regions of the HIV genome are shown in Table A, with numbering relative to 8_5_TV1_C.ZA (SEQ ID NO:33). Thus, the term "Pol" refers to one or more of the following polypeptides: polymerase (p6Pol); protease (prot); reverse transcriptase (p66RT or RT); RNAseH (p15RNAseH); and/or integrase (p31Int or Int).

As used herein, the term "virus-like particle" or "VLP" refers to a nonreplicating, viral shell, derived from any of several viruses discussed further below. VLPs are generally composed of one or more viral proteins, such as, but not limited to those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art and discussed more fully below. The presence of VLPs following recombinant expression of viral proteins can be detected using conventional techniques known in the art, such as by electron microscopy, X-ray crystallography, and the like. See, e.g., Baker et al., *Biophys. J.* (1991) 60:1445-1456; Hagensee et al., *J. Virol.* (1994) 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

By "particle-forming polypeptide" derived from a particular viral protein is meant a full-length or near full-length viral protein, as well as a fragment thereof, or a viral protein with internal deletions, which has the ability to form VLPs under conditions that favor VLP formation. Accordingly, the polypeptide may comprise the full-length sequence, fragments, truncated and partial sequences, as well as analogs and precursor forms of the reference molecule. The term therefore intends deletions, additions and substitutions to the sequence, so long as the polypeptide retains the ability to form a VLP. Thus, the term includes natural variations of the specified polypeptide since variations in coat proteins often occur between viral isolates. The term also includes deletions, additions and substitutions that do not naturally occur in the reference protein, so long as the protein retains the ability to form a VLP. Preferred substitutions are those which are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids.

An "antigen" refers to a molecule containing one or more epitopes (either linear, conformational or both) that will stimulate a host's immune system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term "antigen" denotes both subunit antigens, (i.e., antigens which are separate and discrete from a whole organism with which the antigen is associated in nature), as well as, killed, attenuated or inactivated bacteria, viruses, fungi, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

For purposes of the present invention, antigens can be derived from any of several known viruses, bacteria, parasites and fungi, as described more fully below. The term also intends any of the various tumor antigens. Furthermore, for purposes of the present invention, an "antigen" refers to a protein which includes modifications, such as deletions, additions and substitutions (generally conservative in nature), to the native sequence, so long as the protein maintains the ability to elicit an immunological response, as defined herein. These modifications may be deliberate, as through site-directed mutagenesis, or may be accidental, such as through mutations of hosts which produce the antigens.

An "immunological response" to an antigen or composition is the development in a subject of a humoral and/or a cellular immune response to an antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376. Recent methods of measuring cell-mediated immune response include measurement of intracellular cytokines or cytokine secretion by T-cell populations, or by measurement of epitope specific T-cells (e.g., by the tetramer technique)(reviewed by McMichael, A. J., and O'Callaghan, C. A., *J. Exp. Med.* 187(9)1367-1371, 1998; Mcheyzer-Williams, M. G., et al, *Immunol. Rev.* 150: 5-21, 1996; Lalvani, A., et al, *J. Exp. Med.* 186:859-865, 1997).

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complements, or antibody dependent cell cytotoxicity (ADCC) to provide protection to an immunized host. Such responses can be determined using standard immunoassays and neutralization assays, well known in the art.

An "immunogenic composition" is a composition that comprises an antigenic molecule where administration of the composition to a subject results in the development in the subject of a humoral and/or a cellular immune response to the antigenic molecule of interest. The immunogenic composition can be introduced directly into a recipient subject, such as by injection, inhalation, oral, intranasal and mucosal (e.g., intra-rectally or intra-vaginally) administration.

By "subunit vaccine" is meant a vaccine composition which includes one or more selected antigens but not all antigens, derived from or homologous to, an antigen from a pathogen of interest such as from a virus, bacterium, parasite or fungus. Such a composition is substantially free of intact pathogen cells or pathogenic particles, or the lysate of such cells or particles. Thus, a "subunit vaccine" can be prepared from at least partially purified (preferably substantially purified) immunogenic polypeptides from the pathogen, or analogs thereof. The method of obtaining an antigen included in the subunit vaccine can thus include standard purification techniques, recombinant production, or synthetic production.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence such as a stop codon may be located 3' to the coding sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

A "polynucleotide coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. Exemplary coding sequences are the modified viral polypeptide-coding sequences of the present invention. A transcription termination sequence may be located 3' to the coding sequence. Typical "control elements", include, but are not limited to, transcription regulators, such as promoters, transcription enhancer elements, transcription termination signals, and polyadenylation sequences; and translation regulators, such as sequences for optimization of initiation of translation, e.g., Shine-Dalgamo (ribosome binding site) sequences, Kozak sequences (i.e., sequences for the optimization of translation, located, for example, 5' to the coding sequence), leader sequences, translation initiation codon (e.g., ATG), and translation termination sequences. In certain embodiments, one or more translation regulation or initiation sequences (e.g., the leader sequence) are derived from wild-type translation initiation sequences, i.e., sequences that regulate translation of the coding region in their native state. Wild-type leader sequences that have been modified, using the methods described herein, also find use in the present invention. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is induced by an analyte, cofactor, regulatory protein, etc.), and constitutive promoters.

A "nucleic acid" molecule can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. For example, BLASTN and BLASTP can be used with the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations +Swiss protein +Spupdate +PIR. Details of these programs can be found at the following internet address: ncbi.nlm.gov/cgi-bin/BLAST.

One of skill in the art can readily determine the proper search parameters to use for a given sequence, exemplary preferred Smith Waterman based parameters are presented above. For example, the search parameters may vary based on the size of the sequence in question. Thus, for the polynucleotide sequences of the present invention the length of the polynucleotide sequence disclosed herein is searched against a selected database and compared to sequences of essentially the same length to determine percent identity. For example, a representative embodiment of the present invention would include an isolated polynucleotide having X contiguous nucleotides, wherein (i) the X contiguous nucleotides have at least about a selected level of percent identity relative to Y contiguous nucleotides of the sequences described herein, and (ii) for search purposes X equals Y, wherein Y is a selected reference polynucleotide of defined length.

The sequences of the present invention can include fragments of the sequences, for example, from about 15 nucleotides up to the number of nucleotides present in the full-length sequences described herein (e.g., see the Sequence Listing, Figures, and claims), including all integer values falling within the above-described range. For example, fragments of the polynucleotide sequences of the present invention may be 30-60 nucleotides, 60-120 nucleotides, 120-240 nucleotides, 240-480 nucleotides, 480-1000 nucleotides, and all integer values therebetween.

The synthetic expression cassettes (and purified polynucleotides) of the present invention include related polynucleotide sequences having about 80% to 100%, greater than 80-85%, preferably greater than 90-92%, more preferably greater than 95%, and most preferably greater than 98% up to 100% (including all integer values falling within these described ranges) sequence identity to the synthetic expression cassette (and purified polynucleotide) sequences disclosed herein (for example, to the claimed sequences or other sequences of the present invention) when the sequences of the present invention are used as the query sequence against, for example, a database of sequences.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., supra or Ausubel et al., supra). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., supra or Ausubel et al., supra).

A first polynucleotide is "derived from" second polynucleotide if it has the same or substantially the same basepair sequence as a region of the second polynucleotide, its cDNA, complements thereof, or if it displays sequence identity as described above.

A first polypeptide is "derived from" a second polypeptide if it is (i) encoded by a first polynucleotide derived from a second polynucleotide, or (ii) displays sequence identity to the second polypeptides as described above.

Generally, a viral polypeptide is "derived from" a particular polypeptide of a virus (viral polypeptide) if it is (i) encoded by an open reading frame of a polynucleotide of that virus (viral polynucleotide), or (ii) displays sequence identity to polypeptides of that virus as described above.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence. Further, polyproteins can be constructed by fusing in-frame two or more polynucleotide sequences encoding polypeptide or peptide products. Further, polycistronic coding sequences may be produced by placing two or more polynucleotide sequences encoding polypeptide products adjacent each other, typically under the control of one promoter, wherein each polypeptide coding sequence may be modified to include sequences for internal ribosome binding sites.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

By "nucleic acid immunization" is meant the introduction of a nucleic acid molecule encoding one or more selected antigens into a host cell, for the in vivo expression of an antigen, antigens, an epitope, or epitopes. The nucleic acid molecule can be introduced directly into a recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

"Gene transfer" or "gene delivery" refers to methods or systems for reliably inserting DNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from alphaviruses, pox viruses and vaccinia viruses. When used for immunization, such gene delivery expression vectors may be referred to as vaccines or vaccine vectors.

"T lymphocytes" or "T cells" are non-antibody producing lymphocytes that constitute a part of the cell-mediated arm of the immune system. T cells arise from immature lymphocytes that migrate from the bone marrow to the thymus, where they undergo a maturation process under the direction of thymic hormones. Here, the mature lymphocytes rapidly divide increasing to very large numbers. The maturing T cells become immunocompetent based on their ability to recognize and bind a specific antigen. Activation of immunocompetent T cells is triggered when an antigen binds to the lymphocyte's surface receptors.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) Gene 13:197. Such techniques can be used to introduce one or more exogenous DNA moieties into suitable host cells. The term refers to both stable and transient uptake of the genetic material, and includes uptake of peptide-or antibody-linked DNAs.

A "vector" is capable of transferring gene sequences to target cells (e.g., viral vectors, non-viral vectors, particulate carriers, and liposomes). Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as viral vectors.

Transfer of a "suicide gene" (e.g., a drug-susceptibility gene) to a target cell renders the cell sensitive to compounds or compositions that are relatively nontoxic to normal cells. Moolten, F. L. (1994) *Cancer Gene Ther.* 1:279-287. Examples of suicide genes are thymidine kinase of herpes simplex virus (HSV-tk), cytochrome P450 (Manome et al. (1996) *Gene Therapy* 3:513-520), human deoxycytidine kinase (Manome et al. (1996) *Nature Medicine* 2(5):567-573) and the bacterial enzyme cytosine deaminase (Dong et al. (1996) *Human Gene Therapy* 7:713-720). Cells which express these genes are rendered sensitive to the effects of the relatively nontoxic prodrugs ganciclovir (HSV-tk), cyclophosphamide (cytochrome P450 2B1), cytosine arabinoside (human deoxycytidine kinase) or 5-fluorocytosine (bacterial cytosine deaminase). Culver et al. (1992) *Science* 256:1550-1552, Huber et al. (1994) *Proc. Natl. Acad. Sci. USA* 91:8302-8306.

A "selectable marker" or "reporter marker" refers to a nucleotide sequence included in a gene transfer vector that has no therapeutic activity, but rather is included to allow for simpler preparation, manufacturing, characterization or testing of the gene transfer vector.

A "specific binding agent" refers to a member of a specific binding pair of molecules wherein one of the molecules specifically binds to the second molecule through chemical and/or physical means. One example of a specific binding agent is an antibody directed against a selected antigen.

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

By "physiological pH" or a "pH in the physiological range" is meant a pH in the range of approximately 7.2 to 8.0 inclusive, more typically in the range of approximately 7.2 to 7.6 inclusive.

As used herein, "treatment" refers to any of (I) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

By "co-administration" is meant administration of more than one composition or molecule. Thus, co-administration includes concurrent administration or sequentially administration (in any order), via the same or different routes of administration. Non-limiting examples of co-administration regimes include, co-administration of nucleic acid and polypeptide; co-administration of different nucleic acids (e.g., different expression cassettes as described herein and/or different gene delivery vectors); and co-administration of different polypeptides (e.g., different HIV polypeptides and/or different adjuvants). The term also encompasses multiple administrations of one of the co-administered molecules or compositions (e.g., multiple administrations of one or more of the expression cassettes described herein followed by one or more administrations of a polypeptide-containing composition). In cases where the molecules or compositions are delivered sequentially, the time between each administration can be readily determined by one of skill in the art in view of the teachings herein.

"Lentiviral vector", and "recombinant lentiviral vector" refer to a nucleic acid construct which carries, and within certain embodiments, is capable of directing the expression of a nucleic acid molecule of interest. The lentiviral vector include at least one transcriptional promoter/enhancer or locus defining element(s), or other elements which control gene expression by other means such as alternate splicing, nuclear RNA export, post-translational modification of messenger, or post-transcriptional modification of protein. Such vector constructs must also include a packaging signal, long terminal repeats (LTRS) or portion thereof, and positive and negative strand primer binding sites appropriate to the retrovirus used (if these are not already present in the retroviral vector). Optionally, the recombinant lentiviral vector may also include a signal which directs polyadenylation, selectable markers such as Neo, TK, hygromycin, phleomycin, histidinol, or DHFR, as well as one or more restriction sites and a translation termination sequence. By way of example, such vectors typically include a 5' LTR, a tRNA binding site, a packaging signal, an origin of second strand DNA synthesis, and a 3'LTR or a portion thereof "Lentiviral vector particle" as utilized within the present invention refers to a lentivirus which carries at least one gene of interest. The retrovirus may also contain a selectable marker. The recombinant lentivirus is capable of reverse transcribing its genetic material (RNA) into DNA and incorporating this genetic material into a host cell's DNA upon infection. Lentiviral vector particles may have a lentiviral envelope, a non-lentiviral envelope (e.g., an ampho or VSV-G envelope), or a chimeric envelope.

"Nucleic acid expression vector" or "Expression cassette" refers to an assembly which is capable of directing the expression of a sequence or gene of interest. The nucleic acid expression vector includes a promoter which is operably linked to the sequences or gene(s) of interest. Other control elements may be present as well. Expression cassettes described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

"Packaging cell" refers to a cell which contains those elements necessary for production of infectious recombinant retrovirus which are lacking in a recombinant retroviral vector. Typically, such packaging cells contain one or more expression cassettes which are capable of expressing proteins which encode Gag, pol and env proteins.

"Producer cell" or "vector producing cell" refers to a cell which contains all elements necessary for production of recombinant retroviral vector particles.

2. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

2.1. The HIV Genome

The HIV genome and various polypeptide-encoding regions are shown in Table A. The nucleotide positions are given relative to 8_5_TV1_C.ZA (SEQ ID NO:33, FIG. 11). However, it will be readily apparent to one of ordinary skill in the art in view of the teachings of the present disclosure how to determine corresponding regions in other HIV strains or variants (e.g., isolates $HIV_{IIIb}$, $HIV_{SF2}$, $HIV-1_{SF162}$, $HIV-1_{SF170}$, $HIV_{LAV}$, $HIV_{LAI}$, $HIV_{MN}$, $HIV-1_{CM235}$, $HIV-1_{US4}$, other HIV-1 strains from diverse subtypes(e.g., subtypes, A through G, and O), HIV-2 strains and diverse subtypes (e.g., $HIV-2_{UC1}$ and $HIV-2_{UC2}$), and simian immunodeficiency virus (SIV). (See, e.g., Virology, 3rd Edition (W. K. Joklik ed. 1988); *Fundamental Virology*, 2nd Edition (B. N. Fields and D. M. Knipe, eds. 1991); *Virology*, 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify the various regions).

TABLE A

Regions of the HIV Genome relative to 8_5_TV1_C.ZA

| Region | Position in nucleotide sequence |
|---|---|
| 5'LTR | 1-636 |
| U3 | 1-457 |
| R | 458-553 |
| U5 | 554-636 |
| NFkB II | 340-348 |
| NFkB I | 354-362 |
| Sp1 III | 379-388 |
| Sp1 II | 390-398 |
| Sp1 I | 400-410 |
| TATA Box | 429-433 |
| TAR | 474-499 |
| Poly A signal | 529-534 |
| PBS | 638-655 |
| p7 binding region, packaging signal | 685-791 |

TABLE A-continued

Regions of the HIV Genome relative to 8_5_TV1_C.ZA

| Region | Position in nucleotide sequence |
|---|---|
| Gag: | 792-2285 |
| p17 | 792-1178 |
| p24 | 1179-1871 |
| Cyclophilin A bdg. | 1395-1505 |
| MHR | 1632-1694 |
| p2 | 1872-1907 |
| p7 | 1908-2072 |
| Frameshift slip | 2072-2078 |
| p1 | 2073-2120 |
| p6Gag | 2121-2285 |
| Zn-motif I | 1950-1991 |
| Zn-motif II | 2013-2054 |
| Pol: | 2072-5086 |
| p6Pol | 2072-2245 |
| Prot | 2246-2542 |
| p66RT | 2543-4210 |
| p15RNaseH | 3857-4210 |
| p31Int | 4211-5086 |
| Vif: | 5034-5612 |
| Hydrophilic region | 5292-5315 |
| Vpr: | 5552-5839 |
| Oligomerization | 5552-5677 |
| Amphipathic α-helix | 5597-5653 |
| Tat: | 5823-6038 and 8417-8509 |
| Tat-1 exon | 5823-6038 |
| Tat-2 exon | 8417-8509 |
| N-terminal domain | 5823-5885 |
| Trans-activation domain | 5886-5933 |
| Transduction domain | 5961-5993 |
| Rev: | 5962-6037 and 8416-8663 |
| Rev-1 exon | 5962-6037 |
| Rev-2 exon | 8416-8663 |
| High-affinity bdg. site | 8439-8486 |
| Leu-rich effector domain | 8562-8588 |
| Vpu: | 6060-6326 |
| Transmembrane domain | 6060-6161 |
| Cytoplasmic domain | 6162-6326 |
| Env (gp160): | 6244-8853 |
| Signal peptide | 6244-6324 |
| gp120 | 6325-7794 |
| V1 | 6628-6729 |
| V2 | 6727-6852 |
| V3 | 7150-7254 |
| V4 | 7411-7506 |
| V5 | 7663-7674 |
| C1 | 6325-6627 |
| C2 | 6853-7149 |
| C3 | 7255-7410 |
| C4 | 7507-7662 |
| C5 | 7675-7794 |
| CD4 binding | 7540-7566 |
| gp41 | 7795-8853 |
| Fusion peptide | 7789-7842 |
| Oligomerization domain | 7924-7959 |
| N-terminal heptad repeat | 7921-8028 |
| C-terminal heptad repeat | 8173-8280 |
| Immunodominant region | 8023-8076 |
| Nef: | 8855-9478 |
| Myristoylation | 8858-8875 |
| SH3 binding | 9062-9091 |
| Polypurine tract | 9128-9154 |
| SH3 binding | 9296-9307 |

It will be readily apparent that one of skill in the art can readily align any sequence to that shown in Table A to determine relative locations of any particular HIV gene. For example, using one of the alignment programs described herein (e.g., BLAST), other HIV Type C sequences can be aligned with 8_5_TV1_C.ZA (Table A) and locations of genes determined.

Polypeptide sequences can be similarly aligned. For example, FIG. 103 shows the alignment of Env polypeptide sequences from various strains, relative to SF-162. As described in detail in co-owned WO/39303, Env polypeptides (e.g., gp120, gp140 and gp160) include a "bridging sheet" comprised of 4 anti-parallel β-strands (β-2, β-3, β-20 and β-21) that form a β-sheet. Extruding from one pair of the β-strands (β-2 and β-3) are two loops, V1 and V2. The β-2 sheet occurs at approximately amino acid residue 113 (Cys) to amino acid residue 117 (Thr) while β-3 occurs at approximately amino acid residue 192 (Ser) to amino acid residue 194 (Ile), relative to SF-162 (see, FIG. 103). The "V1/V2 region" occurs at approximately amino acid positions 120 (Cys) to residue 189 (Cys), relative to SF-162. Extruding from the second pair of β-strands (β-20 and β-21) is a "small-loop" structure, also referred to herein as "the bridging sheet small loop." The locations of both the small loop and bridging sheet small loop can be determined relative to HXB-2 following the teachings herein and in WO/39303. Also shown by arrows in FIG. 103A-C are approximate sites for deletions sequence from the beta sheet region. The "*" denotes N-glycosylation sites that can be mutated following the teachings of the present specification.

2.2 Synthetic Expression Cassettes 2.2.1 Modification of HIV-1-Type C Pol-, Prot-, Rt-, Int-, Gag, Env, Tat, Rev, Nef, RnaseH, Vif, Vpr, and Vpu Nucleic Acid Coding Sequences One aspect of the present invention is the generation of HIV-1 type C coding sequences, and related sequences, having improved expression relative to the corresponding wild-type sequences.

2.2.1.1. Modification of GAG Nucleic Acid Coding Sequences

An exemplary embodiment of the present invention is illustrated herein by modifying the Gag protein wild-type sequences obtained from the AF110965 and AF110967 strains of HIV-1, subtype C. (see, for example, Korber et al. (1998) *Human Retroviruses and Aids*, Los Alamos, N.: Los Alamos National Laboratory; Novitsky et al. (1999) *J. Virol.* 73(5):4427-4432, for molecular cloning of various subtype C clones from Botswana). Also illustrated herein is the modification of wild-type sequences from novel isolates 8_5_TV1_C.ZA (also called TV001 or TV1) and 12-5_1_TV2_C.ZA (also called TV002 or TV2). SEQ ID NO:52 shows the wild-type sequence of gag from 8_5_TV 1_C.ZA and SEQ ID NO:54 shows the wild-type sequence of the major homology region of gag (nucleotides 1632-1694 of Table A) of the same strain. SEQ ID NO: 100 shows the wild-type sequence of gag of 12-5_1_TV2_C.ZA Gag sequence obtained from other Type C HIV-1 variants may be manipulated in similar fashion following the teachings of the present specification. Such other variants include, but are not limited to, Gag protein encoding sequences obtained from the isolates of HIV-1 Type C, for example as described in Novitsky et al., (1999), supra; Myers et al., infra; Virology, 3rd Edition (W.K. Joklik ed. 1988); *Fundamental Virology*, 2nd Edition (B.N. Fields and D.M. Knipe, eds. 1991); *Virology*, 3rd Edition (Fields, BN, DM Knipe, PM Howley, Editors, 1996, Lippincott-Raven, Philadelphia, PA and on the World Wide Web (Internet), for example at hiv-web.lan1.gov/cgi-binlhivDB3/public/wdb/ssampublic and hiv-web.lan 1.gov.

First, the HIV-1 codon usage pattern was modified so that the resulting nucleic acid coding sequence was comparable to codon usage found in highly expressed human genes (Example 1). The HIV codon usage reflects a high content of the nucleotides A or T of the codon-triplet. The effect of the HIV-1 codon usage is a high AT content in the DNA sequence that results in a decreased translation ability and instability of the mRNA. In comparison, highly expressed human codons prefer the nucleotides G or C. The gag coding sequences were modified to be comparable to codon usage found in highly expressed human genes.

Second, there are inhibitory (or instability) elements (INS) located within the coding sequences of the Gag coding sequences. The RRE is a secondary RNA structure that interacts with the HIV encoded Rev-protein to overcome the expression down-regulating effects of the INS. To overcome the post-transcriptional activating mechanisms of RRE and Rev, the instability elements can be inactivated by introducing multiple point mutations that do not alter the reading frame of the encoded proteins. Subtype C Gag-encoding sequences having inactivated RRE sites are shown, for example, in FIGS. 1 (SEQ ID NO:3), 2 (SEQ ID NO:4), 5 (SEQ ID NO:20) and 6 (SEQ ID NO:26). Similarly, other synthetic polynucleotides derived from other Subtype C strains can be modified to inactivate the RRE sites.

Modification of the Gag polypeptide coding sequences results in improved expression relative to the wild-type coding sequences in a number of mammalian cell lines (as well as other types of cell lines, including, but not limited to, insect cells). Further, expression of the sequences results in production of virus-like particles (VLPs) by these cell lines (see below).

2.2.1.2 Modification of Env Nucleic Acid Coding Sequences

Similarly, the present invention also includes synthetic Env-encoding polynucleotides and modified Env proteins. Wild-type Env sequences are obtained from the AF110968 and AF110975 strains as well as novel strains 8_5_TV1_C.ZA (SEQ ID NO:33) and 12-5_1_TV2_C.ZA (SEQ ID NO:45) of HIV-1, type C. (see, for example, Novitsky et al. (1999) *J. Virol.* 73(5):4427-4432, for molecular cloning of various subtype C clones from Botswana). Wild-type Env sequences of 8_5_TV1_C.ZA are shown, for example, in SEQ ID NO:48 (wild-type Env common region, nucleotides 7486-7629 as shown in Table A); and SEQ ID NO:50 (wild type gp160, nucleotides 6244-8853 as shown in Table A). Wild-type Env gp160 of 12-5_1_TV2_C.ZA is shown in SEQ ID NO:98. It will be readily apparent from the disclosure herein that polynucleotides encoding fragments of Env gp160 (e.g., gp120, gp41, gp140) can be readily obtained from the larger, full-length sequences disclosed herein. It will also be readily apparent that other modifications can be made, for example deletion of regions such as the V1 and/or V2 region; mutation of the cleavage site and the like (see, Example 1). Exemplary sequences of such modification as shown in SEQ ID NO:119 through 127.

Further, Env sequences obtained from other Type C HIV-1 variants may be manipulated in similar fashion following the teachings of the present specification. Such other variants include, but are not limited to, Env protein encoding sequences obtained from the isolates of HIV-1 Type C, described above.

The codon usage pattern for Env was modified as described above for Gag so that the resulting nucleic acid coding sequence was comparable to codon usage found in highly expressed human genes. Experiments performed in support of the present invention show that the synthetic Env sequences were capable of higher level of protein production relative to the native Env sequences.

Modification of the Env polypeptide coding sequences results in improved expression relative to the wild-type coding sequences in a number of mammalian cell lines (as well as other types of cell lines, including, but not limited to, insect cells). Similar Env polypeptide coding sequences can be obtained, modified and tested for improved expression from a variety of isolates, including those described above for Gag.

Further modifications of Env include, but are not limited to, generating polynucleotides that encode Env polypeptides having mutations and/or deletions therein. For instance, the hypervariable regions, V1 and/or V2, can be deleted as described herein. Additionally, other modifications, for example to the bridging sheet region and/or to N-glycosylation sites within Env can also be performed following the teachings of the present specification. (see, FIG. 103A-C and WO/39303). Various combinations of these modifications can be employed to generate synthetic expression cassettes as described herein.

2.2.1.3 Modification of Sequences Including HIV1 Pol Nucleic Acid Coding Sequences The present invention also includes expression cassettes which include synthetic Pol sequences. As noted above, "Pol" includes, but is not limited to, the protein-encoding regions shown in FIG. 7, for example polymerase, protease, reverse transcriptase and/or integrase-containing sequences. The regions shown in FIG. 7 are described, for example, in Wan et et al (1996) *Biochem. J.* 316:569-573; Kohl et al. (1988) *PNAS USA* 85:4686-4690; Krausslich et al. (1988) *J. Virol.* 62:4393-4397; Coffin, "Retroviridae and their Replication" in Virology, pp 1437-1500 (Raven, N.Y., 1990); Patel et. al. (1995) *Biochemistry* 34:5351-5363. Thus, the synthetic expression cassettes exemplified herein include one or more of these regions and one or more changes to the resulting amino acid sequences.

Wild type Pol sequences were obtained from the AF110975, 8_5_TV1_C.ZA and 12-5_1_TV2_C.ZA strains of HIV-1, type C. (see, for example, Novitsky et al. (1999) *J. Virol.* 73(5):4427-4432, for molecular cloning of various subtype C clones from Botswana). SEQ ID NO:34 shows the wild type sequence of AF110975 from the p2 through p7 region of Pol (see, FIG. 7 and Table A). SEQ ID NO:35 shows the wild type sequence of AF110975 from p1 through the first 6 amino acids of integrase (see, FIG. 7 and Table A). SEQ ID NO:63 and SEQ ID NO:104 show wild-type sequences of Pol from 8_5_TV1_C.ZA and 12-5_1_TV2_C.ZA, respectively (see, also, Table A).

Sequence obtained from other Type C HIV-1 variants may be manipulated in similar fashion following the teachings of the present specification. Such other variants include, but are not limited to, Pol protein encoding sequences obtained from the isolates of HIV-1 Type C described herein.

The codon usage pattern for Pol was modified as described above for Gag and Env so that the resulting nucleic acid coding sequence was comparable to codon usage found in highly expressed human genes.

Table B shows the nucleotide positions of various regions found in the Pol constructs exemplified herein (e.g., SEQ ID NOs: 30-32).

TABLE B

| | Position in nucleotide sequence in construct | | |
|---|---|---|---|
| Region | PR975(+) Seq Id No:30 | PR975YM Seq Id No:31 | PR975(+) YMWM Seq Id No:32 |
| Sal 1 restriction site | 1-6 | 1-6 | 1-6 |
| Kozak start codon | 7-16 | 7-16 | 7-16 |
| p2 | 16-54 | 16-54 | 16-54 |
| p7 | 55-219 | 55-219 | 55-219 |
| p1/p6 pol | 220-375 | 220-375 | 220-375 |
| Insertion mutation for in frame | 225 | 225 | 225 |

TABLE B-continued

| | Position in nucleotide sequence in construct | | |
|---|---|---|---|
| Region | PR975(+) Seq Id No:30 | PR975YM Seq Id No:31 | PR975(+) YMWM Seq Id No:32 |
| p10Protease | 376-672 | 376-672 | 376-672 |
| p66RT | 673-2352 | 673-2346 | 673-2340 |
| p51RT | 673-1992 | 673-1986 | 673-1980 |
| p15RNaseH | 1993-2352 | 1993-2346 | 1993-2340 |
| catalytic center region (YMDD) | 1219-1230 | 1219-1224 | 1219-1224 |
| primer grip region (WMGY) | 1357-1368 | 1351-1362 | 1351-1356 |
| 6aa Integrase | 2353-2370 | 2347-2364 | 2341-2358 |
| YMDD epitope cassette (incl. 5' + 3'Gly) | 2371-2424 | 2365-2418 | 2359-2412 |
| MCS (multiple cloning site) | 2425-2463 | 2419-2457 | 2413-2451 |
| EcoR 1 restriction site | 2464-2469 | 2458-2463 | 2452-2457 |

As shown in Table B, exemplary constructs were modified in various ways. For example, the expression constructs exemplified herein include sequence that encodes the first 6 amino acids of the integrase polypeptide. This 6 amino acid region is believed to provide a cleavage recognition site recognized by HIV protease (see, e.g., McComack et al. (1997) *FEBS Letts* 414:84-88). As noted above, certain constructs exemplified herein include a multiple cloning site (MCS) for insertion of one or more transgenes, typically at the 3' end of the construct. In addition, a cassette encoding a catalytic center epitope derived from the catalytic center in RT is typically included 3' of the sequence encoding 6 amino acids of integrase. This cassette (SEQ ID NO:36) encodes Ile178 through Serine 191 of RT (amino acids 3 through 16 of SEQ ID NO:37) and was added to keep this well conserved region as a possible CTL epitope. Further, the constructs contain an insertion mutations (position 225 of SEQ ID NOs:30 to 32) to preserve the reading frame. (see, e.g., Park et al. (1991) *J. Virol.* 65:5111).

In certain embodiments, the catalytic center and/or primer grip region of RT are modified. The catalytic center and primer grip regions of RT are described, for example, in Patel et al. (1995) Biochem. 34:535 1 and Palaniappan et al. (1997) J. Biol. Chem. 272(17):11157. For example, in the construct designated PR975YM (SEQ ID NO:3 1), wild type sequence encoding the amino acids YMDD (SEQ ID NO: 148) at positions 183-185 of p66 RT, numbered relative to AF 110975, are replaced with sequence encoding the amino acids "AP". In the construct designated PR975YMWM (SEQ ID NO:32), the same mutation in YMDD (SEQ ID NO: 148) is made and, in addition, the primer grip region (amino acids WMGY (SEQ ID NO: 149), residues 229-232 of p66RT, numbered relative to AF 110975) are replaced with sequence encoding the amino acids "PI."

For the Pol sequence, the changes in codon usage are typically restricted to the regions up to the −1 frameshift and starting again at the end of the Gag reading frame; however, regions within the frameshift translation region can be modified as well. Finally, inhibitory (or instability) elements (INS) located within the coding sequences of the protease polypeptide coding sequence can be altered as well.

Experiments can be performed in support of the present invention to show that the synthetic Pol sequences were capable of higher level of protein production relative to the native Pol sequences. Modification of the Pol polypeptide coding sequences results in improved expression relative to the wild-type coding sequences in a number of mammalian cell lines (as well as other types of cell lines, including, but not limited to, insect cells). Similar Pol polypeptide coding sequences can be obtained, modified and tested for improved expression from a variety of isolates, including those described above for Gag and Env.

2.2.1.4 Modification of Other HIV Sequences

The present invention also includes expression cassettes which include synthetic HIV Type C sequences derived HIV genes other than gag, env and pol, including but not limited to, regions within gag, env, pol, as well as, vif, vpr, tat, rev, vpu, and nef for example from 8__5_TY1_C.ZA (SEQ ID NO:33) or 12-5__1_TV2_C.ZA (SEQ ID NO:45). Sequences obtained from other strains can be manipulated in similar fashion following the teachings of the present specification As noted above, the codon usage pattern is modified as described above for Gag, Env and Pol so that the resulting nucleic acid coding sequence is comparable to codon usage found in highly expressed human genes. Experiments can be performed in support of the present invention to show that these synthetic sequences were capable of higher level of protein production relative to the native sequences and that modification of the wild-type polypeptide coding sequences results in improved expression relative to the wild-type coding sequences in a number of mammalian cell lines (as well as other types of cell lines, including, but not limited to, insect cells). Furthermore, the nucleic acid sequence can also be modified to introduce mutations into one or more regions of the gene, for instance to render the gene product non-functional and/or to eliminate the myristoylation site in Nef.

Synthetic expression cassettes exemplified herein include SEQ ID NO:49 and SEQ ID NO:97 (Env gp160-encoding sequences, modified based on 8__5_TV1_C.ZA wild type and 12-5__1_TV2_C.ZA wild-type, respectively); SEQ ID NO:51 and SEQ ID NO:99 (Gag-encoding sequences modified based on 8__5_TV1_C.ZA wild type and 12-5__1_TV2_C.ZA wild-type, respectively); SEQ ID NO:53 (Gag major homology region, modified based on 8__5_TV1_C.ZA wild type); SEQ ID NO:55 and SEQ ID NO:101 (Nef-encoding sequences, modified based on 8__5_TV1_C.ZA wild type and 12-5__1_TV2_C.ZA wild-type, respectively); SEQ ID NO:57 and SEQ ID NO:134 (Nef-encoding sequences with a mutation at position 125 resulting in a non-functional gene product, modified based on 8__5_TV1_C.ZA wild type and 12-5__1_TV2_C.ZA, respectively); SEQ ID NO:58 (RNAseH-encoding sequences, modified based on 8__5_TV1_C.ZA wild type); SEQ ID NO:60 (Integrase-encoding sequences, modified based on 8__5_TV1_C.ZA wild type); SEQ ID NO:62 and SEQ ID NO:103 (Pol-encoding sequences, modified based on 8__5_TV1_C.ZA wild type and 12-5__1_TV2_C.ZA wild-type, respectively); SEQ ID NO:64 (Protease-encoding sequences, modified based on 8__5_TV1_C.ZA wild type); SEQ ID NO:66 (inactivated protease-encoding sequences, modified based on 8__5_TV1_C.ZA wild type); SEQ ID NO:68 (inactivated protease and RT mutated sequences, modified based on 8__5_TV1_C.ZA wild type); SEQ ID NO:70 (protease and reverse-transcriptase-encoding sequences, modified based on 8__5_TV1_C.ZA wild type); SEQ ID NO:72 and SEQ ID NO:105 (exon 1 of Rev, modified based on 8__5_TV1_C.ZA wild type and 12-5__1_TV2_C.ZA wild-type, respectively); SEQ ID NO:74 and SEQ ID NO:107 (exon 2 of Rev, modified based on 8__5_TV1_C.ZA wild type and 12-5__1_TV2_C.ZA wild-type, respectively); SEQ ID NO:76 (reverse transcriptase-encoding sequences, modified based on 8__5_TV1_C.ZA wild type); SEQ ID NO:78 (mutated reverse-transcriptase, modified based on 8__5_TV1_C.ZA wild type); SEQ ID NO:80 (exon 1 of Tat including a mutation that results in non-functional Tat, modified based on 8__5_TV1_C.ZA wild type); SEQ ID NO:81 and SEQ ID NO:109 (exon 1 of Tat, modified based on 8__5_TV1_C.ZA wild type and 12-5__1_TV2_C.ZA wild-type, respectively); SEQ ID NO:83 and SEQ ID NO:111 (exon 2 of Tat, modified based on 8__5_TV1_C.ZA wild type and 12-5__1_TV2_C.ZA wild-type, respectively); SEQ ID NO:85 and SEQ ID NO:113) (Vif-encoding sequences, modified based on 8__5_TV1_C.ZA wild type and 12-5__1_TV2_C.ZA wild-type, respectively); SEQ ID NO:87 and SEQ ID NO:115 (Vpr-encoding sequences, modified based on 8__5_TV1_C.ZA wild type and 12-5__1_TV2_C.ZA wild-type, respectively); SEQ ID NO:89 and SEQ ID NO:117 (Vpu-encoding sequences, modified based on 8__5_TV1_C.ZA wild type and 12-5__1_TV2_C.ZA wild-type, respectively); SEQ ID NO:91 (sequences of exons 1 and 2 of Rev, modified based on 8__5_TV1_C.ZA wild type); SEQ ID NO:93 (sequences of mutated exon 1 of Tat and exon 2 of Tat, where mutation of exon 1 results in non-functional Tat, modified based on 8__5_TV1_C.ZA wild type); SEQ ID NO:94 (sequences of exons 1 and 2 of Tat, modified based on 8__5_TV1_C.ZA wild type); SEQ ID NO:96 and SEQ ID NO:135 (Nef-encoding sequences including a mutation to eliminate myristoylation site, modified based on 8__5_TV1_C.ZA wild type and 12-5__1_TV2_C.ZA, respectively).

2.2.1.5 Further Modification of Sequences Including HIV-1 Nucleic Acid Coding Sequences The Type C HIV polypeptide-encoding expression cassettes described herein may also contain one or more further sequences encoding, for example, one or more transgenes. Further sequences (e.g., transgenes) useful in the practice of the present invention include, but are not limited to, further sequences are those encoding further viral epitopes/antigens {including but not limited to, HCV antigens (e.g., E1, E2; Houghton, M., et al., U.S. Pat. No. 5,714,596, issued Feb. 3, 1998; Houghton, M., et al., U.S. Pat. No. 5,712,088, issued Jan. 27, 1998; Houghton, M., et al., U.S. Pat. No. 5,683,864, issued Nov. 4, 1997; Weiner, A. J., et al., U.S. Pat. No. 5,728,520, issued Mar. 17, 1998; Weiner, A. J., et al., U.S. Pat. No. 5,766,845, issued Jun. 16, 1998; Weiner, A. J., et al., U.S. Pat. No. 5,670,152, issued Sep. 23, 1997; all herein incorporated by reference), HIV antigens (e.g., derived from tat, rev, nef and/or env); and sequences encoding tumor antigens/epitopes. Further sequences may also be derived from non-viral sources, for instance, sequences encoding cytokines such interleukin-2 (IL-2), stem cell factor (SCF), interleukin 3 (IL-3), interleukin 6 (IL-6), interleukin 12 (IL-12), G-CSF, granulocyte macrophage-colony stimulating factor (GM-CSF), interleukin-1 alpha (IL-1I), interleukin-11 (IL-11), MIP-1I, tumor necrosis factor (TNF), leukemia inhibitory factor (LIF), c-kit ligand, thrombopoietin (TPO) and flt3 ligand, commercially available from several vendors such as, for example, Genzyme (Framingham, Mass.), Genentech (South San Francisco, Calif.), Amgen (Thousand Oaks, Calif.), R&D Systems and Immunex (Seattle, Wash.). Additional sequences are described below, for example in Section 2.3. Also, variations on the orientation of the Gag and other coding sequences, relative to each other, are described below.

HIV polypeptide coding sequences can be obtained from other Type C HIV isolates, see, e.g., Myers et al. Los Alamos Database, Los Alamos National Laboratory, Los Alamos, N. Mex. (1992); Myers et al., *Human Retroviruses and Aids,* 1997, Los Alamos, N. Mex.: Los Alamos National Laboratory. Synthetic expression cassettes can be generated using such coding sequences as starting material by following the teachings of the present specification (e.g., see Example 1).

Further, the synthetic expression cassettes of the present invention include related polypeptide sequences having greater than 85%, preferably greater than 90%, more preferably greater than 95%, and most preferably greater than 98% sequence identity to the synthetic expression cassette sequences disclosed herein (for example, (SEQ ID NOs:30-32; SEQ ID NOs: 3, 4, 20, and 21 and SEQ ID NOs:5-17). Various coding regions are indicated in FIGS. 3 and 4, for example in FIG. 3 (AF110968), nucleotides 1-81 (SEQ ID NO:18); nucleotides 82-1512 (SEQ ID NO:6) encode a gp120 polypeptide, nucleotides 1513 to 2547 (SEQ ID NO:10) encode a gp41 polypeptide, nucleotides 82-2025 (SEQ ID NO:7) encode a gp140 polypeptide and nucleotides 82-2547 (SEQ ID NO:8) encode a gp160 polypeptide. Similarly, in FIG. 98 (SEQ ID NO:127, strain 8_2_TV1_C.ZA), nucleotides 1-6 are an EcoRI restriction site; nucleotides 7-87 a encode a wild-type (from 8_2_TV1_C.ZA) leader signal peptide; nucleotides 88 to 1563 encode a gp120 polypeptide; nucleotides 88 to 2064 encode a gp140 polypeptide; nucleotides 88 to 2607 encode a gp160 polypeptide.

2.2.3 Expression of Synthetic Sequences Encoding HIV-1 Subtype C and Related Polypeptides Synthetic HIV-encoding sequences (expression cassettes) of the present invention can be cloned into a number of different expression vectors to evaluate levels of expression and, in the case of Gag, production of VLPs. The synthetic DNA fragments for HIV polypeptides can be cloned into eucaryotic expression vectors, including, a transient expression vector, CMV-promoter-based mammalian vectors, and a shuttle vector for use in baculovirus expression systems. Corresponding wild-type sequences can also be cloned into the same vectors.

These vectors can then be transfected into a several different cell types, including a variety of mammalian cell lines (293, RD, COS-7, and CHO, cell lines available, for example, from the A.T.C.C.). The cell lines are then cultured under appropriate conditions and the levels of any appropriate polypeptide product can be evaluated in supernatants. (see, Table A and Example 2). For example, p24 can be used to evaluate Gag expression; gp160, gp140 or gp120 can be used to evaluate Env expression; p6pol can be used to evaluate Pol expression; prot can be used to evaluate protease; p15 for RNAseH; p31 for Integrase; and other appropriate polypeptides for Vif, Vpr, Tat, Rev, Vpu and Nef. Further, modified polypeptides can also be used, for example, other Env polypeptides include, but are not limited to, for example, native gp160, oligomeric gp140, monomeric gp120 as well as modified and/or synthetic sequences of these polypeptides. The results of these assays demonstrate that expression of synthetic HIV polypeptide-encoding sequences are significantly higher than corresponding wild-type sequences.

Further, Western Blot analysis can be used to show that cells containing the synthetic expression cassette produce the expected protein at higher per-cell concentrations than cells containing the native expression cassette. The HIV proteins can be seen in both cell lysates and supernatants. The levels of production are significantly higher in cell supernatants for cells transfected with the synthetic expression cassettes of the present invention.

Fractionation of the supernatants from mammalian cells transfected with the synthetic expression cassette can be used to show that the cassettes provide superior production of HIV proteins and, in the case of Gag, VLPs, relative to the wild-type sequences.

Efficient expression of these HIV-containing polypeptides in mammalian cell lines provides the following benefits: the polypeptides are free of baculovirus contaminants; production by established methods approved by the FDA; increased purity; greater yields (relative to native coding sequences); and a novel method of producing the Subtype C HIV-containing polypeptides in CHO cells which is not feasible in the absence of the increased expression obtained using the constructs of the present invention. Exemplary Mammalian cell lines include, but are not limited to, BHK, VERO, HT1080, 293, 293T, RD, COS-7, CHO, Jurkat, HUT, SUPT, C8166, MOLT4/clone8, MT-2, MT-4, H9, PM1, CEM, and CEMX174, such cell lines are available, for example, from the A.T.C.C.).

A synthetic Gag expression cassette of the present invention will also exhibit high levels of expression and VLP production when transfected into insect cells. Synthetic expression cassettes described herein also demonstrate high levels of expression in insect cells. Further, in addition to a higher total protein yield, the final product from the synthetic polypeptides consistently contains lower amounts of contaminating baculovirus proteins than the final product from the native Type C sequences.

Further, synthetic expression cassettes of the present invention can also be introduced into yeast vectors which, in turn, can be transformed into and efficiently expressed by yeast cells (*Saccharomyces cerevisea*; using vectors as described in Rosenberg, S. and Tekamp-Olson, P., U.S. Pat. No. RE35,749, issued, Mar. 17, 1998, herein incorporated by reference).

In addition to the mammalian and insect vectors, the synthetic expression cassettes of the present invention can be incorporated into a variety of expression vectors using selected expression control elements. Appropriate vectors and control elements for any given cell type can be selected by one having ordinary skill in the art in view of the teachings of the present specification and information known in the art about expression vectors.

For example, a synthetic expression cassette can be inserted into a vector which includes control elements operably linked to the desired coding sequence, which allow for the expression of the gene in a selected cell-type. For example, typical promoters for mammalian cell expression include the SV40 early promoter, a CMV promoter such as the CMV immediate early promoter (a CMV promoter can include intron A), RSV, HIV-Ltr, the mouse mammary tumor virus LTR promoter (MMLV-ltr), the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook, et al., supra, as well as a bovine growth hormone terminator sequence. Introns, containing splice donor and acceptor sites, may also be designed into the constructs for use with the present invention (Chapman et al., *Nuc. Acids Res.* (1991) 19:3979-3986).

Enhancer elements may also be used herein to increase expression levels of the mammalian constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc.*

*Natl. Acad. Sci. USA* (1982b) 79:6777 and elements derived from human CMV, as described in Boshart et al., *Cell* (1985) 41:521, such as elements included in the CMV intron A sequence (Chapman et al., *Nuc. Acids Res.* (1991) 19:3979-3986).

The desired synthetic polypeptide encoding sequences can be cloned into any number of commercially available vectors to generate expression of the polypeptide in an appropriate host system. These systems include, but are not limited to, the following: baculovirus expression {Reilly, P. R., et al., *BACULOVIRUS EXPRESSION VECTORS: A LABORATORY MANUAL* (1992); Beames, et al., *Biotechniques* 11:378 (1991); Pharmingen; Clontech, Palo Alto, Calif.)}, vaccinia expression {Earl, P. L., et al., "Expression of proteins in mammalian cells using vaccinia" In *Current Protocols in Molecular Biology* (F. M. Ausubel, et al. Eds.), Greene Publishing Associates & Wiley Interscience, New York (1991); Moss, B., et al., U.S. Pat. No. 5,135,855, issued 4 Aug. 1992}, expression in bacteria {Ausubel, F. M., et al., *CURRENT PROTOCOLS IN MOLECULAR BIOLOGY*, John Wiley and Sons, Inc., Media Pa.; Clontech}, expression in yeast {Rosenberg, S. and Tekamp-Olson, P., U.S. Pat. No. RE35,749, issued, Mar. 17, 1998, herein incorporated by reference; Shuster, J. R., U.S. Pat. No. 5,629,203, issued May 13, 1997, herein incorporated by reference; Gellissen, G., et al., *Antonie Van Leeuwenhoek*, 62(1-2):79-93 (1992); Romanos, M. A., et al., *Yeast* 8(6):423-488 (1992); Goeddel, D. V., *Methods in Enzymology* 185 (1990); Guthrie, C., and G. R. Fink, *Methods in Enzymology* 194 (1991)}, expression in mammalian cells {Clontech; Gibco-BRL, Ground Island, N.Y.; e.g., Chinese hamster ovary (CHO) cell lines (Haynes, J., et al., *Nuc. Acid. Res.* 11:687-706 (1983); 1983, Lau, Y. F., et al., *Mol. Cell. Biol.* 4:1469-1475 (1984); Kaufman, R. J., "Selection and coamplification of heterologous genes in mammalian cells," in *Methods in Enzymology*, vol. 185, pp 537-566. Academic Press, Inc., San Diego Calif. (1991)}, and expression in plant cells {plant cloning vectors, Clontech Laboratories, Inc., Palo Alto, Calif., and Pharmacia LKB Biotechnology, Inc., Pistcataway, N.J.; Hood, E., et al., *J. Bacteriol.* 168:1291-1301 (1986); Nagel, R., et al., *FEMS Microbiol. Lett.* 67:325 (1990); An, et al., "Binary Vectors", and others in *Plant Molecular Biology Manual A*3:1-19 (1988); Miki, B. L. A., et al., pp. 249-265, and others in *Plant DNA Infectious Agents* (Hohn, T., et al., eds.) Springer-Verlag, Wien, Austria, (1987); *Plant Molecular Biology: Essential Techniques*, P. G. Jones and J. M. Sutton, New York, J. Wiley, 1997; Miglani, Gurbachan *Dictionary of Plant Genetics and Molecular Biology*, New York, Food Products Press, 1998; Henry, R. J., *Practical Applications of Plant Molecular Biology*, New York, Chapman & Hall, 1997}.

Also included in the invention is an expression vector, containing coding sequences and expression control elements which allow expression of the coding regions in a suitable host. The control elements generally include a promoter, translation initiation codon, and translation and transcription termination sequences, and an insertion site for introducing the insert into the vector. Translational control elements have been reviewed by M. Kozak (e.g., Kozak, M., *Mamm. Genome* 7(8):563-574, 1996; Kozak, M., *Biochimie* 76(9):815-821, 1994; Kozak, M., *J Cell Biol* 108(2):229-241, 1989; Kozak, M., and Shatkin, A. J., *Methods Enzymol* 60:360-375, 1979).

Expression in yeast systems has the advantage of commercial production. Recombinant protein production by vaccinia and CHO cell line have the advantage of being mammalian expression systems. Further, vaccinia virus expression has several advantages including the following: (i) its wide host range; (ii) faithful post-transcriptional modification, processing, folding, transport, secretion, and assembly of recombinant proteins; (iii) high level expression of relatively soluble recombinant proteins; and (iv) a large capacity to accommodate foreign DNA.

The recombinantly expressed polypeptides from synthetic HIV polypeptide-encoding expression cassettes are typically isolated from lysed cells or culture media. Purification can be carried out by methods known in the art including salt fractionation, ion exchange chromatography, gel filtration, size-exclusion chromatography, size-fractionation, and affinity chromatography. Immunoaffinity chromatography can be employed using antibodies generated based on, for example, HIV antigens.

Advantages of expressing the proteins of the present invention using mammalian cells include, but are not limited to, the following: well-established protocols for scale-up production; the ability to produce VLPs; cell lines are suitable to meet good manufacturing process (GMP) standards; culture conditions for mammalian cells are known in the art.

Various forms of the different embodiments of the invention, described herein, may be combined.

2.3 Production of Virus-Like Particles and Use of the Constructs of the Present Invention to Create Packaging Cell Lines.

The group-specific antigens (Gag) of human immunodeficiency virus type-1 (HIV-1) self-assemble into noninfectious virus-like particles (VLP) that are released from various eucaryotic cells by budding (reviewed by Freed, E. O., *Virology* 251:1-15, 1998). The synthetic expression cassettes of the present invention provide efficient means for the production of HIV-Gag virus-like particles (VLPS) using a variety of different cell types, including, but not limited to, mammalian cells.

Viral particles can be used as a matrix for the proper presentation of an antigen entrapped or associated therewith to the immune system of the host.

2.3.1 VLP Production Using the Synthetic Expression Cassettes of the Present Invention Experiments can be performed in support of the present invention to demonstrate that the synthetic expression cassettes of the present invention provide superior production of both Gag proteins and VLPs, relative to native Gag coding sequences. Further, electron microscopic evaluation of VLP production can show that free and budding immature virus particles of the expected size are produced by cells containing the synthetic expression cassettes.

Using the synthetic expression cassettes of the present invention, rather than native Gag coding sequences, for the production of virus-like particles provide several advantages. First, VLPs can be produced in enhanced quantity making isolation and purification of the VLPs easier. Second, VLPs can be produced in a variety of cell types using the synthetic expression cassettes, in particular, mammalian cell lines can be used for VLP production, for example, CHO cells. Production using CHO cells provides (i) VLP formation; (ii) correct myristoylation and budding; (iii) absence of non-mamallian cell contaminants (e.g., insect viruses and/or cells); and (iv) ease of purification. The synthetic expression cassettes of the present invention are also useful for enhanced expression in cell-types other than mammalian cell lines. For example, infection of insect cells with baculovirus vectors encoding the synthetic expression cassettes results in higher levels of total Gag protein yield and higher levels of VLP production (relative to wild-type coding sequences). Further, the final product from insect cells infected with the baculovirus-Gag synthetic expression cassettes consistently contains lower amounts of contaminating insect proteins than the final product when wild-type coding sequences are used.

VLPs can spontaneously form when the particle-forming polypeptide of interest is recombinantly expressed in an appropriate host cell. Thus, the VLPs produced using the synthetic expression cassettes of the present invention are conveniently prepared using recombinant techniques. As discussed below, the Gag polypeptide encoding synthetic expression cassettes of the present invention can include other polypeptide coding sequences of interest (for example, HIV protease, HIV polymerase, HCV core; Env; synthetic Env; see, Example 1). Expression of such synthetic expression cassettes yields VLPs comprising the Gag polypeptide, as well as, the polypeptide of interest.

Once coding sequences for the desired particle-forming polypeptides have been isolated or synthesized, they can be cloned into any suitable vector or replicon for expression. Numerous cloning vectors are known to those of skill in the art, and the selection of an appropriate cloning vector is a matter of choice. See, generally, Sambrook et al, supra. The vector is then used to transform an appropriate host cell. Suitable recombinant expression systems include, but are not limited to, bacterial, mammalian, baculovirus/insect, vaccinia, Semliki Forest virus (SFV), Alphaviruses (such as, Sindbis, Venezuelan Equine Encephalitis (VEE)), mammalian, yeast and Xenopus expression systems, well known in the art. Particularly preferred expression systems are mammalian cell lines, vaccinia, Sindbis, insect and yeast systems.

For example, a number of mammalian cell lines are known in the art and include immortalized cell lines available from the American Type Culture Collection (A.T.C.C.), such as, but not limited to, Chinese hamster ovary (CHO) cells, HeLa cells, baby hamster kidney (BHK) cells, monkey kidney cells (COS), as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*. See, e.g., Summers and Smith, *Texas Agricultural Experiment Station Bulletin No.* 1555 (1987).

Viral vectors can be used for the production of particles in eucaryotic cells, such as those derived from the pox family of viruses, including vaccinia virus and avian poxvirus. Additionally, a vaccinia based infection/transfection system, as described in Tomei et al., *J. Virol.* (1993) 67:4017-4026 and Selby et al., *J. Gen. Virol.* (1993) 74:1103-1113, will also find use with the present invention. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. Alternately, T7 can be added as a purified protein or enzyme as in the "Progenitor" system (Studier and Moffatt, *J. Mol. Biol.* (1986) 189:113-130). The method provides for high level, transient, cytoplasmic production of large quantities of RNA and its translation product(s).

Depending on the expression system and host selected, the VLPS are produced by growing host cells transformed by an expression vector under conditions whereby the particle-forming polypeptide is expressed and VLPs can be formed. The selection of the appropriate growth conditions is within the skill of the art. If the VLPs are formed intracellularly, the cells are then disrupted, using chemical, physical or mechanical means, which lyse the cells yet keep the VLPs substantially intact. Such methods are known to those of skill in the art and are described in, e.g., *Protein Purification Applications: A Practical Approach*, (E. L. V. Harris and S. Angal, Eds., 1990).

The particles are then isolated (or substantially purified) using methods that preserve the integrity thereof, such as, by gradient centrifugation, e.g., cesium chloride (CsCl) sucrose gradients, pelleting and the like (see, e.g., Kirnbauer et al. *J. Virol.* (1993) 67:6929-6936), as well as standard purification techniques including, e.g., ion exchange and gel filtration chromatography.

VLPs produced by cells containing the synthetic expression cassettes of the present invention can be used to elicit an immune response when administered to a subject. One advantage of the present invention is that VLPs can be produced by mammalian cells carrying the synthetic expression cassettes at levels previously not possible. As discussed above, the VLPs can comprise a variety of antigens in addition to the Gag polypeptide (e.g., Gag-protease, Gag-polymerase, Env, synthetic Env, etc.). Purified VLPs, produced using the synthetic expression cassettes of the present invention, can be administered to a vertebrate subject, usually in the form of vaccine compositions. Combination vaccines may also be used, where such vaccines contain, for example, an adjuvant subunit protein (e.g., Env). Administration can take place using the VLPs formulated alone or formulated with other antigens. Further, the VLPs can be administered prior to, concurrent with, or subsequent to, delivery of the synthetic expression cassettes for DNA immunization (see below) and/or delivery of other vaccines. Also, the site of VLP administration may be the same or different as other vaccine compositions that are being administered. Gene delivery can be accomplished by a number of methods including, but are not limited to, immunization with DNA, alphavirus vectors, pox virus vectors, and vaccinia virus vectors.

VLP immune-stimulating (or vaccine) compositions can include various excipients, adjuvants, carriers, auxiliary substances, modulating agents, and the like. The immune stimulating compositions will include an amount of the VLP/antigen sufficient to mount an immunological response. An appropriate effective amount can be determined by one of skill in the art. Such an amount will fall in a relatively broad range that can be determined through routine trials and will generally be an amount on the order of about 0.1 µg to about 1000 µg, more preferably about 1 µg to about 300 µg, of VLP/antigen.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; McGee J P, et al., *J Microencapsul.* 14(2):197-210, 1997; O'Hagan D T, et al., *Vaccine*

11(2):149-54, 1993. Such carriers are well known to those of ordinary skill in the art. Additionally, these carriers may function as immunostimulating agents ("adjuvants"). Furthermore, the antigen may be conjugated to a bacterial toxoid, such as toxoid from diphtheria, tetanus, cholera, etc., as well as toxins derived from *E. coli.*

Adjuvants may also be used to enhance the effectiveness of the compositions. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) oligonucleotides or polymeric molecules encoding immunostimulatory CpG mofifs (Davis, H. L., et al., *J. Immunology* 160:870-876, 1998; Sato, Y. et al., *Science* 273:352-354, 1996) or complexes of antigens/oligonucleotides {Polymeric molecules include double and single stranded RNA and DNA, and backbone modifications thereof, for example, methylphosphonate linkages; or (7) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where senne is substituted for the wild-type amino acid at position 109), and PT-K9/G-129 (where lysine is substituted for the wild-type amino acid at position 9 and glycine substituted at position 129) (see, e.g., International Publication Nos. W093/13202 and W092/19265); and (8) other substances that act as immunostimulating agents to enhance the effectiveness of the composition. Further, such polymeric molecules include alternative polymer backbone structures such as, but not limited to, polyvinyl backbones (Pitha, *Biochem Biophys Acta,* 204:39, 1970a; Pitha, *Biopolymers,* 9:965, 1970b), and morpholino backbones (Summerton, J., et al., U.S. Pat. No. 5,142, 047, issued Aug. 25, 1992; Summerton, J., et al., U.S. Pat. No. 5,185,444 issued Feb. 9, 1993). A variety of other charged and uncharged polynucleotide analogs have been reported. Numerous backbone modifications are known in the art, including, but not limited to, uncharged linkages (e.g., methyl phosphonates, phosphotriesters, phosphoamidates, and carbamates) and charged linkages (e.g., phosphorothioates and phosphorodithioates).}; and (7) other substances that act as immunostimulating agents to enhance the effectiveness of the VLP immune-stimulating (or vaccine) composition. Alum, CpG oligonucleotides, and MF59 are preferred.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetyl-muramyl-L-alanyl-D-isogluatminyl-L-alanine-2-(1'-2'-dipalmtoyl-sn-glycero-3-huydroxyphosphoryloxy)-ethylamine (MTP-PE), etc.

Dosage treatment with the VLP composition may be a single dose schedule or a multiple dose schedule. A multiple dose schedule is one in which a primary course of vaccination may be with 1-10 separate doses, followed by other doses given at subsequent time intervals, chosen to maintain and/or reinforce the immune response, for example at 1-4 months for a second dose, and if needed, a subsequent dose(s) after several months. The dosage regimen will also, at least in part, be determined by the need of the subject and be dependent on the judgment of the practitioner.

If prevention of disease is desired, the antigen carrying VLPs are generally administered prior to primary infection with the pathogen of interest. If treatment is desired, e.g., the reduction of symptoms or recurrences, the VLP compositions are generally administered subsequent to primary infection.

2.3.2 Using the Synthetic Expression Cassettes of the Present Invention to Create Packaging Cell Lines A number of viral based systems have been developed for use as gene transfer vectors for mammalian host cells. For example, retroviruses (in particular, lentiviral vectors) provide a convenient platform for gene delivery systems. A coding sequence of interest (for example, a sequence useful for gene therapy applications) can be inserted into a gene delivery vector and packaged in retroviral particles using techniques known in the art. Recombinant virus can then be isolated and delivered to cells of the subject either in vivo or ex vivo. A number of retroviral systems have been described, including, for example, the following: (U.S. Pat. No. 5,219, 740; Miller et al. (1989) *Bio Techniques* 7:980; Miller, A. D. (1990) *Human Gene Therapy* 1:5; Scarpa et al. (1991) *Virology* 180:849; Burns et al. (1993) *Proc. Natl. Acad. Sci. USA* 90:8033; Boris-Lawrie et al. (1993) *Cur. Opin. Genet. Develop.* 3:102; GB 2200651; EP 0415731; EP 0345242; WO 89/02468; WO 89/05349; WO 89/09271; WO 90/02806; WO 90/07936; WO 90/07936; WO 94/03622; WO 93/25698; WO 93/25234; WO 93/11230; WO 93/10218; WO 91/02805; in U.S. Pat. Nos. 5,219,740; 4,405,712; 4,861,719; 4,980,289 and 4,777,127; in U.S. Ser. No. 07/800,921; and in Vile (1993) *Cancer Res* 53:3860-3864; Vile (1993) *Cancer Res* 53:962-967; Ram (1993) *Cancer Res* 53:83-88; Takamiya (1992) *J Neurosci Res* 33:493-503; Baba (1993) *J Neurosurg* 79:729-735; Mann (1983) *Cell* 33:153; Cane (1984) *Proc Natl Acad Sci USA* 81;6349; and Miller (1990) *Human Gene Therapy* 1.

In other embodiments, gene transfer vectors can be constructed to encode a cytokine or other immunomodulatory molecule. For example, nucleic acid sequences encoding native IL-2 and gamma-interferon can be obtained as described in U.S. Pat. Nos. 4,738,927 and 5,326,859, respectively, while useful muteins of these proteins can be obtained as described in U.S. Pat. No. 4,853,332. Nucleic acid sequences encoding the short and long forms of mCSF can be obtained as described in U.S. Pat. Nos. 4,847,201 and 4,879, 227, respectively. In particular aspects of the invention, retroviral vectors expressing cytokine or immunomodulatory genes can be produced as described herein (for example, employing the packaging cell lines of the present invention)

and in International Application No. PCT US 94/02951, entitled "Compositions and Methods for Cancer Imnmunotherapy."

Examples of suitable immunomodulatory molecules for use herein include the following: IL-1 and IL-2 (Karupiah et al. (1990) *J. Immunology* 144:290-298, Weber et al. (1987) *J. Exp. Med.* 166:1716-1733, Gansbacher et al. (1990) *J. Exp. Med.* 172:1217-1224, and U.S. Pat. No. 4,738,927); IL-3 and IL-4 (Tepper et al. (1989) *Cell* 57:503-512, Golumbek et al. (1991) *Science* 254:713-716, and U.S. Pat. No. 5,017,691); IL-5 and IL-6 (Brakenhof et al. (1987) *J. Immunol.* 139:4116-4121, and International Publication No. WO 90/06370); IL-7 (U.S. Pat. No. 4,965,195); IL-8, IL-9, IL-10, IL-11, IL-12, and IL-13 (*Cytokine Bulletin*, Summer 1994); IL-14 and IL-15; alpha interferon (Finter et al. (1991) *Drugs* 42:749-765, U.S. Pat. Nos. 4,892,743 and 4,966,843, International Publication No. WO 85/02862, Nagata et al. (1980) *Nature* 284:316-320, Familletti et al. (1981) *Methods in Enz.* 78:387-394, Twu et al. (1989) *Proc. Natl. Acad. Sci. USA* 86:2046-2050, and Faktor et al. (1990) *Oncogene* 5:867-872); beta-interferon (Seif et al. (1991) *J. Virol.* 65:664-671); gamma-interferons (Radford et al. (1991) *The American Society of Hepatology* 20082015, Watanabe et al. (1989) *Proc. Natl. Acad. Sci. USA* 86:9456-9460, Gansbacher et al. (1990) *Cancer Research* 50:7820-7825, Maio et al. (1989) *Can. Immunol. Immunother.* 30:34-42, and U.S. Pat. Nos. 4,762,791 and 4,727,138); G-CSF (U.S. Pat. Nos. 4,999,291 and 4,810,643); GM-CSF (International Publication No. WO 85/04188).

Immunomodulatory factors may also be agonists, antagonists, or ligands for these molecules. For example, soluble forms of receptors can often behave as antagonists for these types of factors, as can mutated forms of the factors themselves.

Nucleic acid molecules that encode the above-described substances, as well as other nucleic acid molecules that are advantageous for use within the present invention, may be readily obtained from a variety of sources, including, for example, depositories such as the American Type Culture Collection, or from commercial sources such as British Bio-Technology Limited (Cowley, Oxford England). Representative examples include BBG 12 (containing the GM-CSF gene coding for the mature protein of 127 amino acids), BBG 6 (which contains sequences encoding gamma interferon), A.T.C.C. Deposit No. 39656 (which contains sequences encoding TNF), A.T.C.C. Deposit No. 20663 (which contains sequences encoding alpha-interferon), A.T.C.C. Deposit Nos. 31902, 31902 and 39517 (which contain sequences encoding beta-interferon), A.T.C.C. Deposit No. 67024 (which contains a sequence which encodes Interleukin-1b), A.T.C.C. Deposit Nos. 39405, 39452, 39516, 39626 and 39673 (which contain sequences encoding Interleukin-2), A.T.C.C. Deposit Nos. 59399, 59398, and 67326 (which contain sequences encoding Interleukin-3), A.T.C.C. Deposit No. 57592 (which contains sequences encoding Interleukin-4), A.T.C.C. Deposit Nos. 59394 and 59395 (which contain sequences encoding Interleukin-5), and A.T.C.C. Deposit No. 67153 (which contains sequences encoding Interleukin-6).

Plasmids containing cytokine genes or immunomodulatory genes (International Publication Nos. WO 94/02951 and WO 96/21015, both of which are incorporated by reference in their entirety) can be digested with appropriate restriction enzymes, and DNA fragments containing the particular gene of interest can be inserted into a gene transfer vector using standard molecular biology techniques. (See, e.g., Sambrook et al., supra., or Ausbel et al. (eds) *Current Protocols in Molecular Biology*, Greene Publishing and Wiley-Interscience).

Polynucleotide sequences coding for the above-described molecules can be obtained using recombinant methods, such as by screening cDNA and genomic libraries from cells expressing the gene, or by deriving the gene from a vector known to include the same. For example, plasmids which contain sequences that encode altered cellular products may be obtained from a depository such as the A.T.C.C., or from commercial sources. Plasmids containing the nucleotide sequences of interest can be digested with appropriate restriction enzymes, and DNA fragments containing the nucleotide sequences can be inserted into a gene transfer vector using standard molecular biology techniques.

Alternatively, cDNA sequences for use with the present invention may be obtained from cells which express or contain the sequences, using standard techniques, such as phenol extraction and PCR of cDNA or genomic DNA. See, e.g., Sambrook et al., supra, for a description of techniques used to obtain and isolate DNA. Briefly, mRNA from a cell which expresses the gene of interest can be reverse transcribed with reverse transcriptase using oligo-dT or random primers. The single stranded cDNA may then be amplified by PCR (see U.S. Pat. Nos. 4,683,202, 4,683,195 and 4,800,159, see also *PCR Technology: Principles and Applications for DNA Amplification*, Erlich (ed.), Stockton Press, 1989)) using oligonucleotide primers complementary to sequences on either side of desired sequences.

The nucleotide sequence of interest can also be produced synthetically, rather than cloned, using a DNA synthesizer (e.g., an Applied Biosystems Model 392 DNA Synthesizer, available from ABI, Foster City, Calif.). The nucleotide sequence can be designed with the appropriate codons for the expression product desired. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

The synthetic expression cassettes of the present invention can be employed in the construction of packaging cell lines for use with retroviral vectors.

One type of retrovirus, the murine leukemia virus, or "MLV", has been widely utilized for gene therapy applications (see generally Mann et al. (*Cell* 33:153, 1993), Cane and Mulligan (*Proc, Nat'l. Acad. Sci. USA* 81:6349, 1984), and Miller et al., *Human Gene 2lerapy* 1:5-14,1990.

Lentiviral vectors typically, comprise a 5' lentiviral LTR, a tRNA binding site, a packaging signal, a promoter operably linked to one or more genes of interest, an origin of second strand DNA synthesis and a 3' lentiviral LTR, wherein the lentiviral vector contains a nuclear transport element. The nuclear transport element may be located either upstream (5') or downstream (3') of a coding sequence of interest (for example, a synthetic Gag or Env expression cassette of the present invention). Within certain embodiments, the nuclear transport element is not RRE. Within one embodiment the packaging signal is an extended packaging signal. Within other embodiments the promoter is a tissue specific promoter, or, alternatively, a promoter such as CMV. Within other embodiments, the lentiviral vector further comprises an internal ribosome entry site.

In one embodiment of the present invention synthetic Gag-polymerase expression cassettes are provided comprising a promoter and a sequence encoding synthetic Gag-polymerase protein and at least one of the Vpr, Vpu, Nef or Vif, wherein the promoter is operably linked to Gag-polymerase and vpr, vpu, nef or vif DNA sequences.

Within yet another aspect of the invention, host cells (e.g., packaging cell lines) are provided which contain any of the expression cassettes described herein. For example, within one aspect packaging cell line are provided comprising an expression cassette that comprises a sequence encoding synthetic Gag-polymerase, and a nuclear transport element, wherein the promoter is operably linked to the sequence encoding Gag-polymerase. Packaging cell lines may further comprise a promoter and a sequence encoding Tat, Rev, or an Env, wherein the promoter is operably linked to the sequence Tat, Rev, or an Envor sequences encoding modified versions of these proteins. The packaging cell line may further comprise a sequence encoding any one or more of Nef, Vif, Vpu or Vpr (wild-type or synthetic).

In one embodiment, the expression cassette (carrying, for example, the synthetic Gag-polymerase) is stably integrated. The packaging cell line, upon introduction of a lentiviral vector, typically produces particles. The promoter regulating expression of the synthetic expression cassette may be inducible. Typically, the packaging cell line, upon introduction of a lentiviral vector, produces particles that are essentially free of replication competent virus.

Packaging cell lines are provided comprising an expression cassette which directs the expression of a synthetic *Gag-polymerase* gene or comprising an expression cassette which directs the expression of a synthetic env gene described herein. (See, also, Andre, S., et al., *Journal of Virology* 72(2): 1497-1503, 1998; Haas, J., et al., *Current Biology* 6(3):315-324, 1996) for a description of other modified env gene sequences). A lentiviral vector is introduced into the packaging cell line to produce a vector producing cell line.

As noted above, lentiviral vectors can be designed to carry or express a selected gene(s) or sequences of interest. Lentiviral vectors may be readily constructed from a wide variety of lentiviruses (see RNA Tumor Viruses, Second Edition, Cold Spring Harbor Laboratory, 1985). Representative examples of lentiviruses included HIV, HIV-1, HIV-2, FIV and SIV. Such lentiviruses may either be obtained from patient isolates, or, more preferably, from depositories or collections such as the American Type Culture Collection, or isolated from known sources using available techniques.

Portions of the lentiviral gene delivery vectors (or vehicles) may be derived from different viruses. For example, in a given recombinant lentiviral vector, LTRs may be derived from an HIV, a packaging signal from SIV, and an origin of second strand synthesis from HrV-2. Lentiviral vector constructs may comprise a 5' lentiviral LTR, a tRNA binding site, a packaging signal, one or more heterologous sequences, an origin of second strand DNA synthesis and a 3' LTR, wherein said lentiviral vector contains a nuclear transport element that is not RRE.

Briefly, Long Terminal Repeats ("LTRs") are subdivided into three elements, designated U5, R and U3. These elements contain a variety of signals which are responsible for the biological activity of a retrovirus, including for example, promoter and enhancer elements which are located within U3. LTRs may be readily identified in the provirus (integrated DNA form) due to their precise duplication at either end of the genome. As utilized herein, a 5' LTR should be understood to include a 5' promoter element and sufficient LTR sequence to allow reverse transcription and integration of the DNA form of the vector. The 3' LTR should be understood to include a polyadenylation signal, and sufficient LTR sequence to allow reverse transcription and integration of the DNA form of the vector.

The tRNA binding site and origin of second strand DNA synthesis are also important for a retrovirus to be biologically active, and may be readily identified by one of skill in the art. For example, retroviral tRNA binds to a tRNA binding site by Watson-Crick base pairing, and is carried with the retrovirus genome into a viral particle. The tRNA is then utilized as a primer for DNA synthesis by reverse transcriptase. The tRNA binding site may be readily identified based upon its location just downstream from the 5' LTR. Similarly, the origin of second strand DNA synthesis is, as its name implies, important for the second strand DNA synthesis of a retrovirus. This region, which is also referred to as the poly-purine tract, is located just upstream of the 3' LTR.

In addition to a 5' and 3' LTR, tRNA binding site, and origin of second strand DNA synthesis, recombinant retroviral vector constructs may also comprise a packaging signal, as well as one or more genes or coding sequences of interest. In addition, the lentiviral vectors have a nuclear transport element which, in preferred embodiments is not RRE. Representative examples of suitable nuclear transport elements include the element in Rous sarcoma virus (Ogert, et al., *J Virol* 70, 3834-3843, 1996), the element in Rous sarcoma virus (Liu & Mertz, *Genes & Dev.*, 9, 1766-1789, 1995) and the element in the genome of simian retrovirus type I (Zolotukhin, et al., *J Virol.* 68, 7944-7952, 1994). Other potential elements include the elements in the histone gene (Kedes, *Annu. Rev. Biochem.* 48, 837-870, 1970), the α-interferon gene (Nagata et al., *Nature* 287, 401-408, 1980), the β-adrenergic receptor gene (Koilka, et al., *Nature* 329, 75-79, 1987), and the c-Jun gene (Hattorie, et al., *Proc. Natl. Acad. Sci. USA* 85, 9148-9152, 1988).

Recombinant lentiviral vector constructs typically lack both Gag-polymerase and Env coding sequences. Recombinant lentiviral vector typically contain less than 20, preferably 15, more preferably 10, and most preferably 8 consecutive nucleotides found in Gag-polymerase and Env genes. One advantage of the present invention is that the synthetic Gag-polymerase expression cassettes, which can be used to construct packaging cell lines for the recombinant retroviral vector constructs, have little homology to wild-type Gag-polymerase sequences and thus considerably reduce or eliminate the possibility of homologous recombination between the synthetic and wild-type sequences.

Lentiviral vectors may also include tissue-specific promoters to drive expression of one or more genes or sequences of interest.

Lentiviral vector constructs may be generated such that more than one gene of interest is expressed. This may be accomplished through the use of di-or oligo-cistronic cassettes (e.g., where the coding regions are separated by 80 nucleotides or less, see generally Levin et al., *Gene* 108:167-174, 1991), or through the use of Internal Ribosome Entry Sites ("IRES").

Packaging cell lines suitable for use with the above described recombinant retroviral vector constructs may be readily prepared given the disclosure provided herein. Briefly, the parent cell line from which the packaging cell line is derived can be selected from a variety of mammalian cell lines, including for example, 293, RD, COS-7, CHO, BHK, VERO, HT1080, and myeloma cells.

After selection of a suitable host cell for the generation of a packaging cell line, one or more expression cassettes are introduced into the cell line in order to complement or supply in trans components of the vector which have been deleted.

Representative examples of suitable expression cassettes have been described herein and include synthetic env, synthetic gag, synthetic gag-protease, and synthetic gag-polymerase expression cassettes, which comprise a promoter and a sequence encoding, e.g., Gag-polymerase and at least one of Vpr, Vpu, Nef or Vif, wherein the promoter is operably linked to gag-polymerase and vpr, vpu, nef or vif. As described above, the native and/or synthetic coding sequences may also be utilized in these expression cassettes.

Utilizing the above-described expression cassettes, a wide variety of packaging cell lines can be generated. For example, within one aspect packaging cell line are provided comprising an expression cassette that comprises a sequence encoding synthetic Gage-polymerase, and a nuclear transport element, wherein the promoter is operably linked to the sequence encoding the Gag-polymerase protein. Within other aspects, packaging cell lines are provided comprising a promoter and a sequence encoding Tat, Rev, Env proteins, or other HIV antigens or epitopes derived therefrom, wherein the promoter is operably linked to the sequence encoding Tat, Rev, Env, or the HIV antigen or epitope. Within further embodiments, the packaging cell line may comprise a sequence encoding any one or more of Nef, Vif, Vpu or Vpr. For example, the packaging cell line may contain only Nef, Vif, Vim, or Ypr, Nef and Vif, Nef and Vpu, Nef and Vpr, Vif and Vpu, Vif and Vpr, Vpu and Vpr, NefVif and Vpu, NefVif and Vpr, NefVpu and Vpr, VprVpu and Vpr, or, all four of Nef, Vif, Vpu, and Vpr.

In one embodiment, the expression cassette is stably integrated. Within another embodiment, the packaging cell line, upon introduction of a lentiviral vector, produces particles. Within further embodiments the promoter is inducible. Within certain preferred embodiments of the invention, the packaging cell line, upon introduction of a lentiviral vector, produces particles that are free of replication competent virus.

The synthetic cassettes containing modified coding sequences are transfected into a selected cell line. Transfected cells are selected that (i) carry, typically, integrated, stable copies of the HIV coding sequences, and (ii) are expressing acceptable levels of these polypeptides (expression can be evaluated by methods known in the prior art, e.g., see Examples 1-4). The ability of the cell line to produce VLPs may also be verified.

A sequence of interest is constructed into a suitable viral vector as discussed above. This defective virus is then transfected into the packaging cell line. The packaging cell line provides the viral functions necessary for producing virus-like particles into which the defective viral genome, containing the sequence of interest, are packaged. These VLPs are then isolated and can be used, for example, in gene delivery or gene therapy.

Further, such packaging cell lines can also be used to produce VLPs alone, which can, for example, be used as adjuvants for administration with other antigens or in vaccine compositions. Also, co-expression of a selected sequence of interest encoding a polypeptide (for example, an antigen) in the packaging cell line can also result in the entrapment and/or association of the selected polypeptide in/with the VLPs.

Various forms of the different embodiments of the present invention (e.g., constructs) may be combined.

2.4 DNA Immunization and Gene Delivery

A variety of HIV polypeptide antigens, particularly Type C HIV antigens, can be used in the practice of the present invention. HIV antigens can be included in DNA immunization constructs containing, for example, a synthetic Gag expression cassette fused in-frame to a coding sequence for the polypeptide antigen (synthetic or wild-type), where expression of the construct results in VLPs presenting the antigen of interest.

HIV antigens of particular interest to be used in the practice of the present invention include Tat, Rev, Nef, Vif, Vpu, Vpr, and other HIV antigens or epitopes derived therefrom. These antigens may be synthetic (as described herein) or wild-type. Further, the packaging cell line may contain only Nef and HIV-1 (also known as HTLY-III, LAY, ARY, etc.), including, but not limited to, antigens such as gp120 gp41 , gp160 (both native and modified); Gag; and Pol from a variety of isolates including, but not limited to, $HIV_{IIIb}$, $HIV_{SF2}$, $HIV-1_{SF162}$, $HIV-1_{SF170}$ , $HIV_{LAV}$, $HIV_{LAI}$, $HIV_{MN}$, $HIV-1_{CM235}$, $HIV-1_{US4}$, other HIV-1 strains from diverse subtypes (e.g., subtypes, A through G, and 0), HIV-2 strains and diverse subtypes (e.g., $HIV-2_{UV1}$ and $HIV-_{UC2}$). See, e.g., Myers, et al, Los Alamos Database, Los Alamos National Laboratory, Los Alamos, N.M.; Myers, et al., *Human Retroviruses and Aids*, 1990, Los Alamos, N.M.: Los Alamos National Laboratory.

To evaluate efficacy, DNA immunization using synthetic expression cassettes of the present invention can be performed, for instance as described in Example 4. Mice are immunized with both the Gag (and/or Env) synthetic expression cassette and the Gag (and/or Env) wild type expression cassette. Mouse immunizations with plasmid-DNAs will show that the synthetic expression cassettes provide a clear improvement of immunogenicity relative to the native expression cassettes. Also, the second boost immunization will induce a secondary immune response, for example, after approximately two weeks. Further, the results of CTL assays will show increased potency of synthetic Gag (and/or Env) expression cassettes for induction of cytotoxic T-lymphocyte (CTL) responses by DNA immunization.

It is readily apparent that the subject invention can be used to mount an immune response to a wide variety of antigens and hence to treat or prevent a HIV infection, particularly Type C HIV infection.

2.4.1 Delivery of the Synthetic Expression Cassettes of the Present Invention

Polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from cells and tissues containing the same, using standard techniques, such as phenol extraction and PCR of cDNA or genomic DNA. See, e.g., Sambrook et al., supra, for a description of techniques used to obtain and isolate DNA. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence is assembled from overlapping oligonucleotides prepared by standard methods and assembled into a complete coding sequence. See, e.g., Edge, *Nature* (1981) 292:756; Nambair et al., *Science* (1984) 223: 1299; Jay et al., *J. Biol. Chem*. (1984) 259:6311; Stemmer, W. P. C., (1995) *Gene* 164:49-53.

Next, the gene sequence encoding the desired antigen can be inserted into a vector containing a synthetic expression cassette of the present invention. In certain embodiments, the antigen is inserted into the synthetic Gag coding sequence such that when the combined sequence is expressed it results in the production of VLPs comprising the Gag polypeptide and the antigen of interest, e.g., Env (native or modified) or other antigen(s) (native or modified) derived from HIV. Insertions can be made within the coding sequence or at either end of the coding sequence (5', amino terminus of the expressed Gag polypeptide; or 3', carboxy terminus of the expressed Gag polypeptide)(Wagner, R., et al., *Arch Virol.* 127:117-137, 1992; Wagner, R., et al., *Virology* 200:162-175, 1994; Wu, X., et al., *J. Virol.* 69(6):3389-3398, 1995; Wang, C-T., et al., *Virology* 200:524-534, 1994; Chazal, N., et al., *Virology* 68(1):111-122, 1994; Griffiths, J. C., et al., *J. Virol.* 67(6): 3191-3198, 1993; Reicin, A. S., et al., *J. Virol.* 69(2):642-650, 1995).

Up to 50% of the coding sequences of p55Gag can be deleted without affecting the assembly to virus-like particles and expression efficiency (Borsetti, A., et al, *J. Virol.* 72(11): 9313-9317, 1998; Gamier, L., et al., *J Virol* 72(6):4667-4677, 1998; Zhang, Y., et al., *J Virol* 72(3):1782-1789, 1998; Wang, C., et al., *J Virol* 72(10): 7950-7959, 1998). In one embodiment of the present invention, immunogenicity of the high level expressing synthetic Gag expression cassettes can be increased by the insertion of different structural or non-structural HIV antigens, multiepitope cassettes, or cytokine sequences into deleted regions of Gag sequence. Such deletions may be generated following the teachings of the present invention and information available to one of ordinary skill in the art. One possible advantage of this approach, relative to using full-length sequences fused to heterologous polypeptides, can be higher expression/secretion efficiency of the expression product.

When sequences are added to the amino terminal end of Gag, the polynucletide can contain coding sequences at the 5' end that encode a signal for addition of a myristic moiety to the Gag-containing polypeptide (e.g., sequences that encode Met-Gly).

The ability of Gag-containing polypeptide constructs to form VLPs can be empirically determined following the teachings of the present specification.

The synthetic expression cassettes can also include control elements operably linked to the coding sequence, which allow for the expression of the gene in vivo in the subject species. For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence.

Enhancer elements may also be used herein to increase expression levels of the mammalian constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence.

Furthermore, plasmids can be constructed which include a chimeric antigen-coding gene sequences, encoding, e.g., multiple antigens/epitopes of interest, for example derived from more than one viral isolate.

Typically the antigen coding sequences precede or follow the synthetic coding sequence and the chimeric transcription unit will have a single open reading frame encoding both the antigen of interest and the synthetic coding sequences. Alternatively, multi-cistronic cassettes (e.g., bi-cistronic cassettes) can be constructed allowing expression of multiple antigens from a single mRNA using the EMCV IRES, or the like.

Once complete, the constructs are used for nucleic acid immunization using standard gene delivery protocols. Methods for gene delivery are known in the art. See, e.g., U.S. Pat. Nos. 5,399,346, 5,580,859, 5,589,466. Genes can be delivered either directly to the vertebrate subject or, alternatively, delivered ex vivo, to cells derived from the subject and the cells reimplanted in the subject.

A number of viral based systems have been developed for gene transfer into mammalian cells. For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219, 740; Miller and Rosman, *BioTechniques* (1989) 7:980-990; Miller, A. D., *Human Gene Therapy* (1990) 1:5-14; Scarpa et al., *Virology* (1991) 180:849-852; Bums et al., *Proc. Nat. Acad. Sci. USA* (1993) 90:8033-8037; and Boris-Lawrie and Temin, *Cur. Opin. Genet. Develop.* (1993) 3:102-109.

A number of adenovirus vectors have also been described. Unlike retroviruses which integrate into the host genome, adenoviruses persist extrachromosomally thus minimizing the risks associated with insertional mutagenesis (Haj-Ahmad and Graham, *J. Virol.* (1986) 57:267-274; Bett et al., *J. Virol.* (1993) 67:5911-5921; Mittereder et al., *Human Gene Therapy* (1994) 5:717-729; Seth et al., *J. Virol.* (1994) 68:933-940; Barr et al., *Gene Therapy* (1994) 1:51-58; Berkner, K. L. *BioTechniques* (1988) 6:616-629; and Rich et al., *Human Gene Therapy* (1993) 4:461-476).

Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., *Molec. Cell. Biol.* (1988) 8:3988-3996; Vincent et al., *Vaccines* 90 (1990) (Cold Spring Harbor Laboratory Press); Carter, B. J. *Current Opinion in Biotechnology* (1992) 3:533-539; Muzyczka, N. *Current Topics in Microbiol and Immunol.* (1992) 158:97-129; Kotin, R. M. *Human Gene Therapy* (1994) 5:793-801; Shelling and Smith, *Gene Therapy* (1994) 1:165-169; and Zhou et al., *J. Exp. Med.* (1994) 179:1867-1875.

Another vector system useful for delivering the polynucleotides of the present invention is the enterically administered recombinant poxvirus vaccines described by Small, Jr., P. A., et al. (U.S. Pat. No. 5,676,950, issued Oct. 14, 1997, herein incorporated by reference).

Additional viral vectors which will find use for delivering the nucleic acid molecules encoding the antigens of interest include those derived from the pox family of viruses, including vaccinia virus and avian poxvirus. By way of example, vaccinia virus recombinants expressing the genes can be constructed as follows. The DNA encoding the particular synthetic HIV subtype C polypeptide coding sequence is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the coding sequences of interest into the viral genome. The resulting TK recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., *J. Biol. Chem.* (1993) 268:6866-6869 and Wagner et al., *Proc. Natl. Acad. Sci. USA* (1992) 89:6099-6103, can also be used for gene delivery.

Members of the Alphavirus genus, such as, but not limited to, vectors derived from the Sindbis, Semliki Forest, and Venezuelan Equine Encephalitis viruses, will also find use as viral vectors for delivering the polynucleotides of the present invention (for example, a synthetic Gag-polypeptide encoding expression cassette). For a description of Sindbis-virus derived vectors useful for the practice of the instant methods, see, Dubensky et al., *J. Virol.* (1996) 70:508-519; and International Publication Nos. WO 95/07995 and WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference.

A vaccinia based infection/transfection system can be conveniently used to provide for inducible, transient expression of the coding sequences of interest in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation products. See, e.g., Elroy-Stein and Moss, *Proc. Natl. Acad. Sci. USA* (1990) 87:6743-6747; Fuerst et al., *Proc. Natl. Acad. Sci. USA* (1986) 83:8122-8126.

As an alternative approach to infection with vaccinia or avipox virus recombinants, or to the delivery of genes using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase which in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, *J. Mol. Biol.* (1986) 189:113-130; Deng and Wolff, *Gene* (1994) 143:245-249; Gao et al., *Biochem. Biophys. Res. Commun.* (1994) 200:1201-1206; Gao and Huang, *Nuc. Acids Res.* (1993) 21:2867-2872; Chen et al., *Nuc. Acids Res.* (1994) 22:2114-2120; and U.S. Pat. No. 5,135,855.

Synthetic expression cassettes of interest can also be delivered without a viral vector. For example, the synthetic expression cassette can be packaged in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 1097:1-17; Straubinger et al., in *Methods of Enzymology* (1983), Vol. 101, pp. 512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Felgner et al., *Proc. Natl. Acad. Sci. USA* (1987) 84:7413-7416); mRNA (Malone et al., *Proc. Natl. Acad. Sci. USA* (1989) 86:6077-6081); and purified transcription factors (Debs et al., *J. Biol. Chem.* (1990) 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., *Proc. Natl. Acad. Sci. USA* (1987) 84:7413-7416). Other commercially available lipids include (DDAB/DOPE) and DOTAP/DOPE (Boerhinger). Other cationic liposomes can be prepared from readily available materials using techniques well known in the art. See, e.g., Szoka et al., *Proc. Natl Acad. Sci. USA* (1978) 75:4194-4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as, from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512-527; Szoka et al., *Proc. Natl. Acad. Sci. USA* (1978) 75:4194-4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol. Chem.*

(1980) 255:10431; Szoka and Papahadjopoulos, *Proc. Natl. Acad. Sci. USA* (1978) 75:145; and Schaefer-Ridder et al., *Science* (1982) 215:166.

The DNA and/or protein antigen(s) can also be delivered in cochleate lipid compositions similar to those described by Papahadjopoulos et al., *Biochem. Biophys. Acta*. (1975) 394: 483-491. See, also, U.S. Pat. Nos. 4,663,161 and 4,871,488.

The synthetic expression cassette of interest may also be encapsulated, adsorbed to, or associated with, particulate carriers. Such carriers present multiple copies of a selected antigen to the immune system and promote trapping and retention of antigens in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res*. (1993) 10:362-368; McGee J P, et al., *J Microencapsul*. 14(2):197-210, 1997; O'Hagan D T, et al., *Vaccine* 11(2):149-54, 1993. Suitable microparticles may also be manufactured in the presence of charged detergents, such as anionic or cationic detergents, to yield microparticles with a surface having a net negative or a net positive charge. For example, microparticles manufactured with anionic detergents, such as hexadecyltrimethylammonium bromide (CTAB), i.e. CTAB-PLG microparticles, adsorb negatively charged macromolecules, such as DNA. (see, e.g., Int'l Application Number PCT/US99/17308).

Furthermore, other particulate systems and polymers can be used for the in vivo or ex vivo delivery of the gene of interest. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Felgner, P. L., *Advanced Drug Delivery Reviews* (1990) 5:163-187, for a review of delivery systems useful for gene transfer. Peptoids (Zuckerman, R. N., et al., U.S. Pat. No. 5,831,005, issued Nov. 3, 1998, herein incorporated by reference) may also be used for delivery of a construct of the present invention.

Additionally, biolistic delivery systems employing particulate carriers such as gold and tungsten, are especially useful for delivering synthetic expression cassettes of the present invention. The particles are coated with the synthetic expression cassette(s) to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744. Also, needle-less injection systems can be used (Davis, H. L., et al, *Vaccine* 12:1503-1509, 1994; Bioject, Inc., Portland, Oreg.).

Recombinant vectors carrying a synthetic expression cassette of the present invention are formulated into compositions for delivery to the vertebrate subject. These compositions may either be prophylactic (to prevent infection) or therapeutic (to treat disease after infection). The compositions will comprise a "therapeutically effective amount" of the gene of interest such that an amount of the antigen can be produced in vivo so that an immune response is generated in the individual to which it is administered. The exact amount necessary will vary depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials.

The compositions will generally include one or more "pharmaceutically acceptable excipients or vehicles" such as water, saline, glycerol, polyethyleneglycol, hyaluronic acid, ethanol, etc. Additionally, auxiliary substances, such as wetting or emulsifying agents, pH buffering substances, and the like, may be present in such vehicles. Certain facilitators of nucleic acid uptake and/or expression can also be included in the compositions or coadministered, such as, but not limited to, bupivacaine, cardiotoxin and sucrose.

Once formulated, the compositions of the invention can be administered directly to the subject (e.g., as described above) or, alternatively, delivered ex vivo, to cells derived from the subject, using methods such as those described above. For example, methods for the ex vivo delivery and reimplantation of transformed cells into a subject are known in the art and can include, e.g., dextran-mediated transfection, calcium phosphate precipitation, polybrene mediated transfection, lipofectamine and LT-1 mediated transfection, protoplast fusion, electroporation, encapsulation of the polynucleotide(s) (with or without the corresponding antigen) in liposomes, and direct microinjection of the DNA into nuclei.

Direct delivery of synthetic expression cassette compositions in vivo will generally be accomplished with or without viral vectors, as described above, by injection using either a conventional syringe or a gene gun, such as the Accell® gene delivery system (PowderJect Technologies, Inc., Oxford, England). The constructs can be injected either subcutaneously, epidermally, intradermally, intramucosally such as nasally, rectally and vaginally, intraperitoneally, intravenously, orally or intramuscularly. Delivery of DNA into cells of the epidermis is particularly preferred as this mode of administration provides access to skin-associated lymphoid cells and provides for a transient presence of DNA in the recipient. Other modes of administration include oral and pulmonary administration, suppositories, needle-less injection, transcutaneous and transdermal applications. Dosage treatment may be a single dose schedule or a multiple dose schedule. Administration of nucleic acids may also be combined with administration of peptides or other substances.

2.4.2 Ex Vivo Delivery of the Synthetic Expression Cassettes of the Present Invention In one embodiment, T cells, and related cell types (including but not limited to antigen presenting cells, such as, macrophage, monocytes, lymphoid cells, dendritic cells, B-cells, T-cells, stem cells, and progenitor cells thereof), can be used for ex vivo delivery of the synthetic expression cassettes of the present invention. T cells can be isolated from peripheral blood lymphocytes (PBLs) by a variety of procedures known to those skilled in the art. For example, T cell populations can be "enriched" from a population of PBLs through the removal of accessory and B cells. In particular, T cell enrichment can be accomplished by the elimination of non-T cells using anti-MHC class II monoclonal antibodies. Similarly, other antibodies can be used to deplete specific populations of non-T cells. For example, anti-Ig antibody molecules can be used to deplete B cells and anti-MacI antibody molecules can be used to deplete macrophages.

T cells can be further fractionated into a number of different subpopulations by techniques known to those skilled in the art. Two major subpopulations can be isolated based on their differential expression of the cell surface markers CD4 and CD8. For example, following the enrichment of T cells as described above, CD4+ cells can be enriched using antibodies specific for CD4 (see Coligan et al., supra). The antibodies may be coupled to a solid support such as magnetic beads. Conversely, CD8+ cells can be enriched through the use of antibodies specific for CD4 (to remove CD4+ cells), or can be isolated by the use of CD8 antibodies coupled to a solid support. CD4 lymphocytes from HIV-1 infected patients can be expanded ex vivo, before or after transduction as described by Wilson et. al. (1995) *J. Infect. Dis.* 172:88.

Following purification of T cells, a variety of methods of genetic modification known to those skilled in the art can be performed using non-viral or viral-based gene transfer vectors constructed as described herein. For example, one such approach involves transduction of the purified T cell population with vector-containing supernatant of cultures derived from vector producing cells. A second approach involves co-cultivation of an irradiated monolayer of vector-producing cells with the purified T cells. A third approach involves a similar co-cultivation approach; however, the purified T cells are pre-stimulated with various cytokines and cultured 48 hours prior to the co-cultivation with the irradiated vector producing cells. Pre-stimulation prior to such transduction increases effective gene transfer (Nolta et al. (1992) *Exp. Hematol.* 20:1065). Stimulation of these cultures to proliferate also provides increased cell populations for re-infusion into the patient. Subsequent to co-cultivation, T cells are collected from the vector producing cell monolayer, expanded, and frozen in liquid nitrogen.

Gene transfer vectors, containing one or more synthetic expression cassette of the present invention (associated with appropriate control elements for delivery to the isolated T cells) can be assembled using known methods.

Selectable markers can also be used in the construction of gene transfer vectors. For example, a marker can be used which imparts to a mammalian cell transduced with the gene transfer vector resistance to a cytotoxic agent. The cytotoxic agent can be, but is not limited to, neomycin, aminoglycoside, tetracycline, chloramphenicol, sulfonamide, actinomycin, netropsin, distamycin A, anthracycline, or pyrazinamide. For example, neomycin phosphotransferase II imparts resistance to the neomycin analogue geneticin (G418).

The T cells can also be maintained in a medium containing at least one type of growth factor prior to being selected. A variety of growth factors are known in the art which sustain the growth of a particular cell type. Examples of such growth factors are cytokine mitogens such as rIL-2, IL-10, IL-12, and IL-15, which promote growth and activation of lymphocytes. Certain types of cells are stimulated by other growth factors such as hormones, including human chorionic gonadotropin (hCG) and human growth hormone. The selection of an appropriate growth factor for a particular cell population is readily accomplished by one of skill in the art.

For example, white blood cells such as differentiated progenitor and stem cells are stimulated by a variety of growth factors. More particularly, IL-3, IL-4, IL-5, IL-6, IL-9, GM-CSF, M-CSF, and G-CSF, produced by activated $T_H$ and activated macrophages, stimulate myeloid stem cells, which then differentiate into pluripotent stem cells, granulocyte-monocyte progenitors, eosinophil progenitors, basophil progenitors, megakaryocytes, and erythroid progenitors. Differentiation is modulated by growth factors such as GM-CSF, IL-3, IL-6, IL-11, and EPO.

Pluripotent stem cells then differentiate into lymphoid stem cells, bone marrow stromal cells, T cell progenitors, B cell progenitors, thymocytes, $T_H$ Cells, $T_C$ cells, and B cells. This differentiation is modulated by growth factors such as IL-3, IL-4, IL-6, IL-7, GM-CSF, M-CSF, G-CSF, IL-2, and IL-5.

Granulocyte-monocyte progenitors differentiate to monocytes, macrophages, and neutrophils. Such differentiation is modulated by the growth factors GM-CSF, M-CSF, and IL-8. Eosinophil progenitors differentiate into eosinophils. This process is modulated by GM-CSF and IL-5.

The differentiation of basophil progenitors into mast cells and basophils is modulated by GM-CSF, IL-4, and IL-9. Megakaryocytes produce platelets in response to GM-CSF, EPO, and IL-6. Erythroid progenitor cells differentiate into red blood cells in response to EPO.

Thus, during activation by the CD3-binding agent, T cells can also be contacted with a mitogen, for example a cytokine such as IL-2. In particularly preferred embodiments, the IL-2 is added to the population of T cells at a concentration of about 50 to 100 µg/ml. Activation with the CD3-binding agent can be carried out for 2 to 4 days.

Once suitably activated, the T cells are genetically modified by contacting the same with a suitable gene transfer vector under conditions that allow for transfection of the vectors into the T cells. Genetic modification is carried out when the cell density of the T cell population is between about $0.1 \times 10^6$ and $5 \times 10^6$, preferably between about $0.5 \times 10^6$ and $2 \times 10^6$. A number of suitable viral and nonviral-based gene transfer vectors have been described for use herein.

After transduction, transduced cells are selected away from non-transduced cells using known techniques. For example, if the gene transfer vector used in the transduction includes a selectable marker which confers resistance to a cytotoxic agent, the cells can be contacted with the appropriate cytotoxic agent, whereby non-transduced cells can be negatively selected away from the transduced cells. If the selectable marker is a cell surface marker, the cells can be contacted with a binding agent specific for the particular cell surface marker, whereby the transduced cells can be positively selected away from the population. The selection step can also entail fluorescence-activated cell sorting (FACS) techniques, such as where FACS is used to select cells from the population containing a particular surface marker, or the selection step can entail the use of magnetically responsive particles as retrievable supports for target cell capture and/or background removal.

More particularly, positive selection of the transduced cells can be performed using a FACS cell sorter (e.g. a FACSVantage™ Cell Sorter, Becton Dickinson Immunocytometry Systems, San Jose, Calif.) to sort and collect transduced cells expressing a selectable cell surface marker. Following transduction, the cells are stained with fluorescent-labeled antibody molecules directed against the particular cell surface marker. The amount of bound antibody on each cell can be measured by passing droplets containing the cells through the cell sorter. By imparting an electromagnetic charge to droplets containing the stained cells, the transduced cells can be separated from other cells. The positively selected cells are then harvested in sterile collection vessels. These cell sorting procedures are described in detail, for example, in the FACS-Vantage™ Training Manual, with particular reference to sections 3-11 to 3-28 and 10-1 to 10-17.

Positive selection of the transduced cells can also be performed using magnetic separation of cells based on expression or a particular cell surface marker. In such separation techniques, cells to be positively selected are first contacted with specific binding agent (e.g., an antibody or reagent the interacts specifically with the cell surface marker). The cells are then contacted with retrievable particles (e.g., magnetically responsive particles) which are coupled with a reagent that binds the specific binding agent (that has bound to the positive cells). The cell-binding agent-particle complex can then be physically separated from non-labeled cells, for example using a magnetic field. When using magnetically responsive particles, the labeled cells can be retained in a container using a magnetic filed while the negative cells are removed. These and similar separation procedures are known to those of ordinary skill in the art.

Expression of the vector in the selected transduced cells can be assessed by a number of assays known to those skilled in the art. For example, Western blot or Northern analysis can be employed depending on the nature of the inserted nucleotide sequence of interest. Once expression has been established and the transformed T cells have been tested for the presence of the selected synthetic expression cassette, they are ready for infusion into a patient via the peripheral blood stream.

The invention includes a kit for genetic modification of an ex vivo population of primary mammalian cells. The kit typically contains a gene transfer vector coding for at least one selectable marker and at least one synthetic expression cassette contained in one or more containers, ancillary reagents or hardware, and instructions for use of the kit.

2.4.3 Further Delivery Regimes

Any of the polynucleotides (e.g., expression cassettes) or polypeptides described herein (delivered by any of the methods described above) can also be used in combination with other DNA delivery systems and/or protein delivery systems. Non-limiting examples include co-administration of these molecules, for example, in prime-boost methods where one or more molecules are delivered in a "priming" step and, subsequently, one or more molecules are delivered in a "boosting" step. In certain embodiments, the delivery of one or more nucleic acid-containing compositions and is followed by delivery of one or more nucleic acid-containing compositions and/or one or more polypeptide-containing compositions (e.g., polypeptides comprising HIV antigens). In other embodiments, multiple nucleic acid "primes" (of the same or different nucleic acid molecules) can be followed by multiple polypeptide "boosts" (of the same or different polypeptides). Other examples include multiple nucleic acid administrations and multiple polypeptide administrations.

In any method involving co-administration, the various compositions can be delivered in any order. Thus, in embodiments including delivery of multiple different compositions or molecules, the nucleic acids need not be all delivered before the polypeptides. For example, the priming step may include delivery of one or more polypeptides and the boosting comprises delivery of one or more nucleic acids and/or one more polypeptides. Multiple polypeptide administrations can be followed by multiple nucleic acid administrations or polypeptide and nucleic acid administrations can be performed in any order. In any of the embodiments described herein, the nucleic acid molecules can encode all, some or none of the polypeptides. Thus, one or more or the nucleic acid molecules (e.g., expression cassettes) described herein and/or one or more of the polypeptides described herein can be co-administered in any order and via any administration routes. Therefore, any combination of polynucleotides and/or polypeptides described herein can be used to generate elicit an immune reaction.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Generation of Synthetic Expression Cassettes

A. Modification of HIV-1 Env, Gag Pol Nucleic Acid Coding Sequences

The Pol coding sequences were selected from Type C strain AF110975. The Gag coding sequences were selected from the Type C strains AF110965 and AF110967. The Env coding sequences were selected from Type C strains AF110968 and AF110975. These sequences were manipulated to maximize expression of their gene products.

First, the HIV-1 codon usage pattern was modified so that the resulting nucleic acid coding sequence was comparable to codon usage found in highly expressed human genes. The HIV codon usage reflects a high content of the nucleotides A or T of the codon-triplet. The effect of the HIV-1 codon usage is a high AT content in the DNA sequence that results in a decreased translation ability and instability of the mRNA. In comparison, highly expressed human codons prefer the nucleotides G or C. The coding sequences were modified to be comparable to codon usage found in highly expressed human genes.

Second, there are inhibitory (or instability) elements (INS) located within the coding sequences of the Gag and Gag-protease coding sequences (Schneider R, et al., *J Virol.* 71(7): 4892-4903, 1997). RRE is a secondary RNA structure that interacts with the HIV encoded Rev-protein to overcome the expression down-regulating effects of the INS. To overcome the post-transcriptional activating mechanisms of RRE and Rev, the instability elements are inactivated by introducing multiple point mutations that do not alter the reading frame of the encoded proteins. FIGS. 5 and 6 (SEQ ID Nos: 3, 4, 20 and 21) show the location of some remaining INS in synthetic sequences derived from strains AF110965 and AF110967. The changes made to these sequences are boxed in the Figures. In FIGS. 5 and 6, the top line depicts a modified sequence of Gag polypeptides from the indicated strains. The nucleotide(s) appearing below the line in the boxed region(s) depicts changes made to further remove INS. Thus, when the changes indicated in the boxed regions are made, the resulting sequences correspond to the sequences depicted in FIGS. 1 and 2, respectively.

The synthetic coding sequences are assembled by methods known in the art, for example by companies such as the Midland Certified Reagent Company (Midland, Tex.).

In one embodiment of the invention, sequences encoding Pol-polypeptides are included with the synthetic Gag or Env sequences in order to increase the number of epitopes for virus-like particles expressed by the synthetic, modified Gag/Env expression cassette. Because synthetic HIV-1 Pol expresses the functional enzymes reverse transcriptase (RT) and integrase (INT) (in addition to the structural proteins and protease), it may be helpful in some instances to inactivate RT and INT functions. Several deletions or mutations in the RT and INT coding regions can be made to achieve catalytic nonfunctional enzymes with respect to their RT and INT activity. {Jay. A. Levy (Editor) (1995) *The Retroviridae*, Plenum Press, New York. ISBN 0-306-45033X. Pages 215-20; Grimison, B. and Laurence, J. (1995), *Journal Of Acquired Immune Deficiency Syndromes and Human Retrovirology* 9(1):58-68; Wakefield, J. K., et al., (1992) *Journal Of Virology* 66(11):6806-6812; Esnouf, R., et al., (1995) *Nature Structural Biology* 2(4):303-308; Maignan, S., et al., (1998) *Journal Of Molecular Biology* 282(2):359-368; Katz, R. A.

and Skalka, A. M. (1994) *Annual Review Of Biochemistry* 73 (1994); Jacobo-Molina, A., et al., (1993) *Proceedings Of the National Academy Of Sciences Of the United States Of America* 90(13):6320-6324; Hickman, A. B., et al., (1994) *Journal Of Biological Chemistry* 269(46):29279-29287; Goldgur, Y., et al., (1998) *Proceedings Of the National Academy Of Sciences Of the United States Of America* 95(16): 9150-9154; Goette, M., et al., (1998) *Journal Of Biological Chemistry* 273(17):10139-10146; Gorton, J. L., et al., (1998) *Journal of Virology* 72(6):5046-5055; Engelman, A., et al., (1997) *Journal Of Virology* 71(5):3507-3514; Dyda, F., et al., *Science* 266(5193):1981-1986; Davies, J. F., et al., (1991) *Science* 252(5002):88-95; Bujacz, G., et al., (1996) *Febs Letters* 398(2-3):175-178; Beard, W. A., et al., (1996) *Journal Of Biological Chemistry* 271(21):12213-12220; Kohlstaedt, L. A., et al., (1992) *Science* 256(5065):1783-1790; Krug, M. S. and Berger, S. L. (1991) *Biochemistry* 30(44):10614-10623; Mazumder, A., et al., (1996) *Molecular Pharmacology* 49(4): 621-628; Palaniappan, C., et al., (1997) *Journal Of Biological Chemistry* 272(17):11157-11164; Rodgers, D. W., et al., (1995) *Proceedings Of the National Academy Of Sciences Of the United States Of America* 92(4):1222-1226; Sheng, N. and Dennis, D. (1993) *Biochemistry* 32(18):4938-4942; Spence, R. A., et al., (1995) *Science* 267(5200):988-993.}

Furthermore selected B- and/or T-cell epitopes can be added to the Pol constructs (e.g., 3' of the truncated TNT or within the deletions of the RT-and NT-coding sequence) to replace and augment any epitopes deleted by the functional modifications of RT and NT. Alternately, selected B- and T-cell epitopes (including CTL epitopes) from RT and NT can be included in a minimal VLP formed by expression of the synthetic Gag or synthetic Pol cassette, described above. (For descriptions of known HIV B-and T-cell epitopes see, HIV Molecular Immunology Database CTL Search Interface; Los Alamos Sequence Compendia, 1987-1997 ;Internet address: hiv-web.lan1.gov/immunology/index.htm1.)

The resulting modified coding sequences are presented as a synthetic Env expression cassette; a synthetic Gag expression cassette; a synthetic Pol expression cassette. A common Gag region (Gag-common) extends from nucleotide position 844 to position 903 (SEQ ID NO:1), relative to AF110965 (or from approximately amino acid residues 282 to 301 of SEQ ID NO:17) and from nucleotide position 841 to position 900 (SEQ ID NO:2), relative to AF110967 (or from approximately amino acid residues 281 to 300 of SEQ ID NO:22). A common Env region (Env-common) extends from nucleotide position 1213 to position 1353 (SEQ ID NO:5) and amino acid positions 405 to 451 of SEQ ID NO:23, relative to AF110968 and from nucleotide position 1210 to position 1353 (SEQ ID NO:11) and amino acid positions 404-451 (SEQ ID NO:24), relative to AF110975.

The synthetic DNA fragments for Pol, Gag and Env are cloned into the following eucaryotic expression vectors: pCMVKm2, for transient expression assays and DNA immunization studies, the pCMVKm2 vector is derived from pCMV6a (Chapman et al., *Nuc. Acids Res.* (1991) 19:3979-3986) and comprises a kanamycin selectable marker, a ColE1 origin of replication, a CMV promoter enhancer and Intron A, followed by an insertion site for the synthetic sequences described below followed by a polyadenylation signal derived from bovine growth hormone—the pCMVKm2 vector differs from the pCMV-link vector only in that a polylinker site is inserted into pCMVKm2 to generate pCMV-link; pESN2dhfr and pCMVPLEdhfr, for expression in Chinese Hamster Ovary (CHO) cells; and, pAcC 13, a shuttle vector for use in the Baculovirus expression system (pAcC13, is derived from pAcC12 which is described by Munemitsu S., et al., *Mol Cell Biol.* 10(11):5977-5982, 1990).

Briefly, construction of pCMVPLEdhfr was as follows.

To construct a DHFR cassette, the EMCV IRES (internal ribosome entry site) leader was PCR-amplified from pCite-4a+ (Novagen, Inc., Milwaukee, Wis.) and inserted into pET-23d (Novagen, Inc., Milwaukee, Wis.) as an Xba-Nco fragment to give pET-EMCV. The dhfr gene was PCR-amplified from pESN2dhfr to give a product with a Gly-Gly-Gly-Ser spacer in place of the translation stop codon and inserted as an Nco-BamH1 fragment to give pET-E-DHFR. Next, the attenuated neo gene was PCR amplified from a pSV2Neo (Clontech, Palo Alto, Calif.) derivative and inserted into the unique BamH1 site of pET-E-DHFR to give pET-E-DHFR/$Neo_{(m2)}$. Finally the bovine growth hormone terminator from pCDNA3 (Invitrogen, Inc., Carlsbad, Calif.) was inserted downstream of the neo gene to give pET-E-DHFR/$Neo_{(m2)}$ BGHt. The EMCV-dhfr/neo selectable marker cassette fragment was prepared by cleavage of pET-E-DHFR/$Neo_{(m2)}$ BGHt.

The CMV enhancer/promoter plus Intron A was transferred from pCMV6a (Chapman et al., *Nuc. Acids Res.* (1991) 19:3979-3986) as a HindIII-Sal1 fragment into pUC19 (New England Biolabs, Inc., Beverly, Mass.). The vector backbone of pUC19 was deleted from the Nde1 to the Sap1 sites. The above described DHFR cassette was added to the construct such that the EMCV IRES followed the CMV promoter. The vector also contained an $amp^r$ gene and an SV40 origin of replication.

B. Defining of the Major Homology Region (MHR) of HIV-1 p55Gag

The Major Homology Region (MHR) of HIV-1 p55 (Gag) is located in the p24-CA sequence of Gag. It is a conserved stretch of approximately 20 amino acids. The position in the wild type AF110965 Gag protein is from 282-301 (SEQ ID NO:25) and spans a region from 844-903 (SEQ ID NO:26) for the Gag DNA-sequence. The position in the synthetic Gag protein is also from 282-301 (SEQ ID NO:25) and spans a region from 844-903 (SEQ ID NO:1) for the synthetic Gag DNA-sequence. The position in the wild type and synthetic AF110967 Gag protein is from 281-300 (SEQ ID NO:27) and spans a region from 841-900 (SEQ ID NO:2) for the modified Gag DNA-sequence. Mutations or deletions in the MHR can severely impair particle production (Borsetti, A., et al., *J. Virol.* 72(11):9313-9317, 1998; Mammano, F., et al., *J Virol* 68(8):4927-4936, 1994).

Percent identity to this sequence can be determined, for example, using the Smith-Waterman search algorithm (Time Logic, Incline Village, Nev., with the following exemplary parameters: weight matrix=nuc4×4hb; gap opening penalty=20, gap extension penalty=5.

C. Defining of the Common Sequence Region of HIV-1 Env

The common sequence region (CSR) of HIV-1 Env is located in the C4 sequence of Env. It is a conserved stretch of approximately 47 amino acids. The position in the wild type and synthetic AF110968 Env protein is from approximately amino acid residue 405 to 451 (SEQ ID NO:28) and spans a region from 1213 to 1353 (SEQ ID NO:5) for the Env DNA-sequence. The position in the wild type and synthetic AF110975 Env protein is from approximately amino acid residue 404 to 451 (SEQ ID NO:29) and spans a region from 1210 to 1353 (SEQ ID NO:11) for the Env DNA-sequence.

Percent identity to this sequence can be determined, for example, using the Smith-Waterman search algorithm (Time Logic, Incline Village, Nev.), with the following exemplary parameters: weight matrix=nuc4×4hb; gap opening penalty=20, gap extension penalty=5.

Various forms of the different embodiments of the invention, described herein, may be combined.

D. Exemplary HIV Sequences Derived from South African HIV Type C Strains

HIV coding sequences of novel Type C isolates were obtained. Polypeptide-coding sequences were manipulated to maximize expression of their gene products.

As described above, the HIV-1 codon usage pattern was modified so that the resulting nucleic acid coding sequence was comparable to codon usage found in highly expressed human genes. The HIV codon usage reflects a high content of the nucleotides A or T of the codon-triplet. The effect of the HIV-1 codon usage is a high AT content in the DNA sequence that results in a decreased translation ability and instability of the mRNA. In comparison, highly expressed human codons prefer the nucleotides G or C. The coding sequences were modified to be comparable to codon usage found in highly expressed human genes.

Shown below in Table C are exemplary wild-type and synthetic sequences derived from a novel South African HIV Type C isolate, clone 8_5_TV1_C.ZA. Table D shows exemplary synthetic Env sequences derived from a novel South African HIV Type C isolate, clone 8_2_TV1_C.ZA. Table E shows wild-type and synthetic sequences derived from South African HIV Type C strain 12-5_1_TV2_C.ZA.

TABLE C

| Name | SEQ ID | Description |
| --- | --- | --- |
| C4_Env_TV1_C_ZA_opt short | 46 | synthetic sequence of short Env "common region" |
| C4_Env_TV1_C_ZA_opt | 47 | synthetic sequence of Env "common region" |
| C4_Env_TV1_C_ZA_wt | 48 | wild type 8_5_TV1_C.ZA Env sequence |
| Envgp160_TV1_C_ZAopt | 49 | synthetic Env gp160 |
| Envgp160_TV1_C_ZAwt | 50 | wild type 8_5_TV1_C.ZA Env gp160 sequence |
| Gag_TV1_C_ZAopt | 51 | synthetic sequence of Gag |
| Gag_TV1_C_ZAwt | 52 | wild type 8_5_TV1_C.ZA Gag sequence |
| Gag_TV1_ZA_MHRopt | 53 | synthetic sequence of Gag major homology region |
| Gag_TV1_ZA_MHRwt | 54 | wild type 8_5_TV1_C.ZA Gag major homology region sequence |
| Nef_TV1_C_ZAopt | 55 | synthetic sequence of Nef |
| Nef_TV1_C_ZAwt | 56 | wild type 8_5_TV1_C.ZA Nef sequence |
| NefD125G_TV1_C_ZAopt | 57 | synthetic sequence of Nef, including mutation at position 125 resulting in non-functional gene product |
| p15RNaseH_TV1_C_ZAopt | 58 | synthetic sequence of RNAseH (p15 of Pol) |
| p15RNaseH_TV1_C_ZAwt | 59 | wild type 8_5_TV1_C.ZA RNAseH sequence |
| p31Int_TV1_C_ZAopt | 60 | synthetic sequence of Integrase (p31 of Pol) |
| p31Int_TV1_C_ZAwt | 61 | wild type 8_5_TV1_C.ZA Integrase sequence |
| Pol_TV1_C_ZAopt | 62 | synthetic sequence of Pol |
| Pol_TV1_C_ZAwt | 63 | wild type 8_5_TV1_C.ZA Pol sequence |
| Prot_TV1_C_ZAopt | 64 | synthetic sequence of Prot |
| Prot_TV1_C_ZAwt | 65 | wild type 8_5_TV1_C.ZA Prot sequence |
| Protina_TV1_C_ZAopt | 66 | synthetic sequence of Prot including mutation resulting in inactivation of protease |
| Protina_TV1_C_ZAwt | 67 | wild type 8_5_TV1_C.ZA Prot sequence, including mutation resulting in inactivation of protease. |
| ProtinaRTmut_TV1_C_ZAopt | 68 | synthetic sequence of Prot and reverse transcriptase (RT), including mutation resulting in inactivation of protease and mutation resulting in inactivation of RT. |
| ProtinaRTmut_TV1_C_ZAwt | 69 | wild type 8_5_TV1_C.ZA Prot and RT, mutation resulting in inactivation of protease and mutation resulting in inactivation of RT. |
| ProtwtRTwt_TV1_C_ZAopt | 70 | synthetic sequences of Prot and RT |
| ProtwtRTwt_TV1_C_ZAwt | 71 | wild type 8_5_TV1_C.ZA Prot and RT |
| RevExon1_TV1_C_ZAopt | 72 | synthetic sequence of exon 1 of Rev |
| RevExon1_TV1_C_ZAwt | 73 | wild type 8_5_TV1_C.ZA of exon 1 of Rev |
| RevExon2_TV1_C_ZAopt-2 | 74 | synthetic sequence of exon 2 of Rev |
| RevExon2_TV1_C_ZAwt | 75 | wild type 8_5_TV1_C.ZA of exon 2 of Rev |
| RT_TV1_C_ZAopt | 76 | synthetic sequence of RT |
| RT_TV1_C_ZAwt | 77 | wild type 8_5_TV1_C.ZA RT |
| RTmut_TV1_C_ZAopt | 78 | synthetic sequence of RT, including mutation resulting in inactivation of RT |
| RTmut_TV1_C_ZAwt | 79 | wild type 8_5_TV1_C.ZA RT, including mutation resulting in inactivation of RT |
| TatC22Exon1_TV1_C_ZAopt | 80 | synthetic sequence of exon 1 of Tat, including mutation resulting in non-functional Tat gene product |
| TatExon_TV1_C_ZAopt | 81 | synthetic sequence of exon 1 of Tat |
| TatExon1_TV1_C_ZAwt | 82 | wild type 8_5_TV1_C.ZA exon1 of Tat |
| TatExon2_TV1_C_ZAopt | 83 | synthetic sequence of exon 2 of Tat |
| TatExon2_TV1_C_ZAwt | 84 | wild type 8_5_TV1_C.ZA exon 2 of Tat |

TABLE C-continued

| Name | SEQ ID | Description |
|---|---|---|
| Vif_TV1_C_ZAopt | 85 | synthetic sequence of Vif |
| Vif_TV1_C_ZAwt | 86 | wild type 8_5_TV1_C.ZA Vif |
| Vpr_TV1_C_ZAopt | 87 | synthetic sequence of Vpr |
| Vpr_TV1_C_ZAwt | 88 | wild type 8_5_TV1_C.ZA Vpr |
| Vpu_TV1_C_ZAopt | 89 | synthetic sequence of Vpu |
| Vpu_TV1_C_ZAwt | 90 | wild type 8_5_TV1_C.ZA Vpu |
| revexon1_2 TV1 C ZAopt | 91 | synthetic sequence of exons 1 and 2 of Rev |
| RevExon1_2_TV1_C_ZAwt | 92 | wild type 8_5_TV1_C.ZA Rev (exons 1 and 2) |
| TatC22Exon1_2_TV1_C_ZAopt | 93 | synthetic sequence of exons 1 and 2 of Tat, including mutation in exon 1 resulting in non-functional Tat gene product |
| TatExon1_2_TV1_C_ZAopt | 94 | synthetic sequence of exons 1 and 2 of Tat |
| TatExon1_2_TV1_C_ZAwt | 95 | wild type 8_5_TV1_C.ZA Tat (exons 1 and 2) |
| NefD125G-Myr_TV1_C_ZAopt | 96 | synthetic sequence of Nef, including mutation eliminating myristoylation site. |

TABLE D

| Name | Seq Id | Description |
|---|---|---|
| gp120mod.TV1.delV2 | 119 | synthetic sequence of Env gp120, including V2 deletion and modified leader sequences derived from wild-type 8_2_TV1_C.ZA sequences |
| gp140mod.TV1.delV2 | 120 | synthetic sequence of Env gp140, including V2 deletion and modified leader sequences derived from wild-type 8_2_TV1_C.ZA sequences |
| gp140mod.TV1.mut7.delV2 | 121 | synthetic sequence of Env gp140, including V2 deletion and mutation in cleavage site and modified leader sequences derived from wild-type 8_2_TV1_C.ZA sequences |
| gp160mod.TV1.delV1V2 | 122 | synthetic sequence of Env gp160, including V1/V2 deletion and modified leader derived from wild-type 8_2_TV1_C.ZA sequences |
| gp160mod.TV1.delV2 | 123 | synthetic sequence of Env gp160, including V2 deletion and modified leader sequences derived from wild-type 8_2_TV1_C.ZA sequences |
| gp160mod.TV1.mut7.delV2 | 124 | synthetic sequence of Env gp160, including V2 deletion; a mutation in cleavage site; and modified leader sequences derived from wild-type 8_2_TV1_C.ZA sequences |
| gp160mod.TV1.tpa1 | 125 | synthetic sequence of Env gp160, TPA1 leader |
| gp160mod.TV1 | 126 | synthetic sequence of Env gp160, including modified leader sequences derived from wild-type (8_2_TV1_C.ZA) sequences |
| gp160mod.TV1.wtLnative | 127 | synthetic sequence of Env gp160, including wild type 8_2_TV1_C.ZA (unmodified) leader |
| gp140.mod.TV1.tpa1 | 131 | synthetic sequence of Env gp140, TPA1 leader |
| gp140mod.TV1 | 132 | synthetic sequence of Env gp140, including modified leader sequences derived from wild-type 8_2_TV1_C.ZA sequences |
| gp140mod.TV1.wtLnative | 133 | synthetic sequence of Env gp120, including wild type 8_2_TV1_C.ZA (unmodified) leader sequence. |

As noted above, Env-encoding constructs can be prepared using any of the full-length of gp160 constructs. For example, a gp140 form (SEQ ID NO:132) was made by truncating gp160 (SEQ ID NO:126) at nucleotide 2064; gp120 was made by truncating gp160 (SEQ ID NO:126) at nucleotide 1551 (SEQ ID NO:126). Additional gp140 and gp120 forms can be made using the methods described herein. One or more stop codons are typically added (e.g., nucleotides 2608 to 2610 of SEQ ID NO:126). Further, the wild-type leader sequence can be modified and/or replaced with other leader sequences (e.g, TPA1 leader sequences).

Thus, the polypeptide gp160 includes the coding sequences for gp120 and gp41. The polypeptide gp41 is comprised of several domains including an oligomerization domain (OD) and a transmembrane spanning domain (TM). In the native envelope, the oligomerization domain is required for the non-covalent association of three gp41 polypeptides to form a trimeric structure: through non-covalent interactions with the gp41 trimer (and itself), the gp120 polypeptides are also organized in a trimeric structure. A cleavage site (or cleavage sites) exists approximately between the polypeptide sequences for gp120 and the polypeptide sequences corresponding to gp41. This cleavage site(s) can be mutated to prevent cleavage at the site. The resulting gp140 polypeptide corresponds to a truncated form of gp160 where the transmembrane spanning domain of gp41 has been deleted. This gp140 polypeptide can exist in both monomeric and oligomeric (i.e. trimeric) forms by virtue of the presence of the oligomerization domain in the gp41 moiety. In the situation where the cleavage site has been mutated to prevent cleavage and the transmembrane portion of gp41 has been deleted the resulting polypeptide product is designated "mutated" gp140 (e.g., gp140.mut). As will be apparent to those in the field, the cleavage site can be mutated in a variety of ways. In the exemplary constructs described herein (e.g., SEQ ID NO:121 and SEQ ID NO:124), the mutation in the gp120/gp41 cleavage site changes the wild-type amino acid sequence KRRVVQREKR (SEQ ID NO:129) to ISSVVQSEKS (SEQ ID NO:130).

In yet other embodiments, hypervariable region(s) were deleted, N-glycosylation sites were removed and/or cleavage sites mutated. Exemplary constructs having variable region deletions (V1 and/or V2), V2 deletes were constructed by deleting nucleotides from approximately 499 to approximately 593 (relative to SEQ ID NO:128) and V1/V2 deletes were constructed by deleting nucleotides from approximately 375 to approximately 602 (relative to SEQ ID NO:128). The relative locations of V1 and/or V2 regions can also be readily determined by alignment to the regions shown in Table A. Table E shows wild-type and synthetic sequences derived from South African HIV Type C strain 12-5_1_TV2_C.ZA.

It will be readily apparent that sequences derived from any HIV type C stain or clone can modified as described herein in order to achieve desirable modifications in that strain. Additionally, polyproteins can be constructed by fusing in-frame two or more polynucleotide sequences encoding polypeptide or peptide products. Further, polycistronic coding sequences may be produced by placing two or more polynucleotide sequences encoding polypeptide products adjacent each other, typically under the control of one promoter, wherein each polypeptide coding sequence may be modified to include sequences for internal ribosome binding sites.

The sequences of the present invention, for example, the modified (synthetic) polynucleotide sequences encoding HIV polypeptides, may be modified by deletions, point mutations, substitutions, frame-shifts, and/or further genetic modifications (for example, mutations leading to inactivation of an activity associated with a polypeptide, e.g., mutations that inactivate protease, tat, or reverse transcriptase activity). Such modifications are taught generally in the art and may be applied in the context of the teachings of the present invention. For example, sites corresponding to the "Regions of the HIV Genome" listed in Table A may be modified in the corresponding regions of the novel sequences disclosed herein in order to achieve desirable modifications. Further, the modified (synthetic) polynucleotide sequences of the present invention can be combined for use, e.g., in an composition for generating an immune response in a subject, in a variety of ways, including but not limited to the following ways: multiple individual expression cassettes each comprising one polynucleotide sequence of the present invention (e.g., a gag-expression cassette, an env expression cassette, and a rev expression cassette, or a pol-expression cassette, a vif expression cassette, and a vpr expression cassette, etc.); polyproteins produced by in-frame fusions of multiple poly-

TABLE E

| Name | SEQ ID | Description |
| --- | --- | --- |
| Envgp160_TV2_C_ZAopt | 97 | synthetic sequence of Env gp160 |
| Envgp160_TV2_C_ZAwt | 98 | wildtype 12-5_1_TV2_C.ZA Env gp160. |
| Gag_TV2_C_ZAopt | 99 | synthetic sequence of Gag |
| Gag_TV2_C_ZAwt | 100 | wild type 12-5_1_TV2_C.ZA Gag |
| Nef_TV2_C_ZAopt | 101 | synthetic sequence of Nef |
| Nef_TV2_C_ZAwt | 102 | wild type 12-5_1_TV2_C.ZA Nef |
| Pol_TV2_C_ZAopt | 103 | synthetic sequence of Pol |
| Pol_TV2_C_ZAwt | 104 | wild type 12-5_1_TV2_C.ZA of Pol |
| RevExon1_TV2_C_ZAopt | 105 | synthetic sequence of exon 1 of Rev |
| RevExon1_TV2_C_ZAwt | 106 | wild type 12-5_1_TV2_C.ZA of exon 1 of Rev |
| RevExon2_TV2_C_ZAopt | 107 | synthetic sequence of exon 2 of Rev |
| RevExon2_TV2_C_ZAwt | 108 | wild type 12-5_1_TV2_C.ZA of exon 2 of Rev |
| TatExon1_TV2_C_ZAopt | 109 | synthetic sequence of exon 1 of Tat |
| TatExon1_TV2_C_ZAwt | 110 | wild type 12-5_1_TV2_C.ZA of exon 1 of Tat |
| TatExon2_TV2_C_ZAopt | 111 | synthetic sequence of exon 2 of Tat |
| TatExon2_TV2_C_ZAwt | 112 | wild type 12-5_1_TV2_C.ZA of exon 2 of Tat |
| Vif_TV2_C_ZAopt | 113 | synthetic sequence of Vif |
| Vif_TV2_C_ZAwt | 114 | wild type 12-5_1_TV2_C.ZA of Vif |
| Vpr_TV2_C_ZAopt | 115 | synthetic sequence of Vpr |
| Vpr_TV2_C_ZAwt | 116 | wild type 12-5_1_TV2_C.ZA of Vpr |
| Vpu_TV2_C_ZAopt | 117 | synthetic sequence of Vpu |
| Vpu_TV2_C_ZAwt | 118 | wild type 12-5_1_TV2_C.ZA of Vpu | nucleotides of the present invention, and polycistronic polynucleotides produced using multiple polynuldleotides of the present invention.

EXAMPLE 2

Expression Assays for the Synthetic Coding Sequences

A. Type C HIV Coding Sequences

The wild-type Subtype C HIV coding (for example from AF110965, AF110967, AF110968, AF110975, as well as novel South African strains 8_5_TV1_C.ZA, 8_2_TV1_C.ZA and 12-5_1_TV2_C.ZA) sequences are cloned into expression vectors having the same features as the vectors into which the synthetic sequences are cloned.

Expression efficiencies for various vectors carrying the wild-type and synthetic sequences are evaluated as follows. Cells from several mammalian cell lines (293, RD, COS-7, and CHO; all obtained from the American Type Culture Collection, 10801 University Boulevard, Manassas, Va. 20110-2209) are transfected with 2 μg of DNA in transfection reagent LT1 (PanVera Corporation, 545 Science Dr., Madison, Wis.). The cells are incubated for 5 hours in reduced serum medium (Opti-MEM, Gibco-BRL, Gaithersburg, Md.). The medium is then replaced with normal medium as follows: 293 cells, IMDM, 10% fetal calf serum, 2% glutamine (BioWhittaker, Walkersville, Md.); RD and COS-7 cells, D-MEM, 10% fetal calf serum, 2% glutamine (Opti-MEM, Gibco-BRL, Gaithersburg, Md.); and CHO cells, Ham's F-12, 10% fetal calf serum, 2% glutamine (Opti-MEM, Gibco-BRL, Gaithersburg, Md.). The cells are incubated for either 48 or 60 hours. Cell lysates are collected as described below in Example 3. Supernatants are harvested and filtered through 0.45 μm syringe filters. Supernatants are evaluated using the using 96-well plates coated with a murine monoclonal antibody directed against HIV antigen, for example a Coulter p24-assay (Coulter Corporation, Hialeah, Fla., U.S.). The HIV-1 antigen binds to the coated wells. Biotinylated antibodies against HIV recognize the bound antigen. Conjugated strepavidin-horseradish peroxidase reacts with the biotin. Color develops from the reaction of peroxidase with TMB substrate. The reaction is terminated by addition of 4N $H_2SO_4$. The intensity of the color is directly proportional to the amount of HIV antigen in a sample.

Synthetic HIV Type C expression cassettes provides dramatic increases in production of their protein products, relative to the native (wild-type Subtype C) sequences, when expressed in a variety of cell lines.

B. Signal Peptide Leader Sequences

The ability of various leader sequences to drive expression was tested by transfecting cells with wild type or synthetic Env-encoding expression cassettes operably linked to different leader sequences and evaluating expression of Env polypeptide by ELISA or Western Blot. The amino acid and nucleotide sequence of various signal peptide leader sequences are shown in Table 4.

TABLE 4

| Leader | Amino acid sequence | DNA sequence |
|---|---|---|
| WTnative (8_2_TV1_C.ZA) | MRVMGTQKNCQQWWIWGI LGFWMLMIC (SEQ ID NO:136) | ATGAGAGTGATGGGGACACAGA AGAATTGTCAACAATGGTGGATA TGGGGCATCTTAGGCTTCTGGAT GCTAATGATTTGT (SEQ ID NO:137) |
| WTmod (8_2_TV1_C.ZA) | MRVMGTQKNCQQWWIWGI LGFWMLMIC (SEQ ID NO:136) | ATGCGCGTGATGGGCACCCAGAA GAACTGCCAGCAGTGGTGGATCT GGGGCATCCTGGGCTTCTGGATG CTGATGATCTGC (SEQ ID NO:138) |
| Tpa1 | MDAMKRGLCCVLLLCGAVFVSPS AS (SEQ ID NO:139) | ATGGATGCAATGAAGAGAGGGC TCTGCTGTGTGCTGCTGCTGTGTG GAGCAGTCTTCGTTTCGCCCAGC GCCAGC (SEQ ID NO:140) |
| Tpa2 | MDAMKRGLCCVLLLCGAVFVSPS (SEQ ID NO:141) | ATGGATGCAATGAAGAGAGGGC TCTGCTGTGTGCTGCTGCTGTGTG GAGCAGTCTTCGTTTCGCCCAGC (SEQ ID NO:142) |

293 cells were transiently transfected using standard methods with native and sequence-modified constructs encoding the gp120 and gp140 forms of the 8_2_TV1_C.ZA (TV1c8.2) envelope. Env protein was measure in cell lysates and supernatants using an in-house Env capture ELISA. Results are shown in Table 5 below and indicate that the wild-type signal peptide leader sequence of the TV1c8.2 can be used to efficiently express the encoded envelope protein to levels that are better or comparable to those observed using the heterologous tpa leader sequences. Furthermore, the TV1c8.2 leader works in its native or sequence-modified forms and can be used with native or sequence-modified env genes. All constructs were tested after cloning of the gene cassettes into the EcoR1 and Xho1 sites of the pCMVlink expression vector.

TABLE 5

| TV1c8.2 construct | Supernatant (ng) | Lysate (ng) | Total (ng) |
|---|---|---|---|
| gp140nat.wtL | 532 | 149 | 681 |
| gp140nat.tpa1 | 250 | 20 | 270 |
| gp140nat.tpa2 | 192 | 34 | 226 |
| gp120mod.wtLmod | 6186 | 4576 | 10762 |
| gp120mod.tpa1 | 6932 | 3808 | 10740 |

TABLE 5-continued

| TV1c8.2 construct | Supernatant (ng) | Lysate (ng) | Total (ng) |
|---|---|---|---|
| gp120mod.wtLnat | 6680 | 4174 | 10854 |
| gp140mod.wtLmod | 1844 | 8507 | 10351 |
| gp140mod.tpa1 | 1854 | 2925 | 4779 |
| gp140mod.wtLnat | 1532 | 3015 | 4547 |

The sequence-modified TV1c8.2 envelope variant gene cassettes were subcloned into a Chiron pCMV expression vector for the derivation of stable mammalian cell lines. Stable CHO cell lines expressing the TV1c8.2 envelope proteins were derived using standard methods of transfection, methotrexate amplification, and screening. These cell lines were found to secrete levels of envelope protein that were comparable to those observed for proteins expressed using the tpa leader sequences. Representative results are shown in Table 6 for two cell line clone expressing the TV1c8.2 gp120; they are compared to two reference clones expressing SF162 subtype B gp120 derived in a similar fashion but using the tpa leader. Protein concentrations were determined following densitometry of scanned gels of semi-purified proteins. Standard curves were generated using a highly purified and well-characterized preparation of SF2 gp120 protein and the concentrations of the test proteins were determined.

TABLE 6

| CHO cell line | Clone # | Expression (ng/ml) |
|---|---|---|
| gp120 SF162 | Clone 65 | 921 |
| | Clone 71 | 972 |
| gp120TV1.C8.2 | Clone 159 | 1977 |
| | Clone 210 | 1920 |

The results were also confirmed by Western Blot Analysis, essentially as described in Example 3.

EXAMPLE 3

Western Blot Analysis of Expression

A. HIV Type C Coding Sequences

Human 293 cells are transfected as described in Example 2 with pCMV-based vectors containing native or synthetic HIV Type C expression cassettes. Cells are cultivated for 60 hours post-transfection. Supernatants are prepared as described. Cell lysates are prepared as follows. The cells are washed once with phosphate-buffered saline, lysed with detergent [1% NP40 (Sigma Chemical Co., St. Louis, Mo.) in 0.1 M Tris-HCl, pH 7.5], and the lysate transferred into fresh tubes. SDS-polyacrylamide gels (pre-cast 8-16%; Novex, San Diego, Calif.) are loaded with 20 μl of supernatant or 12.5 μl of cell lysate. A protein standard is also loaded (5 μl, broad size range standard; BioRad Laboratories, Hercules, Calif.). Electrophoresis is carried out and the proteins are transferred using a BioRad Transfer Chamber (BioRad Laboratories, Hercules, Calif.) to Immobilon P membranes (Millipore Corp., Bedford, Mass.) using the transfer buffer recommended by the manufacturer (Millipore), where the transfer is performed at 100 volts for 90 minutes. The membranes are exposed to HIV-1-positive human patient serum and immunostained using o-phenylenediamine dihydrochloride (OPD; Sigma).

Immunoblotting analysis shows that cells containing the synthetic expression cassette produce the expected protein at higher per-cell concentrations than cells containing the native expression cassette. The proteins are seen in both cell lysates and supernatants. The levels of production are significantly higher in cell supernatants for cells transfected with the synthetic expression cassettes of the present invention.

In addition, supernatants from the transfected 293 cells are fractionated on sucrose gradients. Aliquots of the supernatant are transferred to Polyclear™ ultra-centrifuge tubes (Beckman Instruments, Columbia, Md.), under-laid with a solution of 20% (wt/wt) sucrose, and subjected to 2 hours centrifugation at 28,000 rpm in a Beckman SW28 rotor. The resulting pellet is suspended in PBS and layered onto a 20-60% (wt/wt) sucrose gradient and subjected to 2 hours centrifugation at 40,000 rpm in a Beckman SW41ti rotor.

The gradient is then fractionated into approximately 10×1 ml aliquots (starting at the top, 20%-end, of the gradient). Samples are taken from fractions 1-9 and are electrophoresed on 8-16% SDS polyacrylamide gels. The supernatants from 293/synthetic cells give much stronger bands than supernatants from 293/native cells.

EXAMPLE 4

In Vivo Immunogenicity of Synthetic HIV Type C Expression Cassettes

A. Immunization

To evaluate the possibly improved immunogenicity of the synthetic HIV Type C expression cassettes, a mouse study is performed. The plasmid DNA, pCMVKM2 carrying the synthetic Gag expression cassette, is diluted to the following final concentrations in a total injection volume of 100 μl: 20 μg, 2 μg, 0.2 μg, 0.02 and 0.002 μg. To overcome possible negative dilution effects of the diluted DNA, the total DNA concentration in each sample is brought up to 20 μg using the vector (pCMVKM2) alone. As a control, plasmid DNA of the native Gag expression cassette is handled in the same manner. Twelve groups of four to ten Balb/c mice (Charles River, Boston, Mass.) are intramuscularly immunized (50 μl per leg, intramuscular injection into the tibialis anterior) according to the schedule in Table 1.

TABLE 1

| Group | Gag or Env Expression Cassette | Concentration of Gag or Env plasmid DNA (μg) | Immunized at time (weeks): |
|---|---|---|---|
| 1 | Synthetic | 20 | 0[1], 4 |
| 2 | Synthetic | 2 | 0, 4 |
| 3 | Synthetic | 0.2 | 0, 4 |
| 4 | Synthetic | 0.02 | 0, 4 |
| 5 | Synthetic | 0.002 | 0, 4 |
| 6 | Synthetic | 20 | 0 |
| 7 | Synthetic | 2 | 0 |
| 8 | Synthetic | 0.2 | 0 |
| 9 | Synthetic | 0.02 | 0 |
| 10 | Synthetic | 0.002 | 0 |
| 11 | Native | 20 | 0, 4 |
| 12 | Native | 2 | 0, 4 |
| 13 | Native | 0.2 | 0, 4 |
| 14 | Native | 0.02 | 0, 4 |
| 15 | Native | 0.002 | 0, 4 |
| 16 | Native | 20 | 0 |
| 17 | Native | 2 | 0 |
| 18 | Native | 0.2 | 0 |
| 19 | Native | 0.02 | 0 |
| 20 | Native | 0.002 | 0 |

[1]initial immunization at "week 0"

Groups 1-5 and 11-15 are bled at week 0 (before immunization), week 4, week 6, week 8, and week 12. Groups 6-20 and 16-20 are bled at week 0 (before immunization) and at week 4.

B. Humoral Immune Response

The humoral immune response is checked with an anti-HIV antibody ELISAs (enzyme-linked immunosorbent assays) of the mice sera 0 and 4 weeks post immunization (groups 5-12) and, in addition, 6 and 8 weeks post immunization, respectively, 2 and 4 weeks post second immunization (groups 1-4).

The antibody titers of the sera are determined by using the appropriate anti-HIV polypeptide (e.g., anti-Pol, anti-Gag, anti-Env, anti-Vif, anti-Vpu, etc.) antibody ELISA. Briefly, sera from immunized mice are screened for antibodies directed against the HIV proteins (e.g., p55 Gag protein, an Env protein, e.g., gp160 or gp120 or a Pol protein, e.g., p6, prot or RT, etc). ELISA microtiter plates are coated with 0.2 μg of HIV protein per well overnight and washed four times; subsequently, blocking is done with PBS-0.2% Tween (Sigma) for 2 hours. After removal of the blocking solution, 100 μl of diluted mouse serum is added. Sera are tested at 1/25 dilutions and by serial 3-fold dilutions, thereafter. Microtiter plates are washed four times and incubated with a secondary, peroxidase-coupled anti-mouse IgG antibody (Pierce, Rockford, Ill.). ELISA plates are washed and 100 μl of 3, 3', 5, 5'-tetramethyl benzidine (TMB; Pierce) is added per well. The optical density of each well is measured after 15 minutes. The titers reported are the reciprocal of the dilution of serum that gave a half-maximum optical density (O.D.).

Synthetic expression cassettes will provide a clear improvement of immunogenicity relative to the native expression cassettes.

C. Cellular Immune Response

The frequency of specific cytotoxic T-lymphocytes (CTL) is evaluated by a standard chromium release assay of peptide pulsed mouse (Balb/c, CB6F1 and/or C3H) CD4 cells. HIV polypeptide (e.g., Pol, Gag or Env) expressing vaccinia virus infected CD-8 cells are used as a positive control. Briefly, spleen cells (Effector cells, E) are obtained from the mice immunized as described above are cultured, restimulated, and assayed for CTL activity against Gag peptide-pulsed target cells as described (Doe, B., and Walker, C. M., *AIDS* 10(7): 793-794, 1996). Cytotoxic activity is measured in a standard $^{51}$Cr release assay. Target (T) cells are cultured with effector (E) cells at various E:T ratios for 4 hours and the average cpm from duplicate wells are used to calculate percent specific $^{51}$Cr release.

Cytotoxic T-cell (CTL) activity is measured in splenocytes recovered from the mice immunized with HIV Gag or Env DNA. Effector cells from the Gag or Env DNA-immunized animals exhibit specific lysis of HIV polypeptide-pulsed SV-BALB (MHC matched) targets cells, indicative of a CTL response. Target cells that are peptide-pulsed and derived from an MHC-unmatched mouse strain (MC57) are not lysed.

Thus, synthetic expression cassettes exhibit increased potency for induction of cytotoxic T-lymphocyte (CTL) responses by DNA immunization.

EXAMPLE 5

DNA-Immunization of Non-Human Primates Using a Synthetic HIV Type C Expression Cassette Non-human primates are immunized multiple times (e.g., weeks 0, 4, 8 and 24) intradermally, mucosally or bilaterally, intramuscular, into the quadriceps using various doses (e.g., 1-5 mg) and various combinations of synthetic HIV Type C plasmids. The animals are bled two weeks after each immunization and ELISA is performed with isolated plasma. The ELISA is performed essentially as described in Example 4 except the second antibody-conjugate is an anti-human IgG, g-chain specific, peroxidase conjugate (Sigma Chemical Co., St. Louis, Md. 63178) used at a dilution of 1:500. Fifty μg/ml yeast extract is added to the dilutions of plasma samples and antibody conjugate to reduce non-specific background due to preexisting yeast antibodies in the non-human primates.

Further, lymphoproliferative responses to antigen can also be evaluated post-immunization, indicative of induction of T-helper cell functions.

Synthetic plasmid DNA are expected to be immunogenic in non-human primates.

EXAMPLE 6

In Vitro Expression of Recombinant Sindbis RNA and DNA Containing the Synthetic HIV Type C Expression Cassette To evaluate the expression efficiency of the synthetic Pol, Env and Gag expression cassette in Alphavirus vectors, the selected synthetic expression cassette is subcloned into both plasmid DNA-based and recombinant vector particle-based Sindbis virus vectors. Specifically, a cDNA vector construct for in vitro transcription of Sindbis virus RNA vector replicons (pRSIN-luc; Dubensky, et al., *J Virol.* 70:508-519, 1996) is modified to contain a PmeI site for plasmid linearization and a polylinker for insertion of heterologous genes. A polylinker is generated using two oligonucleotides that contain the sites XhoI, PmlI, ApaI, NarI, XbaI, and NotI (XPANXNF, and XPANXNR).

The plasmid pRSIN-luc (Dubensky et al., supra) is digested with XhoI and NotI to remove the luciferase gene insert, blunt-ended using Klenow and dNTPs, and purified from an agarose get using GeneCleanII (Bio101, Vista, Calif.). The oligonucleotides are annealed to each other and ligated into the plasmid. The resulting construct is digested with NotI and SacI to remove the minimal Sindbis 3'-end sequence and $A_{40}$ tract, and ligated with an approximately 0.4 kbp fragment from PKSSIN1-BV (WO 97/38087). This 0.4 kbp fragment is obtained by digestion of pKSSIN1-BV with NotI and SacI, and purification after size fractionation from an agarose gel. The fragment contains the complete Sindbis virus 3'-end, an $A_{40}$ tract and a PmeI site for linearization. This new vector construct is designated SINBVE.

The synthetic HIV coding sequences are obtained from the parental plasmid by digestion with EcoRI, blunt-ending with Klenow and dNTPs, purification with GeneCleanII, digestion with SalI, size fractionation on an agarose gel, and purification from the agarose gel using GeneCleanII. The synthetic HIV polypeptide-coding fragment is ligated into the SINBVE vector that is digested with XhoI and PmtI. The resulting vector is purified using GeneCleanII and is designated SINBVGag. Vector RNA replicons may be transcribed in vitro (Dubensky et al., supra) from SINBVGag and used directly for transfection of cells. Alternatively, the replicons may be packaged into recombinant vector particles by co-transfection with defective helper RNAs or using an alphavirus packaging cell line.

The DNA-based Sindbis virus vector pDCMVSIN-beta-gal (Dubensky, et al., *J Virol.* 70:508-519, 1996) is digested with SalI and XbaI, to remove the beta-galactosidase gene insert, and purified using GeneCleanII after agarose gel size fractionation. The HIV Gag or Env gene is inserted into the pDCMVSIN-beta-gal by digestion of SINBVGag with SalI and XhoI, purification using GeneCleanII of the Gag-containing fragment after agarose gel size fractionation, and ligation. The resulting construct is designated pDSIN-Gag, and may be used directly for in vivo administration or formulated using any of the methods described herein.

BHK and 293 cells are transfected with recombinant Sindbis RNA and DNA, respectively. The supernatants and cell lysates are tested with the Coulter capture ELISA (Example 2).

BHK cells are transfected by electroporation with recombinant Sindbis RNA.

293 cells are transfected using LT-1 (Example 2) with recombinant Sindbis DNA. Synthetic Gag- and/or Env-containing plasmids are used as positive controls. Supernatants and lysates are collected 48 h post transfection.

Type C HIV proteins can be efficiently expressed from both DNA and RNA-based Sindbis vector systems using the synthetic expression cassettes.

EXAMPLE 7

In Vivo Immunogenicity of Recombinant Sindbis Replicon Vectors Containing Synthetic Pol, Gag and/or Env Expression Cassettes A. Immunization To evaluate the immunogenicity of recombinant synthetic HIV Type C expression cassettes in Sindbis replicons, a mouse study is performed. The Sindbis virus DNA vector carrying synthetic expression cassettes (Example 6), is diluted to the following final concentrations in a total injection volume of 100 µl: 20 µg, 2 µg, 0.2 µg, 0.02 and 0.002 µg. To overcome possible negative dilution effects of the diluted DNA, the total DNA concentration in each sample is brought up to 20 µg using the Sindbis replicon vector DNA alone. Twelve groups of four to ten Balb/c mice (Charles River, Boston, Mass.) are intramuscularly immunized (50 µl per leg, intramuscular injection into the tibialis anterior) according to the schedule in Table 2. Alternatively, Sindbis viral particles are prepared at the following doses: $10^3$ pfu, $10^5$ pfu and $10^7$ pfu in 100 µl, as shown in Table 3. Sindbis HIV polypeptide particle preparations are administered to mice using intramuscular and subcutaneous routes (50 µl per site).

TABLE 2

| Group | Gag or Env Expression Cassette | Concentration of Gag or Env DNA (µg) | Immunized at time (weeks): |
|---|---|---|---|
| 1 | Synthetic | 20 | 0[1], 4 |
| 2 | Synthetic | 2 | 0, 4 |
| 3 | Synthetic | 0.2 | 0, 4 |
| 4 | Synthetic | 0.02 | 0, 4 |
| 5 | Synthetic | 0.002 | 0, 4 |
| 6 | Synthetic | 20 | 0 |
| 7 | Synthetic | 2 | 0 |
| 8 | Synthetic | 0.2 | 0 |
| 9 | Synthetic | 0.02 | 0 |
| 10 | Synthetic | 0.002 | 0 |

[1]initial immunization at "week 0"

TABLE 3

| Group | Gag or Env sequence | Concentration of viral particle (pfu) | Immunized at time (weeks): |
|---|---|---|---|
| 1 | Synthetic | $10^3$ | 0[1], 4 |
| 2 | Synthetic | $10^5$ | 0, 4 |
| 3 | Synthetic | $10^7$ | 0, 4 |
| 8 | Synthetic | $10^3$ | 0 |
| 9 | Synthetic | $10^5$ | 0 |
| 10 | Synthetic | $10^7$ | 0 |

[1]initial immunization at "week 0"

Groups are bled and assessment of both humoral and cellular (e.g., frequency of specific CTLs) is performed, essentially as described in Example 4.

EXAMPLE 8

Identification and Sequencing of a Novel HIV Type C Variants

A full-length clone, called 8_5_TV1_C.ZA, encoding an HIV Type C was isolated and sequenced. Briefly, genomic DNA from HIV-1 subtype C infected South African patients was isolated from PBMC (peripheral blood mononuclear cells) by alkaline lysis and anion-exchange columns (Quiagen). To get the genome of full-length clones two halves were amplified, that could later be joined together in frame within the Pol region using an unique Sal 1 site in both fragments. For the amplification, 200-800 ng of genomic DNA were added to the buffer and enzyme mix of the Expand Long Template PCR System after the protocol of the manufacturer (Boehringer Mannheim). The primer were designed after alignments of known full length sequences. For the 5' half a primer mix of 2 forward primers containing either thymidine (S1FCSacTA 5'-GTTTCTTGAGCTCTG-GAAGGGTTAATTTAC TCCAAGAA-3', SEQ ID NO:38) or cytosine on position 20 (S1FTSacTA 5'-GTTTCT-TGAGCTCTGGAAGGGTTAATTTACTCTAAGAA, SEQ ID NO:39) plus Sal 1 site, were used. The reverse primer were also a mix of two primers with either thymidine or cytosine on position 13 (S145RTSalTA 5'-GTTTCTTGTCGACTTGTC-CATGTATGGCTTCCCC T-3', SEQ ID NO:40 and S145RCSalTA 5'-GTTTCTTGTCGACTTGTCCATG-CATGGCTTCCCT-3'SEQ ID NO:41) and contained a Sal 1 site. The forward primer for the 3'half was also a mixture of two primers (S245Basalt 5'-GTTTCTTGTCGACTG-TAGTCCAGGaATATGGCAAT TAG-3'SEQ ID NO:42 and S245Fuscata 5'-GTTTCTTGTCGACTGTAGTCCAGG-gATATG GCAA TTAG-3'SEQ ID NO:43) with Sal 1 site and adenine or guanine on position 12. The reverse primer had a Not 1 site (S2_FullNotTA 5'-GTTTCTTGCGGCCGCT-GCTAGAGATTTTCCACACTACCA-3' SEQ ID NO:44). After amplification the PCR products were purified using a 1% agarose gel and cloned into the per-XL-TOPO vector via TA cloning (Invitrogen). Colonies were checked by restriction analysis and sequence verified. For the full length sequence the sequences of the 5'- and 3'half were combined. The sequence is shown in SEQ ID NO:33. Furthermore, important domains are shown in Table A.

Another clone, designated 12-5_1_TV2_C.ZA was also sequenced and is shown in SEQ ID NO:45. The domains can be readily determined in view of the teachings of the specification, for example by aligning the sequence to those shown in Table A to find the corresponding regions in clone 12-5_1_TV2_C.ZA.

As described above (Example 1, Table C), synthetic expression cassettes were generated using one or more polynucleotide sequences obtained from 8_5_TV1_C.ZA or 12-5_1_TV2_C.ZA.

The polynucleotides described herein have all been deposited at Chiron Corporation, Emeryville, Calif.

Although preferred embodiments of the subject invention have been described in some detail, it is understood that obvious variations can be made without departing from the spirit and the scope of the invention as defined by the appended claims.

The invention claimed is:

1. An expression cassette comprising a polynucleotide comprising a sequence encoding an Env polypeptide and having at least 90% identity to the full-length sequence of the nucleotide sequence SEQ ID NO:120.

2. A method of generating an immune response in a subject, comprising introducing an expression cassette comprising a polynucleotide comprising a sequence encoding an Env polypeptide and having at least 90% identity to the full-length sequence of the nucleotide sequence SEQ ID NO:120 into said subject under conditions that are compatible with expression of said expression cassette in said subject.

3. The method of claim 2, wherein said expression cassette is introduced using a gene delivery vector.

4. The method of claim 3, wherein the gene delivery vector is a non-viral vector.

5. The method of claim 3, wherein said gene delivery vector is a viral vector.

6. The method of claim 3, wherein said gene delivery vector is selected from the group consisting of an adenoviral vector, a vaccinia viral vector, an AAV vector, a retroviral vector, a lentiviral vector and an alphaviral vector.

7. The method of claim 6, wherein said gene delivery vector is a Sindbis-virus derived vector.

8. The method of claim 6, wherein said gene delivery vector is a cDNA vector.

9. The method of claim 6, wherein said gene delivery vector is a eukaryotic layered viral initiation system (ELVIS).

10. The method of claim 3, wherein said composition is delivered using a particulate carrier.

11. The method of claim 3, wherein said composition is coated on a gold or tungsten particle and said coated particle is delivered to said subject using a gene gun.

12. The method of claim 3, wherein said composition is encapsulated in a liposome preparation.

13. The method of claim 3, wherein said subject is a mammal.

14. The method of claim 13, wherein said mammal is a human.

15. The expression cassette of claim 1 wherein the sequence has at least 95% identity to the full-length sequence of the nucleotide sequence SEQ ID NO:120.

16. The expression cassette of claim 1 wherein the sequence has at least 98% identity to the full-length sequence of the nucleotide sequence SEQ ID NO:120.

17. The expression cassette of claim 1 wherein the sequence comprises the nucleotide sequence SEQ ID NO:120.

18. The method of claim 2 wherein the sequence has at least 95% identity to the full-length sequence of the nucleotide sequence SEQ ID NO:120.

19. The method of claim 2 wherein the sequence has at least 98% identity to the full-length sequence of the nucleotide sequence SEQ ID NO:120.

20. The method of claim 2 wherein the sequence comprises the nucleotide sequence SEQ ID NO:120.

\* \* \* \* \*

SEQUENCE LISTING

```
<160> NUMBER OF SEQ ID NOS: 150

<210> SEQ ID NO 1
<211> LENGTH: 60
<212> TYPE: DNA
<213> ORGANISM: Human immunodeficiency virus

<400> SEQUENCE: 1
gacatcaagc agggccccaa ggagcccttc cgcgactacg tggaccgctt cttcaagacc      60

<210> SEQ ID NO 2
<211> LENGTH: 60
<212> TYPE: DNA
<213> ORGANISM: Human immunodeficiency virus

<400> SEQUENCE: 2
gacatccgcc agggccccaa ggagcccttc cgcgactacg tggaccgctt cttcaagacc      60

<210> SEQ ID NO 3
<211> LENGTH: 1479
<212> TYPE: DNA
<213> ORGANISM: Artificial
<220> FEATURE:
<223> OTHER INFORMATION: synthetic Gag of HIV strain AF110965

<400> SEQUENCE: 3
atgggcgccc gcgccagcat cctgcgcggc ggcaagctgg acgcctggga gcgcatccgc      60
ctgcgccccg gcggcaagaa gtgctacatg atgaagcacc tggtgtgggc cagccgcgag     120
ctggagaagt tcgccctgaa ccccggcctg ctggagacca gcgagggctg caagcagatc     180
atccgccagc tgcaccccgc cctgcagacc ggcagcgagg agctgaagag cctgttcaac     240
accgtggcca ccctgtactg cgtgcacgag aagatcgagg tccgcgacac caaggaggcc     300
ctggacaaga tcgaggagga gcagaacaag tgccagcaga agatccagca ggccgaggcc     360
gccgacaagg gcaaggtgag ccagaactac cccatcgtgc agaacctgca gggccagatg     420
gtgcaccagg ccatcagccc ccgcaccctg aacgcctggg tgaaggtgat cgaggagaag     480
gccttcagcc ccgaggtgat ccccatgttc accgccctga gcgagggcgc caccccccag     540
gacctgaaca cgatgttgaa caccgtgggc ggccaccagg ccgccatgca gatgctgaag     600
gacaccatca acgaggaggc cgccgagtgg gaccgcgtgc accccgtgca cgccggcccc     660
atcgcccccg gccagatgcg cgagccccgc ggcagcgaca tcgccggcac caccagcacc     720
ctgcaggagc agatcgcctg gatgaccagc aacccccca tccccgtggg cgacatctac      780
aagcggtgga tcatcctggg cctgaacaag atcgtgcgga tgtacagccc cgtgagcatc     840
ctggacatca agcagggccc caaggagccc ttccgcgact acgtggaccg cttcttcaag     900
accctgcgcg ccgagcagag cacccaggag gtgaagaact ggatgaccga caccctgctg     960
gtgcagaacg ccaaccccga ctgcaagacc atcctgcgcg ctctcggccc cggcgccagc    1020
ctggaggaga tgatgaccgc ctgccagggc gtgggcggcc ccagccacaa ggcccgcgtg    1080
```

-continued

```
ctggccgagg cgatgagcca ggccaacacc agcgtgatga tgcagaagag caacttcaag   1140
ggcccccggc gcatcgtcaa gtgcttcaac tgcggcaagg agggccacat cgcccgcaac   1200
tgccgcgccc cccgcaagaa gggctgctgg aagtgcggca aggagggcca ccagatgaag   1260
gactgcaccg agcgccaggc caacttcctg ggcaagatct ggcccagcca agggccgc    1320 cccggcaact tcctgcagag ccgccccgag cccaccgccc ccccgccga gcttccgc     1380 ttcgaggaga ccaccccggg ccagaagcag gagagcaagg accgcgagac cctgaccagc   1440
ctgaagagcc tgttcggcaa cgacccctg agccagtaa                          1479

<210> SEQ ID NO 4
<211> LENGTH: 1509
<212> TYPE: DNA
<213> ORGANISM: Artificial
<220> FEATURE:
<223> OTHER INFORMATION: synthetic Gag of HIV strain AF110967

<400> SEQUENCE: 4
atgggcgccc gcgccagcat cctgcgcggc gagaagctgg acaagtggga aagatccgc     60 ctgcgccccg gcggcaagaa gcactacatg ctgaagcacc tggtgtgggc cagccgcgag   120
ctggagggct cgccctgaa ccccggcctg ctggagaccg ccgagggctg caagcagatc    180
atgaagcagc tgcagcccgc cctgcagacc ggcaccgagg agctgcgcag cctgtacaac   240
accgtggcca ccctgtactg cgtgcacgcc ggcatcgagg tccgcgacac caaggaggcc   300
ctggacaaga tcgaggagga gcagaacaag tcccagcaga gacccagca ggccaaggag    360 gccgacggca aggtgagcca gaactacccc atcgtgcaga acctgcaggg ccagatggtg   420
caccaggcca tcagcccccg caccctgaac gcctgggtga aggtgatcga ggagaaggcc   480
ttcagccccg aggtgatccc catgttcacc gccctgagcg agggcgccac ccccaggac    540 ctgaacacga tgttgaacac cgtgggcggc caccaggccg ccatgcagat gctgaaggac   600
accatcaacg aggaggccgc cgagtgggac cgcctgcacc ccgtgcaggc cggccccgtg   660
gccccccggc agatgcgcga cccccgcggc agcgacatcg ccggcgccac cagcacctg    720 caggagcaga tcgcctggat gaccagcaac ccccccgtgc ccgtgggcga catctacaag   780
cggtggatca tcctgggcct gaacaagatc gtgcggatgt acagccccgt gagcatcctg   840
gacatccgcc agggccccaa ggagcccttc cgcgactacg tggaccgctt cttcaagacc   900
ctgcgcgccg agcaggccac ccaggacgtg aagaactgga tgaccgagac cctgctggtg   960
cagaacgcca accccgactg caagaccatc ctgcgcgctc tcggccccgg cgccaccctg   1020
gaggagatga tgaccgcctg ccagggcgtg ggcggccccg ccacaaggc ccgcgtgctg   1080 gccgaggcga tgagccaggc caacagcgtg aacatcatga tgcagaagag caacttcaag   1140
ggcccccggc gcaacgtcaa gtgcttcaac tgcggcaagg agggccacat cgccaagaac   1200
tgccgcgccc cccgcaagaa gggctgctgg aagtgcggca aggagggcca ccagatgaag   1260
gactgcaccg agcgccaggc caacttcctg ggcaagatct ggcccagcca agggccgc    1320 cccggcaact tcctgcagaa ccgcagcgag cccgccgccc ccaccgtgcc caccgccccc   1380
cccgccgaga gcttccgctt cgaggagacc accccgccc caagcagga gcccaaggac   1440 cgcgagcct accgcgagcc cctgaccgcc ctgcgcagcc tgttcggcag cggccccctg   1500
agccagtaa                                                          1509

<210> SEQ ID NO 5
<211> LENGTH: 141
```

```
<212> TYPE: DNA
<213> ORGANISM: Artificial
<220> FEATURE:
<223> OTHER INFORMATION: Env common region of HIV strain AF110968

<400> SEQUENCE: 5
accatcacca tcacctgccg catcaagcag atcatcaaca tgtggcagaa ggtgggccgc      60
gccatgtacg ccccccccat cgccggcaac ctgacctgcg agagcaacat caccggcctg     120
ctgctgaccc gcgacggcgg c                                                141

<210> SEQ ID NO 6
<211> LENGTH: 1431
<212> TYPE: DNA
<213> ORGANISM: Artificial
<220> FEATURE:
<223> OTHER INFORMATION: synthetic gp120 coding region of HIV strain
      AF110968

<400> SEQUENCE: 6
agcgtggtgg gcaacctgtg ggtgaccgtg tactacggcg tgcccgtgtg aaggaggcc       60 aagaccaccc tgttctgcac cagcgacgcc aaggcctacg agaccgaggt gcacaacgtg     120
tgggccaccc acgcctgcgt gcccaccgac cccaaccccc aggagatcgt gctggagaac     180
gtgaccgaga acttcaacat gtggaagaac gacatggtgg accagatgca cgaggacatc     240
atcagcctgt gggaccagag cctgaagccc tgcgtgaagc tgaccccccct gtgcgtgacc     300 ctgaagtgcc gcaacgtgaa cgccaccaac aacatcaaca gcatgatcga caacagcaac     360
aagggcgaga tgaagaactg cagcttcaac gtgaccaccg agctgcgcga ccgcaagcag     420
gaggtgcacg ccctgttcta ccgcctggac gtggtgcccc tgcagggcaa caacagcaac     480
gagtaccgcc tgatcaactg caacaccagc gccatcaccc aggcctgccc caaggtgagc     540
ttcgacccca tccccatcca ctactgcacc ccgccggct acgccatcct gaagtgcaac     600
aaccagacct tcaacggcac cggcccctgc aacaacgtga gcagcgtgca gtgcgcccac     660
ggcatcaagc ccgtggtgag cacccagctg ctgctgaacg gcagcctggc caagggcgag     720
atcatcatcc gcagcgagaa cctggccaac aacgccaaga tcatcatcgt gcagctgaac     780
aagcccgtga gatcgtgtg cgtgcgcccc aacaacaaca cccgcaagag cgtgcgcatc     840
ggccccggcc agaccttcta cgccaccggc gagatcatcg gcgacatccg ccaggcctac     900
tgcatcatca acaagaccga gtggaacagc accctgcagg gcgtgagcaa gaagctggag     960
gagcacttca gcaagaaggc catcaagttc gagcccagca gcggcggcga cctggagatc    1020
accacccaca gcttcaactg ccgcggcgag ttcttctact gcgacaccag ccagctgttc    1080
aacagcacct acagcccag cttcaacggc accgagaaca agctgaacgg caccatcacc    1140
atcacctgcc gcatcaagca gatcatcaac atgtggcaga aggtgggccg cgccatgtac    1200 gccccccca tcgccggcaa cctgacctgc gagagcaaca tcaccggcct gctgctgacc    1260
cgcgacggcg gcaagaccgg ccccaacgac accgagatct ccgccccgg cggcggcgac    1320 atgcgcgaca ctggcgcaa cgagctgtac aagtacaagg tggtggagat caagccctg    1380 ggcgtggccc ccaccgaggc caagcgccgc gtggtggagc gcgagaagcg c             1431

<210> SEQ ID NO 7
<211> LENGTH: 1944
<212> TYPE: DNA
<213> ORGANISM: Artificial
<220> FEATURE:
<223> OTHER INFORMATION: synthetic gp140 coding

AF110968

<400> SEQUENCE: 7

```
agcgtggtgg gcaacctgtg ggtgaccgtg tactacggcg tgcccgtgtg gaaggaggcc      60
aagaccaccc tgttctgcac cagcgacgcc aaggcctacg agaccgaggt gcacaacgtg     120
tgggccaccc acgcctgcgt gcccaccgac cccaaccccc aggagatcgt gctggagaac     180
gtgaccgaga acttcaacat gtggaagaac gacatggtgg accagatgca cgaggacatc     240
atcagcctgt gggaccagag cctgaagccc tgcgtgaagc tgacccccct gtgcgtgacc     300
ctgaagtgcc gcaacgtgaa cgccaccaac aacatcaaca gcatgatcga caacagcaac     360
aagggcgaga tgaagaactg cagcttcaac gtgaccaccg agctgcgcga ccgcaagcag     420
gaggtgcacg ccctgttcta ccgcctggac gtggtgcccc tgcagggcaa caacagcaac     480
gagtaccgcc tgatcaactg caacaccagc gccatcaccc aggcctgccc caaggtgagc     540
ttcgacccca tccccatcca ctactgcacc cccgccggct acgccatcct gaagtgcaac     600
aaccagacct tcaacggcac cggccctgc aacaacgtga gcagcgtgca gtgcgcccac     660
ggcatcaagc ccgtggtgag cacccagctg ctgctgaacg gcagcctggc caagggcgag     720
atcatcatcc gcagcgagaa cctggccaac aacgccaaga tcatcatcgt gcagctgaac     780
aagcccgtga gatcgtgtg cgtgcgcccc aacaacaaca cccgcaagag cgtgcgcatc     840
ggccccggcc agaccttcta cgccaccggc gagatcatcg gcgacatccg ccaggcctac     900
tgcatcatca caagaccga gtggaacagc accctgcagg cgtgagcaa gaagctggag     960
gagcacttca gcaagaaggc catcaagttc gagcccagca gcggcggcga cctggagatc    1020
accacccaca gcttcaactg ccgcggcgag ttcttctact gcgacaccag ccagctgttc    1080
aacagcacct acagccccag cttcaacggc accgagaaca agctgaacgg caccatcacc    1140
atcacctgcc gcatcaagca gatcatcaac atgtggcaga aggtgggccg cgccatgtac    1200
gcccccccca tcgccggcaa cctgacctgc gagagcaaca tcaccggcct gctgctgacc    1260
cgcgacggcg gcaagaccgg ccccaacgac accgagatct ccgcccccgg cggcggcgac    1320
atgcgcgaca actggcgcaa cgagctgtac aagtacaagg tggtggagat caagcccctg    1380
ggcgtggccc ccaccgaggc caagcgccgc gtggtggagc gcgagaagcg cgccgtgggc    1440
atcggcgccg tgttcctggg cttcctgggc gccgccggca gcaccatggg cgccgccagc    1500
atcaccctga ccgtgcaggc ccgcctgctg ctgagcggca tcgtgcagca gcagaacaac    1560
ctgctgcgcg ccatcgaggc ccagcagcac ctgctgcagc tgaccgtgtg gggcatcaag    1620
cagctgcaga cccgcatcct ggccgtggag cgctacctga aggaccagca gctgctgggc    1680
atctggggct gcagcggcaa gctgatctgc accaccgccg tgccctggaa cagcagctgg    1740
agcaaccgca gccacgacga gatctgggac aacatgacct ggatgcagtg gaccgcgag    1800
atcaacaact acaccgacac catctaccgc ctgctgagg agagccagaa ccagcaggag    1860
aagaacgaga aggacctgct ggccctggac agctggcaga acctgtggaa ctggttcagc    1920
atcaccaact ggctgtggta catc                                           1944
```

<210> SEQ ID NO 8
<211> LENGTH: 2466
<212> TYPE: DNA
<213> ORGANISM: Artificial
<220> FEATURE:
<223> OTHER INFORMATION: synthetic gp160 coding region of HIV strain AF110968

```
<400> SEQUENCE: 8
agcgtggtgg gcaacctgtg ggtgaccgtg tactacggcg tgcccgtgtg aaggaggcc      60 aagaccaccc tgttctgcac cagcgacgcc aaggcctacg agaccgaggt gcacaacgtg     120
tgggccaccc acgcctgcgt gcccaccgac cccaacccc aggagatcgt gctggagaac      180
gtgaccgaga acttcaacat gtggaagaac gacatggtgg accagatgca cgaggacatc     240
atcagcctgt gggaccagag cctgaagccc tgcgtgaagc tgacccccct gtgcgtgacc     300
ctgaagtgcc gcaacgtgaa cgccaccaac aacatcaaca gcatgatcga caacagcaac     360
aagggcgaga tgaagaactg cagcttcaac gtgaccaccg agctgcgcga ccgcaagcag     420
gaggtgcacg ccctgttcta ccgcctggac gtggtgcccc tgcagggcaa caacagcaac     480
gagtaccgcc tgatcaactg caacaccagc gccatcaccc aggcctgccc caaggtgagc     540
ttcgacccca tccccatcca ctactgcacc cccgccggct acgccatcct gaagtgcaac     600
aaccagacct tcaacggcac cggcccctgc aacaacgtga gcagcgtgca gtgcgcccac     660
ggcatcaagc ccgtggtgag cacccagctg ctgctgaacg gcagcctggc caagggcgag     720
atcatcatcc gcagcgagaa cctggccaac aacgccaaga tcatcatcgt gcagctgaac     780
aagcccgtga agatcgtgtg cgtgcgcccc aacaacaaca cccgcaagag cgtgcgcatc     840 ggcccccggcc agaccttcta cgccaccggc gagatcatcg gcgacatccg ccaggcctac     900
tgcatcatca acaagaccga gtggaacagc accctgcagg gcgtgagcaa gaagctggag     960
gagcacttca gcaagaaggc catcaagttc gagcccagca cggcggcga cctggagatc     1020 accacccaca gcttcaactg ccgcggcgag ttcttctact gcgacaccag ccagctgttc     1080
aacagcacct acagcccag cttcaacggc accgagaaca gctgaacgg caccatcacc      1140 atcacctgcc gcatcaagca gatcatcaac atgtggcaga aggtgggccg cgccatgtac     1200 gccccccca tcgccggcaa cctgacctgc gagagcaaca tcaccggcct gctgctgacc     1260
cgcgacggcg gcaagaccgg ccccaacgac accgagatct ccgcccccgg cggcggcgac     1320
atgcgcgaca ctggcgcaa cgagctgtac aagtacaagg tggtggagat caagcccctg     1380
ggcgtggccc ccaccgaggc caagcgccgc gtggtggagc gcgagaagcg cgccgtgggc     1440
atcggcgccg tgttcctggg cttcctgggc gccgccggca gcaccatggg cgccgccagc     1500
atcaccctga ccgtgcaggc ccgcctgctg ctgagcggca tcgtgcagca gcagaacaac     1560
ctgctgcgcg ccatcgaggc ccagcagcac ctgctgcagc tgaccgtgtg gggcatcaag     1620
cagctgcaga cccgcatcct ggccgtggag cgctacctga aggaccagca gctgctgggc     1680
atctggggct gcagcggcaa gctgatctgc accaccgccg tgccctggaa cagcagctgg     1740
agcaaccgca gccacgacga gatctgggac aacatgacct ggatgcagtg ggaccgcgag     1800
atcaacaact acaccgacac catctaccgc ctgctggagg agagccagaa ccagcaggag     1860
aagaacgaga aggacctgct ggccctggac agctggcaga acctgtggaa ctggttcagc     1920
atcaccaact ggctgtggta catcaagatc ttcatcatga tcgtgggcgg cctgatcggc     1980
ctgcgcatca tcttcgccgt gctgagcatc gtgaaccgcg tgcgccaggg ctacagcccc     2040
ctgcccttcc agaccctgac ccccaacccc cgcgagcccg accgctgggg ccgcatcgag     2100
gaggagggcg gcgagcagga ccgcggccgc agcatccgcc tggtgagcgg cttcctggcc     2160
ctggcctggg acgacctgcg cagcctgtgc ctgttcagct accaccgcct gcgcgacttc     2220
atcctgatcg ccgcccgcgt gctggagctg ctggccagc gcggctggga ggccctgaag     2280
tacctgggca gcctggtgca gtactggggc ctggagctga agaagagcgc catcagcctg     2340
```

```
ctggacacca tcgccatcgc cgtggccgag ggcaccgacc gcatcatcga gttcatccag    2400
cgcatctgcc gcgccatccg caacatcccc cgccgcatcc gccagggctt cgaggccgcc    2460
ctgcag                                                                2466

<210> SEQ ID NO 9
<211> LENGTH: 2547
<212> TYPE: DNA
<213> ORGANISM: Artificial
<220> FEATURE:
<223> OTHER INFORMATION: synthetic signal sequence and gp160 coding
      region of HIV strain AF110968

<400> SEQUENCE: 9
atgcgcgtga tgggcatcct gaagaactac cagcagtggt ggatgtgggg catcctgggc     60
ttctggatgc tgatcatcag cagcgtggtg ggcaacctgt gggtgaccgt gtactacggc    120
gtgcccgtgt ggaaggaggc caagaccacc ctgttctgca ccagcgacgc caaggcctac    180
gagaccgagg tgcacaacgt gtgggccacc cacgcctgcg tgcccaccga ccccaacccc    240
caggagatcg tgctggagaa cgtgaccgag aacttcaaca tgtggaagaa cgacatggtg    300
gaccagatgc acgaggacat catcagcctg tgggaccaga gcctgaagcc ctgcgtgaag    360
ctgacccccc tgtgcgtgac cctgaagtgc cgcaacgtga acgccaccaa caacatcaac    420
agcatgatcg acaacagcaa caagggcgag atgaagaact gcagcttcaa cgtgaccacc    480
gagctgcgcg accgcaagca ggaggtgcac gccctgttct accgcctgga cgtggtgccc    540
ctgcagggca caacagcaa cgagtaccgc ctgatcaact gcaacaccag cgccatcacc    600
caggcctgcc ccaaggtgag cttcgacccc atccccatcc actactgcac cccgccggc     660 tacgccatcc tgaagtgcaa caaccagacc ttcaacggca ccggccctg caacaacgtg    720 agcagcgtgc agtgcgccca cggcatcaag cccgtggtga gcacccagct gctgctgaac    780
ggcagcctgg ccaagggcga gatcatcatc cgcagcgaga acctggccaa cacgccaag    840 atcatcatcg tgcagctgaa caagcccgtg aagatcgtgt gcgtgcgccc caacaacaac    900
acccgcaaga gcgtgcgcat cggccccggc cagaccttct acgccaccgg cgagatcatc    960
ggcgacatcc gccaggccta ctgcatcatc aacaagaccg agtggaacag caccctgcag   1020
ggcgtgagca agaagctgga ggagcacttc agcaagaagg ccatcaagtt cgagcccagc   1080
agcggcggcg acctggagat caccacccac agcttcaact gccgcggcga gttcttctac   1140
tgcgacacca gccagctgtt caacagcacc tacagcccca gcttcaacgg caccgagaac   1200
aagctgaacg gcaccatcac catcacctgc cgcatcaagc agatcatcaa catgtggcag   1260
aaggtgggcc gcgccatgta cgccccccc atcgccggca acctgacctg cgagagcaac   1320
atcaccggcc tgctgctgac ccgcgacggc ggcaagaccg gcccaacga caccgagatc   1380 ttccgccccg gcggcggcga catgcgcgac aactggcgca acgagctgta caagtacaag   1440
gtggtggaga tcaagcccct gggcgtggcc cccaccgagg ccaagcgccg cgtggtggag   1500
cgcgagaagc gcgccgtggg catcggcgcc gtgttcctgg gcttcctggg cgccgccggc   1560
agcaccatgg cgccgccag catcaccctg accgtgcagg cccgcctgct gctgagcggc   1620
atcgtgcagc agcagaacaa cctgctgcgc gccatcgagg cccagcagca cctgctgcag   1680
ctgaccgtgt ggggcatcaa gcagctgcag accgcatcc tggccgtgga gcgctacctg   1740
aaggaccagc agctgctggg catctgggc tgcagcggca gctgatctg caccaccgcc   1800 gtgccctgga acagcagctg gagcaaccgc agccacgacg agatctggga caacatgacc   1860
```

```
tggatgcagt gggaccgcga gatcaacaac tacaccgaca ccatctaccg cctgctggag   1920
gagagccaga accagcagga agaacgag aaggacctgc tggccctgga cagctggcag   1980
aacctgtgga actggttcag catcaccaac tggctgtggt acatcaagat cttcatcatg   2040
atcgtgggcg gcctgatcgg cctgcgcatc atcttcgccg tgctgagcat cgtgaaccgc   2100
gtgcgccagg gctacagccc cctgcccttc cagaccctga cccccaaccc ccgcgagccc   2160
gaccgcctgg gccgcatcga ggaggagggc ggcgagcagg accgcggccg cagcatccgc   2220
ctggtgagcg gcttcctggc cctggcctgg gacgacctgc gcagcctgtg cctgttcagc   2280
taccaccgcc tgcgcgactt catcctgatc gccgcccgcg tgctggagct gctgggccag   2340
cgcggctggg aggccctgaa gtacctgggc agcctggtgc agtactgggg cctggagctg   2400
aagaagagcg ccatcagcct gctggacacc atcgccatcg ccgtggccga gggcaccgac   2460
cgcatcatcg agttcatcca gcgcatctgc cgcgccatcc gcaacatccc ccgccgcatc   2520
cgccagggct cgaggccgc cctgcag                                       2547
```

<210> SEQ ID NO 10
<211> LENGTH: 1035
<212> TYPE: DNA
<213> ORGANISM: Artificial
<220> FEATURE:
<223> OTHER INFORMATION: synthetic a gp41 coding region of HIV strain
      AF110968

<400> SEQUENCE: 10

```
gccgtgggca tcggcgccgt gttcctgggc ttcctgggcg ccgccggcag caccatgggc     60
gccgccagca tcaccctgac cgtgcaggcc cgcctgctgc tgagcggcat cgtgcagcag    120
cagaacaacc tgctgcgcgc catcgaggcc cagcagcacc tgctgcagct gaccgtgtgg    180
ggcatcaagc agctgcagac ccgcatcctg gccgtggagc gctacctgaa ggaccagcag    240
ctgctgggca tctggggctg cagcggcaag ctgatctgca ccaccgccgt gccctggaac    300
agcagctgga gcaaccgcag ccacgacgag atctgggaca catgacctg gatgcagtgg    360 gaccgcgaga tcaacaacta caccgacacc atctaccgcc tgctgaagga gagccagaac    420
cagcaggaga agaacgagaa ggacctgctg gccctggaca gctggcagaa cctgtggaac    480
tggttcagca tcaccaactg gctgtggtac atcaagatct catcatgat cgtgggcggc    540 ctgatcggcc tgcgcatcat cttcgccgtg ctgagcatcg tgaaccgcgt gcgccagggc    600
tacagccccc tgcccttcca gaccctgacc cccaaccccc gcgagccga ccgcctgggc    660 cgcatcgagg aggagggcgg cgagcaggac cgcggccgca gcatccgcct ggtgagcggc    720
ttcctggccc tggcctggga cgacctgcgc agcctgtgcc tgttcagcta ccaccgcctg    780
cgcgacttca tcctgatcgc cgcccgcgtg ctggagctgc tgggccagcg cggctgggag    840
gccctgaagt acctgggcag cctggtgcag tactggggcc tggagctgaa gaagagcgcc    900
atcagcctgc tggacaccat cgccatcgcc gtggccgagg gcaccgaccg catcatcgag    960
ttcatccagc gcatctgccg cgccatccgc aacatccccc gccgcatccg ccagggcttc   1020
gaggccgccc tgcag                                                    1035
```

<210> SEQ ID NO 11
<211> LENGTH: 144
<212> TYPE: DNA
<213> ORGANISM: Artificial
<220> FEATURE:
<223> OTHER INFORMATION: synthetic Env common region of HIV strain

AF110975

<400> SEQUENCE: 11

| agcatcatca cccctgccctg ccgcatcaag cagatcatcg acatgtggca gaaggtgggc | 60 |
| cgcgccatct acgccccccc catcgagggc aacatcacct gcagcagcag catcaccggc | 120 |
| ctgctgctgg cccgcgacgg cggc | 144 |

<210> SEQ ID NO 12
<211> LENGTH: 1437
<212> TYPE: DNA
<213> ORGANISM: Artificial
<220> FEATURE:
<223> OTHER INFORMATION: synthetic gp120 coding region of HIV strain AF110975

<400> SEQUENCE: 12

| agcggcctgg caacctgtg ggtga

-continued

```
agcggcctgg gcaacctgtg ggtgaccgtg tacgacggcg tgcccgtgtg gcgcgaggcc     60
agcaccaccc tgttctgcgc cagcgacgcc aaggcctacg agaaggaggt gcacaacgtg    120
tgggccaccc acgcctgcgt gcccaccgac cccaaccccc aggagatcga gctggacaac    180
gtgaccgaga acttcaacat gtggaagaac gacatggtgg accagatgca cgaggacatc    240
atcagcctgt gggaccagag cctgaagccc cgcgtgaagc tgacccccct gtgcgtgacc    300
ctgaagtgca ccaactacag caccaactac agcaacacca tgaacgccac cagctacaac    360
aacaacacca ccgaggagat caagaactgc accttcaaca tgaccaccga gctgcgcgac    420
aagaagcagc aggtgtacgc cctgttctac aagctggaca tcgtgcccct gaacagcaac    480
agcagcgagt accgcctgat caactgcaac accagcgcca tcacccaggc ctgccccaag    540
gtgagcttcg accccatccc catccactac tgcgcccccg ccggctacgc catcctgaag    600
tgcaagaaca acaccagcaa cggcaccggc ccctgccaga acgtgagcac cgtgcagtgc    660
acccacggca tcaagcccgt ggtgagcacc cccctgctgc tgaacggcag cctggccgag    720
ggcggcgaga tcatcatccg cagcaagaac ctgagcaaca acgcctacac catcatcgtg    780
cacctgaacg acagcgtgga gatcgtgtgc acccgcccca acaacaacac ccgcaagggc    840
atccgcatcg gccccggcca gaccttctac gccaccgaga acatcatcgg cgacatccgc    900
caggcccact gcaacatcag cgccggcgag tggaacaagg ccgtgcagcg cgtgagcgcc    960
aagctgcgcg agcacttccc caacaagacc atcgagttcc agcccagcag cggcggcgac   1020
ctggagatca ccacccacag cttcaactgc cgcggcgagt tcttctactg caacaccagc   1080
aagctgttca acagcagcta caacggcacc agctaccgcg gcaccgagag caacagcagc   1140
atcatcaccc tgccctgccg catcaagcag atcatcgaca tgtggcagaa ggtgggccgc   1200
gccatctacg cccccccat cgagggcaac atcacctgca gcagcagcat caccggcctg   1260
ctgctggccc gcgacggcgg cctggacaac atcaccaccg agatcttccg cccccagggc   1320
ggcgacatga aggacaactg gcgcaacgag ctgtacaagt acaaggtggt ggagatcaag   1380
cccctgggcg tggcccccac cgaggccaag cgccgcgtgg tggagcgcga gaagcgcgcc   1440
gtgggcatcg gcgccgtgat cttcggcttc ctgggcgccg ccggcagcaa catgggcgcc   1500
gccagcatca ccctgaccgc ccaggcccgc cagctgctga gcggcatcgt gcagcagcag   1560
agcaacctgc tgcgcgccat cgaggcccag cagcacatgc tgcagctgac cgtgtggggc   1620
atcaagcagc tgcaggcccg cgtgctggcc atcgagcgct acctgaagga ccagcagctg   1680
ctgggcatct ggggctgcag cggcaagctg atctgcacca ccaccgtgcc ctggaacagc   1740
agctggagca acaagaccca gggcgagatc tgggagaaca tgacctggat gcagtgggac   1800
aaggagatca gcaactacac cggcatcatc taccgcctgc tggaggagag ccagaaccag   1860
caggagcaga acgagaagga cctgctggcc ctggacagcc gcaacaacct gtggagctgg   1920
ttcaacatca gcaactggct gtggtacatc                                    1950
```

<210> SEQ ID NO 14
<211> LENGTH: 2493
<212> TYPE: DNA
<213> ORGANISM: Artificial
<220> FEATURE:
<223> OTHER INFORMATION: synthetic gp160 coding region of HIV strain
AF110975

<400> SEQUENCE: 14

```
agcggcctgg gcaacctgtg ggtgaccgtg tacgacggcg tgcccgtgtg gcgcgaggcc     60
```

-continued

```
agcaccaccc tgttctgcgc cagcgacgcc aaggcctacg agaaggaggt gcacaacgtg    120
tgggccaccc acgcctgcgt gcccaccgac cccaaccccc aggagatcga gctggacaac    180
gtgaccgaga acttcaacat gtggaagaac gacatggtgg accagatgca cgaggacatc    240
atcagcctgt gggaccagag cctgaagccc cgcgtgaagc tgacccccct gtgcgtgacc    300
ctgaagtgca ccaactacag caccaactac agcaacacca tgaacgccac cagctacaac    360
aacaacacca ccgaggagat caagaactgc accttcaaca tgaccaccga gctgcgcgac    420
aagaagcagc aggtgtacgc cctgttctac aagctggaca tcgtgcccct gaacagcaac    480
agcagcgagt accgcctgat caactgcaac accagcgcca tcacccaggc ctgccccaag    540
gtgagcttcg accccatccc catccactac tgcgcccccg ccggctacgc catcctgaag    600
tgcaagaaca acaccagcaa cggcaccggc ccctgccaga cgtgagcac cgtgcagtgc    660
acccacggca tcaagcccgt ggtgagcacc cccctgctgc tgaacggcag cctggccgag    720
ggcggcgaga tcatcatccg cagcaagaac ctgagcaaca cgcctacac catcatcgtg    780
cacctgaacg acagcgtgga gatcgtgtgc acccgcccca caacaacac ccgcaagggc    840
atccgcatcg gccccggcca gaccttctac gccaccgaga acatcatcgg cgacatccgc    900
caggcccact gcaacatcag cgccggcgag tggaacaagg ccgtgcagcg cgtgagcgcc    960
aagctgcgcg agcacttccc caacaagacc atcgagttcc agcccagcag cggcggcgac   1020
ctggagatca ccacccacag cttcaactgc cgcggcgagt tcttctactg caacaccagc   1080
aagctgttca cagcagcta caacggcacc agctaccgcg caccgagag caacagcagc   1140
atcatcaccc tgcccctgcc catcaagcag atcatcgaca tgtggcagaa ggtgggccgc   1200
gccatctacg ccccccccat cgagggcaac atcacctgca agcagcat caccggcctg   1260
ctgctggccc gcgacggcgg cctggacaac atcaccaccg agatcttccg ccccagggc   1320
ggcgacatga aggacaactg cgcaacgag ctgtacaagt acaaggtggt ggagatcaag   1380
cccctgggcg tggcccccac cgaggccaag cgccgcgtgg tggagcgcga aagcgcgcc   1440
gtgggcatcg cgccgtgat cttcggcttc ctgggcgccg ccggcagcaa catgggcgcc   1500
gccagcatca ccctgaccgc ccaggcccgc cagctgctga gcggcatcgt gcagcagcag   1560
agcaacctgc tgcgcgccat cgaggcccag cagcacatgc tgcagctgac cgtgtggggc   1620
atcaagcagc tgcaggcccg cgtgctggcc atcgagcgct acctgaagga ccagcagctg   1680
ctgggcatct ggggctgcag cggcaagctg atctgcacca ccaccgtgcc ctggaacagc   1740
agctggagca acaagaccca gggcgagatc tgggagaaca tgacctggat gcagtgggac   1800
aaggagatca gcaactacac cggcatcatc taccgcctgc tggaggagag ccagaaccag   1860
caggagcaga acgagaagga cctgctggcc ctggacagcc gcaacaacct gtggagctgg   1920
ttcaacatca gcaactggct gtggtacatc aagatcttca tcatgatcgt gggcggcctg   1980
atcggcctgc gcatcatctt cgccgtgctg agcatcgtga accgcgtgcg ccagggctac   2040
agccccctga gcttccagac cctgaccccc aaccccgcg gcctggaccg cctgggccgc   2100
atcgaggagg agggcggcga gcaggaccgc gaccgcagca tccgcctggt gcagggcttc   2160
ctggccctgg cctgggacga cctgcgcagc ctgtgcctgt tcagctacca ccgcctgcgc   2220
gacctgatcc tggtgaccgc ccgcgtggtg agctgctgg gccgcagcag ccccgcggc   2280
ctgcagcgcg gctgggaggc cctgaagtac ctgggcagcc tggtgcagta ctggggcctg   2340
gagctgaaga agagcgccac cagcctgctg gacagcatcg ccatcgccgt ggccgagggc   2400
```

```
accgaccgca tcatcgaggt gatccagcgc atctaccgcg ccttctgcaa catccccgc    2460 cgcgtgcgcc agggcttcga ggccgccctg cag                                2493

<210> SEQ ID NO 15
<211> LENGTH: 2565
<212> TYPE: DNA
<213> ORGANISM: Artificial
<220> FEATURE:
<223> OTHER INFORMATION: synthetic signal sequence and gp160 coding
      region of HIV strain AF110975

<400> SEQUENCE: 15
atgcgcgtgc gcggcatcct gcgcagctgg cagcagtggt ggatctgggg catcctgggc    60
ttctggatct gcagcggcct gggcaacctg tgggtgaccg tgtacgacgg cgtgcccgtg    120
tggcgcgagg ccagcaccac cctgttctgc gccagcgacg ccaaggccta cgagaaggag    180
gtgcacaacg tgtgggccac ccacgcctgc gtgcccaccg accccaaccc caggagatc     240 gagctggaca acgtgaccga gaacttcaac atgtggaaga cgacatggt ggaccagatg     300 cacgaggaca tcatcagcct gtgggaccag agcctgaagc ccgcgtgaa gctgaccccc    360 ctgtgcgtga ccctgaagtg caccaactac agcaccaact cagcaacac catgaacgcc    420 accagctaca acaacaacac caccgaggag atcaagaact gcaccttcaa catgaccacc    480
gagctgcgcg acaagaagca gcaggtgtac gccctgttct acaagctgga catcgtgccc    540
ctgaacagca cagcagcga gtaccgcctg atcaactgca caccagcgc catcaccag     600 gcctgcccca aggtgagctt cgaccccatc cccatccact actgcgcccc cgccggctac    660
gccatcctga gtgcaagaa caacaccagc aacggcaccg cccctgcca gaacgtgagc    720 accgtgcagt gcacccacgg catcaagccc gtggtgagca cccccctgct gctgaacggc    780
agcctggccg agggcggcga gatcatcatc cgcagcaaga acctgagcaa caacgcctac    840
accatcatcg tgcacctgaa cgacagcgtg gagatcgtgt gcacccgccc caacaacaac    900
acccgcaagg gcatccgcat cggccccggc cagaccttct acgccaccga gaacatcatc    960
ggcgacatcc gccaggccca ctgcaacatc agcgccggcg agtggaacaa ggccgtgcag    1020
cgcgtgagcg ccaagctgcg cgagcacttc cccaacaaga ccatcgagtt ccagcccagc    1080
agcggcggcg acctggagat caccacccac agcttcaact gccgcggcga gttcttctac    1140
tgcaacacca gcaagctgtt caacagcagc tacaacggca ccagctaccg cggcaccgag    1200
agcaacagca gcatcatcac cctgccctgc cgcatcaagc agatcatcga catgtggcag    1260
aaggtgggcc gcgccatcta cgccccccc atcgagggca acatcacctg cagcagcagc    1320
atcaccggcc tgctgctggc ccgcgacggc ggcctggaca acatcaccac cgagatcttc    1380
cgcccccagg gcggcgacat gaaggacaac tggcgcaacg agctgtacaa gtacaaggtg    1440
gtggagatca gccccctggg cgtggccccc accgaggcca gcgccgcgt ggtgagcgc     1500 gagaagcgcg ccgtgggcat cggcgccgtg atcttcggct tcctgggcgc cgccggcagc    1560
aacatgggcg ccgccagcat caccctgacc gcccaggccc gccagctgct gagcggcatc    1620
gtgcagcagc agagcaacct gctgcgcgcc atcgaggccc agcagcacat gctgcagctg    1680
accgtgtggg gcatcaagca gctgcaggcc cgcgtgctgg ccatcgagcg ctacctgaag    1740
gaccagcagc tgctgggcat ctggggctgc agcggcaagc tgatctgcac caccaccgtg    1800
ccctggaaca gcagctggag caacaagacc cagggcgaga tctggagaa catgacctgg    1860 atgcagtggg acaaggagat cagcaactac accggcatca tctaccgcct gctggaggag    1920
```

| | | | | |
|---|---|---|---|---|
| agccagaacc | agcaggagca | gaacgagaag | gacctgctgg | ccctggacag ccgcaacaac | 1980 |
| ctgtggagct | ggttcaacat | cagcaactgg | ctgtggtaca | tcaagatctt catcatgatc | 2040 |
| gtgggcggcc | tgatcggcct | gcgcatcatc | ttcgccgtgc | tgagcatcgt gaaccgcgtg | 2100 |
| cgccagggct | acagccccct | gagcttccag | accctgaccc | caaccccccg cggcctggac | 2160 |
| cgcctgggcc | gcatcgagga | ggagggcggc | gagcaggacc | gcgaccgcag catccgcctg | 2220 |
| gtgcagggct | tcctggccct | ggcctgggac | gacctgcgca | gcctgtgcct gttcagctac | 2280 |
| caccgcctgc | gcgacctgat | cctggtgacc | gcccgcgtgg | tggagctgct gggccgcagc | 2340 |
| agcccccgcg | gcctgcagcg | cggctgggag | gccctgaagt | acctgggcag cctggtgcag | 2400 |
| tactggggcc | tggagctgaa | gaagagcgcc | accagcctgc | tggacagcat cgccatcgcc | 2460 |
| gtggccgagg | gcaccgaccg | catcatcgag | gtgatccagc | gcatctaccg cgccttctgc | 2520 |
| aacatccccc | gccgcgtgcg | ccagggcttc | gaggccgccc | tgcag | 2565 |

<210> SEQ ID NO 16
<211> LENGTH: 1056
<212> TYPE: DNA
<213> ORGANISM: Artificial
<220> FEATURE:
<223> OTHER INFORMATION: synthetic a gp41 coding region of HIV strain AF110975

<400> SEQUENCE: 16

| | | | | |
|---|---|---|---|---|
| gccgtgggca | tcggcgccgt | gatcttcggc | ttcctgggcg | ccgccggcag caacatgggc | 60 |
| gccgccagca | tcaccctgac | cgcccaggcc | cgccagctgc | tgagcggcat cgtgcagcag | 120 |
| cagagcaacc | tgctgcgcgc | catcgaggcc | cagcagcaca | tgctgcagct gaccgtgtgg | 180 |
| ggcatcaagc | agctgcaggc | ccgcgtgctg | gccatcgagc | gctacctgaa ggaccagcag | 240 |
| ctgctgggca | tctggggctg | cagcggcaag | ctgatctgca | ccaccaccgt gccctggaac | 300 |
| agcagctgga | gcaacaagac | ccagggcgag | atctgggaga | catgacctg gatgcagtgg | 360 |
| gacaaggaga | tcagcaacta | caccggcatc | atctaccgcc | tgctggagga gagccagaac | 420 |
| cagcaggagc | agaacgagaa | ggacctgctg | ccctggaca | gccgcaacaa cctgtggagc | 480 |
| tggttcaaca | tcagcaactg | gctgtggtac | atcaagatct | tcatcatgat cgtgggcggc | 540 |
| ctgatcggcc | tgcgcatcat | cttcgccgtg | ctgagcatcg | tgaaccgcgt gcgccagggc | 600 |
| tacagccccc | tgagcttcca | gaccctgacc | cccaaccccc | gcggcctgga ccgcctgggc | 660 |
| cgcatcgagg | aggagggcgg | cgagcaggac | cgcgaccgca | gcatccgcct ggtgcagggc | 720 |
| ttcctggccc | tggcctggga | cgacctgcgc | agcctgtgcc | tgttcagcta ccaccgcctg | 780 |
| cgcgacctga | tcctggtgac | cgcccgcgtg | gtggagctgc | tgggccgcag cagcccccgc | 840 |
| ggcctgcagc | gcggctggga | ggccctgaag | tacctgggca | gcctggtgca gtactggggc | 900 |
| ctggagctga | agaagagcgc | caccagcctg | ctggacagca | tcgccatcgc cgtgccgag | 960 |
| ggcaccgacc | gcatcatcga | ggtgatccag | cgcatctacc | gcgccttctg caacatcccc | 1020 |
| cgccgcgtgc | gccagggctt | cgaggccgcc | ctgcag | | 1056 |

<210> SEQ ID NO 17
<211> LENGTH: 492
<212> TYPE: PRT
<213> ORGANISM: Human immunodeficiency virus

<400> SEQUENCE: 17

Met Gly Ala Arg Ala Ser Ile Leu Arg Gly Gly Lys Leu Asp Ala Trp
1               5                   10                  15

```
Glu Arg Ile Arg Leu Arg Pro Gly Gly Lys Lys Cys Tyr Met Met Lys
            20                  25                  30

His Leu Val Trp Ala Ser Arg Glu Leu Glu Lys Phe Ala Leu Asn Pro
            35                  40                  45

Gly Leu Leu Glu Thr Ser Glu Gly Cys Lys Gln Ile Ile Arg Gln Leu
        50                  55                  60

His Pro Ala Leu Gln Thr Gly Ser Glu Glu Leu Lys Ser Leu Phe Asn
65                  70                  75                  80

Thr Val Ala Thr Leu Tyr Cys Val His Glu Lys Ile Glu Val Arg Asp
                85                  90                  95

Thr Lys Glu Ala Leu Asp Lys Ile Glu Glu Gln Asn Lys Cys Gln
            100                 105                 110

Gln Lys Ile Gln Gln Ala Glu Ala Asp Lys Gly Lys Val Ser Gln
            115                 120                 125

Asn Tyr Pro Ile Val Gln Asn Leu Gln Gly Gln Met Val His Gln Ala
        130                 135                 140

Ile Ser Pro Arg Thr Leu Asn Ala Trp Val Lys Val Ile Glu Glu Lys
145                 150                 155                 160

Ala Phe Ser Pro Glu Val Ile Pro Met Phe Thr Ala Leu Ser Glu Gly
                165                 170                 175

Ala Thr Pro Gln Asp Leu Asn Thr Met Leu Asn Thr Val Gly Gly His
            180                 185                 190

Gln Ala Ala Met Gln Met Leu Lys Asp Thr Ile Asn Glu Glu Ala Ala
        195                 200                 205

Glu Trp Asp Arg Val His Pro Val His Ala Gly Pro Ile Ala Pro Gly
210                 215                 220

Gln Met Arg Glu Pro Arg Gly Ser Asp Ile Ala Gly Thr Thr Ser Thr
225                 230                 235                 240

Leu Gln Glu Gln Ile Ala Trp Met Thr Ser Asn Pro Pro Ile Pro Val
                245                 250                 255

Gly Asp Ile Tyr Lys Arg Trp Ile Ile Leu Gly Leu Asn Lys Ile Val
            260                 265                 270

Arg Met Tyr Ser Pro Val Ser Ile Leu Asp Ile Lys Gln Gly Pro Lys
        275                 280                 285

Glu Pro Phe Arg Asp Tyr Val Asp Arg Phe Phe Lys Thr Leu Arg Ala
        290                 295                 300

Glu Gln Ser Thr Gln Glu Val Lys Asn Trp Met Thr Asp Thr Leu Leu
305                 310                 315                 320

Val Gln Asn Ala Asn Pro Asp Cys Lys Thr Ile Leu Arg Ala Leu Gly
                325                 330                 335

Pro Gly Ala Ser Leu Glu Glu Met Met Thr Ala Cys Gln Gly Val Gly
            340                 345                 350

Gly Pro Ser His Lys Ala Arg Val Leu Ala Glu Ala Met Ser Gln Ala
        355                 360                 365

Asn Thr Ser Val Met Met Gln Lys Ser Asn Phe Lys Gly Pro Arg Arg
370                 375                 380

Ile Val Lys Cys Phe Asn Cys Gly Lys Glu Gly His Ile Ala Arg Asn
385                 390                 395                 400

Cys Arg Ala Pro Arg Lys Lys Gly Cys Trp Lys Cys Gly Lys Glu Gly
                405                 410                 415

His Gln Met Lys Asp Cys Thr Glu Arg Gln Ala Asn Phe Leu Gly Lys
            420                 425                 430
```

```
Ile Trp Pro Ser His Lys Gly Arg Pro Gly Asn Phe Leu Gln Ser Arg
        435                 440                 445

Pro Glu Pro Thr Ala Pro Pro Ala Glu Ser Phe Arg Phe Glu Glu Thr
    450                 455                 460

Thr Pro Gly Gln Lys Gln Glu Ser Lys Asp Arg Glu Thr Leu Thr Ser
465                 470                 475                 480

Leu Lys Ser Leu Phe Gly Asn Asp Pro Leu Ser Gln
            485                 490

<210> SEQ ID NO 18
<211> LENGTH: 81
<212> TYPE: DNA
<213> ORGANISM: Artificial
<220> FEATURE:
<223> OTHER INFORMATION: synthetic signal sequence of HIV strain
      AF110968

<400> SEQUENCE: 18
atgcgcgtga tgggcatcct gaagaactac cagcagtggt ggatgtgggg catcctgggc    60
ttctggatgc tgatcatcag c                                             81

<210> SEQ ID NO 19
<211> LENGTH: 72
<212> TYPE: DNA
<213> ORGANISM: Artificial
<220> FEATURE:
<223> OTHER INFORMATION: synthetic signal sequence of HIV strain
      AF110975

<400> SEQUENCE: 19
atgcgcgtgc gcggcatcct gcgcagctgg cagcagtggt ggatctgggg catcctgggc    60
ttctggatct gc                                                       72

<210> SEQ ID NO 20
<211> LENGTH: 1479
<212> TYPE: DNA
<213> ORGANISM: Artificial
<220> FEATURE:
<223> OTHER INFORMATION: synthetic Gag coding sequence of HIV strain
      AF110965

<400> SEQUENCE: 20
atgggcgccc gcgccagcat cctgcgcggc ggcaagctgg acgcctggga gcgcatccgc    60
ctgcgccccg gcggcaagaa gtgctacatg atgaagcacc tggtgtgggc cagccgcgag   120
ctggagaagt tcgccctgaa ccccggcctg ctggagacca gcgagggctg caagcagatc   180
atccgccagc tgcaccccgc cctgcagacc ggcagcgagg agctgaagag cctgttcaac   240
accgtggcca ccctgtactg cgtgcacgag aagatcgagg tgcgcgacac caaggaggcc   300
ctggacaaga tcgaggagga gcagaacaag tgccagcaga gatccagca ggccgaggcc   360 gccgacaagg gcaaggtgag ccagaactac cccatcgtgc agaacctgca gggccagatg   420
gtgcaccagg ccatcagccc ccgcaccctg aacgcctggg tgaaggtgat cgaggagaag   480
gccttcagcc ccgaggtgat ccccatgttc accgccctga gcgagggcgc cacccccag   540 gacctgaaca ccatgctgaa caccgtgggc ggccaccagg ccgccatgca gatgctgaag   600
gacaccatca cgaggaggc cgccgagtgg gaccgcgtgc accccgtgca cgccggcccc   660 atcgccccccg ccagatgcg cgagccccgc ggcagcgaca tcgccggcac caccagcacc   720
ctgcaggagc agatcgcctg gatgaccagc aaccccccca tccccgtggg cgacatctac   780
```

| | |
|---|---|
| aagcgctgga tcatcctggg cctgaacaag atcgtgcgca tgtacagccc cgtgagcatc | 840 |
| ctggacatca agcagggccc caaggagccc ttccgcgact acgtggaccg cttcttcaag | 900 |
| accctgcgcg ccgagcagag cacccaggag gtgaagaact ggatgaccga caccctgctg | 960 |
| gtgcagaacg ccaaccccga ctgcaagacc atcctgcgcg ccctgggccc cggcgccagc | 1020 |
| ctggaggaga tgatgaccgc ctgcagggc gtgggcggcc ccagccacaa ggcccgcgtg | 1080 |
| ctggccgagg ccatgagcca ggccaacacc agcgtgatga tgcagaagag caacttcaag | 1140 |
| ggccccgcc gcatcgtgaa gtgcttcaac tgcggcaagg agggccacat cgcccgcaac | 1200 |
| tgccgcgccc ccgcaagaa gggctgctgg aagtgcggca aggagggcca ccagatgaag | 1260 |
| gactgcaccg agcgccaggc caacttcctg ggcaagatct ggccagcca agggccgc | 1320 |
| cccggcaact tcctgcagag ccgccccgag cccaccgccc ccccgccga gcttccgc | 1380 |
| ttcgaggaga ccaccccgg ccagaagcag gagagcaagg accgcgagac cctgaccagc | 1440 |
| ctgaagagcc tgttcggcaa cgaccccctg agccagtaa | 1479 |

<210> SEQ ID NO 21
<211> LENGTH: 1509
<212> TYPE: DNA
<213> ORGANISM: Artificial
<220> FEATURE:
<223> OTHER INFORMATION: synthetic Gag coding sequence of HIV strain
      AF110967

<400> SEQUENCE: 21

| | |
|---|---|
| atgggcgccc gcgccagcat cctgcgcggc gagaagctgg acaagtggga gaagatccgc | 60 |
| ctgcgccccg gcggcaagaa gcactacatg ctgaagcacc tggtgtgggc cagccgcgag | 120 |
| ctggagggct cgccctgaa ccccggcctg ctggagaccg ccgagggctg caagcagatc | 180 |
| atgaagcagc tgcagcccgc cctgcagacc ggcaccgagg agctgcgcag cctgtacaac | 240 |
| accgtggcca ccctgtactg cgtgcacgcc ggcatcgagg tgcgcgacac caaggaggcc | 300 |
| ctggacaaga tcgaggagga gcagaacaag agccagcaga gacccagca ggccaaggag | 360 |
| gccgacggca aggtgagcca gaactacccc atcgtgcaga acctgcaggg ccagatggtg | 420 |
| caccaggcca tcagcccccg caccctgaac gcctgggtga aggtgatcga ggagaaggcc | 480 |
| ttcagccccg aggtgatccc catgttcacc gccctgagcg agggcgccac cccccaggac | 540 |
| ctgaacacca tgctgaacac cgtgggcggc caccaggccg ccatgcagat gctgaaggac | 600 |
| accatcaacg aggaggccgc cgagtgggac cgcctgcacc ccgtgcaggc cggccccgtg | 660 |
| gccccggcc agatgcgcga ccccgcggc agcgacatcg ccggcgccac cagcacgctg | 720 |
| caggagcaga tcgcctggat gaccagcaac ccccccgtgc ccgtgggcga catctacaag | 780 |
| cgctggatca tcctgggcct gaacaagatc gtgcgcatgt acagccccgt gagcatcctg | 840 |
| gacatccgcc agggccccaa ggagcccttc cgcgactacg tggaccgctt cttcaagacc | 900 |
| ctgcgcgccg agcaggccac ccaggacgtg aagaactgga tgaccgagac cctgctggtg | 960 |
| cagaacgcca accccgactg caagaccatc ctgcgcgccc tgggcccgg cgccaccctg | 1020 |
| gaggagatga tgaccgcctg ccagggcgtg gcggccccg ccacaaggc ccgcgtgctg | 1080 |
| gccgaggcca tgagccaggc caacagcgtg aacatcatga tgcagaagag caacttcaag | 1140 |
| ggccccgcc gcaacgtgaa gtgcttcaac tgcggcaagg agggccacat cgccaagaac | 1200 |
| tgccgcgccc ccgcaagaa gggctgctgg aagtgcggca aggagggcca ccagatgaag | 1260 |
| gactgcaccg agcgccaggc caacttcctg ggcaagatct ggccagcca agggccgc | 1320 |

```
cccggcaact tcctgcagaa ccgcagcgag cccgccgccc ccaccgtgcc caccgccccc   1380
cccgccgaga gcttccgctt cgaggagacc accccgccc caagcagga gcccaaggac    1440 cgcgagccct accgcgagcc cctgaccgcc ctgcgcagcc tgttcggcag cggccccctg   1500
agccagtaa                                                          1509
```

<210> SEQ ID NO 22
<211> LENGTH: 502
<212> TYPE: PRT
<213> ORGANISM: Human immunodeficiency virus

<400> SEQUENCE: 22

```
Met Gly Ala Arg Ala Ser Ile Leu Arg Gly Glu Lys Leu Asp Lys Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Gly Phe Ala Leu Asn Pro
        35                  40                  45

Gly Leu Leu Glu Thr Ala Glu Gly Cys Lys Gln Ile Met Lys Gln Leu
    50                  55                  60

Gln Pro Ala Leu Gln Thr Gly Thr Glu Glu Leu Arg Ser Leu Tyr Asn
65                  70                  75                  80

Thr Val Ala Thr Leu Tyr Cys Val His Ala Gly Ile Glu Val Arg Asp
                85                  90                  95

Thr Lys Glu Ala Leu Asp Lys Ile Glu Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Ala Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val Gln Ala Gly Pro Val Ala Pro Gly Gln
    210                 215                 220

Met Arg Asp Pro Arg Gly Ser Asp Ile Ala Gly Ala Thr Ser Thr Leu
225                 230                 235                 240

Gln Glu Gln Ile Ala Trp Met Thr Ser Asn Pro Pro Val Pro Val Gly
                245                 250                 255

Asp Ile Tyr Lys Arg Trp Ile Ile Leu Gly Leu Asn Lys Ile Val Arg
            260                 265                 270

Met Tyr Ser Pro Val Ser Ile Leu Asp Ile Arg Gln Gly Pro Lys Glu
        275                 280                 285

Pro Phe Arg Asp Tyr Val Asp Arg Phe Phe Lys Thr Leu Arg Ala Glu
    290                 295                 300

Gln Ala Thr Gln Asp Val Lys Asn Trp Met Thr Glu Thr Leu Leu Val
305                 310                 315                 320

Gln Asn Ala Asn Pro Asp Cys Lys Thr Ile Leu Arg Ala Leu Gly Pro
                325                 330                 335
```

```
Gly Ala Thr Leu Glu Glu Met Met Thr Ala Cys Gln Gly Val Gly Gly
            340                 345                 350

Pro Gly His Lys Ala Arg Val Leu Ala Glu Ala Met Ser Gln Ala Asn
        355                 360                 365

Ser Val Asn Ile Met Met Gln Lys Ser Asn Phe Lys Gly Pro Arg Arg
    370                 375                 380

Asn Val Lys Cys Phe Asn Cys Gly Lys Glu Gly His Ile Ala Lys Asn
385                 390                 395                 400

Cys Arg Ala Pro Arg Lys Lys Gly Cys Trp Lys Cys Gly Lys Glu Gly
                405                 410                 415

His Gln Met Lys Asp Cys Thr Glu Arg Gln Ala Asn Phe Leu Gly Lys
            420                 425                 430

Ile Trp Pro Ser His Lys Gly Arg Pro Gly Asn Phe Leu Gln Asn Arg
        435                 440                 445

Ser Glu Pro Ala Ala Pro Thr Val Pro Thr Ala Pro Pro Ala Glu Ser
    450                 455                 460

Phe Arg Phe Glu Glu Thr Thr Pro Ala Pro Lys Gln Glu Pro Lys Asp
465                 470                 475                 480

Arg Glu Pro Tyr Arg Glu Pro Leu Thr Ala Leu Arg Ser Leu Phe Gly
                485                 490                 495

Ser Gly Pro Leu Ser Gln
            500

<210> SEQ ID NO 23
<211> LENGTH: 849
<212> TYPE: PRT
<213> ORGANISM: Human immunodeficiency virus

<400> SEQUENCE: 23

Met Arg Val Met Gly Ile Leu Lys Asn Tyr Gln Gln Trp Trp Met Trp
1               5                   10                  15

Gly Ile Leu Gly Phe Trp Met Leu Ile Ile Ser Ser Val Val Gly Asn
            20                  25                  30

Leu Trp Val Thr Val Tyr Tyr Gly Val Pro Val Trp Lys Glu Ala Lys
        35                  40                  45

Thr Thr Leu Phe Cys Thr Ser Asp Ala Lys Ala Tyr Glu Thr Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Lys Cys Arg Asn Val Asn Ala Thr Asn Asn Ile Asn Ser Met Ile Asp
    130                 135                 140

Asn Ser Asn Lys Gly Glu Met Lys Asn Cys Ser Phe Asn Val Thr Thr
145                 150                 155                 160

Glu Leu Arg Asp Arg Lys Gln Glu Val His Ala Leu Phe Tyr Arg Leu
                165                 170                 175

Asp Val Val Pro Leu Gln Gly Asn Asn Ser Asn Glu Tyr Arg Leu Ile
            180                 185                 190

Asn Cys Asn Thr Ser Ala Ile Thr Gln Ala Cys Pro Lys Val Ser Phe
        195                 200                 205
```

```
Asp Pro Ile Pro Ile His Tyr Cys Thr Pro Ala Gly Tyr Ala Ile Leu
    210                 215                 220

Lys Cys Asn Asn Gln Thr Phe Asn Gly Thr Gly Pro Cys Asn Asn Val
225                 230                 235                 240

Ser Ser Val Gln Cys Ala His Gly Ile Lys Pro Val Val Ser Thr Gln
                245                 250                 255

Leu Leu Leu Asn Gly Ser Leu Ala Lys Gly Glu Ile Ile Ile Arg Ser
                260                 265                 270

Glu Asn Leu Ala Asn Asn Ala Lys Ile Ile Val Gln Leu Asn Lys
                275                 280                 285

Pro Val Lys Ile Val Cys Val Arg Pro Asn Asn Asn Thr Arg Lys Ser
290                 295                 300

Val Arg Ile Gly Pro Gly Gln Thr Phe Tyr Ala Thr Gly Glu Ile Ile
305                 310                 315                 320

Gly Asp Ile Arg Gln Ala Tyr Cys Ile Ile Asn Lys Thr Glu Trp Asn
                325                 330                 335

Ser Thr Leu Gln Gly Val Ser Lys Lys Leu Glu Glu His Phe Ser Lys
                340                 345                 350

Lys Ala Ile Lys Phe Glu Pro Ser Gly Gly Asp Leu Glu Ile Thr
                355                 360                 365

Thr His Ser Phe Asn Cys Arg Gly Glu Phe Phe Tyr Cys Asp Thr Ser
    370                 375                 380

Gln Leu Phe Asn Ser Thr Tyr Ser Pro Ser Phe Asn Gly Thr Glu Asn
385                 390                 395                 400

Lys Leu Asn Gly Thr Ile Thr Ile Thr Cys Arg Ile Lys Gln Ile Ile
                405                 410                 415

Asn Met Trp Gln Lys Val Gly Arg Ala Met Tyr Ala Pro Pro Ile Ala
                420                 425                 430

Gly Asn Leu Thr Cys Glu Ser Asn Ile Thr Gly Leu Leu Leu Thr Arg
                435                 440                 445

Asp Gly Gly Lys Thr Gly Pro Asn Asp Thr Glu Ile Phe Arg Pro Gly
    450                 455                 460

Gly Gly Asp Met Arg Asp Asn Trp Arg Asn Glu Leu Tyr Lys Tyr Lys
465                 470                 475                 480

Val Val Glu Ile Lys Pro Leu Gly Val Ala Pro Thr Glu Ala Lys Arg
                485                 490                 495

Arg Val Val Glu Arg Glu Lys Arg Ala Val Gly Ile Gly Ala Val Phe
                500                 505                 510

Leu Gly Phe Leu Gly Ala Ala Gly Ser Thr Met Gly Ala Ala Ser Ile
    515                 520                 525

Thr Leu Thr Val Gln Ala Arg Leu Leu Leu Ser Gly Ile Val Gln Gln
    530                 535                 540

Gln Asn Asn Leu Leu Arg Ala Ile Glu Ala Gln Gln His Leu Leu Gln
545                 550                 555                 560

Leu Thr Val Trp Gly Ile Lys Gln Leu Gln Thr Arg Ile Leu Ala Val
                565                 570                 575

Glu Arg Tyr Leu Lys Asp Gln Gln Leu Leu Gly Ile Trp Gly Cys Ser
                580                 585                 590

Gly Lys Leu Ile Cys Thr Thr Ala Val Pro Trp Asn Ser Ser Trp Ser
                595                 600                 605

Asn Arg Ser His Asp Glu Ile Trp Asp Asn Met Thr Trp Met Gln Trp
610                 615                 620
```

```
Asp Arg Glu Ile Asn Asn Tyr Thr Asp Thr Ile Tyr Arg Leu Leu Glu
625                 630                 635                 640

Glu Ser Gln Asn Gln Gln Lys Asn Glu Lys Asp Leu Leu Ala Leu
        645                 650                 655

Asp Ser Trp Gln Asn Leu Trp Asn Trp Phe Ser Ile Thr Asn Trp Leu
        660                 665                 670

Trp Tyr Ile Lys Ile Phe Ile Met Ile Val Gly Gly Leu Ile Gly Leu
            675                 680                 685

Arg Ile Ile Phe Ala Val Leu Ser Ile Val Asn Arg Val Arg Gln Gly
        690                 695                 700

Tyr Ser Pro Leu Pro Phe Gln Thr Leu Thr Pro Asn Pro Arg Glu Pro
705                 710                 715                 720

Asp Arg Leu Gly Arg Ile Glu Glu Gly Gly Glu Gln Asp Arg Gly
            725                 730                 735

Arg Ser Ile Arg Leu Val Ser Gly Phe Leu Ala Leu Ala Trp Asp Asp
        740                 745                 750

Leu Arg Ser Leu Cys Leu Phe Ser Tyr His Arg Leu Arg Asp Phe Ile
        755                 760                 765

Leu Ile Ala Ala Arg Val Glu Leu Leu Gly Gln Arg Gly Trp Glu
770                 775                 780

Ala Leu Lys Tyr Leu Gly Ser Leu Val Gln Tyr Trp Gly Leu Glu Leu
785                 790                 795                 800

Lys Lys Ser Ala Ile Ser Leu Leu Asp Thr Ile Ala Ile Ala Val Ala
            805                 810                 815

Glu Gly Thr Asp Arg Ile Ile Glu Phe Ile Gln Arg Ile Cys Arg Ala
                820                 825                 830

Ile Arg Asn Ile Pro Arg Arg Ile Arg Gln Gly Phe Glu Ala Ala Leu
            835                 840                 845

Gln

<210> SEQ ID NO 24
<211> LENGTH: 855
<212> TYPE: PRT
<213> ORGANISM: Human immunodeficiency virus

<400> SEQUENCE: 24

Met Arg Val Arg Gly Ile Leu Arg Ser Trp Gln Gln Trp Trp Ile Trp
1               5                   10                  15

Gly Ile Leu Gly Phe Trp Ile Cys Ser Gly Leu Gly Asn Leu Trp Val
            20                  25                  30

Thr Val Tyr Asp Gly Val Pro Val Trp Arg Glu Ala Ser Thr Thr Leu
        35                  40                  45

Phe Cys Ala Ser Asp Ala Lys Ala Tyr Glu Lys Glu Val His Asn Val
    50                  55                  60

Trp Ala Thr His Ala Cys Val Pro Thr Asp Pro Asn Pro Gln Glu Ile
65                  70                  75                  80

Glu Leu Asp Asn Val Thr Glu Asn Phe Asn Met Trp Lys Asn Asp Met
                85                  90                  95

Val Asp Gln Met His Glu Asp Ile Ile Ser Leu Trp Asp Gln Ser Leu
            100                 105                 110

Lys Pro Arg Val Lys Leu Thr Pro Leu Cys Val Thr Leu Lys Cys Thr
        115                 120                 125

Asn Tyr Ser Thr Asn Tyr Ser Asn Thr Met Asn Ala Thr Ser Tyr Asn
    130                 135                 140
```

```
Asn Asn Thr Thr Glu Glu Ile Lys Asn Cys Thr Phe Asn Met Thr Thr
145                 150                 155                 160

Glu Leu Arg Asp Lys Lys Gln Gln Val Tyr Ala Leu Phe Tyr Lys Leu
            165                 170                 175

Asp Ile Val Pro Leu Asn Ser Asn Ser Ser Glu Tyr Arg Leu Ile Asn
            180                 185                 190

Cys Asn Thr Ser Ala Ile Thr Gln Ala Cys Pro Lys Val Ser Phe Asp
            195                 200                 205

Pro Ile Pro Ile His Tyr Cys Ala Pro Ala Gly Tyr Ala Ile Leu Lys
            210                 215                 220

Cys Lys Asn Asn Thr Ser Asn Gly Thr Gly Pro Cys Gln Asn Val Ser
225                 230                 235                 240

Thr Val Gln Cys Thr His Gly Ile Lys Pro Val Val Ser Thr Pro Leu
                    245                 250                 255

Leu Leu Asn Gly Ser Leu Ala Glu Gly Gly Glu Ile Ile Ile Arg Ser
                260                 265                 270

Lys Asn Leu Ser Asn Asn Ala Tyr Thr Ile Ile Val His Leu Asn Asp
            275                 280                 285

Ser Val Glu Ile Val Cys Thr Arg Pro Asn Asn Asn Thr Arg Lys Gly
290                 295                 300

Ile Arg Ile Gly Pro Gly Gln Thr Phe Tyr Ala Thr Glu Asn Ile Ile
305                 310                 315                 320

Gly Asp Ile Arg Gln Ala His Cys Asn Ile Ser Ala Gly Glu Trp Asn
                325                 330                 335

Lys Ala Val Gln Arg Val Ser Ala Lys Leu Arg Glu His Phe Pro Asn
                340                 345                 350

Lys Thr Ile Glu Phe Gln Pro Ser Ser Gly Gly Asp Leu Glu Ile Thr
                355                 360                 365

Thr His Ser Phe Asn Cys Arg Gly Glu Phe Phe Tyr Cys Asn Thr Ser
            370                 375                 380

Lys Leu Phe Asn Ser Ser Tyr Asn Gly Thr Ser Tyr Arg Gly Thr Glu
385                 390                 395                 400

Ser Asn Ser Ser Ile Ile Thr Leu Pro Cys Arg Ile Lys Gln Ile Ile
                405                 410                 415

Asp Met Trp Gln Lys Val Gly Arg Ala Ile Tyr Ala Pro Pro Ile Glu
            420                 425                 430

Gly Asn Ile Thr Cys Ser Ser Ser Ile Thr Gly Leu Leu Leu Ala Arg
            435                 440                 445

Asp Gly Gly Leu Asp Asn Ile Thr Thr Glu Ile Phe Arg Pro Gln Gly
            450                 455                 460

Gly Asp Met Lys Asp Asn Trp Arg Asn Glu Leu Tyr Lys Tyr Lys Val
465                 470                 475                 480

Val Glu Ile Lys Pro Leu Gly Val Ala Pro Thr Glu Ala Lys Arg Arg
                485                 490                 495

Val Val Glu Arg Glu Lys Arg Ala Val Gly Ile Gly Ala Val Ile Phe
            500                 505                 510

Gly Phe Leu Gly Ala Ala Gly Ser Asn Met Gly Ala Ala Ser Ile Thr
            515                 520                 525

Leu Thr Ala Gln Ala Arg Gln Leu Leu Ser Gly Ile Val Gln Gln Gln
            530                 535                 540

Ser Asn Leu Leu Arg Ala Ile Glu Ala Gln Gln His Met Leu Gln Leu
545                 550                 555                 560

Thr Val Trp Gly Ile Lys Gln Leu Gln Ala Arg Val Leu Ala Ile Glu
```

```
                        565                 570                 575
Arg Tyr Leu Lys Asp Gln Gln Leu Leu Gly Ile Trp Gly Cys Ser Gly
                580                 585                 590

Lys Leu Ile Cys Thr Thr Thr Val Pro Trp Asn Ser Ser Trp Ser Asn
            595                 600                 605

Lys Thr Gln Gly Glu Ile Trp Glu Asn Met Thr Trp Met Gln Trp Asp
        610                 615                 620

Lys Glu Ile Ser Asn Tyr Thr Gly Ile Ile Tyr Arg Leu Leu Glu Glu
625                 630                 635                 640

Ser Gln Asn Gln Gln Glu Gln Asn Glu Lys Asp Leu Leu Ala Leu Asp
                645                 650                 655

Ser Arg Asn Asn Leu Trp Ser Trp Phe Asn Ile Ser Asn Trp Leu Trp
                660                 665                 670

Tyr Ile Lys Ile Phe Ile Met Ile Val Gly Gly Leu Ile Gly Leu Arg
            675                 680                 685

Ile Ile Phe Ala Val Leu Ser Ile Val Asn Arg Val Arg Gln Gly Tyr
        690                 695                 700

Ser Pro Leu Ser Phe Gln Thr Leu Thr Pro Asn Pro Arg Gly Leu Asp
705                 710                 715                 720

Arg Leu Gly Arg Ile Glu Glu Glu Gly Gly Glu Gln Asp Arg Asp Arg
                725                 730                 735

Ser Ile Arg Leu Val Gln Gly Phe Leu Ala Leu Ala Trp Asp Asp Leu
            740                 745                 750

Arg Ser Leu Cys Leu Phe Ser Tyr His Arg Leu Arg Asp Leu Ile Leu
        755                 760                 765

Val Thr Ala Arg Val Val Glu Leu Leu Gly Arg Ser Ser Pro Arg Gly
770                 775                 780

Leu Gln Arg Gly Trp Glu Ala Leu Lys Tyr Leu Gly Ser Leu Val Gln
785                 790                 795                 800

Tyr Trp Gly Leu Glu Leu Lys Lys Ser Ala Thr Ser Leu Leu Asp Ser
                805                 810                 815

Ile Ala Ile Ala Val Ala Glu Gly Thr Asp Arg Ile Ile Glu Val Ile
            820                 825                 830

Gln Arg Ile Tyr Arg Ala Phe Cys Asn Ile Pro Arg Arg Val Arg Gln
        835                 840                 845

Gly Phe Glu Ala Ala Leu Gln
    850                 855

<210> SEQ ID NO 25
<211> LENGTH: 20
<212> TYPE: PRT
<213> ORGANISM: Human immunodeficiency virus

<400> SEQUENCE: 25

Asp Ile Lys Gln Gly Pro Lys Glu Pro Phe Arg Asp Tyr Val Asp Arg
1               5                   10                  15

Phe Phe Lys Thr
            20

<210> SEQ ID NO 26
<211> LENGTH: 60
<212> TYPE: DNA
<213> ORGANISM: Human immunodeficiency virus

<400> SEQUENCE: 26
gacataaaac aaggaccaaa agagcccttt agagactatg tagaccggtt ctttaaaacc    60
```

<210> SEQ ID NO 27
<211> LENGTH: 20
<212> TYPE: PRT
<213> ORGANISM: Human immunodeficiency virus

<400> SEQUENCE: 27

Asp Ile Arg Gln Gly Pro Lys Glu Pro Phe Arg Asp Tyr Val Asp Arg
1               5                   10                  15

Phe Phe Lys Thr
            20

<210> SEQ ID NO 28
<211> LENGTH: 47
<212> TYPE: PRT
<213> ORGANISM: Human immunodeficiency virus

<400> SEQUENCE: 28

Thr Ile Thr Ile Thr Cys Arg Ile Lys Gln Ile Ile Asn Met Trp Gln
1               5                   10                  15

Lys Val Gly Arg Ala Met Tyr Ala Pro Pro Ile Ala Gly Asn Leu Thr
            20                  25                  30

Cys Glu Ser Asn Ile Thr Gly Leu Leu Leu Thr Arg Asp Gly Gly
        35                  40                  45

<210> SEQ ID NO 29
<211> LENGTH: 48
<212> TYPE: PRT
<213> ORGANISM: Human immunodeficiency virus

<400> SEQUENCE: 29

Ser Ile Ile Thr Leu Pro Cys Arg Ile Lys Gln Ile Ile Asp Met Trp
1               5                   10                  15

Gln Lys Val Gly Arg Ala Ile Tyr Ala Pro Pro Ile Glu Gly Asn Ile
            20                  25                  30

Thr Cys Ser Ser Ser Ile Thr Gly Leu Leu Leu Ala Arg Asp Gly Gly
        35                  40                  45

<210> SEQ ID NO 30
<211> LENGTH: 2469
<212> TYPE: DNA
<213> ORGANISM: Artificial
<220> FEATURE:
<223> OTHER INFORMATION: PR975(+)

<400> SEQUENCE: 30
gtcgacgcca ccatggccga ggccatgagc caggccacca cgccaacat cctgatgcag      60 cgcagcaact tcaagggccc caagcgcatc atcaagtgct caactgcgg caaggagggc     120 cacatcgccc gcaactgccg cgcccccgc aagaagggc gctggaagtg cggcaaggag      180
ggccaccaga tgaaggactg caccgagcgc caggccaact tcttccgcga ggacctggcc    240
ttcccccagg caaggcccg cgagttcccc agcgagcaga accgcgccaa cagccccacc     300
agccgcgagc tgcaggtgcg cggcgacaac ccccgcagcg aggccggcgc cgagcgccag    360
ggcaccctga acttccccca gatcaccctg tggcagcgcc ccctggtgag catcaaggtg    420 ggcgccaga tcaaggaggc cctgctggac accggcgccg acgacaccgt gctggaggag    480
atgagcctgc ccggcaagtg gaagcccaag atgatcggcg gcatcggcgg cttcatcaag    540
gtgcgccagt acgaccagat cctgatcgag atctgcggca gaaggccat cggcaccgtg    600

```
ctgatcggcc caccccccgt gaacatcatc ggccgcaaca tgctgaccca gctgggctgc    660
accctgaact tccccatcag ccccatcgag accgtgcccg tgaagctgaa gcccggcatg    720
gacggcccca aggtgaagca gtggcccctg accgaggaga gatcaaggcc cctgaccgcc    780
atctgcgagg agatggagaa ggagggcaag atcaccaaga tcggccccga gaacccctac    840 aacaccccg tgttcgccat caagaagaag gacagcacca gtggcgcaa gctggtggac    900 ttccgcgagc tgaacaagcg cacccaggac ttctgggagg tgcagctggg catcccccac    960
cccgccggcc tgaagaagaa gaagagcgtg accgtgctgg acgtgggcga cgcctacttc   1020
agcgtgcccc tggacgagga cttccgcaag tacaccgcct tcaccatccc cagcatcaac   1080
aacgagaccc ccggcatccg ctaccagtac aacgtgctgc ccagggctg aagggcagc     1140 cccagcatct tccagagcag catgaccaag atcctggagc ccttccgcgc ccgcaacccc   1200
gagatcgtga tctaccagta catggacgac ctgtacgtgg cagcgacct ggagatcggc    1260 cagcaccgcg ccaagatcga ggagctgcgc aagcacctgc tgcgctgggg cttcaccacc   1320
cccgacaaga agcaccagaa ggagcccccc ttcctgtgga tgggctacga gctgcacccc   1380
gacaagtgga ccgtgcagcc catcgagctg cccgagaagg agagctggac cgtgaacgac   1440
atccagaagc tggtgggcaa gctgaactgg gccagccaga tctacccgg catcaaggtg    1500 cgccagctgt gcaagctgct gcgcggcgcc aaggccctga ccgacatcgt gcccctgacc   1560
gaggaggccg agctggagct ggccgagaac cgcgagatcc tgcgcgagcc cgtgcacggc   1620
gtgtactacg accccagcaa ggacctggtg gccgagatcc agaagcaggg ccacgaccag   1680
tggacctacc agatctacca ggagcccttc aagaacctga agaccggcaa gtacgccaag   1740
atgcgcaccg cccacaccaa cgacgtgaag cagctgaccg aggccgtgca gaagatcgcc   1800
atggagagca tcgtgatctg gggcaagacc cccaagttcc gcctgcccat ccagaaggag   1860
acctgggaga cctggtggac cgactactgg caggccacct ggatcccga gtgggagttc    1920 gtgaacaccc cccccctggt gaagctgtgg taccagctgg agaaggagcc catcatcggc   1980
gccgagacct tctacgtgga cggcgccgcc aaccgcgaga ccaagatcgg caaggccggc   2040
tacgtgaccg accggggccg gcagaagatc gtgagcctga ccgagaccac caaccagaag   2100
accgagctgc aggccatcca gctggccctg caggacagcg gcagcgaggt gaacatcgtg   2160
accgacagcc agtacgccct gggcatcatc caggcccagc ccgacaagag cgagagcgag   2220
ctggtgaacc agatcatcga gcagctgatc aagaaggaga aggtgtacct gagctgggtg   2280
cccgcccaca ggggcatcgg cggcaacgag cagatcgaca agctggtgag caagggcatc   2340
cgcaaggtgc tgttcctgga cggcatcgat ggcggcatcg tgatctacca gtacatggac   2400
gacctgtacg tggcagcgg cggccctagg atcgattaaa agcttcccgg ggctagcacc    2460
ggtgaattc                                                           2469

<210> SEQ ID NO 31
<211> LENGTH: 2463
<212> TYPE: DNA
<213> ORGANISM: Artificial
<220> FEATURE:
<223> OTHER INFORMATION: PR975YM

<400> SEQUENCE: 31
gtcgacgcca ccatggccga ggccatgagc caggccacca gcgccaacat cctgatgcag     60
cgcagcaact tcaagggccc caagcgcatc atcaagtgct tcaactgcgg caaggagggc    120
cacatcgccc gcaactgccg cgccccccgc aagaagggct gctggaagtg cggcaaggag    180
```

-continued

```
ggccaccaga tgaaggactg caccgagcgc caggccaact tcttccgcga ggacctggcc    240
ttcccccagg gcaaggcccg cgagttcccc agcgagcaga accgcgccaa cagccccacc    300
agccgcgagc tgcaggtgcg cggcgacaac ccccgcagcg aggccggcgc cgagcgccag    360
ggcaccctga acttccccca gatcaccctg tggcagcgcc cctggtgagc atcaaggtg     420
ggcggccaga tcaaggaggc cctgctggac accggcgccg acgacaccgt gctgaggag     480
atgagcctgc ccggcaagtg gaagcccaag atgatcggcg gcatcggcgg cttcatcaag    540
gtgcgccagt acgaccagat cctgatcgag atctgcggca agaaggccat cggcaccgtg    600
ctgatcggcc ccacccccgt gaacatcatc ggccgcaaca tgctgaccca gctgggctgc    660
accctgaact tccccatcag ccccatcgag accgtgcccg tgaagctgaa gcccggcatg    720
gacggcccca aggtgaagca gtggcccctg accgaggaga gatcaaggc cctgaccgcc     780
atctgcgagg agatggagaa ggagggcaag atcaccaaga tcggccccga gaaccccttac   840
aacaccccg tgttcgccat caagaagaag acagcacca agtggcgcaa gctggtggac     900
ttccgcgagc tgaacaagcg cacccaggac ttctgggagg tgcagctggg catcccccac    960
cccgccggcc tgaagaagaa gaagagcgtg accgtgctgg acgtgggcga cgcctacttc    1020
agcgtgcccc tggacgagga cttccgcaag tacaccgcct tcaccatccc cagcatcaac    1080
aacgagaccc ccggcatccg ctaccagtac aacgtgctgc ccagggctg gaagggcagc    1140
cccagcatct tccagagcag catgaccaag atcctggagc ccttccgcgc ccgcaacccc    1200
gagatcgtga tctaccaggc ccccctgtac gtgggcagcg acctggagat cggccagcac    1260
cgcgccaaga tcgaggagct gcgcaagcac ctgctgcgct ggggcttcac caccccgac    1320
aagaagcacc agaaggagcc ccccttcctg tggatgggct acgagctgca ccccgacaag    1380
tggaccgtgc agcccatcga gctgcccgag aaggagagct ggaccgtgaa cgacatccag    1440
aagctggtgg gcaagctgaa ctgggccagc cagatctacc ccggcatcaa ggtgcgccag    1500
ctgtgcaagc tgctgcgcgg cgccaaggcc ctgaccgaca tcgtgccct gaccgaggag    1560
gccgagctgg agctggccga gaaccgcgag atcctgcgcg agcccgtgca cggcgtgtac    1620
tacgacccca gcaaggacct ggtggccgag atccagaagc agggccacga ccagtggacc    1680
taccagatct accaggagcc cttcaagaac ctgaagaccg gcaagtacgc caagatgcgc    1740
accgcccaca ccaacgacgt gaagcagctg accgaggccg tgcagaagat cgccatggag    1800
agcatcgtga tctggggcaa gacccccaag ttccgcctgc ccatccagaa ggagacctgg    1860
gagacctggt ggaccgacta ctggcaggcc acctggatcc ccgagtggga gttcgtgaac    1920
accccccccc tggtgaagct gtggtaccag ctggagaagg agcccatcat cggcgccgag    1980
accttctacg tggacggcgc cgccaaccgc gagaccaaga tcggcaaggc cggctacgtg    2040
accgaccggg gccggcagaa gatcgtgagc ctgaccgaga ccaccaacca gaagaccgag    2100
ctgcaggcca tccagctggc cctgcaggac agcggcagcg aggtgaacat cgtgaccgac    2160
agccagtacg ccctgggcat catccaggcc cagcccgaca gagcgagag cgagctggtg    2220
aaccagatca tcgagcagct gatcaagaag gagaaggtgt acctgagctg ggtgcccgcc    2280
cacaagggca tcggcggcaa cgagcagatc gacaagctgg tgagcaaggg catccgcaag    2340
gtgctgttcc tggacggcat cgatggcggc atcgtgatct accagtacat ggacgacctg    2400
tacgtgggca gcggcggccc taggatcgat taaaagcttc ccggggctag caccggtgaa    2460
ttc                                                                   2463
```

<210> SEQ ID NO 32
<211> LENGTH: 2457
<212> TYPE: DNA
<213> ORGANISM: Artificial
<220> FEATURE:
<223> OTHER INFORMATION: PR975YMWM

<400> SEQUENCE: 32

| | | | | | | |
|---|---|---|---|---|---|---|
| gtcgacgcca | ccatggccga | ggccatgagc | caggccacca | gcgccaacat | cctgatgcag | 60 |
| cgcagcaact | tcaagggccc | caagcgcatc | atcaagtgct | tcaactgcgg | caaggagggc | 120 |
| cacatcgccc | gcaactgccg | cgccccccgc | aagaagggcg | gctggaagtg | cggcaaggag | 180 |
| ggccaccaga | tgaaggactg | caccgagcgc | caggccaact | tcttccgcga | ggacctggcc | 240 |
| ttcccccagg | gcaaggcccg | cgagttcccc | agcgagcaga | accgcgccaa | cagccccacc | 300 |
| agccgcgagc | tgcaggtgcg | cggcgacaac | ccccgcagcg | aggccggcgc | cgagcgccag | 360 |
| ggcaccctga | acttccccca | gatcaccctg | tggcagcgcc | ccctggtgag | catcaaggtg | 420 |
| ggcggccaga | tcaaggaggc | cctgctggac | accggcgccg | acgacaccgt | gctggaggag | 480 |
| atgagcctgc | ccggcaagtg | gaagcccaag | atgatcggcg | catcggcgg | cttcatcaag | 540 |
| gtgcgccagt | acgaccagat | cctgatcgag | atctgcggca | agaaggccat | cggcaccgtg | 600 |
| ctgatcggcc | caccccccgt | gaacatcatc | ggccgcaaca | tgctgaccca | gctgggctgc | 660 |
| accctgaact | tccccatcag | ccccatcgag | accgtgcccg | tgaagctgaa | gcccggcatg | 720 |
| gacggcccca | aggtgaagca | gtggcccctg | accgaggaga | gatcaaggc | cctgaccgcc | 780 |
| atctgcgagg | agatggagaa | ggagggcaag | atcaccaaga | tcggccccga | gaaccctac | 840 |
| aacacccccg | tgttcgccat | caagaagaag | gacagcacca | gtggcgcaa | gctggtggac | 900 |
| ttccgcgagc | tgaacaagcg | cacccaggac | ttctgggagg | tgcagctggg | catcccccac | 960 |
| cccgccggcc | tgaagaagaa | gaagagcgtg | accgtgctgg | acgtgggcga | cgcctacttc | 1020 |
| agcgtgcccc | tggacgagga | cttccgcaag | tacaccgcct | tcaccatccc | cagcatcaac | 1080 |
| aacgagaccc | ccggcatccg | ctaccagtac | aacgtgctgc | ccagggctg | gaagggcagc | 1140 |
| cccagcatct | tccagagcag | catgaccaag | atcctggagc | ccttccgcgc | ccgcaacccc | 1200 |
| gagatcgtga | tctaccaggc | cccccctgtac | gtgggcagcg | acctggagat | cggccagcac | 1260 |
| cgcgccaaga | tcgaggagct | cgcaagcac | ctgctgcgct | ggggcttcac | cacccccgac | 1320 |
| aagaagcacc | agaaggagcc | ccccttcctg | cccatcgagc | tgcaccccga | caagtggacc | 1380 |
| gtgcagccca | tcgagctgcc | cgagaaggag | agctggaccg | tgaacgacat | ccagaagctg | 1440 |
| gtgggcaagc | tgaactgggc | cagccagatc | taccccggca | tcaaggtgcg | ccagctgtgc | 1500 |
| aagctgctgc | gcgcgccaa | ggccctgacc | gacatcgtgc | ccctgaccga | ggaggccgag | 1560 |
| ctggagctgg | ccgagaaccg | cgagatcctg | cgcgagcccg | tgcacggcgt | gtactacgac | 1620 |
| cccagcaagg | acctggtggc | cgagatccag | aagcagggcc | acgaccagtg | gacctaccag | 1680 |
| atctaccagg | agcccttcaa | gaacctgaag | accggcaagt | acgccaagat | gcgcaccgcc | 1740 |
| cacaccaacg | acgtgaagca | gctgaccgag | gccgtgcaga | gatcgccat | ggagagcatc | 1800 |
| gtgatctggg | gcaagacccc | caagttccgc | ctgcccatcc | agaaggagac | ctgggagacc | 1860 |
| tggtggaccg | actactggca | ggccacctgg | atccccgagt | gggagttcgt | gaacacccc | 1920 |
| cccctggtga | agctgtggta | ccagctggag | aaggagccca | tcatcggcgc | cgagaccttc | 1980 |
| tacgtggacg | cgccgccaa | ccgcgagacc | aagatcggca | aggccggcta | cgtgaccgac | 2040 |
| cggggccggc | agaagatcgt | gagcctgacc | gagaccacca | accagaagac | cgagctgcag | 2100 |

```
gccatccagc tggccctgca ggacagcggc agcgaggtga acatcgtgac cgacagccag   2160
tacgccctgg gcatcatcca ggcccagccc gacaagagcg agagcgagct ggtgaaccag   2220
atcatcgagc agctgatcaa gaaggagaag gtgtacctga gctgggtgcc cgcccacaag   2280
ggcatcggcg gcaacgagca gatcgacaag ctggtgagca agggcatccg caaggtgctg   2340
ttcctggacg gcatcgatgg cggcatcgtg atctaccagt acatggacga cctgtacgtg   2400
ggcagcggcg gccctaggat cgattaaaag cttcccgggg ctagcaccgg tgaattc     2457
```

<210> SEQ ID NO 33
<211> LENGTH: 9781
<212> TYPE: DNA
<213> ORGANISM: Human immunodeficiency virus

<400> SEQUENCE: 33

```
tggaagggtt aatttactcc aagaaaaggc aagaaatcct tgatttgtgg gtctatcaca     60
cacaaggctt cttccctgat tggcaaaact acacaccggg gccaggggtc agatatccac    120
tgacctttgg atggtgctac aagctagtgc cagttgaccc aggggaggtg aagaggccaa    180
acggaggaga agacaactgt ttgctacacc ctatgagcca catggagca gaggatgaag    240 atagagaagt attaaagtgg aagtttgaca gcctcctagc acgcagacac atggcccgcg    300
agctacatcc ggagtattac aaagactgct gacacagaag ggactttccg cctgggactt    360
tccactgggg cgttccggga ggtgtggtct gggcgggact tgggagtggt caaccctcag    420
atgctgcata taagcagctg cttttcgcct gtactgggtc tctctcggta gaccagatct    480
gagcctggga gcctctggc tatctaggga acccactgct taagcctcaa taaagcttgc    540
cttgagtgct ttaagtagtg tgtgcccatc tgttgtgtga ctctggtaac tagagatccc    600
tcagaccctt tgtggtagtg tggaaaatct ctagcagtgg cgcccgaaca gggaccagaa    660
agtgaaagtg agaccagagg agatctctcg acgcaggact cggcttgctg aagtgcacac    720
ggcaagaggc gagaggggcg gctggtgagt acgccaattt tacttgacta gcggaggcta    780
gaaggagaga gatgggtgcg agagcgtcaa tattaagcgg cggaaaatta gataaatggg    840
aaagaattag gttaaggcca gggggaaaga acattatat gttaaaacat ctagtatggg    900
caagcaggga gctggaaaga tttgcactta accctggcct gttagaaaca tcagaaggct    960
gtaaacaaat aataaaacag ctacaaccag ctcttcagac aggaacagag gaacttagat   1020
cattattcaa cacagtagca actctctatt gtgtacataa agggatagag gtacgagaca   1080
ccaaggaagc cttagacaag atagaggaag aacaaaacaa atgtcagcaa aaagcacaac   1140
aggcaaaagc agctgacgaa aaggtcagtc aaaattatcc tatagtacag aatgcccaag   1200
ggcaaatggt acaccaagct atatcaccta gaacattgaa tgcatggata aaagtaatag   1260
aggaaaaggc tttcaatcca gaggaaatac ccatgtttac agcattatca gaaggagcca   1320
ccccacaaga tttaaacaca atgttaaata cagtgggggg acatcaagca gccatgcaaa   1380
tgttaaaaga taccatcaat gaggaggctg cagaatggga taggacacat ccagtacatg   1440
cagggcctgt tgcaccaggc cagatgagag aaccaagggg aagtgacata gcaggaacta   1500
ctagtaccct tcaggaacaa atagcatgga tgacaagtaa tccacctatt ccagtagaag   1560
acatctataa aagatggata attctgggt taaataaaat agtaagaatg tatagccctg   1620
ttagcatttt ggcataaaaa caaggggccaa aagaaccctt tagagactat gtagaccggt   1680
tctttaaaac cttaagagct gaacaagcta cacaagatgt aaagaattgg atgacagaca   1740
```

```
ccttgttggt ccaaaatgcg aacccagatt gtaagaccat tttaagagca ttaggaccag   1800
gggcctcatt agaagaaatg atgacagcat gtcagggagt gggaggacct agccataaag   1860
caagagtgtt ggctgaggca atgagccaag caaacagtaa catactagtg cagagaagca   1920
attttaaagg ctctaacaga attattaaat gtttcaactg tggcaaagta gggcacatag   1980
ccagaaattg cagggcccct aggaaaaagg gctgttggaa atgtggacag aaggacacc    2040 aaatgaaaga ctgtactgag aggcaggcta atttttagg gaaaatttgg ccttcccaca    2100
aggggaggcc agggaatttc ctccagaaca gaccagagcc aacagcccca ccagcagaac   2160
caacagcccc accagcagag agcttcaggt tcgaggagac aaccccgtg ccgaggaagg    2220 agaaagagag ggaaccttta acttccctca aatcactctt tggcagcgac cccttgtctc   2280
aataaaagta gagggccaga taaggaggc tctcttagac acaggagcag atgatacagt    2340
attagaagaa atagatttgc cagggaaatg gaaaccaaaa atgatagggg gaattggagg   2400
ttttatcaaa gtaagacagt atgatcaaat acttatagaa atttgtggaa aaaaggctat   2460
aggtacagta ttagtagggc ctacaccagt caacataatt ggaagaaatc tgttaactca   2520
gcttggatgc acactaaatt ttccaattag tcctattgaa actgtaccag taaaattaaa   2580
accaggaatg gatggcccaa aggtcaaaca atggccattg acagaagaaa aataaaagc    2640 attaacagca atttgtgagg aaatggagaa ggaaggaaaa attacaaaaa ttgggcctga   2700
taatccatat aacactccag tatttgccat aaaaaagaag acagtacta agtggagaaa    2760 attagtagat ttcagggaac tcaataaaag aactcaagac ttttgggaag ttcaattagg   2820
aataccacac ccagcaggat taaaaagaa aaaatcagtg acagtgctag atgtggggga    2880 tgcatattt tcagttcctt tagatgaaag cttcaggaaa tatactgcat tcaccatacc    2940
tagtataaac aatgaaacac cagggattag atatcaatat aatgtgctgc cacagggatg   3000
gaaaggatca ccagcaatat tccagagtag catgacaaaa atcttagagc ccttcagagc   3060
aaaaaatcca gacatagtta tctatcaata tatggatgac ttgtatgtag gatctgactt   3120
agaaataggg caacatagag caaaaataga agagttaagg gaacatttat tgaaatgggg   3180
atttacaaca ccagacaaga aacatcaaaa agaaccccca tttctttgga tggggtatga   3240
actccatcct gacaaatgga cagtacaacc tatactgctg ccagaaaagg atagttggac   3300
tgtcaatgat atacagaagt tagtgggaaa attaaactgg gcaagtcaga tttacccagg   3360
gattaaagta aggcaactct gtaaactcct caggggggcc aaagcactaa cagacatagt   3420
accactaact gaagaagcag aattagaatt ggcagagaac agggaaattt taagagaacc   3480
agtacatgga gtatattatg atccatcaaa agacttgata gctgaaatac agaaacaggg   3540
gcatgaacaa tggacatatc aaatttatca agaaccattt aaaaatctga aaacagggaa   3600
gtatgcaaaa atgaggacta cccacactaa tgatgtaaaa cagttaacag aggcagtgca   3660
aaaaatagcc atgaaagca tagtaatatg gggaaagact cctaaattta gactacccat     3720
ccaaaaagaa acatgggaga catggtggac agactattgg caagccacct ggatccctga   3780
gtgggagttt gttaataccc ctcccctagt aaaattatgg taccaactag aaaaagatcc   3840
catagcagga gtagaaactt tctatgtaga tggagcaact aatagggaag ctaaaatagg   3900
aaaagcaggg tatgttactg acagaggaag gcagaaaatt gttactctaa ctaacacaac   3960
aaatcagaag actgagttac aagcaattca gctagctctg caggattcag gatcagaagt   4020
aaacatagta acagactcac agtatgcatt aggaatcatt caagcacaac cagataagag   4080
tgactcagag atatttaacc aaataataga acagttaata aacaaggaaa gaatctacct   4140
```

```
gtcatgggta ccagcacata aaggaattgg gggaaatgaa caagtagata aattagtaag    4200
taagggaatt aggaaagtgt tgtttctaga tggaatagat aaagctcaag aagagcatga    4260
aaggtaccac agcaattgga gagcaatggc taatgagttt aatctgccac ccatagtagc    4320
aaaagaaata gtagctagct gtgataaatg tcagctaaaa ggggaagcca tacatggaca    4380
agtcgactgt agtccaggga tatgcaatt agattgtacc catttagagg gaaaaatcat    4440
cctggtagca gtccatgtag ctagtggcta catggaagca gaggttatcc cagcagaaac    4500
aggacaagaa acagcatatt ttatattaaa attagcagga agatggccag tcaaagtaat    4560
acatacagac aatggcagta attttaccag tactgcagtt aaggcagcct gttggtgggc    4620
aggtatccaa caggaatttg gaattcccta caatccccaa agtcagggag tggtagaatc    4680
catgaataaa gaattaaaga aaataatagg acaagtaaga gatcaagctg agcaccttaa    4740
gacagcagta caaatggcag tattcattca caattttaaa agaaaagggg gaattggggg    4800
gtacagtgca ggggaaagaa taatagacat aatagcaaca gacatacaaa ctaaagaatt    4860
acaaaaacaa attataagaa ttcaaaattt tcgggtttat tacagagaca gcagagaccc    4920
tatttggaaa ggaccagccg aactactctg gaaaggtgaa ggggtagtag taatagaaga    4980
taaaggtgac ataaaggtag taccaaggag gaaagcaaaa atcattagag attatggaaa    5040
acagatggca ggtgctgatt gtgtggcagg tggacaggat gaagattaga gcatggaata    5100
gtttagtaaa gcaccatatg tatatatcaa ggagagctag tggatgggtc tacagacatc    5160
attttgaaag cagacatcca aaagtaagtt cagaagtaca tatcccatta ggggatgcta    5220
gattagtaat aaaaacatat tggggtttgc agacaggaga aagagattgg catttgggtc    5280
atggagtctc catagaatgg agactgagag aatacagcac acaagtagac cctgacctgg    5340
cagaccagct aattcacatg cattattttg attgttttac agaatctgcc ataagacaag    5400
ccatattagg acacatagtt tttcctaggt gtgactatca agcaggacat aagaaggtag    5460
gatctctgca atacttggca ctgacagcat tgataaaacc aaaaaagaga agccacctc    5520 tgcctagtgt tagaaaatta gtagaggata gatggaacga cccccagaag accaggggcc    5580
gcagagggaa ccatacaatg aatggacact agagattcta gaagaactca gcaggaagc    5640 tgtcagacac tttcctagac catggctcca tagcttagga caatatatct atgaaaccta    5700 tgggatact tggacgggag ttgaagctat aataagagta ctgcaacaac tactgttcat    5760
tcatttcaga attggatgcc aacatagcag aataggcatc ttgcgacaga gaagagcaag    5820
aaatggagcc agtagatcct aaactaaagc cctggaacca tccaggaagc caacctaaaa    5880
cagcttgtaa taattgcttt tgcaaacact gtagctatca ttgtctagtt tgctttcaga    5940
caaaaggttt aggcatttcc tatggcagga agaagcggag acagcgacga agcgctcctc    6000
caagtggtga gatcatcaa aatcctctat caaagcagta agtacacata gtagatgtaa    6060
tggtaagttt aagtttattt aaaggagtag attatagatt aggagtagga cattgatag    6120 tagcactaat catagcaata atagtgtgga ccatagcata tatagaatat aggaaattgg    6180
taagacaaaa gaaaatagac tggttaatta aaagaattag ggaaagagca gaagacagtg    6240
gcaatgagag tgatgggac acagaagaat tgtcaacaat ggtggatatg ggcatctta    6300 ggcttctgga tgctaatgat ttgtaacacg gaggacttgt gggtcacagt ctactatggg    6360
gtacctgtgt ggagagaagc aaaaactact ctattctgtg catcagatgc taaagcatat    6420
gagacagaag tgcataatgt ctgggctaca catgcttgtg tacccacaga ccccaaccca    6480
```

```
caagaaatag ttttgggaaa tgtaacagaa aatttaata tgtggaaaaa taacatggca   6540
gatcagatgc atgaggatat aatcagttta tgggatcaaa gcctaaagcc atgtgtaaag   6600
ttgaccccac tctgtgtcac tttaaactgt acagatacaa atgttacagg taatagaact   6660
gttacaggta atacaaatga taccaatatt gcaaatgcta catataagta tgaagaaatg   6720
aaaaattgct ctttcaatgc aaccacagaa ttaagagata gaaacataa agagtatgca    6780 ctcttttata aacttgatat agtaccactt aatgaaaata gtaacaactt tacatataga   6840
ttaataaatt gcaataccctc aaccataaca caagcctgtc caaggtctc ttttgacccg    6900 attcctatac attactgtgc tccagctgat tatgcgattc taaagtgtaa taataagaca   6960
ttcaatggga caggaccatg ttataatgtc agcacagtac aatgtacaca tggaattaag   7020
ccagtggtat caactcaact actgttaaat ggtagtctag cagaagaagg gataataatt   7080
agatctgaaa atttgacaga gaataccaaa acaataatag tacatcttaa tgaatctgta   7140
gagattaatt gtacaaggcc caacaataat acaaggaaaa gtgtaaggat aggaccagga   7200
caagcattct atgcaacaaa tgacgtaata ggaaacataa gacaagcaca ttgtaacatt   7260
agtacagata gatggaataa aactttacaa caggtaatga aaaaattagg agagcatttc   7320
cctaataaaa caataaaatt tgaaccacat gcaggagggg atctagaaat tacaatgcat   7380
agctttaatt gtagaggaga atttttctat tgcaatacat caaacctgtt taatagtaca   7440
tactacccta agaatggtac atacaaatac aatggtaatt caagcttacc catcacactc   7500
caatgcaaaa taaaacaaat tgtacgcatg tggcaagggg taggacaagc aatgtatgcc   7560
cctcccattg caggaaacat aacatgtaga tcaaacatca caggaatact attgacacgt   7620 gatggggat ttaacaacac aaacaacgac acagaggaga cattcagacc tggaggagga    7680
gatatgaggg ataactggag aagtgaatta tataaatata agtggtaga aattaagcca    7740 ttgggaatag cacccactaa ggcaaaaaga agagtggtgc agagaaaaaa aagagcagtg   7800
ggaataggag ctgtgttcct tgggttcttg ggagcagcag gaagcactat gggcgcagcg   7860
tcaataacgc tgacggtaca ggccagacaa ctgttgtctg gtatagtgca acagcaaagc   7920
aatttgctga aggctataga ggcgcaacag catatgttgc aactcacagt ctggggcatt   7980
aagcagctcc aggcgagagt cctggctata gaaagatacc taaaggatca acagctccta   8040
gggatttggg gctgctctgg aagactcatc tgcaccactg ctgtgccttg gaactccagt   8100
tggagtaata atctgaagc agatatttgg gataacatga cttggatgca gtgggataga   8160
gaaattaata attacacaga acaatattc aggttgcttg aagactcgca aaaccagcag   8220
gaaaagaatg aaaagatt attagaattg gacaagtgga ataatctgtg gaattggttt    8280
gacatatcaa actggctgtg gtatataaaa atattcataa tgatagtagg aggcttgata   8340
ggtttaagaa taatttttgc tgtgctctct atagtgaata gagttaggca gggatactca   8400
cctttgtcat ttcagacccct taccccaagc ccgagggac tcgacaggct cggaggaatc   8460
gaagaagaag gtggagagca agacagagac agatccatac gattggtgag cggattcttg   8520
tcgcttgcct gggacgatct gcggagcctg tgcctcttca gctaccaccg cttgagagac   8580
ttcatattaa ttgcagtgag gcagtggaa cttctgggac acagcagtct caggggacta    8640
cagggggggg gggagatcct taagtatctg ggaagtcttg tgcagtattg ggtctagag    8700 ctaaaaaaga gtgctattag tccgcttgat accatagcaa tagcagtagc tgaaggaaca   8760
gataggatta tagaattggt acaaagaatt tgtagagcta tcctcaacat acctaggaga   8820
ataagacagg gctttgaagc agcttttgcta taaaatggga ggcaagtggt caaaacgcag   8880
```

-continued

| | |
|---|---|
| catagttgga tggcctgcag taagagaaag aatgagaaga actgagccag cagcagaggg | 8940 |
| agtaggagca gcgtctcaag acttagatag acatggggca cttacaagca gcaacacacc | 9000 |
| tgctactaat gaagcttgtg cctggctgca agcacaagag gaggacggag atgtaggctt | 9060 |
| tccagtcaga cctcaggtac ctttaagacc aatgacttat aagagtgcag tagatctcag | 9120 |
| cttcttttta aaagaaaagg ggggactgga agggttaatt tactctagga aaaggcaaga | 9180 |
| aatccttgat ttgtgggtct ataacacaca aggcttcttc cctgattggc aaaactacac | 9240 |
| atcggggcca ggggtccgat tcccactgac ctttggatgg tgcttcaagc tagtaccagt | 9300 |
| tgacccaagg gaggtgaaag aggccaatga aggagaagac aactgtttgc tacaccctat | 9360 |
| gagccaacat ggagcagagg atgaagatag agaagtatta aagtggaagt ttgacagcct | 9420 |
| tctagcacac agacacatgg cccgcgagct acatccggag tattacaaag actgctgaca | 9480 |
| cagaagggac tttccgcctg ggactttcca ctggggcgtt ccgggaggtg tggtctgggc | 9540 |
| gggacttggg agtggtcacc ctcagatgct gcatataagc agctgctttt cgcttgtact | 9600 |
| gggtctctct cggtagacca gatctgagcc tgggagctct ctggctatct agggaaccca | 9660 |
| ctgcttaggc ctcaataaag cttgccttga gtgctctaag tagtgtgtgc ccatctgttg | 9720 |
| tgtgactctg gtaactagag atccctcaga ccctttgtgg tagtgtggaa aatctctagc | 9780 |
| a | 9781 |

<210> SEQ ID NO 34
<211> LENGTH: 203
<212> TYPE: DNA
<213> ORGANISM: Human immunodeficiency virus

<400> SEQUENCE: 34

| | |
|---|---|
| gctgaggcaa tgagccaagc aaccagcgca acatactga tgcagagaag caatttcaaa | 60 |
| ggccctaaaa gaattattaa atgtttcaac tgtggcaagg aagggcacat agctagaaat | 120 |
| tgtagggccc ctaggaaaaa aggctgttgg aaatgtggaa aggaaggaca ccaaatgaaa | 180 |
| gactgtactg agaggcaggc taa | 203 |

<210> SEQ ID NO 35
<211> LENGTH: 2151
<212> TYPE: DNA
<213> ORGANISM: Human immunodeficiency virus

<400> SEQUENCE: 35

| | |
|---|---|
| tttttttaggg aagatttggc cttcccacaa gggaaggcca gggaatttcc ttcagaacag | 60 |
| aacagagcca acagccccac cagcagagag cttcaagttc gaggagacaa ccccgctcc | 120 |
| gaagcaggag ccgaaagaca gggaaccctt aatttccctc aaatcactct ttggcagcga | 180 |
| ccccttgtct caataaaagt aggggggtcaa ataaaggagg ctctcttaga cacaggagct | 240 |
| gatgatacag tattagaaga aatgagtttg ccaggaaaat ggaaaccaaa aatgataggag | 300 |
| ggaattggag gttttatcaa agtaagacag tatgatcaaa tacttataga atttgtgga | 360 |
| aaaaaggcta taggtacagt attaatagga cctacacctg tcaacataat tggaaggaat | 420 |
| atgttgactc agcttggatg cacactaaat tttccaatta gtcccattga aactgtgcca | 480 |
| gtaaaattaa agccaggaat ggatggccca aaggttaaac aatggccatt gacagaagag | 540 |
| aaaataaaag cattaacagc aatttgtgaa gaaatggaga agaaggaaa attacaaaa | 600 |
| attgggcctg aaaatccata taacactcca gtatttgcca taaaaagaa ggacagtact | 660 |

```
aagtggagaa agttagtaga tttcagggaa cttaataaaa gaactcaaga cttttgggaa      720
gttcaattag gaataccaca cccagcaggg ttaaaaaaga aaaaatcagt gacagtactg      780
gatgtggggg atgcatattt ttcagttcct ttagatgagg acttcaggaa atatactgca      840
ttcaccatac ctagtataaa caatgaaaca ccagggatta gatatcaata taatgtgctt      900
ccacagggat ggaaaggatc accatcaata ttccagagta gcatgacaaa atcttagag      960 cccctttagag caagaaatcc agaaatagtc atctatcaat atatggatga cttgtatgta     1020
ggatctgact tagaaatagg gcaacataga gcaaaaatag aggagttaag aaaacatctg     1080
ttaaggtggg gatttaccac accggacaag aaacatcaga agaaccccc atttctttgg     1140 atggggtatg aactccatcc tgacaaatgg acagtacagc ctatagagtt gccagaaaag     1200
gaaagctgga ctgtcaatga tatacagaag ttagtgggaa aattaaattg ggccagtcag     1260
atttacccag gaattaaagt aaggcaactt tgtaaactcc ttagggggc caaagcacta     1320 acagatatag taccactaac tgaagaagca gaattagaat ggcagagaa cagggaaatt     1380 ctaagagaac cagtacatgg agtatattat gacccatcaa agacttggt agctgaaata     1440 cagaaacagg ggcatgacca atggacatat caaatttacc aagaaccatt caaaaacctg     1500
aaaacaggga agtatgcaaa aatgaggact gcccacacta atgatgtaaa acagttaaca     1560
gaggcagtgc aaaaaatagc tatggaaagc atagtaatat ggggaaagac tcctaaattt     1620 agactacccca tccaaaaaga aacatgggag acatggtgga cagactattg gcaagccacc     1680
tggattcctg agtgggagtt tgttaatacc cctcccttag taaaattatg gtaccagcta     1740
gagaaagaac ccataatagg agcagaaact ttctatgtag atggagcagc taatagggaa     1800
actaaaatag gaaaagcagg gtatgttact gacagaggaa ggcagaaaat tgtttctcta     1860
acagaaacaa caaatcagaa gactgaatta caagcaattc agctagcttt gcaagattca     1920
ggatcagaag taaacatagt aacagactca cagtatgcat taggaatcat tcaagcacaa     1980
ccagataaga gtgaatcaga gttagtcaac caaataatag aacaattaat aaaaaaggaa     2040
aaggtctacc tgtcatgggt accagcacat aaaggaattg gaggaaatga acaaatagat     2100
aaattagtaa gtaagggaat caggaaagtg ctgtttctag atggaataga t             2151

<210> SEQ ID NO 36
<211> LENGTH: 54
<212> TYPE: DNA
<213> ORGANISM: Human immunodeficiency virus

<400> SEQUENCE: 36
ggcggcatcg tgatctacca gtacatggac gacctgtacg tgggcagcgg cggc           54

<210> SEQ ID NO 37
<211> LENGTH: 18
<212> TYPE: PRT
<213> ORGANISM: Human immunodeficiency virus

<400> SEQUENCE: 37

Gly Gly Ile Val Ile Tyr Gln Tyr Met Asp Asp Leu Tyr Val Gly Ser
1               5                   10                  15

Gly Gly

<210> SEQ ID NO 38
<211> LENGTH: 38
<212> TYPE: DNA
<213> ORGANISM: Artificial
<220> FEATURE:
```

<223> OTHER INFORMATION: primer S1FCSacTA

<400> SEQUENCE: 38
gtttcttgag ctctggaagg gttaatttac tccaagaa          38

<210> SEQ ID NO 39
<211> LENGTH: 38
<212> TYPE: DNA
<213> ORGANISM: Artificial
<220> FEATURE:
<223> OTHER INFORMATION: primer S1FTSacTA

<400> SEQUENCE: 39
gtttcttgag ctctggaagg gttaatttac tctaagaa          38

<210> SEQ ID NO 40
<211> LENGTH: 35
<212> TYPE: DNA
<213> ORGANISM: Artificial
<220> FEATURE:
<223> OTHER INFORMATION: primer S145RTSalTA

<400> SEQUENCE: 40
gtttcttgtc gacttgtcca tgtatggctt cccct          35

<210> SEQ ID NO 41
<211> LENGTH: 34
<212> TYPE: DNA
<213> ORGANISM: Artificial
<220> FEATURE:
<223> OTHER INFORMATION: primer S145RCSalTA

<400> SEQUENCE: 41
gtttcttgtc gacttgtcca tgcatggctt ccct          34

<210> SEQ ID NO 42
<211> LENGTH: 38
<212> TYPE: DNA
<213> ORGANISM: Artificial
<220> FEATURE:
<223> OTHER INFORMATION: primer S245FASalTA

<400> SEQUENCE: 42
gtttcttgtc gactgtagtc caggaatatg gcaattag          38

<210> SEQ ID NO 43
<211> LENGTH: 38
<212> TYPE: DNA
<213> ORGANISM: Artificial
<220> FEATURE:
<223> OTHER INFORMATION: primer S245FGSalTA

<400> SEQUENCE: 43
gtttcttgtc gactgtagtc cagggatatg gcaattag          38

<210> SEQ ID NO 44
<211> LENGTH: 39
<212> TYPE: DNA
<213> ORGANISM: Artificial
<220> FEATURE:
<223> OTHER INFORMATION: primer S2FullNotTA

<400> SEQUENCE: 44
gtttcttgcg gccgctgcta gagattttcc acactacca          39

<210> SEQ ID NO 45
<211> LENGTH: 9738
<212> TYPE: DNA
<213> ORGANISM: Human immunodeficiency virus

<400> SEQUENCE: 45

```
tggaagggtt aatttactcc aggaaaaggc aagagatcct tgatttatgg gtctatcaca      60
cacaaggcta cttccctgat tggcaaaact acacaccggg accagggtc agatatccac     120
tgacctttgg atggtgcttc aagctagtgc cagttgaccc aagggaagta aagaggcca     180
acggaggaga agacaactgt ttgctacacc ctatgagcca gtatggaatg gatgatgaac     240
acaaagaagt gttacagtgg aagtttgaca gcagcctagc acgcagacac ctggcccgcg     300
agctacatcc ggattattac aaagactgct gacacagaag gactttccg cctgggactt     360
tccactgggg cgttccaggg ggagtggtct gggcgggact gggagtggcc agccctcaga     420
tgctgcatat aagcagcggc ttttcgcctg tactgggtct ctctaggtag accagatccg     480
agcctgggag ctctctgtct atctggggaa cccactgctt aggcctcaat aaagcttgcc     540
ttgagtgctc taagtagtgt gtgcccatct gttgtgtgac tctggtaact ctggtaacta     600
gagatccctc agacccttg tggtagtgtg aaaatctct agcagtggcg cccgaacagg     660
gacttgaaag cgaaagtgag accagagaag atctctcgac gcaggactcg gcttgctgaa     720
gtgcactcgg caagaggcga ggggggcgac tggtgagtac gccaaaattt tttttgacta     780
gcggaggcta aaggagagag gatgggtgcg agagcgtcaa tattaagagg gggaaaatta     840
gacaaatggg aaaaaattag gttacggcca gggggagaa acactatat gctaaaacac     900
ctagtatggg caagcagaga gctggaaaga tttgcagtta accctggcct tttagagaca     960
tcagacggat gtagacaaat aataaaacag ctacaaccag ctcttcagac aggaacagag    1020
gaaattagat cattattta cacagtagca actctctatt gtgtacataa agggatagat    1080
gtacgagaca ccaaggaagc cttagacaag atagaggagg aacaaaacaa atgtcagcaa    1140
aaaacacagc aggcggaagc ggctgacaaa aaggtcagtc aaaattatcc tatagtgcag    1200
aacctccaag gcaaatggt acaccaggcc atatcaccta gaaccttgaa tgcatgggta    1260
aaagtaatag aggagaaggc ttttagccca gaggtaatac ccatgtttac agcattatca    1320
gaaggagcca ccccacaaga tttaaacacc atgttaaata cagtgggggg acatcaagca    1380
gccatgcaaa tgttaaaaga taccatcaat gaggaggctg cagaatggga taggttacat    1440
ccagtacatg cagggcctgt tgcaccaggc cagatgagag aaccaagggg aagtgacata    1500
gcaggaacta ctagtaccct tcaagaacaa atagcatgga tgacaagtaa cccacctatc    1560
ccagtagggg acatctataa aaggtggata attctggggt taaataaaat agtaagaatg    1620
tacagccctg tcagcatttt agacataaaa caaggaccaa ggaacccctt tagagactat    1680
gtagaccggt tctttcaaaac tttaagagct gaacaatcta caagaggt aaaaaattgg    1740
atgacagaca ccttgttagt ccaaaatgcg aacccagatt gtaagaccat tttaagagca    1800
ttaggaccag gggcttcatt agaagaaatg atgacagcat gtcagggagt gggaggacct    1860
agccacaaag caagagtttt ggctgaggca atgagccaag caacaatac aagtgtaatg    1920
atacagaaaa gcaattttaa aggccctaga agagctgtta aatgtttcaa ctgtggcagg    1980
gaagggcaca tagccaggaa ttgcagggcc cctaggaaaa ggggctgttg gaaatgtgga    2040
aaggaaggac accaaatgaa agactgtact gagaggcagg ctaatttttt agggaaaatt    2100
tggccttccc acaaggggag gccagggaat ttccttcaga gcagaccaga gccaacagcc    2160
```

-continued

```
ccaccactag aaccaacagc cccaccagca gagagcttca agttcaagga gactccgaag    2220
caggagccga aagacaggga acctttaact tccctcaaat cactctttgg cagcgacccc    2280
ttgtctcaat aaaagtagcg ggccaaacaa aggaggctct tttagataca ggagcagatg    2340
atacagtact agaagaaata aacttgccag gaaaatggaa accaaaaatg ataggaggaa    2400
ttggaggttt tatcaaagta agacagtatg atcaaatact tatagaaatt tgtggaaaaa    2460
gggctatagg tacagtatta gtaggaccta cacctgtcaa cataattgga agaaatctgt    2520
tgactcagct tggatgcaca ctaaattttc caattagccc cattgaaact gtaccagtaa    2580
aattaaagcc aggaatggat ggcccaaagg ttaaacaatg gccattgaca gaagaaaaaa    2640
taaaagcatt aacagaaatt tgtgaggaaa tggagaagga aggaaaaatt acaaaaattg    2700
ggcctgaaaa tccatataac actccagtat ttgccataaa gaagaaggac agtacaaagt    2760
ggagaaaatt agtagatttc agggaactca ataaaagaac tcaagacttt tgggaagtcc    2820
aattaggaat accacaccca gcagggttaa aaagaaaaaa atcagtgaca gtactggatg    2880
tgggagatgc atattttca gtccctttag atgagagctt cagaaaatat actgcattca    2940
ccatacctag tataaacaat gaaacaccag ggattagata tcaatataat gttcttccac    3000
agggatggaa aggatcacca gcaatattcc agagtagcat gacaagaatc ttagagccct    3060
ttagaacaca aaacccagaa gtagttatct atcaatatat ggatgactta tatgtaggat    3120
ctgacttaga aatagggcaa catagagcaa aaatagagga gttaagagga cacctattga    3180 aatgggggatt taccacacca gacaagaaac atcagaaaga accccccattt ctttggatgg    3240 ggtatgaact ccatcctgac aaatggacag tacagcctat acagctgcca gaaaaggaga    3300
gctggactgt caatgatata cagaagttag tgggaaagtt aaactgggca agtcagattt    3360
acccagggat taaagtaagg caactgtgta aactccttag gggagccaaa gcactaacag    3420
acatagtgcc actgactgaa gaagcagaat tagaattggc tgagaacagg gaaattctaa    3480
aagaaccagt acatggagta tattatgacc catcaaaaga tttaatagct gaaatacaga    3540
aacaggggaa tgaccaatgg acatatcaaa tttaccaaga accatttaaa aatctgagaa    3600
caggaaagta tgcaaaaatg aggactgccc acactaatga tgtgaaacag ttagcagagg    3660
cagtgcaaaa gataacccag gaaagcatag taatatgggg aaaaactcct aaatttagac    3720
tacccatccc aaaagaaaca tgggagacat ggtggtcaga ctattggcaa gccacctgga    3780
ttcctgagtg ggagtttgtc aatacccctc cctagtaaa attgtggtac cagctggaaa    3840
aagaacccat agtaggggca gaaactttct atgtagatgg agcagccaat agggaaacta    3900
aaataggaaa agcagggtat gtcactgaca aggaaggca gaaagttgtt tccttcactg    3960
aaacaacaaa tcagaagact gaattacaag caattcagct agctttgcag gattcagggc    4020
cagaagtaaa catagtaaca gactcacagt atgcattagg aatcattcaa gcacaaccag    4080
ataagagtga atcagaatta gtcagtcaaa taatagaaca gttgataaaa aaggaaaaag    4140
tctacctatc atgggtacca gcacataaag gaattggagg aaatgaacaa gtagacaaat    4200
tagtaagtag tggaatcaga aaagtactgt ttctagatgg aatagataaa gctcaagaag    4260
agcatgaaaa atatcacagc aattggagag caatggctag tgagtttaat ctgccaccca    4320
tagtagcaaa ggaaatagta gccagctgtg ataaatgtca gctaaaaggg gaagccatgc    4380
atggacaagt cgactgtagt ccaggaatat ggcaattaga ctgtacacat ttagaaggaa    4440
aaatcatcct agtagcagtc catgtagcca gtggctacat ggaagcagag gttatcccag    4500
cagaaacagg acaagaaaca gcatacttta tactaaaatt agcaggaaga tggccagtca    4560
```

```
aagtaataca tacagataat ggcagtaatt tcaccagtac cgcagttaag gcagcctgtt    4620
ggtgggcaga tatccaacgg gaatttggaa ttccctacaa tccccaaagt caaggagtag    4680
tagaatccat gaataaagaa ttaaagaaaa tcatagggca agtaagagat caagctgagc    4740
accttaagac agcagtacaa atggcagtat tcattcacaa ttttaaaaga aaggggggga    4800 ttgggggggta cagtgcaggg gagagaataa tagacataat agcatcagac atacaaacta   4860
aagaattaca aaacaaatt ataaaaattc aaaattttcg ggtttattac agagacagca    4920
gagaccctat ttggaaagga ccagccaaac tactctggaa aggtgaaggg gcagtagtaa    4980
tacaagataa tagtgatata aaggtagtac caagaaggaa agcaaaaatc attaaggact   5040
atggaaaaca gatggcaggt gctgattgtg tggcaggtag acaggatgaa gattagaaca   5100
tggcacagtt tagtaaagca ccatatgtat gtttcgagga gagctgatgg atggttctac   5160
agacatcatt atgaaagcag acacccaaaa gtaagttcag aagtacacat cccattagga   5220
gatgccaggt tagtaataaa aacatattgg ggtctgcaga caggagaaag agcttggcat   5280
ttgggtcacg gagtctccat agaatggaga ttgagaagat atagcacaca agtagaccct   5340
gacctgacag accaactaat tcatatgcat tattttgatt gttttgcaga atctgccata   5400
aggaaagcca tactaggaca gatagttagc cctaagtgtg actatcaagc aggacataac   5460
aaggtaggat ctctacaata cttggcactg acagcattga taaaaccaaa aaagataaag   5520
ccacctctgc ctagtgttag gaaattagta gaggatagat ggaacaagcc ccagaagacc   5580
aggggccgca gagggaacca tacaatgaat ggacactaga gcttttagaa gaactcaagc   5640
aggaagctgt cagacacttt cctagaccat ggctccataa cttaggacaa catatctatg   5700
aaacctatgg agatacttgg acaggagttg aagcaataat aagaatcctg caacaattac   5760
tgtttattca tttcaggatt gggtgccatc atagcagaat aggcattttg cgacagagaa   5820
gagcaagaaa tggagccaat agatcctaac ctagaaccct ggaaccatcc aggaagtcag   5880
cctaaaactg cttgtaatgg gtgttactgt aaacgttgca gctatcattg tctagtttgc   5940
tttcagaaaa aaggcttagg catttactat ggcaggaaga agcggagaca gcgacgaagc   6000
gctcctccaa gcaataaaga tcatcaagat cctctaccaa agcagtaagt accgaatagt   6060
atatgtaatg ttagatttaa ctgcaagaat agattctaga ttaggaatag gagcattgat   6120
agtagcacta atcatagcaa taatagtgtg gaccatagta tatatagaat ataggaaatt   6180
ggtaaggcaa aggaaaatag actggttagt taaaaggatt agggaaagag cagaagacag   6240
tggcaatgag agcgaggggg atactgaaga attatcgaca ctggtggata tggggcatct   6300
taggcttttg gatgctaatg atgtgtaatg tgaagggctt gtgggtcaca gtctactacg   6360
gggtacctgt ggggagagaa gcaaaaacta ctctattttg tgcatcagat gctaaagcat   6420
atgagaaaga agtgcataat gtctgggcta cacatgcctg tgtacccaca gaccccaacc   6480
cacaagaagt gattttgggc aatgtaacag aaaattttaa catgtggaaa aatgacatgg   6540
tggatcagat gcaggaagat ataatcagtt tatgggatca aagccttaag ccatgtgtaa   6600
aattgacccc actctgtgtc actttaaact gtacaaatgc aactgttaac tacaataata   6660
cctctaaaga catgaaaaat tgctctttct atgtaaccac agaattaaga gataagaaaa   6720
agaaagaaaa tgcactttttt tatagacttg atatagtacc acttaataat aggaagaatg   6780
ggaatattaa caactataga ttaataaatt gtaatacctc agccataaca caagcctgtc   6840
caaaagtctc gtttgaccca attcctatac attattgtgc tccagctggt tatgcgcctc   6900
```

```
taaaatgtaa taataagaaa ttcaatggaa taggaccatg cgataatgtc agcacagtac    6960
aatgtacaca tggaattaag ccagtggtat caactcaatt actgttaaat ggtagcctag    7020
cagaagaaga gataataatt agatctgaaa atctgacaaa caatgtcaaa acaataatag    7080
tacatcttaa tgaatctata gagattaaat gtacaagacc tggcaataat acaagaaaga    7140
gtgtgagaat aggaccagga caagcattct atgcaacagg agacataata ggagatataa    7200
gacaagcaca ttgtaacatt agtaaaaatg aatggaatac aactttacaa agggtaagtc    7260
aaaaattaca agaactcttc cctaatagta cagggataaa atttgcacca cactcaggag    7320
gggacctaga aattactaca catagcttta attgtggagg agaattttc tattgcaata    7380 caacagacct gtttaatagt acatacagta atggtacatg cactaatggt acatgcatgt    7440
ctaataatac agagcgcatc acactccaat gcagaataaa acaaattata acatgtggc     7500 aggaggtagg acgagcaatg tatgcccctc ccattgcagg aaacataaca tgtagatcaa    7560 atattcagg actactatta acgtgatg gaggagataa taatactgaa acagagacat      7620
tcagacctgg aggaggagac atgagggaca attggagaag tgaattatat aaatacaagg   7680
tggtagaaat taaccatta ggagtagcac ccactgctgc aaaaggaga gtggtggaga     7740 gagaaaaaag agcagtagga ataggagctg tgttccttgg gttcttggga gcagcaggaa   7800
gcactatggg cgcagcatca ataacgctga cggtacaggc cagacaatta ttgtctggta   7860
tagtgcaaca gcaaagtaat ttgctgaggg ctatagaggc gcaacagcat atgttgcaac   7920
tcacggtctg gggcattaag cagctccagg caagagtcct ggctatagag agatacctac   7980
aggatcaaca gctcctagga ctgtggggct gctctggaaa actcatctgc accactaatg   8040
tgctttggaa ctctagttgg agtaataaaa ctcaaagtga tatttgggat aacatgacct   8100
ggatgcagtg ggatagggaa attagtaatt acacaaacac aatatacagg ttgcttgaag   8160
actcgcaaag ccagcaggaa agaaatgaaa aagatttact agcattggac aggtggaaca   8220
atctgtggaa ttggttagc ataacaaatt ggctgtggta tataaaaata ttcataatga    8280
tagtaggagg cttgataggt ttaagaataa tttttgctgt gctctctcta gtaaatagag   8340
ttaggcaggg atactcaccc ttgtcattgc agacccttat cccaaacccg aggggacccg   8400
acaggctcgg aggaatcgaa gaagaaggtg gagagcaaga cagcagcaga tccattcgat   8460
tagtgagcgg attcttgaca cttgcctggg acgacctacg aagcctgtgc ctcttctgct   8520
accaccgatt gagagacttc atattaattg tagtgagagc agtggaactt ctgggacaca   8580
gtagtctcag gggactgcag aggggggtggg gaacccttaa gtatttgggg agtcttgtgc   8640
aatattgggg tctagagtta aaaaagagtg ctattaatct gcttgatact atagcaatag   8700
cagtagctga aggaacagat aggattctag aattcataca aacctttgt agaggtatcc    8760 gcaacgtacc tagaagaata agacagggct tcgaagcagc tttgcaataa aatgggggc    8820 aagtggtcaa aaagcagtat aattggatgg cctgaagtaa gagaaagaat cagacgaact   8880
aggtcagcag cagagggagt aggatcagcg tctcaagact tagagaaaca tggggcactt   8940
acaaccagca acacagccca caacaatgct gcttgcgcct ggctggaagc gcaagaggag   9000
gaaggagaag taggctttcc agtcagacct caggtacctt taagaccaat gacttataaa   9060
gcagcaatag atctcagctt cttttttaaaa gaaaaggggg gactgaaagg gttaatttac   9120
tccaagaaaa ggcaagagat ccttgatttg tgggtttata acacacaagg cttcttccct   9180
gattggcaaa actacacacc gggaccaggg gtcagatttc cactgacctt tggatggtac   9240
ttcaagctag agccagtcga tccaagggaa gtagaagagg ccaatgaagg agaaaacaac   9300
```

```
tgtttactac accctatgag ccagcatgga atggaggatg aagacagaga agtattaaga    9360
tggaagtttg acagtacgct agcacgcaga cacatggccc gcgagctaca tccggagtat    9420
tacaaagact gctgacacag aagggacttt ccgctgggac tttccactgg ggcgttccag    9480
gaggtgtggt ctgggcggga caggggagtg gtcagccctg agatgctgca tataagcagc    9540
tgcttttcgc ctgtactggg tctctctagg tagaccagat ctgagcccgg gagctctctg    9600
gctatctagg gaacccactg cttaagcctc aataaagctt gccttgagtg ccttgagtag    9660
tgtgtgcccg tctgttgtgt gactctggta actagagatc cctcagacca cttgtggtag    9720
tgtggaaaat ctctagca                                                   9738

<210> SEQ ID NO 46
<211> LENGTH: 97
<212> TYPE: DNA
<213> ORGANISM: Artificial
<220> FEATURE:
<223> OTHER INFORMATION: HIV Type C Env Optimized common region short

<400> SEQUENCE: 46
catcaccctg cagtgcaaga tcaagcagat cgtgcgcatg tggcagggcg tgggccaggc    60
catgtacgcc cccccatcg ccggcaacat cacctgc                              97

<210> SEQ ID NO 47
<211> LENGTH: 144
<212> TYPE: DNA
<213> ORGANISM: Artificial
<220> FEATURE:
<223> OTHER INFORMATION: HIV Type C Env Optimized common region

<400> SEQUENCE: 47
ctgcccatca ccctgcagtg caagatcaag cagatcgtgc gcatgtggca gggcgtgggc    60
caggccatgt acgcccccc

-continued

```
accgaggtgc acaacgtgtg ggccacccac gcctgcgtgc ccaccgaccc caaccccag     240 gagatcgtgc tgggcaacgt gaccgagaac ttcaacatgt ggaagaacaa catggccgac    300
cagatgcacg aggacatcat cagcctgtgg gaccagagcc tgaagccctg cgtgaagctg    360
acccccctgt gcgtgaccct gaactgcacc gacaccaacg tgaccggcaa ccgcaccgtg    420
accggcaaca ccaacgacac caacatcgcc aacgccacct acaagtacga ggagatgaag    480
aactgcagct tcaacgccac caccgagctg cgcgacaaga agcacaagga gtacgccctg    540
ttctacaagc tggacatcgt gccctgaac gagaacagca caacttcac ctaccgcctg      600 atcaactgca acaccagcac catcacccag gcctgcccca aggtgagctt cgaccccatc    660
cccatccact actgcgcccc cgccgactac gccatcctga agtgcaacaa caagaccttc    720
aacggcaccg gccctgcta caacgtgagc accgtgcagt gcacccacgg catcaagccc     780
gtggtgagca cccagctgct gctgaacggc agcctggccg aggagggcat catcatccgc    840
agcgagaacc tgaccgagaa caccaagacc atcatcgtgc acctgaacga gagcgtggag    900
atcaactgca cccgccccaa caacaacacc cgcaagagcg tgcgcatcgg ccccggccag    960
gccttctacg ccaccaacga cgtgatcggc aacatccgcc aggcccactg caacatcagc   1020
accgaccgct ggaacaagac cctgcagcag gtgatgaaga gctgggcga gcacttcccc    1080 aacaagacca tcaagttcga gccccacgcc ggcggcgacc tggagatcac catgcacagc   1140
ttcaactgcc gcggcgagtt cttctactgc aacaccagca acctgttcaa cagcacctac   1200
taccccaaga acggcaccta caagtacaac ggcaacagca gcctgcccat caccctgcag   1260
tgcaagatca agcagatcgt gcgcatgtgg cagggcgtgg gccaggccat gtacgccccc   1320
cccatcgccg gcaacatcac ctgccgcagc aacatcaccg gcatcctgct gacccgcgac   1380
ggcggcttca caacaccaa caacgacacc gaggagacct tccgccccgg cggcggcgac    1440
atgcgcgaca ctggcgcag cgagctgtac aagtacaagg tggtggagat caagcccctg   1500
ggcatcgccc ccaccaaggc caagcgccgc gtggtgcagc gcaagaagcg cgccgtgggc   1560
atcggcgccg tgttcctggg cttcctgggc gccgccggca gcaccatggg cgccgccagc   1620
atcaccctga ccgtgcaggc ccgccagctg ctgagcggca tcgtgcagca gcagagcaac   1680
ctgctgaagg ccatcgaggc ccagcagcac atgctgcagc tgaccgtgtg gggcatcaag   1740
cagctgcagg cccgcgtgct ggccatcgag cgctacctga aggaccagca gctgctgggc   1800
atctggggct gcagcggccg cctgatctgc accaccgccg tgccctggaa cagcagctgg   1860
agcaacaaga gcgaggccga catctgggac aacatgacct ggatgcagtg ggaccgcgag   1920
atcaacaact acaccgagac catcttccgc ctgctggagg acagccagaa ccagcaggag   1980
aagaacgaga aggacctgct ggagctggac aagtggaaca acctgtggaa ctggttcgac   2040
atcagcaact ggctgtggta catcaagatc ttcatcatga tcgtgggcgg cctgatcggc   2100
ctgcgcatca tcttcgccgt gctgagcatc gtgaaccgcg tgcgcagggg ctacagcccc   2160
ctgagcttcc agaccctgac ccccagcccc cgcggcctgg accgctgggg cggcatcgag   2220
gaggagggcg gcgagcagga ccgcgaccgc agcatccgcc tggtgagcgg cttcctgagc   2280
ctggcctggg acgacctgcg cagcctgtgc ctgttcagct accaccgcct gcgcgacttc   2340
atcctgatcg ccgtgcgcgc cgtggagctg ctgggccaca gcagcctgcg cggcctgcag   2400
cgcggctggg agatcctgaa gtacctgggc agcctggtgc agtactgggg cctggagctg   2460
aagaagagcg ccatcagccc cctggacacc atcgccatcg ccgtggccga gggcaccgac   2520
cgcatcatcg agctggtgca gcgcatctgc cgcgccatcc tgaacatccc ccgccgcatc   2580
```

```
cgccagggct cgaggccgc cctgctgtaa                                    2610

<210> SEQ ID NO 50
<211> LENGTH: 2610
<212> TYPE: DNA
<213> ORGANISM: Artificial
<220> FEATURE:
<223> OTHER INFORMATION: Type C Envgp160 wild type

<400> SEQUENCE: 50
atgagagtga tggggacaca gaagaattgt caacaatggt

```
aagaatgaaa aagatttatt agaattggac aagtggaata atctgtggaa ttggtttgac    2040
atatcaaact ggctgtggta tataaaaata ttcataatga tagtaggagg cttgataggt    2100
ttaagaataa tttttgctgt gctctctata gtgaatagag ttaggcaggg atactcacct    2160
ttgtcatttc agacccttac cccaagcccg aggggactcg acaggctcgg aggaatcgaa    2220
gaagaaggtg gagagcaaga cagagacaga tccatacgat tggtgagcgg attcttgtcg    2280
cttgcctggg acgatctgcg gagcctgtgc ctcttcagct accaccgctt gagagacttc    2340
atattaattg cagtgagggc agtggaactt ctgggacaca gcagtctcag gggactacag    2400 aggggtggg agatccttaa gtatctggga agtcttgtgc agtattgggg tctagagcta    2460
aaaaagagtg ctattagtcc gcttgatacc atagcaatag cagtagctga aggaacagat    2520
aggattatag aattggtaca aagaatttgt agagctatcc tcaacatacc taggagaata    2580
agacagggct tgaagcagc tttgctataa                                     2610
```

<210> SEQ ID NO 51
<211> LENGTH: 1494
<212> TYPE: DNA
<213> ORGANISM: Artificial
<220> FEATURE:
<223> OTHER INFORMATION: HIV Type C Gag optimized

<400> SEQUENCE: 51

```
atgggcgccc gcgccagcat cctgagcggc ggcaagctgg acaagtggga gcgcatccgc     60
ctgcgccccg gcggcaagaa gcactacatg ctgaagcacc tggtgtgggc cagccgcgag    120
ctggagcgct tcgccctgaa ccccggcctg ctggagacca gcgagggctg caagcagatc    180
atcaagcagc tgcagcccgc cctgcagacc ggcaccgagg agctgcgcag cctgttcaac    240
accgtggcca ccctgtactg cgtgcacaag ggcatcgagg tgcgcgacac caaggaggcc    300
ctggacaaga tcgaggagga gcagaacaag tgccagcaga aggcccagca ggccaaggcc    360
gccgacgaga aggtgagcca gaactacccc atcgtgcaga acgcccaggg ccagatggtg    420
caccaggcca tcagcccccg caccctgaac gcctggatca aggtgatcga ggagaaggcc    480
ttcaaccccg aggagatccc catgttcacc gccctgagcg agggcgccac cccccaggac    540
ctgaacacca tgctgaacac cgtgggcggc caccaggccg ccatgcagat gctgaaggac    600
accatcaacg aggaggccgc cgagtgggac cgcacccacc ccgtgcacgc cggccccgtg    660 gccccgg cc agatgcgcga gcccgcggc agcgacatcg ccggcaccac cagcaccctg    720
caggagcaga tcgcctggat gaccagcaac ccccccatcc ccgtggagga catctacaag    780
cgctggatca tcctgggcct gaacaagatc gtgcgcatgt acagcccgt gagcatcctg    840 gacatcaagc agggcccaa ggagcccttc cgcgactacg tggaccgctt cttcaagacc    900
ctgcgcgccg agcaggccac ccaggacgtg aagaactgga tgaccgacac cctgctggtg    960
cagaacgcca accccgactg caagaccatc ctgcgcgccc tgggccccgg cgccagcctg   1020
gaggagatga tgaccgcctg ccagggcgtg ggcggcccca gccacaaggc ccgcgtgctg   1080
gccgaggcca tgagccaggc caacagcaac atcctggtgc agcgcagcaa cttcaagggc   1140
agcaaccgca tcatcaagtg cttcaactgc ggcaaggtgg ccacatcgc ccgcaactgc   1200 cgcgcccccc gcaagaaggg ctgctggaag tgcggccagg agggccacca gatgaaggac   1260
tgcaccgagc gccaggccaa cttcctgggc aagatctggc ccagccacaa gggccgcccc   1320
ggcaacttcc tgcagaaccg ccccgagccc accgccccc cgccgagcc caccgccccc   1380 cccgccgaga gcttccgctt cgaggagacc accccgtgc ccgcaagga aggagcgc    1440
```

```
gagcccctga ccagcctgaa gagcctgttc ggcagcgacc ccctgagcca gtaa        1494

<210> SEQ ID NO 52
<211> LENGTH: 1494
<212> TYPE: DNA
<213> ORGANISM: Artificial
<220> FEATURE:
<223> OTHER INFORMATION: HIV Type C Gag Wild Type

<400> SEQUENCE: 52
atgggtgcga gagcgtcaat attaagcggc ggaaaattag ataaatggga agaattagg    60 ttaaggccag ggggaaagaa acattatatg ttaaaacatc tagtatgggc aagcagggag   120
ctggaaagat ttgcacttaa ccctggcctg ttagaaacat cagaaggctg taaacaaata   180
ataaaacagc tacaaccagc tcttcagaca ggaacagagg aacttagatc attattcaac   240
acagtagcaa ctctctattg tgtacataaa gggatagagg tacgagacac caaggaagcc   300
ttagacaaga tagaggaaga acaaaacaaa tgtcagcaaa agcacaaca ggcaaaagca    360 gctgacgaaa aggtcagtca aaattatcct atagtacaga atgcccaagg gcaaatggta    420
caccaagcta tatcacctag aacattgaat gcatggataa agtaataga ggaaaaggct    480 ttcaatccag aggaaatacc catgtttaca gcattatcag aaggagccac cccacaagat    540
ttaaacacaa tgttaaatac agtggggggga catcaagcag ccatgcaaat gttaaaagat    600
accatcaatg aggaggctgc agaatgggat aggacacatc cagtacatgc agggcctgtt    660
gcaccaggcc agatgagaga accaagggga agtgacatag caggaactac tagtacccta    720
caggaacaaa tagcatggat gacaagtaat ccacctattc cagtagaaga catctataaa    780
agatggataa ttctggggtt aaataaaata gtaagaatgt atagccctgt tagcattttg    840
gacataaaac aagggccaaa agaacccttt agagactatg tagaccggtt ctttaaaacc    900
ttaagagctg aacaagctac acaagatgta agaattgga tgacagacac cttgttggtc    960
caaaatgcga acccagattg taagaccatt ttaagagcat taggaccagg ggcctcatta   1020
gaagaaatga tgacagcatg tcagggagtg gaggaccta gccataaagc aagagtgttg   1080
gctgaggcaa tgagccaagc aaacagtaac atactagtgc agagaagcaa ttttaaaggc   1140
tctaacagaa ttattaaatg tttcaactgt ggcaaagtag gcacatagc cagaaattgc    1200 agggccccta ggaaaaaggg ctgttggaaa tgtggacagg aaggacacca aatgaaagac   1260
tgtactgaga gcaggctaa ttttttaggg aaaatttggc cttccacaa ggggaggcca    1320 gggaatttcc tccagaacag accagagcca acagccccac cagcagaacc aacagcccca   1380
ccagcagaga gcttcaggtt cgaggagaca acccccgtgc cgaggaagga aaagagagg    1440 gaacctttaa cttccctcaa atcactcttt ggcagcgacc ccttgtctca ataa          1494

<210> SEQ ID NO 53
<211> LENGTH: 60
<212> TYPE: DNA
<213> ORGANISM: Artificial
<220> FEATURE:
<223> OTHER INFORMATION: HIV Type C Gag Major Homology Region Optimized

<400> SEQUENCE: 53
gacatcaagc agggccccaa ggagcccttc cgcgactacg tggaccgctt cttcaagacc    60

<210> SEQ ID NO 54
<211> LENGTH: 60
<212> TYPE: DNA
```

<213> ORGANISM: Artificial
<220> FEATURE:
<223> OTHER INFORMATION: HIV Type C Gag Major Homology Region Wild Type

<400> SEQUENCE: 54

```
gacataaaac aagggccaaa agaacccttt agagactatg tagaccggtt ctttaaaacc        60
```

<210> SEQ ID NO 55
<211> LENGTH: 624
<212> TYPE: DNA
<213> ORGANISM: Artificial
<220> FEATURE:
<223> OTHER INFORMATION: HIV Type C Nef Optimized

<400> SEQUENCE: 55

```
atgggcggca agtggagcaa gcgcagcatc gtgggctggc ccgccgtgcg cgagcgcatg        60
cgccgcaccg agcccgccgc cgagggcgtg ggcgccgcca gcaggacct ggaccgccac       120
ggcgccctga ccagcagcaa cacccccgcc accaacgagg cctgcgcctg ctgcaggcc        180
caggaggagg acggcgacgt gggcttcccc gtgcgccccc agtgcccct cgccccatg         240
acctacaaga gcgccgtgga cctgagcttc ttcctgaagg agaagggcgg cctggagggc       300
ctgatctaca gccgcaagcg ccaggagatc ctggacctgt gggtgtacaa cacccagggc       360
ttcttccccg actggcagaa ctacaccagc ggccccggcg tgcgcttccc cctgaccttc       420
ggctggtgct tcaagctggt gcccgtggac ccccgcgagg tgaaggaggc caacgagggc       480
gaggacaact gcctgctgca ccccatgagc cagcacggcg ccgaggacga ggaccgcgag       540
gtgctgaagt ggaagttcga cagcctgctg gccaccgcc acatggcccg cgagctgcac       600
cccgagtact acaaggactg ctga                                             624
```

<210> SEQ ID NO 56
<211> LENGTH: 624
<212> TYPE: DNA
<213> ORGANISM: Artificial
<220> FEATURE:
<223> OTHER INFORMATION: HIV Type C Nef Wild Type

<400> SEQUENCE: 56

```
atgggaggca agtggtcaaa acgcagcata gttggatggc ctgcagtaag agaaagaatg        60
agaagaactg agccagcagc agagggagta ggagcagcgt ctcaagactt agatagacat       120
ggggcactta caagcagcaa cacacctgct actaatgaag cttgtgcctg gctgcaagca       180
caagaggagg acggagatgt aggctttcca gtcagacctc aggtaccttt aagaccaatg       240
acttataaga gtgcagtaga tctcagcttc tttttaaaag aaaaggggg actggaaggg        300
ttaatttact ctaggaaaag gcaagaaatc cttgatttgt gggtctataa cacacaaggc       360
ttcttccctg attggcaaaa ctacacatcg ggccagggg tccgattccc actgaccttt        420
ggatggtgct tcaagctagt accagttgac ccaaggagg tgaaagaggc caatgaagga       480
gaagacaact gtttgctaca ccctatgagc caacatggag cagaggatga agatagagaa       540
gtattaaagt ggaagtttga cagccttcta gcacacagac acatggcccg cgagctacat       600
ccggagtatt acaaagactg ctga                                             624
```

<210> SEQ ID NO 57
<211> LENGTH: 624
<212> TYPE: DNA
<213> ORGANISM: Artificial
<220> FEATURE:
<223> OTHER INFORMATION: HIV Type C NefD125G Optimized

<400> SEQUENCE: 57

```
atgggcggca agtggagcaa gcgcagcatc gtgggctggc cgccgtgcg cgagcgcatg      60
cgccgcaccg agcccgccgc cgagggcgtg ggcgccgcca gccaggacct ggaccgccac     120
ggcgccctga ccagcagcaa caccccgcc accaacgagg cctgcgcctg gctgcaggcc     180
caggaggagg acgcgacgt gggcttcccc gtgcgcccc aggtgcccct cgcccccatg      240
acctacaaga gcgccgtgga cctgagcttc ttcctgaagg agaagggcgg cctggagggc    300
ctgatctaca gccgcaagcg ccaggagatc ctggacctgt gggtgtacaa cacccagggc    360
ttcttccccg gctggcagaa ctacaccagc ggccccggcg tgcgcttccc cctgaccttc    420
ggctggtgct tcaagctggt gcccgtggac cccgcgagg tgaaggaggc caacgagggc     480
gaggacaact gcctgctgca ccccatgagc cagcacggcg ccgaggacga ggaccgcgag    540
gtgctgaagt ggaagttcga cagcctgctg gcccaccgcc acatggcccg cgagctgcac    600
cccgagtact acaaggactg ctga                                           624
```

<210> SEQ ID NO 58
<211> LENGTH: 354
<212> TYPE: DNA
<213> ORGANISM: Artificial
<220> FEATURE:
<223> OTHER INFORMATION: HIV Type C p15RNaseH Optimized

<400> SEQUENCE: 58

```
accttctacg tggacggcgc caccaaccgc gaggccaaga tcggcaaggc cggctacgtg      60
accgaccgcg ccgccagaa gatcgtgacc ctgaccaaca ccaccaacca gaagaccgag     120
ctgcaggcca tccagctggc cctgcaggac agcggcagcg aggtgaacat cgtgaccgac    180
agccagtacg ccctgggcat catccaggcc cagcccgaca agagcgacag cgagatcttc    240
aaccagatca tcgagcagct gatcaacaag gagcgcatct acctgagctg ggtgcccgcc    300
cacaagggca tcggcggcaa cgagcaggtg acaagctgg tgagcaaggg catc           354
```

<210> SEQ ID NO 59
<211> LENGTH: 354
<212> TYPE: DNA
<213> ORGANISM: Artificial
<220> FEATURE:
<223> OTHER INFORMATION: HIV Type C p15RNaseH Wild Type

<400> SEQUENCE: 59

```
actttctatg tagatggagc aactaatagg gaagctaaaa taggaaaagc agggtatgtt      60
actgacagag gaaggcagaa aattgttact ctaactaaca caacaaatca gaagactgag     120
ttacaagcaa ttcagctagc tctgcaggat tcaggatcag aagtaaacat agtaacagac    180
tcacagtatg cattaggaat cattcaagca caaccagata agagtgactc agagatattt    240
aaccaaataa tagaacagtt aataaacaag gaaagaatct acctgtcatg ggtaccagca    300
cataaaggaa ttgggggaaa tgaacaagta gataaattag taagtaaggg aatt           354
```

<210> SEQ ID NO 60
<211> LENGTH: 876
<212> TYPE: DNA
<213> ORGANISM: Artificial
<220> FEATURE:
<223> OTHER INFORMATION: HIV Type C p31Int Optimized

<400> SEQUENCE: 60

```
cgcaaggtgc tgttcctgga cggcatcgac aaggcccagg aggagcacga gcgctaccac    60
agcaactggc gcgccatggc caacgagttc aacctgcccc ccatcgtggc caaggagatc   120
gtggccagct gcgacaagtg ccagctgaag ggcgaggcca tccacggcca ggtggactgc   180
agccccggca tctggcagct ggactgcacc cacctggagg gcaagatcat cctggtggcc   240
gtgcacgtgg ccagcggcta catggaggcc gaggtgatcc ccgccgagac cggccaggag   300 accgccact  tcatcctgaa gctggccggc cgctggcccg tgaaggtgat ccacaccgac   360
aacggcagca acttcaccag caccgccgtg aaggccgcct gctggtgggc cggcatccag   420
caggagttcg gcatccccta caaccccag  agccagggcg tggtggagag catgaacaag   480
gagctgaaga gatcatcgg ccaggtgcgc gaccaggccg agcacctgaa gaccgccgtg    540
cagatggccg tgttcatcca caacttcaag cgcaagggcg catcggcgg ctacagcgcc    600 ggcgagcgca tcatcgacat catcgccacc gacatccaga ccaaggagct gcagaagcag   660
atcatccgca tccagaactt ccgcgtgtac taccgcgaca gccgcgaccc catcctggaag  720 ggccccgccg agctgctgtg gaagggcgag ggcgtggtgg tgatcgagga caaggcgac    780 atcaaggtgg tgccccgccg caaggccaag atcatccgcg actacggcaa gcagatggcc   840
ggcgccgact gcgtggccgg cggccaggac gaggac                             876
```

<210> SEQ ID NO 61
<211> LENGTH: 876
<212> TYPE: DNA
<213> ORGANISM: Artificial
<220> FEATURE:
<223> OTHER INFORMATION: HIV Type C p31Int Wild Type

<400> SEQUENCE: 61

```
aggaaagtgt tgtttctaga tggaatagat aaagctcaag aagagcatga aaggtaccac    60
agcaattgga gagcaatggc taatgagttt aatctgccac ccatagtagc aaaagaaata   120
gtagctagct gtgataaatg tcagctaaaa ggggaagcca tacatggaca gtcgactgt    180 agtccaggga tatggcaatt agattgtacc catttagagg gaaaaatcat cctggtagca   240
gtccatgtag ctagtggcta catggaagca gaggttatcc cagcagaaac aggacaagaa   300
acagcatatt ttatattaaa attagcagga agatggccag tcaaagtaat acatacagac   360
aatggcagta attttaccag tactgcagtt aaggcagcct gttggtgggc aggtatccaa   420
caggaatttg gaattcccta caatccccaa agtcagggag tggtagaatc catgaataaa   480
gaattaaaga aaataatagg acaagtaaga gatcaagctg agcaccttaa gacagcagta   540
caaatggcag tattcattca cattttaaa  agaaaagggg gaattggggg gtacagtgca    600
ggggaaagaa taatagacat aatagcaaca gacatacaaa ctaaagaatt acaaaaacaa   660
attataagaa ttcaaaattt tcgggtttat tacagagaca gcagagaccc tatttggaaa   720
ggaccagccg aactactctg gaaaggtgaa ggggtagtag taatagaaga taaaggtgac    780
ataaaggtag taccaaggag gaaagcaaaa atcattagag attatggaaa acagatggca   840
ggtgctgatt gtgtggcagg tggacaggat gaagat                             876
```

<210> SEQ ID NO 62
<211> LENGTH: 3015
<212> TYPE: DNA
<213> ORGANISM: Artificial
<220> FEATURE:
<223> OTHER INFORMATION: HIV Type C Pol Optimized

<400> SEQUENCE: 62

```
ttcttccgcg agaacctggc cttccccag ggcgaggccc gcgagttccc ccccgagcag      60
acccgcgcca acagccccac cagccgcacc aacagcccca ccagccgcga gctgcaggtg     120
cgcggcgaca accccgcgc cgaggagggc gagcgcgagg gcaccttcaa cttccccag      180 atcaccctgt ggcagcgccc cctggtgagc atcaaggtgg agggccagat caaggaggcc    240
ctgctggaca ccgcgccga cgacaccgtg ctggaggaga tcgacctgcc cggcaagtgg     300
aagcccaaga tgatcggcgg catcggcggc ttcatcaagg tgcgccagta cgaccagatc    360
ctgatcgaga tctgcggcaa gaaggccatc ggcaccgtgc tggtgggccc cacccccgtg    420
aacatcatcg ccgcaacct gctgacccag ctgggctgca ccctgaactt ccccatcagc    480
cccatcgaga ccgtgccgt gaagctgaag cccggcatgg acggcccaa ggtgaagcag     540 tggcccctga ccgaggagaa gatcaaggcc ctgaccgcca tctgcgagga gatggagaag    600
gagggcaaga tcaccaagat cggccccgac aaccccctaca acaccccgt gttcgccatc    660 aagaagaagg acagcaccaa gtggcgcaag ctggtggact ccgcgagct gaacaagcgc    720 acccaggact tctggaggt gcagctgggc atccccacc ccgccggcct gaagaagaag     780
aagagcgtga ccgtgctgga cgtgggcgac gcctacttca gcgtgcccct ggacgagagc    840
ttccgcaagt acaccgcctt caccatcccc agcatcaaca cgagacccc cggcatccgc    900 taccagtaca acgtgctgcc ccagggctgg aagggcagcc ccgccatctt ccagagcagc    960
atgaccaaga tcctggagcc cttccgcgcc aagaaccccg acatcgtgat ctaccagtac   1020
atggacgacc tgtacgtggg cagcgacctg agatcggcc agcaccgcgc caagatcgag    1080
gagctgcgcg agcacctgct gaagtggggc ttcaccaccc ccgacaagaa gcaccagaag    1140
gagcccccct tcctgtggat gggctacgag ctgcacccg acaagtggac cgtgcagccc    1200
atcctgctgc ccgagaagga cagctggacc gtgaacgaca tccagaagct ggtgggcaag    1260
ctgaactggg ccagccagat ctaccccggc atcaaggtgc gccagctgtg caagctgctg    1320
cgcggcgcca aggccctgac cgacatcgtg cccctgaccg aggaggccga gctggagctg    1380
gccgagaacc gcgagatcct gcgcgagccc gtgcacggcg tgtactacga ccccagcaag    1440
gacctgatcg ccgagatcca gaagcagggc cacgagcagt ggacctacca gatctaccag    1500
gagcccttca gaacctgaa gaccggcaag tacgccaaga tgcgcaccac ccacaccaac    1560
gacgtgaagc agctgaccga ggccgtgcag aagatcgcca tggagagcat cgtgatctgg    1620
ggcaagaccc ccaagttccg cctgcccatc cagaaggaga cctgggagac ctggtggacc    1680
gactactggc aggccaccct gatccccgag tgggagttcg tgaacacccc cccctggtg    1740 aagctgtggt accagctgga gaaggacccc atcgccggcg tggagacctt ctacgtggac    1800
ggcgccacca ccgcgaggc caagatcggc aaggccggct acgtgaccga ccgcggccgc    1860
cagaagatcg tgaccctgac caacaccacc aaccagaaga ccgagctgca ggccatccag    1920
ctggccctgc aggacagcgg cagcgaggtg aacatcgtga ccgacagcca gtacgccctg    1980
ggcatcatcc aggcccagcc cgacaagagc gacagcgaga tcttcaacca gatcatcgag    2040
cagctgatca acaaggagcg catctacctg agctgggtgc ccgcccacaa gggcatcggc    2100
ggcaacgagc aggtggacaa gctggtgagc aagggcatcc gcaaggtgct gttcctggac    2160
ggcatcgaca aggcccagga ggagcacgag cgctaccaca gcaactggcg cgccatggcc    2220
aacgagttca acctgccccc catcgtggcc aaggagatcg tggccagctg cgacaagtgc    2280
cagctgaagg gcgaggccat ccacggccag gtggactgca gccccggcat ctggcagctg    2340
```

| | | | |
|---|---|---|---|
| gactgcaccc | acctggaggg | caagatcatc ctggtggccg | tgcacgtggc cagcggctac | 2400 |
| atggaggccg | aggtgatccc | cgccgagacc ggccaggaga | ccgcctactt catcctgaag | 2460 |
| ctggccggcc | gctggcccgt | gaaggtgatc cacaccgaca | acggcagcaa cttcaccagc | 2520 |
| accgccgtga | aggccgcctg | ctggtgggcc ggcatccagc | aggagttcgg catccectac | 2580 |
| aaccccccaga | gccagggcgt | ggtgagagc atgaacaagg | agctgaagaa gatcatcggc | 2640 |
| caggtgcgcg | accaggccga | gcacctgaag accgccgtgc | agatggccgt gttcatccac | 2700 |
| aacttcaagc | gcaagggcgg | catcggcggc tacagcgccg | gcgagcgcat catcgacatc | 2760 |
| atcgccaccg | acatccagac | caaggagctg cagaagcaga | tcatccgcat ccagaacttc | 2820 |
| cgcgtgtact | accgcgacag | ccgcgacccc atctggaagg | ccccgccga gctgctgtgg | 2880 |
| aagggcgagg | gcgtggtggt | gatcgaggac aagggcgaca | tcaaggtggt gccccgccgc | 2940 |
| aaggccaaga | tcatccgcga | ctacggcaag cagatggccg | cgccgactg cgtggccggc | 3000 |
| ggccaggacg | aggac | | 3015 |

<210> SEQ ID NO 63
<211> LENGTH: 3015
<212> TYPE: DNA
<213> ORGANISM: Artificial
<220> FEATURE:
<223> OTHER INFORMATION: HIV Type C Pol Wild Type

<400> SEQUENCE: 63

| | | | | |
|---|---|---|---|---|
| tttttttaggg | aaaatttggc | cttcccacaa | ggggaggcca | gggaatttcc tccagaacag | 60 |
| accagagcca | acagccccac | cagcagaacc | aacagcccca | ccagcagaga gcttcaggtt | 120 |
| cgaggagaca | acccccgtgc | cgaggaagga | gaaagagagg | gaacctttaa cttcccctcaa | 180 |
| atcactcttt | ggcagcgacc | ccttgtctca | ataaaagtag | agggccagat aaaggaggct | 240 |
| ctcttagaca | caggagcaga | tgatacagta | ttagaagaaa | tagatttgcc agggaaatgg | 300 |
| aaaccaaaaa | tgatagggggg | aattggaggt | tttatcaaag | taagacagta tgatcaaata | 360 |
| cttatagaaa | tttgtggaaa | aaaggctata | ggtacagtat | tagtagggcc tacaccagtc | 420 |
| aacataattg | gaagaaatct | gttaactcag | cttggatgca | cactaaattt tccaattagt | 480 |
| cctattgaaa | ctgtaccagt | aaaattaaaa | ccaggaatgg | atggcccaaa ggtcaaacaa | 540 |
| tggccattga | cagaagaaaa | aataaaagca | ttaacagcaa | tttgtgagga aatggagaag | 600 |
| gaaggaaaaa | ttacaaaaat | tgggcctgat | aatccatata | acactccagt atttgccata | 660 |
| aaaaagaagg | acagtactaa | gtggagaaaa | ttagtagatt | tcagggaact caataaaaga | 720 |
| actcaagact | tttgggaagt | tcaattagga | ataccacacc | cagcaggatt aaaaaagaaa | 780 |
| aaatcagtga | cagtgctaga | tgtggggggat | gcatattttt | cagttccttt agatgaaagc | 840 |
| ttcaggaaat | atactgcatt | caccatacct | agtataaaca | atgaaacacc agggattaga | 900 |
| tatcaatata | atgtgctgcc | acagggatgg | aaaggatcac | cagcaatatt ccagagtagc | 960 |
| atgacaaaaa | tcttagagcc | cttcagagca | aaaaatccag | acatagttat ctatcaatat | 1020 |
| atggatgact | tgtatgtagg | atctgactta | gaaatagggc | aacatagagc aaaaatagaa | 1080 |
| gagttaaggg | aacatttatt | gaaatgggga | tttacaacac | cagacaagaa acatcaaaaa | 1140 |
| gaaccccccat | ttctttggat | ggggtatgaa | ctccatcctg | acaaatggac agtacaacct | 1200 |
| atactgctgc | cagaaaagga | tagttggact | gtcaatgata | tacagaagtt agtgggaaaa | 1260 |
| ttaaactggg | caagtcagat | ttacccaggg | attaaagtaa | ggcaactctg taaactcctc | 1320 |
| aggggggcca | agcactaac | agacatagta | ccactaactg | aagaagcaga attagaattg | 1380 |

```
gcagagaaca gggaaattttt aagagaacca gtacatggag tatattatga tccatcaaaa    1440
gacttgatag ctgaaataca gaaacagggg catgaacaat ggacatatca aatttatcaa    1500
gaaccattta aaaatctgaa acagggaag tatgcaaaaa tgaggactac ccacactaat     1560
gatgtaaaac agttaacaga ggcagtgcaa aaaatagcca tggaaagcat agtaatatgg    1620
ggaaagactc ctaaatttag actacccatc caaaaagaaa catgggagac atggtggaca    1680
gactattggc aagccacctg gatccctgag tgggagtttg ttaatacccc tcccctagta    1740
aaattatggt accaactaga aaagatccc atagcaggag tagaaacttt ctatgtagat     1800
ggagcaacta tagggaagc taaaatagga aaagcagggt atgttactga cagaggaagg    1860
cagaaaattg ttactctaac taacacaaca atcagaaga ctgagttaca agcaattcag     1920
ctagctctgc aggattcagg atcagaagta acatagtaa cagactcaca gtatgcatta    1980
ggaatcattc aagcacaacc agataagagt gactcagaga tatttaacca ataatagaa    2040 cagttaataa acaaggaaag aatctacctg tcatgggtac cagcacataa aggaattggg    2100
ggaaatgaac aagtagataa attagtaagt aagggaatta gaaagtgtt gtttctagat     2160 ggaatagata agctcaaga gagcatgaa aggtaccaca gcaattggag agcaatggct      2220
aatgagttta tctgccacc catagtagca aaagaaatag tagctagctg tgataaatgt    2280
cagctaaaag gggaagccat acatggacaa gtcgactgta gtccagggat atggcaatta    2340
gattgtaccc atttagaggg aaaaatcatc ctggtagcag tccatgtagc tagtggctac    2400
atggaagcag aggttatccc agcagaaaca ggacaagaaa cagcatattt tatattaaaa    2460
ttagcaggaa gatggccagt caaagtaata catacagaca atggcagtaa ttttaccagt    2520
actgcagtta aggcagcctg ttggtgggca ggtatccaac aggaatttgg aattccctac    2580
aatccccaaa gtcagggagt ggtagaatcc atgaataaag aattaaagaa aataatagga    2640
caagtaagag atcaagctga gcaccttaag acagcagtac aaatggcagt attcattcac    2700
aattttaaaa gaaaaggggg aattgggggg tacagtgcag gggaaagaat aatagacata    2760
atagcaacag acatacaaac taagaatta caaaaacaaa ttataagaat tcaaaatttt     2820
cgggtttatt acagagacag cagagaccct atttggaaag gaccagccga actactctgg    2880
aaaggtgaag gggtagtagt aatagaagat aaaggtgaca taaaggtagt accaaggagg    2940
aaagcaaaaa tcattagaga ttatggaaaa cagatggcag gtgctgattg tgtggcaggt    3000
ggacaggatg aagat                                                    3015
```

<210> SEQ ID NO 64
<211> LENGTH: 297
<212> TYPE: DNA
<213> ORGANISM: Artificial
<220> FEATURE:
<223> OTHER INFORMATION: HIV Type C Protease Optimized

<400> SEQUENCE: 64

```
ccccagatca ccctgtggca gcgcccctg gtgagcatca aggtggaggg ccagatcaag      60
gaggccctgc tggacaccgg cgccgacgac accgtgctgg aggagatcga cctgccggc     120 aagtggaagc ccaagatgat cggcggcatc ggcggcttca tcaaggtgcg ccagtacgac    180
cagatcctga tcgagatctg cggcaagaag gccatcggca ccgtgctggt gggccccacc    240
cccgtgaaca tcatcggccg caacctgctg acccagctgg gctgcaccct gaacttc       297
```

<210> SEQ ID NO 65

```
<211> LENGTH: 297
<212> TYPE: DNA
<213> ORGANISM: Artificial
<220> FEATURE:
<223> OTHER INFORMATION: HIV Type C Protease Wild Type

<400> SEQUENCE: 65
cctcaaatca ctctttggca gcgacccctt gtctcaataa aagtagaggg ccagataaag      60
gaggctctct tagacacagg agcagatgat acagtattag aagaaataga tttgccaggg     120
aaatggaaac caaaaatgat aggggaatt ggaggtttta tcaaagtaag acagtatgat      180
caaatactta tagaaatttg tggaaaaaag gctataggta cagtattagt agggcctaca     240
ccagtcaaca taattggaag aaatctgtta actcagcttg gatgcacact aaatttt        297

<210> SEQ ID NO 66
<211> LENGTH: 297
<212> TYPE: DNA
<213> ORGANISM: Artificial
<220> FEATURE:
<223> OTHER INFORMATION: HIV Type C Inactivated Protease Optimized

<400> SEQUENCE: 66 ccccagat

| | |
|---|---|
| atcagcccca tcgagaccgt gcccgtgaag ctgaagcccg gcatggacgg ccccaaggtg | 360 |
| aagcagtggc ccctgaccga ggagaagatc aaggccctga ccgccatctg cgaggagatg | 420 |
| gagaaggagg gcaagatcac caagatcggc cccgacaacc cctacaacac ccccgtgttc | 480 |
| gccatcaaga agaaggacag caccaagtgg cgcaagctgg tggacttccg cgagctgaac | 540 |
| aagcgcaccc aggacttctg ggaggtgcag ctgggcatcc ccacccccgc cggcctgaag | 600 |
| aagaagaaga gcgtgaccgt gctggacgtg ggcgacgcct acttcagcgt gcccctggac | 660 |
| gagagcttcc gcaagtacac cgccttcacc atccccagca tcaacaacga ccccccggc | 720 |
| atccgctacc agtacaacgt gctgccccag ggctggaagg gcagccccgc catcttccag | 780 |
| agcagcatga ccaagatcct ggagcccttc cgcgccaaga ccccgacat cgtgatctac | 840 |
| caggccccc tgtacgtggg cagcgacctg gagatcggcc agcaccgcgc caagatcgag | 900 |
| gagctgcgcg agcacctgct gaagtggggc ttcaccaccc ccgacaagaa gcaccagaag | 960 |
| gagccccct cctgcccat cgagctgcac cccgacaagt ggaccgtgca gcccatcctg | 1020 |
| ctgcccgaga aggacagctg gaccgtgaac gacatccaga gctggtggg caagctgaac | 1080 |
| tgggccagcc agatctaccc cggcatcaag gtgcgccagc tgtgcaagct gctgcgcggc | 1140 |
| gccaaggccc tgaccgacat cgtgcccctg accgaggagg ccgagctgga gctggccgag | 1200 |
| aaccgcgaga tcctgcgcga gcccgtgcac ggcgtgtact acgaccccag caaggacctg | 1260 |
| atcgccgaga tccagaagca gggccacgag cagtggacct accagatcta ccaggagccc | 1320 |
| ttcaagaacc tgaagaccgg caagtacgcc aagatgcgca ccacccacac caacgacgtg | 1380 |
| aagcagctga ccgaggccgt gcagaagatc gccatggaga gcatcgtgat ctggggcaag | 1440 |
| acccccaagt ccgcctgcc catccagaag gagacctggg agacctggtg gaccgactac | 1500 |
| tggcaggcca cctggatccc cgagtgggag ttcgtgaaca ccccccccct ggtgaagctg | 1560 |
| tggtaccagc tggagaagga ccccatcgcc ggcgtggaga ccttctacgt ggacggcgcc | 1620 |
| accaaccgcg aggccaagat cggcaaggcc ggctacgtga ccgaccgcgg ccgccagaag | 1680 |
| atcgtgaccc tgaccaacac caccaaccag aagaccgagc tgcaggccat ccagctggcc | 1740 |
| ctgcaggaca gcggcagcga ggtgaacatc gtgaccgaca gccagtacgc cctgggcatc | 1800 |
| atccaggccc agcccgacaa gagcgacagc gagatcttca ccagatcat cgagcagctg | 1860 |
| atcaacaagg agcgcatcta cctgagctgg gtgcccgccc acaagggcat cggcggcaac | 1920 |
| gagcaggtgg acaagctggt gagcaagggc atccgcaagg tgctg | 1965 |

<210> SEQ ID NO 69
<211> LENGTH: 1965
<212> TYPE: DNA
<213> ORGANISM: Artificial
<220> FEATURE:
<223> OTHER INFORMATION: HIV Type C Inactivated Protease Mutated Reverse
      Transcriptase Wild Type

<400> SEQUENCE: 69

| | |
|---|---|
| cctcaaatca ctctttggca gcgacccctt gtctcaataa aagtagaggg ccagataaag | 60 |
| gaggctctct tagccacagg agcagatgat acagtattag aagaaataga tttgccaggg | 120 |
| aaatggaaac caaaaatgat agggggaatt ggaggtttta tcaaagtaag acagtatgat | 180 |
| caaatactta tagaaatttg tggaaaaaag gctataggta cagtattagt agggcctaca | 240 |
| ccagtcaaca taattggaag aaatctgtta actcagcttg gatgcacact aaatttccca | 300 |
| attagtccta ttgaaactgt accagtaaaa ttaaaaccag gaatggatgg cccaaaggtc | 360 |

```
aaacaatggc cattgacaga agaaaaaata aaagcattaa cagcaatttg tgaggaaatg    420
gagaaggaag gaaaaattac aaaaattggg cctgataatc catataacac tccagtattt    480
gccataaaaa agaaggacag tactaagtgg agaaaattag tagatttcag ggaactcaat    540
aaaagaactc aagacttttg ggaagttcaa ttaggaatac cacacccagc aggattaaaa    600
aagaaaaaat cagtgacagt gctagatgtg ggggatgcat attttt cagt tcctttagat    660 gaaagcttca ggaaatatac tgcattcacc atacctagta taaacaatga acaccaggg    720 attagatatc aatataatgt gctgccacag ggatggaaag gatcaccagc aatattccag    780
agtagcatga caaaaatctt agagcccttc agagcaaaaa atccagacat agttatctat    840
caagccccgt tgtatgtagg atctgactta gaaatagggc aacatagagc aaaatagaa    900 gagttaaggg aacatttatt gaatggggga tttacaacac cagacaagaa acatcaaaaa    960
gaacccccat ttcttcccat cgaactccat cctgacaaat ggacagtaca acctatactg   1020
ctgccagaaa aggatagttg gactgtcaat gatatacaga agttagtggg aaaattaaac   1080
tgggcaagtc agatttaccc agggattaaa gtaaggcaac tctgtaaact cctcagggg    1140 gccaaagcac taacagacat agtaccacta actgaagaag cagaattaga attggcagag   1200
aacagggaaa ttttaagaga accagtacat ggagtatatt atgatccatc aaaagacttg   1260
atagctgaaa tacagaaaca ggggcatgaa caatggacat atcaaattta tcaagaacca   1320
tttaaaaatc tgaaaacagg gaagtatgca aaaatgagga ctacccacac taatgatgta   1380
aaacagttaa cagaggcagt gcaaaaaata gccatggaaa gcatagtaat atggggaaag   1440
actcctaaat ttagactacc catccaaaaa gaaacatggg agacatggtg gacagactat   1500
tggcaagcca cctggatccc tgagtgggag tttgttaata ccccctcccct agtaaaatta   1560 tggtaccaac tagaaaaaga tcccatagca ggagtagaaa ctttctatgt agatggagca   1620
actaataggg aagctaaaat aggaaaagca gggtatgtta ctgacagagg aaggcagaaa   1680
attgttactc taactaacac aacaaatcag aagactgagt tacaagcaat tcagctagct   1740
ctgcaggatt caggatcaga agtaaacata gtaacagact cacagtatgc attaggaatc   1800
attcaagcac aaccagataa gagtgactca gagatattta accaaataat agaacagtta   1860
ataaacaagg aaagaatcta cctgtcatgg gtaccagcac ataaaggaat tgggggaaat   1920
gaacaagtag ataaattagt aagtaaggga attaggaaag tgttg                   1965
```

<210> SEQ ID NO 70
<211> LENGTH: 1977
<212> TYPE: DNA
<213> ORGANISM: Artificial
<220> FEATURE:
<223> OTHER INFORMATION: HIV Type C Protease and Reverse Transcriptase
      Optimized

<400> SEQUENCE: 70

```
ccccagatca ccctgtggca gcgcccctg gtgagcatca aggtggaggg ccagatcaag     60
gaggccctgc tggacaccgg cgccgacgac accgtgctgg aggagatcga cctgcccggc    120
aagtggaagc ccaagatgat cggcggcatc ggcggcttca tcaaggtgcg ccagtacgac    180
cagatcctga tcgagatctg cggcaagaag gccatcggca ccgtgctggt gggcccacc    240 cccgtgaaca tcatcggccg caacctgctg acccagctgg gctgcaccct gaacttcccc    300
atcagcccca tcgagaccgt gcccgtgaag ctgaagcccg gcatggacgg ccccaaggtg    360
aagcagtggc ccctgaccga ggagaagatc aaggccctga ccgccatctg cgaggagatg    420
```

```
gagaaggagg gcaagatcac caagatcggc cccgacaacc cctacaacac ccccgtgttc      480
gccatcaaga agaaggacag caccaagtgg cgcaagctgg tggacttccg cgagctgaac      540
aagcgcaccc aggacttctg ggaggtgcag ctgggcatcc cccacccgc cggcctgaag       600 aagaagaaga gcgtgaccgt gctggacgtg ggcgacgcct acttcagcgt gcccctggac      660
gagagcttcc gcaagtacac cgccttcacc atccccagca tcaacaacga ccccccggc      720 atccgctacc agtacaacgt gctgcccag ggctggaagg gcagcccgc catcttccag        780 agcagcatga ccaagatcct ggagcccttc gcgccaaga ccccgacat cgtgatctac        840 cagtacatgg acgacctgta cgtgggcagc gacctggaga tcggccagca ccgcgccaag     900
atcgaggagc tgcgcgagca cctgctgaag tggggcttca ccaccccga caagaagcac     960 cagaaggagc ccccttcct gtggatgggc tacgagctgc accccgacaa gtggaccgtg     1020
cagcccatcc tgctgcccga aggacagc tggaccgtga cgacatcca gaagctggtg       1080 ggcaagctga actgggccag ccagatctac cccggcatca aggtgcgcca gctgtgcaag    1140
ctgctgcgcg cgccaaggc cctgaccgac atcgtgcccc tgaccgagga ggccgagctg     1200
gagctggccg agaaccgcga gatcctgcgc gagcccgtgc acggcgtgta ctacgacccc    1260
agcaaggacc tgatcgccga gatccagaag cagggccacg agcagtggac ctaccagatc    1320
taccaggagc ccttcaagaa cctgaagacc ggcaagtacg ccaagatgcg caccacccac    1380
accaacgacg tgaagcagct gaccgaggcc gtgcagaaga tcgccatgga gagcatcgtg    1440
atctggggca agacccccaa gttccgcctg cccatccaga ggagacctg ggagacctgg     1500 tggaccgact actggcaggc cacctggatc cccgagtggg agttcgtgaa caccccccc     1560 ctggtgaagc tgtggtacca gctggagaag acccccatcg ccggcgtgga gaccttctac    1620
gtggacggcg ccaccaaccg cgaggccaag atcggcaagg ccggctacgt gaccgaccgc    1680
ggccgccaga gatcgtgac cctgaccaac accaccaacc agaagaccga gctgcaggcc     1740
atccagctgg ccctgcagga cagcggcagc gaggtgaaca tcgtgaccga cagccagtac    1800
gccctgggca tcatccaggc ccagcccgac aagagcgaca gcgagatctt caaccagatc    1860
atcgagcagc tgatcaacaa ggagcgcatc tacctgagct gggtgcccgc ccacaagggc    1920
atcggcggca acgagcaggt ggacaagctg gtgagcaagg catccgcaa ggtgctg        1977
```

<210> SEQ ID NO 71
<211> LENGTH: 1977
<212> TYPE: DNA
<213> ORGANISM: Artificial
<220> FEATURE:
<223> OTHER INFORMATION: HIV Type C Protease and Reverse Transcriptase
      Wild Type

<400> SEQUENCE: 71

```
cctcaaatca ctctttggca gcgacccctt gtctcaataa aagtagaggg ccagataaag      60
gaggctctct tagacacagg agcagatgat acagtattag aagaaataga tttgccaggg     120
aaatggaaac caaaaatgat aggggggaatt ggaggtttta tcaaagtaag acagtatgat    180
caaatactta tagaaatttg tggaaaaaag gctataggta cagtattagt agggcctaca    240
ccagtcaaca taattggaag aaatctgtta actcagcttg gatgcacact aaattttcca    300
attagtccta ttgaaactgt accagtaaaa ttaaaaccag gaatggatgg cccaaaggtc    360
aaacaatggc cattgacaga agaaaaaata aaagcattaa cagcaatttg tgaggaaatg    420
gagaaggaag gaaaaattac aaaaattggg cctgataatc catataacac tccagtattt    480
```

```
gccataaaaa agaaggacag tactaagtgg agaaaattag tagatttcag ggaactcaat      540
aaaagaactc aagacttttg ggaagttcaa ttaggaatac cacacccagc aggattaaaa      600
aagaaaaaat cagtgacagt gctagatgtg ggggatgcat attttttcagt tcctttagat    660 gaaagcttca ggaaatatac tgcattcacc atacctagta taaacaatga acaccaggg      720 attagatatc aatataatgt gctgccacag ggatggaaag gatcaccagc aatattccag     780
agtagcatga caaaaatctt agagcccttc agagcaaaaa atccagacat agttatctat    840
caatatatgg atgacttgta tgtaggatct gacttagaaa tagggcaaca tagagcaaaa   900
atagaagagt taagggaaca tttattgaaa tggggattta caacaccaga caagaaacat  960 caaaagaac ccccatttct ttggatgggg tatgaactcc atcctgacaa atggacagta   1020
caacctatac tgctgccaga aaaggatagt tggactgtca atgatataca gaagttagtg  1080
ggaaaattaa actgggcaag tcagatttac ccagggatta agtaaggca actctgtaaa  1140 ctcctcaggg gggccaaagc actaacagac atagtaccac taactgaaga agcagaatta  1200
gaattggcag agaacaggga aattttaaga gaaccagtac atggagtata ttatgatcca  1260
tcaaaagact tgatagctga aatacagaaa caggggcatg aacaatggac atatcaaatt  1320
tatcaagaac catttaaaaa tctgaaaaca ggagaagtatg caaaaatgag gactacccac  1380
actaatgatg taaaacagtt aacagaggca gtgcaaaaaa tagccatgga aagcatagta  1440
atatggggaa agactcctaa atttagacta cccatccaaa aagaaacatg ggagacatgg  1500
tggacagact attggcaagc cacctggatc cctgagtggg agtttgttaa tacccctccc  1560
ctagtaaaat tatggtacca actagaaaaa gatcccatag caggagtaga aactttctat  1620
gtagatggag caactaatag ggaagctaaa ataggaaaag cagggtatgt tactgacaga  1680
ggaaggcaga aaattgttac tctaactaac acaacaaatc agaagactga gttacaagca  1740
attcagctag ctctgcagga ttcaggatca gaagtaaaca tagtaacaga ctcacagtat  1800
gcattaggaa tcattcaagc acaaccagat aagagtgact cagagatatt taaccaaata  1860
atagaacagt taataaacaa ggaaagaatc tacctgtcat gggtaccagc acataaagga  1920
attgggggaa atgaacaagt agataaatta gtaagtaagg gaattaggaa agtgttg     1977

<210> SEQ ID NO 72
<211> LENGTH: 75
<212> TYPE: DNA
<213> ORGANISM: Artificial
<220> FEATURE:
<223> OTHER INFORMATION: HIV Type C RevExon1 Optimized

<400> SEQUENCE: 72
atggccggcc gcagcggcga cagcgacgag gccctgctgc aggtggtgaa gatcatcaag   60
atcctgtacc agagc                                                   75

<210> SEQ ID NO 73
<211> LENGTH: 76
<212> TYPE: DNA
<213> ORGANISM: Artificial
<220> FEATURE:
<223> OTHER INFORMATION: HIV Type C RevExon1 Wild Type

<400> SEQUENCE: 73
atggcaggaa gaagcggaga cagcgacgaa gcgctcctcc aagtggtgaa gatcatcaaa   60
atcctctatc aaagca                                                   76
```

<210> SEQ ID NO 74
<211> LENGTH: 246
<212> TYPE: DNA
<213> ORGANISM: Artificial
<220> FEATURE:
<223> OTHER INFORMATION: HIV Type C RevExon2 Optimized

<400> SEQUENCE: 74

```
ccctacccca agcccgaggg caccgccag gcccgccgca accgccgccg ccgctggcgc      60
gcccgccagc gccagatcca caccatcggc gagcgcatcc tggtggcctg cctgggccgc     120
agcgccgagc ccgtgccct gcagctgccc ccctggagc gcctgcacat caactgcagc      180
gagggcagcg gcaccagcgg cacccagcag agccagggca ccaccgaggg cgtgggcgac    240
ccctaa                                                                246
```

<210> SEQ ID NO 75
<211> LENGTH: 248
<212> TYPE: DNA
<213> ORGANISM: Artificial
<220> FEATURE:
<223> OTHER INFORMATION: HIV Type C RevExon2 Wild Type

<400> SEQUENCE: 75

```
acccttaccc caagcccgag gggactcgac aggctcggag gaatcgaaga agaaggtgga     60
gagcaagaca gagacagatc catacgattg gtgagcggat tcttgtcgct tgcctgggac    120
gatctgcgga gcctgtgcct cttcagctac caccgcttga gagacttcat attaattgca    180
gtgagggcag tggaacttct gggacacagc agtctcaggg gactacagag ggggtgggag    240
atccttaa                                                              248
```

<210> SEQ ID NO 76
<211> LENGTH: 1680
<212> TYPE: DNA
<213> ORGANISM: Artificial
<220> FEATURE:
<223> OTHER INFORMATION: HIV Type C Reverse Transcriptase Optimized

<400> SEQUENCE: 76

```
cccatcagcc ccatcgagac cgtgcccgtg aagctgaagc ccggcatgga cggccccaag     60
gtgaagcagt ggcccctgac cgaggagaag atcaaggccc tgaccgccat ctgcgaggag    120
atggagaagg agggcaagat caccaagatc ggcccccgaca accccctacaa cacccccgtg   180
ttcgccatca agaagaagga cagcaccaag tggcgcaagc tggtggactt ccgcgagctg     240
aacaagcgca cccaggactt ctgggaggtg cagctgggca tcccccaccc cgccggcctg    300
aagaagaaga gagcgtgac cgtgctggac gtgggcgacg cctacttcag cgtgcccctg      360
gacgagagct tccgcaagta caccgccttc accatcccca gcatcaacaa cgagaccccc    420
ggcatccgct accagtacaa cgtgctgccc cagggctgga agggcagccc cgccatcttc    480
cagagcagca tgaccaagat cctggagccc ttccgcgcca gaaccccga catcgtgatc     540
taccagtaca tggacgacct gtacgtgggc agcgacctgg agatcggcca gcaccgcgcc    600
aagatcgagg agctgcgcga gcacctgctg aagtggggct caccacccc cgacaagaag    660
caccagaagg agcccccctt cctgtggatg ggctacgagc tgcaccccga caagtggacc    720
gtgcagccca tcctgctgcc cgagaaggac agctggaccg tgaacgacat ccagaagctg    780
gtgggcaagc tgaactgggc cagcagatc taccccggca tcaaggtgcg ccagctgtgc    840
aagctgctgc gcggcgccaa ggccctgacc gacatcgtgc ccctgaccga ggaggccgag    900
```

```
ctggagctgg ccgagaaccg cgagatcctg cgcgagcccg tgcacggcgt gtactacgac    960
cccagcaagg acctgatcgc cgagatccag aagcagggcc acgagcagtg gacctaccag   1020
atctaccagg agcccttcaa gaacctgaag accggcaagt acgccaagat gcgcaccacc   1080
cacaccaacg acgtgaagca gctgaccgag gccgtgcaga agatcgccat ggagagcatc   1140
gtgatctggg gcaagacccc caagttccgc ctgcccatcc agaaggagac ctgggagacc   1200
tggtggaccg actactggca ggccacctgg atccccgagt gggagttcgt gaacaccccc   1260
cccctggtga gctgtggta ccagctggag aaggacccca cgccggcgt ggagaccttc   1320
tacgtggacg gcgccaccaa ccgcgaggcc aagatcggca aggccggcta cgtgaccgac   1380
cgcggccgcc agaagatcgt gaccctgacc aacaccacca ccagaagac cgagctgcag   1440
gccatccagc tggccctgca ggacagcggc agcgaggtga acatcgtgac cgacagccag   1500
tacgccctgg gcatcatcca ggcccagccc gacaagagcg acagcgagat cttcaaccag   1560
atcatcgagc agctgatcaa caaggagcgc atctacctga gctgggtgcc cgcccacaag   1620
ggcatcggcg gcaacgagca ggtggacaag ctggtgagca agggcatccg caaggtgctg   1680
```

<210> SEQ ID NO 77
<211> LENGTH: 1680
<212> TYPE: DNA
<213> ORGANISM: Artificial
<220> FEATURE:
<223> OTHER INFORMATION: HIV Type C Reverse Transcriptase Wild Type

<400> SEQUENCE: 77

```
ccaattagtc ctattgaaac tgtaccagta aaattaaaac caggaatgga tgcccaaag     60
gtcaaacaat ggccattgac agaagaaaaa ataaaagcat taacagcaat tgtgaggaa    120
atggagaagg aaggaaaaat tacaaaaatt gggcctgata atccatataa cactccagta    180
tttgccataa aaagaagga cagtactaag tggagaaaat tagtagattt cagggaactc    240
aataaaagaa ctcaagactt tgggaagtt caattaggaa taccacaccc agcaggatta    300
aaaagaaaa atcagtgac agtgctagat gtggggatg catattttc agttccttta      360
gatgaaagct tcaggaaata tactgcattc accataccta gtataaacaa tgaaacacca    420
gggattagat atcaatataa tgtgctgcca cagggatgga aaggatcacc agcaatattc    480
cagagtagca tgacaaaaat cttagagccc ttcagagcaa aaaatccaga catagttatc    540
tatcaatata tggatgactt gtatgtagga tctgacttag aaatagggca acatagagca    600
aaaatagaag agttaaggga acatttattg aaatggggat ttacaacacc agacaagaaa    660
catcaaaaag acccccatt tctttggatg gggtatgaac tccatcctga caatggaca     720
gtacaaccta tactgctgcc agaaaaggat agttggactg tcaatgatat acagaagtta    780
gtgggaaaat taaactgggc aagtcagatt tacccaggga ttaaagtaag gcaactctgt    840
aaactcctca gggggccaa agcactaaca gacatagtac cactaactga agaagcagaa    900
ttagaattgg cagagaacag ggaaattta agagaaccag tacatggagt atattatgat    960
ccatcaaaag acttgatagc tgaaatacag aaacagggg atgaacaatg acatatcaa   1020
atttatcaag aaccatttaa aaatctgaaa acagggaagt atgcaaaaat gaggactacc   1080
cacactaatg atgtaaaaca gttaacagag gcagtgcaaa aatagccat ggaaagcata   1140
gtaatatggg gaaagactcc taaatttaga ctacccatcc aaaaagaaac atgggagaca   1200
tggtggacag actattggca agccacctgg atccctgagt gggagtttgt taatacccct   1260
ccctagtaa aattatggta ccaactagaa aaagatccca tagcaggagt agaaactttc   1320
```

-continued

| | |
|---|---|
| tatgtagatg gagcaactaa tagggaagct aaaataggaa aagcagggta tgttactgac | 1380 |
| agaggaaggc agaaaattgt tactctaact aacacaacaa atcagaagac tgagttacaa | 1440 |
| gcaattcagc tagctctgca ggattcagga tcagaagtaa acatagtaac agactcacag | 1500 |
| tatgcattag gaatcattca agcacaacca gataagagtg actcagagat atttaaccaa | 1560 |
| ataatagaac agttaataaa caaggaaaga atctacctgt catgggtacc agcacataaa | 1620 |
| ggaattgggg gaaatgaaca agtagataaa ttagtaagta agggaattag gaaagtgttg | 1680 |

<210> SEQ ID NO 78
<211> LENGTH: 1668
<212> TYPE: DNA
<213> ORGANISM: Artificial
<220> FEATURE:
<223> OTHER INFORMATION: HIV Type C Mutated Reverse Transcriptase Optimized

<400> SEQUENCE: 78

| | |
|---|---|
| cccatcagcc ccatcgagac cgtgcccgtg aagctgaagc ccggcatgga cggccccaag | 60 |
| gtgaagcagt ggcccctgac cgaggagaag atcaaggccc tgaccgccat ctgcgaggag | 120 |
| atggagaagg agggcaagat caccaagatc ggccccgaca acccctacaa caccccgtg | 180 |
| ttcgccatca agaagaagga cagcaccaag tggcgcaagc tggtggactt ccgcgagctg | 240 |
| aacaagcgca cccaggactt ctgggaggtg cagctgggca tcccccaccc cgccggcctg | 300 |
| aagaagaaga gagcgtgac cgtgctggac gtgggcgacg cctacttcag cgtgcccctg | 360 |
| gacgagagct tccgcaagta caccgccttc accatcccca gcatcaacaa cgagaccccc | 420 |
| ggcatccgct accagtacaa cgtgctgccc cagggctgga agggcagccc cgccatcttc | 480 |
| cagagcagca tgaccaagat cctggagccc ttccgcgcca gaaccccga catcgtgatc | 540 |
| taccaggccc ccctgtacgt gggcagcgac ctggagatcg ccagcaccg cgccaagatc | 600 |
| gaggagctgc gcgagcacct gctgaagtgg ggcttcacca cccccgacaa gaagcaccag | 660 |
| aaggagcccc ccttcctgcc catcgagctg caccccgaca gtggaccgt gcagcccatc | 720 |
| ctgctgcccg agaaggacag ctggaccgtg aacgacatcc agaagctggt gggcaagctg | 780 |
| aactgggcca gccagatcta ccccggcatc aaggtgcgcc agctgtgcaa gctgctgcgc | 840 |
| ggcgccaagg ccctgaccga catcgtgccc ctgaccgagg aggccagct ggagctggcc | 900 |
| gagaaccgcg agatcctgcg cgagcccgtg cacggcgtgt actacgaccc cagcaaggac | 960 |
| ctgatcgccg agatccagaa gcagggccac gagcagtgga cctaccagat ctaccaggag | 1020 |
| cccttcaaga acctgaagac cggcaagtac gccaagatgc gcaccaccca caccaacgac | 1080 |
| gtgaagcagc tgaccgaggc cgtgcagaag atcgccatgg agagcatcgt gatctggggc | 1140 |
| aagaccccca gttccgcct gcccatccag aaggagacct gggagacctg tggaccgac | 1200 |
| tactggcagg ccacctggat ccccgagtgg gagttcgtga cacccccc cctggtgaag | 1260 |
| ctgtggtacc agctggagaa ggaccccatc gccggcgtgg agaccttcta cgtggacggc | 1320 |
| gccaccaacc gcgaggccaa gatcggcaag gccggctacg tgaccgaccg cggccgccag | 1380 |
| aagatcgtga ccctgaccaa caccaccaac cagaagaccg agctgcaggc catccagctg | 1440 |
| gccctgcagg acagcggcag cgaggtgaac atcgtgaccg acagccagta cgccctgggc | 1500 |
| atcatccagg cccagcccga caagagcgac agcgagatct caaccagat catcgagcag | 1560 |
| ctgatcaaca aggagcgcat ctacctgagc tgggtgcccg cccacaaggg catcggcggc | 1620 |
| aacgagcagg tggacaagct ggtgagcaag ggcatccgca aggtgctg | 1668 |

<210> SEQ ID NO 79
<211> LENGTH: 1668
<212> TYPE: DNA
<213> ORGANISM: Artificial
<220> FEATURE:
<223> OTHER INFORMATION: HIV Type C Mutated Reverse Transcriptase Wild
      Type

<400> SEQUENCE: 79

```
ccaattagtc ctattgaaac tgtaccagta aaattaaaac caggaatgga tggcccaaag      60
gtcaaacaat ggccattgac agaagaaaaa ataaaagcat taacagcaat ttgtgaggaa     120
atggagaagg aaggaaaaat tacaaaaatt gggcctgata atccatataa cactccagta     180
tttgccataa aaagaaagga cagtactaag tggagaaaat tagtagattt cagggaactc     240
aataaaagaa ctcaagactt ttgggaagtt caattaggaa taccacaccc agcaggatta     300
aaaaagaaaa aatcagtgac agtgctagat gtgggggatg catattttc agttccttta     360
gatgaaagct tcaggaaata tactgcattc accataccta gtataaacaa tgaaacacca     420
gggattagat atcaatataa tgtgctgcca cagggatgga aaggatcacc agcaatattc     480
cagagtagca tgacaaaaat cttagagccc ttcagagcaa aaaatccaga catagttatc     540
tatcaagccc cgttgtatgt aggatctgac ttagaaatag gcaacatag agcaaaaata     600
gaagagttaa gggaacattt attgaaatgg ggatttacaa caccagacaa gaaacatcaa     660
aaagaaccc catttcttcc catcgaactc catcctgaca aatggacagt acaacctata     720
ctgctgccag aaaaggatag ttggactgtc aatgatatac agaagttagt gggaaaatta     780
aactgggcaa gtcagattta cccagggatt aaagtaaggc aactctgtaa actcctcagg     840
ggggccaaag cactaacaga catagtacca ctaactgaag aagcagaatt agaattggca     900
gagaacaggg aaattttaag agaaccagta catggagtat attatgatcc atcaaaagac     960
ttgatagctg aaatacagaa acaggggcat gaacaatgga catatcaaat ttatcaagaa    1020
ccatttaaaa atctgaaaac agggaagtat gcaaaaatga ggactaccca cactaatgat    1080
gtaaaacagt taacagaggc agtgcaaaaa atagccatgg aaagcatagt aatatgggga    1140
aagactccta aatttagact acccatccaa aaagaaacat gggagacatg gtggacagac    1200
tattggcaag ccacctggat ccctgagtgg gagtttgtta taccccctcc cctagtaaaa    1260
ttatggtacc aactagaaaa agatcccata gcaggagtag aaactttcta tgtagatgga    1320
gcaactaata gggaagctaa aataggaaaa gcagggtatg ttactgacag aggaaggcag    1380
aaaattgtta ctctaactaa cacaacaaat cagaagactg agttacaagc aattcagcta    1440
gctctgcagg attcaggatc agaagtaaac atagtaacag actcacagta tgcattagga    1500
atcattcaag cacaaccaga taagagtgac tcagagatat taaccaaat aatagaacag    1560
ttaataaaca aggaaagaat ctacctgtca tgggtaccag cacataaagg aattggggga    1620
aatgaacaag tagataaatt agtaagtaag ggaattagga aagtgttg                 1668
```

<210> SEQ ID NO 80
<211> LENGTH: 216
<212> TYPE: DNA
<213> ORGANISM: Artificial
<220> FEATURE:
<223> OTHER INFORMATION: HIV Type C TatC22Exon1 Optimized

<400> SEQUENCE: 80

```
atggagcccg tggaccccaa gctgaagccc tggaaccacc ccggcagcca gcccaagacc      60
```

```
gccggcaaca actgcttctg caagcactgc agctaccact gcctggtgtg cttccagacc    120
aagggcctgg gcatcagcta cggccgcaag aagcgccgcc agcgccgcag cgccccccccc   180 agcggcgagg accaccagaa ccccctgagc aagcag                              216
```

```
<210> SEQ ID NO 81
<211> LENGTH: 216
<212> TYPE: DNA
<213> ORGANISM: Artificial
<220> FEATURE:
<223> OTHER INFORMATION: HIV Type C TatExon1 Optimized

<400> SEQUENCE: 81
atggagcccg tggaccccaa gctgaagccc tggaaccacc ccggcagcca gcccaagacc    60
gcctgcaaca actgcttctg caagcactgc agctaccact gcctggtgtg cttccagacc   120
aagggcctgg gcatcagcta cggccgcaag aagcgccgcc agcgccgcag cgccccccccc  180 agcggcgagg accaccagaa ccccctgagc aagcag                              216
```

```
<210> SEQ ID NO 82
<211> LENGTH: 216
<212> TYPE: DNA
<213> ORGANISM: Artificial
<220> FEATURE:
<223> OTHER INFORMATION: HIV Type C TatExon1 Wild Type

<400> SEQUENCE: 82
atggagccag tagatcctaa actaaagccc tggaaccatc caggaagcca acctaaaaca    60
gcttgtaata attgcttttg caaacactgt agctatcatt gtctagtttg ctttcagaca   120
aaaggtttag gcatttccta tggcaggaag aagcggagac agcgacgaag cgctcctcca   180
agtggtgaag atcatcaaaa tcctctatca aagcag                              216
```

```
<210> SEQ ID NO 83
<211> LENGTH: 93
<212> TYPE: DNA
<213> ORGANISM: Artificial
<220> FEATURE:
<223> OTHER INFORMATION: HIV Type C TatExon2 Optimized

<400> SEQUENCE: 83
cccctgcccc aggcccgcgg cgacagcacc ggcagcgagg agagcaagaa gaaggtggag    60
agcaagaccg agaccgaccc ctacgactgg tga                                 93
```

```
<210> SEQ ID NO 84
<211> LENGTH: 93
<212> TYPE: DNA
<213> ORGANISM: Artificial
<220> FEATURE:
<223> OTHER INFORMATION: HIV Type C TatExon2 Wild Type

<400> SEQUENCE: 84
cccttacccc aagcccgagg ggactcgaca ggctcggagg aatcgaagaa gaaggtggag    60
agcaagacag agacagatcc atacgattgg tga                                 93
```

```
<210> SEQ ID NO 85
<211> LENGTH: 579
<212> TYPE: DNA
<213> ORGANISM: Artificial
<220> FEATURE:
<223> OTHER INFORMATION: HIV Type C Vif Optimized
```

-continued

```
<400> SEQUENCE: 85
atggagaacc gctggcaggt gctgatcgtg tggcaggtgg accgcatgaa gatccgcgcc      60
tggaacagcc tggtgaagca ccacatgtac atcagccgcc gcgccagcgg ctgggtgtac     120
cgccaccact tcgagagccg ccaccccaag gtgagcagcg aggtgcacat ccccctgggc     180
gacgcccgcc tggtgatcaa gacctactgg ggcctgcaga ccggcgagcg cgactggcac     240
ctgggccacg gcgtgagcat cgagtggcgc ctgcgcgagt acagcaccca ggtggacccc     300
gacctggccg accagctgat ccacatgcac tacttcgact gcttcaccga gagcgccatc     360
cgccaggcca tcctgggcca catcgtgttc ccccgctgcg actaccaggc cggccacaag     420
aaggtgggca gcctgcagta cctggccctg accgccctga tcaagcccaa gaagcgcaag     480
ccccccctgc ccagcgtgcg caagctggtg gaggaccgct ggaacgaccc ccagaagacc     540
cgcggccgcc gcggcaacca ccatgaac ggccactag                              579

<210> SEQ ID NO 86
<211> LENGTH: 579
<212> TYPE: DNA
<213> ORGANISM: Artificial
<220> FEATURE:
<223> OTHER INFORMATION: HIV Type C Vif Wild Type

<400> SEQUENCE: 86
atggaaaaca gatggcaggt gctgattgtg tggcaggtgg acaggatgaa gattagagca      60
tggaatagtt tagtaaagca ccatatgtat atatcaagga gagctagtgg atgggtctac     120
agacatcatt ttgaaagcag acatccaaaa gtaagttcag aagtacatat cccattaggg     180
gatgctagat tagtaataaa aacatattgg ggtttgcaga caggagaaag agattggcat     240
ttgggtcatg gagtctccat agaatggaga ctgagagaat acagcacaca agtagaccct     300
gacctggcag accagctaat tcacatgcat tattttgatt gttttacaga atctgccata     360
agacaagcca tattaggaca catagttttt cctaggtgtg actatcaagc aggacataag     420
aaggtaggat ctctgcaata cttggcactg acagcattga taaaaccaaa aaagagaaag     480
ccacctctgc ctagtgttag aaaattagta gaggatagat ggaacgaccc ccagaagacc     540
aggggccgca gagggaacca tacaatgaat ggacactag                             579

<210> SEQ ID NO 87
<211> LENGTH: 288
<212> TYPE: DNA
<213> ORGANISM: Artificial
<220> FEATURE:
<223> OTHER INFORMATION: HIV Type C Vpr  Optimized

<400> SEQUENCE: 87
atggagcgcc cccccgagga ccagggcccc cagcgcgagc cctacaacga gtggaccctg      60
gagatcctgg aggagctgaa gcaggaggcc gtgcgccact cccccgccc ctggctgcac      120 agcctgggcc agtacatcta cgagacctac ggcgacacct ggaccggcgt ggaggccatc     180
atccgcgtgc tgcagcagct gctgttcatc cacttccgca tcggctgcca gcacagccgc     240
atcggcatcc tgcgccagcg ccgcgcccgc aacggcgcca gccgcagc                  288

<210> SEQ ID NO 88
<211> LENGTH: 288
<212> TYPE: DNA
<213> ORGANISM: Artificial
<220> FEATURE:
<223> OTHER INFORMATION: HIV Type C Vpr Wild Type
```

<400> SEQUENCE: 88

```
atggaacgac ccccagaaga ccaggggccg cagagggaac catacaatga atggacacta      60
gagattctag aagaactcaa gcaggaagct gtcagacact tcctagacc atggctccat      120 agcttaggac aatatatcta tgaaacctat ggggatactt ggacgggagt tgaagctata      180
ataagagtac tgcaacaact actgttcatt catttcagaa ttggatgcca acatagcaga      240
ataggcatct tgcgacagag aagagcaaga aatggagcca gtagatcc                  288
```

<210> SEQ ID NO 89
<211> LENGTH: 267
<212> TYPE: DNA
<213> ORGANISM: Artificial
<220> FEATURE:
<223> OTHER INFORMATION: HIV Type C Vpu Optimized

<400> SEQUENCE: 89

```
atggtgagcc tgagcctgtt caagggcgtg gactaccgcc tgggcgtggg cgccctgatc      60
gtggccctga tcatcgccat catcgtgtgg accatcgcct acatcgagta ccgcaagctg      120
gtgcgccaga agaagatcga ctggctgatc aagcgcatcc gcgagcgcgc cgaggacagc      180
ggcaacgaga gcgacggcga caccgaggag ctgagcacca tggtggacat gggccacctg      240
cgcctgctgg acgccaacga cctgtaa                                         267
```

<210> SEQ ID NO 90
<211> LENGTH: 267
<212> TYPE: DNA
<213> ORGANISM: Artificial
<220> FEATURE:
<223> OTHER INFORMATION: HIV Type C Vpu Wild Type

<400> SEQUENCE: 90

```
atggtaagtt taagttttatt taaaggagta gattatagat taggagtagg agcattgata      60
gtagcactaa tcatagcaat aatagtgtgg accatagcat atatagaata taggaaattg      120
gtaagacaaa agaaaataga ctggttaatt aaaagaatta gggaaagagc agaagacagt      180
ggcaatgaga gtgatgggga cacagaagaa ttgtcaacaa tggtggatat ggggcatctt      240
aggcttctgg atgctaatga tttgtaa                                         267
```

<210> SEQ ID NO 91
<211> LENGTH: 321
<212> TYPE: DNA
<213> ORGANISM: Artificial
<220> FEATURE:
<223> OTHER INFORMATION: HIV Type C RevExon 1 and 2 Optimized

<400> SEQUENCE: 91

```
atggccggcc gcagcggcga cagcgacgag gccctgctgc aggtggtgaa gatcatcaag      60
atcctgtacc agagccccta ccccaagccc gagggcaccc gccaggcccg ccgcaaccgc      120
cgccgccgct ggcgcgcccg ccagcgccag atccacacca tcggcgagcg catcctggtg      180
gcctgcctgg gccgcagcgc cgagcccgtg cccctgcagc tgccccccct ggagcgcctg      240
cacatcaact gcagcgaggg cagcggcacc agcggcaccc agcagagcca gggcaccacc      300
gagggcgtgg gcgaccccta a                                               321
```

<210> SEQ ID NO 92
<211> LENGTH: 324
<212> TYPE: DNA

<213> ORGANISM: Artificial
<220> FEATURE:
<223> OTHER INFORMATION: HIV Type C RevExon 1 and 2 Wild Type

<400> SEQUENCE: 92

```
atggcaggaa gaagcggaga cagcgacgaa gcgctcctcc aagtggtgaa gatcatcaaa      60
atcctctatc aaagcaaccc ttaccccaag cccgagggga ctcgacaggc tcggaggaat     120
cgaagaagaa ggtggagagc aagacagaga cagatccata cgattggtga gcggattctt    180
gtcgcttgcc tgggacgatc tgcggagcct gtgcctcttc agctaccacc gcttgagaga    240
cttcatatta attgcagtga gggcagtgga acttctggga cacagcagtc tcaggggact    300
acagaggggg tgggagatcc ttaa                                            324
```

<210> SEQ ID NO 93
<211> LENGTH: 309
<212> TYPE: DNA
<213> ORGANISM: Artificial
<220> FEATURE:
<223> OTHER INFORMATION: HIV Type C TatC22 Exon 1 and 2 Optimized

<400> SEQUENCE: 93

```
atggagcccg tggaccccaa gctgaagccc tggaaccacc ccggcagcca gcccaagacc      60
gccggcaaca actgcttctg caagcactgc agctaccact gcctggtgtg cttccagacc     120
aagggcctgg gcatcagcta cggccgcaag aagcgccgcc agcgccgcag cgcccccccc    180
agcggcgagg accaccagaa ccccctgagc aagcagcccc tgcccaggc ccgcggcgac     240
agcaccggca gcgaggagag caagaagaag gtggagagca gaccgagac cgacccctac    300
gactggtga                                                             309
```

<210> SEQ ID NO 94
<211> LENGTH: 309
<212> TYPE: DNA
<213> ORGANISM: Artificial
<220> FEATURE:
<223> OTHER INFORMATION: HIV Type C Tat Exon 1 and 2 Optimized

<400> SEQUENCE: 94

```
atggagcccg tggaccccaa gctgaagccc tggaaccacc ccggcagcca gcccaagacc      60
gcctgcaaca actgcttctg caagcactgc agctaccact gcctggtgtg cttccagacc    120
aagggcctgg gcatcagcta cggccgcaag aagcgccgcc agcgccgcag cgcccccccc   180
agcggcgagg accaccagaa ccccctgagc aagcagcccc tgcccaggc ccgcggcgac     240
agcaccggca gcgaggagag caagaagaag gtggagagca gaccgagac cgacccctac    300
gactggtga                                                             309
```

<210> SEQ ID NO 95
<211> LENGTH: 309
<212> TYPE: DNA
<213> ORGANISM: Artificial
<220> FEATURE:
<223> OTHER INFORMATION: HIV Type C Tat Exon 1 and 2 Wild Type

<400> SEQUENCE: 95

```
atggagccag tagatcctaa actaaagccc tggaaccatc caggaagcca acctaaaaca      60
gcttgtaata attgcttttg caaacactgt agctatcatt gtctagtttg ctttcagaca    120
aaaggtttag gcatttccta tggcaggaag aagcggagac agcgacgaag cgctcctcca    180
agtggtgaag atcatcaaaa tcctctatca aagcagccct taccccaagc ccgaggggac    240
```
tcgacaggct cggaggaatc gaagaagaag gtggagagca agacagagac agatccatac    300
gattggtga                                                           309

<210> SEQ ID NO 96
<211> LENGTH: 624
<212> TYPE: DNA
<213> ORGANISM: Artificial
<220> FEATURE:
<223> OTHER INFORMATION: HIV Type C NefD125g Optimized  Myristalization
      Modification

<400> SEQUENCE: 96
atggccggca agtggagcaa gcgcagcatc gtgggctggc cgccgtgcg cgagcgcatg     60 cgccgcaccg agcccgccgc cgagggcgtg ggcgccgcca gcaggacct ggaccgccac    120 ggcgccctga ccagcagcaa cacccccgcc accaacgagg cctgcgcctg gctgcaggcc   180
caggaggagg acgcgacgt gggcttcccc gtgcgccccc aggtgcccct gcgccccatg    240
acctacaaga gcgccgtgga cctgagcttc ttcctgaagg agaagggcgg cctggagggc   300
ctgatctaca gccgcaagcg ccaggagatc ctggacctgt gggtgtacaa cacccagggc   360
ttcttccccg gctggcagaa ctacaccagc ggccccggcg tgcgcttccc cctgaccttc   420
ggctggtgct tcaagctggt gcccgtggac cccgcgagg tgaaggaggc caacgagggc    480
gaggacaact gcctgctgca ccccatgagc cagcacggcg ccgaggacga ggaccgcgag   540
gtgctgaagt ggaagttcga cagcctgctg gcccaccgcc acatggcccg cgagctgcac   600
cccgagtact acaaggactg ctga                                         624

<210> SEQ ID NO 97
<211> LENGTH: 2565
<212> TYPE: DNA
<213> ORGANISM: Artificial
<220> FEATURE:
<223> OTHER INFORMATION: Envgp160_TV2_C_ZAopt

<400> SEQUENCE: 97
atgcgcgccc gcggcatcct gaagaactac cgccactggt ggatctgggg catcctgggc    60
ttctggatgc tgatgatgtg caacgtgaag ggcctgtggg tgaccgtgta ctacggcgtg   120
cccgtgggcc gcgaggccaa gaccaccctg ttctgcgcca gcgacgccaa ggcctacgag   180
aaggaggtgc acaacgtgtg gccaccac gcctgcgtgc ccaccgaccc caaccccag    240 gaggtgatcc tgggcaacgt gaccgagaac ttcaacatgt ggaagaacga catggtggac   300
cagatgcagg aggacatcat cagcctgtgg gaccagagcc tgaagccctg cgtgaagctg   360
acccccctgt gcgtgaccct gaactgcacc aacgccaccg tgaactacaa caacaccagc   420
aaggacatga gaactgcag cttctacgtg accaccgagc tgcgcgacaa gaagaagaag   480
gagaacgccc tgttctaccg cctggacatc gtgcccctga caaccgcaa gaacggcaac    540 atcaacaact accgcctgat caactgcaac accagcgcca tcacccaggc ctgccccaag   600
gtgagcttcg accccatccc catccactac tgcgccccg ccggctacgc cccctgaag     660 tgcaacaaca agaagttcaa cggcatcggc ccctgcgaca acgtgagcac cgtgcagtgc   720
acccacggca tcaagcccgt ggtgagcacc cagctgctgc tgaacggcag cctggccgag   780
gaggagatca tcatccgcag cgagaacctg accaacaacg tgaagaccat catcgtgcac   840
ctgaacgaga gcatcgagat caagtgcacc cgccccggca caacacccg caagagcgtg   900 cgcatcggcc ccggccaggc cttctacgcc accgcgaca tcatcggcga catccgccag   960

-continued

```
gcccactgca acatcagcaa gaacgagtgg aacaccaccc tgcagcgcgt gagccagaag    1020
ctgcaggagc tgttccccaa cagcaccggc atcaagttcg ccccccacag cggcggcgac    1080
ctggagatca ccacccacag cttcaactgc ggcggcgagt tcttctactg caacaccacc    1140
gacctgttca acagcaccta cagcaacggc acctgcacca acggcacctg catgagcaac    1200
aacaccgagc gcatcaccct gcagtgccgc atcaagcaga tcatcaacat gtggcaggag    1260
gtgggccgcg ccatgtacgc cccccccatc gccggcaaca tcacctgccg cagcaacatc    1320
accgccctgc tgctgacccg cgacggcggc gacaacaaca ccgagaccga gaccttccgc    1380
cccggcggcg gcgacatgcg cgacaactgg cgcagcgagc tgtacaagta caaggtggtg    1440
gagatcaagc ccctgggcgt ggcccccacc gccgccaagc gccgcgtggt ggagcgcgag    1500
aagcgcgccg tgggcatcgg cgccgtgttc ctgggcttcc tgggcgccgc cggcagcacc    1560
atgggcgccg ccagcatcac cctgaccgtg caggcccgcc agctgctgag cggcatcgtg    1620
cagcagcaga gcaacctgct gcgcgccatc gaggcccagc agcacatgct gcagctgacc    1680
gtgtggggca tcaagcagct gcaggcccgc gtgctggcca tcgagcgcta cctgcaggac    1740
cagcagctgc tgggcctgtg gggctgcagc ggcaagctga tctgcaccac caacgtgctg    1800
tggaacagca gctggagcaa caagacccag agcgacatct gggacaacat gacctggatg    1860
cagtgggacc gcgagatcag caactacacc aacaccatct accgcctgct ggaggacagc    1920
cagagccagc aggagcgcaa cgagaaggac ctgctggccc tggaccgctg gaacaacctg    1980
tggaactggt tcagcatcac caactggctg tggtacatca gatcttcat catgatcgtg    2040 ggcggcctga tcggcctgcg catcatcttc gccgtgctga gcctggtgaa ccgcgtgcgc    2100
cagggctaca gccccctgag cctgcagacc ctgatcccca ccccccgcgg ccccgaccgc    2160
ctgggcggca tcgaggagga gggcggcgag caggacagca gccgcagcat ccgcctggtg    2220
agcggcttcc tgaccctggc ctgggacgac ctgcgcagcc tgtgcctgtt ctgctaccac    2280
cgcctgcgcg acttcatcct gatcgtggtg cgcgccgtgg agctgctggg ccacagcagc    2340
ctgcgcggcc tgcagcgcgg ctggggcacc ctgaagtacc tgggcagcct ggtgcagtac    2400
tggggcctgg agctgaagaa gagcgccatc aacctgctgg acaccatcgc catcgccgtg    2460
gccgagggca ccgaccgcat cctggagttc atccagaacc tgtgccgcgg catccgcaac    2520
gtgccccgcc gcatccgcca gggcttcgag gccgccctgc agtaa    2565
```

<210> SEQ ID NO 98
<211> LENGTH: 2565
<212> TYPE: DNA
<213> ORGANISM: Artificial
<220> FEATURE:
<223> OTHER INFORMATION: Envgp160_TV2_C_ZAwt

<400> SEQUENCE: 98

```
atgagagcga gggggatact gaagaattat cgacactggt ggatatgggg catcttaggc      60
ttttggatgc taatgatgtg taatgtgaag ggcttgtggg tcacagtcta ctacggggta     120
cctgtgggga gagaagcaaa aactactcta ttttgtgcat cagatgctaa agcatatgag     180
aaagaagtgc ataatgtctg gctacacat gcctgtgtac ccacagaccc caacccacaa     240
gaagtgattt tgggcaatgt aacagaaaat tttaacatgt ggaaaaatga catggtggat     300
cagatgcagg aagatataat cagtttatgg gatcaaagcc ttaagccatg tgtaaaattg     360 acccactct gtgtcacttt aaactgtaca atgcaactg ttaactacaa taatacctct     420
```

-continued

```
aaagacatga aaaattgctc tttctatgta accacagaat taagagataa gaaaagaaa      480 gaaaatgcac ttttttatag acttgatata gtaccactta ataataggaa gatgggaat      540 attaacaact atagattaat aaattgtaat acctcagcca taacacaagc ctgtccaaaa     600
gtctcgtttg acccaattcc tatacattat tgtgctccag ctggttatgc gcctctaaaa    660
tgtaataata agaaattcaa tggaatagga ccatgcgata atgtcagcac agtacaatgt    720
acacatggaa ttaagccagt ggtatcaact caattactgt taaatggtag cctagcagaa    780
gaagagataa taattagatc tgaaaatctg acaaacaatg tcaaaacaat aatagtacat    840
cttaatgaat ctatagagat taaatgtaca agacctggca ataatacaag aaagagtgtg    900
agaataggac caggacaagc attctatgca acaggagaca ataggagata taagacaa     960 gcacattgta acattagtaa aaatgaatgg aatacaactt tacaaagggt aagtcaaaaa    1020
ttacaagaac tcttccctaa tagtacaggg ataaaatttg caccacactc aggaggggac    1080
ctagaaatta ctacacatag ctttaattgt ggaggagaat ttttctattg caatacaaca    1140
gacctgttta atagtacata cagtaatggt acatgcacta atggtacatg catgtctaat    1200
aatacagagc gcatcacact ccaatgcaga ataaaacaaa ttataaacat gtggcaggag    1260
gtaggacgag caatgtatgc ccctcccatt gcaggaaaca taacatgtag atcaaatatt    1320
acaggactac tattaacacg tgatggagga gataataata ctgaaacaga gacattcaga    1380
cctggaggag gagacatgag ggacaattgg agaagtgaat tatataaata caaggtggta    1440
gaaattaaac cattaggagt agcacccact gctgcaaaaa ggagagtggt ggagagagaa    1500
aaaagagcag taggaatagg agctgtgttc cttgggttct gggagcagc aggaagcact    1560 atgggcgcag catcaataac gctgacggta caggccagac aattattgtc tggtatagtg    1620
caacagcaaa gtaatttgct gagggctata gaggcgcaac agcatatgtt gcaactcacg    1680
gtctggggca ttaagcagct ccaggcaaga gtcctggcta tagagagata cctacaggat    1740
caacagctcc taggactgtg gggctgctct ggaaaactca tctgcaccac taatgtgctt    1800
tggaactcta gttggagtaa taaaactcaa agtgatattt gggataacat gacctggatg    1860
cagtgggata gggaaattag taattacaca aacacaatat acaggttgct tgaagactcg    1920
caaagccagc aggaaagaaa tgaaaaagat ttactagcat tggacaggtg gaacaatctg    1980
tggaattggt ttagcataac aaaattggctg tggtatataa aaatattcat aatgatagta    2040
ggaggcttga taggtttaag aataattttt gctgtgctct ctctagtaaa tagagttagg    2100
cagggatact caccccttgtc attgcagacc cttatcccaa acccgagggg acccgacagg    2160
ctcggaggaa tcgaagaaga aggtggagag caagacagca gcagatccat tcgattagtg    2220
agcggattct tgacacttgc ctgggacgac ctacgaagcc tgtgcctctt ctgctaccac    2280
cgattgagag acttcatatt aattgtagtg agagcagtgg aacttctggg acacagtagt    2340 ctcagggac tgcagagggg gtggggaacc cttaagtatt tggggagtct tgtgcaatat    2400
tggggtctag agttaaaaaa gagtgctatt aatctgcttg atactatagc aatagcagta    2460
gctgaaggaa cagataggat tctagaattc atacaaaacc tttgtagagg tatccgcaac    2520
gtacctagaa gaataagaca gggcttcgaa gcagctttgc aataa                    2565
```

```
<210> SEQ ID NO 99
<211> LENGTH: 1491
<212> TYPE: DNA
<213> ORGANISM: Artificial
<220> FEATURE:
<223> OTHER INFORMATION: Gag_TV2_C_ZAopt
```

<400> SEQUENCE: 99

```
atgggcgccc gcgccagcat cctgcgcggc ggcaagctgg acaagtggga gaagatccgc      60
ctgcgccccg gcggccgcaa gcactacatg ctgaagcacc tggtgtgggc cagccgcgag     120
ctggagcgct tcgccgtgaa ccccggcctg ctggagacca gcgacggctg ccgccagatc     180
atcaagcagc tgcagcccgc cctgcagacc ggcaccgagg agatccgcag cctgttcaac     240
accgtggcca ccctgtactg cgtgcacaag ggcatcgacg tgcgcgacac caaggaggcc     300
ctggacaaga tcgaggagga gcagaacaag tgccagcaga gacccagca ggccgaggcc      360
gccgacaaga aggtgagcca gaactacccc atcgtgcaga acctgcaggg ccagatggtg     420
caccaggcca tcagccccg cacccctgaac gcctgggtga aggtgatcga ggagaaggcc     480
ttcagccccg aggtgatccc catgttcacc gccctgagcg agggcgccac ccccaggac      540
ctgaacacca tgctgaacac cgtgggcggc caccaggccg ccatgcagat gctgaaggac     600
accatcaacg aggaggccgc cgagtgggac cgcctgcacc ccgtgcacgc cggccccgtg     660
gccccggcc agatgcgcga gccccgcggc agcgacatcg ccggcaccac cagcaccctg     720
caggagcaga tcgcctggat gaccagcaac cccccatcc ccgtgggcga catctacaag      780
cgctggatca tcctgggcct gaacaagatc gtgcgcatgt acagcccgt gagcatcctg      840
gacatcaagc agggcccccaa ggagcccttc gcgactacg tggaccgctt cttcaagacc     900
ctgcgcgccg agcagagcac ccaggaggtg aagaactgga tgaccgacac cctgctggtg     960
cagaacgcca accccgactg caagaccatc ctgcgcgccc tgggccccgg cgccagcctg    1020
gaggagatga tgaccgcctg ccagggcgtg ggcggcccca gccacaaggc ccgcgtgctg    1080
gccgaggcca tgagccaggc caacaacacc agcgtgatga tccagaagag caacttcaag    1140
ggccccgcc gcgccgtgaa gtgcttcaac tgcggccgcg agggccacat cgcccgcaac    1200
tgccgcgccc ccgcaagcg cggctgctgg aagtgcggca aggagggcca ccagatgaag    1260
gactgcaccg agcgccaggc caacttcctg ggcaagatct ggccagcca aagggccgc    1320
cccggcaact tcctgcagag ccgccccgag cccaccgccc ccccctgga gcccaccgcc    1380
cccccgccg agagcttcaa gttcaaggag accccaagc aggagcccaa ggaccgcgag    1440
cccctgacca gcctgaagag cctgttcggc agcgaccccc tgagccagta a             1491
```

<210> SEQ ID NO 100
<211> LENGTH: 1491
<212> TYPE: DNA
<213> ORGANISM: Artificial
<220> FEATURE:
<223> OTHER INFORMATION: Gag_TV2_C_ZAwt

<400> SEQUENCE: 100

```
atgggtgcga gagcgtcaat attaagaggg ggaaaattag acaaatggga aaaaattagg      60
ttacggccag gggggagaaa acactatatg ctaaaacacc tagtatgggc aagcagagag     120
ctggaaagat ttgcagttaa ccctggcctt ttagagacat cagacggatg tagacaaata     180
ataaaacagc tacaaccagc tcttcagaca ggaacagagg aaattagatc attatttaac     240
acagtagcaa ctctctattg tgtacataaa gggatagatg tacgagacac caaggaagcc     300
ttagacaaga tagaggagga acaaaacaaa tgtcagcaaa aaacacagca ggcggaagcg     360
gctgacaaaa aggtcagtca aaattatcct atagtgcaga acctccaagg gcaaatggta     420
caccaggcca tatcacctag aaccttgaat gcatgggtaa agtaataga ggagaaggct      480
```

```
tttagcccag aggtaatacc catgtttaca gcattatcag aaggagccac cccacaagat    540
ttaaacacca tgttaaatac agtgggggga catcaagcag ccatgcaaat gttaaaagat    600
accatcaatg aggaggctgc agaatgggat aggttacatc cagtacatgc agggcctgtt    660
gcaccaggcc agatgagaga accaagggga agtgacatag caggaactac tagtacccct    720
caagaacaaa tagcatggat gacaagtaac ccacctatcc cagtagggga catctataaa    780
aggtggataa ttctggggtt aaataaaata gtaagaatgt acagccctgt cagcatttta    840
gacataaaac aaggaccaaa ggaaccccttt agagactatg tagaccggtt cttcaaaact    900
ttaagagctg aacaatctac acaagaggta aaaaattgga tgacagacac cttgttagtc    960
caaaatgcga acccagattg taagaccatt ttaagagcat taggaccagg ggcttcatta   1020
gaagaaatga tgacagcatg tcagggagtg ggaggaccta gccacaaagc aagagttttg   1080
gctgaggcaa tgagccaagc aaacaataca agtgtaatga tacagaaaag caattttaaa   1140
ggccctagaa gagctgttaa atgtttcaac tgtggcaggg aagggcacat agccaggaat   1200
tgcagggccc ctaggaaaag gggctgttgg aaatgtggaa aggaaggaca ccaaatgaaa   1260
gactgtactg agaggcaggc taattttta gggaaaattt ggccttccca caaggggagg   1320
ccagggaatt ccttcagag cagaccagag ccaacagccc caccactaga accaacagcc   1380
ccaccagcag agagcttcaa gttcaaggag actccgaagc aggagccgaa agacagggaa   1440
cctttaactt ccctcaaatc actctttggc agcgacccct tgtctcaata a            1491

<210> SEQ ID NO 101
<211> LENGTH: 624
<212> TYPE: DNA
<213> ORGANISM: Artificial
<220> FEATURE:
<223> OTHER INFORMATION: Nef_TV2_C_ZAopt

<400> SEQUENCE: 101
atgggcggca agtggagcaa gagcagcatc atcggctggc ccgaggtgcg cgagcgcatc     60
cgccgcaccc gcagcgccgc cgagggcgtg ggcagcgcca gccaggacct ggagaagcac    120
ggcgccctga ccaccagcaa caccgcccac aacaacgccg cctgcgcctg gctggaggcc    180
caggaggagg agggcgaggt gggcttcccc gtgcgccccc agtgcccct gcgccccatg    240 acctacaagg ccgccatcga cctgagcttc ttcctgaagg agaagggcgg cctggagggc    300
ctgatctaca gcaagaagcg ccaggagatc ctggacctgt gggtgtacaa cacccagggc    360
ttcttccccg actggcagaa ctacacccc ggccccggc tgcgcttccc cctgaccttc    420
ggctggtact tcaagctgga gcccgtggac cccgcgagg tggaggaggc caacgagggc    480
gagaacaact gcctgctgca ccccatgagc agcacggca tggaggacga ggaccgcgag    540
gtgctgcgct ggaagttcga cagcacctg gccgccgcc acatggcccg cgagctgcac    600
cccgagtact acaaggactg ctga                                          624

<210> SEQ ID NO 102
<211> LENGTH: 624
<212> TYPE: DNA
<213> ORGANISM: Artificial
<220> FEATURE:
<223> OTHER INFORMATION: Nef_TV2_C_ZA_wt

<400> SEQUENCE: 102 atgggggggca agtggtcaaa aagcagtata attggatggc ctgaagtaag agaaagaatc     60
agacgaacta ggtcagcagc agagggagta ggatcagcgt ctcaagactt agagaaacat    120
```

| | |
|---|---|
| ggggcactta caaccagcaa cacagcccac aacaatgctg cttgcgcctg gctggaagcg | 180 |
| caagaggagg aaggagaagt aggctttcca gtcagacctc aggtaccttt aagaccaatg | 240 |
| acttataaag cagcaataga tctcagcttc tttttaaaag aaaaggggg actgaaggg | 300 |
| ttaatttact ccaagaaaag gcaagagatc cttgatttgt gggtttataa cacacaaggc | 360 |
| ttcttccctg attggcaaaa ctacacaccg ggaccagggg tcagatttcc actgaccttt | 420 |
| ggatggtact tcaagctaga gccagtcgat ccaagggaag tagaagaggc caatgaagga | 480 |
| gaaaacaact gtttactaca ccctatgagc cagcatggaa tggaggatga agacagagaa | 540 |
| gtattaagat ggaagtttga cagtacgcta gcacgcagac acatggcccg cgagctacat | 600 |
| ccggagtatt acaaagactg ctga | 624 |

```
<210> SEQ ID NO 103
<211> LENGTH: 3009
<212> TYPE: DNA
<213> ORGANISM: Artificial
<220> FEATURE:
<223> OTHER INFORMATION: Pol_TV2_C_ZAopt

<400> SEQUENCE: 103
```

| | |
|---|---|
| ttcttccgcg agaacctggc cttccccag ggcgaggccc gcgagttccc cagcgagcag | 60 |
| acccgcgcca acagccccac cacccgcacc aacagcccca ccagccgcga gctgcaggtg | 120 |
| cagggcgaca cgcgaggccgg cgccgagcgc cagggcacct tcaacttccc ccagatcacc | 180 |
| ctgtggcagc gcccctggt gagcatcaag gtggccggcc agaccaagga ggccctgctg | 240 |
| gacaccggcg ccgacgacac cgtgctggag gagatcaacc tgcccggcaa gtggaagccc | 300 |
| aagatgatcg gcggcatcgg cggcttcatc aaggtgcgcc agtacgacca gatcctgatc | 360 |
| gagatctgcg gcaagcgcgc catcggcacc gtgctggtgg ccccaccccc cgtgaacatc | 420 |
| atcggccgca acctgctgac ccagctgggc tgcaccctga acttccccat cagccccatc | 480 |
| gagaccgtgc ccgtgaagct gaagcccggc atggacggcc ccaaggtgaa gcagtggccc | 540 |
| ctgaccgagg agaagatcaa ggccctgacc gagatctgcg aggagatgga aggagggc | 600 |
| aagatcacca gatcggccc cgagaacccc tacaacaccc ccgtgttcgc catcaagaag | 660 |
| aaggacagca ccagtggcg caagctggtg gacttccgcg agctgaacaa gcgcaccag | 720 |
| gacttctggg aggtgcagct gggcatcccc caccccgccg gcctgaagaa gaagaagagc | 780 |
| gtgaccgtgc tggacgtggg cgacgcctac ttcagcgtgc ccctgacga gcttccgc | 840 |
| aagtacaccg ccttcaccat ccccagcatc aacaacgaga ccccggcat ccgctaccag | 900 |
| tacaacgtgc tgccccaggg ctggaagggc agccccgcca tcttccagag cagcatgacc | 960 |
| cgcatcctgg agcccttccg cacccagaac cccgaggtgg tgatctacca gtacatggac | 1020 |
| gacctgtacg tgggcagcga cctggagatc ggccagcacc gcgccaagat cgaggagctg | 1080 |
| cgcggccacc tgctgaagtg gggcttcacc acccccgaca agaagcacca aaggagccc | 1140 |
| cccttcctgt ggatgggcta cgagctgcac cccgacaagt ggaccgtgca gcccatccag | 1200 |
| ctgcccgaga aggagagctg gaccgtgaac gacatccaga gctggtggg caagctgaac | 1260 |
| tgggccagcc agatctaccc cggcatcaag gtgcgccagc tgtgcaagct gctgcgcggc | 1320 |
| gccaaggccc tgaccgacat cgtgccctg accgaggagg ccgagctgga gctggccgag | 1380 |
| aaccgcgaga tcctgaagga gcccgtgcac ggcgtgtact acgacccag caaggacctg | 1440 |
| atcgccgaga tccagaagca gggcaacgac cagtggacct accagatcta ccaggagccc | 1500 |

```
ttcaagaacc tgcgcaccgg caagtacgcc aagatgcgca ccgcccacac caacgacgtg    1560
aagcagctgg ccgaggccgt gcagaagatc acccaggaga gcatcgtgat ctggggcaag    1620
acccccaagt tccgcctgcc catccccaag gagacctggg agacctggtg gagcgactac    1680
tggcaggcca cctggatccc cgagtgggag ttcgtgaaca cccccccct ggtgaagctg     1740 tggtaccagc tggagaagga gcccatcgtg ggcgccgaga ccttctacgt ggacggcgcc    1800
gccaaccgcg agaccaagat cggcaaggcc ggctacgtga ccgacaaggg ccgccagaag    1860
gtggtgagct tcaccgagac caccaaccag aagaccgagc tgcaggccat ccagctggcc    1920
ctgcaggaca gcgcccccga ggtgaacatc gtgaccgaca ccagtacgc cctgggcatc     1980 atccaggccc agcccgacaa gagcgagagc gagctggtga ccagatcat cgagcagctg     2040 atcaagaagg agaaggtgta cctgagctgg gtgcccgccc acaagggcat cggcggcaac    2100
gagcaggtgg acaagctggt gagcagcggc atccgcaagg tgctgttcct ggacggcatc    2160
gacaaggccc aggaggagca cgagaagtac cacagcaact ggcgcgccat ggccagcgag    2220
ttcaacctgc cccccatcgt ggccaaggag atcgtggcca gctgcgacaa gtgccagctg    2280
aagggcgagg ccatgcacgg ccaggtggac tgcagccccg gcatctggca gctggactgc    2340
acccacctgg agggcaagat catcctggtg gccgtgcacg tggccagcgg ctacatggag    2400
gccgaggtga tccccgccga gaccggccag gagaccgcct acttcatcct gaagctggcc    2460
ggccgctggc ccgtgaaggt gatccacacc gacaacggca gcaacttcac cagcaccgcc    2520
gtgaaggccg cctgctggtg ggccgacatc agcgcgagt tcggcatccc ctacaacccc     2580
cagagccagg gcgtggtgga gagcatgaac aaggagctga agaagatcat cggccaggtg    2640
cgcgaccagg ccgagcacct gaagaccgcc gtgcagatgg ccgtgttcat ccacaacttc    2700
aagcgcaagg gcggcatcgg cggctacagc gccggcgagc gcatcatcga catcatcgcc    2760
agcgacatcc agaccaagga gctgcagaag cagatcatca gatccagaa cttccgcgtg     2820 tactaccgcg acagccgcga ccccatctgg aagggccccg ccaagctgct gtggaagggc    2880
gagggcgccg tggtgatcca ggacaacagc gacatcaagg tggtgccccg ccgcaaggcc    2940
aagatcatca aggactacgg caagcagatg gccggcgccg actgcgtggc cggccgccag    3000
gacgaggac                                                            3009
```

<210> SEQ ID NO 104
<211> LENGTH: 3009
<212> TYPE: DNA
<213> ORGANISM: Artificial
<220> FEATURE:
<223> OTHER INFORMATION: Pol_TV2_C_ZAwt

<400> SEQUENCE: 104

```
tttttaggg aaaatttggc cttcccacaa ggggaggcca gggaatttcc ttcagagcag       60
accagagcca acagccccac cactagaacc aacagcccca ccagcagaga gcttcaagtt     120
caaggagact ccgaagcagg agccgaaaga cagggaacct ttaacttccc tcaaatcact     180
ctttggcagc gacccccttgt ctcaataaaa gtagcgggcc aaacaaagga ggctcttta    240 gatacaggag cagatgatac agtactagaa gaaataaact tgccaggaaa atggaaacca    300
aaaatgatag gaggaattgg aggttttatc aaagtaagac agtatgatca atactatata    360
gaaatttgtg gaaaagggc tataggtaca gtattagtag gacctacacc tgtcaacata     420
attggaagaa atctgttgac tcagcttgga tgcacactaa attttccaat tagccccatt    480
gaaactgtac cagtaaaatt aaagccagga atggatggcc caaaggttaa acaatggcca    540
```

```
ttgacagaag aaaaaataaa agcattaaca gaaatttgtg aggaaatgga gaaggaagga    600
aaaattacaa aaattgggcc tgaaaatcca tataacactc cagtatttgc cataaagaag    660
aaggacagta caaagtggag aaaattagta gatttcaggg aactcaataa aagaactcaa    720
gactttgggg aagtccaatt aggaatacca cacccagcag ggttaaaaaa gaaaaaatca    780
gtgacagtac tggatgtggg agatgcatat ttttcagtcc ctttagatga gagcttcaga    840
aaatatactg cattcaccat acctagtata acaatgaaa caccagggat tagatatcaa     900
tataatgttc ttccacaggg atggaaagga tcaccagcaa tattccagag tagcatgaca    960
agaatcttag agccctttag aacacaaaac ccagaagtag ttatctatca atatatggat   1020
gacttatatg taggatctga cttagaaata gggcaacata gagcaaaaat agaggagtta   1080
agaggacacc tattgaaatg gggatttacc acaccagaca gaaacatca gaaagaaccc    1140
ccatttcttt ggatggggta tgaactccat cctgacaaat ggacagtaca gcctatacag   1200
ctgccagaaa aggagagctg gactgtcaat gatatacaga agttagtggg aaagttaaac   1260
tgggcaagtc agatttaccc agggattaaa gtaaggcaac tgtgtaaact ccttagggga   1320
gccaaagcac taacagacat agtgccactg actgaagaag cagaattaga attggctgag   1380
aacagggaaa ttctaaaaga accagtacat ggagtatatt atgacccatc aaaagattta   1440
atagctgaaa tacagaaaca ggggaatgac caatggacat atcaaattta ccaagaacca   1500
tttaaaaatc tgagaacagg aaagtatgca aaaatgagga ctgcccacac taatgatgtg   1560
aaacagttag cagaggcagt gcaaaagata acccaggaaa gcatagtaat atggggaaaa   1620
actcctaaat ttagactacc catcccaaaa gaaacatggg agacatggtg gtcagactat   1680
tggcaagcca cctggattcc tgagtgggag tttgtcaata cccctcccct agtaaaattg   1740
tggtaccagc tggaaaaaga acccatagta ggggcagaaa ctttctatgt agatggagca   1800
gccaataggg aaactaaaat aggaaaagca gggtatgtca ctgacaaagg aaggcagaaa   1860
gttgtttcct tcactgaaac aacaaatcag aagactgaat tacaagcaat tcagctagct   1920
ttgcaggatt cagggccaga agtaaacata gtaacagact cacagtatgc attaggaatc   1980
attcaagcac aaccagataa gagtgaatca gaattagtca gtcaaataat agaacagttg   2040
ataaaaaagg aaaagtctta cctatcatgg gtaccagcac ataaaggaat tggaggaaat   2100
gaacaagtag acaaattagt aagtagtgga atcagaaaag tactgtttct agatggaata   2160
gataaagctc aagaagagca tgaaaaatat cacagcaatt ggagagcaat ggctagtgag   2220
tttaatctgc cacccatagt agcaaaggaa atagtagcca gctgtgataa atgtcagcta   2280
aaaggggaag ccatgcatgg acaagtcgac tgtagtccag gaatatgcca attagactgt   2340
acacatttag aaggaaaaat catcctagta gcagtccatg tagccagtgg ctacatggaa   2400
gcagaggtta tcccagcaga aacaggacaa gaaacagcat actttatact aaaattagca   2460
ggaagatggc cagtcaaagt aatacataca gataatggca gtaatttcac cagtaccgca   2520
gttaaggcag cctgttggtg ggcagatatc caacgggaat tggaattccc tacaatccc    2580
caaagtcaag gagtagtaga atccatgaat aaagaattaa agaaaatcat agggcaagta   2640
agagatcaag ctgagcacct taagacagca gtacaaatgg cagtattcat tcacaatttt   2700
aaaagaaaag ggggattggg gggtacagtg cagggggaga ataatagaca taatagcag    2760
tcagacatac aaactaaaga attacaaaaa caaattataa aaattcaaaa ttttcgggtt   2820
tattacagag acagcagaga cccatttggg aaaggaccag ccaaactact ctggaaaggt   2880
```

```
gaaggggcag tagtaataca agataatagt gatataaagg tagtaccaag aaggaaagca    2940
aaaatcatta aggactatgg aaaacagatg gcaggtgctg attgtgtggc aggtagacag    3000
gatgaagat                                                           3009

<210> SEQ ID NO 105
<211> LENGTH: 75
<212> TYPE: DNA
<213> ORGANISM: Artificial
<220> FEATURE:
<223> OTHER INFORMATION: RevExon1_TV2_C_ZAopt

<400> SEQUENCE: 105
atggccggcc gcagcggcga cagcgacgag gccctgctgc aggccatcaa gatcatcaag    60
atcctgtacc agagc                                                    75

<210> SEQ ID NO 106
<211> LENGTH: 76
<212> TYPE: DNA
<213> ORGANISM: Artificial
<220> FEATURE:
<223> OTHER INFORMATION: RevExon1_TV2_C_ZAwt

<400> SEQUENCE: 106
atggcaggaa gaagcggaga cagcgacgaa gcgctcctcc aagcaataaa gatcatcaag    60
atcctctacc aaagca                                                   76

<210> SEQ ID NO 107
<211> LENGTH: 246
<212> TYPE: DNA
<213> ORGANISM: Artificial
<220> FEATURE:
<223> OTHER INFORMATION: RevExon2_TV2_C_ZAopt

<400> SEQUENCE: 107
ccctacccca agcccgaggg cacccgccag gcccgccgca accgccgccg ccgctggcgc    60
gcccgccagc agcagatcca cagcatcagc gagcgcatcc tggacacctg cctgggccgc    120
cccaccaagc ccgtgccccct gctgctgccc cccatcgagc gcctgcacat caactgcagc   180
gagagcagcg gcaccagcgg cacccagtag agccagggca ccgccgaggg cgtgggcaac    240
ccctaa                                                              246

<210> SEQ ID NO 108
<211> LENGTH: 248
<212> TYPE: DNA
<213> ORGANISM: Artificial
<220> FEATURE:
<223> OTHER INFORMATION: RevExon2_TV2_C_ZAwt

<400> SEQUENCE: 108
acccttatcc caaacccgag gggacccgac aggctcggag gaatcgaaga agaaggtgga    60
gagcaagaca gcagcagatc cattcgatta gtgagcggat tcttgacact tgcctgggac    120
gacctacgaa gcctgtgcct cttctgctac caccgattga gagacttcat attaattgta    180
gtgagagcag tggaacttct gggacacagt agtctcaggg gactgcagag ggggtgggga    240
acccttaa                                                            248

<210> SEQ ID NO 109
<211> LENGTH: 216
<212> TYPE: DNA
<213> ORGANISM: Artificial
```

```
<220> FEATURE:
<223> OTHER INFORMATION: TatExon1_TV2_C_ZAopt

<400> SEQUENCE: 109
atggagccca tcgaccccaa cctggagccc tggaaccacc ccggcagcca gcccaagacc     60
gcctgcaacg gctgctactg caagcgctgc agctaccact gcctggtgtg cttccagaag    120
aagggcctgg gcatctacta cggccgcaag aagcgccgcc agcgccgcag cgcccccccc    180
agcaacaagg accaccagga cccctgccc aagcag                               216

<210> SEQ ID NO 110
<211> LENGTH: 216
<212> TYPE: DNA
<213> ORGANISM: Artificial
<220> FEATURE:
<223> OTHER INFORMATION: TatExon1_TV2_C_ZAwt

<400> SEQUENCE: 110
atggagccaa tagatcctaa cctagaaccc tggaaccatc caggaagtca gcctaaaact     60
gcttgtaatg gttgttactg taaacgttgc agctatcatt gtctagtttg ctttcagaaa    120
aaaggcttag gcatttacta tggcaggaag aagcggagac agcgacgaag cgctcctcca    180
agcaataaag atcatcaaga tcctctacca aagcag                              216

<210> SEQ ID NO 111
<211> LENGTH: 90
<212> TYPE: DNA
<213> ORGANISM: Artificial
<220> FEATURE:
<223> OTHER INFORMATION: TatExon2_TV2_C_ZAopt

<400> SEQUENCE: 111
cccctgagcc agacccgcgg cgaccccacc ggcagcgagg agagcaagaa gaaggtggag     60
agcaagaccg ccgccgaccc cttcgactag                                      90

<210> SEQ ID NO 112
<211> LENGTH: 90
<212> TYPE: DNA
<213> ORGANISM: Artificial
<220> FEATURE:
<223> OTHER INFORMATION: TatExon2_TV2_C_ZAwt

<400> SEQUENCE: 112
cccttatccc aaacccgagg ggacccgaca ggctcggagg aatcgaagaa gaaggtggag     60
agcaagacag cagcagatcc attcgattag                                      90

<210> SEQ ID NO 113
<211> LENGTH: 579
<212> TYPE: DNA
<213> ORGANISM: Artificial
<220> FEATURE:
<223> OTHER INFORMATION: Vif_TV2_C_ZAopt

<400> SEQUENCE: 113
atggagaacc gctggcaggt gctgatcgtg tggcaggtgg accgcatgaa gatccgcacc     60
tggcacagcc tggtgaagca ccacatgtac gtgagccgcc gcgccgacgg ctggttctac    120
cgccaccact acgagagccg ccaccccaag gtgagcagca ggtgcacat cccctgggc     180 gacgcccgcc tggtgatcaa gacctactgg ggcctgcaga ccggcgagcg cgcctggcac    240
ctgggccacg gcgtgagcat cgagtggcgc ctgcgccgct acagcaccca ggtggacccc    300
```

```
gacctgaccg accagctgat ccacatgcac tacttcgact gcttcgccga gagcgccatc    360
cgcaaggcca tcctgggcca gatcgtgagc cccaagtgcg actaccaggc cggccacaac    420
aaggtgggca gcctgcagta cctggccctg accgccctga tcaagcccaa gaagatcaag    480
ccccccctgc ccagcgtgcg caagctggtg gaggaccgct ggaacaagcc ccagaagacc    540
cgcggccgcc gcggcaacca caccatgaac ggccactag                          579
```

<210> SEQ ID NO 114
<211> LENGTH: 579
<212> TYPE: DNA
<213> ORGANISM: Artificial
<220> FEATURE:
<223> OTHER INFORMATION: Vif_TV2_C_ZAwt

<400> SEQUENCE: 114

```
atggaaaaca gatggcaggt gctgattgtg tggcaggtag acaggatgaa gattagaaca     60
tggcacagtt tagtaaagca ccatatgtat gtttcgagga gagctgatgg atggttctac    120
agacatcatt atgaaagcag cacccaaaaa gtaagttcag aagtacacat cccattagga    180
gatgccaggt tagtaataaa aacatattgg ggtctgcaga caggagaaag agcttggcat    240
ttgggtcacg gagtctccat agaatggaga ttgagaagat atagcacaca gtagaccct    300 gacctgacag accaactaat tcatatgcat tattttgatt gttttgcaga atctgccata    360
aggaaagcca tactaggaca gatagttagc cctaagtgtg actatcaagc aggacataac    420
aaggtaggat ctctacaata cttggcactg acagcattga taaaaccaaa aaagataaag    480
ccacctctgc ctagtgttag gaaattagta gaggatagat ggaacaagcc ccagaagacc    540 agggggccgca gagggaacca tacaatgaat ggacactag                          579
```

<210> SEQ ID NO 115
<211> LENGTH: 288
<212> TYPE: DNA
<213> ORGANISM: Artificial
<220> FEATURE:
<223> OTHER INFORMATION: Vpr_TV2_C_ZAopt

<400> SEQUENCE: 115

```
atggagcagg cccccgagga ccagggcccc cagcgcgagc cctacaacga gtggaccctg     60
gagctgctgg aggagctgaa gcaggaggcc gtgcgccact ccccccgccc ctggctgcac    120
aacctgggcc agcacatcta cgagacctac ggcgacacct ggaccggcgt ggaggccatc    180
atccgcatcc tgcagcagct gctgttcatc cacttccgca tcggctgcca ccacagccgc    240
atcggcatcc tgcgccagcg ccgcgcccgc aacggcgcca ccgcagc                  288
```

<210> SEQ ID NO 116
<211> LENGTH: 288
<212> TYPE: DNA
<213> ORGANISM: Artificial
<220> FEATURE:
<223> OTHER INFORMATION: Vpr_TV2_C_ZAwt

<400> SEQUENCE: 116

```
atggaacaag ccccagaaga ccaggggccg cagagggaac catacaatga atggacacta     60
gagcttttag aagaactcaa gcaggaagct gtcagacact tcctagacc atggctccat    120 aacttaggac aacatatcta tgaaacctat ggagatactt ggacaggagt tgaagcaata    180
ataagaatcc tgcaacaatt actgtttatt catttcagga ttgggtgcca tcatagcaga    240
ataggcattt tgcgacagag aagagcaaga aatggagcca atagatcc                 288
```

<210> SEQ ID NO 117
<211> LENGTH: 261
<212> TYPE: DNA
<213> ORGANISM: Artificial
<220> FEATURE:
<223> OTHER INFORMATION: Vpu_TV2_C_ZAopt

<400> SEQUENCE: 117

```
atgctggacc tgaccgcccg catcgacagc cgcctgggca tcggcgccct gatcgtggcc      60
ctgatcatcg ccatcatcgt gtggaccatc gtgtacatcg agtaccgcaa gctggtgcgc     120
cagcgcaaga tcgactggct ggtgaagcgc atccgcgagc gcgccgagga cagcggcaac     180
gagagcgagg cgacaccgga ggagctgagc accctggtgg acatgggcca cctgcgcctg     240
ctggacgcca acgacgtgta a                                               261
```

<210> SEQ ID NO 118
<211> LENGTH: 261
<212> TYPE: DNA
<213> ORGANISM: Artificial
<220> FEATURE:
<223> OTHER INFORMATION: Vpu_TV2_C_ZAwt

<400> SEQUENCE: 118

```
atgttagatt taactgcaag aatagattct agattaggaa taggagcatt gatagtagca      60
ctaatcatag caataatagt gtggaccata gtatatatag aatataggaa attggtaagg     120
caaaggaaaa tagactggtt agttaaaagg attagggaaa gagcagaaga cagtggcaat     180
gagagcgagg gggatactga agaattatcg acactggtgg atatggggca tcttaggctt     240
ttggatgcta atgatgtgta a                                               261
```

<210> SEQ ID NO 119
<211> LENGTH: 1473
<212> TYPE: DNA
<213> ORGANISM: Artificial
<220> FEATURE:
<223> OTHER INFORMATION: gp120mod.TV1.delV2

<400> SEQUENCE: 119

```
gaattcatgc gcgtgatggg cacccagaag aactgccagc agtggtggat ctggggcatc      60
ctgggcttct ggatgctgat gatctgcaac accgaggacc tgtgggtgac cgtgtactac     120
ggcgtgcccg tgtggcgcga cgccaagacc accctgttct gcgccagcga cgccaaggcc     180
tacgagaccg aggtgcacaa cgtgtgggcc acccacgcct gcgtgcccac cgaccccaac     240
cccaggaga tcgtgctggg caacgtgacc gagaacttca catgtggaa gaacgacatg     300
gccgaccaga tgcacgagga cgtgatcagc ctgtgggacc agagcctgaa gcctgcgtg      360
aagctgaccc cctgtgcgt gaccctgaac tgcaccgaca ccaacgtgac cggcaaccgc     420
accgtgaccg gcaacagcac caacaacacc aacggcaccg catctacaa catcgaggag     480
atgaagaact gcagcttcaa cgccggcgcc ggccgcctga tcaactgcaa caccagcacc     540
atcacccagg cctgccccaa ggtgagcttc gaccccatcc ccatccacta ctgcgccccc     600
gccggctacg ccatcctgaa gtgcaacaac aagaccttca cggcaccgg ccctgctac       660
aacgtgagca ccgtgcagtg cacccacggc atcaagcccg tggtgagcac ccagctgctg     720
ctgaacggca gcctggccga ggagggcatc atcatccgca gcgagaacct gaccgagaac     780
accaagacca tcatcgtgca cctgaacgag agcgtggaga tcaactgcac ccgccccaac     840
```

| | |
|---|---|
| aacaacaccc gcaagagcgt gcgcatcggc cccggccagg ccttctacgc caccaacgac | 900 |
| gtgatcggca acatccgcca ggcccactgc aacatcagca ccgaccgctg gaacaagacc | 960 |
| ctgcagcagg tgatgaagaa gctgggcgag cacttcccca acaagaccat ccagttcaag | 1020 |
| ccccacgccg gcggcgacct ggagatcacc atgcacagct tcaactgccg cggcgagttc | 1080 |
| ttctactgca acaccagcaa cctgttcaac agcacctacc acagcaacaa cggcaccta | 1140 |
| aagtacaacg gcaacagcag cagccccatc accctgcagt gcaagatcaa gcagatcgtg | 1200 |
| cgcatgtggc agggcgtggg ccaggccacc tacgccccccc catcgccgg caacatcacc | 1260 |
| tgccgcagca acatcaccgg catcctgctg acccgcgacg gcggcttcaa caccaccaac | 1320 |
| aacaccgaga ccttccgccc cggcggcggc gacatgcgcg acaactggcg cagcgagctg | 1380 |
| tacaagtaca aggtggtgga gatcaagccc ctgggcatcg cccccaccaa ggccaagcgc | 1440 |
| cgcgtggtgc agcgcgagaa gcgctaactc gag | 1473 |

<210> SEQ ID NO 120
<211> LENGTH: 1986
<212> TYPE: DNA
<213> ORGANISM: Artificial
<220> FEATURE:
<223> OTHER INFORMATION: gp140mod.TV1.delV2

<400> SEQUENCE: 120

| | |
|---|---|
| gaattcatgc gcgtgatggg cacccagaag aactgccagc agtggtggat ctggggcatc | 60 |
| ctgggcttct ggatgctgat gatctgcaac accgaggacc tgtgggtgac cgtgtactac | 120 |
| ggcgtgcccg tgtggcgcga cgccaagacc accctgttct gcgccagcga cgccaaggcc | 180 |
| tacgagaccg aggtgcacaa cgtgtgggcc acccacgcct gcgtgcccac cgaccccaac | 240 |
| ccccaggaga tcgtgctggg caacgtgacc gagaacttca acatgtggaa gaacgacatg | 300 |
| gccgaccaga tgcacgagga cgtgatcagc ctgtgggacc agagcctgaa gccctgcgtg | 360 |
| aagctgaccc ccctgtgcgt gaccctgaac tgcaccgaca ccaacgtgac cggcaaccgc | 420 |
| accgtgaccg caacagcac caacaacacc aacggcaccg gcatctacaa catcgaggag | 480 |
| atgaagaact gcagcttcaa cgccggcgcc ggccgcctga tcaactgcaa caccagcacc | 540 |
| atcacccagg cctgccccaa ggtgagcttc gaccccatcc ccatccacta ctgcgccccc | 600 |
| gccggctacg ccatcctgaa gtgcaacaac aagaccttca cggcaccgg ccctgctac | 660 |
| aacgtgagca ccgtgcagtg cacccacggc atcaagcccg tggtgagcac ccagctgctg | 720 |
| ctgaacggca gcctggccga ggagggcatc atcatccgcg gcgagaacct gaccgagaac | 780 |
| accaagacca tcatcgtgca cctgaacgag agcgtggaga tcaactgcac ccgccccaac | 840 |
| aacaacaccc gcaagagcgt gcgcatcggc cccggccagg ccttctacgc caccaacgac | 900 |
| gtgatcggca acatccgcca ggcccactgc aacatcagca ccgaccgctg gaacaagacc | 960 |
| ctgcagcagg tgatgaagaa gctgggcgag cacttcccca acaagaccat ccagttcaag | 1020 |
| ccccacgccg gcggcgacct ggagatcacc atgcacagct tcaactgccg cggcgagttc | 1080 |
| ttctactgca acaccagcaa cctgttcaac agcacctacc acagcaacaa cggcaccta | 1140 |
| aagtacaacg gcaacagcag cagccccatc accctgcagt gcaagatcaa gcagatcgtg | 1200 |
| cgcatgtggc agggcgtggg ccaggccacc tacgccccccc catcgccgg caacatcacc | 1260 |
| tgccgcagca acatcaccgg catcctgctg acccgcgacg gcggcttcaa caccaccaac | 1320 |
| aacaccgaga ccttccgccc cggcggcggc gacatgcgcg acaactggcg cagcgagctg | 1380 |
| tacaagtaca aggtggtgga gatcaagccc ctgggcatcg cccccaccaa ggccaagcgc | 1440 |

```
cgcgtggtgc agcgcgagaa gcgcgccgtg ggcatcggcg ccgtgttcct gggcttcctg    1500
ggcgccgccg gcagcaccat gggcgccgcc agcatcaccc tgaccgtgca ggcccgccag    1560
ctgctgagcg gcatcgtgca gcagcagagc aacctgctga aggccatcga ggcccagcag    1620
cacatgctgc agctgaccgt gtggggcatc aagcagctgc aggcccgcgt gctggccatc    1680
gagcgctacc tgaaggacca gcagctgctg ggcatctggg gctgcagcgg ccgcctgatc    1740
tgcaccaccg ccgtgccctg aacagcagc tggagcaaca agagcgagaa ggacatctgg    1800
gacaacatga cctggatgca gtgggaccgc gagatcagca actacaccgg cctgatctac    1860
aacctgctgg aggacagcca gaaccagcag gagaagaacg agaaggacct gctggagctg    1920
gacaagtgga caacctgtg gaactggttc gacatcagca actggccctg gtacatctaa    1980
ctcgag                                                                1986
```

<210> SEQ ID NO 121
<211> LENGTH: 1986
<212> TYPE: DNA
<213> ORGANISM: Artificial
<220> FEATURE:
<223> OTHER INFORMATION: gp140mod.TV1.mut7.delV2

<400> SEQUENCE: 121

```
gaattcatgc gcgtgatggg cacccagaag aactgccagc agtggtggat ctggggcatc      60
ctgggcttct ggatgctgat gatctgcaac accgaggacc tgtgggtgac cgtgtactac     120
ggcgtgcccg tgtggcgcga cgccaagacc accctgttct cgccagcga cgccaaggcc     180 tacgagaccg aggtgcacaa cgtgtgggcc acccacgcct gcgtgcccac cgaccccaac     240 cccaggaga tcgtgctggg caacgtgacc gagaacttca acatgtggaa gaacgacatg     300
gccgaccaga tgcacgagga cgtgatcagc ctgtgggacc agagcctgaa gccctgcgtg     360
aagctgaccc cctgtgcgt gaccctgaac tgcaccgaca ccaacgtgac cggcaaccgc     420
accgtgaccg gcaacagcac caacaacacc aacggcaccg gcatctacaa catcgaggag     480
atgaagaact gcagcttcaa cgccggcgcc ggccgcctga tcaactgcaa caccagcacc     540
atcacccagg cctgccccaa ggtgagcttc gaccccatcc ccatccacta ctgcgccccc     600
gccggctacg ccatcctgaa gtgcaacaac aagaccttca acggcaccgg ccctgctac     660 aacgtgagca ccgtgcagtg cacccacggc atcaagcccg tggtgagcac ccagctgctg     720
ctgaacggca gcctggccga ggagggcatc atcatccgca gcgagaacct gaccgagaac     780
accaagacca tcatcgtgca cctgaacgag agcgtggaga tcaactgcac ccgccccaac     840
aacaacaccc gcaagagcgt gcgcatcggc ccgggccagg ccttctacgc caccaacgac     900
gtgatcggca acatccgcca ggcccactgc aacatcagca ccgaccgctg gaacaagacc     960
ctgcagcagg tgatgaagaa gctgggcgag cacttcccca acaagaccat ccagttcaag    1020
ccccacgccg gcggcgacct ggagatcacc atgcacagct tcaactgccg cggcgagttc    1080
ttctactgca acaccagcaa cctgttcaac agcacctacc acagcaacaa cggcaccctac   1140 aagtacaacg gcaacagcag cagccccatc accctgcagt gcaagatcaa gcagatcgtg    1200
cgcatgtggc agggcgtggg ccaggccacc tacgcccccc catcgccgg caacatcacc    1260 tgccgcagca acatcaccgg catcctgctg acccgcgacg gcggcttcaa caccaccaac    1320
aacaccgaga ccttccgccc cggcggcggc gacatgcgcg acaactggcg cagcgagctg    1380
tacaagtaca aggtggtgga gatcaagccc ctgggcatcg cccccaccaa ggccatcagc    1440
```

-continued

```
agcgtggtgc agagcgagaa gagcgccgtg ggcatcggcg ccgtgttcct gggcttcctg      1500
ggcgccgccg gcagcaccat gggcgccgcc agcatcaccc tgaccgtgca ggcccgccag      1560
ctgctgagcg gcatcgtgca gcagcagagc aacctgctga aggccatcga ggcccagcag      1620
cacatgctgc agctgaccgt gtggggcatc aagcagctgc aggcccgcgt gctggccatc      1680
gagcgctacc tgaaggacca gcagctgctg ggcatctggg gctgcagcgg ccgcctgatc      1740
tgcaccaccg ccgtgccctg aacagcagc tggagcaaca gagcgagaa ggacatctgg       1800 gacaacatga cctggatgca gtgggaccgc gagatcagca actacaccgg cctgatctac      1860
aacctgctgg aggacagcca gaaccagcag gagaagaacg agaaggacct gctggagctg      1920
gacaagtgga caacctgtg gaactggttc gacatcagca ctggccctg gtacatctaa       1980 ctcgag                                                                 1986
```

<210> SEQ ID NO 122
<211> LENGTH: 2397
<212> TYPE: DNA
<213> ORGANISM: Artificial
<220> FEATURE:
<223> OTHER INFORMATION: gp160mod.TV1.delV1V2

<400> SEQUENCE: 122

```
gaattcatgc gcgtgatggg cacccagaag aactgccagc agtggtggat ctggggcatc        60
ctgggcttct ggatgctgat gatctgcaac accgaggacc tgtgggtgac cgtgtactac       120
ggcgtgcccg tgtggcgcga cgccaagacc accctgttct cgccagcga cgccaaggcc        180 tacgagaccg aggtgcacaa cgtgtgggcc acccacgcct gcgtgccac cgaccccaac        240 cccaggaga tcgtgctggg caacgtgacc gagaacttca acatgtggaa gaacgacatg        300
gccgaccaga tgcacgagga cgtgatcagc ctgtgggacc agagcctgaa gccctgcgtg       360
aagctgaccc ccctgtgcgt gggcgccggc aactgcaaca ccagcaccat cacccaggcc      420
tgccccaagg tgagcttcga ccccatcccc atccactact gcgccccgc cggctacgcc        480 atcctgaagt gcaacaacaa gaccttcaac ggcaccggcc cctgctacaa cgtgagcacc      540
gtgcagtgca cccacggcat caagcccgtg gtgagcaccc agctgctgct gaacggcagc      600
ctggccgagg agggcatcat catccgcagc gagaacctga ccgagaacac caagaccatc      660
atcgtgcacc tgaacgagag cgtggagatc aactgcaccc gccccaacaa caacacccgc      720
aagagcgtgc gcatcggccc cggccaggcc ttctacgcca ccaacgacgt gatcggcaac      780
atccgccagg cccactgcaa catcagcacc gaccgctgga caagaccct gcagcaggtg      840 atgaagaagc tgggcgagca cttccccaac aagaccatcc agttcaagcc ccacgccggc      900
ggcgacctgg agatcaccat gcacagcttc aactgccgcg gcgagttctt ctactgcaac      960
accagcaacc tgttcaacag cacctaccac agcaacaacg gcacctacaa gtacaacggc     1020
aacagcagca gccccatcac cctgcagtgc aagatcaag agatcgtgcg catgtggcag      1080
ggcgtgggcc aggccaccta cgccccccc atcgccggca acatcacctg ccgcagcaac      1140
atcaccggca tcctgctgac ccgcgacggc ggcttcaaca ccaccaacaa caccgagacc     1200
ttccgccccg gcggcggcga catgcgcgac aactggcgca gcgagctgta caagtacaag     1260
gtggtggaga tcaagcccct gggcatcgcc cccaccaagg ccaagcgccg cgtggtgcag     1320
cgcgagaagc gcgccgtggg catcggcgcc gtgttcctgg gcttcctggg cgccgccggc     1380
agcaccatgg gcgccgccag catcaccctg accgtgcagg cccgccagct gctgagcggc      1440
atcgtgcagc agcagagcaa cctgctgaag gccatcgagg cccagcagca catgctgcag      1500
```

```
ctgaccgtgt ggggcatcaa gcagctgcag gcccgcgtgc tggccatcga gcgctacctg   1560
aaggaccagc agctgctggg catctggggc tgcagcggcc gcctgatctg caccaccgcc   1620
gtgccctgga acagcagctg gagcaacaag agcgagaagg acatctggga caacatgacc   1680
tggatgcagt gggaccgcga gatcagcaac tacaccggcc tgatctacaa cctgctggag   1740
gacagccaga accagcagga gaagaacgag aaggacctgc tggagctgga caagtggaac   1800
aacctgtgga actggttcga catcagcaac tggccctggt acatcaagat cttcatcatg   1860
atcgtgggcg gcctgatcgg cctgcgcatc atcttcgccg tgctgagcat cgtgaaccgc   1920
gtgcgccagg gctacagccc cctgagcttc cagaccctga cccccagccc ccgcggcctg   1980
gaccgcctgg gcggcatcga ggaggagggc ggcgagcagg accgcgaccg cagcatccgc   2040
ctggtgagcg gcttcctgag cctggcctgg gacgacctgc gcaacctgtg cctgttcagc   2100
taccaccgcc tgcgcgactt catcctgatc gccgtgcgcg ccgtggagct gctgggccac   2160
agcagcctgc gcggcctgca gcgcggctgg gagatcctga agtacctggg cagcctggtg   2220
cagtactggg gcctggagct gaagaagagc gccatcagcc tgctggacac catcgccatc   2280
accgtggccg agggcaccga ccgcatcatc gagctggtgc agcgcatctg ccgcgccatc   2340
ctgaacatcc ccgccgcat ccgccagggc ttcgaggccg ccctgctgta actcgag      2397
```

<210> SEQ ID NO 123
<211> LENGTH: 2529
<212> TYPE: DNA
<213> ORGANISM: Artificial
<220> FEATURE:
<223> OTHER INFORMATION: gp160mod.TV1.delV2

<400> SEQUENCE: 123

```
gaattcatgc gcgtgatggg cacccagaag aactgccagc agtggtggat ctggggcatc     60
ctgggcttct ggatgctgat gatctgcaac accgaggacc tgtgggtgac cgtgtactac    120
ggcgtgcccg tgtggcgcga cgccaagacc accctgttct gcgccagcga cgccaaggcc    180
tacgagaccg aggtgcacaa cgtgtgggcc acccacgcct gcgtgcccac cgaccccaac    240 cccaggaga tcgtgctggg caacgtgacc gagaacttca acatgtggaa gaacgacatg    300
gccgaccaga tgcacgagga cgtgatcagc ctgtgggacc agagcctgaa gcccctgcgtg    360 aagctgaccc ccctgtgcgt gaccctgaac tgcaccgaca ccaacgtgac cggcaaccgc   420
accgtgaccg gcaacagcac caacaacacc aacggcaccg gcatctacaa catcgaggag   480
atgaagaact gcagcttcaa cgccggcgcc ggccgcctga tcaactgcaa caccagcacc   540
atcacccagg cctgccccaa ggtgagcttc gaccccatcc ccatccacta ctgcgccccc   600
gccggctacg ccatcctgaa gtgcaacaac aagaccttca acggcaccgg ccctgctac   660 aacgtgagca ccgtgcagtg cacccacggc atcaagcccg tggtgagcac ccagctgctg   720
ctgaacggca gcctggccga ggagggcatc atcatccgca gcgagaacct gaccgagaac   780
accaagacca tcatcgtgca cctgaacgag agcgtggaga tcaactgcac ccgccccaac   840 aacaacacc gcaagagcgt gcgcatcggc cccggccagg ccttctacgc caccaacgac   900
gtgatcggca acatccgcca ggcccactgc aacatcagca ccgaccgctg gaacaagacc   960
ctgcagcagg tgatgaagaa gctgggcgag cacttcccca caagaccat ccagttcaag  1020 ccccacgccg cggcgaccct ggagatcacc atgcacagct tcaactgccg cggcgagttc  1080
ttctactgca acaccagcaa cctgttcaac agcacctacc acagcaacaa cggcacctac  1140
```

-continued

```
aagtacaacg gcaacagcag cagccccatc accctgcagt gcaagatcaa gcagatcgtg   1200
cgcatgtggc agggcgtggg ccaggccacc tacgcccccc ccatcgccgg caacatcacc   1260
tgccgcagca acatcaccgg catcctgctg acccgcgacg gcggcttcaa caccaccaac   1320
aacaccgaga ccttccgccc cggcggcggc gacatgcgcg acaactggcg cagcgagctg   1380
tacaagtaca aggtggtgga gatcaagccc ctgggcatcg cccccaccaa ggccaagcgc   1440
cgcgtggtgc agcgcgagaa gcgcgccgtg ggcatcggcg ccgtgttcct gggcttcctg   1500
ggcgccgccg gcagcaccat gggcgccgcc agcatcaccc tgaccgtgca ggcccgccag   1560
ctgctgagcg gcatcgtgca gcagcagagc aacctgctga aggccatcga ggcccagcag   1620
cacatgctgc agctgaccgt gtggggcatc aagcagctgc aggcccgcgt gctggccatc   1680
gagcgctacc tgaaggacca gcagctgctg ggcatctggg gctgcagcgg ccgcctgatc   1740
tgcaccaccg ccgtgccctg gaacagcagc tggagcaaca agagcgagaa ggacatctgg   1800
gacaacatga cctggatgca gtgggaccgc gagatcagca actacaccgg cctgatctac   1860
aacctgctgg aggacagcca gaaccagcag gagaagaacg agaaggacct gctggagctg   1920
gacaagtgga acaacctgtg gaactggttc gacatcagca actggccctg gtacatcaag   1980
atcttcatca tgatcgtggg cggcctgatc ggcctgcgca tcatcttcgc cgtgctgagc   2040
atcgtgaacc gcgtgcgcca gggctacagc cccctgagct tccagaccct gacccccagc   2100
ccccgcggcc tggaccgcct gggcggcatc gaggaggagg gcggcgagca ggaccgcgac   2160
cgcagcatcc gcctggtgag cggcttcctg agcctggcct gggacgacct gcgcaacctg   2220
tgcctgttca gctaccaccg cctgcgcgac ttcatcctga tcgccgtgcg cgccgtggag   2280
ctgctgggcc acagcagcct gcgcggcctg cagcgcggct gggagatcct gaagtacctg   2340
ggcagcctgg tgcagtactg ggcctggag ctgaagaaga gcgccatcag cctgctggac   2400
accatcgcca tcaccgtggc cgagggcacc gaccgcatca tcgagctggt gcagcgcatc   2460
tgccgcgcca tcctgaacat cccccgccgc atccgccagg gcttcgaggc cgccctgctg   2520
taactcgag                                                           2529
```

<210> SEQ ID NO 124
<211> LENGTH: 2529
<212> TYPE: DNA
<213> ORGANISM: Artificial
<220> FEATURE:
<223> OTHER INFORMATION: gp160mod.TV1.mut7.delV2

<400> SEQUENCE: 124

```
gaattcatgc gcgtgatggg cacccagaag aactgccagc agtggtggat ctggggcatc     60
ctgggcttct ggatgctgat gatctgcaac accgaggacc tgtgggtgac cgtgtactac    120
ggcgtgcccg tgtggcgcga cgccaagacc accctgttct gcgccagcga cgccaaggcc    180
tacgagaccg aggtgcacaa cgtgtgggcc acccacgcct gcgtgcccac cgaccccaac    240
ccccaggaga tcgtgctggg caacgtgacc gagaacttca acatgtggaa gaacgacatg    300
gccgaccaga tgcacgagga cgtgatcagc ctgtgggacc agagcctgaa gccctgcgtg    360
aagctgaccc ccctgtgcgt gaccctgaac tgcaccgaca ccaacgtgac cggcaaccgc    420
accgtgaccg gcaacagcac caacaacacc aacggcaccg gcatctacaa catcgaggag    480
atgaagaact gcagcttcaa cgccggcgcc ggccgcctga tcaactgcaa caccagcacc    540
atcacccagg cctgccccaa ggtgagcttc gaccccatcc ccatccacta ctgcgccccc    600
gccggctacg ccatcctgaa gtgcaacaac aagaccttca acggcaccgg cccctgctac    660
```

```
aacgtgagca ccgtgcagtg cacccacggc atcaagcccg tggtgagcac ccagctgctg        720
ctgaacggca gcctggccga ggagggcatc atcatccgca gcgagaacct gaccgagaac        780
accaagacca tcatcgtgca cctgaacgag agcgtggaga tcaactgcac ccgccccaac        840
aacaacaccc gcaagagcgt gcgcatcggc cccggccagg ccttctacgc caccaacgac        900
gtgatcggca catccgcca ggcccactgc aacatcagca ccgaccgctg gaacaagacc         960
ctgcagcagg tgatgaagaa gctgggcgag cacttcccca acaagaccat ccagttcaag       1020
ccccacgccg gcggcgacct ggagatcacc atgcacagct tcaactgccg cggcgagttc       1080
ttctactgca acaccagcaa cctgttcaac agcacctacc acagcaacaa cggcacctac       1140
aagtacaacg caacagcag cagcccatc accctgcagt gcaagatcaa gcagatcgtg         1200
cgcatgtggc agggcgtggg ccaggccacc tacgcccccc catcgccgg caacatcacc        1260 tgccgcagca acatcaccgg catcctgctg acccgcacg gcggcttcaa caccaccaac        1320
aacaccgaga ccttccgccc cggcggcggc gacatgcgcg acaactggcg cagcgagctg       1380
tacaagtaca aggtggtgga gatcaagccc ctgggcatcg cccccaccaa ggccatcagc       1440
agcgtggtgc agagcgagaa gagcgccgtg ggcatcggcg ccgtgttcct gggcttcctg       1500
ggcgccgccg gcagcaccat gggcgccgcc agcatcaccc tgaccgtgca ggcccgccag       1560
ctgctgagcg gcatcgtgca gcagcagagc aacctgctga aggccatcga ggcccagcag       1620
cacatgctgc agctgaccgt gtggggcatc aagcagctgc aggcccgcgt gctggccatc       1680
gagcgctacc tgaaggacca gcagctgctg ggcatctggg gctgcagcgg ccgcctgatc       1740
tgcaccaccg ccgtgccctg aacagcagc tggagcaaca agagcgagaa ggacatctgg        1800
gacaacatga cctggatgca gtgggaccgc gagatcagca actacaccgg cctgatctac       1860
aacctgctgg aggacagcca gaaccagcag gagaagaacg agaaggacct gctggagctg       1920
gacaagtgga caacctgtg gaactggttc gacatcagca actggccctg gtacatcaag        1980
atcttcatca tgatcgtggg cggcctgatc ggcctgcgca tcatcttcgc cgtgctgagc       2040
atcgtgaacc gcgtgcgcca gggctacagc cccctgagct ccagaccct gaccccagc         2100 ccccgcggcc tggaccgcct gggcggcatc gaggaggagg cggcgagca ggaccgcgac        2160 cgcagcatcc gcctggtgag cggcttcctg agcctggcct gggacgacct gcgcaacctg       2220
tgcctgttca gctaccaccg cctgcgcgac ttcatcctga tcgccgtgcg cgccgtggag       2280
ctgctgggcc acagcagcct gcgcggcctg cagcgcggct gggagatcct gaagtacctg       2340
ggcagcctgg tgcagtactg gggcctggag ctgaagaaga gcgccatcag cctgctggac       2400
accatcgcca tcaccgtggc cgagggcacc gaccgcatca tcgagctggt gcagcgcatc       2460
tgccgcgcca tcctgaacat ccccgccgc atccgccagg gcttcgaggc cgccctgctg       2520
taactcgag                                                              2529

<210> SEQ ID NO 125
<211> LENGTH: 2613
<212> TYPE: DNA
<213> ORGANISM: Artificial
<220> FEATURE:
<223> OTHER INFORMATION: gp160mod.TV1.tpa1

<400> SEQUENCE: 125
gtcgacgcca ccatggatgc aatgaagaga gggctctgct gtgtgctgct gctgtgtgga         60
gcagtcttcg tttcgcccag cgccagcacc gaggacctgt gggtgaccgt gtactacggc        120
```

```
gtgcccgtgt ggcgcgacgc caagaccacc ctgttctgcg ccagcgacgc caaggcctac    180
gagaccgagg tgcacaacgt gtgggccacc cacgcctgcg tgcccaccga ccccaacccc    240
caggagatcg tgctgggcaa cgtgaccgag aacttcaaca tgtggaagaa cgacatggcc    300
gaccagatgc acgaggacgt gatcagcctg tgggaccaga gcctgaagcc ctgcgtgaag    360
ctgacccccc tgtgcgtgac cctgaactgc accgacacca acgtgaccgg caaccgcacc    420
gtgaccggca acagcaccaa caacaccaac ggcaccggca tctacaacat cgaggagatg    480
aagaactgca gcttcaacgc caccaccgag ctgcgcgaca agaagcacaa ggagtacgcc    540
ctgttctacc gcctggacat cgtgcccctg aacgagaaca gcgacaactt cacctaccgc    600
ctgatcaact gcaacaccag caccatcacc caggcctgcc ccaaggtgag cttcgacccc    660
atccccatcc actactgcgc ccccgccggc tacgccatcc tgaagtgcaa caacaagacc    720
ttcaacggca ccggcccctg ctacaacgtg agcaccgtgc agtgcaccca cggcatcaag    780
cccgtggtga gcacccagct gctgctgaac ggcagcctgg ccgaggaggg catcatcatc    840
cgcagcgaga acctgaccga gaacaccaag accatcatcg tgcacctgaa cgagagcgtg    900
gagatcaact gcacccgccc caacaacaac acccgcaaga gcgtgcgcat cggcccggc    960 caggccttct acgccaccaa cgacgtgatc ggcaacatcc gccaggccca ctgcaacatc    1020
agcaccgacc gctggaacaa gaccctgcag caggtgatga agaagctggg cgagcacttc    1080
cccaacaaga ccatccagtt caagccccac gccggcggcg acctggagat caccatgcac    1140
agcttcaact gccgcggcga gttcttctac tgcaacacca gcaacctgtt caacagcacc    1200
taccacagca acaacggcac ctacaagtac aacggcaaca gcagcagccc catcaccctg    1260
cagtgcaaga tcaagcagat cgtgcgcatg tggcagggcg tgggccaggc cacctacgcc    1320 cccccccatcg ccggcaacat cacctgccgc agcaacatca ccggcatcct gctgacccgc    1380
gacggcggct tcaacaccac caacaacacc gagaccttcc gccccggcgg cggcgacatg    1440
cgcgacaact ggcgcagcga gctgtacaag tacaaggtgg tggagatcaa gcccctgggc    1500
atcgccccca ccaaggccaa cgccgccgtg gtgcagcgcg agaagcgcgc cgtgggcatc    1560
ggcgccgtgt tcctgggctt cctgggcgcc gccggcagca ccatgggcgc cgccagcatc    1620
accctgaccg tgcaggcccg ccagctgctg agcggcatcg tgcagcagca gagcaacctg    1680
ctgaaggcca tcgaggccca gcagcacatg ctgcagctga ccgtgtgggg catcaagcag    1740
ctgcaggccc gcgtgctggc catcgagcgc tacctgaagg accagcagct gctgggcatc    1800
tggggctgca gcggccgcct gatctgcacc accgccgtgc cctggaacag cagctggagc    1860
aacaagagcg agaaggacat ctgggacaac atgacctgga tgcagtggga ccgcgagatc    1920
agcaactaca accggcctgat ctacaacctg ctggaggaca ccagaaccca gcaggagaag    1980
aacgagaagg acctgctgga gctgacaag tggaacaacc tgtggaactg gttcgacatc    2040
agcaactggc cctggtacat caagatcttc atcatgatcg tgggcggcct gatcggcctg    2100
cgcatcatct cgccgtgct gagcatcgtg aaccgcgtgc gccagggcta cagcccctg    2160 agcttccaga ccctgacccc cagcccccgc ggcctggacc gctgggcgg catcgaggag    2220 gagggcggcg agcaggaccg cgaccgcagc atccgcctgg tgagcggctt cctgagcctg    2280
gcctgggacg acctgcgcaa cctgtgcctg ttcagctacc accgcctgcg cgacttcatc    2340
ctgatcgccg tgcgcgccgt ggagctgctg ggccacagca gcctgcgcgg cctgcagcgc    2400
ggctgggaga tcctgaagta cctgggcagc ctggtgcagt actggggcct ggagctgaag    2460
aagagcgcca tcagcctgct ggacaccatc gccatcaccg tggccgaggg caccgaccgc    2520
```

```
atcatcgagc tggtgcagcg catctgccgc gccatcctga acatccccg ccgcatccgc    2580 cagggcttcg aggccgccct gctgtaactc gag                                 2613

<210> SEQ ID NO 126
<211> LENGTH: 2616
<212> TYPE: DNA
<213> ORGANISM: Artificial
<220> FEATURE:
<223> OTHER INFORMATION: gp160mod.TV1

<400> SEQUENCE: 126
gaattcatgc gcgtgatggg cacccagaag aactgccagc agtggtggat ctggggcatc      60
ctgggcttct ggatgctgat gatctgcaac accgaggacc tgtgggtgac cgtgtactac     120
ggcgtgcccg tgtggcgcga cgccaagacc accctgttct gcgccagcga cgccaaggcc     180
tacgagaccg aggtgcacaa cgtgtgggcc acccacgcct gcgtgcccac cgaccccaac     240
ccccaggaga tcgtgctggg caacgtgacc gagaacttca acatgtggaa gaacgacatg     300
gccgaccaga tgcacgagga cgtgatcagc ctgtgggacc agagcctgaa gccctgcgtg     360
aagctgaccc ccctgtgcgt gaccctgaac tgcaccgaca ccaacgtgac cggcaaccgc     420
accgtgaccg gcaacagcac caacaacacc aacggcaccg catctacaa catcgaggag     480 atgaagaact gcagcttcaa cgccaccacc gagctgcgcg acaagaagca aggagtac      540 gccctgttct accgcctgga catcgtgccc ctgaacgaga cagcgacaa cttcacctac     600 cgcctgatca actgcaacac cagcaccatc acccaggcct gccccaaggt gagcttcgac     660
cccatcccca tccactactg cgcccccgcc ggctacgcca tcctgaagtg caacaacaag     720
accttcaacg gcaccggccc ctgctacaac gtgagcaccg tgcagtgcac ccacggcatc     780
aagcccgtgg tgagcaccca gctgctgctg aacggcagcc tggccgagga gggcatcatc     840
atccgcagcg agaacctgac cgagaacacc aagaccatca tcgtgcacct gaacgagagc     900
gtggagatca actgcacccg ccccaacaac aacacccgca gagcgtgcg catcggcccc     960 ggccaggcct ctacgccac caacgacgtg atcggcaaca tccgccaggc ccactgcaac    1020
atcagcaccg accgctggaa caagaccctg cagcaggtga tgaagaagct gggcgagcac    1080
ttccccaaca gaccatcca gttcaagccc acgccggcg cgacctgga gatcaccatg    1140 cacagcttca actgccgcgg cgagttcttc tactgcaaca ccagcaacct gttcaacagc    1200
acctaccaca gcaacaacgg cacctacaag tacaacggca acagcagcag ccccatcacc    1260
ctgcagtgca gatcaagca gatcgtgcgc atgtggcagg gcgtgggcca ggccacctac    1320 gccccccca tcgccggcaa catcacctgc cgcagcaaca tcaccggcat cctgctgacc    1380
cgcgacggcg gcttcaacac caccaacaac accgagacct tccgccccgg cggcggcgac    1440
atgcgcgaca ctggcgcag cgagctgtac aagtacaagg tggtggagat caagcccctg    1500
ggcatcgccc ccaccaaggc caagcgccgc gtggtgcagc gcgagaagcg cgccgtgggc    1560
atcggcgccc tgttcctggg cttcctgggc gccgccggca gcaccatggg cgccgccagc    1620
atcaccctga ccgtgcaggc cgccagctg ctgagcggca tcgtgcagca gcagagcaac    1680
ctgctgaagg ccatcgaggc ccagcagcac atgctgcagc tgaccgtgtg ggcatcaag    1740 cagctgcagg cccgcgtgct ggccatcgag cgctacctga aggaccagca gctgctgggc    1800
atctggggct gcagcggccg cctgatctgc accaccgccg tgccctggaa cagcagctgg    1860
agcaacaaga gcgagaagga catctgggac aacatgacct ggatgcagtg ggaccgcgag    1920
```

-continued

| | |
|---|---|
| atcagcaact acaccggcct gatctacaac ctgctggagg acagccagaa ccagcaggag | 1980 |
| aagaacgaga aggacctgct ggagctggac aagtggaaca acctgtggaa ctggttcgac | 2040 |
| atcagcaact ggccctggta catcaagatc ttcatcatga tcgtgggcgg cctgatcggc | 2100 |
| ctgcgcatca tcttcgccgt gctgagcatc gtgaaccgcg tgcgccaggg ctacagcccc | 2160 |
| ctgagcttcc agaccctgac ccccagcccc cgcggcctgg accgcctggg cggcatcgag | 2220 |
| gaggagggcg gcgagcagga ccgcgaccgc agcatccgcc tggtgagcgg cttcctgagc | 2280 |
| ctggcctggg acgacctgcg caacctgtgc ctgttcagct accaccgcct gcgcgacttc | 2340 |
| atcctgatcg ccgtgcgcgc cgtggagctg ctgggccaca gcagcctgcg cggcctgcag | 2400 |
| cgcggctggg agatcctgaa gtacctgggc agcctggtgc agtactgggg cctggagctg | 2460 |
| aagaagagcg ccatcagcct gctggacacc atcgccatca ccgtggccga gggcaccgac | 2520 |
| cgcatcatcg agctggtgca gcgcatctgc cgcgccatcc tgaacatccc cgccgcatc | 2580 |
| cgccagggct cgaggccgc cctgctgtaa ctcgag | 2616 |

<210> SEQ ID NO 127
<211> LENGTH: 2616
<212> TYPE: DNA
<213> ORGANISM: Artificial
<220> FEATURE:
<223> OTHER INFORMATION: gp160mod.TV1.wtLnative

<400> SEQUENCE: 127

| | |
|---|---|
| gaattcatga gagtgatggg gacacagaag aattgtcaac aatggtggat atggggcatc | 60 |
| ttaggcttct ggatgctaat gatttgtaac accgaggacc tgtgggtgac cgtgtactac | 120 |
| ggcgtgcccg tgtggcgcga cgccaagacc accctgttct cgccagcga cgccaaggcc | 180 |
| tacgagaccg aggtgcacaa cgtgtgggcc acccacgcct gcgtgccac cgaccccaac | 240 |
| ccccaggaga tcgtgctggg caacgtgacc gagaacttca catgtggaa gaacgacatg | 300 |
| gccgaccaga tgcacgagga cgtgatcagc ctgtgggacc agagcctgaa gccctgcgtg | 360 |
| aagctgaccc ccctgtgcgt gaccctgaac tgcaccgaca ccaacgtgac cggcaaccgc | 420 |
| accgtgaccg gcaacagcac caacaacacc aacggcaccg gcatctacaa catcgaggag | 480 |
| atgaagaact gcagcttcaa cgccaccacc gagctgcgcg acaagaagca caggagtac | 540 |
| gccctgttct accgcctgga catcgtgccc ctgaacgaga cagcgacaa cttcacctac | 600 |
| cgcctgatca actgcaacac cagcaccatc ccccaggcct gccccaaggt gagcttcgac | 660 |
| cccatcccca tccactactg cgccccgcc ggctacgcca tcctgaagtg caacaacaag | 720 |
| accttcaacg gcaccggccc ctgctacaac gtgagcaccg tgcagtgcac ccacggcatc | 780 |
| aagcccgtgg tgagcaccca gctgctgctg aacggcagcc tggccgagga gggcatcatc | 840 |
| atccgcagcg agaacctgac cgagaacacc aagaccatca tcgtgcacct gaacgagagc | 900 |
| gtggagatca actgcacccg ccccaacaac aacacccgca gagcgtgcg catcggcccc | 960 |
| ggccaggcct tctacgccac caacgacgtg atcggcaaca tccgccaggc ccactgcaac | 1020 |
| atcagcaccg accgctggaa caagaccctg cagcaggtga tgaagaagct gggcgagcac | 1080 |
| ttccccaaca gaccatcca gttcaagccc cacgccggcg gcgacctgga gatcaccatg | 1140 |
| cacagcttca ctgccgcgg cgagttcttc tactgcaaca ccagcaacct gttcaacagc | 1200 |
| acctaccaca gcaacaacgg cacctacaag tacaacggca acagcagcag ccccatcacc | 1260 |
| ctgcagtgca gatcaagca gatcgtgcgc atgtggcagg gcgtgggcca ggccacctac | 1320 |
| gccccccca tcgccggcaa catcacctgc cgcagcaaca tcaccggcat cctgctgacc | 1380 |

-continued

```
cgcgacggcg gcttcaacac caccaacaac accgagacct tccgcccggg cggcggcgac    1440
atgcgcgaca actggcgcag cgagctgtac aagtacaagg tggtggagat caagcccctg    1500
ggcatcgccc ccaccaaggc caagcgccgc gtggtgcagc gcgagaagcg cgccgtgggc    1560
atcggcgccg tgttcctggg cttcctgggc gccgccggca gcaccatggg cgccgccagc    1620
atcaccctga ccgtgcaggc cgccagctgc ctgagcggca tcgtgcagca gcagagcaac    1680
ctgctgaagg ccatcgaggc ccagcagcac atgctgcagc tgaccgtgtg gggcatcaag    1740
cagctgcagg cccgcgtgct ggccatcgag cgctacctga aggaccagca gctgctgggc    1800
atctggggct gcagcggccg cctgatctgc accaccgccg tgccctggaa cagcagctgg    1860
agcaacaaga gcgagaagga catctgggac aacatgacct ggatgcagtg ggaccgcgag    1920
atcagcaact acaccggcct gatctacaac ctgctggagg acagccagaa ccagcaggag    1980
aagaacgaga aggacctgct ggagctggac aagtggaaca acctgtggaa ctggttcgac    2040
atcagcaact ggccctggta catcaagatc ttcatcatga tcgtgggcgg cctgatcggc    2100
ctgcgcatca tcttcgccgt gctgagcatc gtgaaccgcg tgcgccaggg ctacagcccc    2160
ctgagcttcc agaccctgac ccccagcccc cgcggcctgg accgcctggg cggcatcgag    2220
gaggagggcg gcgagcagga ccgcgaccgc agcatccgcc tggtgagcgg cttcctgagc    2280
ctggcctggg acgacctgcg caacctgtgc ctgttcagct accaccgcct gcgcgacttc    2340
atcctgatcg ccgtgcgcgc cgtggagctg ctgggccaca gcagcctgcg cggcctgcag    2400
cgcggctggg agatcctgaa gtacctgggc agcctggtgc agtactgggg cctggagctg    2460
aagaagagcg ccatcagcct gctggacacc atcgccatca ccgtggccga gggcaccgac    2520
cgcatcatcg agctggtgca gcgcatctgc cgcgccatcc tgaacatccc ccgccgcatc    2580
cgccagggct tcgaggccgc cctgctgtaa ctcgag                              2616
```

<210> SEQ ID NO 128
<211> LENGTH: 2604
<212> TYPE: DNA
<213> ORGANISM: Artificial
<220> FEATURE:
<223> OTHER INFORMATION: Wild-type Env gp160 (8_2_ZA)

<400> SEQUENCE: 128

```
atgagagtga tggggacaca gaagaattgt caacaatggt ggatatgggg catcttaggc      60
ttctggatgc taatgatttg taacacggag gacttgtggg tcacagtcta ctatggggta     120
cctgtgtgga gagacgcaaa aactactcta ttctgtgcat cagatgctaa agcatatgag     180
acagaagtgc ataatgtctg gctacacat gcctgtgtac ccacagaccc caacccacaa     240
gaaatagttt tgggaaatgt aacagaaaat tttaatatgt ggaaaaatga catggcagat     300
cagatgcatg aggatgtaat cagtttatgg gatcaaagcc taaagccatg tgtaaagttg     360
accccactct gtgtcacttt aaactgtaca gatacaaatg ttacaggtaa tagaactgtt     420
acaggtaata gtaccaataa tacaaatggt acaggtattt ataacattga gaaatgaaa     480 aattgctctt tcaatgcaac cacagaatta agagataaga acataaaga gtatgcactc     540 ttttatagac ttgatatagt accacttaat gagaatagtg caactttac atatagatta     600 ataaattgca ataccctcaac cataacacaa gcctgtccaa aggtctcttt tgacccgatt     660
cctatacatt actgtgctcc agctggttat gcgattctaa agtgtaataa taagacattc     720
aatgggacag gaccatgtta taatgtcagc acagtacaat gtacacatgg aattaagcca     780
```

-continued

```
gtggtatcaa ctcaattact gttaaatggt agtctagcag aagaagggat aataattaga      840
tctgaaaatt tgacagagaa taccaaaaca ataatagtac accttaatga atctgtagag      900
attaattgta caagacccaa caataataca agaaaaagtg taaggatagg accaggacaa      960
gcattctatg caacaaatga tgtaatagga aacataagac aagcacattg taacattagt     1020
acagatagat ggaacaaaac tttacaacag gtaatgaaaa aattaggaga gcatttccct     1080
aataaaacaa tacaatttaa accacatgca ggaggggatc tagaaattac aatgcatagc     1140
tttaattgta gaggagaatt tttctattgt aatacatcaa acctgtttaa tagcacatac     1200
cactctaata atggtacata caaatacaat ggtaattcaa gctcacccat cacactccaa     1260
tgtaaaataa aacaaattgt acgcatgtgg caaggggtag acaagcaac gtatgcccct      1320 cccattgcag gaaacataac atgtagatca aacatcacag gaatactatt gacacgtgat     1380
ggaggattta acaccacaaa caacacagag acattcagac ctggaggagg agatatgagg     1440
gataactgga gaagtgaatt atataaatat aaagtagtag aaattaagcc attgggaata     1500
gcacccacta aggcaaaaag aagagtggtg cagagagaaa aaagagcagt gggaatagga     1560
gctgtgttcc ttgggttctt gggagcagca ggaagcacta tgggcgcagc gtcaataacg     1620
ctgacggtac aggccagaca actgttgtct ggtatagtgc aacagcaaag caatttgctg     1680
aaggctatag aggcgcaaca gcatatgttg caactcacag tctggggcat taagcagctc     1740
caggcgagag tcctggctat agaaagatac ctaaaggatc aacagctcct agggatttgg     1800
ggctgctctg gaaagactcat ctgcaccact gctgtgcctt ggaactccag ttggagtaat     1860
aaatctgaaa agatatttg ggataacatg acttggatgc agtgggatag agaaattagt      1920
aattacacag gcttaatata caatttgctt gaagactcgc aaaaccagca ggaaaagaat     1980 gaaaagagatt tattagaatt ggacaagtgg aacaatctgt ggaattggtt tgacatatca     2040
aactggccgt ggtatataaa aatattcata atgatagtag gaggcttgat aggtttaaga     2100
ataatttttg ctgtgctttc tatagtgaat agagttaggc agggatactc accttttgtca    2160 tttcagaccc ttaccccaag cccgagggga ctcgacaggc tcggaggaat cgaagaagaa     2220
ggtggagagc aagacagaga cagatccata cgattggtga gcggattctt gtcgcttgcc     2280
tgggacgatc tgcggaacct gtgcctcttc agctaccacc gcttgagaga cttcatatta     2340
attgcagtga gggcagtgga acttctggga cacagcagtc tcaggggact acagaggggg     2400
tgggaaatcc ttaagtatct gggaagtctt gtgcaatatt ggggtctaga gctaaaaaag     2460
agtgctatta gtctgcttga taccatagca ataacagtag ctgaaggaac agataggatt     2520
atagaattag tacaaagaat ttgtagagct atcctcaaca tacctagaag aataagacag     2580
ggctttgaag cagctttgct ataa                                            2604
```

<210> SEQ ID NO 129
<211> LENGTH: 10
<212> TYPE: PRT
<213> ORGANISM: Artificial
<220> FEATURE:
<223> OTHER INFORMATION: wild-type amino acid sequence changed by
    mutation in gp120/gp41 cleavage site

<400> SEQUENCE: 129

Lys Arg Arg Val Val Gln Arg Glu Lys Arg
1               5                   10

<210> SEQ ID NO 130
<211> LENGTH: 10

```
<212> TYPE: PRT
<213> ORGANISM: Artificial
<220> FEATURE:
<223> OTHER INFORMATION: wild-type amino acid sequence changed by
      mutation in gp120/gp41 cleavage site

<400> SEQUENCE: 130

Ile Ser Ser Val Val Gln Ser Glu Lys Ser
1               5                   10

<210> SEQ ID NO 131
<211> LENGTH: 2052
<212> TYPE: DNA
<213> ORGANISM: Artificial
<220> FEATURE:
<223> OTHER INFORMATION: gp140mod.TV1.tpa1

<400> SEQUENCE: 131
atggatgcaa tgaagagagg gctctgctgt gtgctgctgc tgtgtggagc agtcttcgtt      60
tcgcccagcg ccagcaccga ggacctgtgg gtgaccgtgt actacggcgt gcccgtgtgg     120
cgcgacgcca agaccaccct gttctgcgcc agcgacgcca aggcctacga gaccgaggtg     180
cacaacgtgt gggccaccca cgcctgcgtg cccaccgacc caaccccca ggagatcgtg      240 ctgggcaacg tgaccgagaa cttcaacatg tggaagaacg acatggccga ccagatgcac     300
gaggacgtga tcagcctgtg ggaccagagc ctgaagccct gcgtgaagct gaccccctg      360 tgcgtgaccc tgaactgcac cgacaccaac gtgaccggca ccgcaccgt gaccggcaac      420 agcaccaaca caccaacgg caccggcatc tacaacatcg aggagatgaa gaactgcagc     480
ttcaacgcca ccaccgagct gcgcgacaag aagcacaagg agtacgccct gttctaccgc     540
ctggacatcg tgcccctgaa cgagaacagc gacaacttca cctaccgcct gatcaactgc     600
aacaccagca ccatcacccca ggcctgcccc aaggtgagct ccgaccccat ccccatccac     660
tactgcgccc ccgccggcta cgccatcctg aagtgcaaca acaagacctt caacggcacc     720
ggcccctgct acaacgtgag caccgtgcag tgcacccacg gcatcaagcc cgtggtgagc     780
acccagctgc tgctgaacgg cagcctggcc gaggagggca tcatcatccg cagcgagaac     840
ctgaccgaga caccaagac catcatcgtg cacctgaacg agagcgtgga gatcaactgc     900
acccgcccca caacaacac ccgcaagagc gtgcgcatcg ccccggcca ggccttctac       960 gccaccaacg acgtgatcgg caacatccgc caggcccact gcaacatcag caccgaccgc    1020
tggaacaaga ccctgcagca ggtgatgaag aagctgggcg agcactttcc caacaagacc    1080
atccagttca gccccaccgc cggcggcgac ctggagatca ccatgcacag cttcaactgc    1140
cgcggcgagt tcttctactg caacaccagc aacctgttca cagcaccta ccacagcaac    1200 aacggcacct acaagtacaa cggcaacagc agcagcccca tcaccctgca gtgcaagatc    1260
aagcagatcg tgcgcatgtg gcagggcgtg ggccaggcca cctacgcccc cccatcgcc    1320 ggcaacatca cctgccgcag caacatcacc ggcatcctgc tgacccgcga cggcggcttc    1380
aacaccacca caacaccga gaccttccgc cccggcggcg gcgacatgcg cgacaactgg    1440
cgcagcgagc tgtacaagta caaggtggtg gagatcaagc cctgggcat cgcccccacc    1500 aaggccaagc gccgcgtggt gcagcgcgag aagcgcgccg tgggcatcgg cgccgtgttc    1560
ctgggcttcc tgggcgccgc cggcagcacc atggcgccg ccagcatcac cctgaccgtg    1620
caggcccgcc agctgctgag cggcatcgtg cagcagcaga gcaacctgct gaaggccatc    1680
gaggcccagc agcacatgct gcagctgacc gtgtggggca tcaagcagct gcaggcccgc    1740
```

```
gtgctggcca tcgagcgcta cctgaaggac cagcagctgc tgggcatctg ggctgcagc    1800 ggccgcctga tctgcaccac cgccgtgccc tggaacagca gctggagcaa caagagcgag   1860
aaggacatct gggacaacat gacctggatg cagtgggacc gcgagatcag caactacacc   1920
ggcctgatct acaacctgct ggaggacagc cagaaccagc aggagaagaa cgagaaggac   1980
ctgctggagc tggacaagtg gaacaacctg tggaactggt tcgacatcag caactggccc   2040
tggtacatct aa                                                       2052
```

<210> SEQ ID NO 132
<211> LENGTH: 2073
<212> TYPE: DNA
<213> ORGANISM: Artificial
<220> FEATURE:
<223> OTHER INFORMATION: gp140mod.TV1

<400> SEQUENCE: 132

```
gaattcatgc gcgtgatggg cacccagaag aactgccagc agtggtggat ctggggcatc     60
ctgggcttct ggatgctgat gatctgcaac accgaggacc tgtgggtgac cgtgtactac    120
ggcgtgcccg tgtggcgcga cgccaagacc accctgttct cgccagcga cgccaaggcc    180 tacgagaccg aggtgcacaa cgtgtgggcc acccacgcct gcgtgccac cgaccccaac    240 cccaggaga tcgtgctggg caacgtgacc gagaacttca acatgtggaa gaacgacatg    300
gccgaccaga tgcacgagga cgtgatcagc ctgtgggacc agagcctgaa gccctgcgtg    360
aagctgaccc ccctgtgcgt gaccctgaac tgcaccgaca ccaacgtgac cggcaaccgc    420
accgtgaccg gcaacagcac caacaacacc aacggcaccg gcatctacaa catcgaggag    480
atgaagaact gcagcttcaa cgccaccacc gagctgcgcg acaagaagca caaggagtac    540
gccctgttct accgcctgga catcgtgccc ctgaacgaga cagcgacaa cttcacctac    600 cgcctgatca actgcaacac cagcaccatc ccccaggcct gccccaaggt gagcttcgac    660
cccatcccca tccactactg cgcccccgcc ggctacgcca tcctgaagtg caacaacaag    720
accttcaacg gcaccggccc tgctacaac gtgagcaccg tgcagtgcac ccacggcatc    780
aagcccgtgg tgagcaccca gctgctgctg aacggcagcc tggccgagga gggcatcatc    840
atccgcagcg agaacctgac cgagaacacc aagaccatca tcgtgcacct gaacgagagc    900
gtggagatca actgcacccg ccccaacaac aacacccgca gagcgtgcg catcggcccc    960 ggccaggcct tctacgccac caacgacgtg atcggcaaca tccgccaggc ccactgcaac   1020
atcagcaccg accgctggaa caagaccctg cagcaggtga tgaagaagct gggcgagcac   1080
ttccccaaca agaccatcca gttcaagccc cacgccggcg cgacctgga gatcaccatg    1140 cacagcttca actgccgcgg cgagttcttc tactgcaaca ccagcaacct gttcaacagc    1200
acctaccaca gcaacaacgg cacctacaag tacaacggca acagcagcag ccccatcacc    1260
ctgcagtgca gatcaagca gatcgtgcgc atgtggcagg gcgtgggcca ggccacctac    1320 gccccccca tcgccggcaa catcacctgc cgcagcaaca tcaccggcat cctgctgacc    1380
cgcgacggcg gcttcaacac caccaacaac accgagacct tccgcccgg cggcggcgac    1440 atgcgcgaca ctggcgcag cgagctgtac aagtacaagg tggtggagat caagcccctg    1500
ggcatcgccc ccaccaaggc caagcgccg tgtcgcagc gcgagaagcg cgccgtgggc    1560
atcggcgccg tgttcctggg cttcctgggc gccgccggca gcaccatggg cgccgccagc    1620
atcaccctga ccgtgcaggc ccgccagctg ctgagcggca tcgtgcagca gcagagcaac    1680
ctgctgaagg ccatcgaggc ccagcagcac atgctgcagc tgaccgtgtg gggcatcaag    1740
```

| | |
|---|---|
| cagctgcagg cccgcgtgct ggccatcgag cgctacctga aggaccagca gctgctgggc | 1800 |
| atctggggct gcagcggccg cctgatctgc accaccgccg tgccctggaa cagcagctgg | 1860 |
| agcaacaaga gcgagaagga catctgggac aacatgacct ggatgcagtg ggaccgcgag | 1920 |
| atcagcaact acaccggcct gatctacaac ctgctggagg acagccagaa ccagcaggag | 1980 |
| aagaacgaga aggacctgct ggagctggac aagtggaaca acctgtggaa ctggttcgac | 2040 |
| atcagcaact ggccctggta catctaactc gag | 2073 |

<210> SEQ ID NO 133
<211> LENGTH: 2073
<212> TYPE: DNA
<213> ORGANISM: Artificial
<220> FEATURE:
<223> OTHER INFORMATION: gp140mod.TV1.wtLnative

<400> SEQUENCE: 133

| | |
|---|---|
| gaattcatga gagtgatggg gacacagaag aattgtcaac aatggtggat atggggcatc | 60 |
| ttaggcttct ggatgctaat gatttgtaac accgaggacc tgtgggtgac cgtgtactac | 120 |
| ggcgtgcccg tgtggcgcga cgccaagacc accctgttct gcgccagcga cgccaaggcc | 180 |
| tacgagaccg aggtgcacaa cgtgtgggcc acccacgcct gcgtgcccac cgaccccaac | 240 |
| cccaggaga tcgtgctggg caacgtgacc gagaacttca catgtggaa gaacgacatg | 300 |
| gccgaccaga tgcacgagga cgtgatcagc ctgtgggacc agagcctgaa gccctgcgtg | 360 |
| aagctgaccc ccctgtgcgt gaccctgaac tgcaccgaca ccaacgtgac cggcaaccgc | 420 |
| accgtgaccg gcaacagcac caacaacacc aacggcaccg catctacaa catcgaggag | 480 |
| atgaagaact gcagcttcaa cgccaccacc gagctgcgcg acaagaagca caaggagtac | 540 |
| gccctgttct accgcctgga catcgtgccc ctgaacgaga cagcgacaa cttcacctac | 600 |
| cgcctgatca actgcaacac cagcaccatc acccaggcct gccccaaggt gagcttcgac | 660 |
| cccatcccca tccactactg cgcccccgcc ggctacgcca tcctgaagtg caacaacaag | 720 |
| accttcaacg gcaccggccc ctgctacaac gtgagcaccg tgcagtgcac ccacggcatc | 780 |
| aagcccgtgg tgagcaccca gctgctgctg aacggcagcc tggccgagga gggcatcatc | 840 |
| atccgcagcg agaacctgac cgagaacacc aagaccatca tcgtgcacct gaacgagagc | 900 |
| gtggagatca actgcacccg ccccaacaac aacacccgca gagcgtgcg catcggcccc | 960 |
| ggccaggcct ctacgccac caacgacgtg atcggcaaca tccgccaggc ccactgcaac | 1020 |
| atcagcaccg accgctggaa caagaccctg cagcaggtga tgaagaagct gggcgagcac | 1080 |
| ttccccaaca agaccatcca gttcaagccc acgccggcg cgacctgga gatcaccatg | 1140 |
| cacagcttca actgccgcgg cgagttcttc tactgcaaca ccagcaacct gttcaacagc | 1200 |
| acctaccaca gcaacaacgg cacctacaag tacaacggca acagcagcag ccccatcacc | 1260 |
| ctgcagtgca agatcaagca gatcgtgcgc atgtggcagg gcgtgggcca ggccacctac | 1320 |
| gcccccccca tcgccggcaa catcacctgc cgcagcaaca tcaccggcat cctgctgacc | 1380 |
| cgcgacggcg gcttcaacac caccaacaac accgagacct tccgccccgg cggcggcgac | 1440 |
| atgcgcgaca ctggcgcag cgagctgtac aagtacaagg tggtggagat caagcccctg | 1500 |
| ggcatcgccc ccaccaaggc caagcgccgc gtggtgcagc gcgagaagcg cgccgtgggc | 1560 |
| atcggcgccg tgttcctggg cttcctgggc gccgccggca gcaccatggg cgccgccagc | 1620 |
| atcaccctga ccgtgcaggc ccgccagctg ctgagcggca tcgtgcagca gcagagcaac | 1680 |

-continued

```
ctgctgaagg ccatcgaggc ccagcagcac atgctgcagc tgaccgtgtg gggcatcaag     1740
cagctgcagg cccgcgtgct ggccatcgag cgctacctga aggaccagca gctgctgggc     1800
atctggggct gcagcggccg cctgatctgc accaccgccg tgccctggaa cagcagctgg     1860
agcaacaaga gcgagaagga catctgggac aacatgacct ggatgcagtg ggaccgcgag     1920
atcagcaact acaccggcct gatctacaac ctgctggagg acagccagaa ccagcaggag     1980
aagaacgaga aggacctgct ggagctggac aagtggaaca acctgtggaa ctggttcgac     2040
atcagcaact ggcccctggta catctaactc gag                                 2073
```

<210> SEQ ID NO 134
<211> LENGTH: 624
<212> TYPE: DNA
<213> ORGANISM: Artificial
<220> FEATURE:
<223> OTHER INFORMATION: NefD125G_TV2_C_ZAopt

<400> SEQUENCE: 134

```
atgggcggca agtggagcaa gagcagcatc atcggctggc ccgaggtgcg cgagcgcatc       60
cgccgcaccc gcagcgccgc cgagggcgtg ggcagcgcca gccaggacct ggagaagcac      120
ggcgccctga ccaccagcaa caccgcccac aacaacgccg cctgcgcctg gctggaggcc      180
caggaggagg agggcgaggt gggcttcccc gtgcgccccc aggtgcccct gcgccccatg      240
acctacaagg ccgccatcga cctgagcttc ttcctgaagg agaagggcgg cctggagggc      300
ctgatctaca gcaagaagcg ccaggagatc ctggacctgt gggtgtacaa cacccagggc      360
ttcttccccg ctggcagaa ctacaccccc ggccccggcg tgcgcttccc cctgaccttc       420
ggctggtact tcaagctgga gcccgtggac cccgcgagg tggaggaggc caacgagggc       480
gagaacaact gcctgctgca ccccatgagc cagcacggca tggaggacga ggaccgcgag      540
gtgctgcgct ggaagttcga cagcaccctg gcccgccgcc acatggcccg cgagctgcac      600
cccgagtact acaaggactg ctga                                             624
```

<210> SEQ ID NO 135
<211> LENGTH: 624
<212> TYPE: DNA
<213> ORGANISM: Artificial
<220> FEATURE:
<223> OTHER INFORMATION: NefD125G-Myr_TV2_C_ZAopt

<400> SEQUENCE: 135

```
atggccggca agtggagcaa gagcagcatc atcggctggc ccgaggtgcg cgagcgcatc       60
cgccgcaccc gcagcgccgc cgagggcgtg ggcagcgcca gccaggacct ggagaagcac      120
ggcgccctga ccaccagcaa caccgcccac aacaacgccg cctgcgcctg gctggaggcc      180
caggaggagg agggcgaggt gggcttcccc gtgcgccccc aggtgcccct gcgccccatg      240
acctacaagg ccgccatcga cctgagcttc ttcctgaagg agaagggcgg cctggagggc      300
ctgatctaca gcaagaagcg ccaggagatc ctggacctgt gggtgtacaa cacccagggc      360
ttcttccccg ctggcagaa ctacaccccc ggccccggcg tgcgcttccc cctgaccttc       420
ggctggtact tcaagctgga gcccgtggac cccgcgagg tggaggaggc caacgagggc       480
gagaacaact gcctgctgca ccccatgagc cagcacggca tggaggacga ggaccgcgag      540
gtgctgcgct ggaagttcga cagcaccctg gcccgccgcc acatggcccg cgagctgcac      600
cccgagtact acaaggactg ctga                                             624
```

<210> SEQ ID NO 136
<211> LENGTH: 27
<212> TYPE: PRT
<213> ORGANISM: Artificial
<220> FEATURE:
<223> OTHER INFORMATION: TV1c8.2 signal peptide leader sequence

<400> SEQUENCE: 136

Met Arg Val Met Gly Thr Gln Lys Asn Cys Gln Gln Trp Trp Ile Trp
1               5                   10                  15

Gly Ile Leu Gly Phe Trp Met Leu Met Ile Cys
            20                  25

<210> SEQ ID NO 137
<211> LENGTH: 81
<212> TYPE: DNA
<213> ORGANISM: Artificial
<220> FEATURE:
<223> OTHER INFORMATION: WTnative (8-2_TV1_C.ZA) signal peptide leader
      sequence

<400> SEQUENCE: 137
atgagagtga tggggacaca gaagaattgt caacaatggt ggatatgggg catcttaggc        60
ttctggatgc taatgatttg t                                                 81

<210> SEQ ID NO 138
<211> LENGTH: 81
<212> TYPE: DNA
<213> ORGANISM: Artificial
<220> FEATURE:
<223> OTHER INFORMATION: WTmod (8-2_TV1_C.ZA) signal peptide leader
      sequence

<400> SEQUENCE: 138
atgcgcgtga tgggcaccca gaagaactgc cagcagtggt ggatctgggg catcctgggc        60
ttctggatgc tgatgatctg c                                                 81

<210> SEQ ID NO 139
<211> LENGTH: 25
<212> TYPE: PRT
<213> ORGANISM: Artificial
<220> FEATURE:
<223> OTHER INFORMATION: Tpa1 signal peptide leader sequence

<400> SEQUENCE: 139

Met Asp Ala Met Lys Arg Gly Leu Cys Cys Val Leu Leu Leu Cys Gly
1               5                   10                  15

Ala Val Phe Val Ser Pro Ser Ala Ser
            20                  25

<210> SEQ ID NO 140
<211> LENGTH: 75
<212> TYPE: DNA
<213> ORGANISM: Artificial
<220> FEATURE:
<223> OTHER INFORMATION: Tpa1 signal peptide leader sequence

<400> SEQUENCE: 140
atggatgcaa tgaagagagg gctctgctgt gtgctgctgc tgtgtggagc agtcttcgtt        60
tcgcccagcg ccagc                                                        75

<210> SEQ ID NO 141
<211> LENGTH: 23
<212> TYPE: PRT

```
<213> ORGANISM: Artificial
<220> FEATURE:
<223> OTHER INFORMATION: Tpa2 signal peptide leader sequence

<400> SEQUENCE: 141

Met Asp Ala Met Lys Arg Gly Leu Cys Cys Val Leu Leu Cys Gly
1               5                   10                  15

Ala Val Phe Val Ser Pro Ser
            20

<210> SEQ ID NO 142
<211> LENGTH: 69
<212> TYPE: DNA
<213> ORGANISM: Artificial
<220> FEATURE:
<223> OTHER INFORMATION: Tpa2 signal peptide leader sequence

<400> SEQUENCE: 142
atggatgcaa tgaagagagg gctctgctgt gtgctgctgc tgtgtggagc agtcttcgtt    60
tcgcccagc                                                           69

<210> SEQ ID NO 143
<211> LENGTH: 842
<212> TYPE: PRT
<213> ORGANISM: Human immunodeficiency virus SF162

<400> SEQUENCE: 143

Met Asp Ala Met Lys Arg Gly Leu Cys Cys Val Leu Leu Cys Gly
1               5                   10                  15

Ala Val Phe Val Ser Pro Ser Ala Val Glu Lys Leu Trp Val Thr Val
            20                  25                  30

Tyr Tyr Gly Val Pro Val Trp Lys Glu Ala Thr Thr Thr Leu Phe Cys
        35                  40                  45

Ala Ser Asp Ala Lys Ala Tyr Asp Thr Glu Val His Asn Val Trp Ala
    50                  55                  60

Thr His Ala Cys Val Pro Thr Asp Pro Asn Pro Gln Glu Ile Val Leu
65                  70                  75                  80

Glu Asn Val Thr Glu Asn Phe Asn Met Trp Lys Asn Asn Met Val Glu
                85                  90                  95

Gln Met His Glu Asp Ile Ile Ser Leu Trp Asp Gln Ser Leu Lys Pro
            100                 105                 110

Cys Val Lys Leu Thr Pro Leu Cys Val Thr Leu His Cys Thr Asn Leu
        115                 120                 125

Lys Asn Ala Thr Asn Thr Lys Ser Ser Asn Trp Lys Glu Met Asp Arg
    130                 135                 140

Gly Glu Ile Lys Asn Cys Ser Phe Lys Val Thr Thr Ser Ile Arg Asn
145                 150                 155                 160

Lys Met Gln Lys Glu Tyr Ala Leu Phe Tyr Lys Leu Asp Val Val Pro
                165                 170                 175

Ile Asp Asn Asp Asn Thr Ser Tyr Lys Leu Ile Asn Cys Asn Thr Ser
            180                 185                 190

Val Ile Thr Gln Ala Cys Pro Lys Val Ser Phe Glu Pro Ile Pro Ile
        195                 200                 205

His Tyr Cys Ala Pro Ala Gly Phe Ala Ile Leu Lys Cys Asn Asp Lys
    210                 215                 220

Lys Phe Asn Gly Ser Gly Pro Cys Thr Asn Val Ser Thr Val Gln Cys
225                 230                 235                 240
```

-continued

Thr His Gly Ile Arg Pro Val Ser Thr Gln Leu Leu Asn Gly
                245                 250                 255

Ser Leu Ala Glu Glu Gly Val Val Ile Arg Ser Glu Asn Phe Thr Asp
            260                 265                 270

Asn Ala Lys Thr Ile Ile Val Gln Leu Lys Glu Ser Val Glu Ile Asn
        275                 280                 285

Cys Thr Arg Pro Asn Asn Asn Thr Arg Lys Ser Ile Thr Ile Gly Pro
290                 295                 300

Gly Arg Ala Phe Tyr Ala Thr Gly Asp Ile Ile Gly Asp Ile Arg Gln
305                 310                 315                 320

Ala His Cys Asn Ile Ser Gly Glu Lys Trp Asn Asn Thr Leu Lys Gln
                325                 330                 335

Ile Val Thr Lys Leu Gln Ala Gln Phe Gly Asn Lys Thr Ile Val Phe
            340                 345                 350

Lys Gln Ser Ser Gly Gly Asp Pro Glu Ile Val Met His Ser Phe Asn
        355                 360                 365

Cys Gly Gly Glu Phe Phe Tyr Cys Asn Ser Thr Gln Leu Phe Asn Ser
370                 375                 380

Thr Trp Asn Asn Thr Ile Gly Pro Asn Asn Thr Asn Gly Thr Ile Thr
385                 390                 395                 400

Leu Pro Cys Arg Ile Lys Gln Ile Ile Asn Arg Trp Gln Glu Val Gly
                405                 410                 415

Lys Ala Met Tyr Ala Pro Pro Ile Arg Gly Gln Ile Arg Cys Ser Ser
            420                 425                 430

Asn Ile Thr Gly Leu Leu Leu Thr Arg Asp Gly Gly Lys Glu Ile Ser
        435                 440                 445

Asn Thr Thr Glu Ile Phe Arg Pro Gly Gly Gly Asp Met Arg Asp Asn
        450                 455                 460

Trp Arg Ser Glu Leu Tyr Lys Tyr Lys Val Val Lys Ile Glu Pro Leu
465                 470                 475                 480

Gly Val Ala Pro Thr Lys Ala Lys Arg Arg Val Val Gln Arg Glu Lys
                485                 490                 495

Arg Ala Val Thr Leu Gly Ala Met Phe Leu Gly Phe Leu Gly Ala Ala
            500                 505                 510

Gly Ser Thr Met Gly Ala Arg Ser Leu Thr Leu Thr Val Gln Ala Arg
        515                 520                 525

Gln Leu Leu Ser Gly Ile Val Gln Gln Gln Asn Asn Leu Leu Arg Ala
        530                 535                 540

Ile Glu Ala Gln Gln His Leu Leu Gln Leu Thr Val Trp Gly Ile Lys
545                 550                 555                 560

Gln Leu Gln Ala Arg Val Leu Ala Val Glu Arg Tyr Leu Lys Asp Gln
                565                 570                 575

Gln Leu Leu Gly Ile Trp Gly Cys Ser Gly Lys Leu Ile Cys Thr Thr
            580                 585                 590

Ala Val Pro Trp Asn Ala Ser Trp Ser Asn Lys Ser Leu Asp Gln Ile
        595                 600                 605

Trp Asn Asn Met Thr Trp Met Glu Trp Glu Arg Glu Ile Asp Asn Tyr
610                 615                 620

Thr Asn Leu Ile Tyr Thr Leu Ile Glu Glu Ser Gln Asn Gln Gln Glu
625                 630                 635                 640

Lys Asn Glu Gln Glu Leu Leu Glu Leu Asp Lys Trp Ala Ser Leu Trp
                645                 650                 655

Asn Trp Phe Asp Ile Ser Lys Trp Leu Trp Tyr Ile Lys Ile Phe Ile

```
                    660                 665                 670
Met Ile Val Gly Gly Leu Val Gly Leu Arg Ile Val Phe Thr Val Leu
                675                 680                 685

Ser Ile Val Asn Arg Val Arg Gln Gly Tyr Ser Pro Leu Ser Phe Gln
                690                 695                 700

Thr Arg Phe Pro Ala Pro Arg Gly Pro Asp Arg Pro Glu Gly Ile Glu
705                 710                 715                 720

Glu Glu Gly Gly Glu Arg Asp Arg Asp Arg Ser Ser Pro Leu Val His
                        725                 730                 735

Gly Leu Leu Ala Leu Ile Trp Asp Asp Leu Arg Ser Leu Cys Leu Phe
                740                 745                 750

Ser Tyr His Arg Leu Arg Asp Leu Ile Leu Ile Ala Ala Arg Ile Val
                755                 760                 765

Glu Leu Leu Gly Arg Arg Gly Trp Glu Ala Leu Lys Tyr Trp Gly Asn
            770                 775                 780

Leu Leu Gln Tyr Trp Ile Gln Glu Leu Lys Asn Ser Ala Val Ser Leu
785                 790                 795                 800

Phe Asp Ala Ile Ala Ile Ala Val Ala Glu Gly Thr Asp Arg Ile Ile
                        805                 810                 815

Glu Val Ala Gln Arg Ile Gly Arg Ala Phe Leu His Ile Pro Arg Arg
                820                 825                 830

Ile Arg Gln Gly Phe Glu Arg Ala Leu Leu
                835                 840

<210> SEQ ID NO 144
<211> LENGTH: 867
<212> TYPE: PRT
<213> ORGANISM: Human immunodeficiency virus TV1.8_2

<400> SEQUENCE: 144

Met Arg Val Met Gly Thr Gln Lys Asn Cys Gln Gln Trp Trp Ile Trp
1               5                   10                  15

Gly Ile Leu Gly Phe Trp Met Leu Met Ile Cys Asn Thr Glu Asp Leu
                20                  25                  30

Trp Val Thr Val Tyr Tyr Gly Val Pro Val Trp Arg Asp Ala Lys Thr
            35                  40                  45

Thr Leu Phe Cys Ala Ser Asp Ala Lys Ala Tyr Glu Thr Glu Val His
        50                  55                  60

Asn Val Trp Ala Thr His Ala Cys Val Pro Thr Asp Pro Asn Pro Gln
65                  70                  75                  80

Glu Ile Val Leu Gly Asn Val Thr Glu Asn Phe Asn Met Trp Lys Asn
                85                  90                  95

Asp Met Ala Asp Gln Met His Glu Asp Val Ile Ser Leu Trp Asp Gln
                100                 105                 110

Ser Leu Lys Pro Cys Val Lys Leu Thr Pro Leu Cys Val Thr Leu Asn
            115                 120                 125

Cys Thr Asp Thr Asn Val Thr Gly Asn Arg Thr Val Thr Gly Asn Ser
        130                 135                 140

Thr Asn Asn Thr Asn Gly Thr Gly Ile Tyr Asn Ile Glu Glu Met Lys
145                 150                 155                 160

Asn Cys Ser Phe Asn Ala Thr Thr Glu Leu Arg Asp Lys Lys His Lys
                165                 170                 175

Glu Tyr Ala Leu Phe Tyr Arg Leu Asp Ile Val Pro Leu Asn Glu Asn
                180                 185                 190
```

```
Ser Asp Asn Phe Thr Tyr Arg Leu Ile Asn Cys Asn Thr Ser Thr Ile
    195                 200                 205

Thr Gln Ala Cys Pro Lys Val Ser Phe Asp Pro Ile Pro Ile His Tyr
210                 215                 220

Cys Ala Pro Ala Gly Tyr Ala Ile Leu Lys Cys Asn Asn Lys Thr Phe
225                 230                 235                 240

Asn Gly Thr Gly Pro Cys Tyr Asn Val Ser Thr Val Gln Cys Thr His
                245                 250                 255

Gly Ile Lys Pro Val Val Ser Thr Gln Leu Leu Asn Gly Ser Leu
                260                 265                 270

Ala Glu Glu Gly Ile Ile Ile Arg Ser Glu Asn Leu Thr Glu Asn Thr
            275                 280                 285

Lys Thr Ile Ile Val His Leu Asn Glu Ser Val Glu Ile Asn Cys Thr
290                 295                 300

Arg Pro Asn Asn Asn Thr Arg Lys Ser Val Arg Ile Gly Pro Gly Gln
305                 310                 315                 320

Ala Phe Tyr Ala Thr Asn Asp Val Ile Gly Asn Ile Arg Gln Ala His
                325                 330                 335

Cys Asn Ile Ser Thr Asp Arg Trp Asn Lys Thr Leu Gln Gln Val Met
            340                 345                 350

Lys Lys Leu Gly Glu His Phe Pro Asn Lys Thr Ile Gln Phe Lys Pro
            355                 360                 365

His Ala Gly Gly Asp Leu Glu Ile Thr Met His Ser Phe Asn Cys Arg
    370                 375                 380

Gly Glu Phe Phe Tyr Cys Asn Thr Ser Asn Leu Phe Asn Ser Thr Tyr
385                 390                 395                 400

His Ser Asn Asn Gly Thr Tyr Lys Tyr Asn Gly Asn Ser Ser Ser Pro
                405                 410                 415

Ile Thr Leu Gln Cys Lys Ile Lys Gln Ile Val Arg Met Trp Gln Gly
                420                 425                 430

Val Gly Gln Ala Thr Tyr Ala Pro Pro Ile Ala Gly Asn Ile Thr Cys
            435                 440                 445

Arg Ser Asn Ile Thr Gly Ile Leu Leu Thr Arg Asp Gly Gly Phe Asn
450                 455                 460

Thr Thr Asn Asn Thr Glu Thr Phe Arg Pro Gly Gly Gly Asp Met Arg
465                 470                 475                 480

Asp Asn Trp Arg Ser Glu Leu Tyr Lys Tyr Lys Val Val Glu Ile Lys
                485                 490                 495

Pro Leu Gly Ile Ala Pro Thr Lys Ala Lys Arg Arg Val Val Gln Arg
                500                 505                 510

Glu Lys Arg Ala Val Gly Ile Gly Ala Val Phe Leu Gly Phe Leu Gly
            515                 520                 525

Ala Ala Gly Ser Thr Met Gly Ala Ala Ser Ile Thr Leu Thr Val Gln
    530                 535                 540

Ala Arg Gln Leu Leu Ser Gly Ile Val Gln Gln Ser Asn Leu Leu
545                 550                 555                 560

Lys Ala Ile Glu Ala Gln Gln His Met Leu Gln Leu Thr Val Trp Gly
                565                 570                 575

Ile Lys Gln Leu Gln Ala Arg Val Leu Ala Ile Glu Arg Tyr Leu Lys
            580                 585                 590

Asp Gln Gln Leu Leu Gly Ile Trp Gly Cys Ser Gly Arg Leu Ile Cys
    595                 600                 605

Thr Thr Ala Val Pro Trp Asn Ser Ser Trp Ser Asn Lys Ser Glu Lys
```

```
                610                 615                 620
Asp Ile Trp Asp Asn Met Thr Trp Met Gln Trp Asp Arg Glu Ile Ser
625                 630                 635                 640

Asn Tyr Thr Gly Leu Ile Tyr Asn Leu Leu Glu Asp Ser Gln Asn Gln
                645                 650                 655

Gln Glu Lys Asn Glu Lys Asp Leu Leu Glu Leu Asp Lys Trp Asn Asn
                660                 665                 670

Leu Trp Asn Trp Phe Asp Ile Ser Asn Trp Pro Trp Tyr Ile Lys Ile
                675                 680                 685

Phe Ile Met Ile Val Gly Gly Leu Ile Gly Leu Arg Ile Ile Phe Ala
690                 695                 700

Val Leu Ser Ile Val Asn Arg Val Arg Gln Gly Tyr Ser Pro Leu Ser
705                 710                 715                 720

Phe Gln Thr Leu Thr Pro Ser Pro Arg Gly Leu Asp Arg Leu Gly Gly
                725                 730                 735

Ile Glu Glu Glu Gly Gly Glu Gln Asp Arg Asp Arg Ser Ile Arg Leu
                740                 745                 750

Val Ser Gly Phe Leu Ser Leu Ala Trp Asp Asp Leu Arg Asn Leu Cys
                755                 760                 765

Leu Phe Ser Tyr His Arg Leu Arg Asp Phe Ile Leu Ile Ala Val Arg
                770                 775                 780

Ala Val Glu Leu Leu Gly His Ser Ser Leu Arg Gly Leu Gln Arg Gly
785                 790                 795                 800

Trp Glu Ile Leu Lys Tyr Leu Gly Ser Leu Val Gln Tyr Trp Gly Leu
                805                 810                 815

Glu Leu Lys Lys Ser Ala Ile Ser Leu Leu Asp Thr Ile Ala Ile Thr
                820                 825                 830

Val Ala Glu Gly Thr Asp Arg Ile Ile Glu Leu Val Gln Arg Ile Cys
                835                 840                 845

Arg Ala Ile Leu Asn Ile Pro Arg Arg Ile Arg Gln Gly Phe Glu Ala
                850                 855                 860

Ala Leu Leu
865

<210> SEQ ID NO 145
<211> LENGTH: 869
<212> TYPE: PRT
<213> ORGANISM: Human immunodeficiency virus TV1.8_5

<400> SEQUENCE: 145

Met Arg Val Met Gly Thr Gln Lys Asn Cys Gln Gln Trp Trp Ile Trp
1               5                   10                  15

Gly Ile Leu Gly Phe Trp Met Leu Met Ile Cys Asn Thr Glu Asp Leu
                20                  25                  30

Trp Val Thr Val Tyr Tyr Gly Val Pro Val Trp Arg Glu Ala Lys Thr
                35                  40                  45

Thr Leu Phe Cys Ala Ser Asp Ala Lys Ala Tyr Glu Thr Glu Val His
                50                  55                  60

Asn Val Trp Ala Thr His Ala Cys Val Pro Thr Asp Pro Asn Pro Gln
65                  70                  75                  80

Glu Ile Val Leu Gly Asn Val Thr Glu Asn Phe Asn Met Trp Lys Asn
                85                  90                  95

Asn Met Ala Asp Gln Met His Glu Asp Ile Ile Ser Leu Trp Asp Gln
                100                 105                 110
```

```
Ser Leu Lys Pro Cys Val Lys Leu Thr Pro Leu Cys Val Thr Leu Asn
        115                 120                 125

Cys Thr Asp Thr Asn Val Thr Gly Asn Arg Thr Val Thr Gly Asn Thr
    130                 135                 140

Asn Asp Thr Asn Ile Ala Asn Ala Thr Tyr Lys Tyr Glu Glu Met Lys
145                 150                 155                 160

Asn Cys Ser Phe Asn Ala Thr Thr Glu Leu Arg Asp Lys Lys His Lys
                165                 170                 175

Glu Tyr Ala Leu Phe Tyr Lys Leu Asp Ile Val Pro Leu Asn Glu Asn
            180                 185                 190

Ser Asn Asn Phe Thr Tyr Arg Leu Ile Asn Cys Asn Thr Ser Thr Ile
        195                 200                 205

Thr Gln Ala Cys Pro Lys Val Ser Phe Asp Pro Ile Pro Ile His Tyr
    210                 215                 220

Cys Ala Pro Ala Asp Tyr Ala Ile Leu Lys Cys Asn Asn Lys Thr Phe
225                 230                 235                 240

Asn Gly Thr Gly Pro Cys Tyr Asn Val Ser Thr Val Gln Cys Thr His
                245                 250                 255

Gly Ile Lys Pro Val Val Ser Thr Gln Leu Leu Leu Asn Gly Ser Leu
            260                 265                 270

Ala Glu Glu Gly Ile Ile Ile Arg Ser Glu Asn Leu Thr Glu Asn Thr
        275                 280                 285

Lys Thr Ile Ile Val His Leu Asn Glu Ser Val Glu Ile Asn Cys Thr
    290                 295                 300

Arg Pro Asn Asn Asn Thr Arg Lys Ser Val Arg Ile Gly Pro Gly Gln
305                 310                 315                 320

Ala Phe Tyr Ala Thr Asn Asp Val Ile Gly Asn Ile Arg Gln Ala His
                325                 330                 335

Cys Asn Ile Ser Thr Asp Arg Trp Asn Lys Thr Leu Gln Gln Val Met
            340                 345                 350

Lys Lys Leu Gly Glu His Phe Pro Asn Lys Thr Ile Lys Phe Glu Pro
        355                 360                 365

His Ala Gly Gly Asp Leu Glu Ile Thr Met His Ser Phe Asn Cys Arg
    370                 375                 380

Gly Glu Phe Phe Tyr Cys Asn Thr Ser Asn Leu Phe Asn Ser Thr Tyr
385                 390                 395                 400

Tyr Pro Lys Asn Gly Thr Tyr Lys Tyr Asn Gly Asn Ser Ser Leu Pro
                405                 410                 415

Ile Thr Leu Gln Cys Lys Ile Lys Gln Ile Val Arg Met Trp Gln Gly
            420                 425                 430

Val Gly Gln Ala Met Tyr Ala Pro Pro Ile Ala Gly Asn Ile Thr Cys
        435                 440                 445

Arg Ser Asn Ile Thr Gly Ile Leu Leu Thr Arg Asp Gly Gly Phe Asn
    450                 455                 460

Asn Thr Asn Asn Asp Thr Glu Glu Thr Phe Arg Pro Gly Gly Gly Asp
465                 470                 475                 480

Met Arg Asp Asn Trp Arg Ser Glu Leu Tyr Lys Tyr Lys Val Val Glu
                485                 490                 495

Ile Lys Pro Leu Gly Ile Ala Pro Thr Lys Ala Lys Arg Arg Val Val
            500                 505                 510

Gln Arg Lys Lys Arg Ala Val Gly Ile Gly Ala Val Phe Leu Gly Phe
        515                 520                 525

Leu Gly Ala Ala Gly Ser Thr Met Gly Ala Ala Ser Ile Thr Leu Thr
```

```
                530             535             540
Val Gln Ala Arg Gln Leu Leu Ser Gly Ile Val Gln Gln Ser Asn
545                 550                 555                 560

Leu Leu Lys Ala Ile Glu Ala Gln Gln His Met Leu Gln Leu Thr Val
                565                 570                 575

Trp Gly Ile Lys Gln Leu Gln Ala Arg Val Leu Ala Ile Glu Arg Tyr
                580                 585                 590

Leu Lys Asp Gln Gln Leu Leu Gly Ile Trp Gly Cys Ser Gly Arg Leu
                595                 600                 605

Ile Cys Thr Thr Ala Val Pro Trp Asn Ser Ser Trp Ser Asn Lys Ser
                610                 615                 620

Glu Ala Asp Ile Trp Asp Asn Met Thr Trp Met Gln Trp Asp Arg Glu
625                 630                 635                 640

Ile Asn Asn Tyr Thr Glu Thr Ile Phe Arg Leu Leu Glu Asp Ser Gln
                645                 650                 655

Asn Gln Gln Glu Lys Asn Glu Lys Asp Leu Leu Glu Leu Asp Lys Trp
                660                 665                 670

Asn Asn Leu Trp Asn Trp Phe Asp Ile Ser Asn Trp Leu Trp Tyr Ile
                675                 680                 685

Lys Ile Phe Ile Met Ile Val Gly Gly Leu Ile Gly Leu Arg Ile Ile
                690                 695                 700

Phe Ala Val Leu Ser Ile Val Asn Arg Val Arg Gln Gly Tyr Ser Pro
705                 710                 715                 720

Leu Ser Phe Gln Thr Leu Thr Pro Ser Pro Arg Gly Leu Asp Arg Leu
                725                 730                 735

Gly Gly Ile Glu Glu Glu Gly Gly Glu Gln Asp Arg Asp Arg Ser Ile
                740                 745                 750

Arg Leu Val Ser Gly Phe Leu Ser Leu Ala Trp Asp Asp Leu Arg Ser
                755                 760                 765

Leu Cys Leu Phe Ser Tyr His Arg Leu Arg Asp Phe Ile Leu Ile Ala
                770                 775                 780

Val Arg Ala Val Glu Leu Leu Gly His Ser Ser Leu Arg Gly Leu Gln
785                 790                 795                 800

Arg Gly Trp Glu Ile Leu Lys Tyr Leu Gly Ser Leu Val Gln Tyr Trp
                805                 810                 815

Gly Leu Glu Leu Lys Lys Ser Ala Ile Ser Pro Leu Asp Thr Ile Ala
                820                 825                 830

Ile Ala Val Ala Glu Gly Thr Asp Arg Ile Ile Glu Leu Val Gln Arg
                835                 840                 845

Ile Cys Arg Ala Ile Leu Asn Ile Pro Arg Arg Ile Arg Gln Gly Phe
850                 855                 860

Glu Ala Ala Leu Leu
865

<210> SEQ ID NO 146
<211> LENGTH: 854
<212> TYPE: PRT
<213> ORGANISM: Human immunodeficiency virus TV2.12-5/1

<400> SEQUENCE: 146

Met Arg Ala Arg Gly Ile Leu Lys Asn Tyr Arg His Trp Trp Ile Trp
1               5                   10                  15

Gly Ile Leu Gly Phe Trp Met Leu Met Cys Asn Val Lys Gly Leu
                20                  25                  30
```

-continued

```
Trp Val Thr Val Tyr Tyr Gly Val Pro Val Gly Arg Glu Ala Lys Thr
         35                  40                  45

Thr Leu Phe Cys Ala Ser Asp Ala Lys Ala Tyr Glu Lys Glu Val His
         50                  55                  60

Asn Val Trp Ala Thr His Ala Cys Val Pro Thr Asp Pro Asn Pro Gln
 65                  70                  75                  80

Glu Val Ile Leu Gly Asn Val Thr Glu Asn Phe Asn Met Trp Lys Asn
                 85                  90                  95

Asp Met Val Asp Gln Met Gln Glu Asp Ile Ile Ser Leu Trp Asp Gln
             100                 105                 110

Ser Leu Lys Pro Cys Val Lys Leu Thr Pro Leu Cys Val Thr Leu Asn
         115                 120                 125

Cys Thr Asn Ala Thr Val Asn Tyr Asn Asn Thr Ser Lys Asp Met Lys
     130                 135                 140

Asn Cys Ser Phe Tyr Val Thr Thr Glu Leu Arg Asp Lys Lys Lys Lys
145                 150                 155                 160

Glu Asn Ala Leu Phe Tyr Arg Leu Asp Ile Val Pro Leu Asn Asn Arg
                 165                 170                 175

Lys Asn Gly Asn Ile Asn Asn Tyr Arg Leu Ile Asn Cys Asn Thr Ser
             180                 185                 190

Ala Ile Thr Gln Ala Cys Pro Lys Val Ser Phe Asp Pro Ile Pro Ile
         195                 200                 205

His Tyr Cys Ala Pro Ala Gly Tyr Ala Pro Leu Lys Cys Asn Asn Lys
     210                 215                 220

Lys Phe Asn Gly Ile Gly Pro Cys Asp Asn Val Ser Thr Val Gln Cys
225                 230                 235                 240

Thr His Gly Ile Lys Pro Val Val Ser Thr Gln Leu Leu Leu Asn Gly
                 245                 250                 255

Ser Leu Ala Glu Glu Ile Ile Ile Arg Ser Glu Asn Leu Thr Asn
             260                 265                 270

Asn Val Lys Thr Ile Ile Val His Leu Asn Glu Ser Ile Glu Ile Lys
         275                 280                 285

Cys Thr Arg Pro Gly Asn Asn Thr Arg Lys Ser Val Arg Ile Gly Pro
     290                 295                 300

Gly Gln Ala Phe Tyr Ala Thr Gly Asp Ile Ile Gly Asp Ile Arg Gln
305                 310                 315                 320

Ala His Cys Asn Ile Ser Lys Asn Glu Trp Asn Thr Thr Leu Gln Arg
                 325                 330                 335

Val Ser Gln Lys Leu Gln Glu Leu Phe Pro Asn Ser Thr Gly Ile Lys
             340                 345                 350

Phe Ala Pro His Ser Gly Gly Asp Leu Glu Ile Thr Thr His Ser Phe
         355                 360                 365

Asn Cys Gly Gly Glu Phe Phe Tyr Cys Asn Thr Thr Asp Leu Phe Asn
     370                 375                 380

Ser Thr Tyr Ser Asn Gly Thr Cys Thr Asn Gly Thr Cys Met Ser Asn
385                 390                 395                 400

Asn Thr Glu Arg Ile Thr Leu Gln Cys Arg Ile Lys Gln Ile Ile Asn
                 405                 410                 415

Met Trp Gln Glu Val Gly Arg Ala Met Tyr Ala Pro Pro Ile Ala Gly
             420                 425                 430

Asn Ile Thr Cys Arg Ser Asn Ile Thr Gly Leu Leu Leu Thr Arg Asp
         435                 440                 445

Gly Gly Asp Asn Asn Thr Glu Thr Glu Thr Phe Arg Pro Gly Gly Gly
```

-continued

```
        450                 455                 460
Asp Met Arg Asp Asn Trp Arg Ser Glu Leu Tyr Lys Tyr Lys Val Val
465                 470                 475                 480

Glu Ile Lys Pro Leu Gly Val Ala Pro Thr Ala Ala Lys Arg Arg Val
                485                 490                 495

Val Glu Arg Glu Lys Arg Ala Val Gly Ile Gly Ala Val Phe Leu Gly
            500                 505                 510

Phe Leu Gly Ala Ala Gly Ser Thr Met Gly Ala Ala Ser Ile Thr Leu
        515                 520                 525

Thr Val Gln Ala Arg Gln Leu Leu Ser Gly Ile Val Gln Gln Gln Ser
530                 535                 540

Asn Leu Leu Arg Ala Ile Glu Ala Gln Gln His Met Leu Gln Leu Thr
545                 550                 555                 560

Val Trp Gly Ile Lys Gln Leu Gln Ala Arg Val Leu Ala Ile Glu Arg
                565                 570                 575

Tyr Leu Gln Asp Gln Gln Leu Leu Gly Leu Trp Gly Cys Ser Gly Lys
            580                 585                 590

Leu Ile Cys Thr Thr Asn Val Leu Trp Asn Ser Ser Trp Ser Asn Lys
        595                 600                 605

Thr Gln Ser Asp Ile Trp Asp Asn Met Thr Trp Met Gln Trp Asp Arg
610                 615                 620

Glu Ile Ser Asn Tyr Thr Asn Thr Ile Tyr Arg Leu Leu Glu Asp Ser
625                 630                 635                 640

Gln Ser Gln Gln Glu Arg Asn Glu Lys Asp Leu Leu Ala Leu Asp Arg
                645                 650                 655

Trp Asn Asn Leu Trp Asn Trp Phe Ser Ile Thr Asn Trp Leu Trp Tyr
            660                 665                 670

Ile Lys Ile Phe Ile Met Ile Val Gly Gly Leu Ile Gly Leu Arg Ile
        675                 680                 685

Ile Phe Ala Val Leu Ser Leu Val Asn Arg Val Arg Gln Gly Tyr Ser
690                 695                 700

Pro Leu Ser Leu Gln Thr Leu Ile Pro Asn Pro Arg Gly Pro Asp Arg
705                 710                 715                 720

Leu Gly Gly Ile Glu Glu Gly Gly Glu Gln Asp Ser Ser Arg Ser
                725                 730                 735

Ile Arg Leu Val Ser Gly Phe Leu Thr Leu Ala Trp Asp Asp Leu Arg
            740                 745                 750

Ser Leu Cys Leu Phe Cys Tyr His Arg Leu Arg Asp Phe Ile Leu Ile
        755                 760                 765

Val Val Arg Ala Val Glu Leu Leu Gly His Ser Ser Leu Arg Gly Leu
770                 775                 780

Gln Arg Gly Trp Gly Thr Leu Lys Tyr Leu Gly Ser Leu Val Gln Tyr
785                 790                 795                 800

Trp Gly Leu Glu Leu Lys Lys Ser Ala Ile Asn Leu Leu Asp Thr Ile
                805                 810                 815

Ala Ile Ala Val Ala Glu Gly Thr Asp Arg Ile Leu Glu Phe Ile Gln
            820                 825                 830

Asn Leu Cys Arg Gly Ile Arg Asn Val Pro Arg Arg Ile Arg Gln Gly
        835                 840                 845

Phe Glu Ala Ala Leu Gln
    850
```

<210> SEQ ID NO 147

```
<211> LENGTH: 875
<212> TYPE: PRT
<213> ORGANISM: Artificial
<220> FEATURE:
<223> OTHER INFORMATION: HIV Env consensus sequence
<220> FEATURE:
<221> NAME/KEY: misc_feature
<222> LOCATION: (148)..(149)
<223> OTHER INFORMATION: Xaa can be any naturally occurring amino acid
<220> FEATURE:
<221> NAME/KEY: misc_feature
<222> LOCATION: (151)..(151)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: misc_feature
<222> LOCATION: (155)..(156)
<223> OTHER INFORMATION: Xaa can be any naturally occurring amino acid
<220> FEATURE:
<221> NAME/KEY: misc_feature
<222> LOCATION: (192)..(192)
<223> OTHER INFORMATION: Xaa can be any naturally occurring amino acid
<220> FEATURE:
<221> NAME/KEY: misc_feature
<222> LOCATION: (366)..(366)
<223> OTHER INFORMATION: Xaa can be any naturally occurring amino acid
<220> FEATURE:
<221> NAME/KEY: misc_feature
<222> LOCATION: (406)..(409)
<223> OTHER INFORMATION: Xaa can be any naturally occurring amino acid
<220> FEATURE:
<221> NAME/KEY: misc_feature
<222> LOCATION: (421)..(421)
<223> OTHER INFORMATION: Xaa can be any naturally occurring amino acid
<220> FEATURE:
<221> NAME/KEY: misc_feature
<222> LOCATION: (475)..(476)
<223> OTHER INFORMATION: Xaa can be any naturally occurring amino acid

<400> SEQUENCE: 147

Met Arg Val Met Gly Thr Gln Lys Asn Cys Gln Gln Trp Trp Ile Trp
1               5                   10                  15

Gly Ile Leu Gly Phe Trp Met Leu Met Ile Cys Asn Val Glu Asp Leu
            20                  25                  30

Trp Val Thr Val Tyr Tyr Gly Val Pro Val Trp Arg Glu Ala Lys Thr
        35                  40                  45

Thr Leu Phe Cys Ala Ser Asp Ala Lys Ala Tyr Glu Thr Glu Val His
    50                  55                  60

Asn Val Trp Ala Thr His Ala Cys Val Pro Thr Asp Pro Asn Pro Gln
65                  70                  75                  80

Glu Ile Val Leu Gly Asn Val Thr Glu Asn Phe Asn Met Trp Lys Asn
                85                  90                  95

Asn Met Val Asp Gln Met His Glu Asp Ile Ile Ser Leu Trp Asp Gln
            100                 105                 110

Ser Leu Lys Pro Cys Val Lys Leu Thr Pro Leu Cys Val Thr Leu Asn
        115                 120                 125

Cys Thr Asn Thr Asn Val Thr Gly Asn Arg Thr Val Thr Gly Asn Ser
    130                 135                 140

Asn Ser Asn Xaa Xaa Ala Xaa Ala Xaa Tyr Xaa Xaa Glu Glu Met Lys
145                 150                 155                 160

Asn Cys Ser Phe Asn Val Thr Glu Leu Arg Asp Lys Lys His Lys
                165                 170                 175

Glu Tyr Ala Leu Phe Tyr Lys Leu Asp Ile Val Pro Leu Asn Asn Xaa
            180                 185                 190
```

-continued

```
Glu Asn Ser Asn Asn Phe Thr Tyr Arg Leu Ile Asn Cys Asn Thr Ser
            195                 200                 205

Thr Ile Thr Gln Ala Cys Pro Lys Val Ser Phe Asp Pro Ile Pro Ile
        210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Tyr Asn Val Ser Thr Val Gln Cys
                245                 250                 255

Thr His Gly Ile Lys Pro Val Val Ser Thr Gln Leu Leu Asn Gly
            260                 265                 270

Ser Leu Ala Glu Glu Gly Ile Ile Ile Arg Ser Glu Asn Leu Thr Glu
        275                 280                 285

Asn Thr Lys Thr Ile Ile Val His Leu Asn Glu Ser Val Glu Ile Asn
        290                 295                 300

Cys Thr Arg Pro Asn Asn Asn Thr Arg Lys Ser Val Arg Ile Gly Pro
305                 310                 315                 320

Gly Gln Ala Phe Tyr Ala Thr Asn Asp Ile Ile Gly Asn Ile Arg Gln
                325                 330                 335

Ala His Cys Asn Ile Ser Thr Asp Arg Trp Asn Lys Thr Leu Gln Gln
            340                 345                 350

Val Met Lys Lys Leu Gln Glu His Phe Pro Asn Lys Thr Xaa Ile Lys
        355                 360                 365

Phe Lys Pro His Ala Gly Gly Asp Leu Glu Ile Thr Met His Ser Phe
        370                 375                 380

Asn Cys Arg Gly Glu Phe Phe Tyr Cys Asn Thr Ser Asn Leu Phe Asn
385                 390                 395                 400

Ser Thr Tyr His Asn Xaa Xaa Xaa Xaa Asn Gly Thr Tyr Lys Tyr Asn
                405                 410                 415

Gly Asn Ser Ser Xaa Pro Ile Thr Leu Gln Cys Lys Ile Lys Gln Ile
            420                 425                 430

Ile Arg Met Trp Gln Gly Val Gly Gln Ala Met Tyr Ala Pro Pro Ile
        435                 440                 445

Ala Gly Asn Ile Thr Cys Arg Ser Asn Ile Thr Gly Ile Leu Leu Thr
450                 455                 460

Arg Asp Gly Gly Phe Asn Asn Thr Asn Thr Xaa Xaa Thr Glu Thr Phe
465                 470                 475                 480

Arg Pro Gly Gly Gly Asp Met Arg Asp Asn Trp Arg Ser Glu Leu Tyr
                485                 490                 495

Lys Tyr Lys Val Val Glu Ile Lys Pro Leu Gly Ile Ala Pro Thr Lys
            500                 505                 510

Ala Lys Arg Arg Val Val Gln Arg Glu Lys Arg Ala Val Gly Ile Gly
        515                 520                 525

Ala Val Phe Leu Gly Phe Leu Gly Ala Ala Gly Ser Thr Met Gly Ala
        530                 535                 540

Ala Ser Ile Thr Leu Thr Val Gln Ala Arg Gln Leu Leu Ser Gly Ile
545                 550                 555                 560

Val Gln Gln Gln Ser Asn Leu Leu Lys Ala Ile Glu Ala Gln Gln His
                565                 570                 575

Met Leu Gln Leu Thr Val Trp Gly Ile Lys Gln Leu Gln Ala Arg Val
            580                 585                 590

Leu Ala Ile Glu Arg Tyr Leu Lys Asp Gln Gln Leu Leu Gly Ile Trp
        595                 600                 605
```

-continued

```
Gly Cys Ser Gly Lys Leu Ile Cys Thr Thr Ala Val Pro Trp Asn Ser
    610                 615                 620

Ser Trp Ser Asn Lys Ser Glu Ala Asp Ile Trp Asp Asn Met Thr Trp
625                 630                 635                 640

Met Gln Trp Asp Arg Glu Ile Ser Asn Tyr Thr Asn Thr Ile Tyr Arg
                645                 650                 655

Leu Leu Glu Asp Ser Gln Asn Gln Gln Glu Lys Asn Glu Lys Asp Leu
            660                 665                 670

Leu Glu Leu Asp Lys Trp Asn Asn Leu Trp Asn Trp Phe Asp Ile Ser
        675                 680                 685

Asn Trp Leu Trp Tyr Ile Lys Ile Phe Ile Met Ile Val Gly Gly Leu
690                 695                 700

Ile Gly Leu Arg Ile Ile Phe Ala Val Leu Ser Ile Val Asn Arg Val
705                 710                 715                 720

Arg Gln Gly Tyr Ser Pro Leu Ser Phe Gln Thr Leu Thr Pro Ser Pro
                725                 730                 735

Arg Gly Pro Asp Arg Leu Gly Gly Ile Glu Glu Gly Gly Glu Gln
            740                 745                 750

Asp Arg Asp Arg Ser Ile Arg Leu Val Ser Gly Phe Leu Ser Leu Ala
        755                 760                 765

Trp Asp Asp Leu Arg Ser Leu Cys Leu Phe Ser Tyr His Arg Leu Arg
770                 775                 780

Asp Phe Ile Leu Ile Ala Val Arg Ala Val Glu Leu Leu Gly His Ser
785                 790                 795                 800

Ser Leu Arg Gly Leu Gln Arg Gly Trp Glu Ile Leu Lys Tyr Leu Gly
                805                 810                 815

Ser Leu Val Gln Tyr Trp Gly Leu Glu Leu Lys Lys Ser Ala Ile Ser
            820                 825                 830

Leu Leu Asp Thr Ile Ala Ile Ala Val Ala Glu Gly Thr Asp Arg Ile
        835                 840                 845

Ile Glu Leu Val Gln Arg Ile Cys Arg Ala Ile Leu Asn Ile Pro Arg
850                 855                 860

Arg Ile Arg Gln Gly Phe Glu Ala Ala Leu Leu
865                 870                 875
```

<210> SEQ ID NO 148
<211> LENGTH: 4
<212> TYPE: PRT
<213> ORGANISM: Artificial
<220> FEATURE:
<223> OTHER INFORMATION: Epitope Tag

<400> SEQUENCE: 148

Tyr Met Asp Asp

<210> SEQ ID NO 149
<211> LENGTH: 4
<212> TYPE: PRT
<213> ORGANISM: Artificial
<220> FEATURE:
<223> OTHER INFORMATION: Epitope Tag

<400> SEQUENCE: 149

Trp Met Gly Tyr

<210> SEQ ID NO 150
<211> LENGTH: 4
<212> TYPE: PRT

```
<213> ORGANISM: Artificial
<220> FEATURE:
<223> OTHER INFORMATION: Epitope Tag

<400> SEQUENCE: 150

Gly Pro Gly Arg
```